United States Patent
Freeze et al.

(10) Patent No.: US 10,323,018 B2
(45) Date of Patent: Jun. 18, 2019

(54) QUINAZOLINE AND QUINOLINE COMPOUNDS AND USES THEREOF

(71) Applicant: Millennium Pharmaceuticals, Inc., Cambridge, MA (US)

(72) Inventors: Brian Scott Freeze, Boston, MA (US); Kenneth M. Gigstad, Westford, MA (US); David A. Janowick, Quincy, MA (US); Hong Myung Lee, Cambridge, MA (US); Zhan Shi, Concord, MA (US); Francois Soucy, Stoneham, MA (US); Stepan Vyskocil, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/544,192

(22) PCT Filed: Jan. 20, 2016

(86) PCT No.: PCT/US2016/014026
§ 371 (c)(1),
(2) Date: Jul. 17, 2017

(87) PCT Pub. No.: WO2016/118565
PCT Pub. Date: Jul. 28, 2016

(65) Prior Publication Data
US 2018/0009784 A1   Jan. 11, 2018

Related U.S. Application Data

(60) Provisional application No. 62/105,387, filed on Jan. 20, 2015.

(51) Int. Cl.

| | | |
|---|---|---|
| *C07D 401/14* | (2006.01) | |
| *A61K 31/47* | (2006.01) | |
| *C07D 403/12* | (2006.01) | |
| *C07D 405/14* | (2006.01) | |
| *C07D 401/12* | (2006.01) | |
| *C07D 403/14* | (2006.01) | |
| *C07D 409/14* | (2006.01) | |
| *C07D 471/04* | (2006.01) | |
| *C07D 495/04* | (2006.01) | |
| *A61K 31/4709* | (2006.01) | |
| *A61K 31/501* | (2006.01) | |
| *A61K 31/517* | (2006.01) | |
| *A61K 31/541* | (2006.01) | |
| *C07D 215/233* | (2006.01) | |

(Continued)

(52) U.S. Cl.
CPC .......... *C07D 401/14* (2013.01); *A61K 31/47* (2013.01); *A61K 31/4709* (2013.01); *A61K 31/501* (2013.01); *A61K 31/517* (2013.01); *A61K 31/541* (2013.01); *C07D 215/233* (2013.01); *C07D 401/04* (2013.01); *C07D 401/12* (2013.01); *C07D 403/12* (2013.01); *C07D 403/14* (2013.01); *C07D 405/14* (2013.01); *C07D 409/14* (2013.01); *C07D 417/12* (2013.01); *C07D 471/04* (2013.01); *C07D 495/04* (2013.01)

(58) Field of Classification Search
CPC .. C07D 401/14; C07D 401/12; C07D 401/04; C07D 403/12; C07D 403/14; C07D 405/14; C07D 409/14; C07D 471/04; C07D 495/04; C07D 215/233; C07D 417/12; A61K 31/47; A61K 31/4709; A61K 31/501; A61K 31/417; A61K 31/541
See application file for complete search history.

(56) References Cited

U.S. PATENT DOCUMENTS

| | | |
|---|---|---|
| 6,548,499 B1 | 4/2003 | Carson et al. |
| 7,189,724 B2 | 3/2007 | An et al. |

(Continued)

FOREIGN PATENT DOCUMENTS

| | | | |
|---|---|---|---|
| JP | 2007 099641 | | 4/2007 |
| JP | 2013032343 | * | 2/2013 |

(Continued)

OTHER PUBLICATIONS

Busso, PLoS ONE, vol. 3(5), e2267 p. 1-10, 2008. (Year: 2008).*

(Continued)

*Primary Examiner* — D Margaret M Seaman
(74) *Attorney, Agent, or Firm* — McNeill Baur PLLC

(57) ABSTRACT

This invention provides compounds of formula (I) or a pharmaceutically acceptable salt thereof, wherein T, J, R, $R^4$, $R^q$, o, $R^A$, W and $R^B$ and subsets thereof are as described in the specification. The compounds are inhibitors of NAMPT and are thus useful for treating cancer, inflammatory conditions, and/or T-cell mediated autoimmune disease.

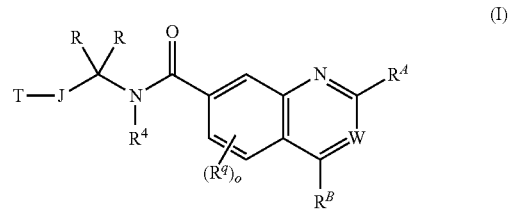

(I)

23 Claims, No Drawings

(51) Int. Cl.
*C07D 401/04* (2006.01)
*C07D 417/12* (2006.01)

(56) References Cited

U.S. PATENT DOCUMENTS

| | | | |
|---|---|---|---|
| 10,144,742 | B2 | 12/2018 | Gigstad et al. |
| 2005/0026923 | A1 | 2/2005 | An et al. |
| 2009/0170840 | A1 | 7/2009 | Roth et al. |
| 2011/0275643 | A1 | 11/2011 | Liou et al. |
| 2012/0003156 | A1 | 1/2012 | Dang et al. |
| 2012/0010172 | A1 | 1/2012 | Christensen et al. |
| 2012/0122924 | A1 | 5/2012 | Curtin et al. |
| 2012/0165318 | A1 | 6/2012 | McCall et al. |
| 2012/0220589 | A1 | 8/2012 | McCall et al. |
| 2012/0225846 | A1 | 9/2012 | McCall et al. |
| 2012/0232056 | A1 | 9/2012 | McCall et al. |
| 2012/0264755 | A1 | 10/2012 | Christensen et al. |
| 2012/0277224 | A1 | 11/2012 | McCall et al. |
| 2013/0273034 | A1 | 10/2013 | Bair et al. |
| 2013/0274286 | A1 | 10/2013 | Kumaravel et al. |
| 2013/0295051 | A1 | 11/2013 | Bair et al. |
| 2013/0303508 | A1 | 11/2013 | Clark et al. |
| 2013/0303509 | A1 | 11/2013 | Hansen et al. |
| 2013/0303510 | A1 | 11/2013 | Hansen et al. |
| 2013/0303511 | A1 | 11/2013 | Clark et al. |
| 2013/0317027 | A1 | 11/2013 | Willardsen et al. |
| 2014/0336167 | A1 | 11/2014 | Sweis et al. |

FOREIGN PATENT DOCUMENTS

| | | |
|---|---|---|
| WO | WO 1999/042461 | 8/1999 |
| WO | WO 2004/043950 | 5/2004 |
| WO | WO 2004/089416 | 10/2004 |
| WO | WO 2005/007099 | 1/2005 |
| WO | WO 2010/023307 | 3/2010 |
| WO | WO 2010/142735 | 12/2010 |
| WO | WO 2011/109441 | 9/2011 |
| WO | WO 2011/121055 | 10/2011 |
| WO | WO 2011/121434 | 10/2011 |
| WO | WO 2012/031196 | 3/2012 |
| WO | WO 2012/031197 | 3/2012 |
| WO | WO 2012/031199 | 3/2012 |
| WO | WO 2012/087861 | 6/2012 |
| WO | WO 2012/150952 | 11/2012 |
| WO | WO 2012/154194 | 11/2012 |
| WO | WO 2012/177782 | 12/2012 |
| WO | WO 2013/067710 | 5/2013 |
| WO | WO 2013/082150 | 6/2013 |
| WO | WO 2013/127267 | 9/2013 |
| WO | WO 2013/127268 | 9/2013 |
| WO | WO 2013/130935 | 9/2013 |
| WO | WO 2013/130943 | 9/2013 |
| WO | WO 2013/158649 | 10/2013 |
| WO | WO 2013/170112 | 11/2013 |
| WO | WO 2013/170113 | 11/2013 |
| WO | WO 2013/170115 | 11/2013 |
| WO | WO 2013/170118 | 11/2013 |
| WO | WO 2013/170191 | 11/2013 |
| WO | WO 2014/004884 | 1/2014 |
| WO | WO 2015/100322 | 7/2015 |

OTHER PUBLICATIONS

Esposito, J Neuroinflammation, vol. 9(66), 1-11, 2012. (Year: 2012).*
Galli, J Med Chem, vol. 56, 6279-6296, 2013. (Year: 2013).*
International Search Report for PCT/US2016/014026, dated Mar. 30, 2016, 16 pages.
Bi et al., "Overexpression of Nampt in Gastric Cancer and Chemopotentiating Effects of the Nampt Inhibitor FK866 in Combination with Fluorouracil," Oncology Reports, 2011, 26:1251-1257.
Bowlby et al., "Nicotinamide Phosphoribosyl Transferase (Nampt) is Required for De Novo Lipogenesis in Tumor Cells," PLoS ONE, 2012, 7(6):e40195.
Chemical Abstracts Service, Online Database Registry, XP002772406, Aug. 21, 2006.
Chemical Abstracts Service, Online Database Registry, XP002772407, Aug. 21, 2006.
Chemical Abstracts Service, Online Database Registry, XP002772408, Jun. 25, 2009.
Christensen et al., "Nicotinamide Phosphoribosyltransferase Inhibitors, Design, Preparation and SAR," J. Med. Chem., 2013, 1-55.
Dragovich et al., "Fragment-based Design of 3-aminopyridine-derived Amides as Potent Inhibitors of Human Nicotinamide Phosphoribosyltransferase (NAMPT)," Bioorganic & Medicinal Chemistry Letters, 2013, 24(3):954-962.
Ekelund et al., "Interactions Between the New Cytotoxic Drug CHS 828 and Amiloride and Mitomycin C in a Human Tumour Cell Line and in Tumour Cells from Patients," Chemotherapy, 2002, 48:196-204.
Extended European Search Report received in European Patent Application No. 15779407.4, dated Aug. 9, 2017, 21 pages.
Extended European Search Report received in European Patent Application No. 16740634.7, dated Sep. 19, 2018, 7 pages.
Galli et al., "Medicinal Chemistry of Nicotinamide Phosphoribosyltransferase (Nampt) Inhibitors," J. Med. Chem, 2013, Review, A-R.
Giannetti et al., "Fragment-Based Identification of Amides Derived from Trans-2-(Pyridin-3-yl)Cyclopropanecarboxylic Acid as Potent Inhibitors of Human Nicotinamide Phosphoribosyltransferase (NAMPT)," J. Med. Chem, 2014, 1-94.
Gunzer-Toste et al., "Discovery of Potent and Efficacious Urea-Containing Nicotinamide Phosphoribosyltransferase (NAMPT) Inhibitors with Reduced CYP2C9 Inhibition Properties," Bioorganic & Medicinal Chemistry Letters, 2013, 23:3531-3538.
Hajduk et al., "Privileged Molecules for Protein Binding Identified from NMR-Based Screening," J. Med. Chem., 2000, 43:3443-3447.
Hupkes et al., "Identification of Novel Bacterial M.SssI DNA Methyltransferase Inhibitors," Journal of Biomolecular Screening, 2012, 18(3):348-355.
International Search Report for PCT/US2015/026275 dated Jul. 9, 2015, 8 pages.
Martinsson et al., "The Combination of the Antitumoural Pyridyl Cyanoguanidine CHS 828 and Etoposide in vitro—from Cytotoxic Synergy to Complete Inhibition of Apoptosis," British Journal of Pharmacology, 2002, 137:568-573.
McMahon, "VEGF Receptor Signaling in Tumor Angiogenesis," The Oncologist, 2000, 5(suppl1):3-10.
Muruganandham et al, "Metabolic Signatures Associated with a NAD Synthesis Inhibitor-Induced Tumor Apoptosis Identified by $^1$H-Decoupled-$^{31}$P Magnetic Resonance Spectroscopy," Clin. Cancer Res., 2005, 11:3503-3513.
Pinedo et al, "Translational Research: The Role of VEGF in Tumor Angiogenesis," The Oncologist, 2000, 5(suppl1):1-2.
Pogrebniak et al., "Chemopotentiating Effects of a Novel NAD Biosynthesis Inhibitor, FK866, in Combination with Antineoplastic Agents," Eur. J. Med. Res., 2006, 11:313-321.
Rongvaux et al., "Nicotinamide Phosphoribosyl Transferase/Pre-B Cell Colony-Enhancing Factor/Visfatin is Required for Lymphocyte Development and Cellular Resistance to Genotoxic Stress," Jour. Immunol., 2008, 181:4685-4695.
Takeuchi et al., "Discovery of a Novel Nicotinamide Phosphoribosyl Transferase (NAMPT) Inhibitor via in Silico Screening," Biol. Pharm. Bull., 2014, 37(1):31-36.
Zak et al., "Identification of Nicotinamide Phosphoribosyltransferase (NAMPT) Inhibitors with no Evidence of CYP3A4 Time-Dependent Inhibition and Improved Aqueous Solubility," Bioorg. Med. Chem. Lett., 2015, 25:529-541.
Zheng et al., "Structure-Based Discovery of Novel Amide-Containing Nicotinamide Phosphoribosyltransferase (Nampt) Inhibitors," J. Med. Chem., 2013, 56:6413-6433.
Zheng et al., "Structure-Based Identification of Ureas as Novel Nicotinamide Phosphoribosyltransferase (Nampt) Inhibitors," J. Med. Chem, 2013, 56:4921-4937.

(56) References Cited

OTHER PUBLICATIONS

Zheng et al., "Identification of Amides Derived from 1H-Pyrazolo[3,4-b]Pyridine-5-Carboxylic Acid as Potent Inhibitors of Human Nicotinamide Phosphoribosyltransferase (NAMPT)," Bioorg. Med. Chem. Lett., 2013, 23:5488-5497.
Zheng et al., "Discovery of Potent and Efficacious Cyanoguanidine-Containing Nicotinamide Phosphoribosyltransferase (NAMPT) Inhibitors," Bioorg. Med. Chem. Lett., 2014, 24:337-343.
Zoppoli et al., "Potent Synergistic Interaction Between the Nampt Inhibitor APO866 and the Apoptosis Activator TRAIL in Human Leukemia Cells," Experimental Hematology, 2010, 38:979-988.

* cited by examiner

QUINAZOLINE AND QUINOLINE COMPOUNDS AND USES THEREOF

BACKGROUND OF THE INVENTION

Nicotinamide phosphoribosyltransferase (NAMPT; also known as visfatin and pre-B-cell colony-enhancing factor 1 (PBEF)) is an enzyme that catalyzes the condensation of nicotinamide (NaM) with 5-phosphoribosyl-1-pyrophosphate to yield nicotinamide mononucleotide. This is the first and rate-limiting step in one biosynthetic pathway that cells use to make nicotinamide adenine dinucleotide (NAD+). NAD+ is a critical cofactor for multiple enzymes involved in cell metabolism and homeostasis.

Inhibition of NAMPT results in the lowering of cellular concentrations of NAD+(Beauparlant et al (2007) AACR-NCI-EORTC International Conference on Molecular Targets and Cancer Therapeutics, 2007 Oct. 22-26 Abstract nr A82; and Roulson et al (2007) AACR-NCI-EORTC International Conference on Molecular Targets and Cancer Therapeutics, 2007 Oct. 22-26 Abstract nr A81). Cancer cells have a higher basal turnover of NAD+ and also display higher energy requirements compared with normal cells. Small-molecule inhibitors of NAMPT have been shown to cause depletion of intracellular NAD+ levels and ultimately induce tumor cell death (Hansen, C M et al. Anticancer Res. 20, 42111-4220, 2000) as well as inhibit tumor growth in xenograft models (Olese, U. H. et al. Mol Cancer Ther. 9, 1609-1617, 2010).

Compounds of the invention inhibit the activity of NAMPT, and therefore, may be useful for the treatment of cancer. Cases where NAMPT inhibition has been linked to cancer, a disease where the compounds of the invention may have a therapeutic benefit, include but are not limited to colorectal cancer (Van Beijnum, J. R. et al. Int. J. Cancer 101, 118-127, 2002) and NAMPT is involved in angiogenesis (Kim, S. R. et al. Biochem. Biophys. Res. Commun. 357, 150-156, 2007), multiple myeloma (Chauhan, D. et al., Blood, 2012, 120, 3519-3529), breast cancer (Lord, C. J. EMBO Mol. Med. 2012, 4, 1087-1096), leukemia (Thakur, B. K. et al. Int. J. Cancer 2013, 132, 766-774), non-small cell lung (NSCL) cancer (Okumura, S. J. Thorac. Oncol. 2012, 7, 49-56), gastric cancer (Bi, T. Q. et al. Oncol. Rep. 2011, 26, 1251-1257), neuroblastoma (Travelli, C. et al. J. Pharmacol. Exp. Ther. 2011, 338, 829-840), bladder cancer (Yang, H. J. Exp. Biol. Med. 2010, 235, 869-876), mammary carcinoma (Muruganandham, M. et al. Clin. Cancer Res. 2005, 11, 3503-3513), liver carcinoma (Hasmann, M. Cancer Res. 2003, 63, 7436-7442), renal carcinoma (Drevs, J. Anticancer Res. 2003, 23, 4853-4858, cervix adenocarcinoma (Pittelli, M. et al. J. Biol. Chem. 2010, 285, 34106-34114), glioma (Pitelli, N. et al), lymphoma (Le, A. et al. Proc. Natl. Acad. Sci. U.S.A. 2010, 107, 2037-2042), pancreatic cancer (Le, A. et al.), ovarian cancer (Olesen, U. H. et al. Mol. Cancer Ther. 2010, 9, 1609-1617), melanoma (Maldi, E. et al. Pigm. Cell Melanoma Res. 2013, 26, 144-146), prostate cancer (Zerp, S. F. et al. Radiother. and Oncol. 10, 2014, 110, 348).

Other cases, where a compound of the invention may have a therapeutic benefit as a NAMPT inhibitor, include inflammatory conditions such as rheumatoid arthritis, inflammatory bowel disease, asthma, COPD (chronic obstructive pulmonary disease), osteoarthritis, osteoporosis, sepsis, lupus, spinal cord injury and infection (Galli, M. et al Cancer Res. 70, 8-11, 2010). For example, NAMPT is the predominant enzyme in T and B lymphocytes. Selective inhibition of NAMPT leads to NAD+ depletion in lymphocytes blocking the expansion that accompanies autoimmune disease progression whereas cell types expressing the other NAD+ generating pathways might be spared. A small molecule NAMPT inhibitor (FK866) has been shown to selectively block proliferation and induce apoptosis of activated T cells and was efficacious in animal models of arthritis (collagen-induced arthritis) (Busso, N. et al. Plos One 3, e2267, 2008). FK866, a small molecule NAMPT inhibitor, ameliorated the manifestations of experimental autoimmune encephalomyelitis (EAE), a model of T-cell mediated autoimmune disorders. (Bruzzone, S et al. Plos One 4, e7897, 2009). NAMPT activity increases NF-kB transcriptional activity in human vascular endothelial cell, resulting in MMP-2 and MMP-9 activation, suggesting a role for NAMPT inhibitors in the prevention of inflammatory mediated complications of obesity and type 2 diabetes (Adya, R. et. Al. Diabetes Care, 31, 758-760, 2).

Clearly, it would be beneficial to provide novel NAMPT inhibitors that possess good therapeutic properties, especially for the treatment of cancer, inflammatory conditions, and/or T-cell mediated autoimmune disease.

1. General Description of Compounds of the Invention

This invention provides compounds that are inhibitors of NAMPT and accordingly are useful for the treatment of cancer, inflammatory conditions, and/or T-cell mediated autoimmune disease. The invention relates to the following:

Embodiment [1]

A compound of formula I:

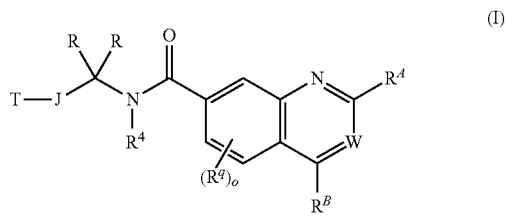

or a pharmaceutically acceptable salt of formula I, wherein:
$R^A$ is

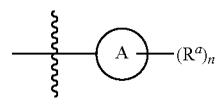

or $YR^C R^D R^E$;
$R^B$ is $XR^1 R^2 R^3$;
W is N, CH or $CR^{q1}$;
Y is selected from C, O, S, and N, provided that (1) when Y is N, then one of $R^C$, $R^D$, and $R^E$ is absent and the remaining two of $R^C$, $R^D$, and $R^E$ are both not hydrogen and (2) when Y is O or S, then two of $R^C$, $R^D$, and $R^E$ are absent and the remaining one of $R^C$, $R^D$, and $R^E$ is not hydrogen;
$R^C$, $R^D$, and $R^E$ are each independently selected from hydrogen; linear or branched $C_{1-6}$aliphatic, wherein 1 or 2 methylene units of the $C_{1-6}$ aliphatic are optionally and independently replaced by O, S, S(O), S(O)$_2$, or N($R^{25}$); $(CH_2)_q$-6-10-membered aryl; $(CH_2)_r$-3-10-membered cycloaliphatic; $(CH_2)_x$-4-10-membered heterocycle having 1-5 heteroatoms independently selected from nitrogen, oxygen, and sulfur, and $(CH_2)_b$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^e$;

X is selected from halogen, C, O, S, and N, provided that (1) when X is N, then one of $R^1$, $R^2$, and $R^3$ is absent; (2) when X is halogen, then $R^1$, $R^2$, and $R^3$ are absent, and (3) when X is O or S, then two of $R^1$, $R^2$, and $R^3$ are absent and the remaining one of $R^1$, $R^2$, and $R^3$ is not hydrogen;

$R^1$, $R^2$, and $R^3$ are each independently selected from hydrogen; linear or branched $C_{1-6}$ aliphatic, wherein 1 or 2 methylene units of the $C_{1-6}$ aliphatic are optionally and independently replaced by O, S, S(O), $S(O)_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^k$;

or wherein any two of $R^1$, $R^2$, and $R^3$ taken together with the atom X to which they are bound, when X is C or N, form a ring selected from 4-10-membered heterocycle ring having 1-5 heteroatoms independently selected from nitrogen, oxygen and sulfur, and 3-10-membered cycloaliphatic, wherein the ring is optionally substituted with one or more $R^b$;

or wherein $R^1$, $R^2$, and $R^3$ taken together with the atom X to which they are bound, when X is C, form a ring selected from 5-10-membered heteroaryl having 1-4 heteroatoms independently selected from nitrogen, oxygen, and sulfur, and 6-10-membered aryl, wherein the ring is optionally substituted with one or more $R^b$;

or wherein $R^1$, $R^2$, and $R^3$ taken together with the atom X to which they are bound, when X is N, form a 5-10-membered heteroaryl ring having 1-5 heteroatoms independently selected from nitrogen, oxygen, and sulfur, wherein the ring is optionally substituted with one or more $R^b$;

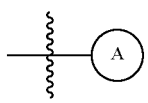

is a ring selected from 3-7-membered saturated, partially unsaturated, and aromatic monocyclic ring having 0-3 heteroatoms independently selected from nitrogen, oxygen, and sulfur and 8-10-membered saturated, partially unsaturated, and aromatic bicyclic ring having 0-5 heteroatoms independently selected from nitrogen, oxygen, and sulfur;

each occurrence of $R^a$ is independently selected from linear or branched $C_{1-6}$ aliphatic and $Z_1$—$R^8$;

or wherein two $R^a$ taken together with the atom or atoms to which they are bound, form a ring selected from 4-10-membered heterocycle having 1-5 heteroatoms independently selected from nitrogen, oxygen, and sulfur and 3-6-membered cycloaliphatic, wherein the ring is optionally substituted with one or more $R^p$;

each occurrence of $R^p$ is independently selected from CN, $CH_3$, $CF_3$, $CH_2F$, $CF_2H$, $NH_2$, NH(linear or branched $C_{1-3}$ aliphatic), N(linear or branched $C_{1-3}$ aliphatic)$_2$, OH, halogen, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $Z_1$ is independently selected from a direct bond, $C_{1-3}$ alkylene chain, O, $N(R^{16})$, S, S(O), $S(O)_2$, C(O), $CO_2$, $C(O)NR^{16}$, $N(R^{16})C(O)$, $N(R^{16})CO_2$, $S(O)_2NR^{16}$, $N(R^{16})S(O)_2$, $OC(O)N(R^{16})$, $N(R^{16})C(O)NR^{16}$, $N(R^{16})S(O)_2N(R^{16})$, and OC(O), wherein the alkylene chain is optionally substituted with one or more $R^h$;

each occurrence of $R^h$ is independently selected from CN, $CH_3$, $CF_3$, $CH_2F$, $CF_2H$, OH, halogen, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $R^b$ is independently selected from linear or branched $C_{1-6}$ aliphatic and $Z_2$—$R^6$;

or wherein two $R^b$ taken together with the atom or atoms to which they are bound, form a 3-7-membered saturated, partially unsaturated, or aromatic monocyclic ring having 0-3 heteroatoms independently selected from nitrogen, oxygen, and sulfur, wherein the ring is optionally substituted with one or more $R^c$;

each occurrence of $R^c$ is independently selected from linear or branched $C_{1-6}$ aliphatic, $CF_3$, $CF_2H$, $CH_2F$, halogen, $OR^{12}$, $(CH_2)_v$—$C(O)R^9$, and $(CH_2)_w$—$NR^{10}C(O)R^{11}$;

each occurrence of $Z_2$ is independently selected from direct bond, $C_{1-3}$ alkylene chain, O, $N(R^{17})$, S, S(O), $S(O)_2$, C(O), $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2N(R^{17})$, and OC(O), wherein the alkylene chain is optionally substituted with one or more $R^i$;

each occurrence of $R^i$ is independently selected from CN, $CH_3$, $CF_3$, $CH_2F$, $CF_2H$, halogen, OH, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $R^k$ is independently selected from linear or branched $C_{1-6}$ aliphatic and $Z_3$—$R^{23}$;

each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and OC(O), wherein the alkylene chain is optionally substituted with one or more $R^n$;

each occurrence of $R^n$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

each occurrence of $R^e$ is independently selected from linear or branched $C_{1-6}$ aliphatic and $Z_4$—$R^{22}$;

each occurrence of $Z_4$ is independently selected from direct bond, $C_{1-3}$ alkylene chain, O, $N(R^{20})$, S, S(O), $S(O)_2$, C(O), $CO_2$, $C(O)NR^{20}$, $N(R^{20})C(O)$, $N(R^{20})CO_2$, $S(O)_2NR^{20}$, $N(R^{20})S(O)_2$, $OC(O)N(R^{20})$, $N(R^{20})C(O)NR^{20}$, $N(R^{20})S(O)_2N(R^{20})$, and OC(O), wherein the alkylene chain is optionally substituted with one or more $R^t$;

each occurrence of $R^t$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

J is selected from a direct bond; linear or branched $C_{1-6}$ aliphatic, wherein 1 or 2 methylene units of J are optionally and independently replaced by O, S, or $N(R^{13})$ and further wherein the $C_{1-6}$ aliphatic is optionally substituted with one or more $R^j$;

each occurrence of $R^j$ is independently selected from fluorine, $CH_3$, $CF_3$, $CH_2F$, $CF_2H$, OH, $OCH_3$, $OCF_3$, $OCH_2F$, $OCF_2H$, O(linear or branched $C_{2-3}$ aliphatic), $NH_2$, NH(linear or branched $C_{1-3}$aliphatic), N(linear or branched $C_{1-3}$ aliphatic)$_2$, and linear or branched $C_{2-3}$ aliphatic, wherein the $C_{2-3}$ aliphatic is optionally substituted with one or more F;

or wherein two $R^j$ taken together with the atom or atoms to which they are bound form a ring selected from 3-6-membered heterocycle having 1 heteroatom selected from nitrogen, oxygen, and sulfur and 3-6-membered cycloaliphatic ring, wherein the ring is optionally substituted with one or more $R^m$;

each occurrence of R is independently selected from hydrogen and linear or branched $C_{1-3}$ aliphatic, wherein the $C_{1-3}$ aliphatic is optionally substituted with one or more F;

or wherein one of $R^j$ and one of R taken together with the atoms to which they are bound form a ring selected from 3-6-membered heterocycle having 1 heteroatom selected from nitrogen, oxygen, and sulfur and 3-6-membered cycloaliphatic, wherein the ring is optionally substituted with one or more $R^m$;

$R^4$ is selected from hydrogen and linear or branched $C_{1-6}$ aliphatic;

or wherein one of R and $R^4$ taken together with the atoms to which they are bound, form a ring selected from 4-10-membered heterocycle having 1-5 heteroatoms independently selected from nitrogen, oxygen, and sulfur, wherein the ring is optionally substituted with one or more $R^m$;

or wherein one of $R^j$ and $R^4$ taken together with the atoms to which they are bound, form a ring selected from 4-10-membered heterocycle having 1-5 heteroatoms independently selected from nitrogen, oxygen, and sulfur, wherein the ring is optionally substituted with one or more $R^m$;

each occurrence of $R^m$ is independently selected from halogen, $CF_3$, $CF_2H$, $CH_2F$, and linear or branched $C_{1-6}$ aliphatic, or wherein two $R^m$ taken together with the atom or atoms to which they are bound, form a ring selected from 3-7-membered saturated, partially unsaturated, or aromatic monocyclic ring having 1-3 heteroatoms independently selected from nitrogen, oxygen, and sulfur, wherein the ring is optionally substituted with one or more $R^h$;

each occurrence of $R^h$ is independently selected from halogen, $CF_3$, $CF_2H$, $CH_2F$, linear or branched $C_{1-6}$ aliphatic, $C(O)N(R^{18})_2$, OH, and O(linear or branched $C_{1-6}$ aliphatic);

each occurrence of $R^5$ is independently selected from hydrogen, $CF_3$, $CF_2H$, $CH_2F$, and linear or branched $C_{1-6}$aliphatic;

each occurrence of $R^6$ is independently selected from CN, halogen, $OR^7$, $N(R^{19})_2$, linear or branched $C_{1-6}$ aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the aryl, heteroaryl, heterocycle, and cycloaliphatic are optionally substituted with one or more $R^c$;

each occurrence of $R^7$ is independently selected from hydrogen, $CF_3$, $CF_2H$, $CH_2F$, linear or branched $C_{1-6}$ aliphatic, and 6-10-membered aryl;

each occurrence of $R^8$ is independently selected from CN, halogen, $OR^5$, $N(R^{21})_2$, linear or branched $C_{1-6}$ aliphatic, 6-10-membered aryl, 3-10-membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein the aryl, cycloaliphatic, heteroaryl, and heterocycle are optionally substituted with one or more $R^g$;

each occurrence of $R^g$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $R^9$ is independently selected from OH, O(linear or branched $C_{1-6}$ aliphatic), $N(R^5)_2$, and linear or branched $C_{1-6}$ aliphatic;

each occurrence of $R^{10}$ is independently selected from hydrogen and linear or branched $C_{1-6}$ aliphatic;

each occurrence of $R^{11}$ is independently selected from OH, $OC_{1-6}$aliphatic, $N(R^4)_2$, and $C_{1-6}$ aliphatic;

each occurrence of $R^{12}$ is independently selected from hydrogen and linear or branched $C_{1-6}$ aliphatic;

each occurrence of $R^{13}$ is independently selected from hydrogen and linear or branched $C_{1-6}$ aliphatic;

each occurrence of $R^{14}$ is independently selected from hydrogen and linear or branched $C_{1-6}$ aliphatic;

each occurrence of $R^{15}$ is independently selected from hydrogen and linear or branched $C_{1-6}$ aliphatic;

each occurrence of $R^{16}$ is independently selected from hydrogen and linear or branched $C_{1-6}$ aliphatic;

each occurrence of $R^{17}$ is independently selected from hydrogen and linear or branched $C_{1-6}$ aliphatic;

each occurrence of $R^{18}$ is independently selected from hydrogen and linear or branched $C_{1-6}$ aliphatic;

each occurrence of $R^{19}$ is independently selected from hydrogen and linear or branched $C_{1-3}$ aliphatic;

each occurrence of $R^{20}$ is independently selected from hydrogen and linear or branched $C_{1-6}$ aliphatic;

each occurrence of $R^{21}$ is independently selected from hydrogen and linear or branched $C_{1-6}$ aliphatic;

each occurrence of $R^{22}$ is independently selected from CN, halogen, $OR^{28}$, $N(R^{29})_2$, and linear or branched $C_{1-6}$ aliphatic; 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic;

each occurrence of $R^{23}$ is independently selected from CN, halogen, $OR^{30}$, $SR^{30}$, $N(R^{26})_2$, and linear or branched $C_{1-6}$aliphatic;

each occurrence of $R^{24}$ is independently selected from hydrogen and linear or branched $C_{1-6}$ aliphatic;

each occurrence of $R^{25}$ is independently selected from hydrogen and linear or branched $C_{1-3}$ aliphatic;

each occurrence of $R^{26}$ is independently selected from hydrogen and linear or branched $C_{1-3}$ aliphatic;

each occurrence of $R^{27}$ is independently selected from hydrogen and linear or branched $C_{1-3}$ aliphatic;

each occurrence of $R^{28}$ is independently selected from hydrogen, $CF_3$, $CF_2H$, $CH_2F$, linear or branched $C_{1-6}$ aliphatic, and 6-10-membered aryl;

each occurrence of $R^{29}$ is independently selected from hydrogen and linear or branched $C_{1-3}$ aliphatic; each occurrence of $R^{30}$ is independently selected from hydrogen, $CF_3$, $CF_2H$, $CH_2F$, linear or branched $C_{1-6}$ aliphatic, and 6-10-membered aryl;

T is $(CH_2)_s$-6-10-membered aryl or $(CH_2)_z$-5-10-membered monocyclic or bicyclic heteroaryl having 1-5 heteroatoms independently selected from nitrogen, oxygen, and sulfur, wherein the aryl and heteroaryl are optionally substituted with one or more $R^d$, each occurrence of $R^d$ is independently selected from CN, halogen, $N(R^{27})_2$, and linear or branched $C_{1-6}$ aliphatic; or wherein taken together two $R^d$ together with the atom or atoms to which they are bound, form a 4-10-membered heterocycle ring having 1-5 heteroatoms independently selected from nitrogen, oxygen, and sulfur;

each occurrence of $R^{q1}$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

b is 0, 1, 2, or 3;
n is 0, 1, 2, 3, 4, or 5;
o is 0, 1, 2, or 3;
p is 0, 1, 2, or 3;
r is 0, 1, 2, or 3;
s is 0, 1, 2, or 3;
t is 0, 1, 2, or 3;
q is 0, 1, 2, or 3;
u is 0, 1, 2, or 3;
x is 0, 1, 2, or 3;
v is 0, 1, 2, or 3;
w is 0, 1, 2, or 3; and
z is 0, 1, 2, or 3, further provided that when $R^B$ is a tertiary amine or methyl and J is a direct bond, then T is not phenyl or 3-pyridine, wherein the phenyl and 3-pyridine are optionally substituted with one of more $R^d$.

DETAILED DESCRIPTION OF THE INVENTION

2. Compounds and Definitions

Compounds of this invention include those described generally above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of 3 to 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having 3 to 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. In one aspect, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. In one aspect, the aralkyl group is $C_{6-10}$ aryl$C_{1-6}$ alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, for example 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, in one aspect, mono-, bi-, or tricyclic, in another aspect, mono- or bicyclic. The term "heteroatom" refers to nitrogen, oxygen, or sulfur, and includes any oxidized form of nitrogen or sulfur, and any quaternized form of a basic nitrogen atom. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Non-limiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen atom. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, in one aspect, mono-, bi-, or tricyclic, in another aspect, mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, in one aspect from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, $-NO_2$, $-CN$, $-R^+$, $-C(R^+)=C(R^+)_2$, $-C\equiv C-R^+$, $-OR^+$, $-SR°$, $-S(O)R°$, $-SO_2R°$, $-SO_3R^+$, $-SO_2N(R^+)_2$, $-N(R^+)_2$, $-NR^+C(O)R^+$, $-NR^+C(S)R^+$, $-NR^+C(O)N(R^+)_2$, $-NR^+C(S)N(R^+)_2$, $-N(R^+)C(=NR^+)-N(R^+)_2$, $-N(R^+)C(=NR^+)-R°$, $-NR^+CO_2R^+$, $-NR^+SO_2R°$, $-NR^+SO_2N(R^+)_2$, $-O-C(O)R^+$, $-O-CO_2R^+$, $-OC(O)N(R^+)_2$, $-C(O)R^+$, $-C(S)R°$, $-CO_2R^+$, $-C(O)-C(O)R^+$, $-C(O)N(R^+)_2$, $-C(S)N(R^+)_2$, $-C(O)N(R^+)-OR^+$, $-C(O)N(R^+)C(=NR^+)-N(R^+)_2$, $-N(R^+)C(=NR^+)-N(R^+)-C(O)R^+$, $-C(=NR^+)-N(R^+)_2$, $-C(=NR^+)-OR^+$, $-N(R^+)-N(R^+)_2$, $-C(=NR^+)-N(R^+)-OR^+$, $-C(R°)=N-OR^+$, $-P(O)(R^+)_2$, $-P(O)(OR^+)_2$, $-O-P(O)-OR^+$, and $-P(O)(NR^+)-N(R^+)_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R°$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: $-SH$, $=O$, $=S$, $=C(R^*)_2$, $=N-N(R^*)_2$, $=N-OR^*$, $=N-NHC(O)R^*$, $=N-NHCO_2R°$, $=N-NHSO_2R°$ or $=N-R^*$ where $R°$ is defined above, and each $R^*$ is independently selected from hydrogen or an optionally substituted $C_{1-6}$ aliphatic group.

In addition to the substituents defined above and herein, optional substituents on the nitrogen of a non-aromatic heterocyclic ring also include and are generally selected from
$-R^+$, $-N(R^+)_2$, $-C(O)R^+$, $-C(O)OR^+$, $-C(O)C(O)R^+$, $-C(O)CH_2C(O)R^+$, $-S(O)_2R^+$, $-S(O)_2N(R^+)_2$, $-C(S)N(R^+)_2$, $-C(=NH)-N(R^+)_2$, or $-N(R^+)S(O)_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of $R^+$ (or any other variable similarly defined in the specification and claims herein), are taken together with their intervening atom(s) include, but are not limited to the following: a) two independent occurrences of $R^+$ (or any other variable similarly defined in the specification or claims herein) that are bound to the same atom and are taken together with that atom to form a ring, for example, $N(R^+)_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of $OR^+$

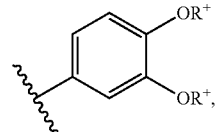

these two occurrences of $R^+$ are taken together with the oxygen atoms to which they are bound to form a fused 6-membered oxygen containing ring:

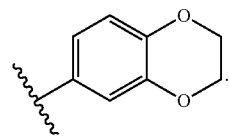 [SMILES: *c1ccc2c(c1)OCCO2]

It will be appreciated that a variety of other rings (e.g., spiro and bridged rings) can be formed when two independent occurrences of $R^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this invention. Such compounds are useful, as a nonlimiting example, as analytical tools or probes in biological assays.

It is to be understood that, when a disclosed compound has at least one chiral center, the present invention encompasses one enantiomer of compound free from the corresponding optical isomer, racemic mixture of the compound and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the invention encompasses a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

Embodiment [2]

A compound of formula Ia or Ib:

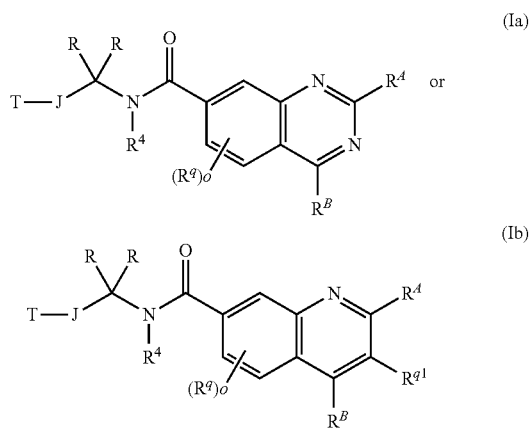

or a pharmaceutically acceptable salt of formula Ia or Ib, wherein T, J, R, $R^4$, $R^q$, o, $R^A$, and $R^B$ are as defined herein for formula I; and $R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [3]

A compound of formula II or III:

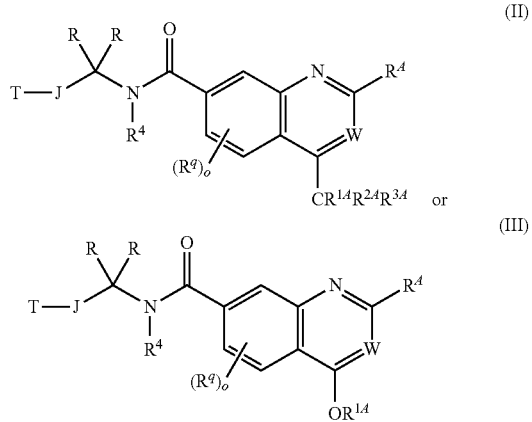

or a pharmaceutically acceptable salt of formula II or III, wherein T, J, R, $R^4$, $R^q$, o, W, and $R^A$ are as defined herein for formula I;

$R^{1A}$, $R^{2A}$, and $R^{3A}$ are each independently selected from hydrogen; linear or branched $C_{1-6}$ aliphatic, wherein 1 or 2 methylene units of the $C_{1-6}$ aliphatic are optionally and independently replaced by O, S, S(O), S(O)$_2$, or N($R^{19}$); $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^k$, provided that for formula III, $R^{1A}$ is not hydrogen and provided that for formula II, when $R^{1A}$, $R^{2A}$, and $R^{3A}$ are each hydrogen and J is a direct bond, the T is not phenyl or 3-pyridine, wherein the phenyl and 3-pyridine are optionally substituted with one or more $R^d$;

or wherein any two of $R^{1A}$, $R^{2A}$, and $R^{3A}$ taken together with the carbon atom to which they are bound, form a ring selected from 4-10-membered heterocycle having 1-5 heteroatoms independently selected from nitrogen, oxygen and sulfur and 3-10-membered cycloaliphatic, wherein the ring is optionally substituted with one or more $R^b$;

or wherein $R^{1A}$, $R^{2A}$, and $R^{3A}$ taken together with the carbon atom to which they are bound form a ring selected from 5-10-membered heteroaryl having 1-4 heteroatoms independently selected from nitrogen, oxygen, and sulfur, and 6-10-membered aryl, wherein the ring is optionally substituted with one or more $R^b$;

each occurrence of $R^b$ is independently selected from linear or branched $C_{1-6}$ aliphatic and $Z_2$—$R^6$;

or wherein two $R^b$ taken together with the atom or atoms to which they are bound, form a ring selected from 3-7-membered saturated, partially unsaturated, or aromatic monocyclic ring having 0-3 heteroatoms independently selected from nitrogen, oxygen, and sulfur, wherein the ring is optionally substituted with one or more $R^c$;

each occurrence of $R^c$ is independently selected from linear or branched $C_{1-6}$ aliphatic, $CF_3$, $CF_2H$, $CH_2F$, halogen, $OR^{12}$, $(CH_2)_v$—$C(O)R^9$, and $(CH_2)_w$—$NR^{10}C(O)R^{11}$;

each occurrence of $Z_2$ is independently selected from direct bond, $C_{1-3}$ alkylene chain, O, $N(R^{17})$, S, $S(O)$, $S(O)_2$, $C(O)$, $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2N(R^{17})$, and $OC(O)$, wherein the alkylene chain is optionally substituted with one or more $R^i$;

each occurrence of $R^i$ is independently selected from CN, $CH_3$, $CF_3$, $CH_2F$, $CF_2H$, halogen, OH, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $R^k$ is independently selected from linear or branched $C_{1-6}$ aliphatic and $Z_3$—$R^{23}$;

each occurrence of $Z_3$ is independently selected from direct bond, $C_{1-3}$ alkylene chain, O, $N(R^{24})$, S, $S(O)$, $S(O)_2$, $C(O)$, $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and $OC(O)$, wherein the alkylene chain is optionally substituted with one or more $R^n$;

each occurrence of $R^n$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

each occurrence of $R^6$ is independently selected from CN, halogen, $OR^7$, $N(R^{19})_2$, linear or branched $C_{1-6}$ aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the aryl, heteroaryl, heterocycle, and cycloaliphatic is optionally substituted with one or more $R^c$;

each occurrence of $R^7$ is independently selected from hydrogen, $CF_3$, $CF_2H$, $CH_2F$, linear or branched $C_{1-6}$ aliphatic, and 6-10-membered aryl;

each occurrence of $R^9$ is independently selected from OH, O(linear or branched $C_{1-6}$ aliphatic), $N(R^{15})_2$, and linear or branched $C_{1-6}$ aliphatic;

each occurrence of $R^{10}$ is independently selected from hydrogen and linear or branched $C_{1-6}$ aliphatic;

each occurrence of $R^{11}$ is independently selected from OH, $OC_{1-6}$aliphatic, $N(R^4)_2$, and $C_{1-6}$ aliphatic;

each occurrence of $R^{12}$ is independently selected from hydrogen and linear or branched $C_{1-6}$ aliphatic;

each occurrence of $R^{14}$ is independently selected from hydrogen and linear or branched $C_{1-6}$ aliphatic;

each occurrence of $R^{15}$ is independently selected from hydrogen and linear or branched $C_{1-6}$ aliphatic;

each occurrence of $R^{17}$ is independently selected from hydrogen and linear or branched $C_{1-6}$ aliphatic;

each occurrence of $R^{19}$ is independently selected from hydrogen and linear or branched $C_{1-3}$ aliphatic;

each occurrence of $R^{23}$ is independently selected from CN, halogen, $OR^{30}$, $SR^{30}$, $N(R^{26})_2$, and linear or branched $C_{1-6}$aliphatic;

each occurrence of $R^{24}$ is independently selected from hydrogen and linear or branched $C_{1-6}$ aliphatic;

each occurrence of $R^{26}$ is independently selected from hydrogen and linear or branched $C_{1-3}$ aliphatic;

each occurrence of $R^{30}$ is independently selected from hydrogen, $CF_3$, $CF_2H$, $CH_2F$, linear or branched $C_{1-6}$ aliphatic, and 6-10-membered aryl;

p is 0, 1, 2, or 3;
s is 0, 1, 2, or 3;
t is 0, 1, 2, or 3;
u is 0, 1, 2, or 3;
v is 0, 1, 2, or 3; and
w is 0, 1, 2, or 3.

Embodiment [4]

A compound of formula II:

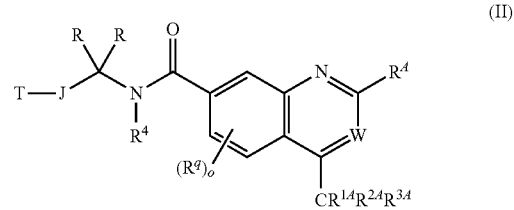

or a pharmaceutically acceptable salt of formula II, wherein T, J,

R, $R^4$, $R^q$, o, W, and $R^A$ are as defined herein for formula I; and $R^{1A}$, $R^{2A}$, and $R^{3A}$ are as defined herein for formula II.

Embodiment [5]

A compound of formula IIa or IIb:

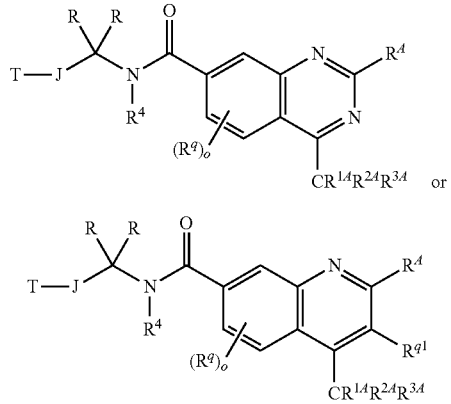

or a pharmaceutically acceptable salt of formula IIa or IIb, wherein T, J, R, $R^4$, $R^9$, o, and $R^A$ are as defined herein for formula I;
$R^{1A}$, $R^{2A}$, and $R^{3A}$ are as defined herein for formula II; and
$R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [6]

The compound of any one of embodiments [3]-[5], wherein $R^{1A}$, $R^{2A}$, and $R^{3A}$ are each independently selected from hydrogen; linear or branched $C_{1-6}$aliphatic, wherein 1 or 2 methylene units of the $C_{1-6}$ aliphatic are optionally and independently replaced by O; $(CH_2)_r$-3-7-membered cycloaliphatic; $(CH_2)_s$-6-membered aryl; and $(CH_2)_u$-4-6-membered heterocycle having 1-3 heteroatoms independently selected from nitrogen, oxygen, and sulfur, wherein the $C_{1-6}$aliphatic, cycloaliphatic, aryl, and heterocycle are optionally substituted with one or more $R_k$, provided that when $R^{1A}$, $R^{2A}$, and $R^{3A}$ are each hydrogen and J is a direct bond, the T is not phenyl or 3-pyridine, wherein the phenyl and 3-pyridine are optionally substituted with one or more $R^d$;
or wherein $R^{1A}$, $R^{2A}$, and $R^{3A}$ taken together with the carbon atom to which they are bound, form a ring selected from 5-6-membered heteroaryl having 1-4 heteroatoms independently selected from nitrogen, oxygen, and sulfur and 6-membered aryl, wherein the ring is optionally substituted with one or more $R^b$.

Embodiment [7]

The compound of any one of embodiments [3]-[6], wherein $CR^{1A}R^{2A}R^{3A}$ is selected from

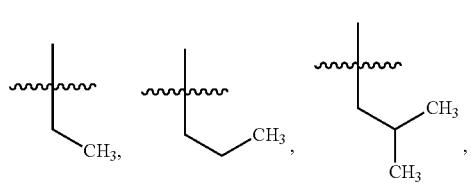

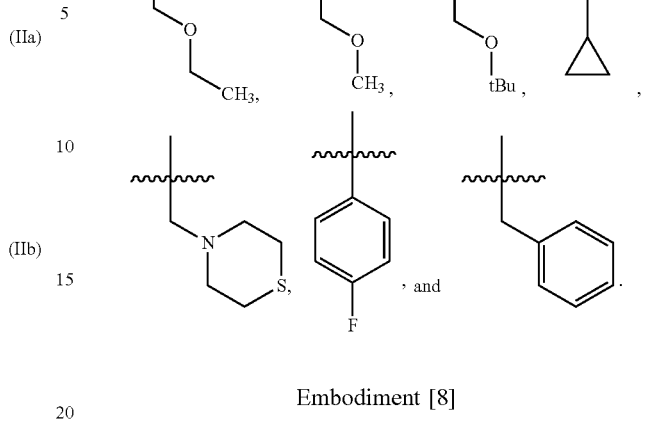

Embodiment [8]

The compound of any one of embodiments [3]-[7], wherein $CR^{1A}R^{2A}R^{3A}$ is selected from

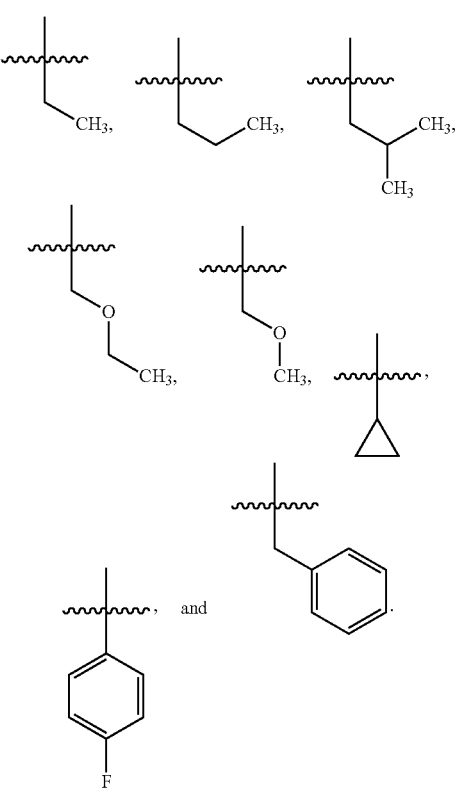

Embodiment [9]

The compound of any one of embodiments [3]-[6], wherein $R^{1A}$, $R^{2A}$, and $R^{3A}$ are each independently selected from hydrogen and linear or branched $C_{1-6}$aliphatic, wherein 1 or 2 methylene units of the $C_{1-6}$ aliphatic are optionally and independently replaced by O.

Embodiment [10]

The compound of any one of embodiments [3]-[9], wherein $CR^{1A}R^{2A}R^{3A}$ is selected from

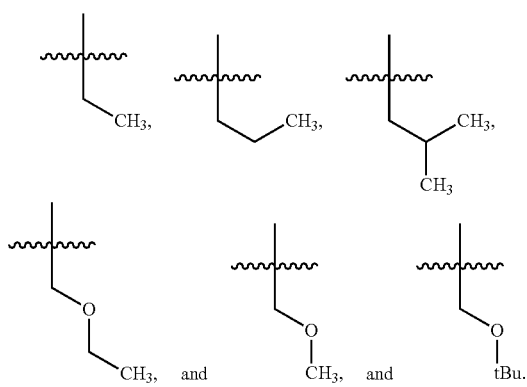

Embodiment [11]

The compound of any one of embodiments [3]-[10], wherein $CR^{1A}R^{2A}R^{3A}$ is selected from

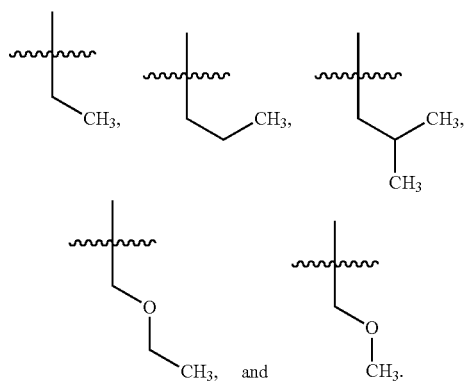

Embodiment [12]

The compound of any one of embodiments [3]-[6], wherein $R^{1A}$, $R^{2A}$, and $R^{3A}$ are each independently selected from hydrogen and linear or branched $C_{1-6}$aliphatic, provided that when $R^{1A}$, $R^{2A}$, and $R^{3A}$ are each hydrogen and J is a direct bond, the T is not phenyl or 3-pyridine, wherein the phenyl and 3-pyridine are optionally substituted with one or more $R^d$.

Embodiment [13]

The compound of any one of embodiments [3]-[12], wherein $CR^{1A}R^{2A}R^{3A}$ is selected from

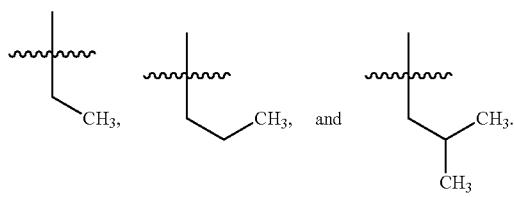

Embodiment [14]

The compound of any one of embodiments [3]-[13], wherein $CR^{1A}R^{2A}R^{3A}$ is selected from

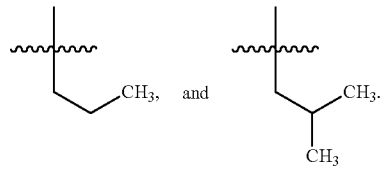

Embodiment [15]

A compound of formula III:

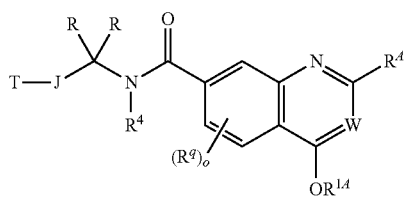

or a pharmaceutically acceptable salt of formula III, wherein
T, J, R,
$R^4$, $R^q$, o, W, and $R^A$ are as defined herein for formula I;
$R^{1A}$ is selected from linear or branched $C_{1-6}$aliphatic, wherein 1 or 2 methylene units of the $C_{1-6}$ aliphatic are optionally and independently replaced by O, S, S(O), $S(O)_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^k$;
each occurrence of $R^k$ is independently selected from linear or branched $C_{1-6}$ aliphatic and $Z_3-R^{23}$;
each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and OC(O), wherein the alkylene chain is optionally substituted with one or more $R^n$;
each occurrence of $R^n$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;
each occurrence of $R^{19}$ is independently selected from hydrogen and linear or branched $C_{1-3}$ aliphatic;
each occurrence of $R^{23}$ is independently selected from CN, halogen, $OR^{30}$, $SR^{30}$, $N(R^{26})_2$, and linear or branched $C_{1-6}$aliphatic;
each occurrence of $R^{24}$ is independently selected from hydrogen and linear or branched $C_{1-6}$ aliphatic;
each occurrence of $R^{26}$ is independently selected from hydrogen and linear or branched $C_{1-3}$ aliphatic;

each occurrence of $R^{30}$ is independently selected from hydrogen, $CF_3$, $CF_2H$, $CH_2F$, linear or branched $C_{1-6}$ aliphatic, and 6-10-membered aryl;
p is 0, 1, 2, or 3;
s is 0, 1, 2, or 3;
t is 0, 1, 2, or 3, and
u is 0, 1, 2, or 3.

Embodiment [15-1]

The compound of formula (III) of embodiment [15] or a pharmaceutically acceptable salt thereof, wherein $R^4$, $R^5$, $R^{13}$, $R^d$, o, $R^{26}$ and $R^{30}$ are as defined herein for formula I;
J is linear $C_{1-6}$ aliphatic, wherein 1-2 methylene units of J are optionally and independently replaced by O, S, or $N(R^{13})$;
T is 5-10-membered heteroaryl having 1-5 nitrogen, wherein the heteroaryl is optionally substituted with one or more $R^d$;
R is hydrogen;
$R^A$ is

[structure: —A—(R^a)_n]

wherein

[structure: —A]

is a 5- or 6-membered aromatic monocyclic ring having 0-3 nitrogen;
n is 0, 1, 2, or 3;
$R^a$ is $Z_1$—$R^8$;
$Z_1$ is a direct bond;
$R^8$ is independently selected from halogen, $R^5$ and $OR^5$;
W is CH;
$R^q$ is hydrogen;
$R^{1A}$ is linear or branched $C_{1-6}$ aliphatic, wherein 1 or 2 methylene units of the $C_{1-6}$ aliphatic are optionally and independently replaced by O, S, or $N(R^{19})$; and wherein the $C_{1-6}$ aliphatic is optionally substituted with one or more $R^k$;
each occurrence of $R^k$ is independently selected from linear or branched $C_{1-6}$ aliphatic and $Z_3$—$R^{23}$;
each occurrence of $Z_3$ is independently selected from direct bond, and $C_{1-3}$ alkylene chain; and
each occurrence of $R^{23}$ is independently selected from CN, halogen, $OR^{30}$, $SR^{30}$, $N(R^{26})_2$, and linear or branched $C_{1-6}$aliphatic.

Embodiment [15-2]

The compound of embodiment [15-1] or a pharmaceutically acceptable salt thereof, wherein $R^{26}$ is as defined herein for formula I;

[structure: T—J—C(R)(R)—N(R^4)— is]

[structure: imidazole-CH2CH2CH2—NH—]

$R^A$ is

[structure: 4-fluorophenyl];

and
$R^{1A}$ is linear or branched $C_{1-6}$ aliphatic, wherein 1 or 2 methylene units of the $C_{1-6}$ aliphatic are optionally and independently replaced by O, S, or NH.

Embodiment [16]

A compound of formula IIIa or IIIb:

[structure (IIIa): T—J—C(R)(R)—N(R^4)—C(O)—quinazoline with $R^A$ and $OR^{1A}$, $(R^q)_o$]

[structure (IIIb): T—J—C(R)(R)—N(R^4)—C(O)—quinoline with $R^A$, $R^{q1}$, $OR^{1A}$, $(R^q)_o$]

or a pharmaceutically acceptable salt of formula IIIa or IIIb, wherein T, J, R, $R^4$, $R^q$, o, and $R^A$ are as defined herein for formula I;
$R^{1A}$ is as defined herein for formula III; and
$R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [17]

The compound of any one of embodiments [15]-[16], wherein $R^{1A}$ is selected from a linear or branched $C_{1-6}$aliphatic, wherein 1 or 2 methylene units of the $C_{1-6}$ aliphatic are optionally and independently replaced by O and $(CH_2)_r$-3-7-membered cycloaliphatic.

Embodiment [17-1]

The compound of any one of embodiments [15]-[16], wherein $R^{14}$ is linear or branched $C_{1-6}$ aliphatic, wherein 1 or 2 methylene units of the $C_{1-6}$ aliphatic are optionally replaced by O; and wherein the $C_{1-6}$ aliphatic is optionally substituted with OH, SH, or $N(R^{26})_2$.

Embodiment [18]

The compound of any one of embodiments [15]-[17], wherein $OR^{14}$ is selected from

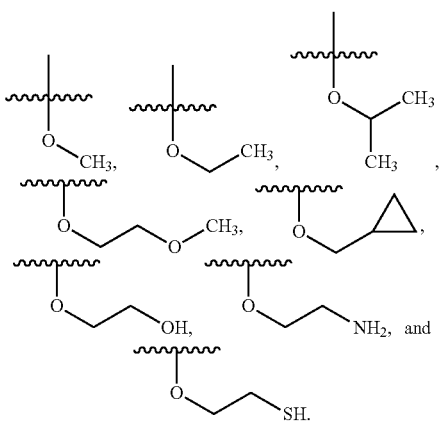

For example, $OR^{14}$ is selected from

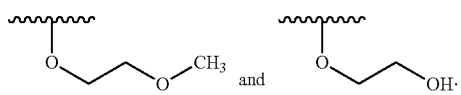

Embodiment [19]

A compound of formula (IV):

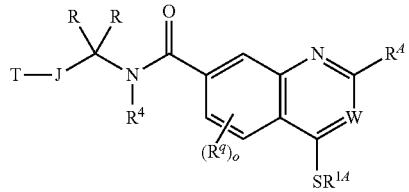

or a pharmaceutically acceptable salt of formula (IV), wherein T, J, R, $R^4$, $R^9$, o, W, and $R^A$ are as defined herein for formula I;
$R^{14}$ is selected from linear or branched $C_{1-6}$ aliphatic, wherein 1 or 2 methylene units of the $C_{1-6}$ aliphatic are optionally and independently replaced by O, S, S(O), $S(O)_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^k$;
each occurrence of $R^k$ is independently selected from linear or branched $C_{1-6}$ aliphatic and $Z_3$—$R^{23}$;
each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and OC(O), wherein the alkylene chain is optionally substituted with one or more $R''$;
each occurrence of $R''$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;
each occurrence of $R^{19}$ is independently selected from hydrogen and linear or branched $C_{1-3}$ aliphatic;
each occurrence of $R^{23}$ is independently selected from CN, halogen, $OR^{30}$, $SR^{30}$, $N(R^{26})_2$, and linear or branched $C_{1-6}$ aliphatic;
each occurrence of $R^{24}$ is independently selected from hydrogen and linear or branched $C_{1-6}$ aliphatic;
each occurrence of $R^{26}$ is independently selected from hydrogen and linear or branched $C_{1-3}$ aliphatic;
each occurrence of $R^{30}$ is independently selected from hydrogen, $CF_3$, $CF_2H$, $CH_2F$, linear or branched $C_{1-6}$ aliphatic, and 6-10-membered aryl;
p is 0, 1, 2, or 3;
s is 0, 1, 2, or 3;
t is 0, 1, 2, or 3, and
u is 0, 1, 2, or 3.

Embodiment [20]

A compound of formula IVa or IVb:

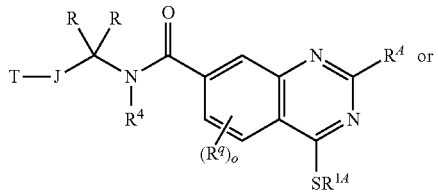

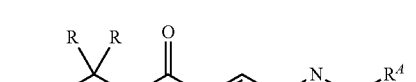

or a pharmaceutically acceptable salt of formula IVa or IVb, wherein T, J, R, $R^4$, $R^q$, o, and $R^A$ are as defined herein for formula I;
$R^{14}$ is as defined herein for formula IV; and
$R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [21]

The compound of any one of embodiments [19]-[20], wherein $R^{14}$ is selected from linear or branched $C_{1-6}$aliphatic, wherein 1 or 2 methylene units of the $C_{1-6}$ aliphatic are optionally and independently replaced by O.

Embodiment [22]

The compound of any one of embodiments [19]-[21], wherein $SR^{1A}$ is

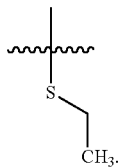

Embodiment [23]

A compound of formula V:

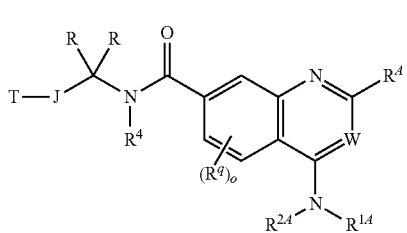

or a pharmaceutically acceptable salt of formula V, wherein T, J, R, $R^4$, R, o, $R^A$ and W are as defined herein for formula I;

$R^{1A}$ and $R^{2A}$ are each independently selected from hydrogen; linear or branched $C_{1-6}$aliphatic, wherein 1 or 2 methylene units of the $C_{1-6}$ aliphatic are optionally and independently replaced by O, S, S(O), $S(O)_2$, or $N(R^{19})$; $(CH_2)_s$-6-10-membered aryl; $(CH_2)_t$-3-10-membered cycloaliphatic; $(CH_2)_u$-4-10-membered heterocycle having 1-5 heteroatoms independently selected from nitrogen, oxygen, and sulfur, and $(CH_2)_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^k$, or wherein $R^{1A}$ and $R^{2A}$ taken together with the nitrogen atom to which they are bound, form a 4-10-membered heterocycle ring having 1-5 heteroatoms independently selected from nitrogen, oxygen and sulfur, wherein the ring is optionally substituted with one or more $R^b$;

or wherein $R^{1A}$ and $R^{2A}$ taken together with the nitrogen atom to which they are bound form a 5-10-membered heteroaryl ring having 1-5 heteroatoms independently selected from nitrogen, oxygen, and sulfur, wherein the ring is optionally substituted with one or more $R^b$;

each occurrence of $R^b$ is independently selected from linear or branched $C_{1-6}$ aliphatic and $Z_2$—$R^6$;

or wherein two $R^b$ taken together with the atom or atoms to which they are bound, form a 3-7-membered saturated, partially unsaturated, or aromatic monocyclic ring having 0-3 heteroatoms independently selected from nitrogen, oxygen, and sulfur, wherein the ring is optionally substituted with one or more $R^c$;

each occurrence of $R^c$ is independently selected from linear or branched $C_{1-6}$ aliphatic, $CF_3$, $CF_2H$, $CH_2F$, halogen, $OR^{12}$, $(CH_2)_v$—$C(O)R^9$, and $(CH_2)_w$—$NR^{10}C(O)R^{11}$;

each occurrence of $Z_2$ is independently selected from direct bond, $C_{1-3}$ alkylene chain, O, $N(R^{17})$, S, S(O), $S(O)_2$, C(O), $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2N(R^{17})$, and OC(O), wherein the alkylene chain is optionally substituted with one or more $R^i$;

each occurrence of $R^i$ is independently selected from CN, $CH_3$, $CF_3$, $CH_2F$, $CF_2H$, halogen, OH, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $R^k$ is independently selected from linear or branched $C_{1-6}$ aliphatic and $Z_3$—$R^{23}$;

each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and OC(O), wherein the alkylene chain is optionally substituted with one or more $R''$;

each occurrence of $R''$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

each occurrence of $R^6$ is independently selected from CN, halogen, $OR^7$, $N(R^{19})_2$, linear or branched $C_{1-6}$ aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the aryl, heteroaryl, heterocycle, and cycloaliphatic is optionally substituted with one or more $R^c$;

each occurrence of $R^7$ is independently selected from hydrogen, $CF_3$, $CF_2H$, $CH_2F$, linear or branched $C_{1-6}$ aliphatic, and 6-10-membered aryl;

each occurrence of $R^9$ is independently selected from OH, O(linear or branched $C_{1-6}$ aliphatic), $N(R^5)_2$, and linear or branched $C_{1-6}$ aliphatic;

each occurrence of $R^{10}$ is independently selected from hydrogen and linear or branched $C_{1-6}$ aliphatic;

each occurrence of $R^{11}$ is independently selected from OH, $OC_{1-6}$aliphatic, $N(R^{14})_2$, and $C_{1-6}$ aliphatic;

each occurrence of $R^{12}$ is independently selected from hydrogen and linear or branched $C_{1-6}$ aliphatic;

each occurrence of $R^{14}$ is independently selected from hydrogen and linear or branched $C_{1-6}$ aliphatic;

each occurrence of $R^{15}$ is independently selected from hydrogen and linear or branched $C_{1-6}$ aliphatic;

each occurrence of $R^{17}$ is independently selected from hydrogen and linear or branched $C_{1-6}$ aliphatic;

each occurrence of $R^{19}$ is independently selected from hydrogen and linear or branched $C_{1-3}$ aliphatic;

each occurrence of $R^{23}$ is independently selected from CN, halogen, $OR^{30}$, $SR^{30}$, $N(R^{26})_2$, and linear or branched $C_{1-6}$aliphatic;

each occurrence of $R^{24}$ is independently selected from hydrogen and linear or branched $C_{1-6}$ aliphatic;

each occurrence of $R^{26}$ is independently selected from hydrogen and linear or branched $C_{1-3}$ aliphatic;

each occurrence of $R^{30}$ is independently selected from hydrogen, $CF_3$, $CF_2H$, $CH_2F$, linear or branched $C_{1-6}$ aliphatic, and 6-10-membered aryl;

p is 0, 1, 2, or 3;

s is 0, 1, 2, or 3;
t is 0, 1, 2, or 3;
u is 0, 1, 2, or 3;
v is 0, 1, 2, or 3; and
w is 0, 1, 2, or 3,
provided that $R^{1A}$ and $R^{2A}$ are not both hydrogen and
provided that when $NR^{1A}R^{2A}$ is a tertiary amine and J is a direct bond, then T is not phenyl or 3-pyridine, wherein the phenyl and 3-pyridine are optionally substituted with one of more $R^d$.

Embodiment [24]

A compound of formula Va or Vb:

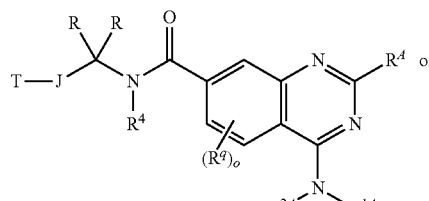

(Va)

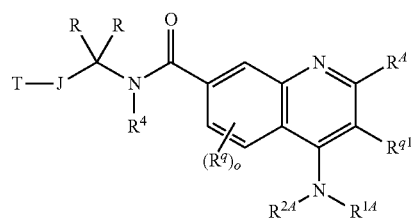

(Vb)

or a pharmaceutically acceptable salt of formula Va or Vb, wherein T, J, R, $R^4$, $R^q$, o, and $R^A$ are as defined herein for formula I;
$R^{1A}$ and $R^{2A}$ are as defined for formula V; and
$R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [25]

The compound of any one of embodiments [23]-[24], wherein $R^{1A}$ and $R^{2A}$ are each independently selected from linear or branched $C_{1-6}$ aliphatic.

Embodiment [26]

The compound of any one of embodiments [23]-[25], wherein $NR^{1A}R^{2A}$ is selected from

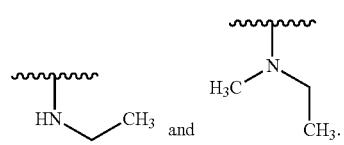

Embodiment [27]

A compound of formula VI:

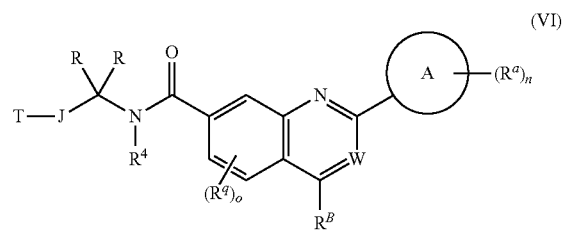

(VI)

or a pharmaceutically acceptable salt of formula VI wherein T, J, R, $R^4$, $R^q$, o, $R^B$, W, and

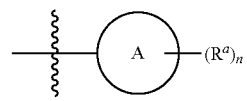

are as defined herein for formula I.

Embodiment [28]

A compound of formula VIa or VIb:

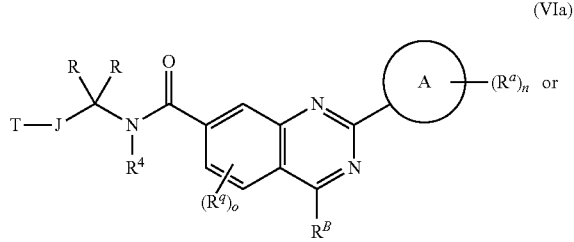

(VIa)

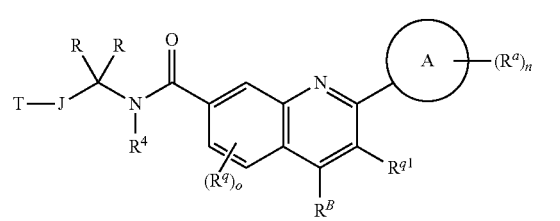

(VIb)

or a pharmaceutically acceptable salt of formula VIa or VIb, wherein T, J, R, $R^4$, $R^q$, o, $R^B$;

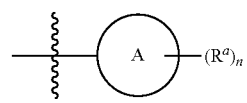

are as defined herein for formula I; and
$R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [29]

The compound of any one of embodiments [1]-[28], wherein

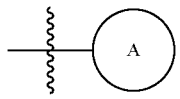

is a 5- or 6-membered saturated, partially unsaturated, monocyclic ring having 0-3 heteroatoms independently selected from nitrogen, oxygen, and sulfur.

Embodiment [30]

The compound of any one of embodiments [1]-[29], wherein

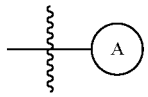

is a 5- or 6-membered aromatic monocyclic ring having 0-3 heteroatoms independently selected from nitrogen, oxygen, and sulfur and n is 0, 1, 2, or 3. For example,

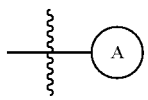

is a 5- or 6-membered aromatic monocyclic ring having 0-3 nitrogen and n is 0, 1, 2, or 3.

Embodiment [31]

The compound of any one of embodiments [1]-[30], wherein

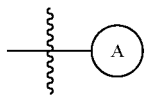

is a selected from phenyl, thiophene, pyrazole, furan, pyrrole, pyridine, pyrazine, thiazole, imidazole, imidazopyridine, indole, and benzoimidazole and n is 0, 1, 2, or 3.

Embodiment [32]

The compound of any one of embodiments [1]-[30], wherein

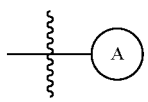

is a 6-membered aromatic monocyclic ring having 0-3 heteroatoms independently selected from nitrogen, oxygen, and sulfur and n is 0, 1, 2, or 3.

Embodiment [33]

The compound of any one of embodiments [1]-[30] or [32], wherein

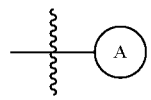

is a phenyl ring and n is 0, 1, 2, or 3.

Embodiment [34]

The compound of any one of embodiments [1]-[33], wherein n is 0.

Embodiment [35]

The compound of any one of embodiments [1]-[33], wherein n is 1 or 2.

Embodiment [36]

The compound of any one of embodiments [1]-[33], wherein n is 1.

Embodiment [37]

A compound of formula VII:

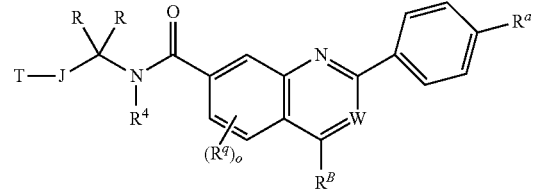

(VII)

or a pharmaceutically acceptable salt of formula VII, wherein T, J, R, $R^4$, $R^q$, o, $R^B$, W, and $R^a$ are as defined herein for formula I.

Embodiment [38]

A compound of formula VIIa or VIIb:

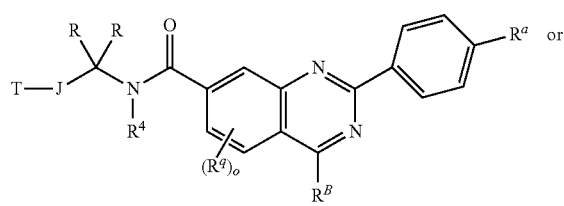

(VIIa) or

-continued

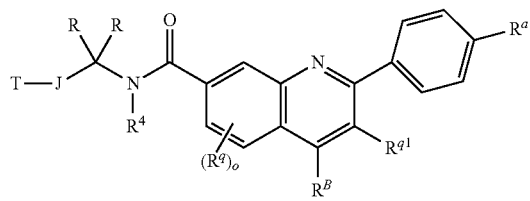
(VIIb)

or a pharmaceutically acceptable salt of formula VIIa or VIIb, wherein T, J, R, $R^4$, $R^q$, o, $R^B$, and $R^a$ are as defined herein for formula I; and $R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [39]

The compound of any one of embodiments [1]-[30], wherein

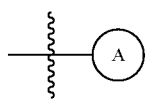

is selected from 5 or 6-membered aromatic monocyclic ring having one heteroatom selected from nitrogen, oxygen, and sulfur and n is 0, 1, 2, or 3.

Embodiment [40]

The compound of any one of embodiments [1]-[30] or [39], wherein

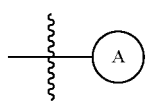

is a 5-membered aromatic monocyclic ring having having one heteroatom selected from nitrogen, oxygen, and sulfur and n is 0, 1, 2, or 3.

Embodiment [41]

The compound of any one of embodiments [1]-[30] or [39]-[40], wherein

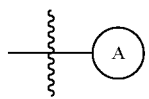

is thiophene and n is 0, 1, or 2.

Embodiment [42]

A compound of formula VIII:

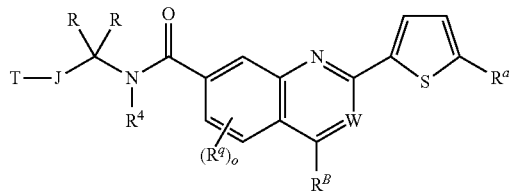
(VIII)

or a pharmaceutically acceptable salt of formula VIII, wherein T, J, R, $R^4$, $R^q$, o, $R^B$, W, and $R^a$ are as defined herein for formula I.

Embodiment [43]

A compound of formula VIIIa or VIIIb:

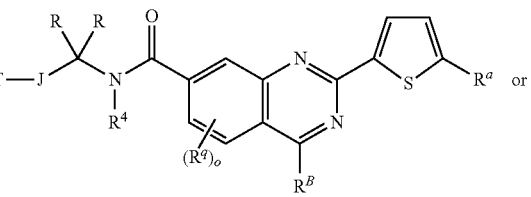
(VIIIa)

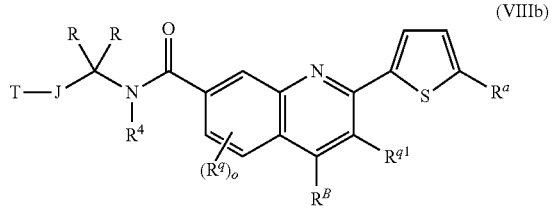
(VIIIb)

or a pharmaceutically acceptable salt of formula VIIIa or VIIIb, wherein T, J, R, $R^4$, $R^q$, o, $R^B$, and $R^a$ are as defined herein for formula I; and $R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [44]

The compound of any one of embodiments [1]-[29], wherein

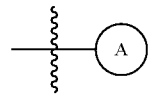

is selected from a 5- or 6-membered saturated monocyclic ring having 0-3 heteroatoms independently selected from nitrogen, oxygen, and sulfur and n is 0, 1, 2, or 3.

Embodiment [45]

The compound of any one of embodiments [1]-[29] or [44], wherein

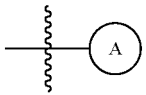

is a 5-membered saturated monocyclic ring having having one heteroatom selected from nitrogen, oxygen, and sulfur and n is 0, 1, 2, or 3.

Embodiment [46]

The compound of any one of embodiments [1]-[29] or [44]-[45], wherein

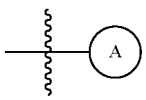

is pyrrolidine and n is 0, 1, or 2.

Embodiment [47]

The compound of any one of embodiments [1]-[46], wherein each occurrence of $R^a$ is $Z_1$—$R^8$.

Embodiment [48]

The compound of any one of embodiments [1]-[47], wherein $Z_1$ is a direct bond.

Embodiment [49]

The compound of any one of embodiments [1]-[48], wherein each occurrence of $R^8$ is independently selected from halogen, $R^5$ and $OR^5$.

Embodiment [50]

The compound of any one of embodiments [1]-[49], wherein each occurrence of $R^8$ is independently selected from chlorine, fluorine, methyl and methoxy.

Embodiment [51]

The compound of any one of embodiments [1]-[50], wherein each occurrence of $R^8$ is independently selected from chlorine and fluorine.

Embodiment [52]

The compound of any one of embodiments [1]-[51], wherein $R^8$ is chlorine.

Embodiment [53]

The compound of any one of embodiments [1]-[51], wherein $R^8$ is fluorine.

Embodiment [54]

The compound of any one of embodiments [1]-[33] or [37]-[53], wherein n is 1 and $R^a$ is chlorine.

Embodiment [55]

The compound of any one of embodiments [1]-[33] or [37]-[53], wherein n is 1 and $R^a$ is fluorine.

Embodiment [56]

The compound of any one of embodiments [1]-[33] or [37]-[53], wherein n is 2 and one $R^a$ is fluorine and the other $R^a$ is chlorine.

Embodiment [57]

The compound of any one of embodiments [1]-[26], wherein $R^4$ is selected from

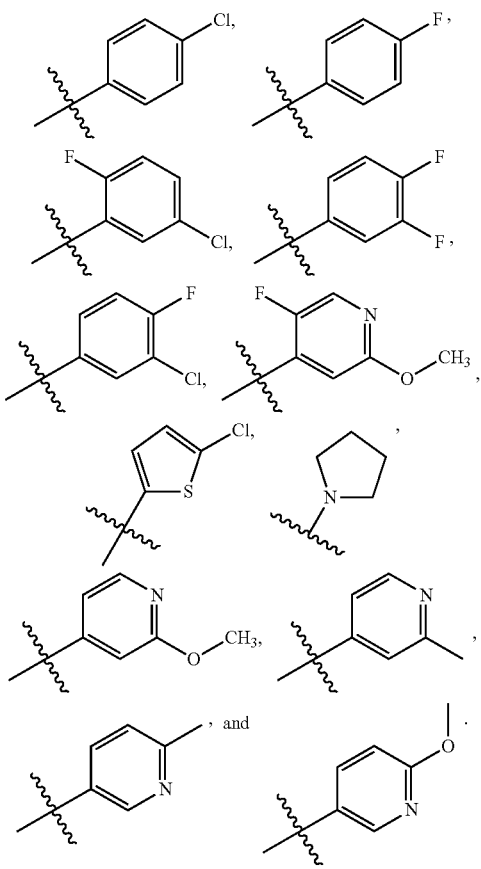

For example, $R^4$ is selected from

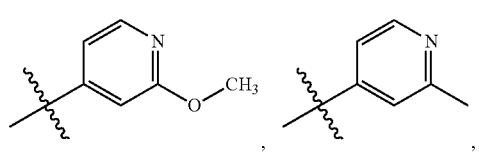

-continued

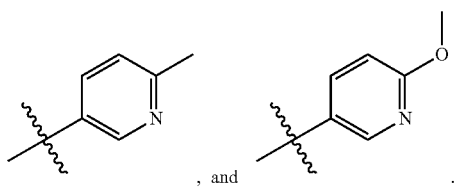

, and

Embodiment [58]

The compound of any one of embodiments [1]-[26] or [57], wherein $R^4$ is selected from

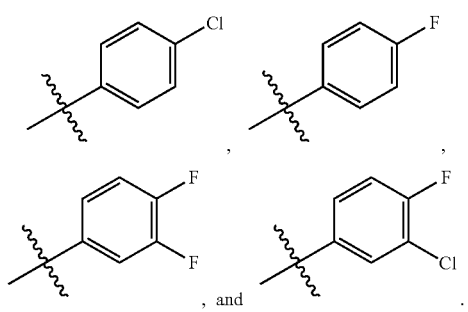

, and

Embodiment [59]

A compound of formula IX:

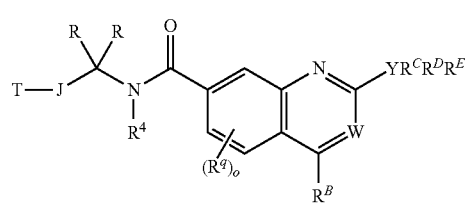
(IX)

or a pharmaceutically acceptable salt of formula IX, wherein T, J, R, $R^4$, $R^q$, o, $R^B$, W, Y, $R^C$, $R^D$, and $R^E$ are as defined herein for formula I.

Embodiment [60]

A compound of formula IXa or IXb:

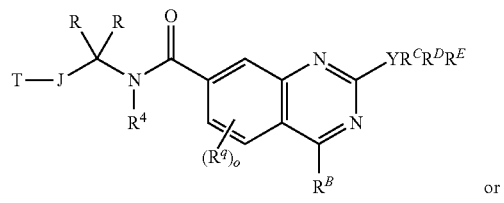
(IXa)

or

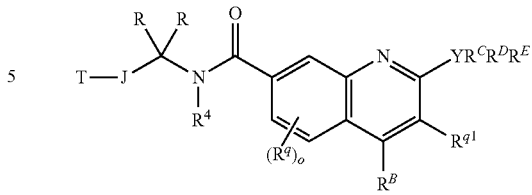
(IXb)

or a pharmaceutically acceptable salt of formula IXa or IXb, wherein T, J, R, $R^4$, $R^q$, o, $R^B$, Y, $R^C$, $R^D$, and $R^E$ are as defined herein for formula I; and
$R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [61]

A compound of formula X or XI:

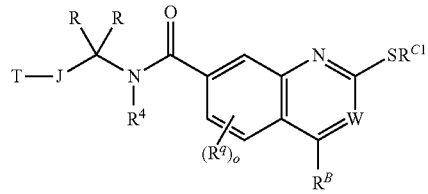
(X)

or

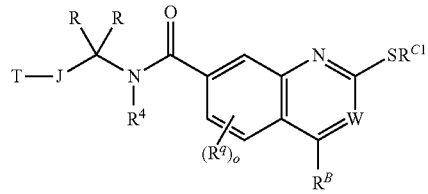
(XI)

or a pharmaceutically acceptable salt of formula X or XI, wherein T, J, R, $R^4$, $R^q$, o, $R^B$, and W are as defined herein for formula I;
$R^{C1}$ is selected from linear or branched $C_{1-6}$aliphatic, wherein 1 or 2 methylene units of the $C_{1-6}$ aliphatic are optionally and independently replaced by O, S, S(O), $S(O)_2$, or $N(R^{25})$; $(CH_2)_q$-6-10-membered aryl; $(CH_2)_r$-3-10-membered cycloaliphatic; $(CH_2)_x$-4-10-membered heterocycle having 1-5 heteroatoms independently selected from nitrogen, oxygen, and sulfur, and $(CH_2)_b$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl is optionally substituted with one or more $R^e$;
each occurrence of $R^e$ is independently selected from linear or branched $C_{1-6}$ aliphatic and $Z_4$—$R^{22}$;
each occurrence of $Z_4$ is independently selected from direct bond, $C_{1-3}$ alkylene chain, O, $N(R^{20})$, S, S(O), $S(O)_2$, C(O), $CO_2$, $C(O)NR^{20}$, $N(R^{20})C(O)$, $N(R^{20})CO_2$, $S(O)_2NR^{20}$, $N(R^{20})S(O)_2$, $OC(O)N(R^{20})$, $N(R^{20})C(O)NR^{20}$, $N(R^{20})S(O)_2N(R^{20})$, and OC(O), wherein the alkylene chain is optionally substituted with one or more $R^t$;
each occurrence of $R^t$ is independently selected from CN, $CH_3$, $CF_3$, $CF_2H$, $CH_2F$, halogen, OH, $OCH_3$, $OCF_3$, OCH$_2$F, OCF$_2$H, O(linear or branched C$_{2-3}$ aliphatic), and linear or branched C$_{2-3}$ aliphatic, wherein the C$_{2-3}$ aliphatic is optionally substituted with one or more F;

each occurrence of R$^{20}$ is independently selected from hydrogen and linear or branched C$_{1-6}$ aliphatic;

each occurrence of R$^{22}$ is independently selected from CN, halogen, OR$^{28}$, N(R$^{29}$)$_2$, and linear or branched C$_{1-6}$ aliphatic; 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic;

each occurrence of R$^{25}$ is independently selected from hydrogen and linear or branched C$_{1-3}$ aliphatic;

each occurrence of R$^{28}$ is independently selected from hydrogen, CF$_3$, CF$_2$H, CH$_2$F, linear or branched C$_{1-6}$ aliphatic, and 6-10-membered aryl;

each occurrence of R$^{29}$ is independently selected from hydrogen and linear or branched C$_{1-3}$ aliphatic;

b is 0, 1, 2, or 3;
r is 0, 1, 2, or 3;
q is 0, 1, 2, or 3, and
x is 0, 1, 2, or 3.

Embodiment [62]

A compound of formula Xa or Xb:

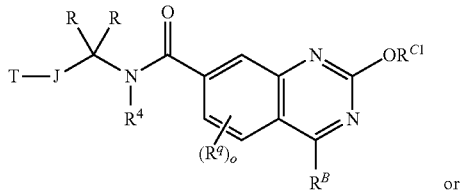

(Xa)

or

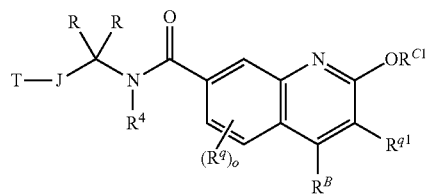

(Xb)

or a pharmaceutically acceptable salt of formula Xa or Xb, wherein T, J, R, R$^4$, R$^q$, o, and R$^B$ are as defined herein for formula I;

R$^{C1}$ is as defined herein for formula X; and

R$^{q1}$ is selected from hydrogen, CN, CH$_3$, CF$_3$, CF$_2$H, CH$_2$F, halogen, OH, OCH$_3$, OCF$_3$, OCH$_2$F, OCF$_2$H, O(linear or branched C$_{2-3}$ aliphatic), and linear or branched C$_{2-3}$ aliphatic, wherein the C$_{2-3}$ aliphatic is optionally substituted with one or more F.

Embodiment [63]

A compound of formula XIa or XIb:

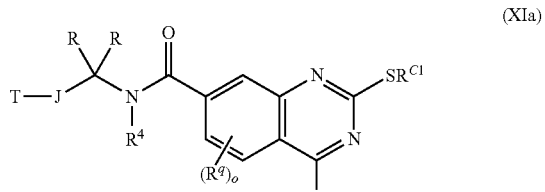

(XIa)

or

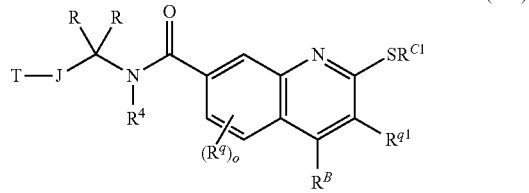

(XIb)

or a pharmaceutically acceptable salt of formula XIa or XIb, wherein T, J, R, R$^4$, R$^q$, o, and R$^B$; R$^{C1}$ is as defined herein for formula X; and R$^{q1}$ is selected from hydrogen, CN, CH$_3$, CF$_3$, CF$_2$H, CH$_2$F, halogen, OH, OCH$_3$, OCF$_3$, OCH$_2$F, OCF$_2$H, O(linear or branched C$_{2-3}$ aliphatic), and linear or branched C$_{2-3}$ aliphatic, wherein the C$_{2-3}$ aliphatic is optionally substituted with one or more F.

Embodiment [64]

The compound of any one of embodiments [61]-[63], wherein R$^{c1}$ is linear or branched C$_{1-6}$aliphatic.

Embodiment [65]

A compound of formula XII:

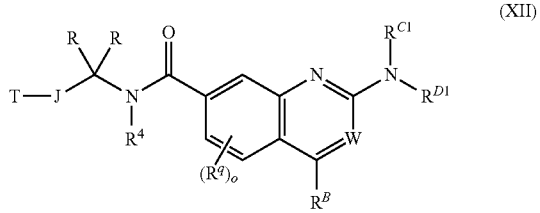

(XII)

or a pharmaceutically acceptable salt of formula XII, wherein T, J, R, R$^4$, R$^q$, o, W, and R$^B$ are as defined herein for formula I and R$^{C1}$ and R$^{D1}$ are each independently selected from hydrogen, linear or branched C$_{1-6}$aliphatic, wherein 1 or 2 methylene units of the C$_{1-6}$ aliphatic are optionally and independently replaced by O, S, S(O), S(O)$_2$, or N(R$^{25}$); (CH$_2$)$_q$-6-10-membered aryl; (CH$_2$)$_r$-3-10-membered cycloaliphatic; (CH$_2$)$_x$-4-10-membered heterocycle having 1-5 heteroatoms independently selected from nitrogen, oxygen, and sulfur, and (CH$_2$)$_b$-5-10-membered heteroaryl having 1-5 heteroatoms independently selected from nitrogen, oxygen, and sulfur, wherein the C$_{1-6}$ aliphatic, aryl, cycloaliphatic, heterocycle, and heteroaryl is optionally substituted with one or more R$^e$;

each occurrence of R$^e$ is independently selected from linear or branched C$_{1-6}$ aliphatic and Z$_4$—R$^{22}$;

each occurrence of $Z_4$ is independently selected from direct bond, $C_{1-3}$ alkylene chain, O, $N(R^{20})$, S, S(O), $S(O)_2$, C(O), $CO_2$, $C(O)NR^{20}$, $N(R^{20})C(O)$, $N(R^{20})CO_2$, $S(O)_2NR^{20}$, $N(R^{20})S(O)_2$, $OC(O)N(R^{20})$, $N(R^{20})C(O)NR^{20}$, $N(R^{20})S(O)_2N(R^{20})$, and OC(O), wherein the alkylene chain is optionally substituted with one or more $R^t$;

each occurrence of $R^t$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

each occurrence of $R^{20}$ is independently selected from hydrogen and linear or branched $C_{1-6}$ aliphatic;

each occurrence of $R^{22}$ is independently selected from CN, halogen, $OR^{28}$, $N(R^{29})_2$, and linear or branched $C_{1-6}$ aliphatic; 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic;

each occurrence of $R^{25}$ is independently selected from hydrogen and linear or branched $C_{1-3}$ aliphatic;

each occurrence of $R^{28}$ is independently selected from hydrogen, $CF_3$, $CF_2H$, $CH_2F$, linear or branched $C_{1-6}$ aliphatic, and 6-10-membered aryl;

each occurrence of $R^{29}$ is independently selected from hydrogen and linear or branched $C_{1-3}$ aliphatic;

b is 0, 1, 2, or 3;
r is 0, 1, 2, or 3;
q is 0, 1, 2, or 3, and
x is 0, 1, 2, or 3,
provided that $R^{C1}$ and $R^{D1}$ are not both hydrogen.

Embodiment [66]

A compound of formula XIIa or XIIb:

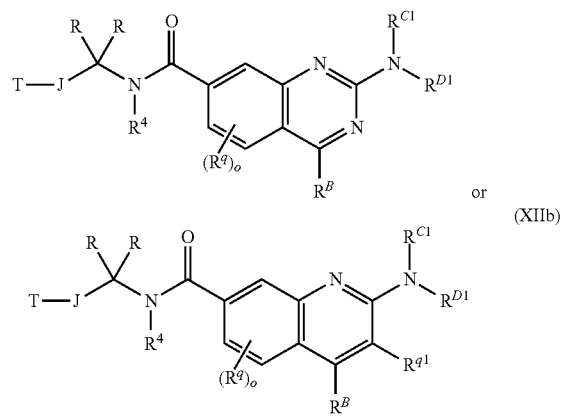

or a pharmaceutically acceptable salt of formula XIIa or XIIb, wherein T, J, R, $R^4$, $R^q$, o, and $R^B$ are as defined herein for formula I;

$R^{C1}$ and $R^{D1}$ are as defined herein for formula XII; and $R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [67]

The compound of any one of embodiments [65]-[66], wherein $R^{C1}$ and $R^{D1}$ are each independently selected from hydrogen and linear or branched $C_{1-6}$ aliphatic, provided that $R^{C1}$ and $R^{D1}$ are not both hydrogen.

Embodiment [68]

The compound of any one of embodiments [65]-[67], wherein $R^{C1}$ and $R^{D1}$ are each independently selected from hydrogen and linear $C_{1-3}$ aliphatic, provided that $R^{C1}$ and $R^{D1}$ are not both hydrogen.

Embodiment [69]

The compound of any one of embodiments [65]-[60], wherein $YR^{C1}R^{D1}$ is selected from

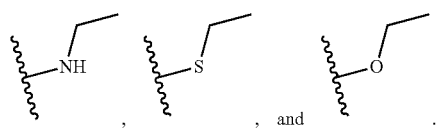

Embodiment [70]

A compound of formula XIII:

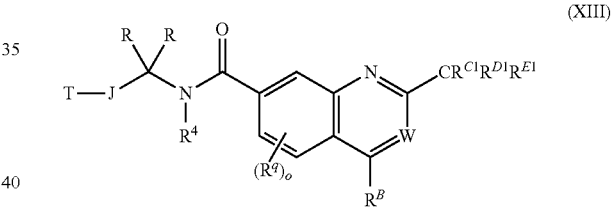

or a pharmaceutically acceptable salt of formula XIII, wherein T, J, R, $R^4$, $R^q$, o, W, and $R^B$ are as defined herein for formula I;

$R^{C1}$, $R^{D1}$ and $R^{E1}$ are each independently selected from hydrogen, linear or branched $C_{1-6}$ aliphatic, wherein 1 or 2 methylene units of the $C_{1-6}$ aliphatic are optionally and independently replaced by O, S, S(O), $S(O)_2$, or $N(R^{25})$; $(CH_2)_q$-6-10-membered aryl; $(CH_2)_r$-3-10-membered cycloaliphatic; $(CH_2)_x$-4-10-membered heterocycle having 1-5 heteroatoms independently selected from nitrogen, oxygen, and sulfur, and $(CH_2)_b$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl is optionally substituted with one or more $R^e$;

each occurrence of $R^e$ is independently selected from linear or branched $C_{1-6}$ aliphatic and $Z_4$—$R^{22}$;

each occurrence of $Z_4$ is independently selected from direct bond, $C_{1-3}$ alkylene chain, O, $N(R^{20})$, S, S(O), $S(O)_2$, C(O), $CO_2$, $C(O)NR^{20}$, $N(R^{20})C(O)$, $N(R^{20})CO_2$, $S(O)_2NR^{20}$, $N(R^{20})S(O)_2$, $OC(O)N(R^{20})$, $N(R^{20})C(O)NR^{20}$, $N(R^{20})S(O)_2N(R^{20})$, and OC(O), wherein the alkylene chain is optionally substituted with one or more $R^t$;

each occurrence of $R^t$ is independently selected from CN, $CH_3$, $CF_3$, $CF_2H$, $CH_2F$, halogen, OH, $OCH_3$, $OCF_3$, OCH₂F, OCF₂H, O(linear or branched C$_{2-3}$ aliphatic), and linear or branched C$_{2-3}$ aliphatic, wherein the C$_{2-3}$ aliphatic is optionally substituted with one or more F;

each occurrence of R$^{20}$ is independently selected from hydrogen and linear or branched C$_{1-6}$ aliphatic;

each occurrence of R$^{22}$ is independently selected from CN, halogen, OR$^{28}$, N(R$^{29}$)$_2$, and linear or branched C$_{1-6}$ aliphatic; 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic;

each occurrence of R$^{25}$ is independently selected from hydrogen and linear or branched C$_{1-3}$ aliphatic;

each occurrence of R$^{28}$ is independently selected from hydrogen, CF$_3$, CF$_2$H, CH$_2$F, linear or branched C$_{1-6}$ aliphatic, and 6-10-membered aryl;

each occurrence of R$^{29}$ is independently selected from hydrogen and linear or branched C$_{1-3}$ aliphatic;

b is 0, 1, 2, or 3;
r is 0, 1, 2, or 3;
q is 0, 1, 2, or 3, and
x is 0, 1, 2, or 3.

Embodiment [71]

A compound of formula XIIIa or XIIIb:

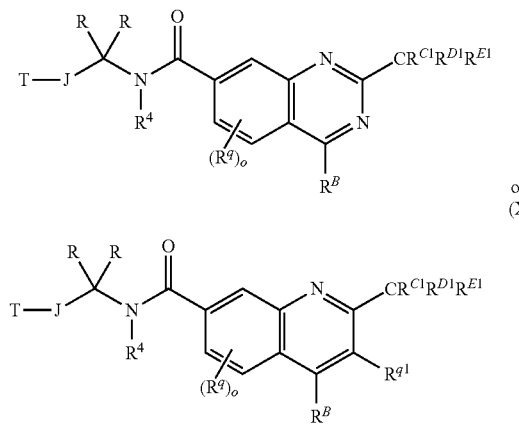

or a pharmaceutically acceptable salt of formula XIIIa or XIIIb, wherein T, J, R, R$^4$, R, o, and R$^B$ are as defined herein for formula I;

R$^{C1}$, R$^{D1}$, and R$^{E1}$ are as defined herein for formula XIII; and

R$^{q1}$ is selected from hydrogen, CN, CH$_3$, CF$_3$, CF$_2$H, CH$_2$F, halogen, OH, OCH$_3$, OCF$_3$, OCH$_2$F, OCF$_2$H, O(linear or branched C$_{2-3}$ aliphatic), and linear or branched C$_{2-3}$ aliphatic, wherein the C$_{2-3}$ aliphatic is optionally substituted with one or more F.

Embodiment [72]

The compound of any one of embodiments [70]-[71], wherein R$^{C1}$, R$^{D1}$, and R$^{E1}$ are each independently selected from hydrogen and linear or branched C$_{1-6}$aliphatic.

Embodiment [73]

The compound of any one of embodiments [1]-[26] or wherein R$^A$ is selected from

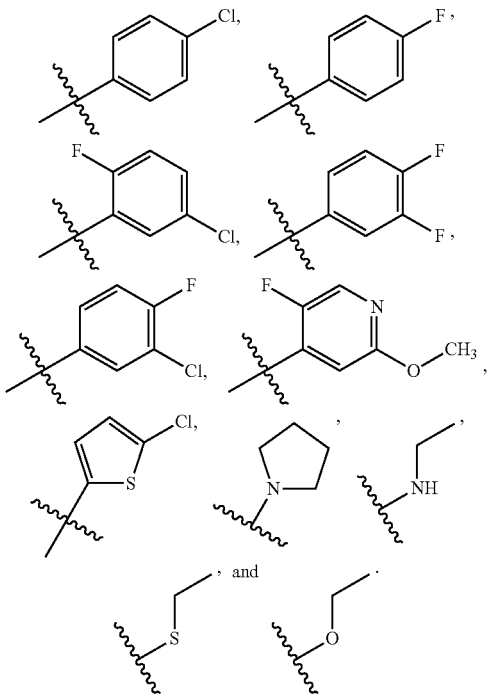

Embodiment [74]

The compound of any one of embodiments [1]-[26] or [73], wherein R$^A$ is selected from

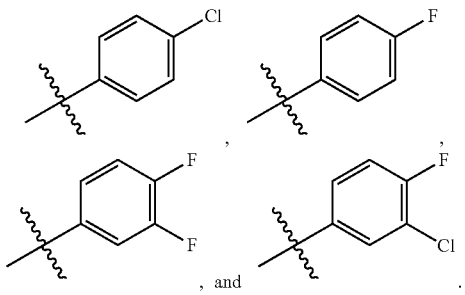

Embodiment [75]

The compound of any one of embodiments [1]-[74], wherein J is selected from direct bond, C$_1$ aliphatic, and C$_2$ aliphatic and further wherein, the aliphatic are optionally substituted with one or more R$^j$; or J is selected from C$_1$ aliphatic and C$_2$ aliphatic, wherein the aliphatic are substituted with one or more R$^j$ and one of R$^j$ and one of R taken together with the atoms to which they are bound form a 3-6-membered cycloaliphatic ring; or J is C$_2$ aliphatic, wherein the aliphatic is substituted with two or more R$^j$ and two R$^j$ taken together with the atom or atoms to which they are bound form a 3-6-membered cycloaliphatic ring.

Embodiment [76]

A compound of formula XIV or XV:

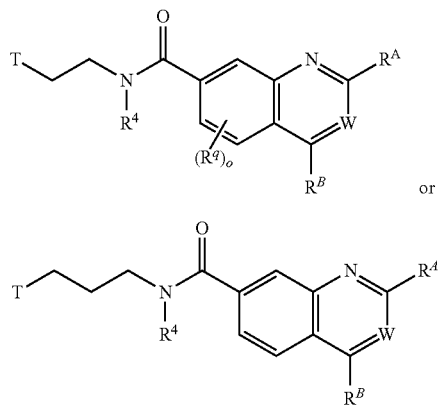

or a pharmaceutically acceptable salt of formula XIV or XV, wherein T, $R^4$, $R^9$, o, W, $R^A$, and $R^B$ are as defined herein for formula I.

Embodiment [77]

A compound of formula XVIa, XVIb, XVa, or XVb:

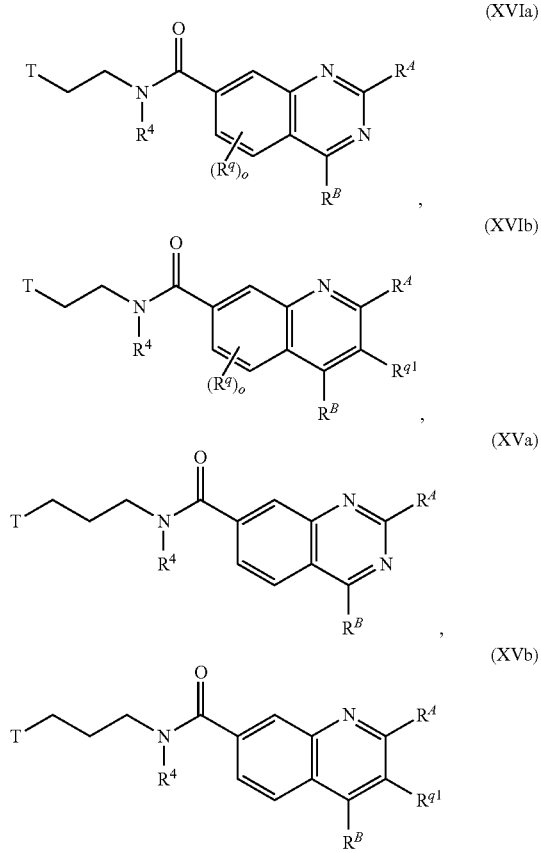

or a pharmaceutically acceptable salt of formula XVIa, XVIb, XVa, or XVb, wherein T, $R^4$, $R^A$, and $R^B$ are as defined herein for formula I; and $R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [78]

The compound of any one of embodiments [1]-[74], wherein J is linear $C_{1-6}$ aliphatic, wherein 1-2 methylene units of J are optionally and independently replaced by O, S, or $N(R^{13})$.

Embodiment [79]

The compound of any one of embodiments [1]-[74] or [78], wherein J is linear $C_{1-6}$ aliphatic, wherein 1-2 methylene units of J are replaced by O.

Embodiment [80]

The compound of any one of embodiments [1]-[74] or [78]-[79], wherein J is linear $C_{1-6}$ aliphatic, wherein 1 methylene unit of J is replaced by O.

Embodiment [81]

The compound of any one of embodiments [1]-[74] or [78]-[80], wherein J is linear $C_2$ aliphatic, wherein 1 methylene unit of J is replaced by O.

Embodiment [82]

The compound of any one of embodiments [1]-[74] or [78]-[81], wherein J is a linear $C_2$ aliphatic substituted with two $R^j$.

Embodiment [83]

The compound of any one of embodiments [1]-[74] or [78]-[82], wherein J is a linear $C_2$ aliphatic substituted with two $R^j$, wherein said two $R^j$ taken together with the atom or atoms to which they are bound form a 3-6-membered cycloaliphatic ring.

Embodiment [84]

The compound of any one of embodiments [1]-[74] or [78]-[83], wherein J is a linear $C_2$ aliphatic substituted with two $R^j$, wherein said two $R^j$ taken together with the atom or atoms to which they are bound form a cyclopropyl ring.

Embodiment [85]

The compound of any one of embodiments [1]-[74] or [82]-[84], wherein

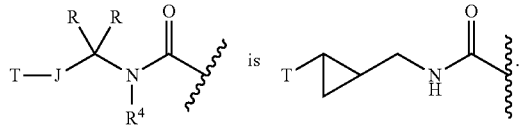

Embodiment [86]

The compound of any one of embodiments [1]-[74] or [82]-[85], wherein

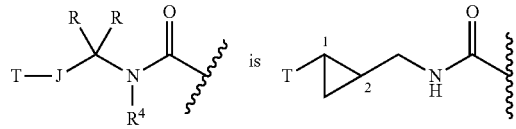

and the substitution at the cyclopropyl ring is trans and the configuration of the stereocenters labeled 1 and 2 is R,R.

Embodiment [87]

The compound of any one of embodiments [1]-[74] or [82]-[85], wherein

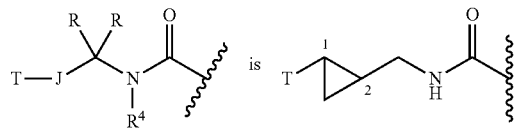

and the substitution at the cyclopropyl ring is trans and the configuration of the stereocenters labeled 1 and 2 is S,S.

Embodiment [88]

The compound of any one of embodiments [1]-[74] or [82]-[85], wherein

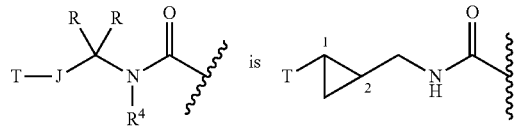

and the substitution at the cyclopropyl ring is trans and the compound is the first eluting enantiomer on a Chiralpak ID column.

Embodiment [89]

The compound of any one of embodiments [1]-[74] or [82]-[85], wherein

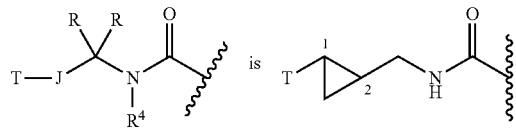

and the substitution at the cyclopropyl ring is trans and the compound is the second eluting enantiomer on a Chiralpak ID column.

Embodiment [90]

The compound of any one of embodiments [1]-[74] or [82]-[84], wherein

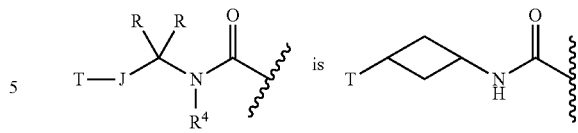

and the substitution at the cyclobutyl ring is cis

Embodiment [91]

The compound of any one of embodiments [1]-[90], wherein T is selected from $(CH_2)_s$-6-10-membered aryl or 5-10-membered heteroaryl having 1-5 heteroatoms independently selected from nitrogen, oxygen, and sulfur, wherein the aryl and heteroaryl are optionally substituted with one or more $R^d$. For example, T is 5-10-membered heteroaryl having 1-3 nitrogen, wherein the heteroaryl is optionally substituted with one or more $R^d$.

Embodiment [92]

The compound of any one of embodiments [1]-[91], wherein T is $(CH_2)_s$-6-10-membered aryl, wherein the aryl is optionally substituted with one or more $R^d$.

Embodiment [93]

A compound of formula XVI:

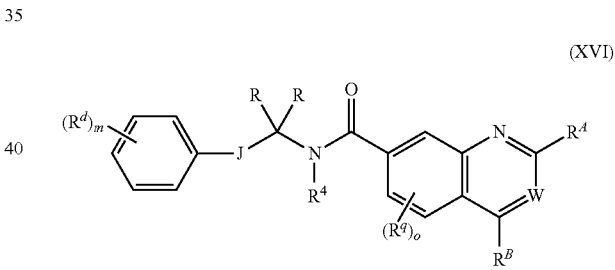

(XVI)

or a pharmaceutically acceptable salt of formula XVI, wherein $R^d$, J, R, $R^4$, $R^q$, o, W, $R^A$, and $R^B$ are as defined herein for formula I; and m is 0, 1, 2, 3, 4, or 5.

Embodiment [94]

A compound of formula XVIa or XVIb:

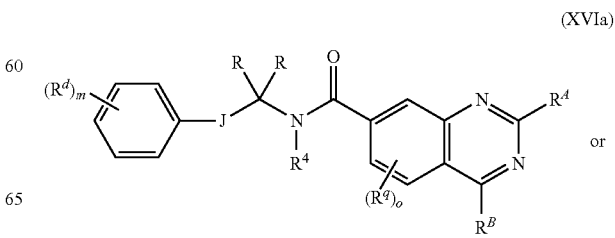

(XVIa)

or (XVIb)

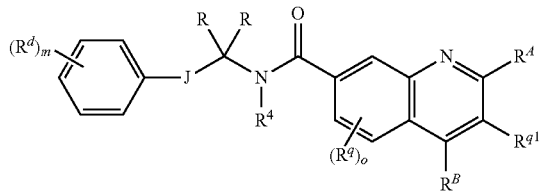

pharmaceutically acceptable salt of formula XVIa or XVIb, wherein $R^d$, J, R, $R^4$, $R^q$, o, $R^A$, and $R^B$ are as defined herein for formula I;
m is 0, 1, 2, 3, 4, or 5; and
$R^{q1}$ is selected from hydrogen, CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F.

Embodiment [95]

The compound of any one of embodiments [1]-[91], wherein T is a 5-9-membered heteroaryl ring having 1-3 heteroatoms independently selected from nitrogen and sulfur, wherein the ring is optionally substituted with one or more $R^d$.

Embodiment [96]

The compound of any one of embodiments [1]-[91] or [95], wherein T is a 5-6 membered heteroaryl ring having 1-3 heteroatoms independently selected from nitrogen and sulfur and the ring is optionally substituted with one or more $R^d$.

Embodiment [97]

The compound of any one of embodiments [1]-[91] or [95]-[96], wherein T is a 5-membered heteroaryl ring having 1-3 heteroatoms independently selected from nitrogen and sulfur and the ring is optionally substituted with one or more $R^d$.

Embodiment [98]

The compound of any one of embodiments [1]-[91] or [95]-[97], wherein T is a 5-membered heteroaryl ring having two nitrogen heteroatoms and the ring is optionally substituted with one or more $R^d$.

Embodiment [99]

The compound of any one of embodiments [1]-[91] or [96], wherein T is a 6-membered heteroaryl ring having one nitrogen heteroatom and the ring is optionally substituted with one or more $R^d$.

Embodiment [100]

The compound of any one of embodiments [1]-[91] or [95], wherein T is selected from

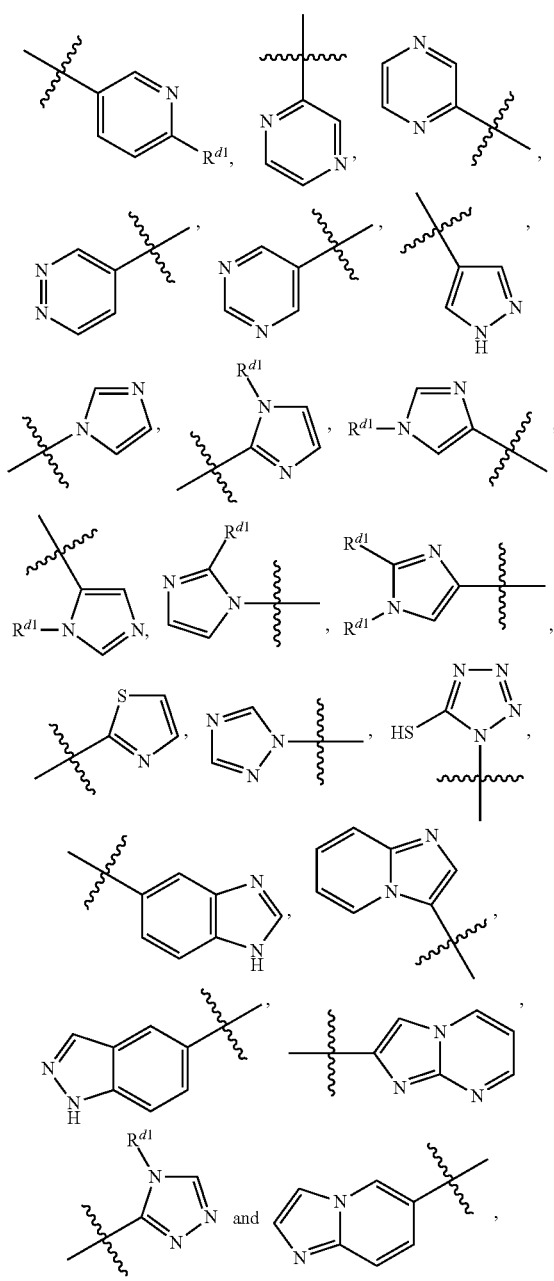

wherein $R^{d1}$ is selected from hydrogen, CN, halogen, $N(R^{27})_2$, and linear or branched $C_{1-6}$ aliphatic and each occurrence of $R^{27}$ is independently selected from hydrogen and linear or branched $C_{1-3}$ aliphatic.

Embodiment [101]

The compound of embodiment [100], wherein $R^{d1}$ is hydrogen or $CH_3$.

Embodiment [102]

The compound of embodiment [100], wherein $R^{d1}$ is hydrogen.

Embodiment [103]

The compound of any one of embodiments [1]-[91] or [95], wherein T is selected from

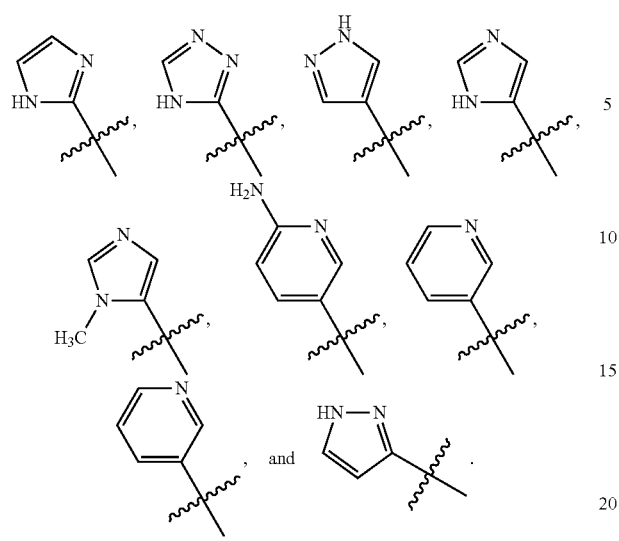

Embodiment [104]

The compound of any one of embodiments [1]-[75], wherein J is a direct bond.

Embodiment [105]

The compound of any one of embodiments [1]-[75] or [104], wherein T is a 8-10-membered bicyclic heteroaryl ring having 1-5 heteroatoms independently selected from nitrogen, oxygen, and sulfur, wherein the bicyclic ring is optionally substituted with one or more $R^d$ or a 5-6-membered monocyclic heteroaryl ring having 1-5 heteroatoms independently selected from nitrogen, oxygen, and sulfur, wherein the monocyclic ring is substituted with two $R^d$ taken together with the atom or atoms to which they are bound, forms a 4-10-membered heterocycle ring having 1-5 heteroatoms independently selected from nitrogen, oxygen, and sulfur.

Embodiment [106]

The compound of any one of embodiments [1]-[75] or [104]-[105], wherein T is a 8-10-membered bicyclic heteroaryl ring having 1-5 heteroatoms independently selected from nitrogen, oxygen, and sulfur, wherein the bicyclic ring is optionally substituted with one or more $R^d$.

Embodiment [107]

The compound of any one of embodiments [1]-[75] or [104]-[106], wherein T is selected from

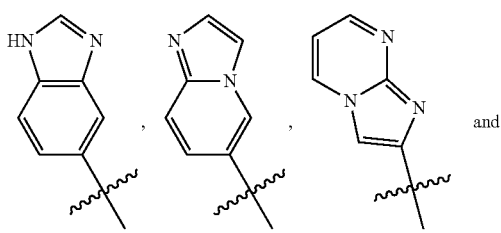

and

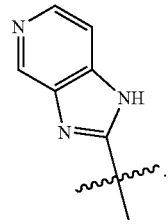

Embodiment [108]

The compound of any one of embodiments [1]-[74], wherein

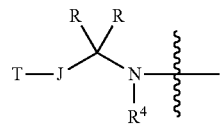

is selected from

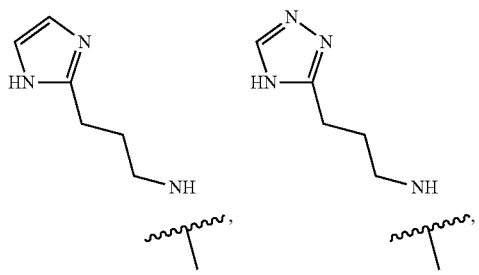

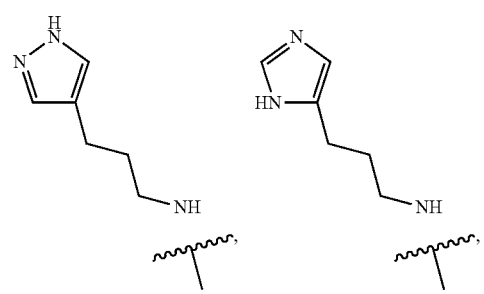

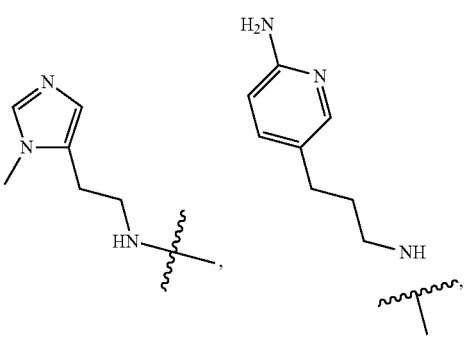

-continued

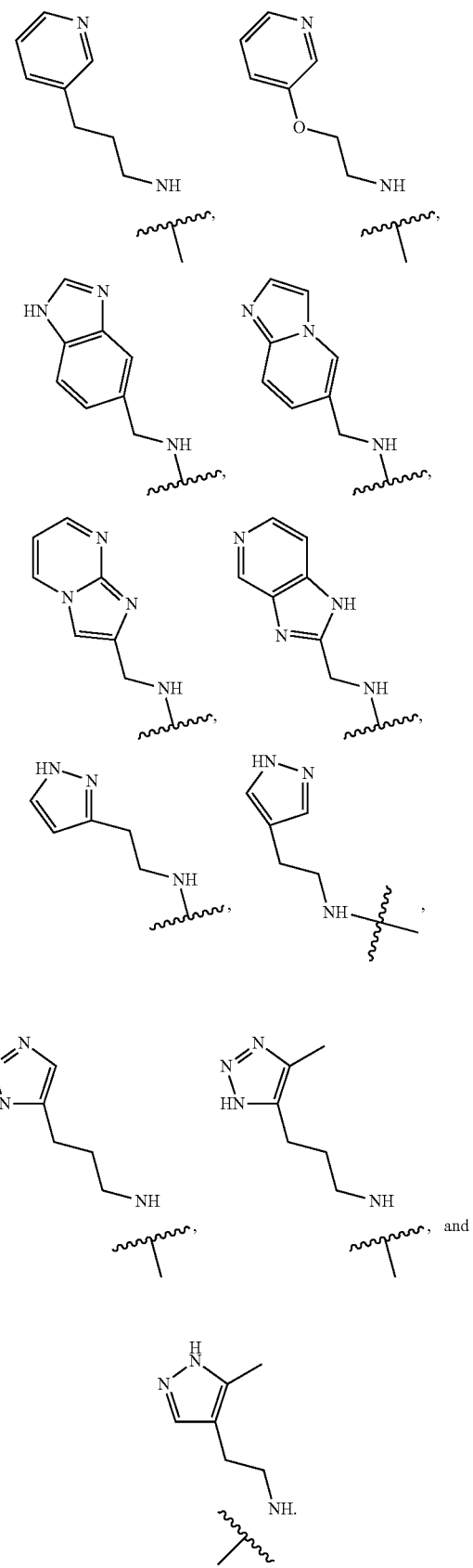

For example,

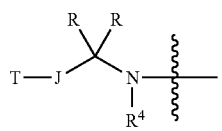

is selected from

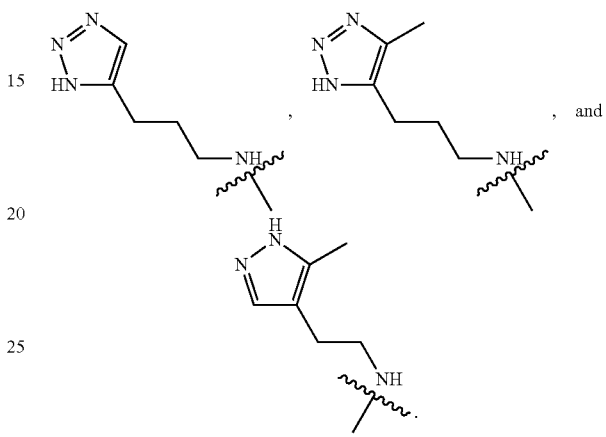

Embodiment [109]

The compound of any one of embodiments [1], [3]-[4], [6]-[15], [17]-[19], [21]-[23], [26]-[27], [29]-[37], [39]-[42], [44]-[59], [61], [64]-[65], [67]-[70], [72]-[76], [78]-[93], or [95]-[108], wherein W is selected from CH and $CR^1$ and wherein $R^{q1}$ is halogen.

Embodiment [110]

The compound of any one of embodiments [1], [3]-[4], [6]-[15], [17]-[19], [21]-[23], [26]-[27], [29]-[37], [39]-[42], [44]-[59], [61], [64]-[65], [67]-[70], [72]-[76], [78]-[93], or [95]-[108], wherein W is CH.

Embodiment [111]

The compound of any one of embodiments [1], [3]-[4], [6]-[15], [17]-[19], [21]-[23], [26]-[27], [29]-[37], [39]-[42], [44]-[59], [61], [64]-[65], [67]-[70], [72]-[76], [78]-[93], or [95]-[108], wherein W is $CR^{q1}$ and wherein $R^{q1}$ is halogen.

Embodiment [112]

The compound of any one of embodiments [2], [5], [6]-[14], [16]-[18], [20]-[22], [24]-[26], [28]-[36], [38]-[41], [43]-[58], [60], [62]-[64], [66]-[69], [71]-[75], [77]-[92], or [94]-[108], wherein $R^{q1}$ is hydrogen or halogen.

Embodiment [113]

The compound of any one of embodiments [2], [5], [6]-[14], [16]-[18], [20]-[22], [24]-[26], [28]-[36], [38]-[41], [43]-[58], [60], [62]-[64], [66]-[69], [71]-[75], [77]-[92], or [94]-[108], wherein $R^{q1}$ is hydrogen.

Embodiment [114]

The compound of any one of embodiments [2], [5], [6]-[14], [16]-[18], [20]-[22], [24]-[26], [28]-[36], [38]-[41],

[43]-[58], [60], [62]-[64], [66]-[69], [71]-[75], [77]-[92], or [94]-[108], wherein $R^{q1}$ is halogen.

4. Uses, Formulation and Administration

As discussed above, the invention provides compounds that are useful as inhibitors of the enzyme NAMPT. The NAMPT inhibition of a compound of the invention can be measured using a variety of methods known in the art. For example, the ability of a compound of the invention to inhibit NAMPT enzyme activity can be measured using a homogeneous time resolved fluorescence (HTRF) assay using hNAMPT protein and anti 6His-Tb in buffer treated with a compound of the invention (or control e.g., DMSO) and BodiPY ligand. The TR-FRET signal can be measured using a high throughput microplate reader (e.g., Pherastar). Excitation can be carried out at 320 nm. The percent inhibition value at a single concentration of compound of the invention can be calculated relative to a control treated sample. A concentration response curve can be generated for each compound of the invention and the curve fitted to generate an $IC_{50}$ value. In one embodiment, compounds of the invention inhibit NAMPT with an $IC_{50}$ value of <10 nM. In one embodiment, compounds of the invention inhibit NAMPT with an $IC_{50}$ value of <50 nM. In one embodiment, compounds of the invention inhibit NAMPT with an $IC_{50}$ value of <100 nM.

The invention also provides compounds that inhibit cell growth. The ability of a compound of the invention to inhibit the growth of cells can be measured using a variety of methods known in the art. For example, the ability of a compound of the invention to inhibit the growth of PC3 cells can be measured. PC3 cells can be plated and incubated overnight under $CO_2$. For each measurement, a compound of the invention (or vehicle e.g., DMSO) can be diluted with AIM serum free medium and added to the cell plate. The cell plate can then be incubated for 72 h under $CO_2$. Cell-titer glo solution can be added and the plates can be incubated protected from light and the amount of luminescences can be measured. Concentration response curves can be generated by calculating the luminescence increase in test compound treated samples relative to DMSO-treated controls. Percentage remaining viability values at a single concentration can be measured. Growth inhibition ($GI_{50}$) or cell viability ($LD_{50}$) values can be determined from thoses curves. In one embodiment, compounds of the invention have a percent viability in PC3 line @ 1.667 uM of <1%. In one embodiment, compounds of the invention have a percent viability in PC3 line @ 1.667 uM of <2%. In one embodiment, compounds of the invention have a percent viability in PC3 line @ 1.667 uM of <3%. In one embodiment, compounds of the invention have a percent viability in PC3 line @ 1.667 uM of <4%. In one embodiment, compounds of the invention have a percent viability in PC3 line @ 1.667 uM of <5%. In one embodiment, compounds of the invention have a percent viability in PC3 line @ 1.667 uM of <10%. In one embodiment, compounds of the invention have a percent viability in PC3 line @ 1.667 uM of <50%. In one embodiment, compounds of the invention do not include compounds having a cell viability in PC3 line @ 1.667 uM of >50%.

The invention also provides conjugates (e.g., antibody-drug conjugates) that contain target-binding agents (e.g., antibodies) and the compounds of this invention (or pharmaceutically acceptable salts thereof). Such conjugates bind to a target (e.g., an antigen such as HER2 and CD30) and internalize into the cells containing such target, which leads to release of the compounds of this invention in the cells and apoptosis of such cells. Because of the presence of the target-binding agents, such conjugates specifically bind and kill target-containing cells. Specifically, the conjugates can contain a linker group, which covalently connects a target-binding agent (e.g., an antibody) and a compound of this invention. The linker group can contain at least two functional groups with one connecting to the target-binding agent and the other one connecting to the compound of this invention. For example, the linker group can be a polymeric scaffold. See, e.g., U.S. Pat. No. 8,808,679, which is incorporated herein by reference.

The compounds of the invention are useful for treating diseases, disorders, and symptoms that will respond to therapy with a NAMPT inhibitor. Consequently, the invention provides therapeutic methods for treating cancer, inflammatory conditions, and/or T-cell mediated autoimmune disease. These therapeutic methods involve treating a patient (either a human or another animal) in need of such treatment, with a therapeutically effective amount of one or more of the compounds of the invention or a pharmaceutical composition comprising a therapeutically effective amount of one or more of the compounds of the invention. Additionally, the invention provides the use of one or more of the compounds of the invention for the manufacture of a medicament useful for human therapy.

In some embodiments, the therapeutic method comprises a method of inhibiting abnormal cell growth or treating or preventing a hyperproliferative disorder in a subject comprising administering to the subject an effective amount of a compound of the invention or a pharmaceutically acceptable salt thereof. In some embodiments, the therapeutic method comprises therapy for the delaying the onset of, or reducing the symptoms of, cancer, an inflammatory disorder, or T-cell mediated autoimmune disease in a subject comprising administering to the subject an effective amount of a compound of the invention or a pharmaceutically acceptable salt thereof.

The invention also comprises treating isolated cells with a therapeutically effective amount of one or more of the compounds of the invention.

As used herein, the phrase "treating . . . with . . . a compound" means either administering one or more of the compounds of the invention directly to isolated cells or to a patient (animal or human).

In some embodiments, the invention provides a method of treating cancer, comprising administering a therapeutically effective amount of one or more compounds of the invention to a patient. In some embodiments, the patient is a human patient.

There are reports of NAMPT over-expression in colon cancers (Hufton et al., FEBS Lett. 463(1-2):77-82 (1999), Van Beijnum et al., Int. J. Cancer. 101(2):118-27 (2002)), ovarian cancers (Shackelford et al., Int J. Clin. Exp. Pathol. 3(5): 522-527 (2010)), prostate cancers (Wang et al., Oncogene 30: 907-921 (2011)) and glioblastoma multiforme (GBM) cancers (Reddy et al., Cancer Biol. Ther. 7(5):663-8 (2008)). Immunohistochemistry analyses suggest strong expression of NAMPT occurs in greater than 20% of biopsies of: breast, lung, malignant lymphoma, ovarian, pancreatic, prostate and testicular cancers (www.proteinatlas.org). Furthermore, the NAMPT transcript is known to be upregulated in colon cancers (van Beijnum J R, et al.; and Hufton S E, et al.) and glioblastoma cancers (Reddy P S, et al.).

In some embodiments, the invention provides a method of treating a cancer that overexpresses NAMPT, comprising administering a therapeutically effective amount of one or more compounds of the invention to a patient.

In view of the above, it is believed that inhibition of NAMPT activity would be effective in treating a wide range of cancers. The invention provides methods of treating a wide range of cancers by administering therapeutically effective amounts of one or more of the compounds of the invention. For example, cancer cell types corresponding to gastrointestinal, prostate, breast, testicular, sarcoma, renal, skin, myeloma, ovarian, leukemia, lymphoma, lung, cervical or brain cancers can be killed by a compound of the invention.

In one aspect, the invention provides a method of treating cancer comprising administering a therapeutically effective amount of one or more compounds of the invention to a patient. In one aspect, the cancer is gastrointestinal cancer. In one aspect, the cancer is liver. In one aspect, the cancer is pancreatic. In one aspect, cancer is stomach (gastric). In one aspect, the cancer is esophageal. In one aspect, the cancer is colon. In one aspect, the cancer is large intestine cancer. In one aspect, the cancer is small intestine cancer. In one aspect, the cancer is prostate. In one aspect, the cancer is breast. In one aspect, the cancer is testicular. In one aspect, the cancer is lung. In one aspect, the cancer is non-small cell lung cancer (NSCLC). In one aspect, cancer is small cell lung cancer (SCLC). In one aspect, the cancer is sarcoma. In one aspect, the cancer is renal. In one aspect, the cancer is skin. In one aspect, the cancer is myeloma. In one aspect, the cancer is ovarian. In one aspect, the cancer is leukemia. In one aspect, the cancer is lymphoma. In one aspect, the cancer is cervical. In one aspect, the cancer is brain. In one aspect, the cancer is glioma.

In some embodiments, a method of the invention involves treating cancers that have been found to respond favorably to treatment with NAMPT inhibitors. Further, "treating cancer" should be understood as encompassing treating a patient who is at any one of the several stages of cancer, including diagnosed but as yet asymptomatic cancer.

Specific cancers that can be treated by the methods of the invention are those cancers that respond favorably to treatment with a NAMPT inhibitor. Such cancers include, but are not limited to, colon carcinoma, stomach carcinoma, malignant pancreatic insulinoma, pancreatic carcinoma, esophageal carcinoma, liver carcinoma, prostatic carcinoma, breast carcinoma, Wilms' tumor, renal cell carcinoma, melanoma, multiple myeloma, ovarian carcinoma, acute lymphocytic leukemia, chronic lymphocytic leukemia, acute myeloid leukemia, chronic granulocytic leukemia, acute granulocytic leukemia, hairy cell leukemia, Hodgkin's disease, non-Hodgkin's lymphoma, mantle-cell lymphoma, mycosis fungoides, essential primary macroglobulinemia, lung carcinoma, small-cell lung carcinoma, non-small cell carcinoma, cervical carcinoma, cervix adenocarcinoma, glioma, neuroblastoma, primary brain carcinoma, glioblastoma multiforme (GBM), testicular carcinoma, bladder carcinoma, malignant carcinoid carcinoma, choriocarcinoma, head or neck carcinoma, genitourinary carcinoma, thyroid carcinoma, endometrial carcinoma, thrombocytosis, adrenal cortex carcinoma, mammary carcinoma, soft-tissue sarcoma, osteogenic sarcoma, rhabdomyosarcoma, or Kaposi's sarcoma. Other disorders that can be treated by the methods of the invention are malignant hypercalcemia, cervical hyperplasia, or polycythemia vera.

Importantly, NAD+ can be generated by several NAMPT-independent pathways as well, including: (1) de novo synthesis from L-tryptophan via the kynurenine pathway; (2) from nicotinic acid (NA) via the Preiss-Handler pathway; and (3) from nicotinamide riboside or nicotinic acid riboside via nicotinamide/nicotinic acid riboside kinases (reviewed in Khan, J. A. et al. Expert Opin. Ther. Targets. 11(5):695-705 (2007)). However, these different routes of NAD+ synthesis are generally tissue specific: The de novo pathway is present in liver, brain, and immune cells, the Priess-Handler pathway is primarily active in the liver, kidney, and heart, and Nrk2, of the nicotinamide riboside kinase pathway, is expressed in brain, heart, and skeletal muscle (Bogan, K. L. and Brenner, C. Annu. Rev. Nutr. 28:115-30 (2008) and Tempel, W. et al., PLoS Biol. 5(10):e263 (2007)).

Of these alternative pathways of NAD+ synthesis, the Preiss-Handler pathway is perhaps the most important for cancer cells. The first and rate-limiting step of this pathway, the conversion of nicotinic acid (NA) to nicotinic acid mononucleotide (NAMN), is catalyzed by the enzyme NAPRT 1.

Some embodiments include a method of treating cancer, wherein cells of the cancer exhibit low levels of NAPRT1 expression. In one aspect, NAPRT1 expression is least in brain cancers, lung cancers, lymphoma, myeloma and osteosarcoma. For example, glioblastoma and sarcoma cell lines have been found to have reduced NAPRT1 expression (Watson, et al. Mol. Cell. Biol. 29(21):5872-88 (2009)). Thus, in some embodiments, the invention provides a method of treating a cancer that exhibits low levels of NAPRT1 expression, comprising administering a therapeutically effective amount of one or more compounds of the invention to a patient. In one aspect, the cancer is brain, such as glioblastoma. In one aspect, the cancer is lung. In one aspect, the cancer is osteosarcoma.

While those cancers with reduced or absent levels of NAPRT1 expression may be more susceptible to treatment with the NAMPT inhibitors of the invention, administration of NA to patients having such cancers could prevent toxicity in other tissues associated with NAMPT inhibition. To support this concept, experiments can be conducted to show that mice given NA survive doses of a NAMPT inhibitor above the maximum tolerated dose (see also Beauparlant P., et al. Anticancer Drugs. 20(5):346-54 (2009) and Watson, et al. Mol. Cell. Biol. 29(21):5872-88 (2009)). This phenomenon is referred to in the art as "NA rescue." Accordingly, in some embodiments, the methods of treating cancer disclosed herein further comprise administering nicotinic acid, or a compound that could form nicotinic acid or provide nicotinamide dinucleotide (NAD) from an alternate pathway, such as quinolinic acid (Sahm, F., et al. Cancer Res 73:3225 (2013); Henderson, T. D. et al. J. Biol. Chem. 170:261 (1947); Pittelli, M. et al. J. Biol. Chem. 285(44): 34106 (2010)) to the patient in addition to administering a compound of the invention. In some of such embodiments, the compound of the invention can be administered at dose that exceeds the maximum tolerated dose for that particular compound of the invention as determined for mono-therapy. In some embodiments, administering NA may include administering NA prior to administering one or more of the compounds of the invention, co-administering NA with one or more of the compounds of the invention, or first treating the patient with one or more of the compounds of the invention, followed by thereafter administering NA.

NAMPT expression in visceral adipose tissue has been found to correlate with the expression of proinflammatory genes, CD68 and TNF-alpha (Chang et al.; Metabolism. 59(1):93-9 (2010)). Several studies have noted an increase in reactive oxygen species and activation of NF-kappaB in response to NAMPT expression (Oita et al.; Pflugers Arch. (2009); Romacho et al.; Diabetologia. 52(11):2455-63

(2009)). NAMPT serum levels were found to have been increased in patients with inflammatory bowel diseases and correlated with disease activity (Moschen et al.; Mutat. Res. (2009)). One study has even suggested a specific mechanism for NAMPT in inflammation: High levels of NAMPT increase cellular NAD+ levels leading to a post-transcriptional upregulation of TNF via the NAD-dependent deacetylase, SirT6 (Van Gool et al. Nat. Med. 15(2):206-10 (2009)). Further, inhibition of NAMPT reduced levels of inflammatory cytokines IL-6 and TNF-alph. (Busso et al. PLoS One. 21; 3(5):e2267 (2008)). In another study, NAMPT inhibition was found to prevent TNF-alpha and IFN-gamma production in T-lymphocytes (Bruzzone et al.; PLoS One; 4(11): e7897 (2009)).

In view of the above, it is believed that inhibition of NAMPT activity would be effective in treating inflammatory conditions e.g., systemic or chronic inflammation resulting from a wide range of causes. Consequently, the invention provides methods of treating an inflammatory condition by administering therapeutically effective amounts of one or more of the compounds of the invention. NAMPT levels increased in a mouse model of arthritis and treatment of these mice with a NAMPT inhibitor reduced the arthritis symptoms (Busso et al. PLoS One. 21; 3(5):e2267 (2008)). In one aspect, the invention provides methods of treating rheumatoid arthritis by administering therapeutically effective amounts of one or more of the compounds of the invention to a patient.

In one aspect, the invention provides a method of treating an inflammatory condition comprising administering a therapeutically effective amount of one or more compounds of the invention to a patient. In one aspect, the inflammatory condition is rheumatoid arthritis. In one aspect, the inflammatory condition is inflammatory bowl disease. In one aspect, the inflammatory condition is asthma. In one aspect, the inflammatory condition is COPD (chronic obstructive pulmonary disease). In one aspect, the inflammatory condition is osteoarthritis. In one aspect, the inflammatory condition is osteoporosis. In one aspect, the inflammatory condition is sepsis. In one aspect, the inflammatory condition is related to a spinal cord injury. In one aspect, the inflammatory condition is related to an infection NAMPT expression has been shown to be upregulated in activated T-cells (Rongavaux et al.; J. Immunol. 181(7): 4685-95 2008)) and Phase I clinical trials report lymphopenia in patients treated with NAMPT inhibitors (reviewed in von Heideman et al.; Cancer Chemother. Pharmacol. (2009)). Additionally, in a mouse model of a T-cell autoimmune disease, experimental autoimmune encephalomyelitis (EAE), NAMPT inhibition reduced the clinical disease score and demyelination in the spinal cord (Bruzzone et al.; PLoS One. 4(11):e7897 (2009)). In view of the above, it is believed that inhibition of NAMPT activity would be effective in treating T-cell mediated autoimmune disease. Consequently, the invention provides methods of treating T-cell mediated autoimmune disease by administering therapeutically effective amounts of one or more of the compounds of the invention to a patient. In one aspect, the autoimmune disease is EAE. In one aspect, the autoimmune disease is lupus.

While one or more of the compounds of the invention may be used in an application of monotherapy to treat a disorder, disease, or symptom, the compounds of the invention also may be used in combination therapy, in which the use of a compound of the invention is combined with the use of one or more other therapeutic agents for treating the same and/or other types of disorders, diseases, or symptoms. Combination therapy includes administration of the therapeutic agents concurrently or sequentially. Alternatively, the therapeutic agents can be combined into one composition which is administered to the patient. In some embodiments, the compounds of the invention are used in combination with other therapeutic agents, such as other inhibitors of NAMPT.

NAMPT inhibition has been shown to sensitize cells to the effects of various chemotherapeutic or cytotoxic agents. Specifically, NAMPT inhibition has been shown to sensitize cells to amiloride, mitomycin C, etoposide, mechlorethamine, streptozotocin, 5-fluorouracil, raltitrexed, methotrexate, bortezomib, dasatinib, olaparib, TRAIL, cyclosporine A, valproate, temozolomide (TMZ), methoxyamine hydrochloride (MX), cisplatin, FX 11 (3-dihydroxy-6-methyl-7-(phenylmethyl)-4-propylnaphthalene-1-carboxylic acid), rituximab (RTX), Sirtinol, 1-methyl-D-tryptophan, and L-1-methyl tryptophan (Ekelund, S. et al. Chemotherapy 48:196-204 (2002) (lymphoma); Rongvaux, A. et al. The Journal of Immunology 181(7):4685-95 (2008); Martinsson, P. et al. British Journal of Pharmacology 137: 568-73 (2002) (lymphoma); Pogrebniak, A. et al. European Journal of Medical Research 11(8):313-21 (2006) (leukemia), Myrexis US 2013/0317027 (cancer); Bi, T., et al., Oncology Reports 26(5): 1251-1257 (2011) (gastric); Bajrami, I., et al., EMBO Molecular Medicine 4(10):1087-1097 (2012) (TN breast cancer); Zoppoli, G., et al., Experimental Hematology, 38(11):979-988 (2010) (leukemia); Cea, M., et al., Haematologica 2009; 94[suppl. 2]:495 abs. 1237(leukemia); Goellner, E., et al. Cancer Research, 71:2308-2317 (2011); Travelli, C., et al., The Journal of Pharmacology, 338(3): 829-840 (2011) (neuroblastoma); Le, A., et al., PNAS 2009 107(5):2037-2042(lymphoma and pancreatic); Nahimana, A., et al. Leuk & Lymphoma, early online: 1-10 (2014) (B-cell lymphoma) Bowlby, S. et al., PLOS, 7(6): e40195 (2012) (prostate); Watson, M. et al., Molecular and Cellular Biology, 29(21) 5872 (2009); and Goellner, E. et al, Cancer Research, 71: 2308 (2011). NAMPT inhibition has also been shown to increase the radiation sensitivity of certain tumors (Muruganandham, M., et al. Clin Cancer Res 11:3503-3513 (2005) (mammory carcinoma); Zerp, S. F. et al., Radiotherapy and Oncology ePub (prostate)).

In some embodiments, a compound of the invention is administered in combination with a second therapeutic agent. In one embodiment, the second therapeutic agent is amiloride, mitomycin C, etoposide, mechlorethamine, streptozotocin, 5-fluorouracil, raltitrexed, methotrexate, bortezomib, dasatinib, olaparib, TRAIL, cyclosporine A, valproate, temozolomide (TMZ), methoxyamine hydrochloride (MX), cisplatin, FX 11 (3-dihydroxy-6-methyl-7-(phenylmethyl)-4-propylnaphthalene-1-carboxylic acid), rituximab (RTX), Sirtinol, 1-methyl-D-tryptophan, and L-1-methyl tryptophan. In some embodiments, the invention provides a method of treating cancer, comprising administering a therapeutically effective amount of one or more compounds of the present invention and one or more second agents selected from the second therapeutic agents described above. In one aspect, the cancer is any cancer described herein. In one aspect, the cancer is lymphoma, leukemia, gastric, breast, neuroblastoma, or pancreatic cancer.

Another aspect of the invention relates to inhibiting NAMPT activity in a biological sample or a patient, which method comprises administering to the patient, or contacting said biological sample with a compound of the invention or a composition comprising said compound. The term "biological sample", as used herein, generally includes in vivo, in vitro, and ex vivo materials, and also includes, without limitation, cell cultures or extracts thereof, biopsied material obtained from a mammal or extracts thereof, and blood, saliva, urine, feces, semen, tears, or other body fluids or extracts thereof.

Still another aspect of this invention is to provide a kit comprising separate containers in a single package, wherein the compounds of the invention, compositions and/or salts thereof are used in combination with pharmaceutically acceptable carriers to treat disorders, symptoms and diseases where NAMPT plays a role.

Accordingly, in another aspect of the invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of the invention or an inhibitorily active metabolite or residue thereof. As used herein, the term "inhibitorily active metabolite or residue thereof" means that a metabolite or residue thereof is also an inhibitor of NAMPT.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of the invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, or cardiovascular disorder is provided comprising administering an effective amount of a compound or a pharmaceutical composition to a subject in need thereof. In certain embodiments of the present invention an "effective amount" of the compound or pharmaceutical composition is that amount effective for treating cancer, an inflammatory condition or T-cell mediated autoimmune disease or is that amount effective for treating cancer. In other embodiments, an "effective amount" of a compound is an amount which inhibits NAMPT and thereby blocks the resulting production of NAD+.

The compounds and compositions, according to the method of the invention, may be administered using any amount and any route of administration effective for treating the disease. The exact amount required will vary from subject to subject, depending on the species, age, and general condition of the subject, the severity of the disease, the particular agent, its mode of administration, and the like. In one aspect, the compounds of the invention are formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, in one aspect, a mammal, and in another aspect, a human.

The pharmaceutically acceptable compositions of the invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease being treated. In certain embodiments, a compound of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In one aspect, compositions for rectal or vaginal administration are suppositories which can be prepared by mixing a compound of the invention with suitable non-irritating excipient or carrier such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

While one or more of the compounds of the invention may be used in an application of monotherapy to treat a disorder, disease or symptom, one or more of the compounds of the invention may also may be used in combination therapy, in which the use of a compound of the invention or composition (therapeutic agent) is combined with the use of one or more other therapeutic agents for treating the same and/or other types of disorders, symptoms and diseases. Combination therapy includes administration of the therapeutic agents concurrently or sequentially. Alternatively, the therapeutic agents can be combined into one composition which is administered to the patient.

EXPERIMENTAL PROCEDURES

I-A. Preparation of Certain Exemplary Compounds:

Compounds 1 through 229 (Shown in Table 1 below) were prepared using the general methods and specific examples described directly below.

1. General Synthetic Methods and Intermediates

The compounds of the present invention can be prepared by methods known to one of ordinary skill in the art and/or by reference to the schemes shown below and the synthetic examples. Exemplary synthetic routes are set forth in Schemes below and in the Examples.

Scheme 1: General method for the preparation of compounds of formula iii

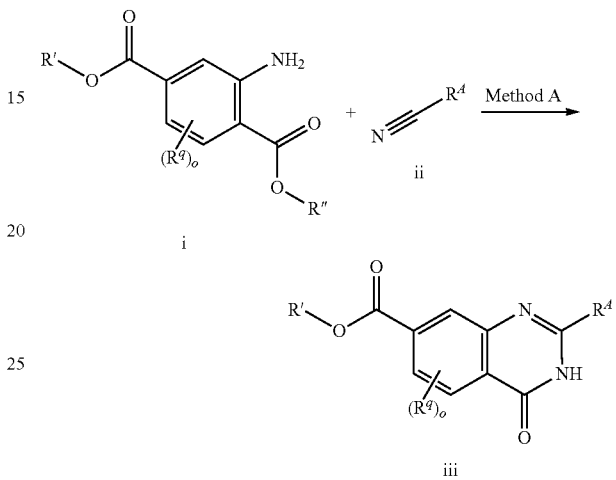

Scheme 1 shows a general route for the preparation of compounds of formula iii. Commercially available aminoterephthalate i (R' and R" are $C_{1-6}$ aliphatic) can be treated with nitrile ii in the presence of an acid, such as HCl in a suitable solvent, for example dioxane at elevated temperature, for example, in a sealed reaction vessel (Method A) to provide 4-oxo-3,4-dihydroquinazoline 7-carboxylate iii.

Scheme 2: General method for the preparation of compounds of formula iv

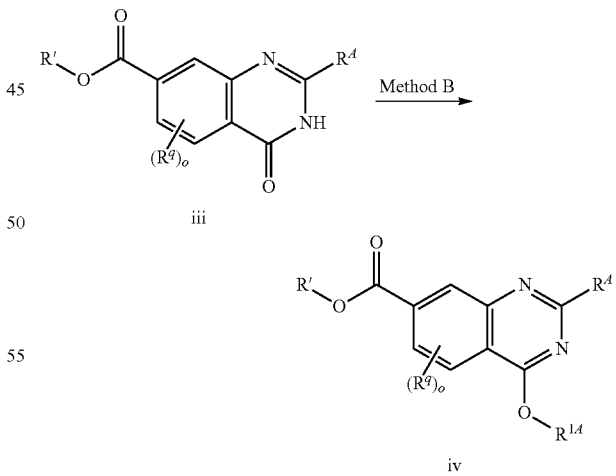

Scheme 2 shows a general route for the preparation of compounds of formula iv. Compound iii can be treated with an alkyl halide, for example ethyl iodide, a suitable base, such as potassium carbonate in an appropriate solvent, such as DMF (Method B) to afford a quinazoline of formula iv ($R^{1A}$ is $C_{1-6}$ aliphatic).

Scheme 3: General method for the preparation of compounds of formula vi

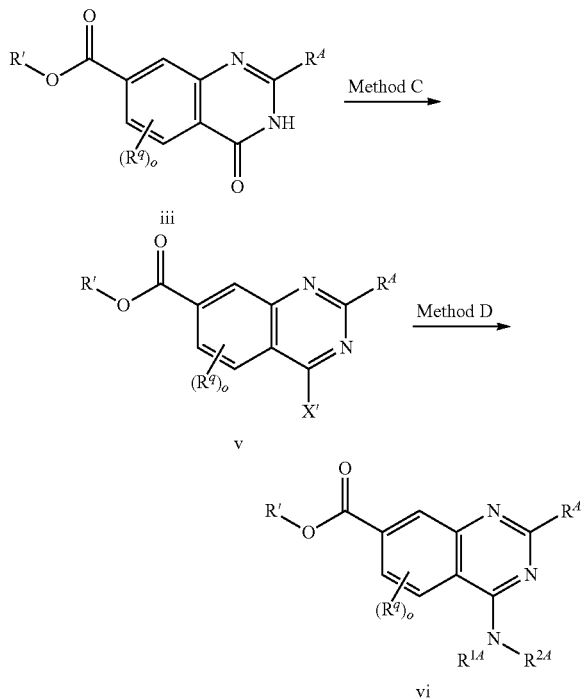

Scheme 3 shows a general route for the preparation of compounds of formula vi. Compound iii can be treated with a suitable halogenating agent, for example PCl$_5$ in an appropriate solvent, such as dichloroethane. The halogenation reaction can be performed at elevated temperature with thermal heating or microwave irradiation (Method C) to afford halide v (R' is C$_{1-6}$ aliphatic and X' is halogen). Compound v can then be treated with amine in a suitable solvent, for example DCM, at room or elevated temperature (Method D) to afford aminoquinazoline vi.

Scheme 4: General method for the preparation of compounds of formula vii

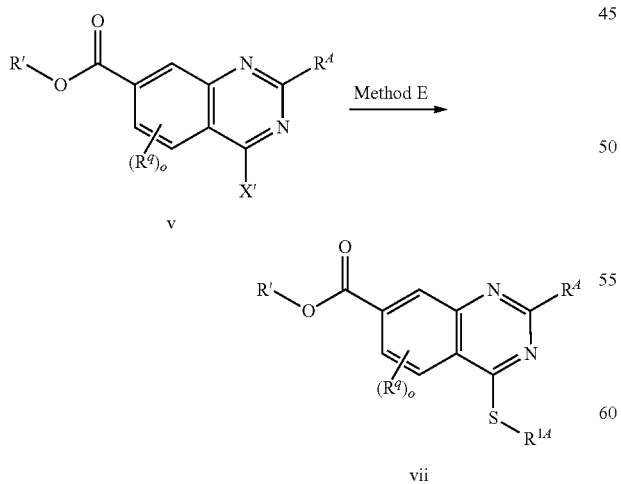

Scheme 4 shows a general route for the preparation of compounds of formula vii. Compound v (R' is C$_{1-6}$ aliphatic and X' is halogen) can be treated with an alkylthiolate salt, for example sodium ethanethiolate in a suitable solvent, such as DMF (Method E) to afford alkylthioquinazoline vii.

Scheme 5: General method for the preparation of compounds of formula viii

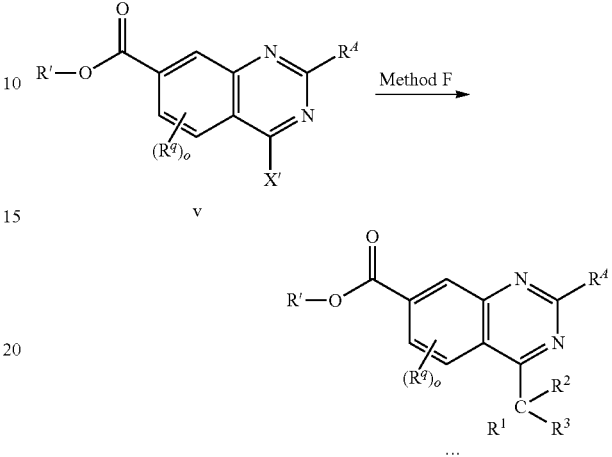

Scheme 5 shows a general route for the preparation of compounds of formula viii, wherein R$^1$, R$^2$ and R$^3$ are C$_{1-6}$ aliphatic or H. Compound v (R' is C$_{1-6}$ aliphatic and X' is halogen) can be treated with an alkylmagnesium halide, for example ethylmagnesium chloride, using a catalyst such as Fe(acac)$_3$ in a suitable solvent, for example THF with cooling or at room temperature (Method F) to provide a compound of formula viii (R$^1$, R$^2$ and R$^3$ are C$_{1-6}$ aliphatic or H).

Scheme 6: General method for the preparation of compounds of formula viii

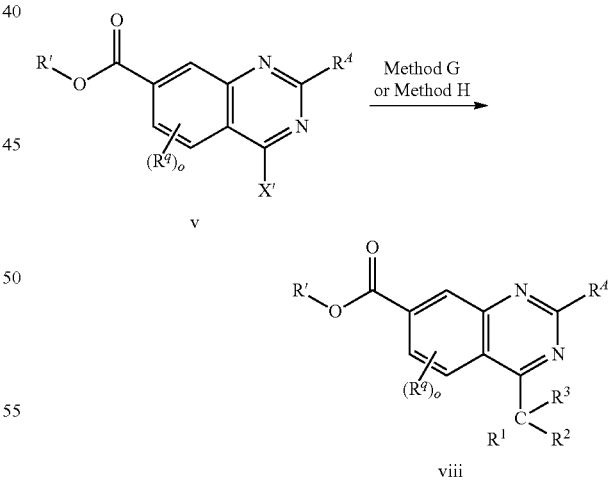

Scheme 6 shows a general route for the preparation of compounds of formula viii, wherein R$^1$, R$^2$ and R$^3$ taken together with the carbon atom to which they are bound form aryl or heteroaryl or any two of R$^1$, R$^2$ and R$^3$ taken together with the carbon atom to which they are bound form cycloaliphatic or heterocycle, or each R$^1$, R$^2$, and R$^3$ represents an optionally substituted C$_{1-6}$ aliphatic or H. Compound v (R' is C$_{1-6}$ aliphatic and X' is halogen) can be treated under Suzuki coupling conditions with aryl or benzylboronic acid with a suitable catalyst, for example dppf/Pd complex and an appropriate base, such as potassium carbonate in a suitable solvent, for example dioxane at elevated temperature (Method G) to provide a compound of formula viii. Alternatively, a trifluoroborate salt can be used, for example potassium methoxymethyltrifluoroborate with a suitable catalyst, for example SiliaCat® DPP-Pd, a base, such as cesium carbonate in a suitable solvent, for example dioxane at elevated temperature with thermal heating or microwave irradiation (Method H) to afford a compound of formula viii ($R^1$, $R^2$ and $R^3$ taken together with the carbon atom to which they are bound form aryl, heteroaryl, cycloaliphatic, or heterocycle, or each $R^1$, $R^2$, and $R^3$ represents an optionally substituted $C_{1-6}$ aliphatic or H).

Scheme 7: General method for the preparation of compounds of formula xii

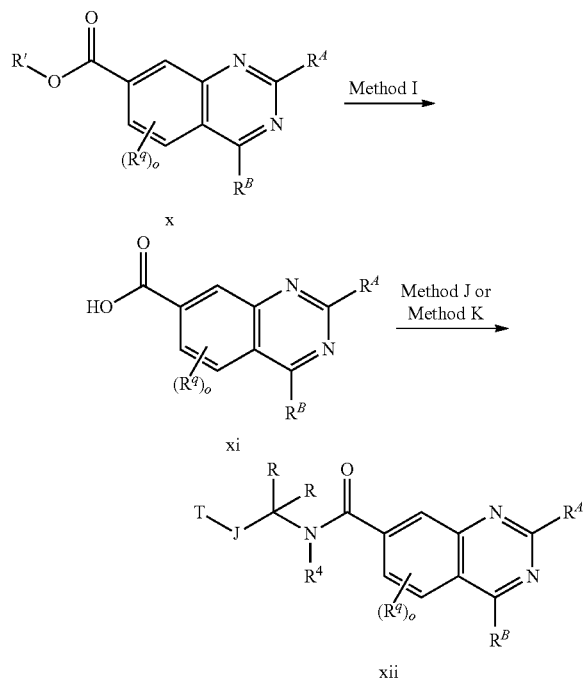

reagents, for example HATU, T3P®, TBTU, EDCI, with a suitable base such as diisopropylethylamine or triethylamine in a suitable solvent, such as THF, DMF, pyridine or DMSO.

Scheme 8: Alternative method for the preparation of compounds of formula xii

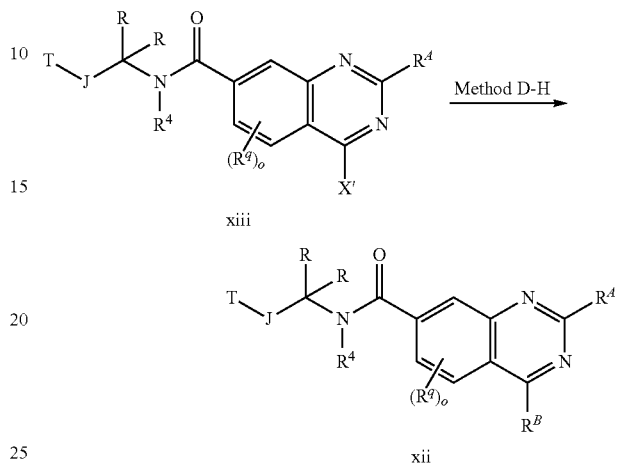

Scheme 8 shows an alternative route for the preparation of compounds of formula xii. Quinazoline halide xiii (X' is halogen) can be transformed to compound xii using Methods D, E, F, G, or H as described in Schemes 3-6.

Scheme 9: General method for the preparation of compounds of formula xxi

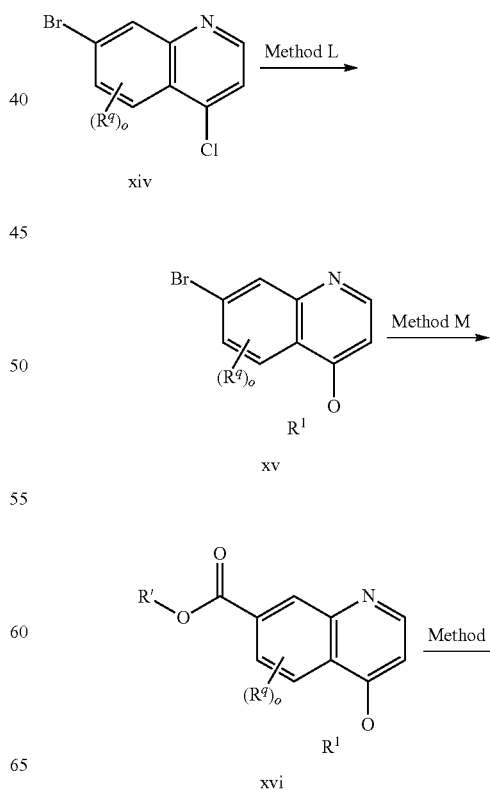

Scheme 7 shows a general route for the preparation of compounds of formula xii. Compound x (R' is $C_{1-6}$ aliphatic) can be hydrolyzed to carboxylic acid xi using standard conditions, for example NaOH in a suitable aqueous solvent mixture, such as THF at room temperature or elevated temperature with an optional co-solvent, such as MeOH (Method I). Compound xi can then be transformed to an amide xii using Method J or K. Method J involves the initial formation of an acid halide using suitable conditions, for example thionyl chloride or oxalyl chloride in DCE, DCM with catalytic amount of DMF, at elevated temperature. The resulting acid halide can be then coupled with an amine in a suitable solvent, for example THF or DMF. When the amine utilized in the coupling reaction is a salt, excess base is added, for example triethylamine can be added as a base. When $R^B$ in compound xi is a hydroxyl group (or compound xi is the corresponding tautomeric oxo-dihydroquinazoline), Method J also can be utilized for introduction of a halide at $R^B$ position followed by subsequent transformations described in Schemes 3-6. Method K is direct coupling of carboxylic acid xi with amine using amide coupling

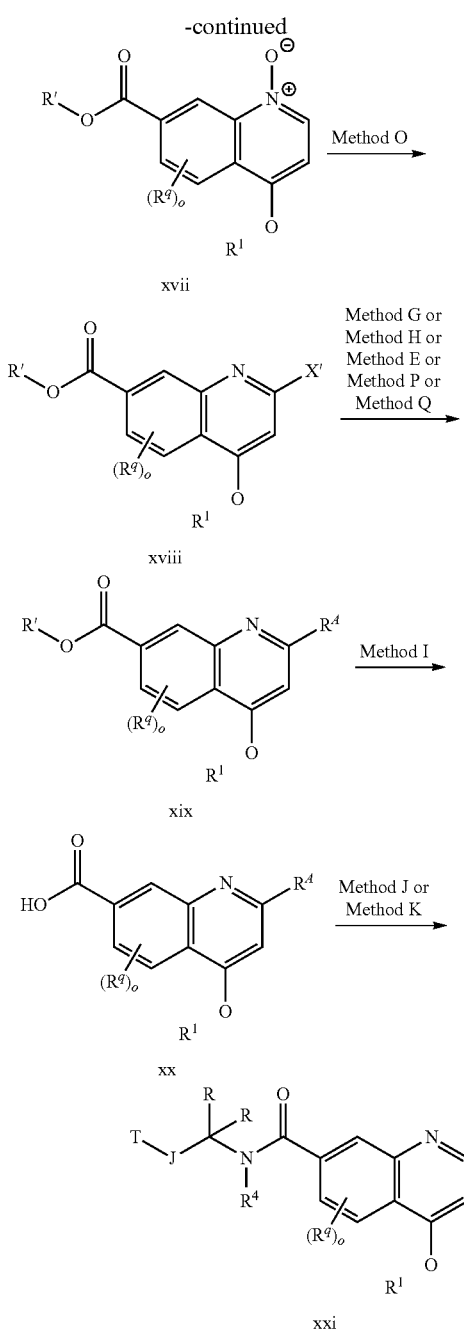

Scheme 9 shows a general route for the synthesis of compounds of formula xxi. Commercially available 7-bromo-4-chloroquinoline xiv can be treated with an alkaline metal, for example sodium alkoxide in a suitable solvent, such as NMP (Method L) to provide the O-substituted compound of formula xv. Alkoxycarbonylation of xv can be achieved for example, using carbon monoxide; an alcohol, such as methanol; a base, for example TEA; and a transition metal catalyst, for example palladium (II) acetate/bis(diphenylphosphino)propane, in a suitable solvent, for example DMSO at elevated temperature (Method M) to give ester xvi. Introduction of a halogen into the 2-position can be achieved using a 2-step procedure. Compound xvi can be first N-oxidized using a suitable oxidizing reagent, such as mCPBA in an appropriate solvent, such as DCM (Method N). The resulting N-oxide xvii can then be transformed into a 2-halogenated quinoline xviii using for example oxalyl chloride and DMF in a suitable solvent, such as DCM (Method O). Compounds xviii (X' is halogen) can be transformed into the 2-substituted compound xix using one of a variety of different methods (e.g., Method G, H, E, P, or Q). Arylation can be achieved using Suzuki coupling conditions with a boronic acid or ester, for example using SiliaCat DPP-Pd or Pd/dppf, a suitable base, such as cesium carbonate in an appropriate solvent, such as dioxane (with or without water), at elevated temperature with thermal heating or microwave irradiation (Method G). Alternatively, a trifluoroborate salt can be used, for example potassium methoxymethyltrifluoroborate, or potassium cyclopropyltrifluoroborate, with a suitable catalyst, for example SiliaCat DPP-Pd, a base, such as cesium carbonate in a suitable solvent, for example dioxane, at elevated temperature with thermal heating or microwave irradiation (Method H). Alkyloxy substitution at the 2-position can be achieved using an alkaline metal alkoxide, for example sodium ethoxide in a suitable solvent, such as ethanol at elevated temperature (Method P). A 2-substituted thioether can be prepared by treating compound xviii with an alkaline metal alkylthiolate, for example sodium ethanethiolate in a suitable solvent, such as DMF (Method E). 2-Aminoquinoline can be prepared by treatment of xviii with an amine, either neat (without solvent) or with a suitable co-solvent, such as DMA or NMP at elevated temperature with thermal heating or microwave irradiation (Method Q). Compound xix can be hydrolyzed to the carboxylic acid xx using Method I as described in Scheme 7. The resulting carboxylic acid xx can then be coupled with for example, an amine from any one of Schemes 12-16 and transformed into amide xxi using Method J or K as described in Scheme 7.

Scheme 10: General method for the preparation of compounds of formula xxiii amd xxiv

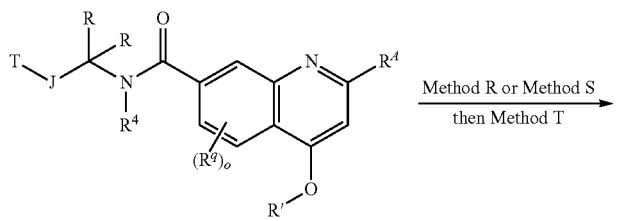

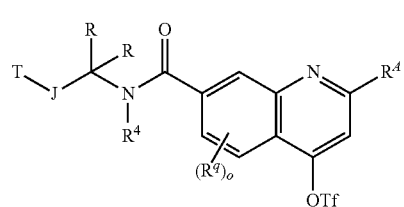

xxii

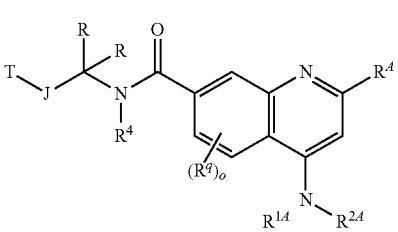

xxiv

Method G or Method H

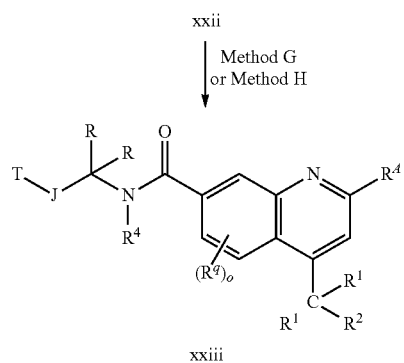

xxiii

Scheme 10 shows a general method for preparation of compounds of formula xxiii and xxiv. Compound xxi, where R' is a group that can be deprotected, such as a $C_{1-6}$ aliphatic group e.g., methyl or a benzyl group, can be utilized as starting material. The first step can be removal of the protecting group e.g., the methyl ether can be deprotected using $BBr_3$ or $BCl_3$ in a suitable solvent, such as DCM with cooling or at room temperature (Method R). Alternatively, the benzyl group can be removed by a transition metal catalyzed hydrogenation, for example treatment with Pd, under hydrogen gas pressure in a suitable solvent, such as ethyl acetate, methanol, with optional addition of acetic acid (Method S). The resulting phenol can then be converted to triflate xxii, for example using triflic anhydride and a base, such as pyridine, TEA, in a suitable solvent, such as DCM (Method T). The triflate xxii can then be subjected to Suzuki coupling conditions with a boronic acid or ester to provide a compound of formula xxiii using a suitable catalyst, such as Pd/dppf or Pd/dpePhos, a suitable base, such as cesium carbonate in an appropriate solvent, such as dioxane with or without water, at elevated temperature with thermal heating or microwave irradiation (Method G). Alternatively, a trifluoroborate salt can be used, for example potassium methoxymethyltrifluoroborate, or potassium cyclopropyltrifluoroborate, with a suitable catalyst, for example SiliaCat® DPP-Pd, a base, such as cesium carbonate in a suitable solvent, for example dioxane at elevated temperature with thermal heating or microwave irradiation (Method H). Triflate xxii can also be converted to amine xxiv using Buchwald-Hartwig conditions, using $HN(R^{1A}R^{2A})$, $Pd_2dba_3$/BINAP, $Pd_2dba_3$/X-Phos or another suitable Pd based catalyst, with a suitable base, such as NaOtBu or $Cs_2CO_3$ in a suitable solvent, such as toluene or dioxane at elevated temperature or using microwave irradiation (Method U).

Scheme 11: General method for the preparation of compounds of formula xxvii

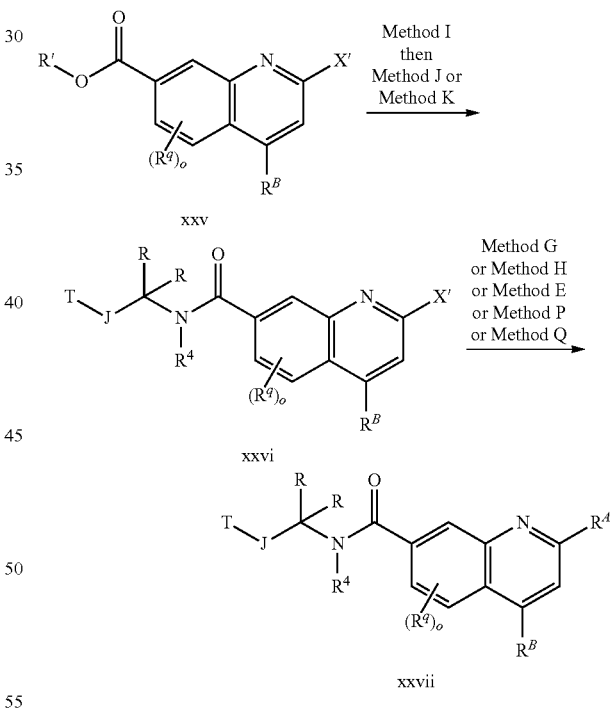

Scheme 11 shows an alternative procedure for the preparation of compounds of formula xxvii. The ester group of 2-haloquinoline xxv (X' is halogen) can be hydrolyzed to a carboxylic acid using Method I as described in Scheme 7, and the resulting carboxylic acid can be coupled with an amine from any one of Schemes 12-16 and converted in to amide xxvi using a variety of methods e.g., Method J or K as described in Scheme 7. The halogen atom in xxvi can then be utilized in a coupling reaction for the preparation of a compound of formula xxvii, wherein $R^A$ is attached to the quinoline via C-substitution (Methods G, H), S-substitution (Method E), O-substitution (Method P) or N-substitution (Method Q). Methods G, H, E, P, and Q are described in Scheme 7.

Scheme 12: General method for the preparation of 2-imidazolyl compounds of formula xxxi

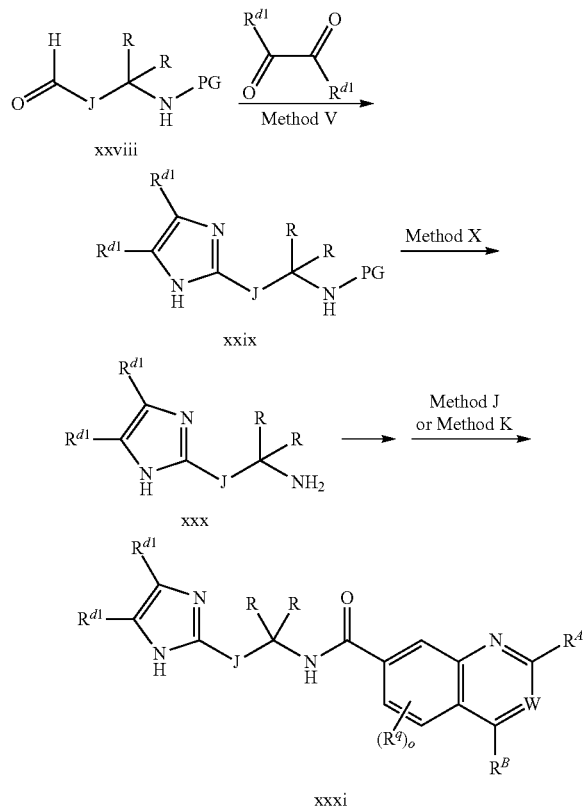

Scheme 12 shows a general procedure for the synthesis of imidazole-containing compounds of formula xxxi. Aldehyde xxviii can be prepared from the corresponding amino-alcohol compound, wherein the amine can be protected with a suitable amine protecting group (PG), such as a Boc group, and the alcohol can be oxidized to an aldehyde using a suitable oxidizing reagent, such as DMSO. Aldehyde xxviii can be condensed with a dicarbonyl compound, such as a diketone, ketoaldehyde, or glyoxal, in the presence of an appropriate ammonia source, such as ammonium acetate or ammonia, in a solvent such as methanol to form the imidazole of formula xxix (Method V). The amine protecting group can then be removed under appropriate conditions, for example TFA/DCM treatment for Boc group removal (Method X) to provide amine xxx, that can be coupled with for example an ester or an acid from any one of Schemes 1-7; 19-21 to form amide xxxi using Method J or K as described above.

Scheme 13: General method for the preparation of triazolyl compounds of formula xxxv

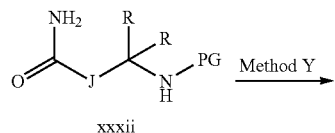

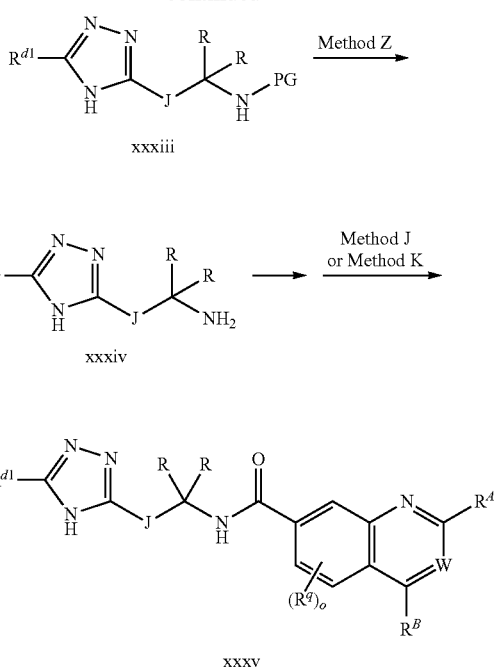

Scheme 13 shows a general procedure for the synthesis of triazole-containing compounds of formula xxxv. The carboxamide xxxii can be prepared from the corresponding amino-alcohol compound, wherein the amine can be protected with a suitable amine protecting group (PG), such as a Boc group, and the alcohol can be oxidized using a suitable oxidizing reagent, such as oxalyl chloride and DMSO. The resulting carboxamide xxxii can be treated with a dialkyl-amide-dialkylacetal, such as DMFDMA at elevated temperature or under microwave irradiation (Method Y) to give an intermediate amidine that can be transformed into a 1,2,4-triazole xxxiii e.g., using hydrazine in acetic acid at elevated temperature or under microwave irradiation (Method Z). The amine can be deprotected to produce xxxiv under suitable conditions, for example, TFA in DCM for removal of a Boc group (Method X). The resulting amine xxxiv can then be coupled with for example an acid or an ester from any one of Schemes 1-7; 19-21 to form an amide xxxv using Method J or K as described above.

Scheme 14: General method for the preparation of compounds of formula xxxix

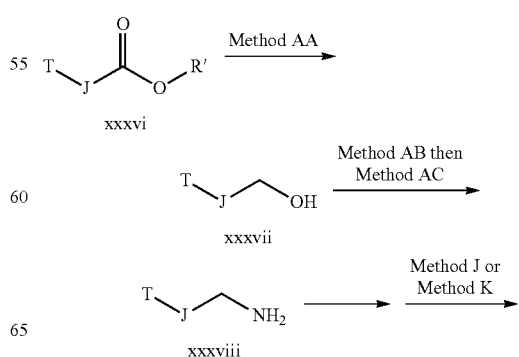

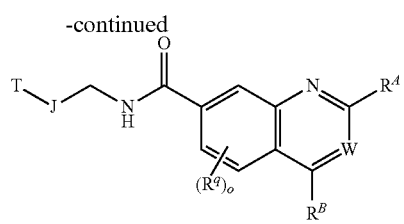

xxxix

Scheme 14 shows a general procedure for the synthesis of compounds of formula xxxix. The ester xxxvi (R' is $C_{1-6}$ aliphatic) can be treated with a suitable reducing agent, such as LAH or DIBAL in a suitable solvent, for example diethyl ether or THF (Method AA) to provide alcohol xxxvii. Alcohol xxxvii can then be converted to amine xxxviii, for example under Mitsunobu conditions, using phthalimide, triphenylphosphine, DEAD in a suitable solvent, such as THF (Method AB) followed by amine release, for example using hydrazine in ethanol at elevated temperature to remove the phthalimide protecting group (Method AC). The resulting amine can then be coupled to with an ester or an acid from any one of Schemes 1-7 to form amide xxxix using Method J or K as described above.

Scheme 15: General method for the preparation of compounds of formula xliv

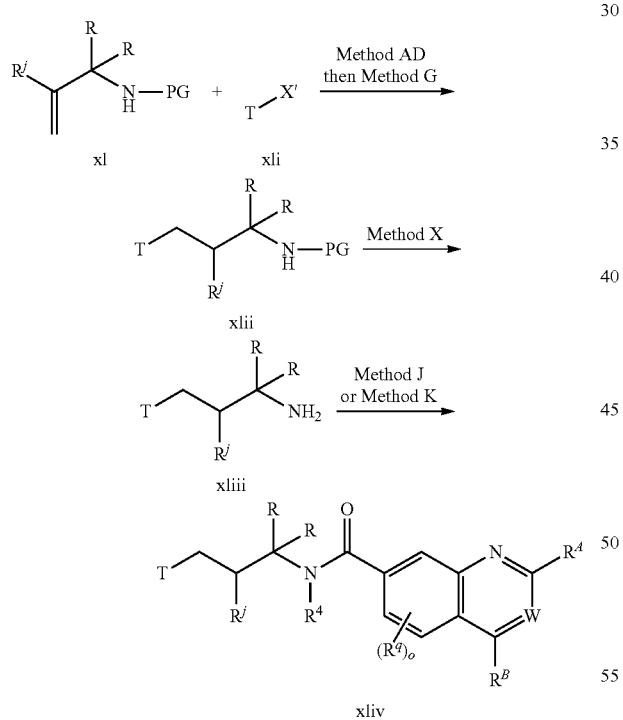

Scheme 15 shows a general procedure for the synthesis of compounds of formula xliv. The suitably protected (for example Boc protected) allylamine xl can be converted to a boronic acid via hydroboration with a suitable reagent, such as 9-BBN in a suitable solvent, for example THF, followed by treatment with sodium hydroxide (Method AD). The intermediate boronic acid can then be coupled with an aryl or heteroaryl halide xli under Suzuki conditions, using a catalyst for example $Pd(PPh_3)_4$ in a suitable solvent, for example THF at elevated temperature (Method G) to provide compound xlii. Deprotection of the amine can afford compound xliii. The deprotection can be carried out under suitable conditions, using for example TFA in DCM for deprotection of a Boc group (Method X). The resulting amine can then be coupled with for example an ester or an acid from any one of Schemes 1-7; 19-21 to form amide xliv using Method J or K as described above.

Scheme 16: General method for the preparation of compounds of formula xlix

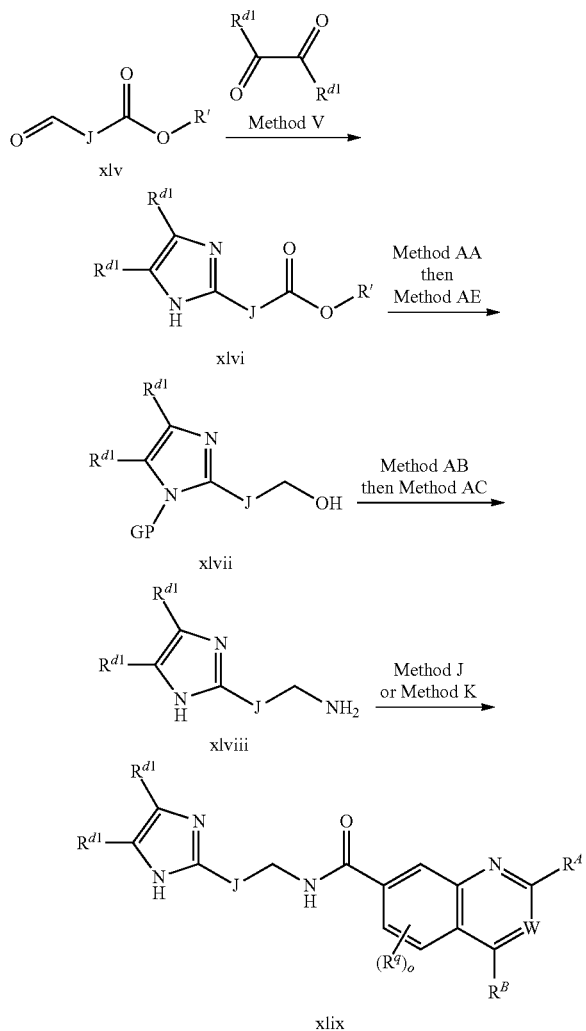

Scheme 16 shows a general method for the synthesis of compounds of formula xlix. The aldehyde group in compound xlv (R' is $C_{1-6}$ aliphatic) can be converted to an optionally substituted imidazole xlvi using Method V described in Scheme 12. The ester group in xlvi can be treated with a suitable reducing agent, such as LAH or DIBAL in a suitable solvent, for example diethyl ether or THF (Method AA) to provide an alcohol followed by subsequent imidazole protection with a suitable protecting group (PG), for example a tosylate group (Ts). Appropriate reagent, such as TsCl and a base, for example $K_2CO_3$ in an appropriate solvent, such as THF/water (Method AE) can be used to provide a compound of formula xlvii (PG=protecting group). Alcohol xlvii can then be converted onto amine xlviii under Mitsunobu conditions, using for example phthalimide, triphenylphosphine, DEAD in a suitable solvent, such as THF (Method AB) followed by deprotection of both the phthalimide and tosylate groups, for example using hydrazine in ethanol at elevated temperature (Method AC). The resulting amine xlviii can then be coupled with for example an ester or an acid from any one of Schemes 1-7; 19-21 to form amide xlix using Method J or K as described above.

Scheme 17: General method for the preparation of compounds of formula lii

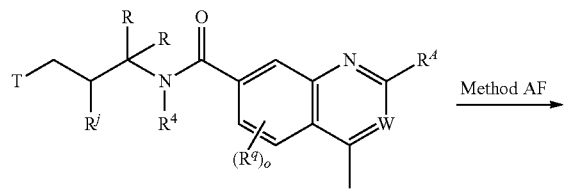

l

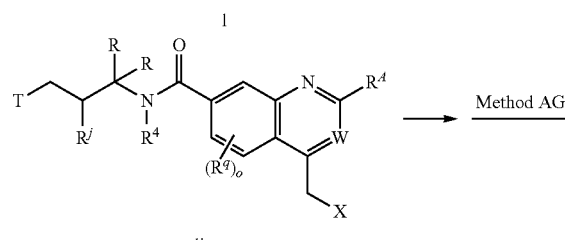

li

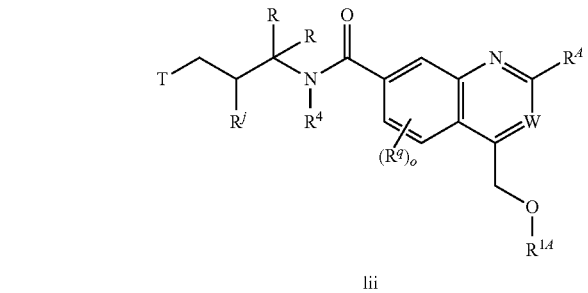

lii

Scheme 17 shows a general method for the synthesis of compounds of formula lii. Methyl substituted heteroaromatic compounds 1 can be halogenated under standard conditions, for example bromine in acetic acid with heating (Method AF). The formed alkyl halides li can be then treated with alcohols in the presence of a suitable base, such as aqueous sodium hydroxide (Method AG). Reaction can be run at room or elevated temperature with an optional co-solvent, such as dioxane or THF to provide ethers of formula lii.

Scheme 18: General method for the preparation of compounds of formula liv

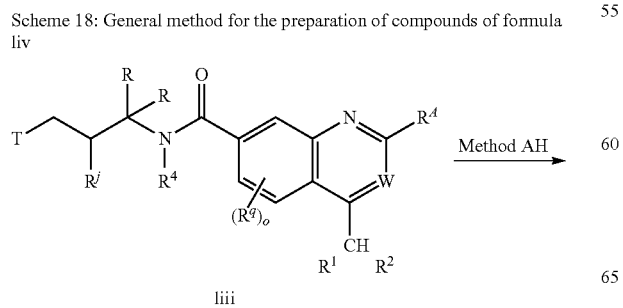

liii

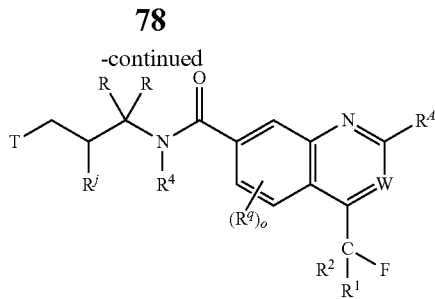

liv

Scheme 18 shows a general method for the synthesis of compounds of formula liv. Alkyl substituted heteroaromatic compounds liii can be treated with suitable fluorinating agent, such as N-fluoro-N'-chloromethyl-triethylenediamine-bis(tetrafluoroborate) (F-TEDA-BF$_4$) (Selectfluor) in a suitable solvent, for example MeCN to afford compounds of formula liv (Method AH)

Scheme 19: General method for the preparation of compounds of formula xxvii

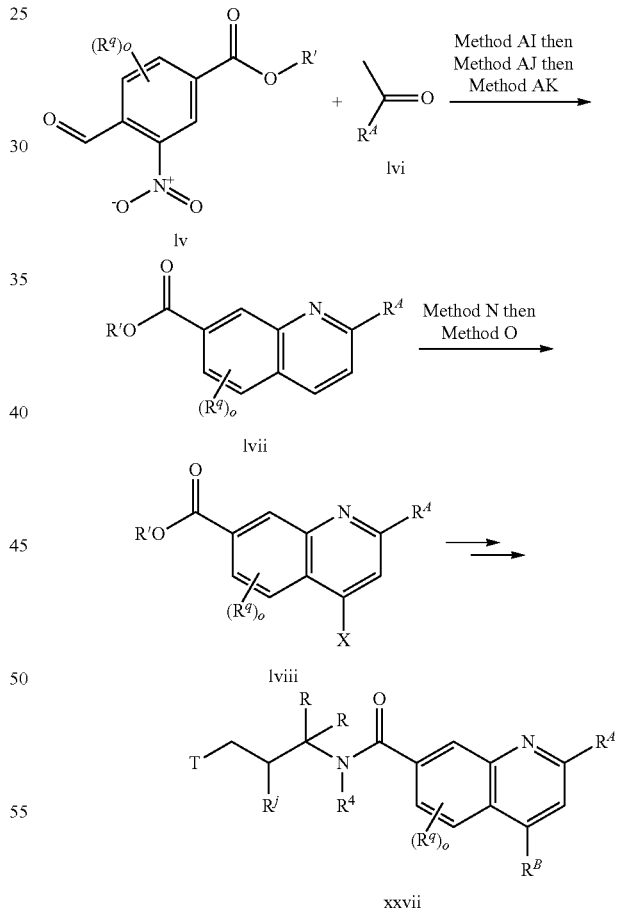

Scheme 19 shows a general method for the synthesis of compounds of formula xxvii. Optionally substituted formyl nitobenzoates lv (R' is $C_{1-6}$ aliphatic) can be reduced to intermediate formyl aminobenzoates using general conditions, such as iron powder in aqueous HCl at elevated temperature (Method AI), followed by treatment with arylmethyl ketones lvi premixed with an excess of a suitable base, for example potassium hydroxide (Method AJ) to afford carboxylic acid intermediates that can be subsequently esterified to esters lvii using general conditions, such as oxalyl chloride, DMF, THF and an alcohol, such as methanol (Method AK). Esters lvii can be then halogenated using a 2-step procedure, starting with N-oxidation with a suitable reagent, for example mCPBA in DCM (Method N), followed by treatment with an appropriate halogenting agent, such as oxalyl chloride in a suitable solvent, for example DMF/DCM mixture (Method O). Resulting compounds lviii can be then converted to compounds xxvii using sequences described above, such as introduction of $R^B$ using methods G, H, L, U, and conversion of ester function to amide using Methods I followed by J or K.

Scheme 20: General method for the preparation of compounds of formula xxvii

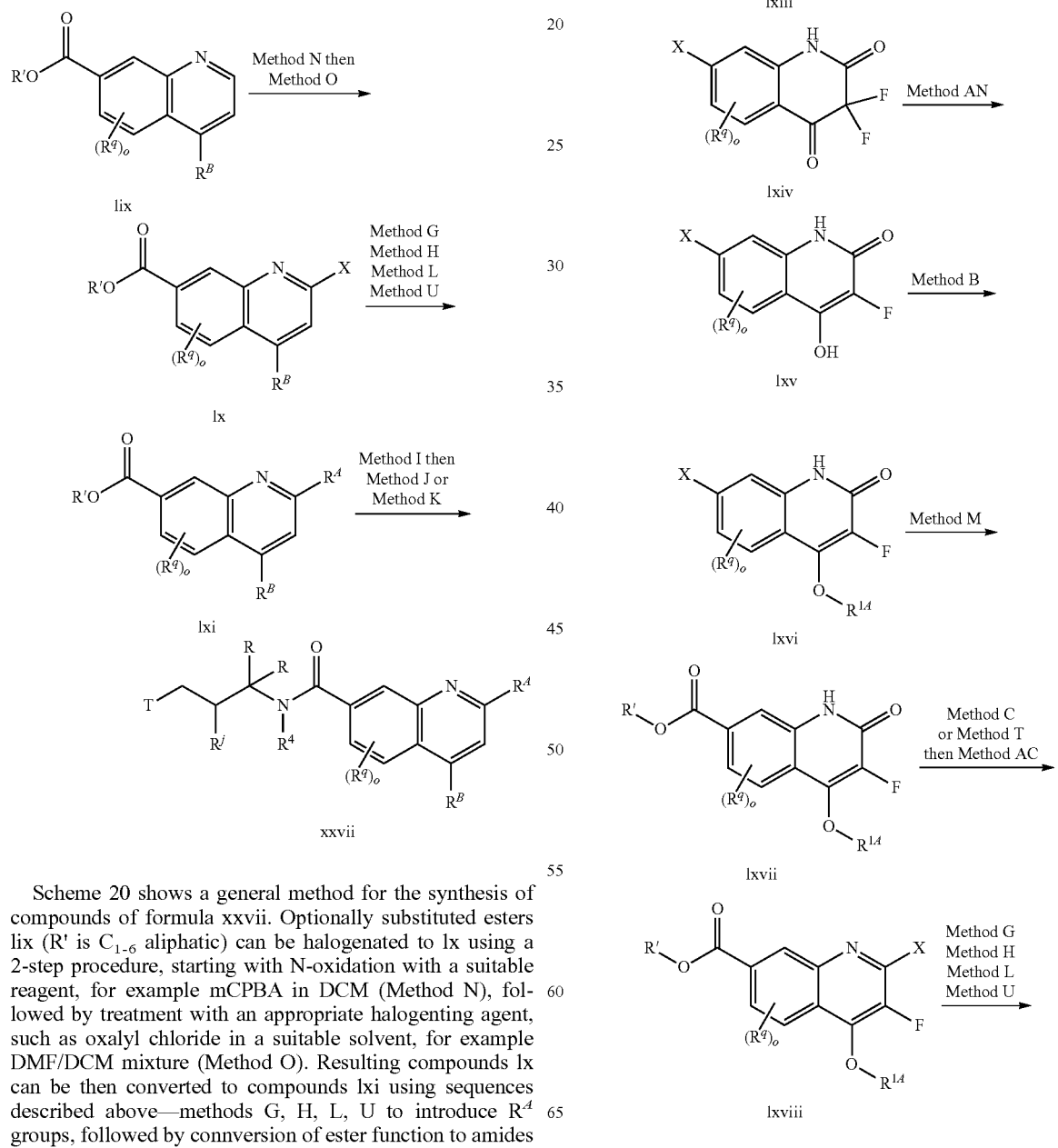

Scheme 20 shows a general method for the synthesis of compounds of formula xxvii. Optionally substituted esters lix (R' is $C_{1-6}$ aliphatic) can be halogenated to lx using a 2-step procedure, starting with N-oxidation with a suitable reagent, for example mCPBA in DCM (Method N), followed by treatment with an appropriate halogenating agent, such as oxalyl chloride in a suitable solvent, for example DMF/DCM mixture (Method O). Resulting compounds lx can be then converted to compounds lxi using sequences described above—methods G, H, L, U to introduce $R^A$ groups, followed by connversion of ester function to amides xxvii using Methods I and then J or K.

Scheme 21: General method for the preparation of compounds of formula lxx

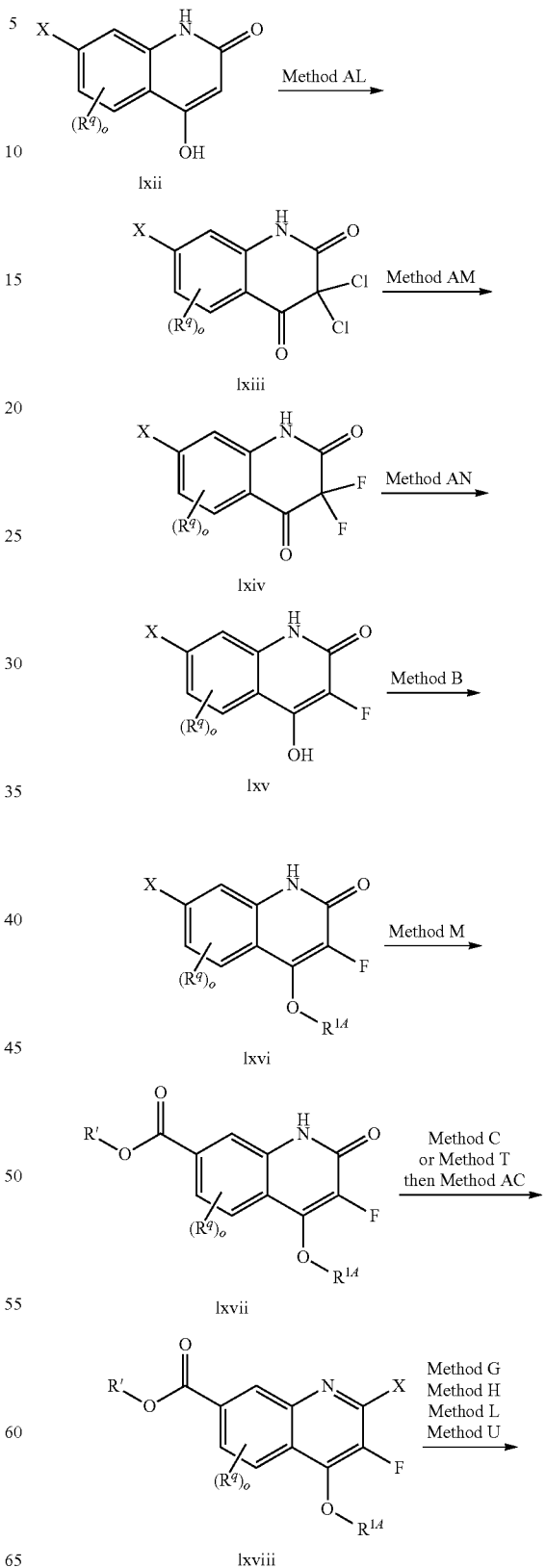

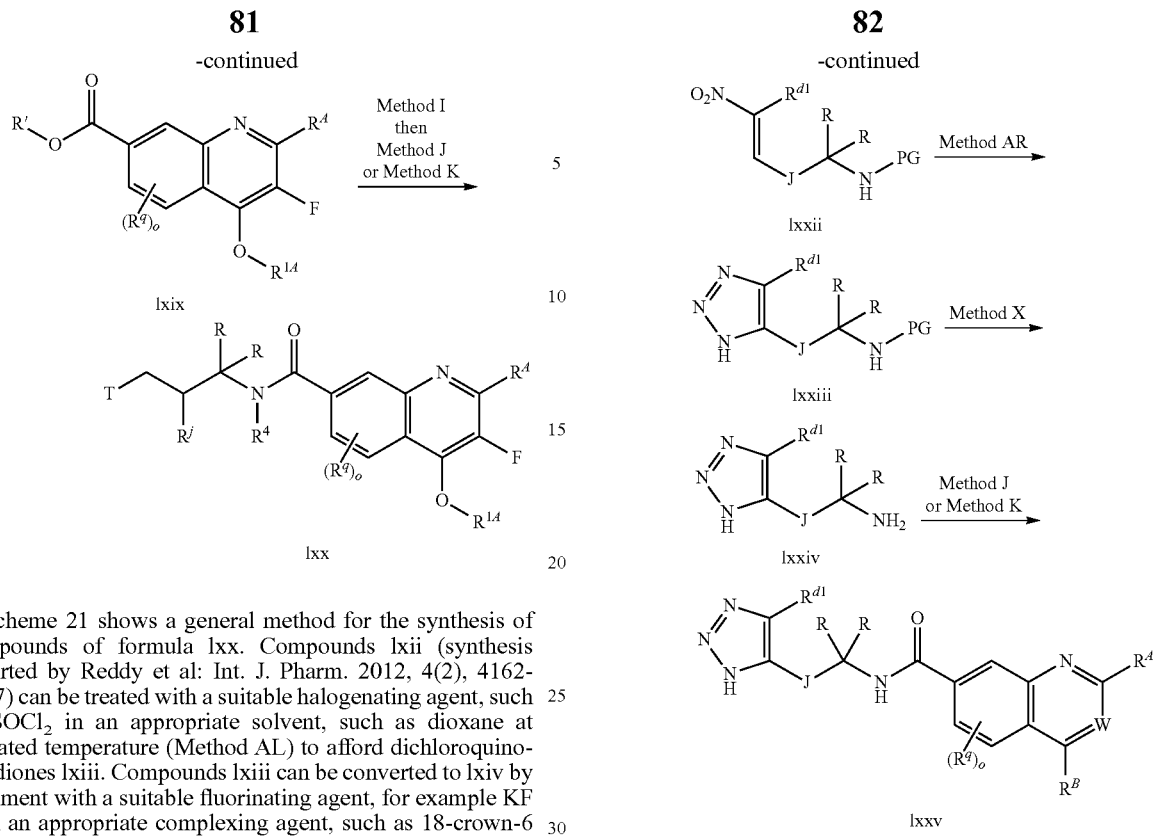

Scheme 21 shows a general method for the synthesis of compounds of formula lxx. Compounds lxii (synthesis reported by Reddy et al: Int. J. Pharm. 2012, 4(2), 4162-4167) can be treated with a suitable halogenating agent, such as SOCl$_2$ in an appropriate solvent, such as dioxane at elevated temperature (Method AL) to afford dichloroquinolinediones lxiii. Compounds lxiii can be converted to lxiv by treatment with a suitable fluorinating agent, for example KF with an appropriate complexing agent, such as 18-crown-6 in MeCN at elevated temperature (Method AM). Compounds lxiv can be then converted to monofluorohydroxyquinolinones lxv using an appropriate method, such as zinc in acetic acid at elevated temperature (Method AN). Compounds lxv can be then converted to ethers lxvi by treatment with alkyl halides, such as ethyl iodide with a suitable base, for example K$_2$CO$_3$ in an appropriate solvent, such as DMF at elevated temperature (Method B). Conversion of halides in lxvi to esters lxvii (R' is C$_{1-6}$ aliphatic) can be achieved as described in Scheme 9, Method M. Introduction of halide towards compounds of formula lxviii can be achieved using direct halogenation of lxvii as described in Scheme 3, Method C, or using a two-step procedure starting with triflate formation according to Method T described in Scheme 10, followed by exchange with a halogenating reagent, for example anhydrous HCl in a suitable solvent, for example EtOAc (Method AO). Resulting compounds lxviii can be then converted to compounds lxix using sequences described above—methods G, H, L, U to introduce R$^A$ groups, followed by conversion of ester function to amides lxx using Methods I and then J or K.

Scheme 22: General method for the preparation of compounds of formula lxv

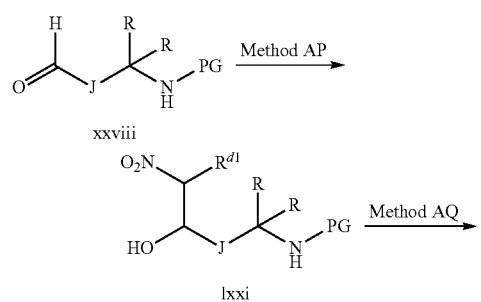

Scheme 22 shows a general method for the synthesis of compounds of formula lxxv. The aldehyde group in compounds xxviii can be converted to optionally substituted nitroalcohols lxxi using treatment with nitroalkanes, for example nitroethane and a suitable base, such as TEA (Method AP). Elimination towards nitroalkenes lxxii can be achieved for example by treatment with methanesulfonyl chloride and a suitable base, such as TEA in DCM (Method AQ). Nitroalkenes lxxii can be then converted to triazoles lxxiii using treatment with sodium azide in DMSO (Method AR). Removal of the protecting group (PG) can be achieved using methods described above, for example using hydrazine in ethanol at elevated temperature to remove phthalimide group (Method AC), or Boc group removal using TFA/DCM or HCl/dioxane (Method X). The resulting amines lxxiv can then be coupled with an ester or an acid from any one of Schemes 1-7; 19-21 to form amides lxxv using Method J or K as described above.

Scheme 23: General method for the preparation of compounds of formula lxxix

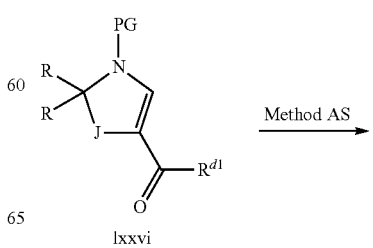

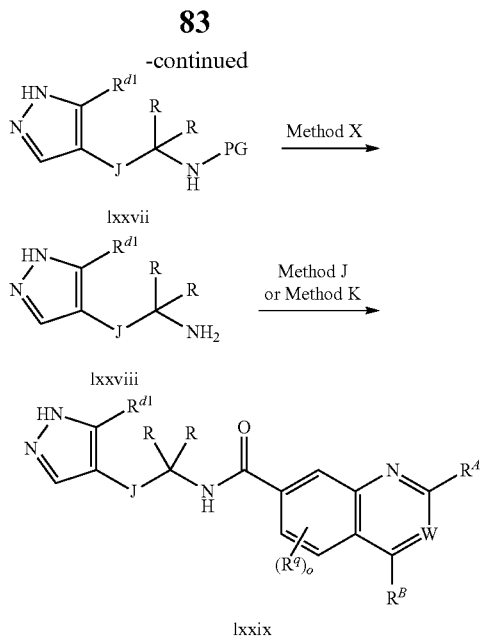

Scheme 23 shows a general method for the synthesis of compounds of formula lxxix. Compounds lxxvi can be converted to protected pyrazoles lxxvii using treatment with hydrazine in a suitable solvent such as butanol at elevated temperature (Method AS). Removal of the protecting group (PG) can be achieved using methods described above, for example Boc group removal using TFA/DCM or HCl/dioxane (Method X). The resulting amines lxxviii can then be coupled with an ester or an acid from any one of Schemes 1-7; 19-21 to form amides lxxix using Method J or K as described above.

Scheme 24: General method for the preparation of compounds of formula lxxxiii

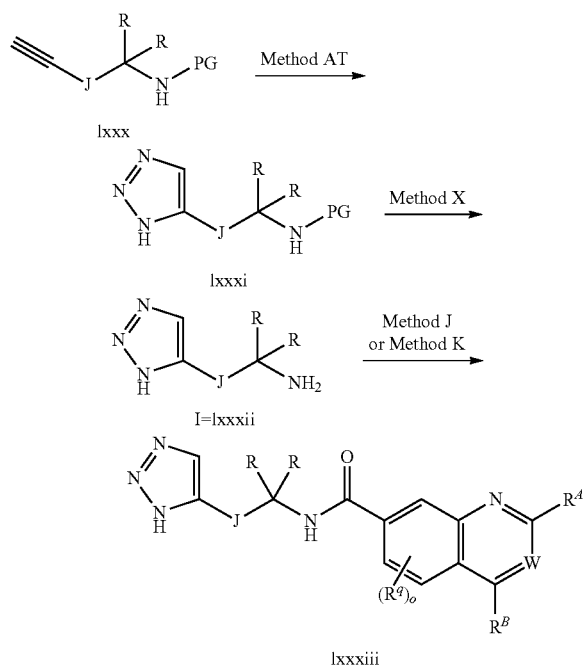

Scheme 24 shows a general method for the synthesis of compounds of formula lxxxiii. Conversion of alkynes lxxx to triazoles lxxxi can be for example achieved by treatment of aqueous formaldehyde in acetic acid with sodium azide, followed by addition of alkynes lxxx and sodium ascorbate/cupric sulfate catalyst (Method AT). Removal of the protecting group (PG) can be achieved using methods described above, for example Boc group removal using TFA/DCM or HCl/dioxane (Method X). The resulting amines lxxxii can then be coupled with an ester or an acid from any one of Schemes 1-7; 19-21 to form amides lxxxiii using Method J or K as described above.

Scheme 25: General method for the preparation of compounds of formula lxxxviii

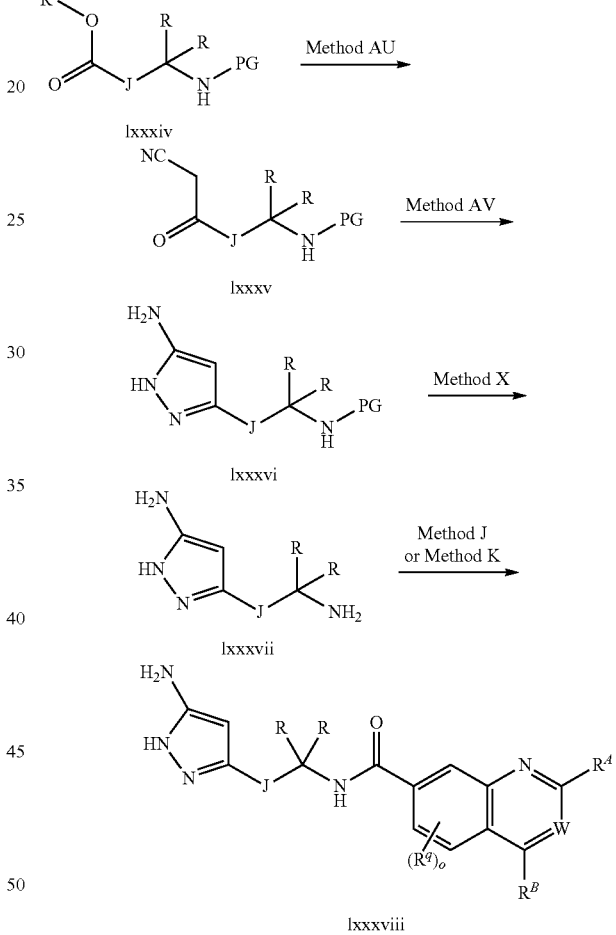

Scheme 25 shows a general method for the synthesis of compounds of formula lxxxviii. Conversion of esters lxxxiv (R' is $C_{1-6}$ aliphatic) to α-cyanoketones lxxxv can be achieved by treatment with deprotonated acetonitrile, obtained for example by treatment of acetonitrile with n-BuLi in THF at low temperature (Method AU). Compounds lxxxv can be converted to aminopyrazoles lxxxvi using treatment with hydrazine in a suitable solvent, such as EtOH (Method AV). Removal of the protecting group (PG) can be achieved using methods described above, for example Boc group removal using TFA/DCM or HCl/dioxane (Method X). The resulting amines lxxxvii can then be coupled with an ester or an acid from any one of Schemes 1-7; 19-21 to form amides lxxxviii using Method J or K as described above.

EXAMPLES
Table 1 below depicts certain compounds represented by compounds of formula I.
TABLE 1
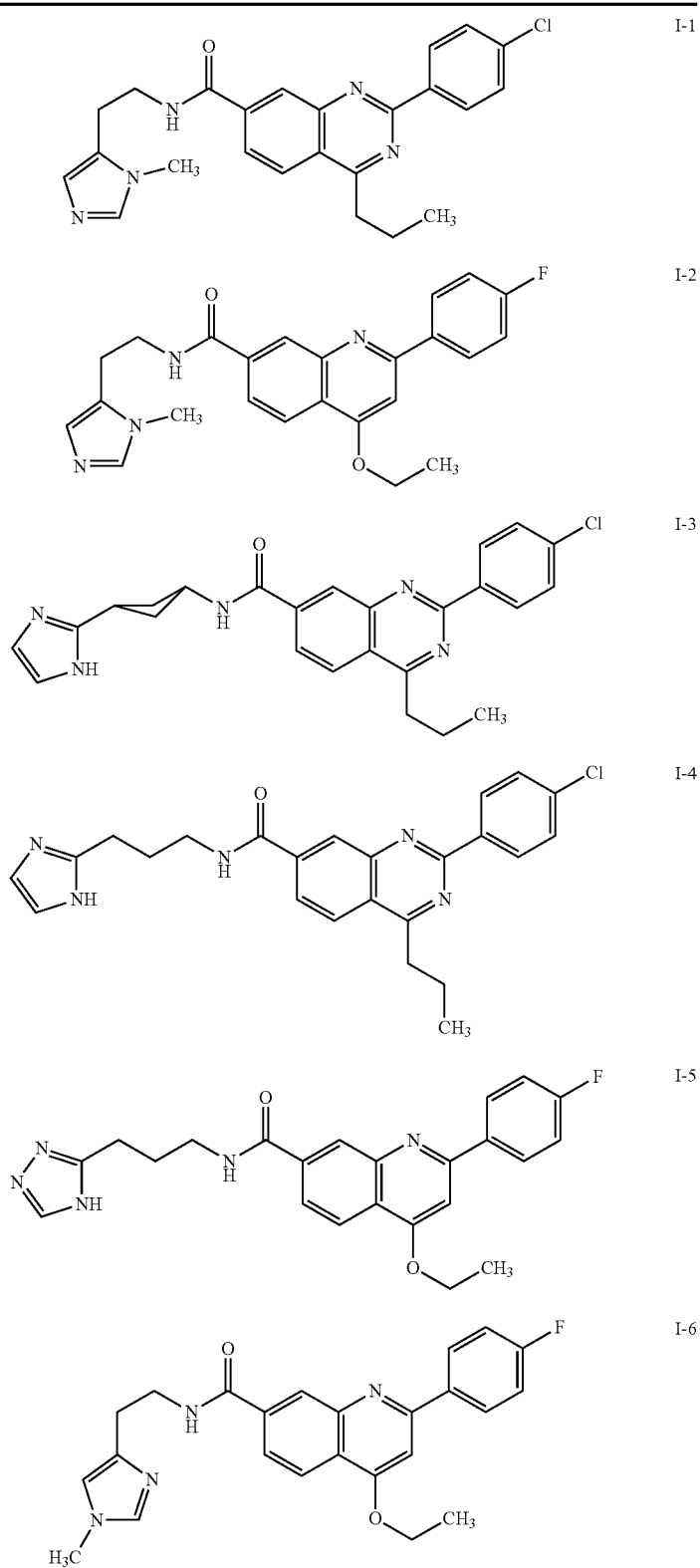

TABLE 1-continued
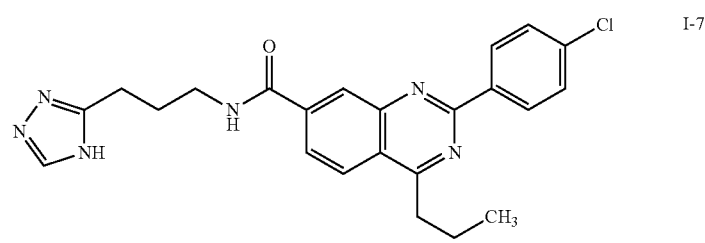
I-7
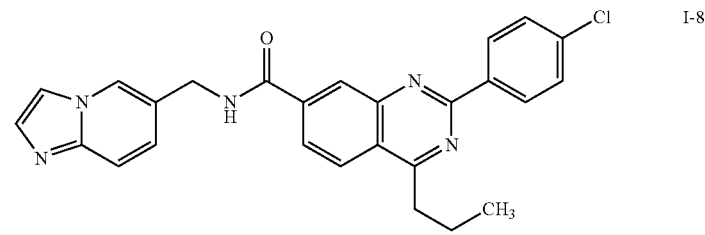
I-8
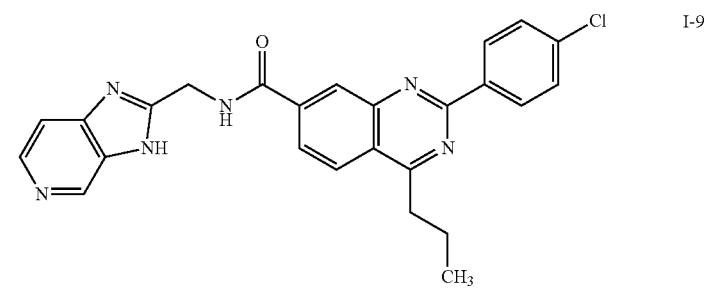
I-9
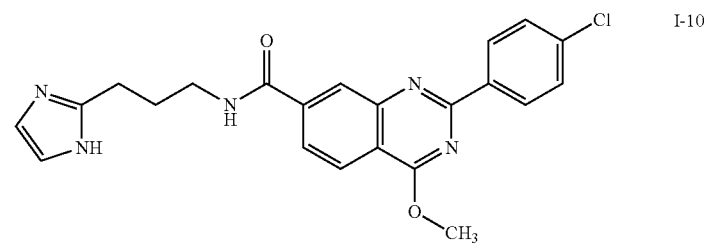
I-10
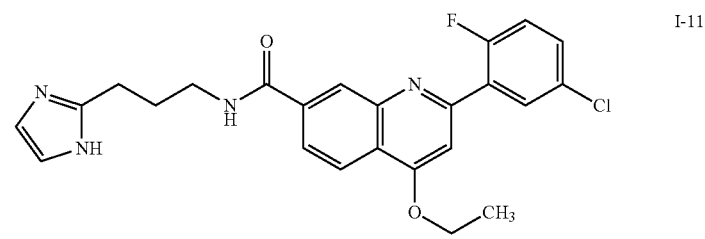
I-11
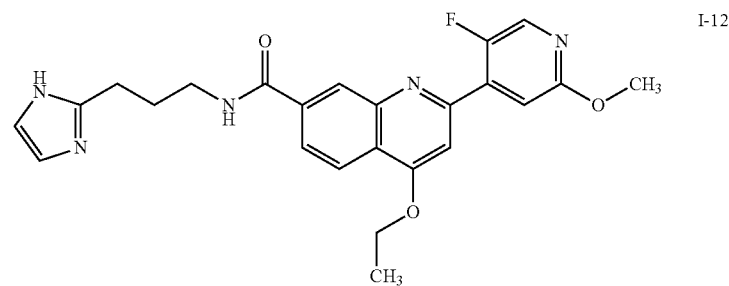
I-12

TABLE 1-continued
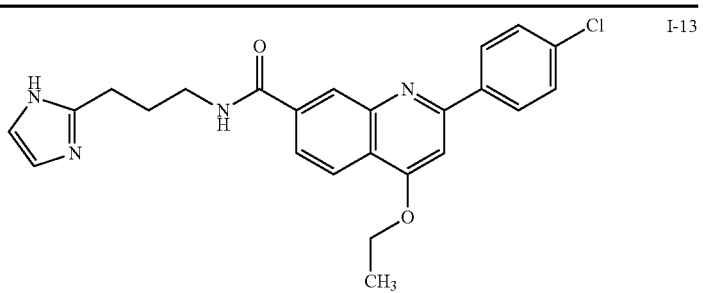
I-13
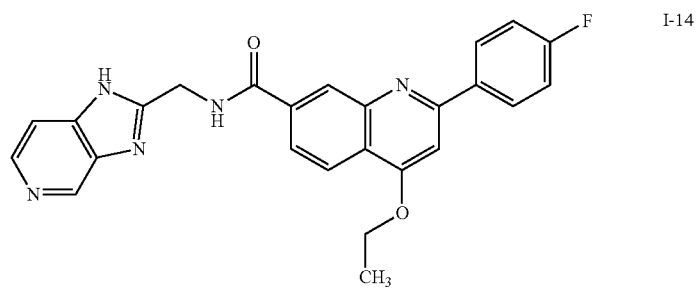
I-14
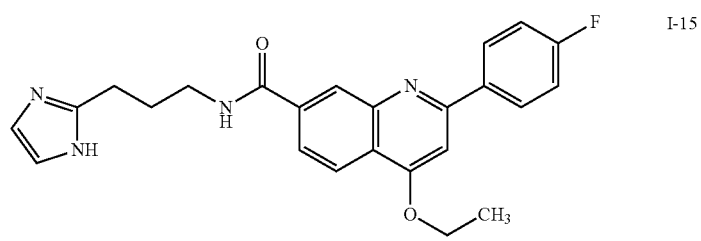
I-15
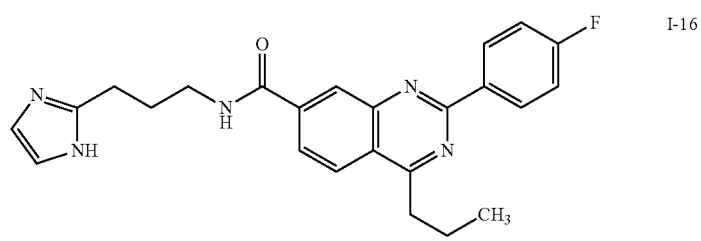
I-16
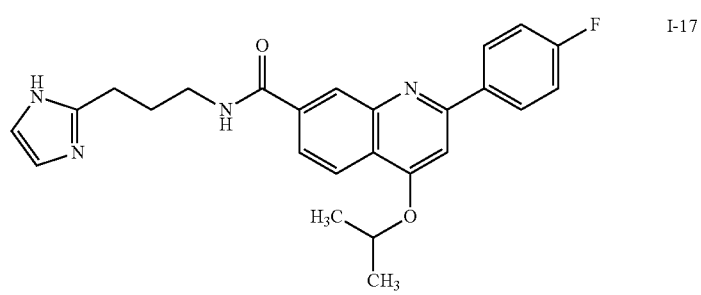
I-17
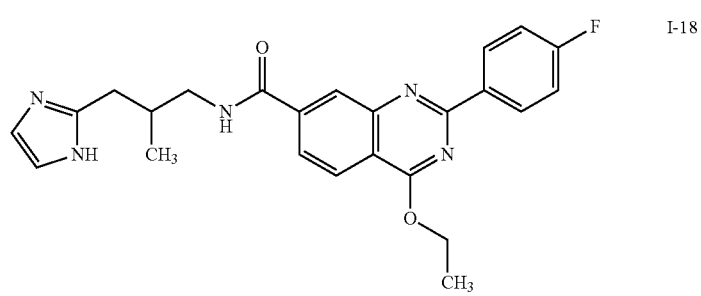
I-18

TABLE 1-continued
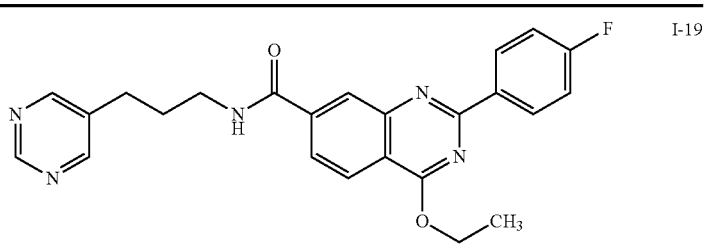 I-19
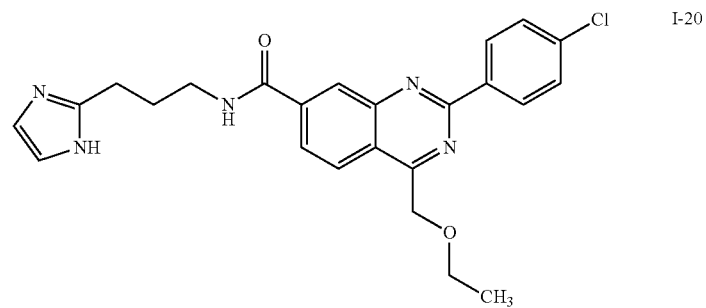 I-20
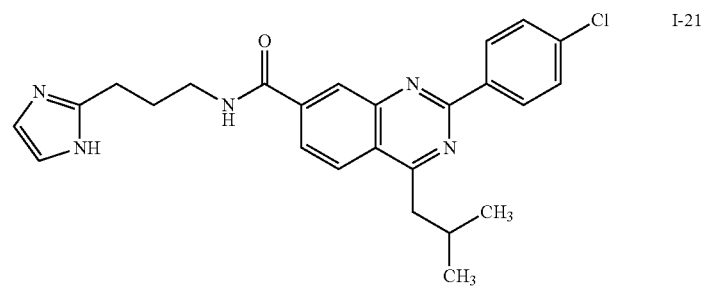 I-21
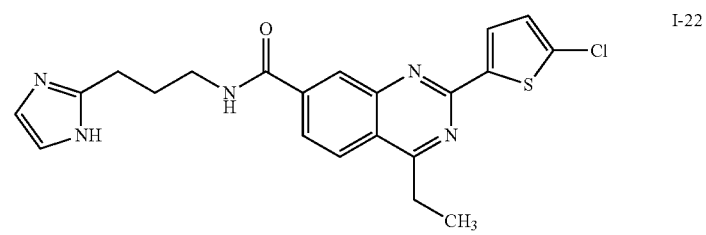 I-22
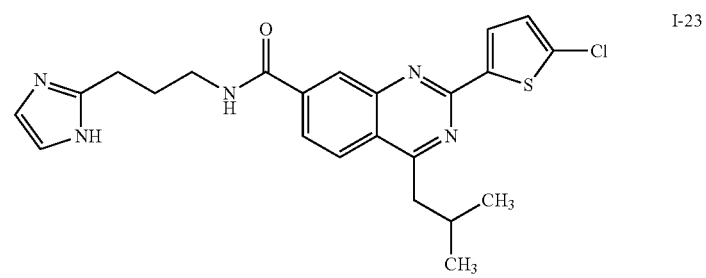 I-23
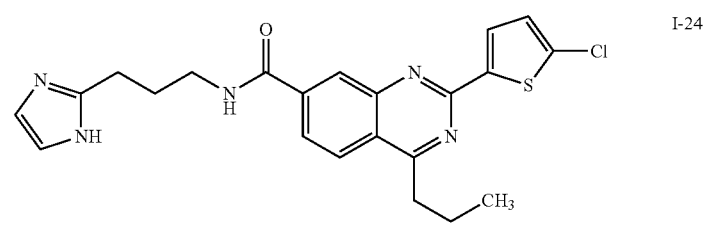 I-24

TABLE 1-continued
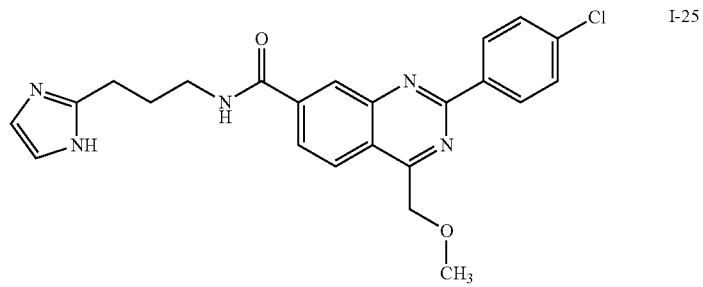
I-25
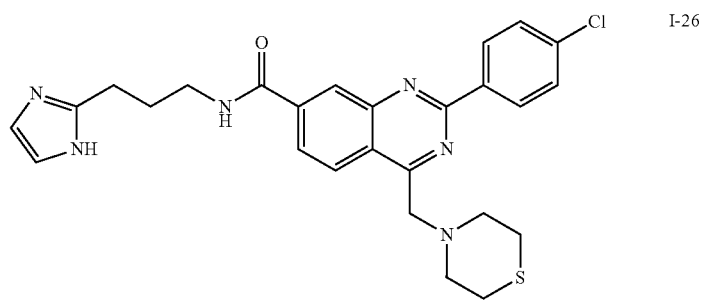
I-26
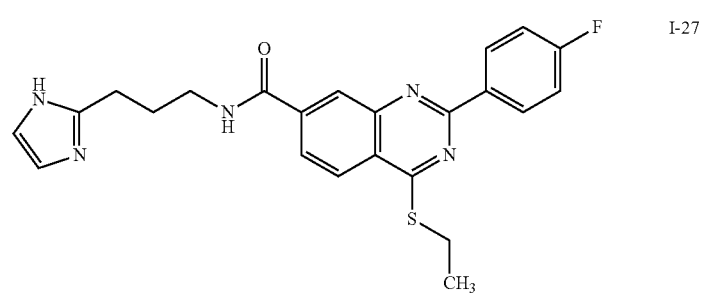
I-27
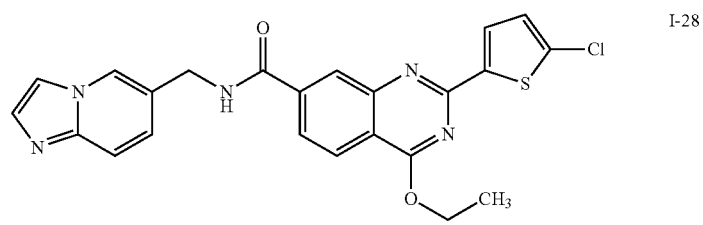
I-28
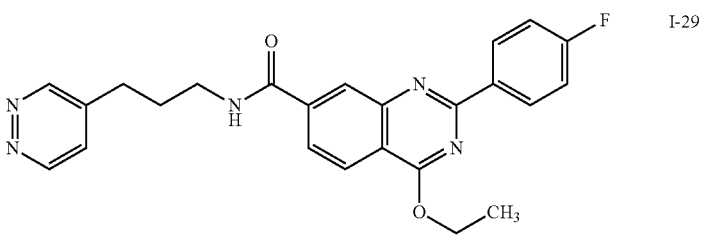
I-29
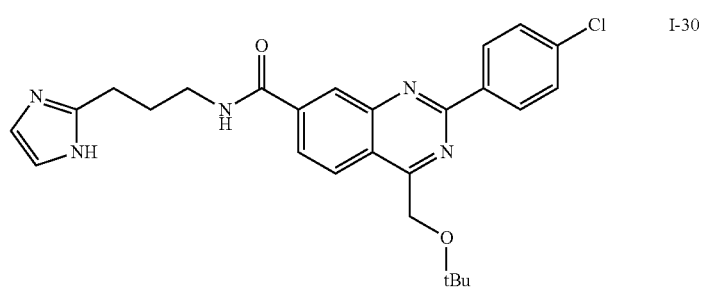
I-30

TABLE 1-continued
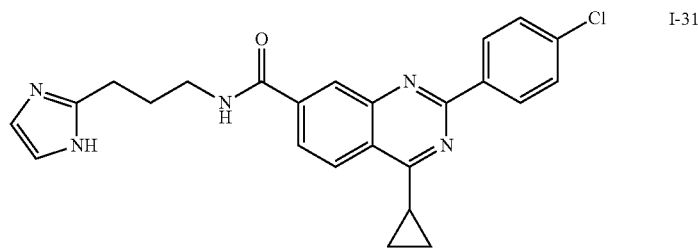 I-31
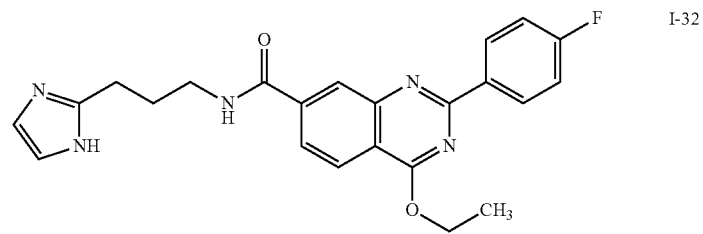 I-32
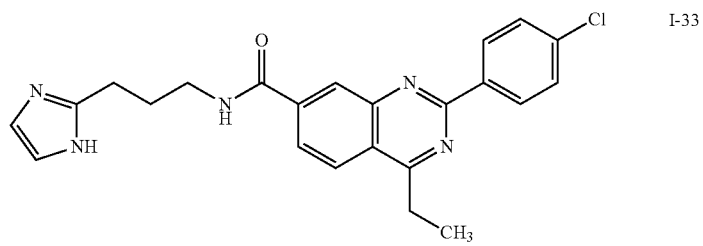 I-33
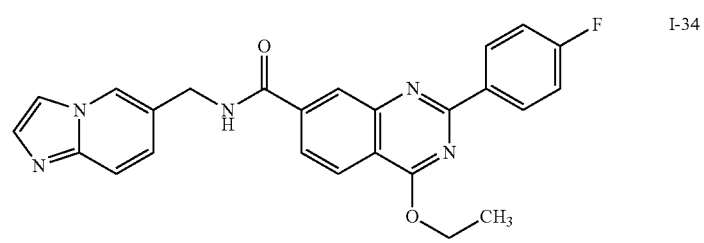 I-34
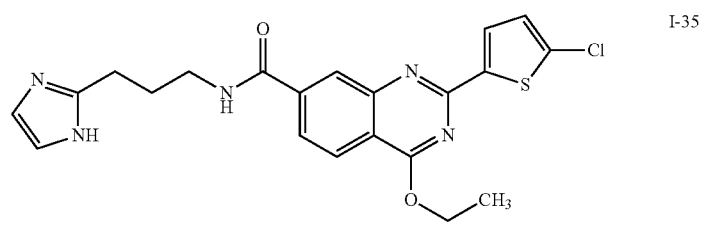 I-35
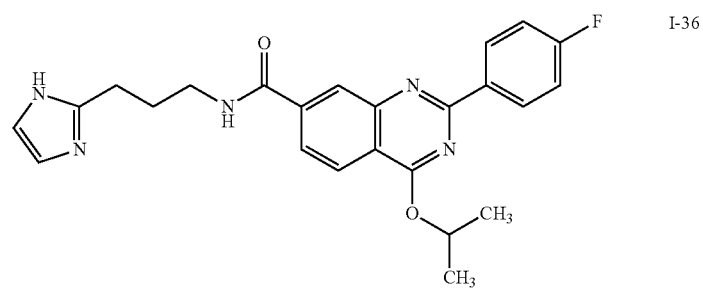 I-36

TABLE 1-continued
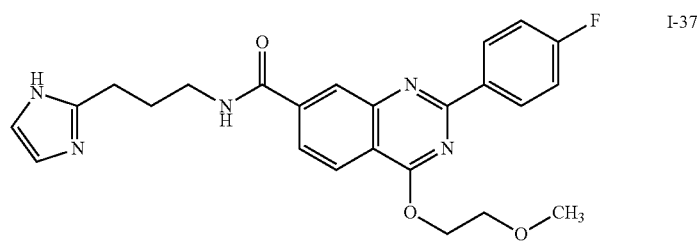 I-37
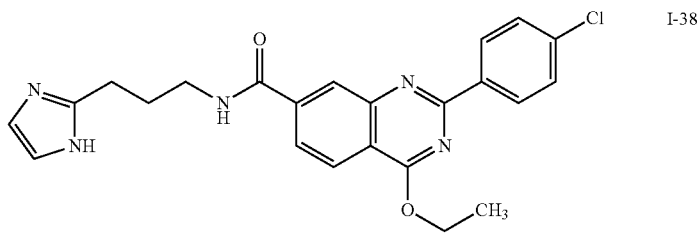 I-38
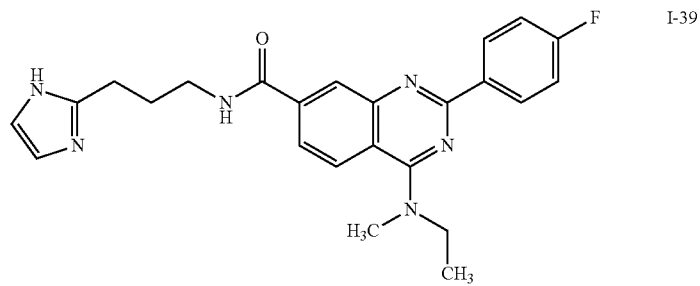 I-39
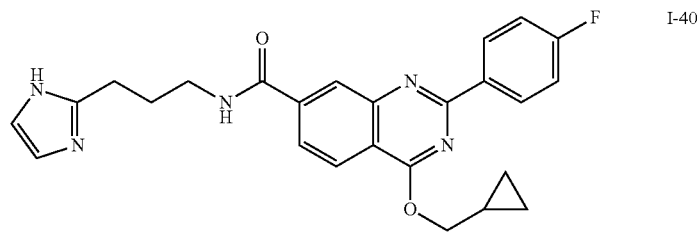 I-40
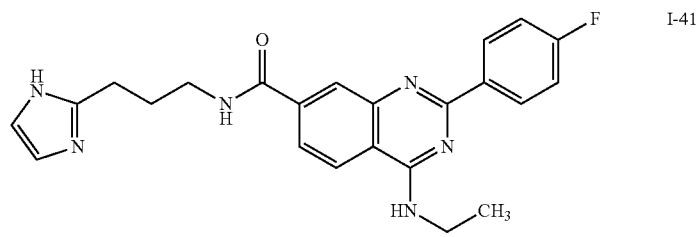 I-41
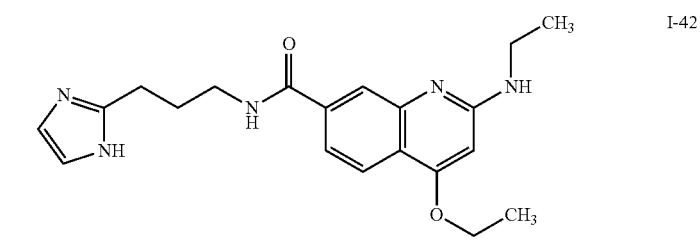 I-42

TABLE 1-continued
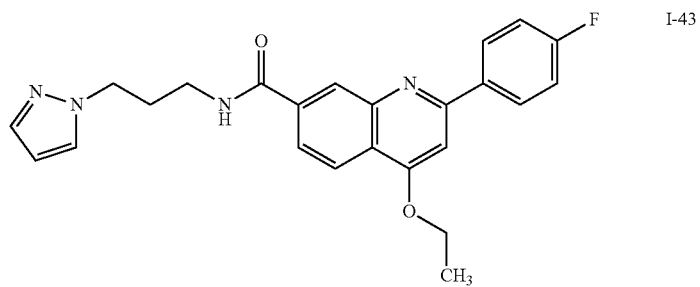
I-43
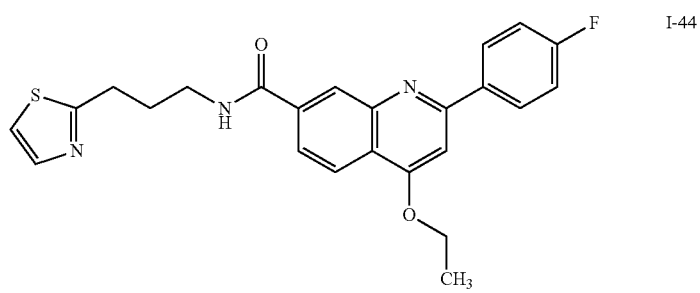
I-44
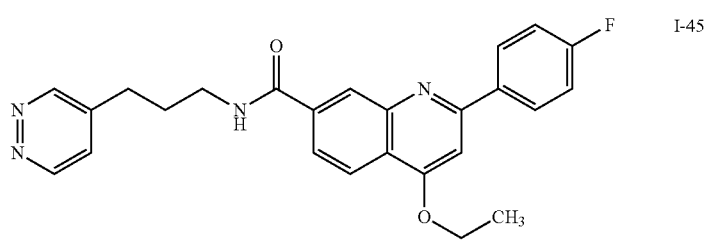
I-45
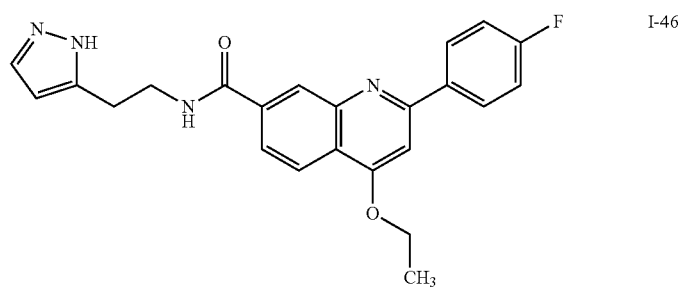
I-46
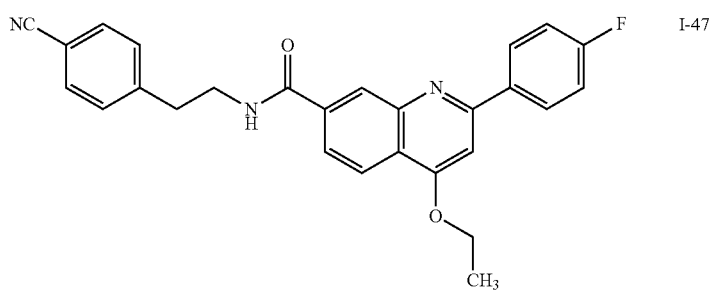
I-47

TABLE 1-continued
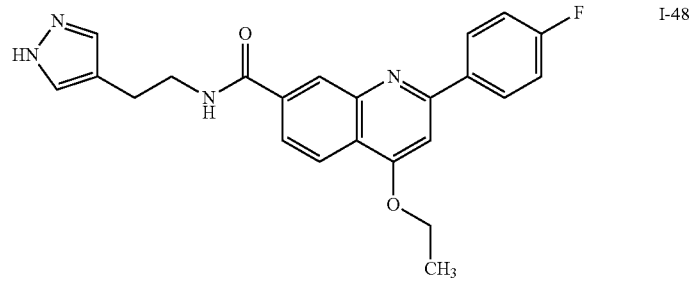
I-48
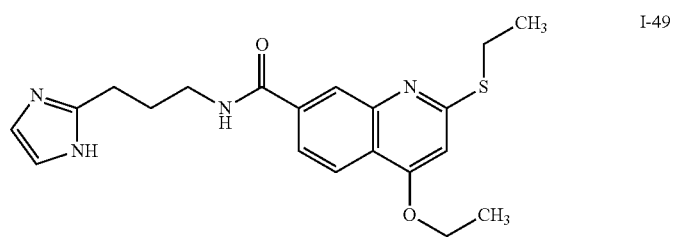
I-49
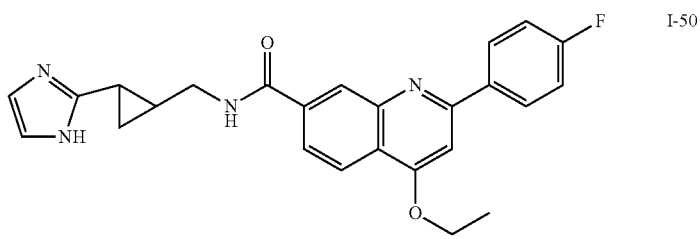
I-50
trans cyclopropyl (first eluting enantiomer, Chiralpak ID Peak 1)
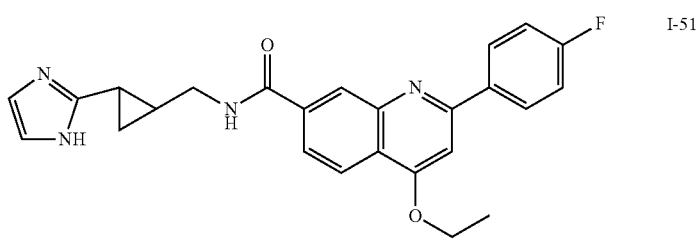
I-51
trans cyclopropyl (second eluting enantiomer, Chiralpak ID Peak 2)
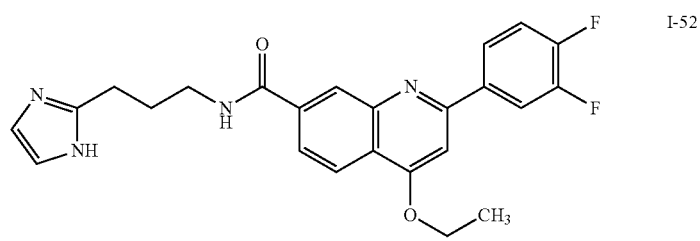
I-52
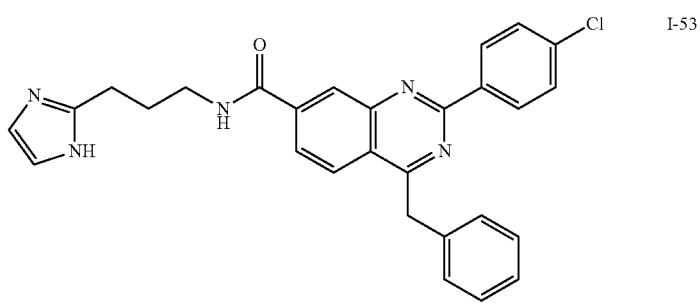
I-53

TABLE 1-continued
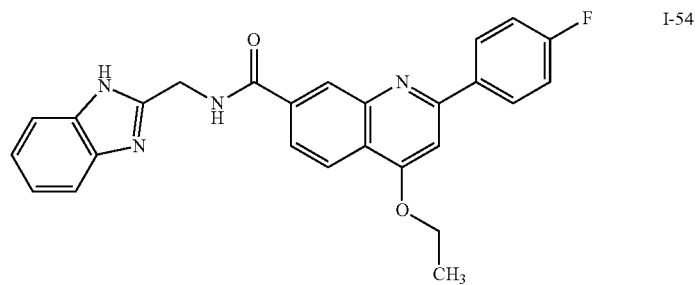
I-54
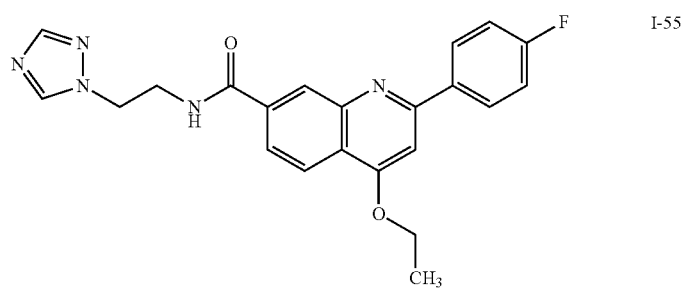
I-55
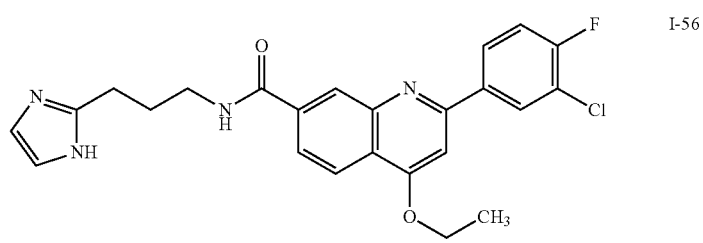
I-56
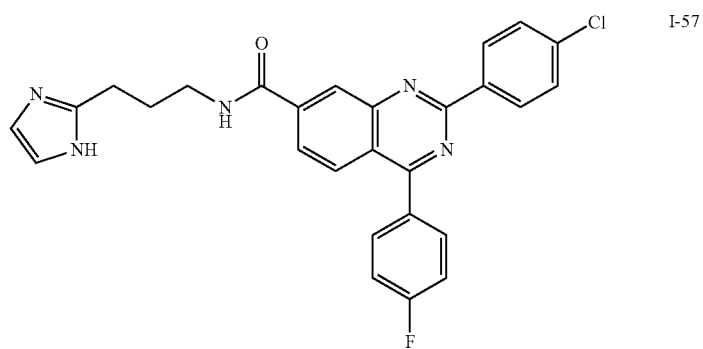
I-57
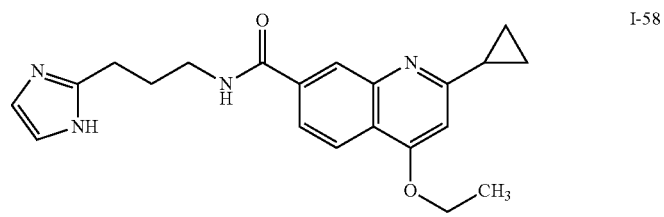
I-58

TABLE 1-continued
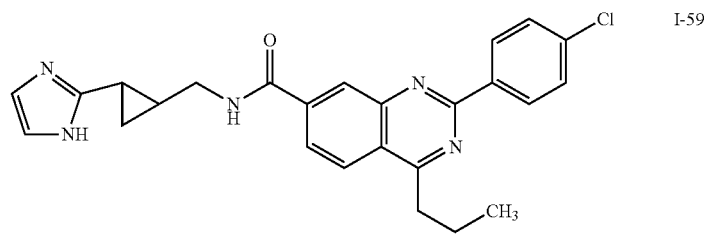
I-59
trans cyclopropyl (racemic)
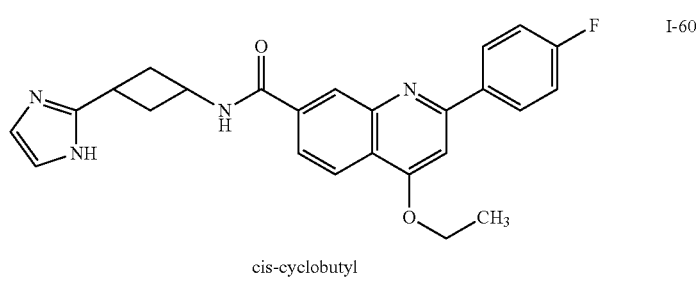
I-60
cis-cyclobutyl
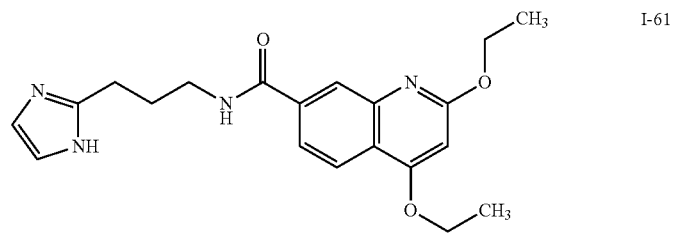
I-61
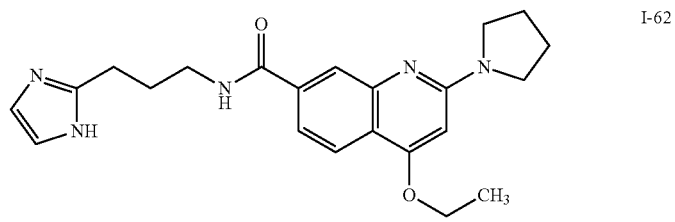
I-62
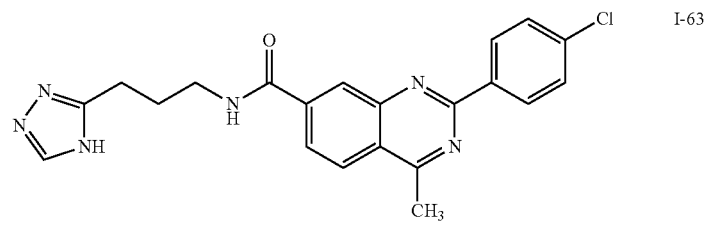
I-63
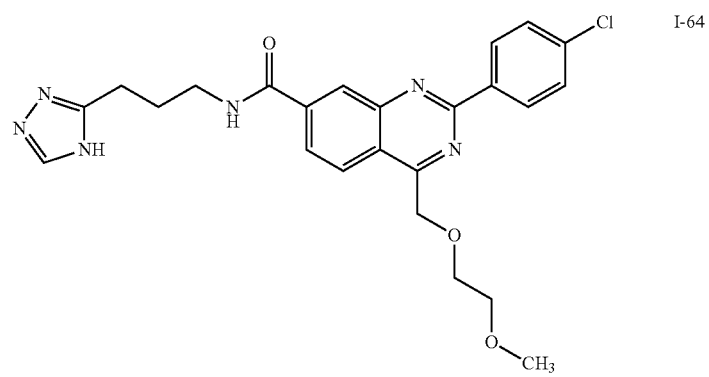
I-64

TABLE 1-continued
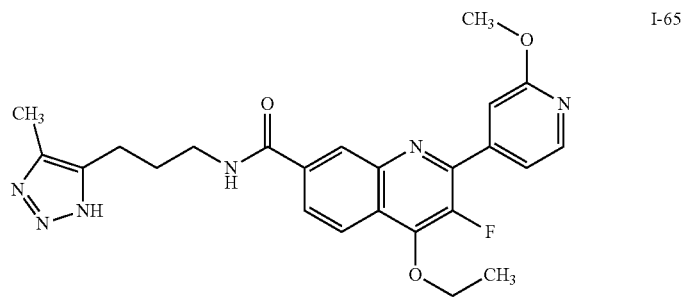
I-65
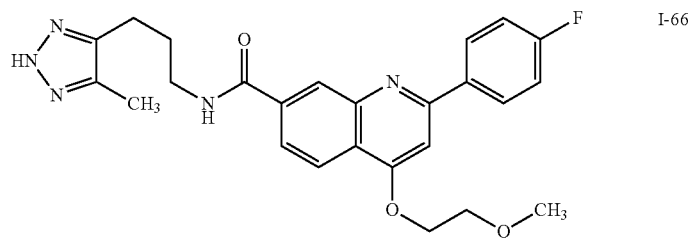
I-66
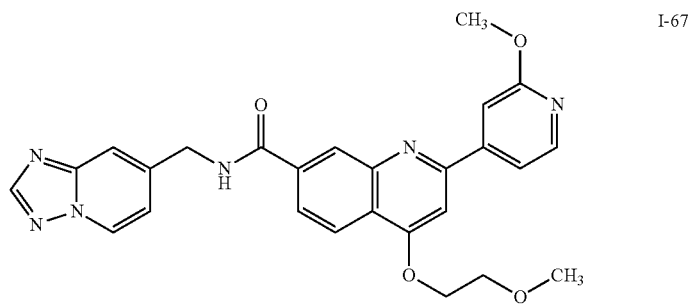
I-67
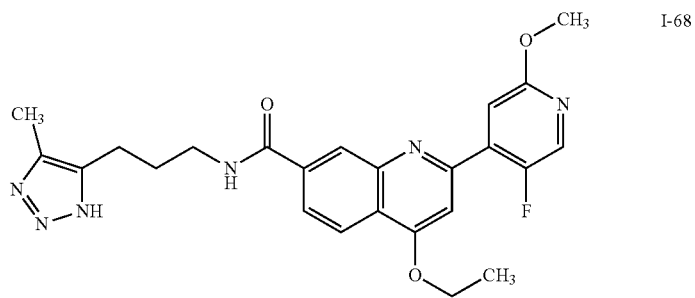
I-68
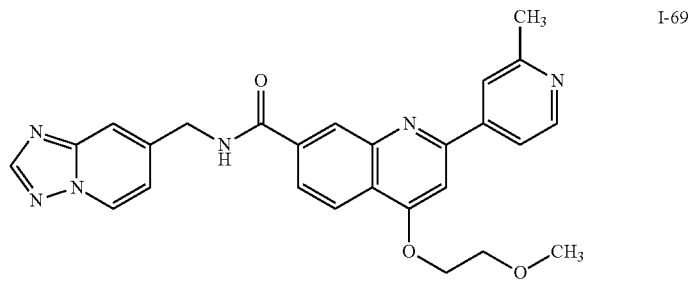
I-69

TABLE 1-continued
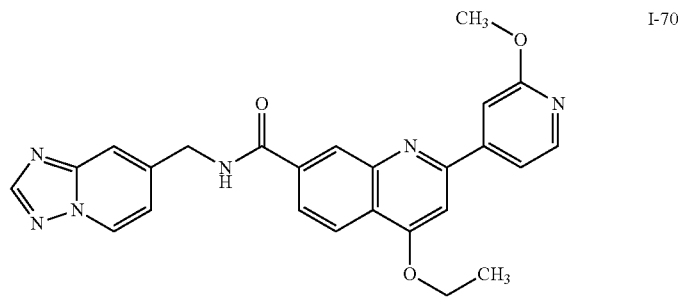
I-70
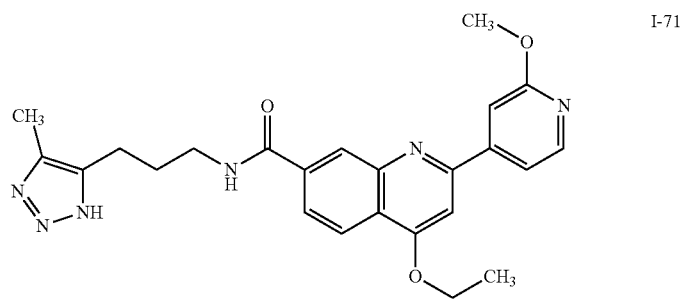
I-71
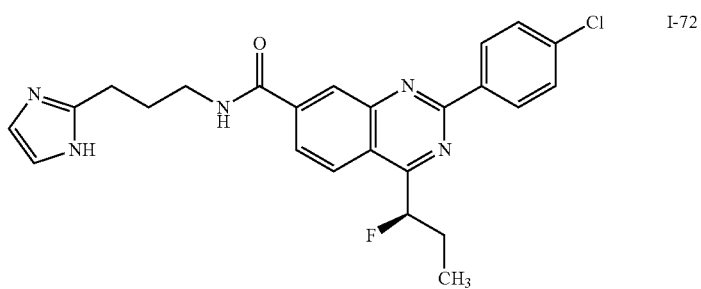
I-72
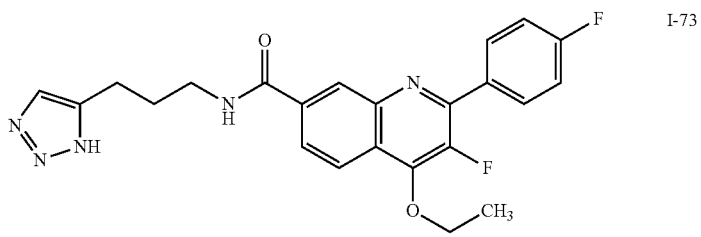
I-73
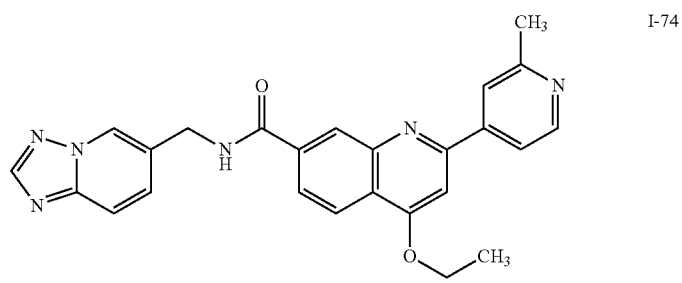
I-74

TABLE 1-continued
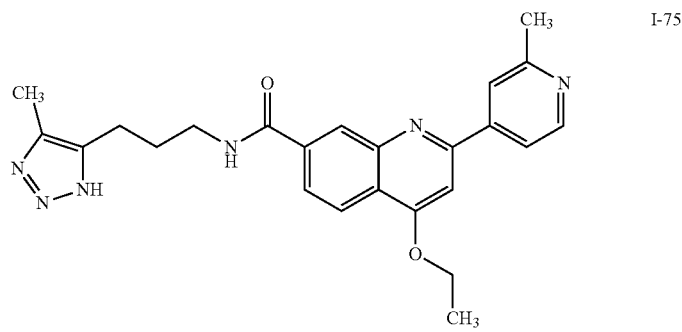
I-75
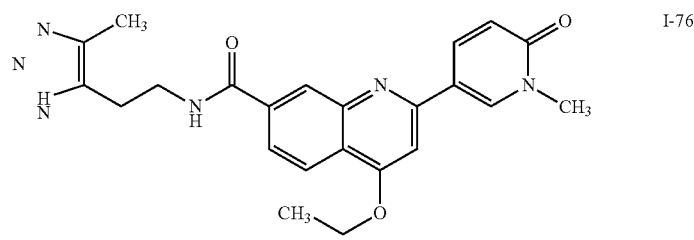
I-76
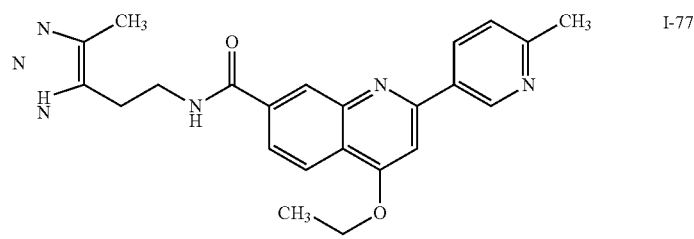
I-77
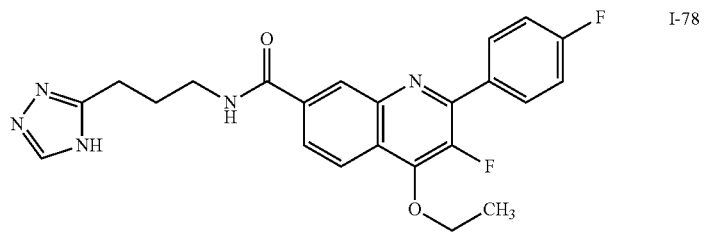
I-78
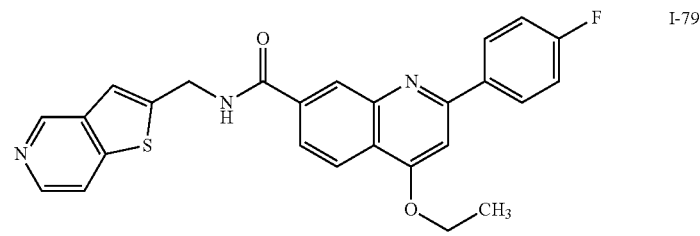
I-79
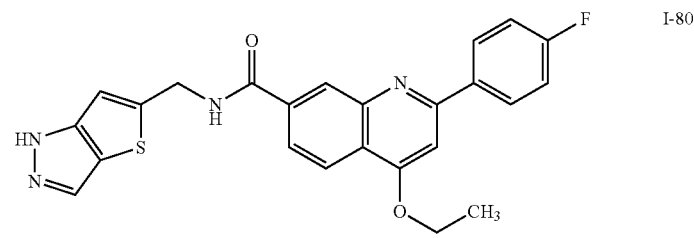
I-80

TABLE 1-continued
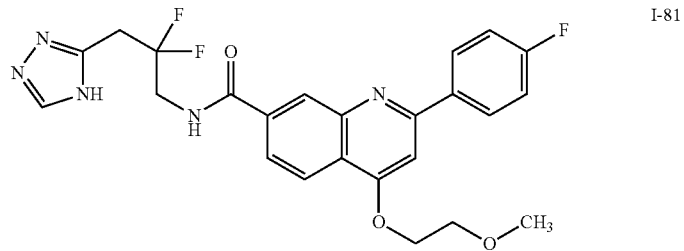
I-81
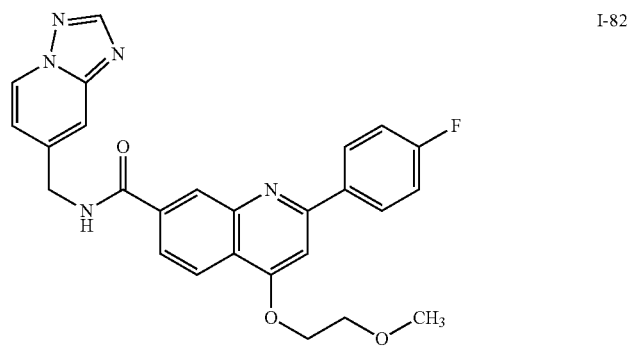
I-82
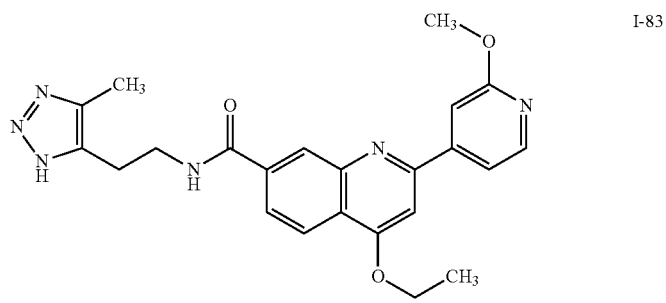
I-83
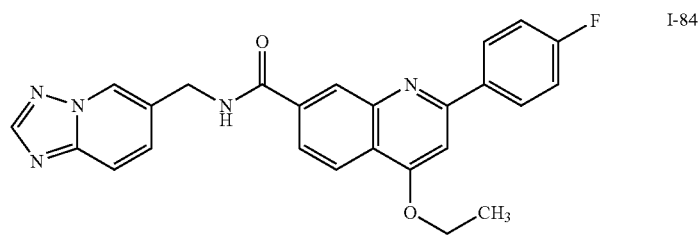
I-84
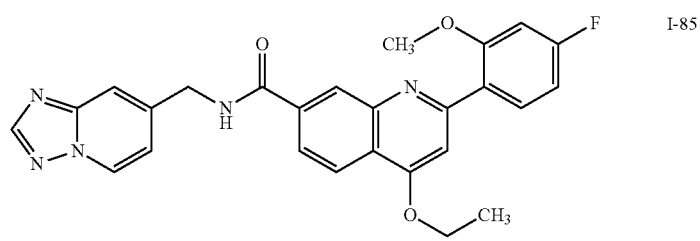
I-85

TABLE 1-continued
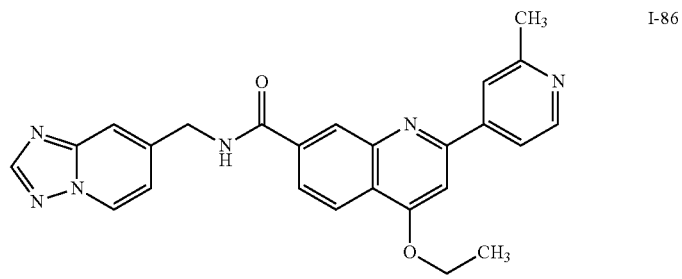
I-86
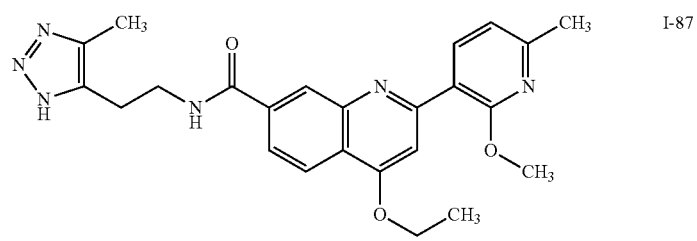
I-87
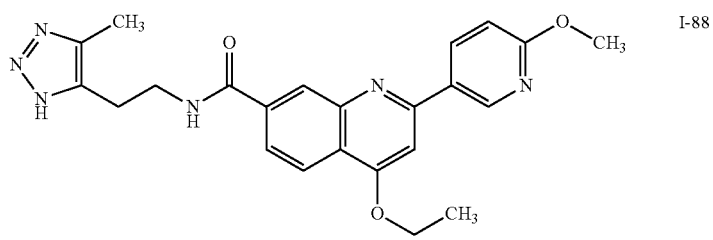
I-88
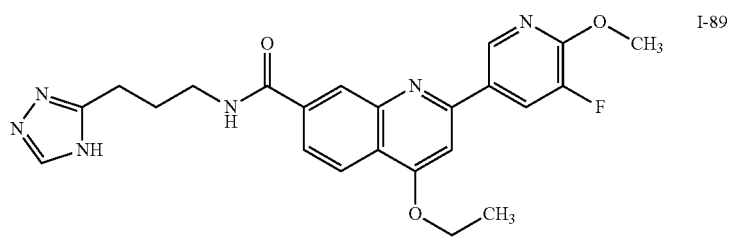
I-89
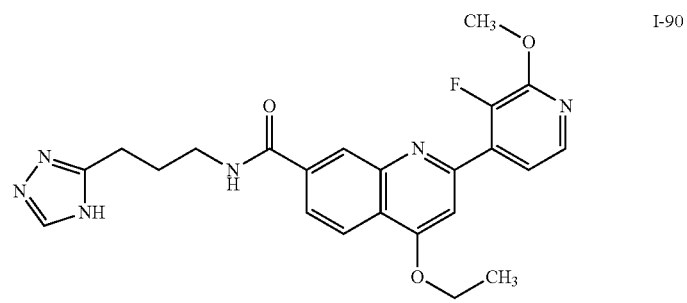
I-90
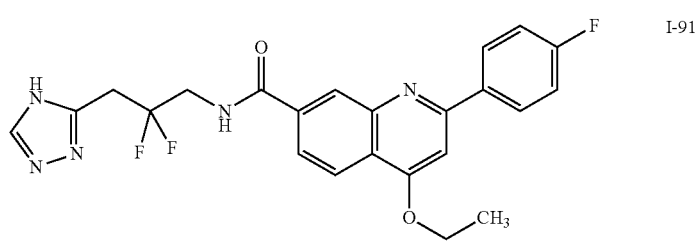
I-91

TABLE 1-continued
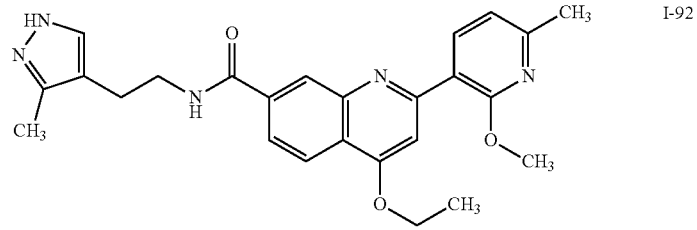
I-92
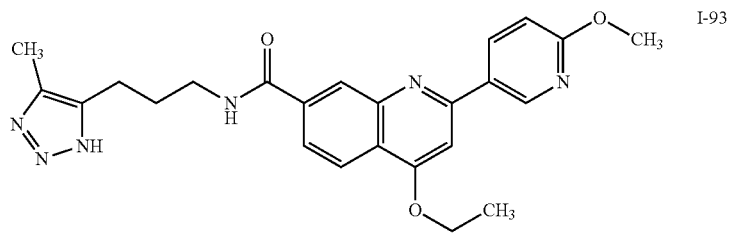
I-93
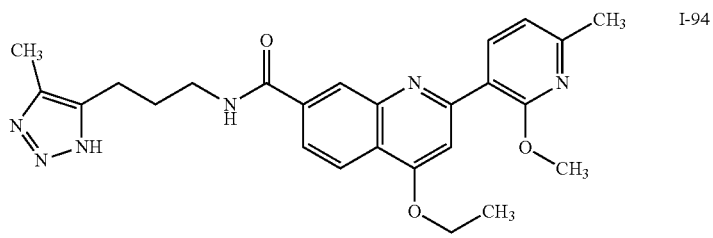
I-94
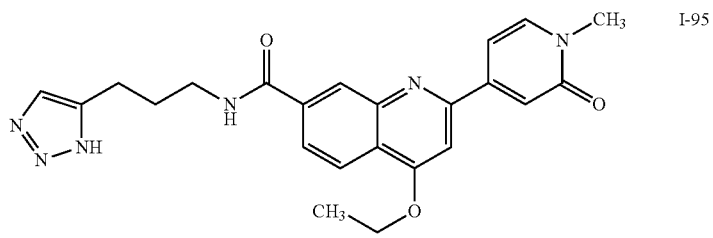
I-95
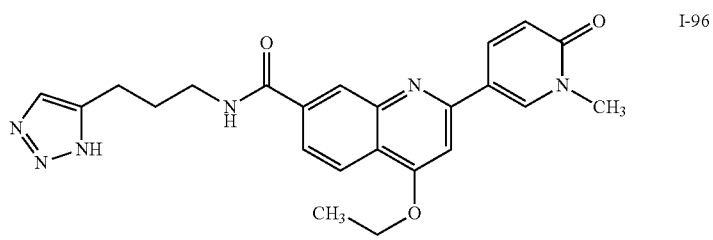
I-96
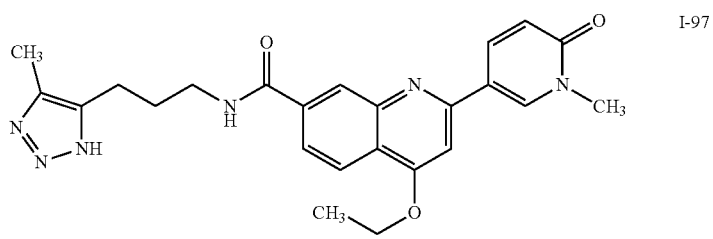
I-97

TABLE 1-continued
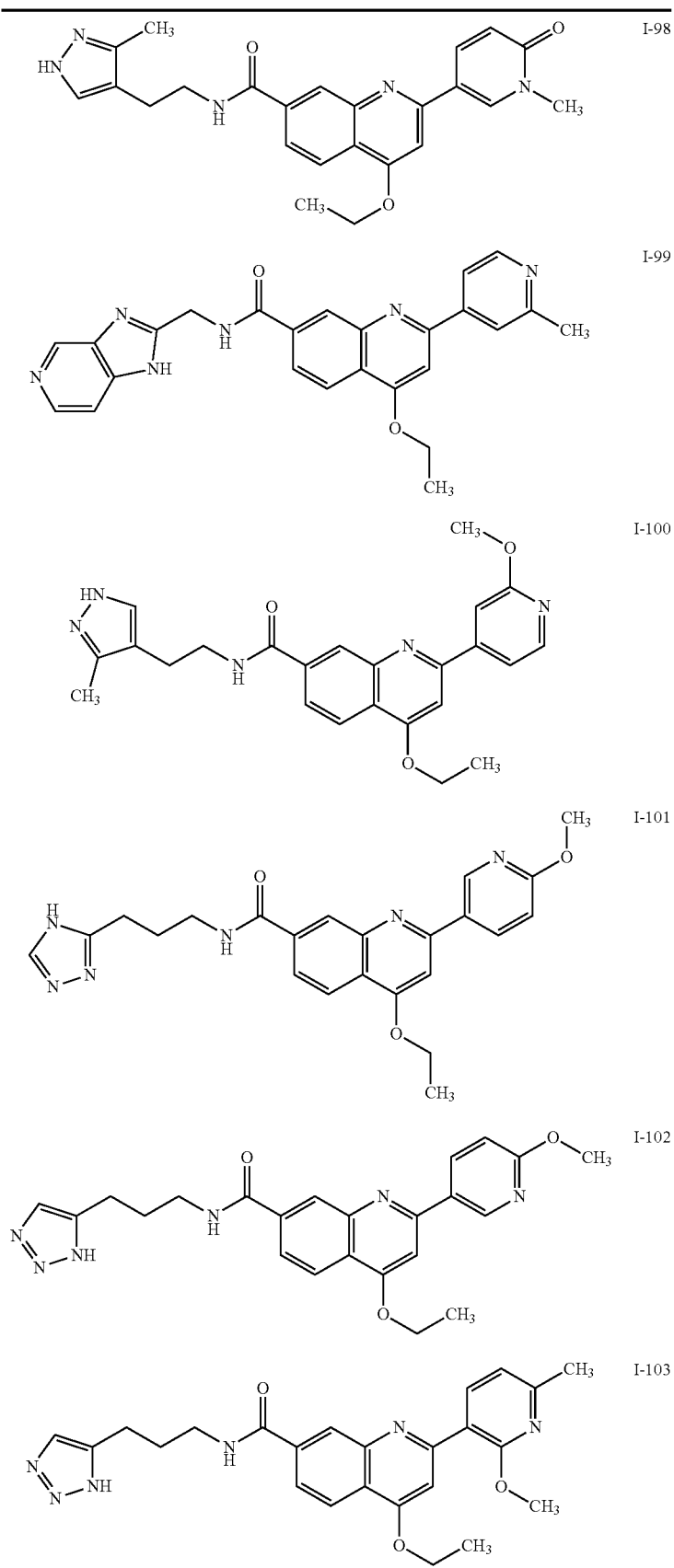

TABLE 1-continued
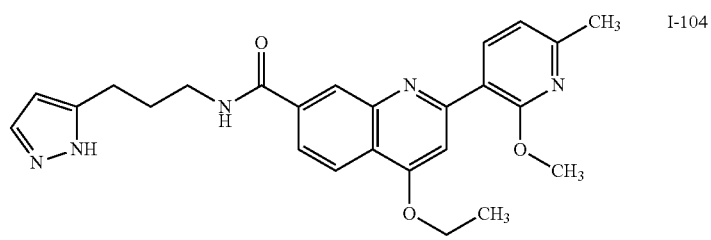
I-104
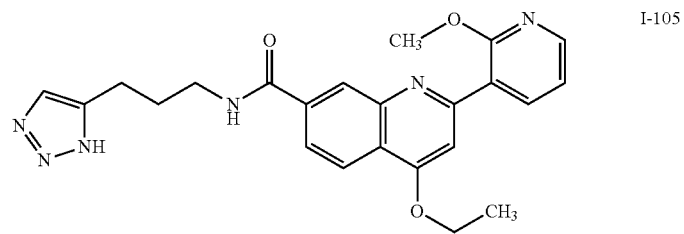
I-105
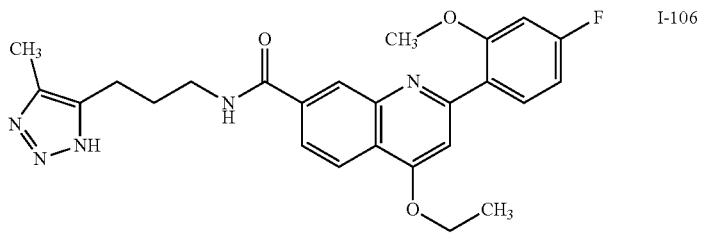
I-106
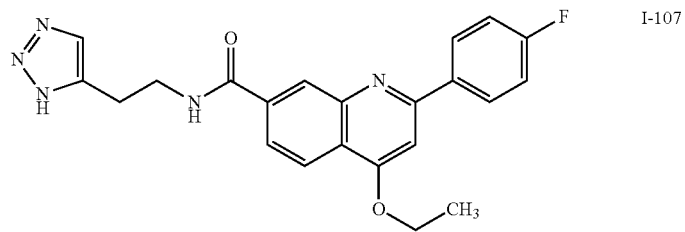
I-107
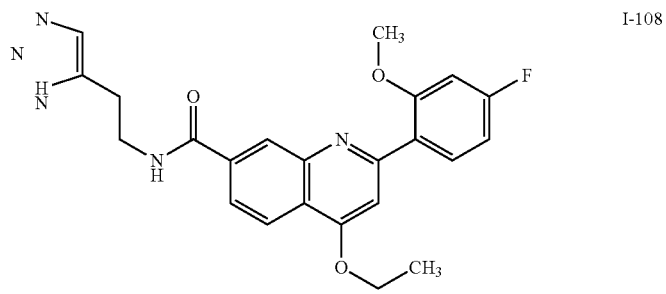
I-108
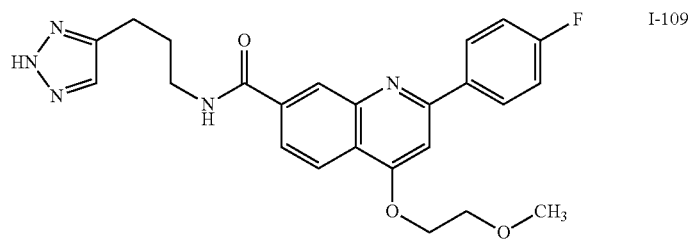
I-109

TABLE 1-continued
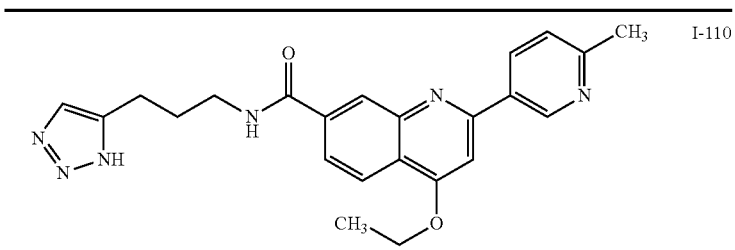 I-110
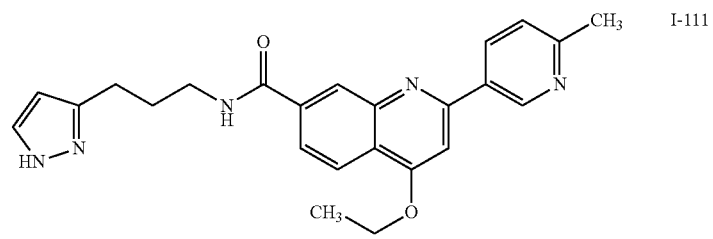 I-111
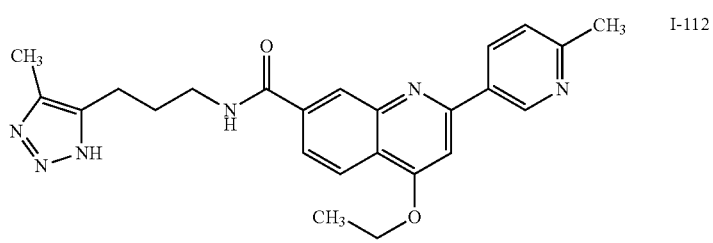 I-112
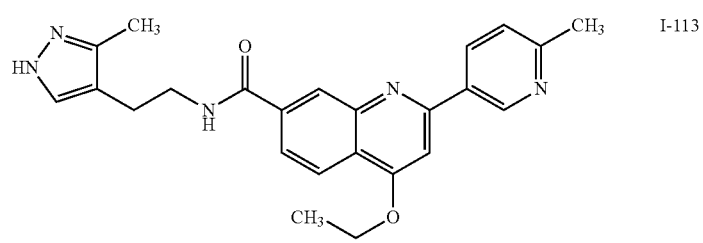 I-113
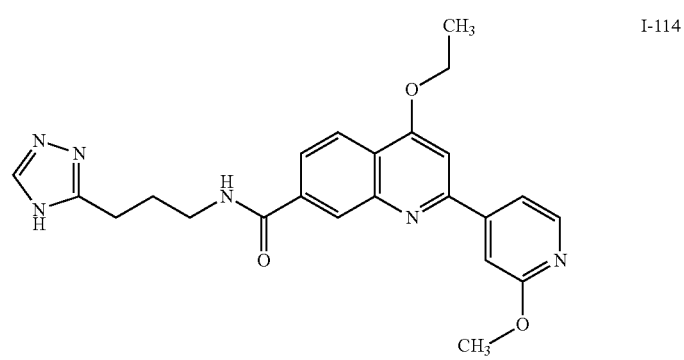 I-114
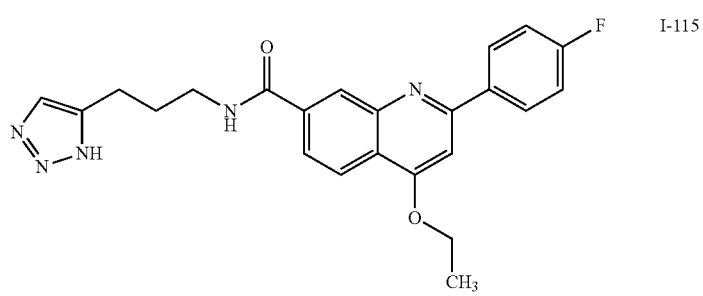 I-115

TABLE 1-continued
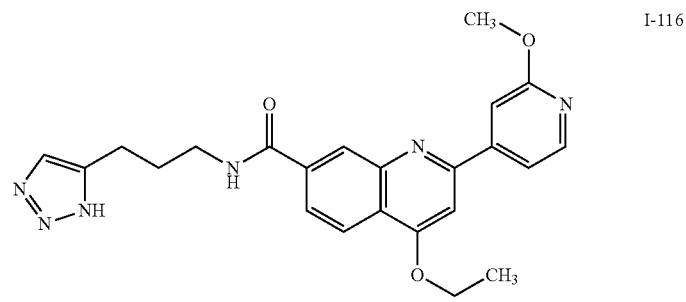
I-116
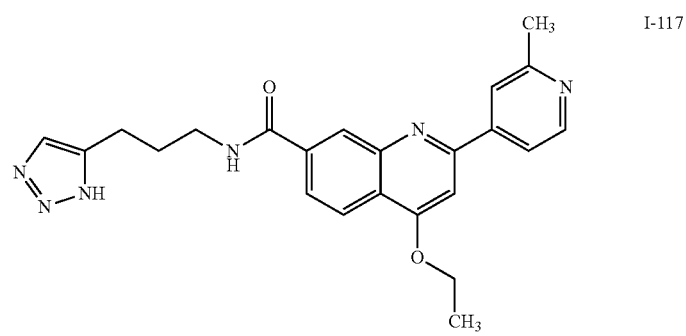
I-117
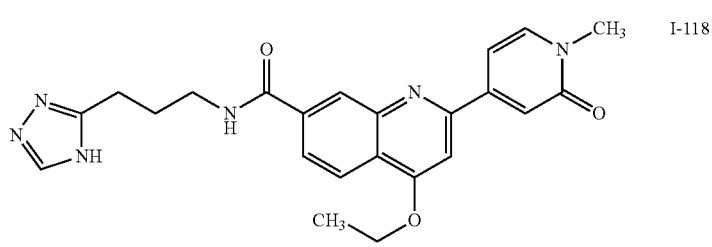
I-118
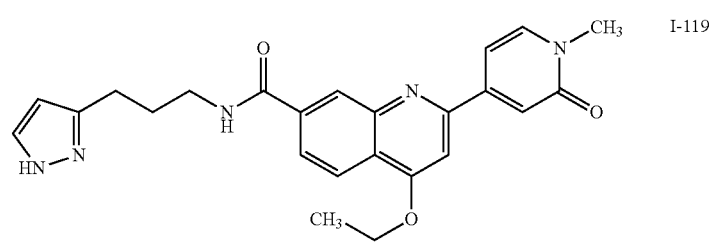
I-119
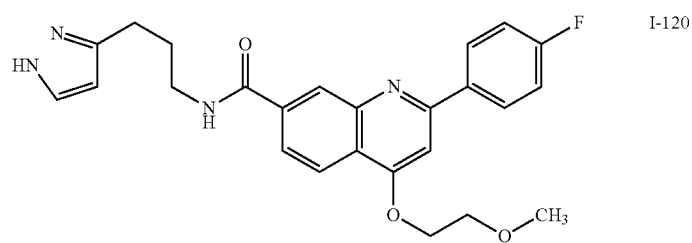
I-120
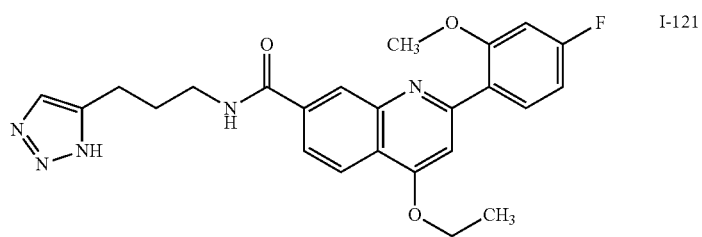
I-121

TABLE 1-continued
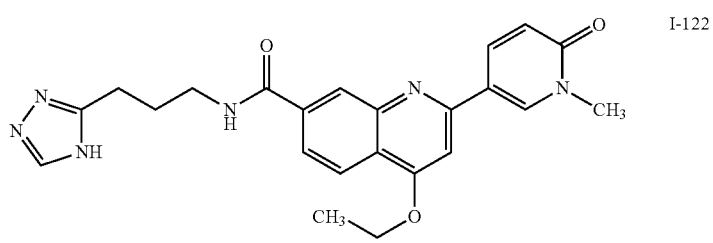
I-122
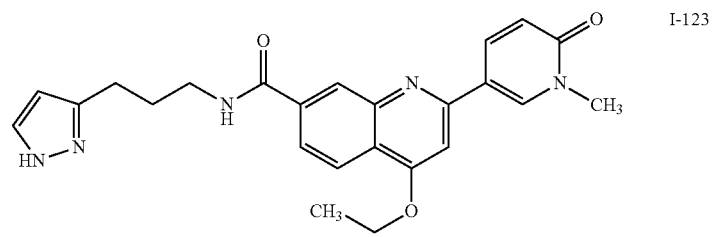
I-123
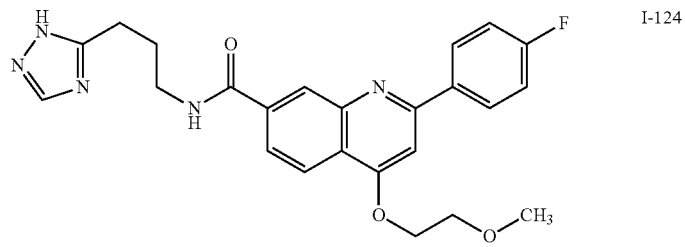
I-124
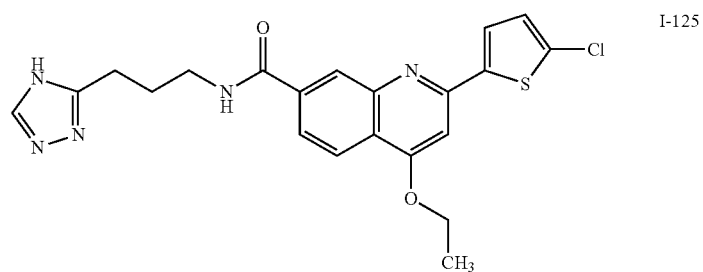
I-125
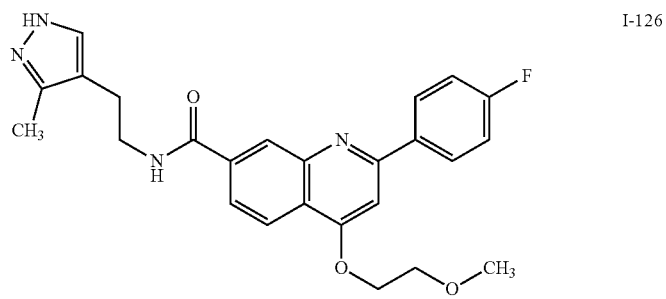
I-126
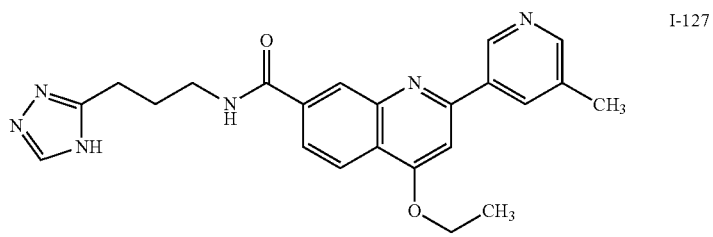
I-127

TABLE 1-continued
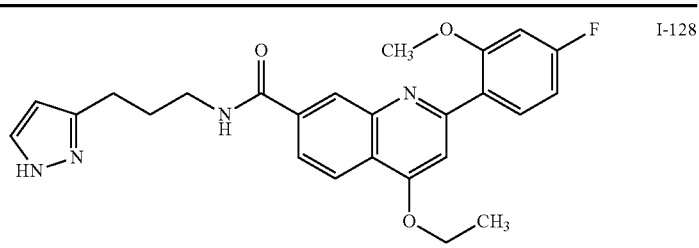
I-128
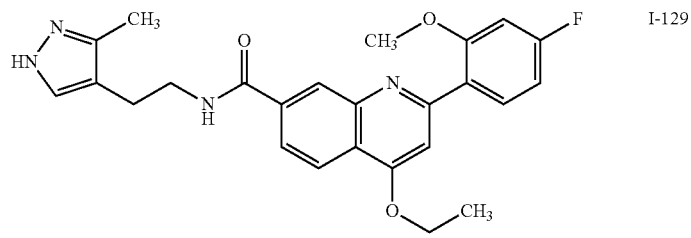
I-129
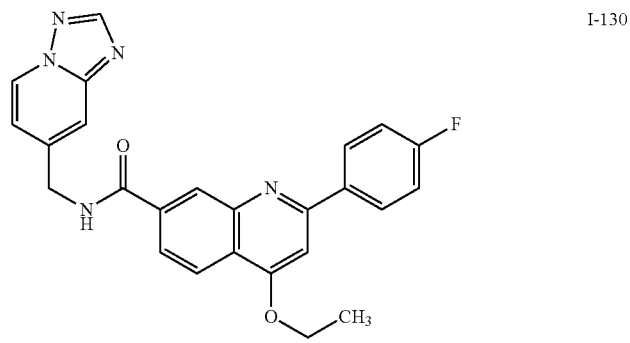
I-130
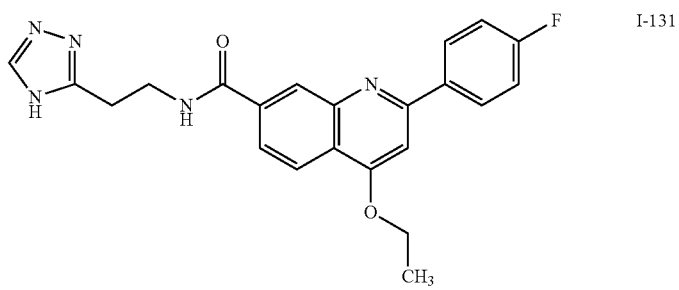
I-131
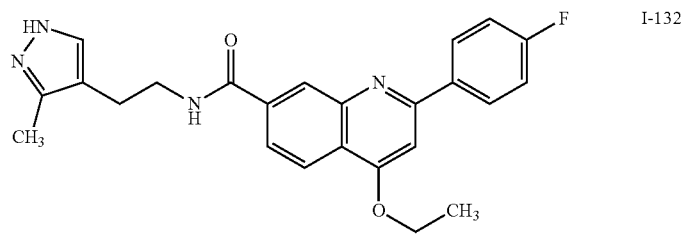
I-132
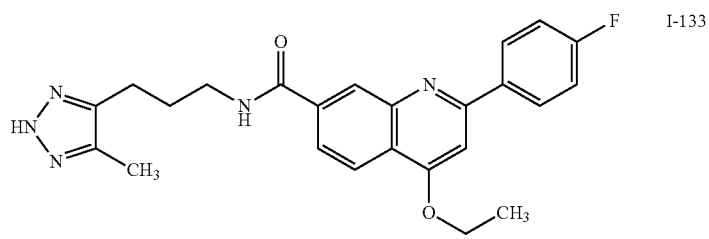
I-133

TABLE 1-continued
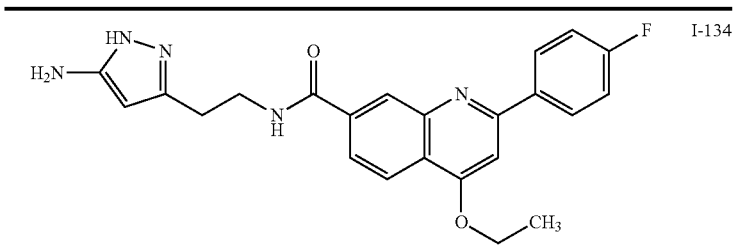 I-134
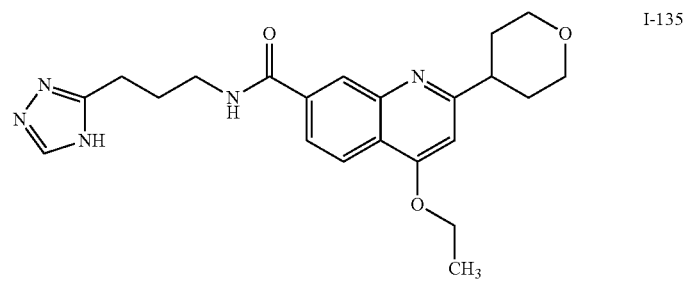 I-135
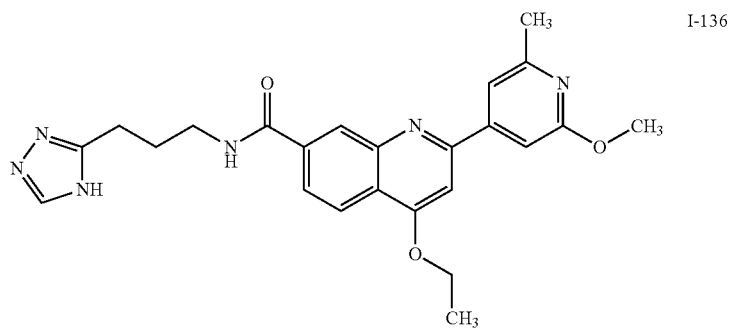 I-136
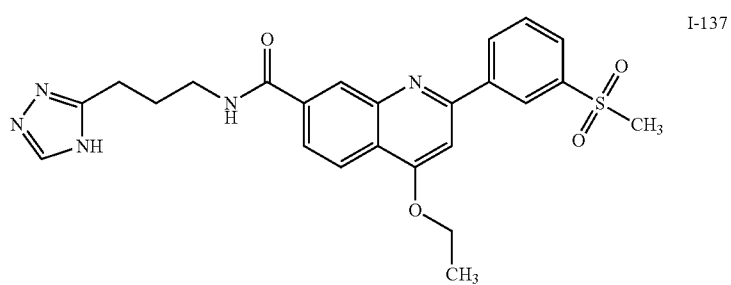 I-137
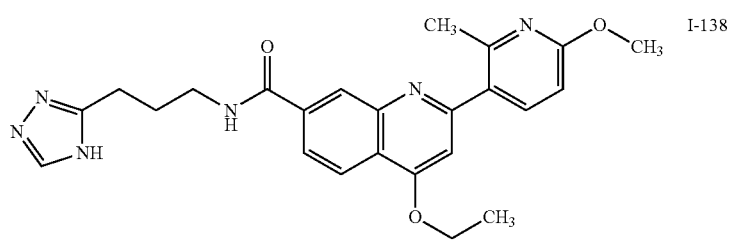 I-138
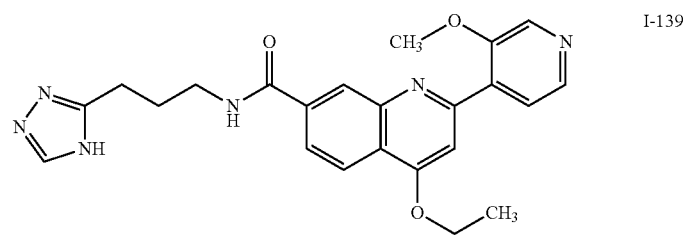 I-139

TABLE 1-continued
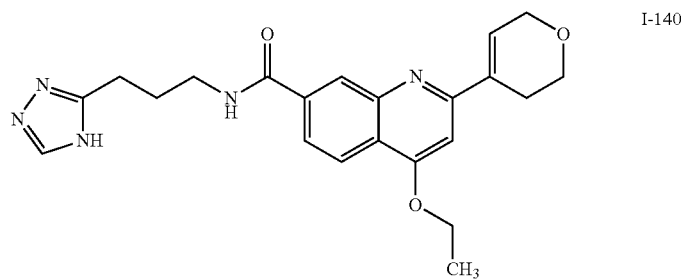 I-140
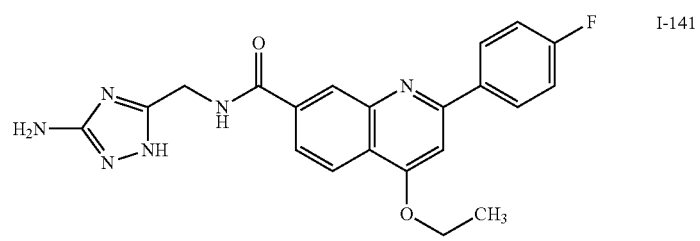 I-141
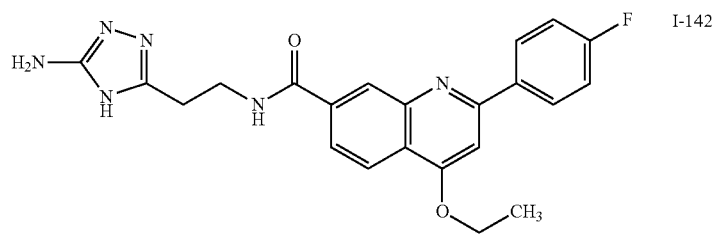 I-142
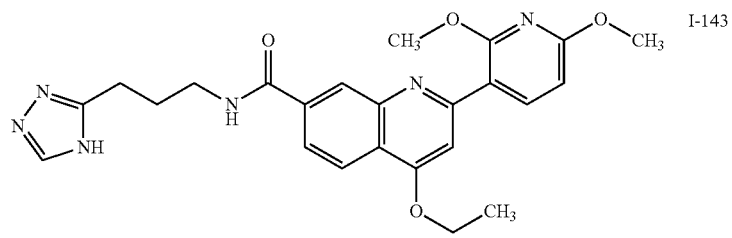 I-143
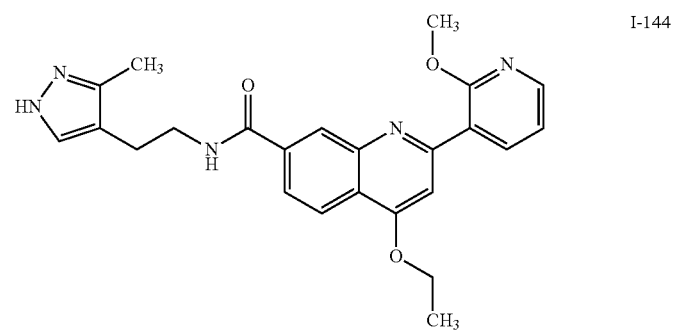 I-144
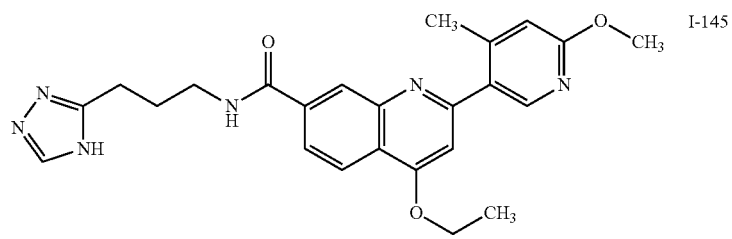 I-145

TABLE 1-continued
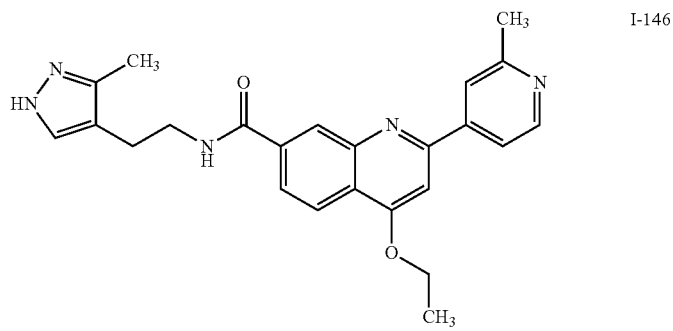
I-146
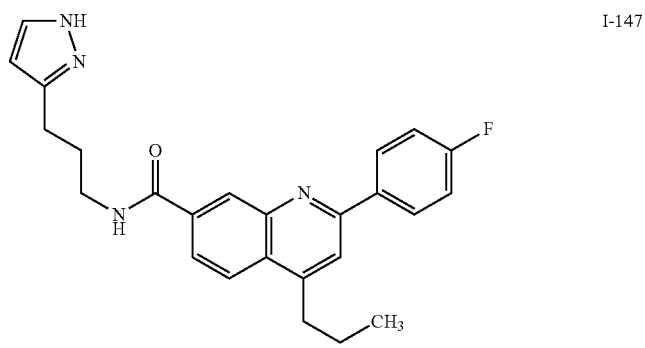
I-147
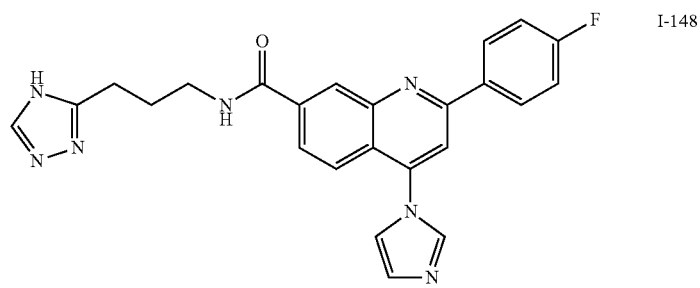
I-148
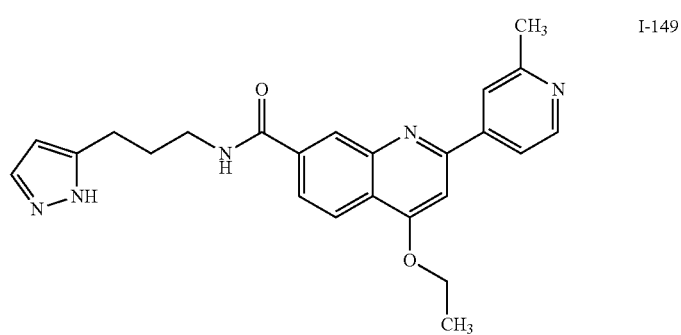
I-149
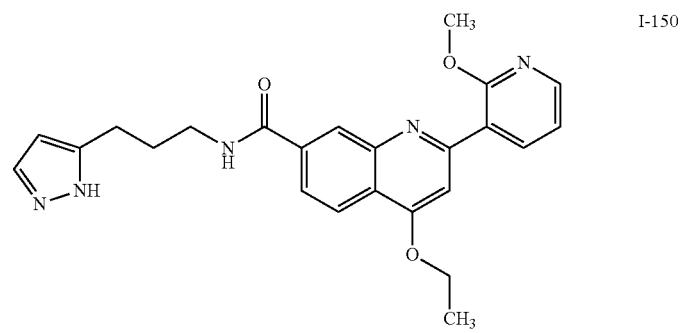
I-150

TABLE 1-continued
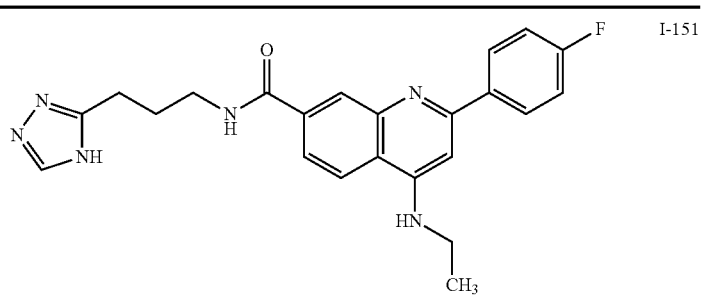
I-151
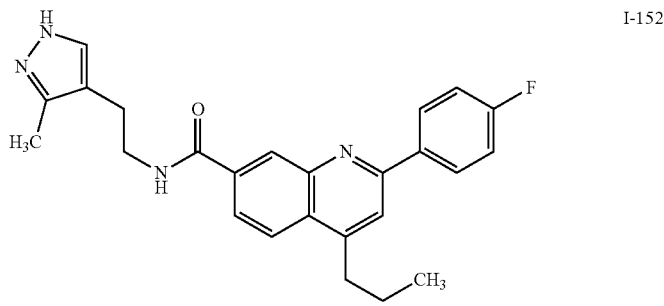
I-152
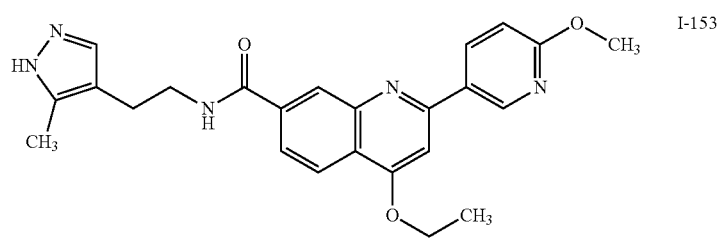
I-153
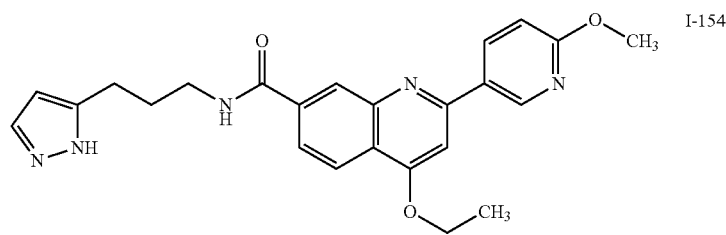
I-154
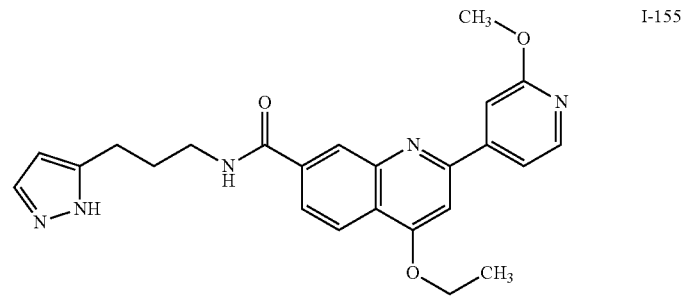
I-155
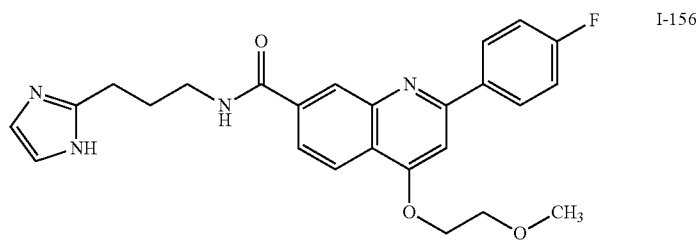
I-156

TABLE 1-continued
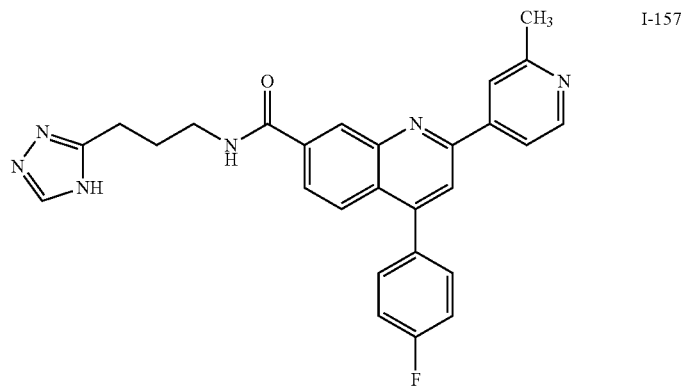
I-157
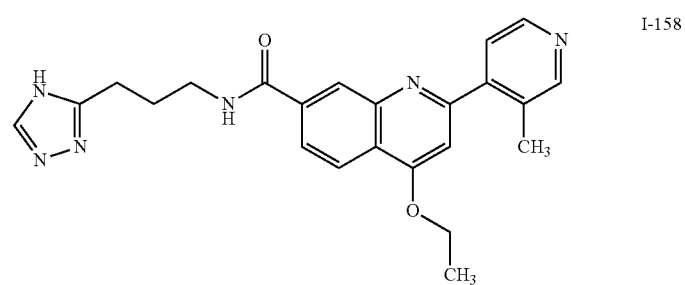
I-158
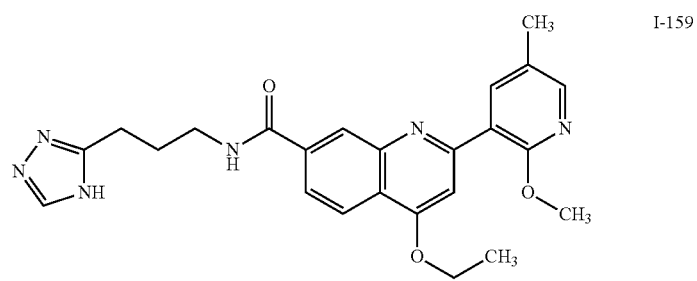
I-159
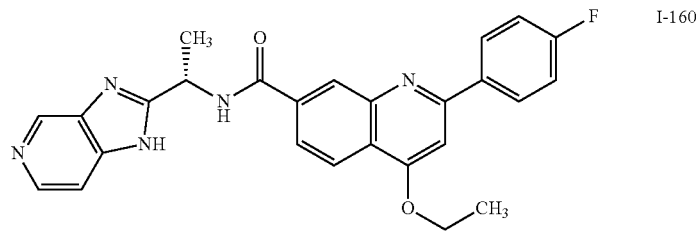
I-160
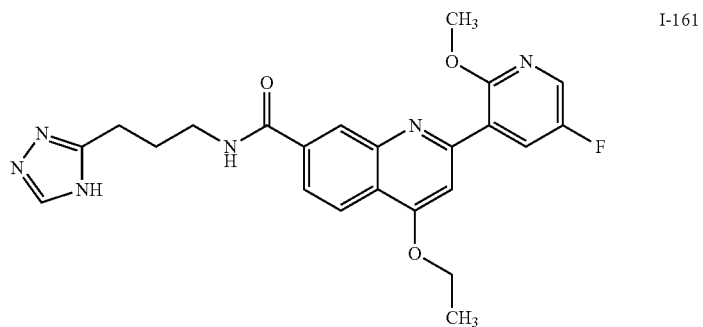
I-161

TABLE 1-continued
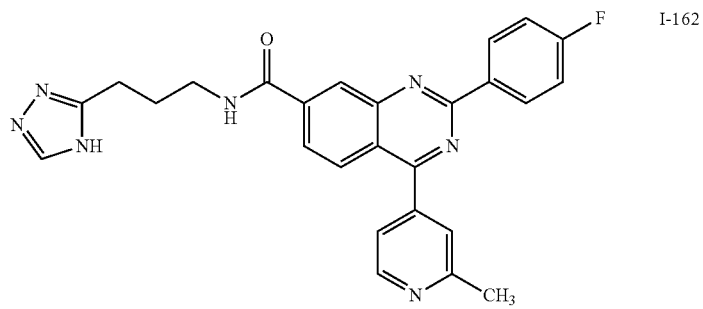
I-162
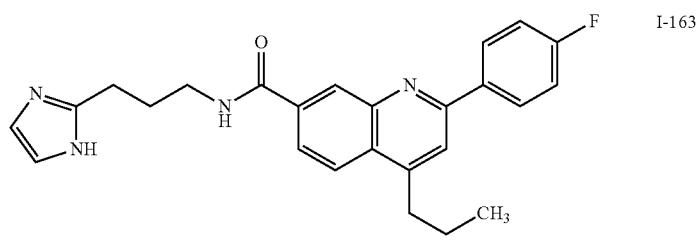
I-163
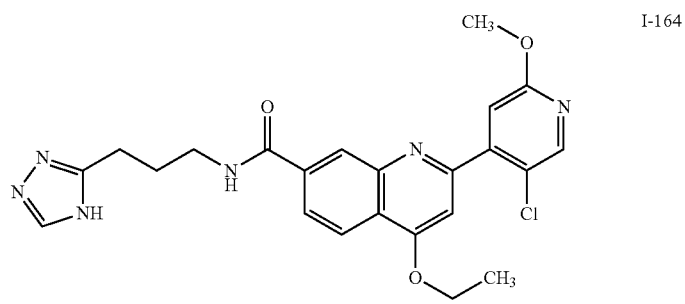
I-164
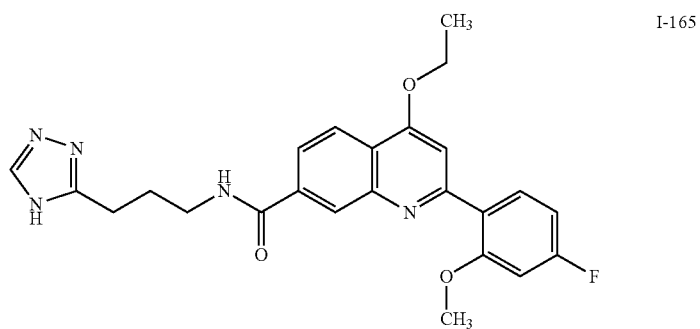
I-165
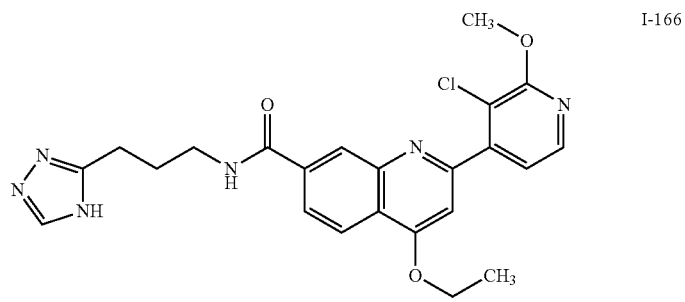
I-166

TABLE 1-continued
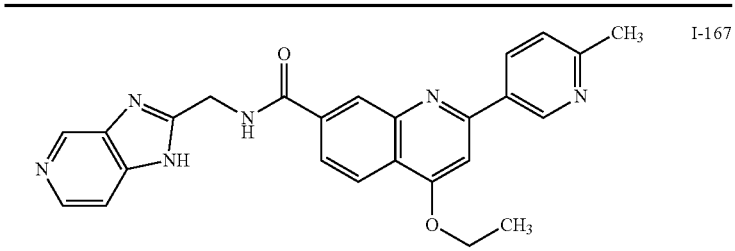 I-167
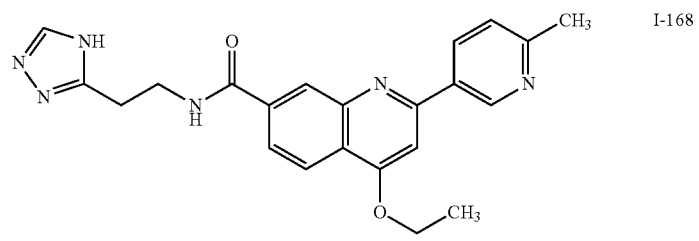 I-168
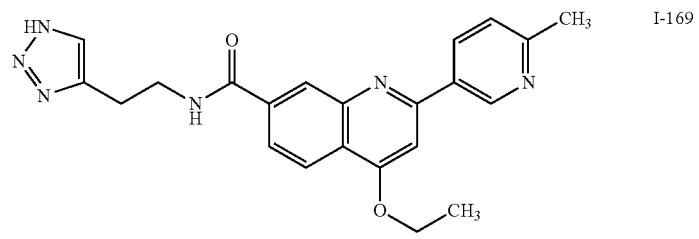 I-169
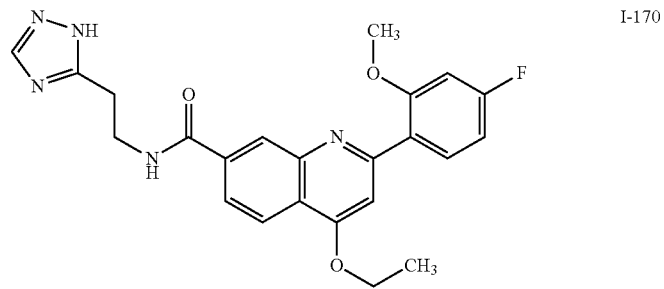 I-170
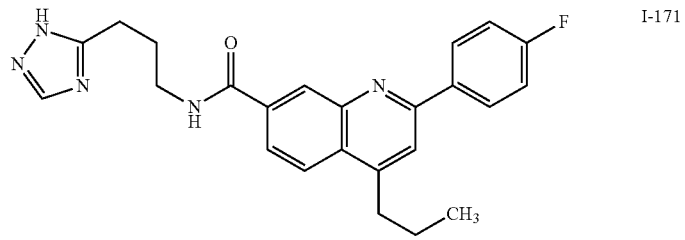 I-171
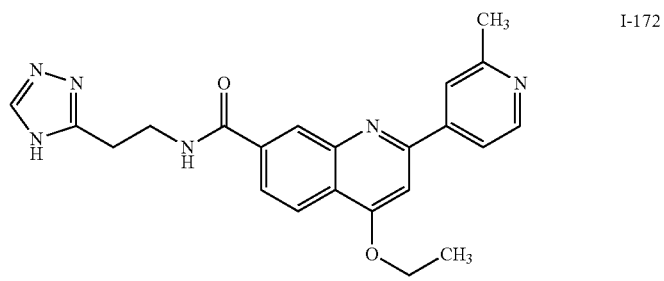 I-172

TABLE 1-continued
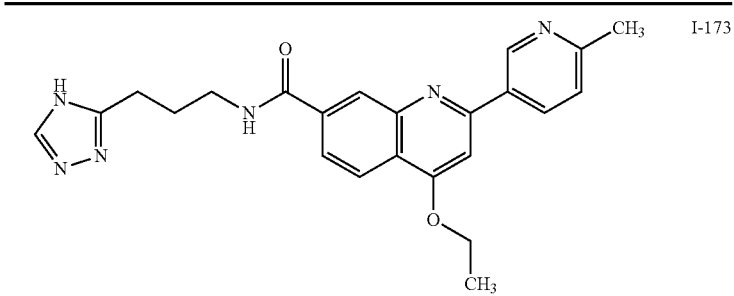 I-173
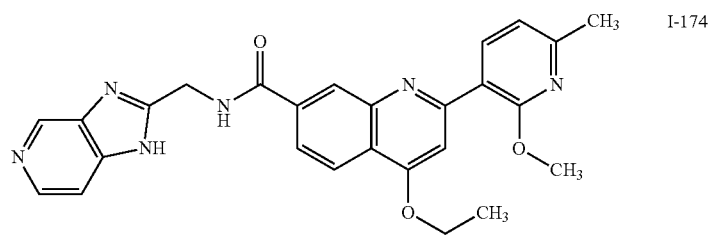 I-174
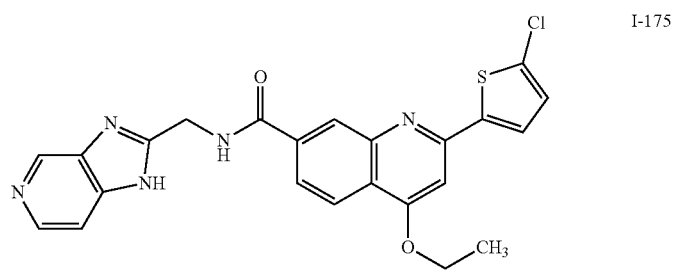 I-175
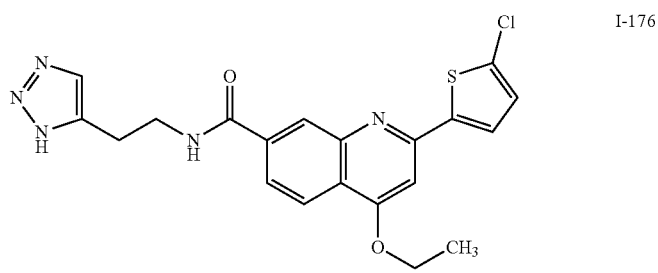 I-176
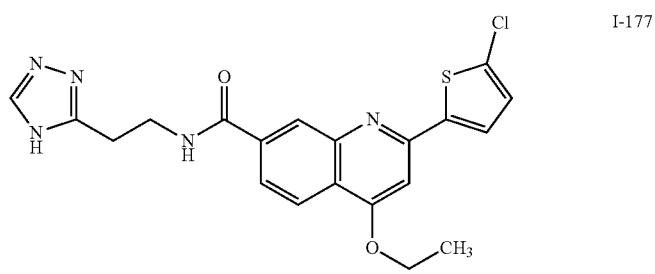 I-177
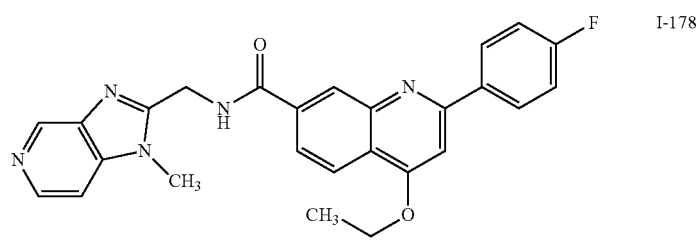 I-178

147 148
TABLE 1-continued
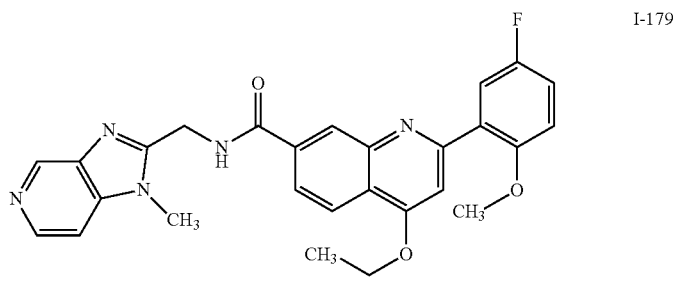
I-179
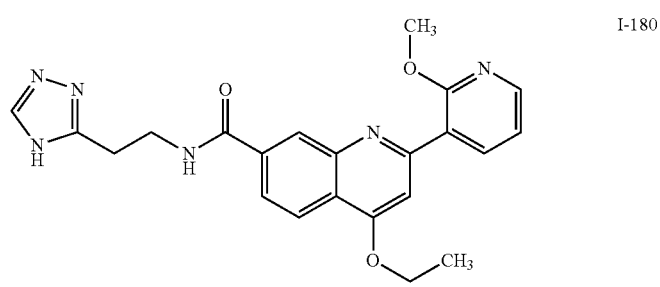
I-180
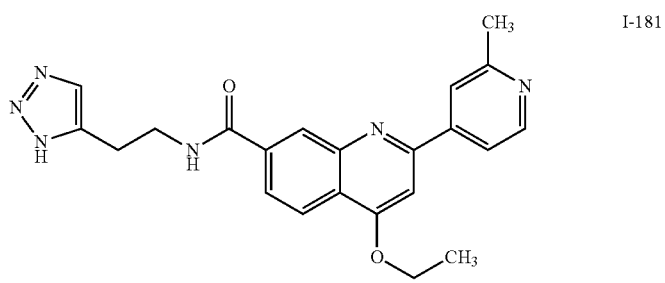
I-181
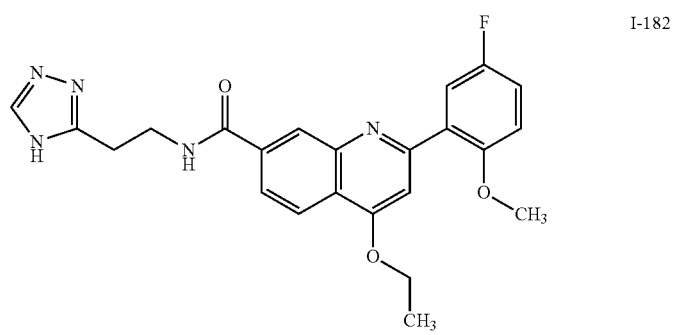
I-182
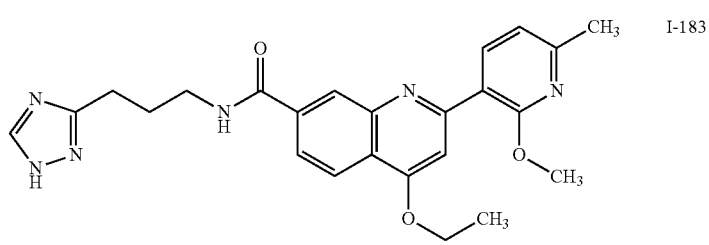
I-183

TABLE 1-continued
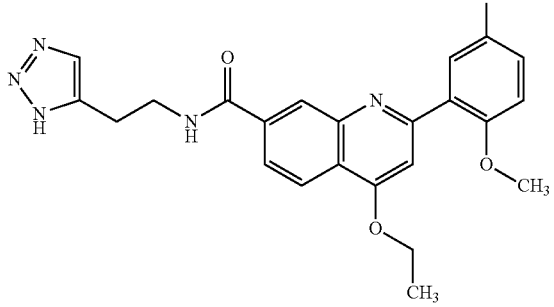 I-184
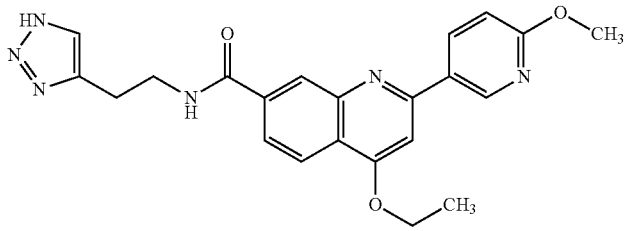 [SMILES: CCOc1cc(-c2ccc(OC)nc2)nc2cc(C(=O)NCCc3c[nH]nn3)ccc12] I-185
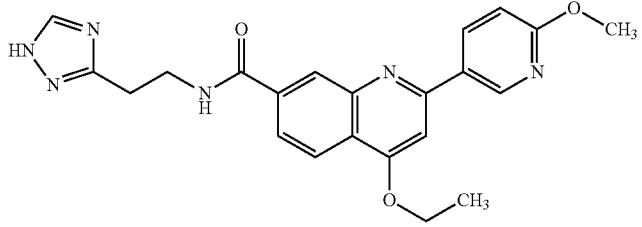 [SMILES: CCOc1cc(-c2ccc(OC)nc2)nc2cc(C(=O)NCCc3nc[nH]n3)ccc12] I-186
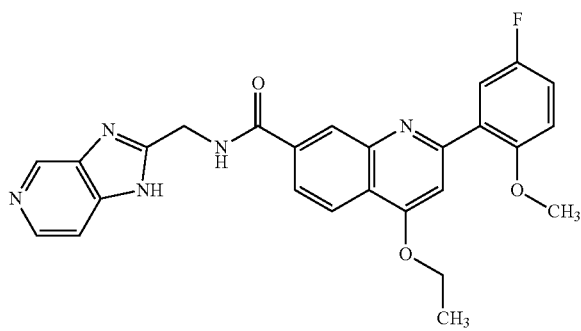 [SMILES: CCOc1cc(-c2cc(F)ccc2OC)nc2cc(C(=O)NCc3nc4cnccc4[nH]3)ccc12] I-187
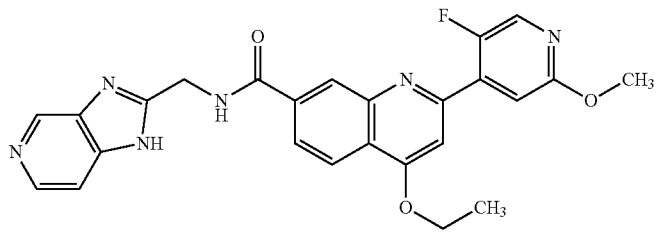 [SMILES: CCOc1cc(-c2cc(OC)ncc2F)nc2cc(C(=O)NCc3nc4cnccc4[nH]3)ccc12] I-188
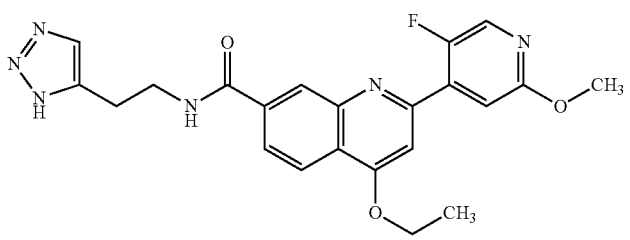 [SMILES: CCOc1cc(-c2cc(OC)ncc2F)nc2cc(C(=O)NCCc3cnn[nH]3)ccc12] I-189

TABLE 1-continued
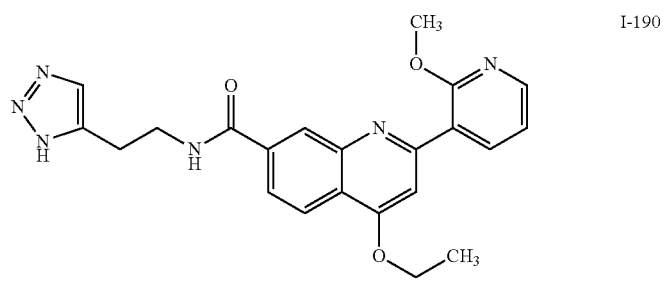
I-190
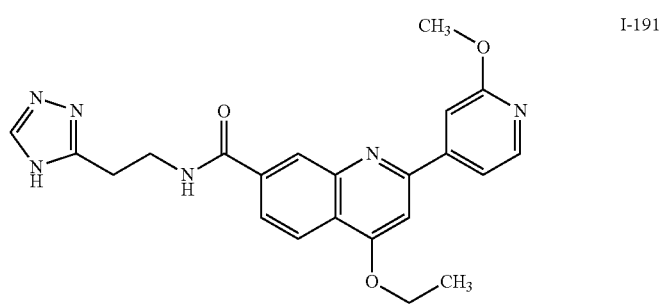
I-191
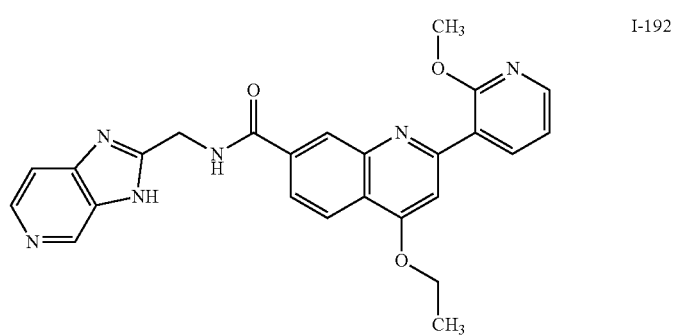
I-192
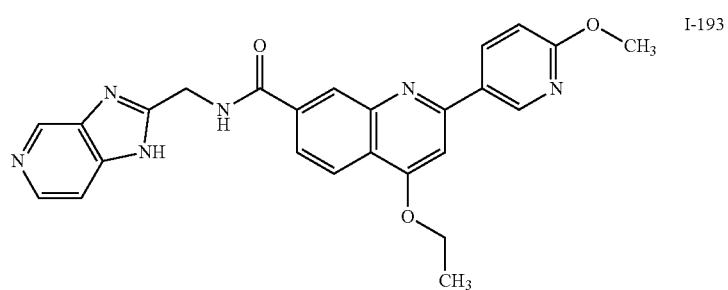
I-193
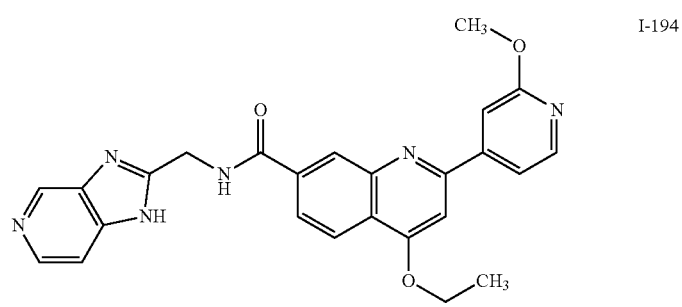
I-194

TABLE 1-continued
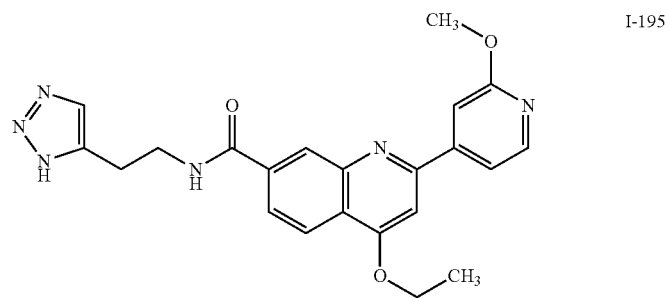 I-195
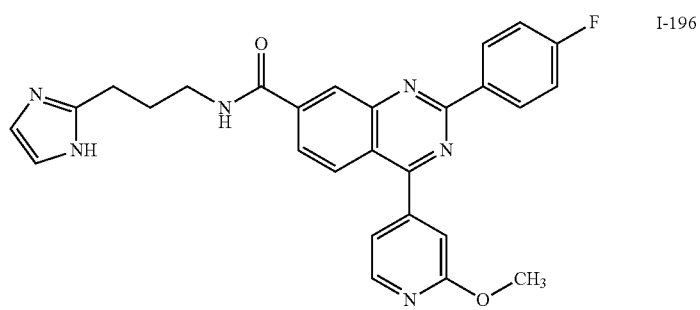 I-196
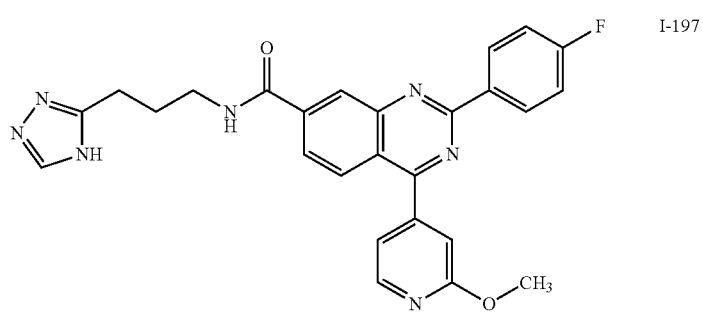 I-197
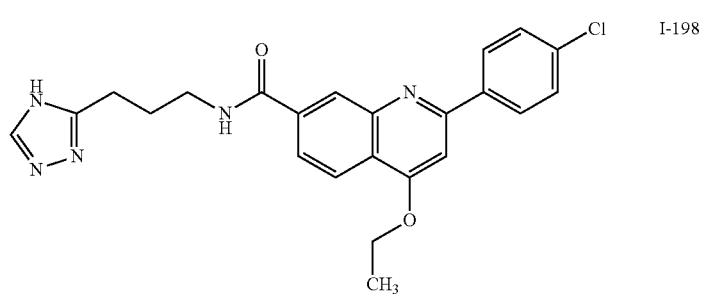 I-198
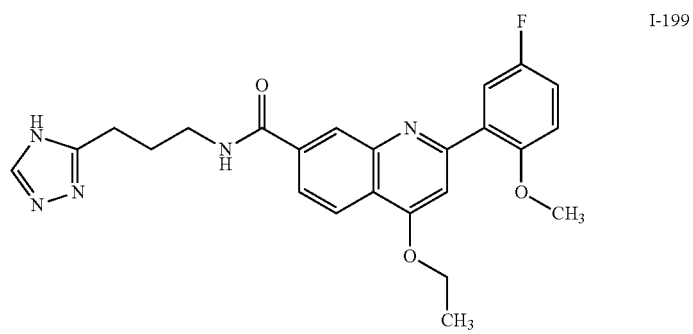 I-199

TABLE 1-continued
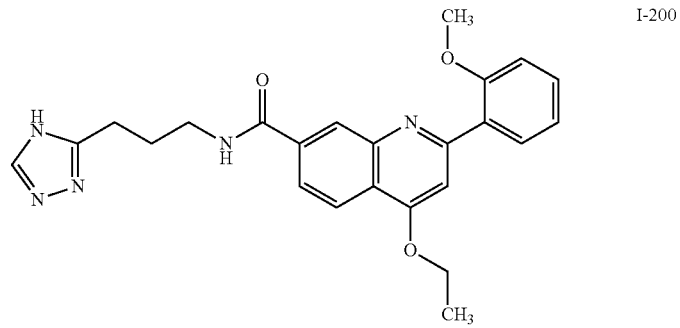
I-200
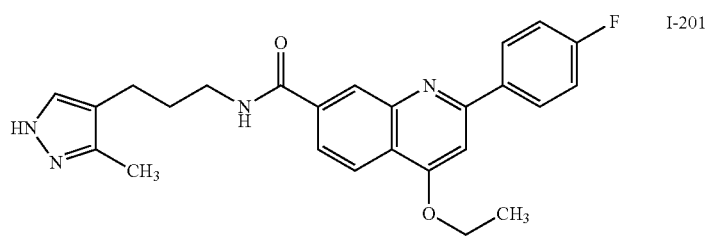
I-201
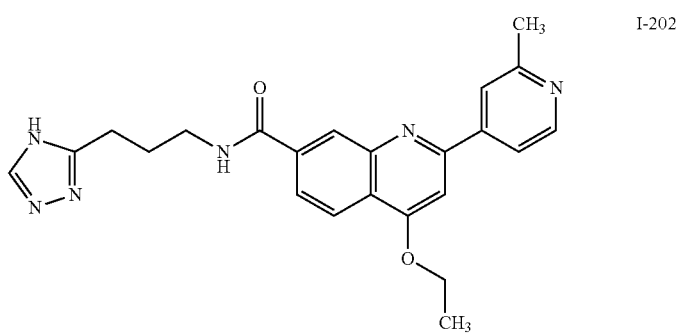
I-202
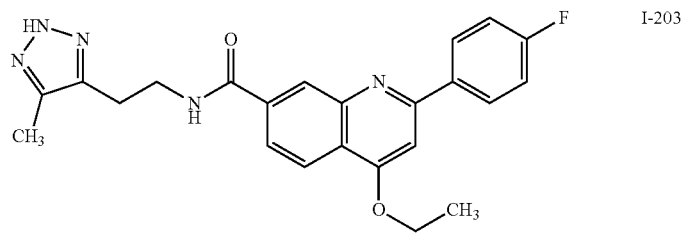
I-203
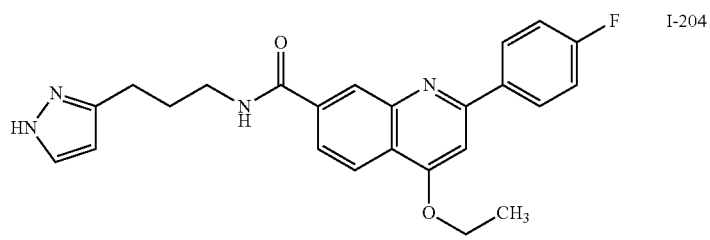
I-204

TABLE 1-continued
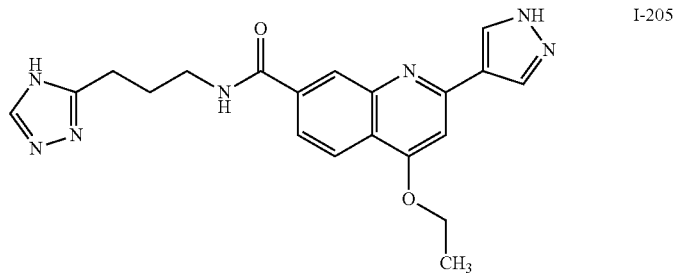
I-205
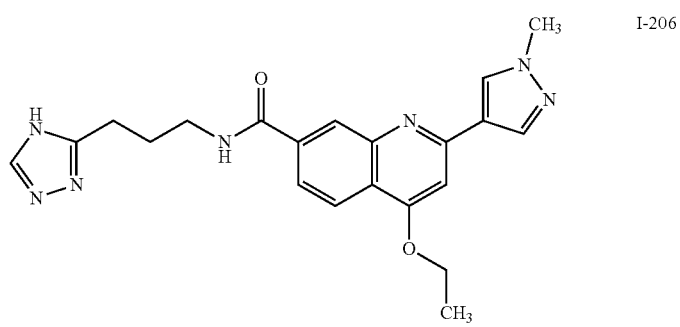
I-206
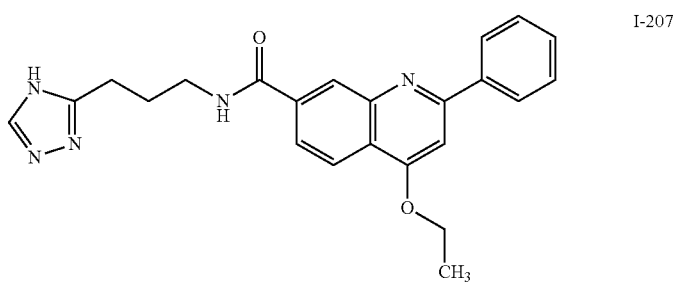
I-207
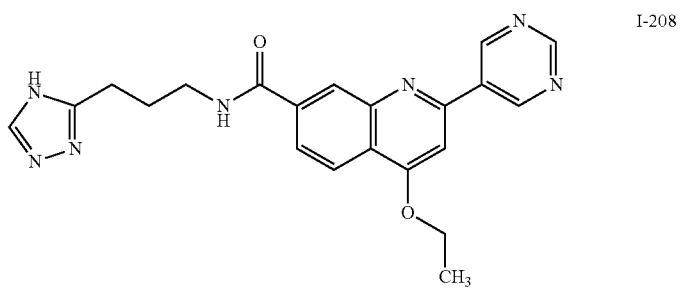
I-208
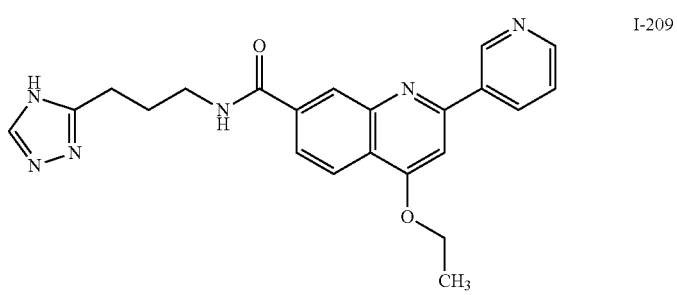
I-209

TABLE 1-continued
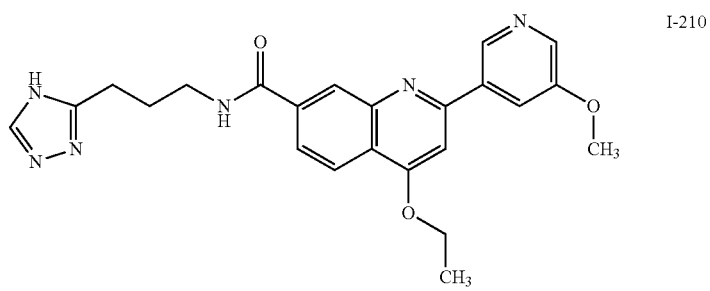
I-210
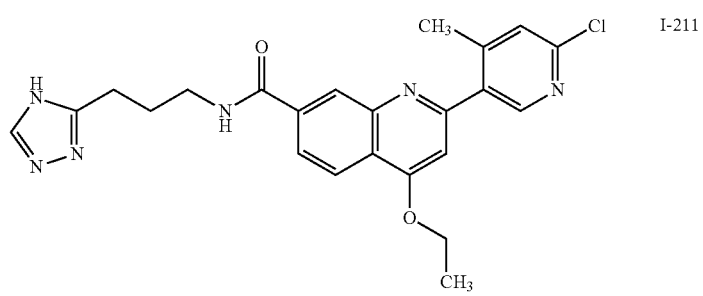
I-211
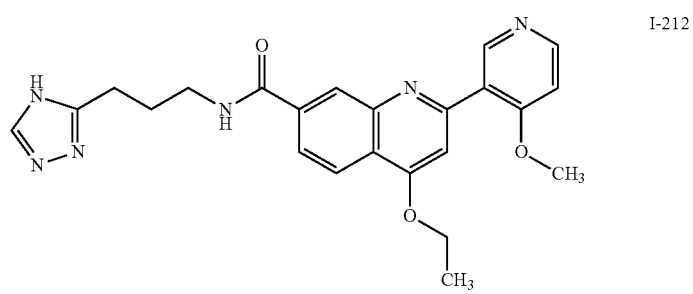
I-212
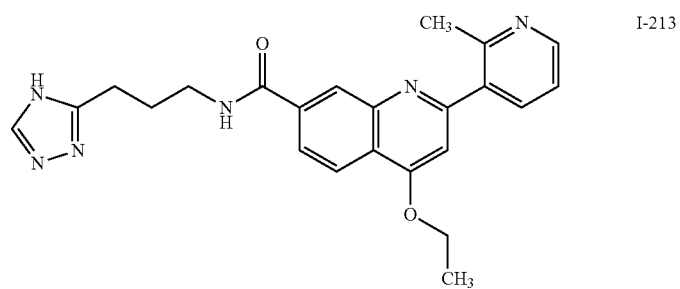
I-213
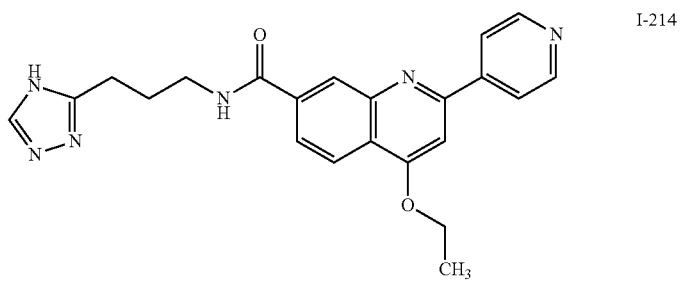
I-214

TABLE 1-continued
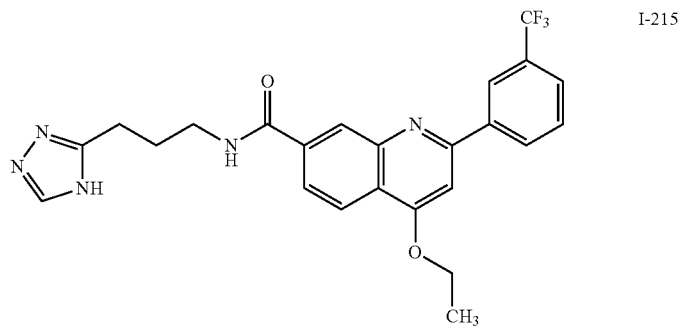 I-215
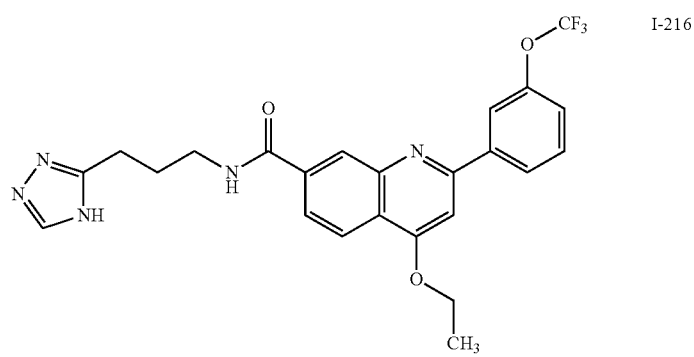 I-216
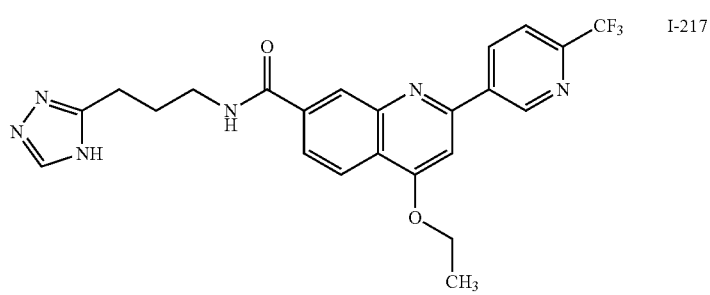 I-217
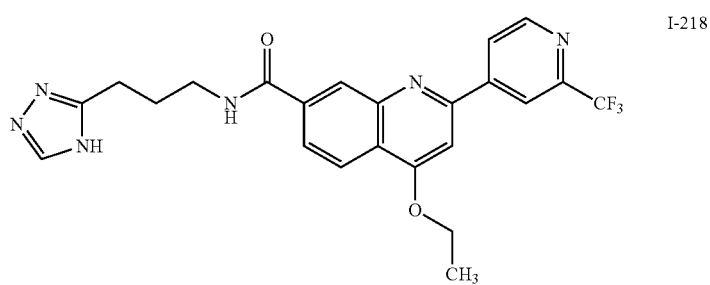 I-218
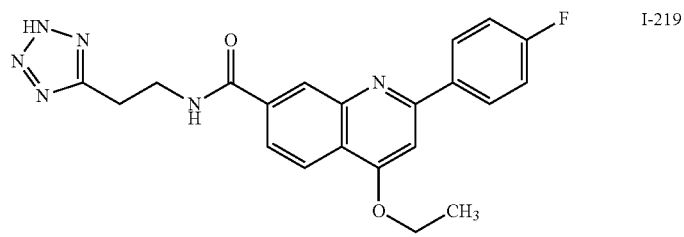 I-219

TABLE 1-continued
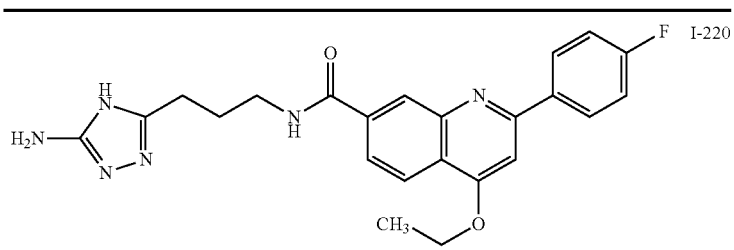 I-220
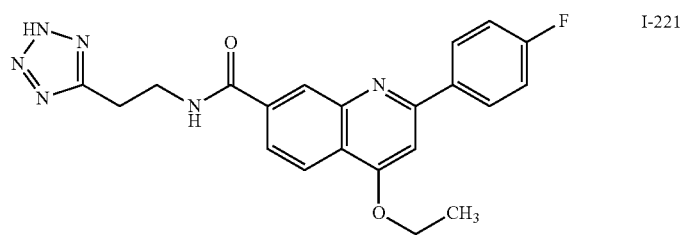 I-221
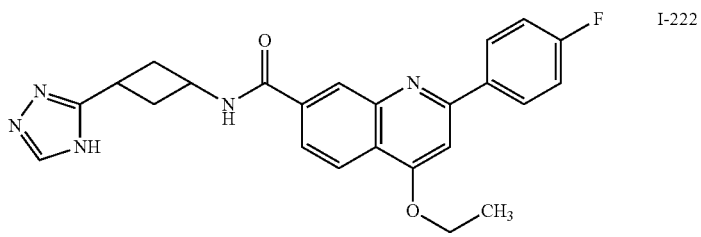 I-222
cis-cyclobutyl
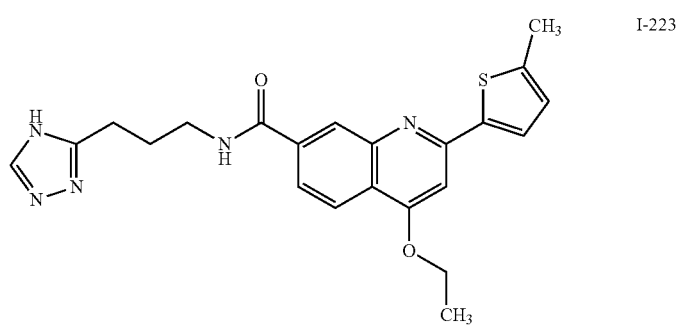 I-223
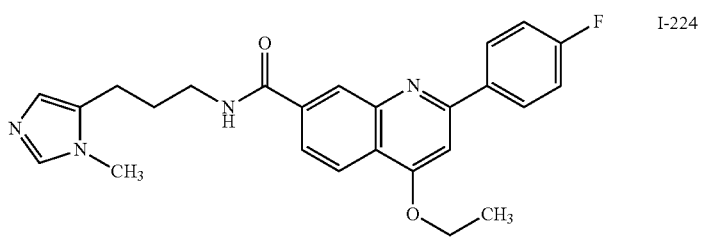 I-224
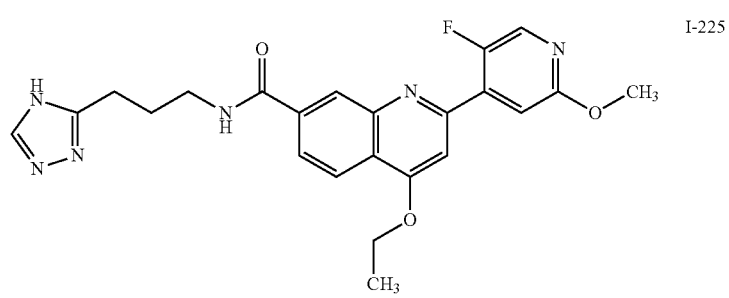 I-225

TABLE 1-continued

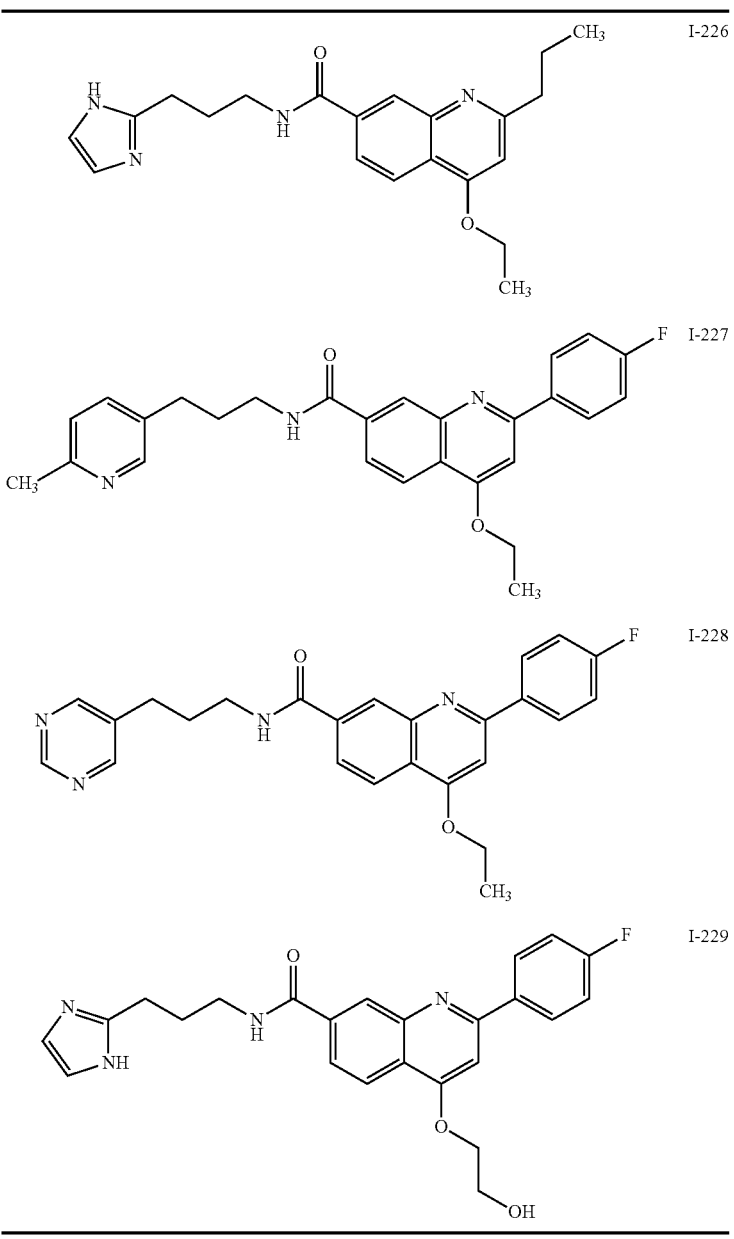

| Index | IUPAC Name |
|---|---|
| I-1 | 2-(4-chlorophenyl)-N-[2-(1-methyl-1H-imidazol-5-yl)ethyl]-4-propylquinazoline-7-carboxamide |
| I-2 | 4-ethoxy-2-(4-fluorophenyl)-N-[2-(1-methyl-1H-imidazol-5-yl)ethyl]quinoline-7-carboxamide |
| I-3 | 2-(4-chlorophenyl)-N-[cis-3-(1H-imidazol-2-yl)cyclobutyl]-4-propylquinazoline-7-carboxamide |
| I-4 | 2-(4-chlorophenyl)-N-[3-(1H-imidazol-2-yl)propyl]-4-propylquinazoline-7-carboxamide |
| I-5 | 4-ethoxy-2-(4-fluorophenyl)-N-[3-(4H-1,2,4-triazol-3-yl)propyl]quinoline-7-carboxamide |
| I-6 | 4-ethoxy-2-(4-fluorophenyl)-N-[2-(1-methyl-1H-imidazol-4-yl)ethyl]quinoline-7-carboxamide |
| I-7 | 2-(4-chlorophenyl)-4-propyl-N-[3-(4H-1,2,4-triazol-3-yl)propyl]quinazoline-7-carboxamide |
| I-8 | 2-(4-chlorophenyl)-N-(imidazo[1,2-a]pyridin-6-ylmethyl)-4-propylquinazoline-7-carboxamide |
| I-9 | 2-(4-chlorophenyl)-N-(3H-imidazo[4,5-c]pyridin-2-ylmethyl)-4-propylquinazoline-7-carboxamide |
| I-10 | 2-(4-chlorophenyl)-N-[3-(1H-imidazol-2-yl)propyl]-4-methoxyquinazoline-7-carboxamide |
| I-11 | 2-(5-chloro-2-fluorophenyl)-4-ethoxy-N-[3-(1H-imidazol-2-yl)propyl]quinoline-7-carboxamide |
| I-12 | 4-ethoxy-2-(5-fluoro-2-methoxypyridin-4-yl)-N-[3-(1H-imidazol-2-yl)propyl]quinoline-7-carboxamide |
| I-13 | 2-(4-chlorophenyl)-4-ethoxy-N-[3-(1H-imidazol-2-yl)propyl]quinoline-7-carboxamide |
| I-14 | 4-ethoxy-2-(4-fluorophenyl)-N-(1H-imidazo[4,5-c]pyridin-2-ylmethyl)quinoline-7-carboxamide |
| I-15 | 4-ethoxy-2-(4-fluorophenyl)-N-[3-(1H-imidazol-2-yl)propyl]quinoline-7-carboxamide |
| I-16 | 2-(4-fluorophenyl)-N-[3-(1H-imidazol-2-yl)propyl]-4-propylquinazoline-7-carboxamide |

-continued

| Index | IUPAC Name |
|---|---|
| I-17 | 2-(4-fluorophenyl)-N-[3-(1H-imidazol-2-yl)propyl]-4-isopropoxyquinoline-7-carboxamide |
| I-18 | 4-ethoxy-2-(4-fluorophenyl)-N-[3-(1H-imidazol-2-yl)-2-methylpropyl]quinazoline-7-carboxamide |
| I-19 | 4-ethoxy-2-(4-fluorophenyl)-N-[3-(pyrimidin-5-yl)propyl]quinazoline-7-carboxamide |
| I-20 | 2-(4-chlorophenyl)-4-(ethoxymethyl)-N-[3-(1H-imidazol-2-yl)propyl]quinazoline-7-carboxamide |
| I-21 | 2-(4-chlorophenyl)-N-[3-(1H-imidazol-2-yl)propyl]-4-isobutylquinazoline-7-carboxamide |
| I-22 | 2-(5-chloro-2-thienyl)-4-ethyl-N-[3-(1H-imidazol-2-yl)propyl]quinazoline-7-carboxamide |
| I-23 | 2-(5-chloro-2-thienyl)-N-[3-(1H-imidazol-2-yl)propyl]-4-isobutylquinazoline-7-carboxamide |
| I-24 | 2-(5-chloro-2-thienyl)-N-[3-(1H-imidazol-2-yl)propyl]-4-propylquinazoline-7-carboxamide |
| I-25 | 2-(4-chlorophenyl)-N-[3-(1H-imidazol-2-yl)propyl]-4-(methoxymethyl)quinazoline-7-carboxamide |
| I-26 | 2-(4-chlorophenyl)-N-[3-(1H-imidazol-2-yl)propyl]-4-(thiomorpholin-4-ylmethyl)quinazoline-7-carboxamide |
| I-27 | 4-(ethylsulfanyl)-2-(4-fluorophenyl)-N-[3-(1H-imidazol-2-yl)propyl]quinazoline-7-carboxamide |
| I-28 | 2-(5-chloro-2-thienyl)-4-ethoxy-N-(imidazo[1,2-a]pyridin-6-ylmethyl)quinazoline-7-carboxamide |
| I-29 | 4-ethoxy-2-(4-fluorophenyl)-N-[3-(pyridazin-4-yl)propyl]quinazoline-7-carboxamide |
| I-30 | 4-(tert-butoxymethyl)-2-(4-chlorophenyl)-N-[3-(1H-imidazol-2-yl)propyl]quinazoline-7-carboxamide |
| I-31 | 2-(4-chlorophenyl)-4-cyclopropyl-N-[3-(1H-imidazol-2-yl)propyl]quinazoline-7-carboxamide |
| I-32 | 4-ethoxy-2-(4-fluorophenyl)-N-[3-(1H-imidazol-2-yl)propyl]quinazoline-7-carboxamide |
| I-33 | 2-(4-chlorophenyl)-4-ethyl-N-[3-(1H-imidazol-2-yl)propyl]quinazoline-7-carboxamide |
| I-34 | 4-ethoxy-2-(4-fluorophenyl)-N-(imidazo[1,2-a]pyridin-6-ylmethyl)quinazoline-7-carboxamide |
| I-35 | 2-(5-chloro-2-thienyl)-4-ethoxy-N-[3-(1H-imidazol-2-yl)propyl]quinazoline-7-carboxamide |
| I-36 | 2-(4-fluorophenyl)-N-[3-(1H-imidazol-2-yl)propyl]-4-isopropoxyquinazoline-7-carboxamide |
| I-37 | 2-(4-fluorophenyl)-N-[3-(1H-imidazol-2-yl)propyl]-4-(2-methoxyethoxy)quinazoline-7-carboxamide |
| I-38 | 2-(4-chlorophenyl)-4-ethoxy-N-[3-(1H-imidazol-2-yl)propyl]quinazoline-7-carboxamide |
| I-39 | 4-[ethyl(methyl)amino]-2-(4-fluorophenyl)-N-[3-(1H-imidazol-2-yl)propyl]quinazoline-7-carboxamide |
| I-40 | 4-(cyclopropylmethoxy)-2-(4-fluorophenyl)-N-[3-(1H-imidazol-2-yl)propyl]quinazoline-7-carboxamide |
| I-41 | 4-(ethylamino)-2-(4-fluorophenyl)-N-[3-(1H-imidazol-2-yl)propyl]quinazoline-7-carboxamide |
| I-42 | 4-ethoxy-2-(ethylamino)-N-[3-(1H-imidazol-2-yl)propyl]quinoline-7-carboxamide |
| I-43 | 4-ethoxy-2-(4-fluorophenyl)-N-[3-(1H-pyrazol-1-yl)propyl]quinoline-7-carboxamide |
| I-44 | 4-ethoxy-2-(4-fluorophenyl)-N-[3-(1,3-thiazol-2-yl)propyl]quinoline-7-carboxamide |
| I-45 | 4-ethoxy-2-(4-fluorophenyl)-N-[3-(pyridazin-4-yl)propyl]quinoline-7-carboxamide |
| I-46 | 4-ethoxy-2-(4-fluorophenyl)-N-[2-(1H-pyrazol-5-yl)ethyl]quinoline-7-carboxamide |
| I-47 | N-[2-(4-cyanophenyl)ethyl]-4-ethoxy-2-(4-fluorophenyl)quinoline-7-carboxamide |
| I-48 | 4-ethoxy-2-(4-fluorophenyl)-N-[2-(1H-pyrazol-4-yl)ethyl]quinoline-7-carboxamide |
| I-49 | 4-ethoxy-2-(ethylsulfanyl)-N-[3-(1H-imidazol-2-yl)propyl]quinoline-7-carboxamide |
| I-50 | 4-ethoxy-2-(4-fluorophenyl)-N-{[trans-(1,2)-2-(1H-imidazol-2-yl)cyclopropyl]methyl}quinoline-7-carboxamide (trans cyclopropyl, first eluting enantiomer, Chiralpak ID Peak 1) |
| I-51 | 4-ethoxy-2-(4-fluorophenyl)-N-{[trans-(1,2)-2-(1H-imidazol-2-yl)cyclopropyl]methyl}quinoline-7-carboxamide (trans cyclopropyl, second eluting enantiomer, Chiralpak ID Peak 2) |
| I-52 | 2-(3,4-difluorophenyl)-4-ethoxy-N-[3-(1H-imidazol-2-yl)propyl]quinoline-7-carboxamide |
| I-53 | 4-benzyl-2-(4-chlorophenyl)-N-[3-(1H-imidazol-2-yl)propyl]quinazoline-7-carboxamide |
| I-54 | N-(1H-benzimidazol-2-ylmethyl)-4-ethoxy-2-(4-fluorophenyl)quinoline-7-carboxamide |
| I-55 | 4-ethoxy-2-(4-fluorophenyl)-N-[2-(1H-1,2,4-triazol-1-yl)ethyl]quinoline-7-carboxamide |
| I-56 | 2-(3-chloro-4-fluorophenyl)-4-ethoxy-N-[3-(1H-imidazol-2-yl)propyl]quinoline-7-carboxamide |
| I-57 | 2-(4-chlorophenyl)-4-(4-fluorophenyl)-N-[3-(1H-imidazol-2-yl)propyl]quinazoline-7-carboxamide |
| I-58 | 2-cyclopropyl-4-ethoxy-N-[3-(1H-imidazol-2-yl)propyl]quinoline-7-carboxamide |
| I-59 | 2-(4-chlorophenyl)-N-{[trans-(1,2)-2-(1H-imidazol-2-yl)cyclopropyl]methyl}-4-propylquinazoline-7-carboxamide (trans cyclopropyl racemic) |
| I-60 | 4-ethoxy-2-(4-fluorophenyl)-N-[cis-3-(1H-imidazol-2-yl)cyclobutyl]quinoline-7-carboxamide |
| I-61 | 2,4-diethoxy-N-[3-(1H-imidazol-2-yl)propyl]quinoline-7-carboxamide |
| I-62 | 4-ethoxy-N-[3-(1H-imidazol-2-yl)propyl]-2-(pyrrolidin-1-yl)quinoline-7-carboxamide |
| I-63 | 2-(4-chlorophenyl)-4-methyl-N-[3-(4H-1,2,4-triazol-3-yl)propyl]quinazoline-7-carboxamide |
| I-64 | 2-(4-chlorophenyl)-4-[(2-methoxyethoxy)methyl]-N-[3-(4H-1,2,4-triazol-3-yl)propyl]quinazoline-7-carboxamide |
| I-65 | 4-ethoxy-3-fluoro-2-(2-methoxypyridin-4-yl)-N-[3-(4-methyl-1H-1,2,3-triazol-5-yl)propyl]quinoline-7-carboxamide |
| I-66 | 2-(4-fluorophenyl)-4-(2-methoxyethoxy)-N-[3-(5-methyl-2H-1,2,3-triazol-4-yl)propyl]quinoline-7-carboxamide |
| I-67 | 4-ethoxy-2-(4-fluorophenyl)-N-[3-(6-methylpyridin-3-yl)propyl]quinoline-7-carboxamide |
| I-68 | 4-ethoxy-2-(5-fluoro-2-methoxypyridin-4-yl)-N-[3-(4-methyl-1H-1,2,3-triazol-5-yl)propyl]quinoline-7-carboxamide |
| I-70 | 4-ethoxy-2-(2-methoxypyridin-4-yl)-N-([1,2,4]triazolo[1,5-a]pyridin-7-ylmethyl)quinoline-7-carboxamide |
| I-71 | 4-ethoxy-2-(2-methoxypyridin-4-yl)-N-[3-(4-methyl-1H-1,2,3-triazol-5-yl)propyl]quinoline-7-carboxamide |
| I-72 | 2-(4-chlorophenyl)-4-(1-fluoropropyl)-N-[3-(1H-imidazol-2-yl)propyl]quinazoline-7-carboxamide |
| I-73 | 4-ethoxy-3-fluoro-2-(4-fluorophenyl)-N-[3-(1H-1,2,3-triazol-5-yl)propyl]quinoline-7-carboxamide |
| I-74 | 4-ethoxy-2-(2-methylpyridin-4-yl)-N-([1,2,4]triazolo[1,5-a]pyridin-6-ylmethyl)quinoline-7-carboxamide |
| I-75 | 4-ethoxy-2-(2-methoxypyridin-4-yl)-N-[3-(4-methyl-1H-1,2,3-triazol-5-yl)propyl]quinoline-7-carboxamide |
| I-76 | 4-ethoxy-2-(1-methyl-6-oxo-1,6-dihydropyridin-3-yl)-N-[2-(4-methyl-1H-1,2,3-triazol-5-yl)ethyl]quinoline-7-carboxamide |
| I-77 | 4-ethoxy-2-(6-methylpyridin-3-yl)-N-[2-(4-methyl-1H-1,2,3-triazol-5-yl)ethyl]quinoline-7-carboxamide |
| I-78 | 4-ethoxy-3-fluoro-2-(4-fluorophenyl)-N-[3-(4H-1,2,4-triazol-3-yl)propyl]quinoline-7-carboxamide |
| I-79 | 4-ethoxy-2-(4-fluorophenyl)-N-(thieno[3,2-c]pyridin-2-ylmethyl)quinoline-7-carboxamide |
| I-80 | 4-ethoxy-2-(4-fluorophenyl)-N-(1H-thieno[3,2-c]pyrazol-5-ylmethyl)quinoline-7-carboxamide |
| I-81 | N-[2,2-difluoro-3-(4H-1,2,4-triazol-3-yl)propyl]-2-(4-fluorophenyl)-4-(2-methoxyethoxy)quinoline-7-carboxamide |
| I-82 | 2-(4-fluorophenyl)-4-(2-methoxyethoxy)-N-([1,2,4]triazolo[1,5-a]pyridin-7-ylmethyl)quinoline-7-carboxamide |
| I-83 | 4-ethoxy-2-(2-methoxypyridin-4-yl)-N-[2-(4-methyl-1H-1,2,3-triazol-5-yl)ethyl]quinoline-7-carboxamide |
| I-84 | 4-ethoxy-2-(4-fluorophenyl)-N-([1,2,4]triazolo[1,5-a]pyridin-6-ylmethyl)quinoline-7-carboxamide |
| I-85 | 4-ethoxy-2-(4-fluoro-2-methoxyphenyl)-N-([1,2,4]triazolo[1,5-a]pyridin-7-ylmethyl)quinoline-7-carboxamide |
| I-86 | 4-ethoxy-2-(2-methylpyridin-4-yl)-N-([1,2,4]triazolo[1,5-a]pyridin-7-ylmethyl)quinoline-7-carboxamide |
| I-87 | 4-ethoxy-2-(2-methoxy-6-methylpyridin-3-yl)-N-[2-(4-methyl-1H-1,2,3-triazol-5-yl)ethyl]quinoline-7-carboxamide |
| I-88 | 4-ethoxy-2-(6-methoxypyridin-3-yl)-N-[2-(4-methyl-1H-1,2,3-triazol-5-yl)ethyl]quinoline-7-carboxamide |
| I-89 | 4-ethoxy-2-(5-fluoro-6-methoxypyridin-3-yl)-N-[3-(4H-1,2,4-triazol-3-yl)propyl]quinoline-7-carboxamide |
| I-90 | 4-ethoxy-3-fluoro-2-(2-methoxypyridin-4-yl)-N-[3-(4H-1,2,4-triazol-3-yl)propyl]quinoline-7-carboxamide |
| I-91 | N-[2,2-difluoro-3-(4H-1,2,4-triazol-3-yl)propyl]-4-ethoxy-2-(4-fluorophenyl)quinoline-7-carboxamide |
| I-92 | 4-ethoxy-2-(2-methoxy-6-methylpyridin-3-yl)-N-[2-(3-methyl-1H-pyrazol-4-yl)ethyl]quinoline-7-carboxamide |

| Index | IUPAC Name |
|---|---|
| I-93 | 4-ethoxy-2-(6-methoxypyridin-3-yl)-N-[3-(4-methyl-1H-1,2,3-triazol-5-yl)propyl]quinoline-7-carboxamide |
| I-94 | 4-ethoxy-2-(2-methoxy-6-methylpyridin-3-yl)-N-[3-(4-methyl-1H-1,2,3-triazol-5-yl)propyl]quinoline-7-carboxamide |
| I-95 | 4-ethoxy-2-(1-methyl-2-oxo-1,2-dihydropyridin-4-yl)-N-[3-(1H-1,2,3-triazol-5-yl)propyl]quinoline-7-carboxamide |
| I-96 | 4-ethoxy-2-(1-methyl-6-oxo-1,6-dihydropyridin-3-yl)-N-[3-(1H-1,2,3-triazol-5-yl)propyl]quinoline-7-carboxamide |
| I-97 | 4-ethoxy-2-(1-methyl-6-oxo-1,6-dihydropyridin-3-yl)-N-[3-(4-methyl-1H-1,2,3-triazol-5-yl)propyl]quinoline-7-carboxamide |
| I-98 | 4-ethoxy-2-(1-methyl-6-oxo-1,6-dihydropyridin-3-yl)-N-[2-(3-methyl-1H-pyrazol-4-yl)ethyl]quinoline-7-carboxamide |
| I-99 | 4-ethoxy-N-(1H-imidazo[4,5-c]pyridin-2-ylmethyl)-2-(2-methylpyridin-4-yl)quinoline-7-carboxamide |
| I-100 | 4-ethoxy-2-(2-methoxypyridin-4-yl)-N-[2-(3-methyl-1H-pyrazol-4-yl)ethyl]quinoline-7-carboxamide |
| I-101 | 4-ethoxy-2-(6-methoxypyridin-3-yl)-N-[3-(4H-1,2,4-triazol-3-yl)propyl]quinoline-7-carboxamide |
| I-102 | 4-ethoxy-2-(6-methoxypyridin-3-yl)-N-[3-(1H-1,2,3-triazol-5-yl)propyl]quinoline-7-carboxamide |
| I-103 | 4-ethoxy-2-(2-methoxy-6-methylpyridin-3-yl)-N-[3-(1H-1,2,3-triazol-5-yl)propyl]quinoline-7-carboxamide |
| I-104 | 4-ethoxy-2-(2-methoxy-6-methylpyridin-3-yl)-N-[3-(1H-pyrazol-5-yl)propyl]quinoline-7-carboxamide |
| I-105 | 4-ethoxy-2-(2-methoxypyridin-3-yl)-N-[3-(1H-1,2,3-triazol-5-yl)propyl]quinoline-7-carboxamide |
| I-106 | 4-ethoxy-2-(4-fluoro-2-methoxyphenyl)-N-[3-(4-methyl-1H-1,2,3-triazol-5-yl)propyl]quinoline-7-carboxamide |
| I-107 | 4-ethoxy-2-(4-fluorophenyl)-N-[2-(1H-1,2,3-triazol-5-yl)ethyl]quinoline-7-carboxamide |
| I-108 | 4-ethoxy-2-(4-fluoro-2-methoxyphenyl)-N-[2-(1H-1,2,3-triazol-5-yl)ethyl]quinoline-7-carboxamide |
| I-109 | 2-(4-fluorophenyl)-4-(methoxyethoxy)-N-[3-(2H-1,2,3-triazol-4-yl)propyl]quinoline-7-carboxamide |
| I-110 | 4-ethoxy-2-(6-methylpyridin-3-yl)-N-[3-(1H-1,2,3-triazol-5-yl)propyl]quinoline-7-carboxamide |
| I-111 | 4-ethoxy-2-(6-methylpyridin-3-yl)-N-[3-(1H-pyrazol-3-yl)propyl]quinoline-7-carboxamide |
| I-112 | 4-ethoxy-2-(6-methylpyridin-3-yl)-N-[3-(4-methyl-1H-1,2,3-triazol-5-yl)propyl]quinoline-7-carboxamide |
| I-113 | 4-ethoxy-N-[2-(3-methyl-1H-pyrazol-4-yl)ethyl]-2-(6-methylpyridin-3-yl)quinoline-7-carboxamide |
| I-114 | 4-ethoxy-2-(2-methoxypyridin-4-yl)-N-[3-(4H-1,2,4-triazol-3-yl)propyl]quinoline-7-carboxamide |
| I-115 | 4-ethoxy-2-(4-fluorophenyl)-N-[3-(1H-1,2,3-triazol-5-yl)propyl]quinoline-7-carboxamide |
| I-116 | 4-ethoxy-2-(2-methoxypyridin-4-yl)-N-[3-(1H-1,2,3-triazol-5-yl)propyl]quinoline-7-carboxamide |
| I-117 | 4-ethoxy-2-(2-methylpyridin-4-yl)-N-[3-(1H-1,2,3-triazol-5-yl)propyl]quinoline-7-carboxamide |
| I-118 | 4-ethoxy-2-(1-methyl-2-oxo-1,2-dihydropyridin-4-yl)-N-[3-(4H-1,2,4-triazol-3-yl)propyl]quinoline-7-carboxamide |
| I-119 | 4-ethoxy-2-(1-methyl-2-oxo-1,2-dihydropyridin-4-yl)-N-[3-(1H-pyrazol-3-yl)propyl]quinoline-7-carboxamide |
| I-120 | 2-(4-fluorophenyl)-4-(2-methoxyethoxy)-N-[3-(1H-pyrazol-3-yl)propyl]quinoline-7-carboxamide |
| I-121 | 4-ethoxy-2-(4-fluoro-2-methoxyphenyl)-N-[3-(1H-1,2,3-triazol-5-yl)propyl]quinoline-7-carboxamide |
| I-122 | 4-ethoxy-2-(1-methyl-6-oxo-1,6-dihydropyridin-3-yl)-N-[3-(4H-1,2,4-triazol-3-yl)propyl]quinoline-7-carboxamide |
| I-123 | 4-ethoxy-2-(1-methyl-6-oxo-1,6-dihydropyridin-3-yl)-N-[3-(1H-pyrazol-3-yl)propyl]quinoline-7-carboxamide |
| I-124 | 2-(4-fluorophenyl)-4-(2-methoxyethoxy)-N-[3-(1H-1,2,4-triazol-5-yl)propyl]quinoline-7-carboxamide |
| I-125 | 2-(5-chloro-2-thienyl)-4-ethoxy-N-[3-(4H-1,2,4-triazol-3-yl)propyl]quinoline-7-carboxamide |
| I-126 | 2-(4-fluorophenyl)-4-(2-methoxyethoxy)-N-[2-(3-methyl-1H-pyrazol-4-yl)ethyl]quinoline-7-carboxamide |
| I-127 | 4-ethoxy-2-(5-methylpyridin-3-yl)-N-[3-(4H-1,2,4-triazol-3-yl)propyl]quinoline-7-carboxamide |
| I-128 | 4-ethoxy-2-(4-fluoro-2-methoxyphenyl)-N-[3-(1H-pyrazol-3-yl)propyl]quinoline-7-carboxamide |
| I-129 | 4-ethoxy-2-(4-fluoro-2-methoxyphenyl)-N-[2-(3-methyl-1H-pyrazol-4-yl)ethyl]quinoline-7-carboxamide |
| I-130 | 4-ethoxy-2-(4-fluorophenyl)-N-([1,2,4]triazolo[1,5-a]pyridin-7-ylmethyl)quinoline-7-carboxamide |
| I-131 | 4-ethoxy-2-(4-fluorophenyl)-N-[2-(4H-1,2,4-triazol-3-yl)ethyl]quinoline-7-carboxamide |
| I-132 | 4-ethoxy-2-(4-fluorophenyl)-N-[2-(3-methyl-1H-pyrazol-4-yl)ethyl]quinoline-7-carboxamide |
| I-133 | 4-ethoxy-2-(4-fluorophenyl)-N-[3-(5-methyl-2H-1,2,3-triazol-4-yl)propyl]quinoline-7-carboxamide |
| I-134 | N-[2-(5-amino-1H-pyrazol-3-yl)ethyl]-4-ethoxy-2-(4-fluorophenyl)quinoline-7-carboxamide |
| I-135 | 4-ethoxy-2-(tetrahydro-2H-pyran-4-yl)-N-[3-(4H-1,2,4-triazol-3-yl)propyl]quinoline-7-carboxamide |
| I-136 | 4-ethoxy-2-(2-methoxy-6-methylpyridin-4-yl)-N-[3-(4H-1,2,4-triazol-3-yl)propyl]quinoline-7-carboxamide |
| I-137 | 4-ethoxy-2-[3-(methylsulfonyl)phenyl]-N-[3-(4H-1,2,4-triazol-3-yl)propyl]quinoline-7-carboxamide |
| I-138 | 4-ethoxy-2-(6-methoxy-2-methylpyridin-3-yl)-N-[3-(4H-1,2,4-triazol-3-yl)propyl]quinoline-7-carboxamide |
| I-139 | 4-ethoxy-2-(3-methoxypyridin-4-yl)-N-[3-(4H-1,2,4-triazol-3-yl)propyl]quinoline-7-carboxamide |
| I-140 | 2-(3,6-dihydro-2H-pyran-4-yl)-4-ethoxy-N-[3-(4H-1,2,4-triazol-3-yl)propyl]quinoline-7-carboxamide |
| I-141 | N-[(3-amino-1H-1,2,4-triazol-5-yl)methyl]-4-ethoxy-2-(4-fluorophenyl)quinoline-7-carboxamide |
| I-142 | N-[2-(5-amino-4H-1,2,4-triazol-3-yl)ethyl]-4-ethoxy-2-(4-fluorophenyl)quinoline-7-carboxamide |
| I-143 | 2-(2,6-dimethoxypyridin-3-yl)-4-ethoxy-N-[3-(4H-1,2,4-triazol-3-yl)propyl]quinoline-7-carboxamide |
| I-144 | 4-ethoxy-2-(2-methoxypyridin-3-yl)-N-[2-(3-methyl-1H-pyrazol-4-yl)ethyl]quinoline-7-carboxamide |
| I-145 | 4-ethoxy-2-(6-methoxy-4-methyl-3-pyridyl)-N-[3-(4H-1,2,4-triazol-3-yl)propyl]quinoline-7-carboxamide |
| I-146 | 4-ethoxy-N-[2-(3-methyl-1H-pyrazol-4-yl)ethyl]-2-(2-methylpyridin-4-yl)quinoline-7-carboxamide |
| I-147 | 2-(4-fluorophenyl)-4-propyl-N-[3-(1H-pyrazol-3-yl)propyl]quinoline-7-carboxamide |
| I-148 | 2-(4-fluorophenyl)-4-(1H-imidazol-1-yl)-N-[3-(4H-1,2,4-triazol-3-yl)propyl]quinoline-7-carboxamide |
| I-149 | 4-ethoxy-2-(2-methylpyridin-4-yl)-N-[3-(1H-pyrazol-5-yl)propyl]quinoline-7-carboxamide |
| I-150 | 4-ethoxy-2-(2-methoxypyridin-3-yl)-N-[3-(1H-pyrazol-5-yl)propyl]quinoline-7-carboxamide |
| I-151 | 4-(ethylamino)-2-(4-fluorophenyl)-N-[3-(4H-1,2,4-triazol-3-yl)propyl]quinoline-7-carboxamide |
| I-152 | 2-(4-fluorophenyl)-N-[2-(3-methyl-1H-pyrazol-4-yl)ethyl]-4-propylquinoline-7-carboxamide |
| I-153 | 4-ethoxy-2-(6-methoxypyridin-3-yl)-N-[2-(5-methyl-1H-pyrazol-4-yl)ethyl]quinoline-7-carboxamide |
| I-154 | 4-ethoxy-2-(6-methoxypyridin-3-yl)-N-[3-(1H-pyrazol-5-yl)propyl]quinoline-7-carboxamide |
| I-155 | 4-ethoxy-2-(2-methoxypyridin-4-yl)-N-[3-(1H-pyrazol-5-yl)propyl]quinoline-7-carboxamide |
| I-156 | 2-(4-fluorophenyl)-N-[3-(1H-imidazol-2-yl)propyl]-4-(2-methoxyethoxy)quinoline-7-carboxamide |
| I-157 | 4-(4-fluorophenyl)-2-(2-methylpyridin-4-yl)-N-[3-(4H-1,2,4-triazol-3-yl)propyl]quinoline-7-carboxamide |
| I-158 | 4-ethoxy-2-(3-methylpyridin-4-yl)-N-[3-(4H-1,2,4-triazol-3-yl)propyl]quinoline-7-carboxamide |
| I-159 | 4-ethoxy-2-(2-methoxy-5-methylpyridin-3-yl)-N-[3-(4H-1,2,4-triazol-3-yl)propyl]quinoline-7-carboxamide |
| I-160 | 4-ethoxy-2-(4-fluorophenyl)-N-[(1S)-1-(1H-imidazo[4,5-c]pyridin-2-yl)ethyl]quinoline-7-carboxamide |
| I-161 | 4-ethoxy-2-(5-fluoro-2-methoxypyridin-3-yl)-N-[3-(4H-1,2,4-triazol-3-yl)propyl]quinoline-7-carboxamide |
| I-162 | 2-(4-fluorophenyl)-4-(2-methylpyridin-4-yl)-N-[3-(4H-1,2,4-triazol-3-yl)propyl]quinazoline-7-carboxamide |
| I-163 | 2-(4-fluorophenyl)-N-[3-(1H-imidazol-2-yl)propyl]-4-propylquinoline-7-carboxamide |
| I-164 | 2-(5-chloro-2-methoxypyridin-4-yl)-4-ethoxy-N-[3-(4H-1,2,4-triazol-3-yl)propyl]quinoline-7-carboxamide |
| I-165 | 4-ethoxy-2-(4-fluoro-2-methoxyphenyl)-N-[3-(4H-1,2,4-triazol-3-yl)propyl]quinoline-7-carboxamide |
| I-166 | 2-(3-chloro-2-methoxypyridin-4-yl)-4-ethoxy-N-[3-(4H-1,2,4-triazol-3-yl)propyl]quinoline-7-carboxamide |
| I-167 | 4-ethoxy-N-(1H-imidazo[4,5-c]pyridin-2-ylmethyl)-2-(6-methylpyridin-3-yl)quinoline-7-carboxamide |
| I-168 | 4-ethoxy-2-(6-methylpyridin-3-yl)-N-[2-(4H-1,2,4-triazol-3-yl)ethyl]quinoline-7-carboxamide |
| I-169 | 4-ethoxy-2-(6-methylpyridin-3-yl)-N-[2-(1H-1,2,3-triazol-4-yl)ethyl]quinoline-7-carboxamide |

| Index | IUPAC Name |
|---|---|
| I-170 | 4-ethoxy-2-(4-fluoro-2-methoxyphenyl)-N-[2-(1H-1,2,4-triazol-5-yl)ethyl]quinoline-7-carboxamide |
| I-171 | 2-(4-fluorophenyl)-4-propyl-N-[3-(1H-1,2,4-triazol-5-yl)propyl]quinoline-7-carboxamide |
| I-172 | 4-ethoxy-2-(2-methylpyridin-4-yl)-N-[2-(4H-1,2,4-triazol-3-yl)ethyl]quinoline-7-carboxamide |
| I-173 | 4-ethoxy-2-(6-methylpyridin-3-yl)-N-[3-(4H-1,2,4-triazol-3-yl)propyl]quinoline-7-carboxamide |
| I-174 | 4-ethoxy-N-(1H-imidazo[4,5-c]pyridin-2-ylmethyl)-2-(2-methoxy-6-methylpyridin-3-yl)quinoline-7-carboxamide |
| I-175 | 2-(5-chloro-2-thienyl)-4-ethoxy-N-(1H-imidazo[4,5-c]pyridin-2-ylmethyl)quinoline-7-carboxamide |
| I-176 | 2-(5-chloro-2-thienyl)-4-ethoxy-N-[2-(1H-1,2,3-triazol-5-yl)ethyl]quinoline-7-carboxamide |
| I-177 | 2-(5-chloro-2-thienyl)-4-ethoxy-N-[2-(4H-1,2,4-triazol-3-yl)ethyl]quinoline-7-carboxamide |
| I-178 | 4-ethoxy-2-(4-fluorophenyl)-N-[(1-methyl-1H-imidazo[4,5-c]pyridin-2-yl)methyl]quinoline-7-carboxamide |
| I-179 | 4-ethoxy-2-(5-fluoro-2-methoxyphenyl)-N-[(1-methyl-1H-imidazo[4,5-c]pyridin-2-yl)methyl]quinoline-7-carboxamide |
| I-180 | 4-ethoxy-2-(2-methoxypyridin-3-yl)-N-[2-(4H-1,2,4-triazol-3-yl)ethyl]quinoline-7-carboxamide |
| I-181 | 4-ethoxy-2-(2-methylpyridin-4-yl)-N-[2-(1H-1,2,3-triazol-5-yl)ethyl]quinoline-7-carboxamide |
| I-182 | 4-ethoxy-2-(5-fluoro-2-methoxyphenyl)-N-[2-(4H-1,2,4-triazol-3-yl)ethyl]quinoline-7-carboxamide |
| I-183 | 4-ethoxy-2-(2-methoxy-6-methylpyridin-3-yl)-N-[3-(1H-1,2,4-triazol-3-yl)propyl]quinoline-7-carboxamide |
| I-184 | 4-ethoxy-2-(5-fluoro-2-methoxyphenyl)-N-[2-(1H-1,2,3-triazol-5-yl)ethyl]quinoline-7-carboxamide |
| I-185 | 4-ethoxy-2-(6-methoxypyridin-3-yl)-N-[2-(1H-1,2,3-triazol-4-yl)ethyl]quinoline-7-carboxamide |
| I-186 | 4-ethoxy-2-(6-methoxypyridin-3-yl)-N-[2-(1H-1,2,4-triazol-3-yl)ethyl]quinoline-7-carboxamide |
| I-187 | 4-ethoxy-2-(5-fluoro-2-methoxyphenyl)-N-(1H-imidazo[4,5-c]pyridin-2-ylmethyl)quinoline-7-carboxamide |
| I-188 | 4-ethoxy-2-(5-fluoro-2-methoxypyridin-4-yl)-N-(1H-imidazo[4,5-c]pyridin-2-ylmethyl)quinoline-7-carboxamide |
| I-189 | 4-ethoxy-2-(5-fluoro-2-methoxypyridin-4-yl)-N-[2-(1H-1,2,3-triazol-5-yl)ethyl]quinoline-7-carboxamide |
| I-190 | 4-ethoxy-2-(2-methoxypyridin-3-yl)-N-[2-(1H-1,2,3-triazol-5-yl)ethyl]quinoline-7-carboxamide |
| I-191 | 4-ethoxy-2-(2-methoxypyridin-4-yl)-N-[2-(4H-1,2,4-triazol-3-yl)ethyl]quinoline-7-carboxamide |
| I-192 | 4-ethoxy-N-(3H-imidazo[4,5-c]pyridin-2-ylmethyl)-2-(2-methoxypyridin-3-yl)quinoline-7-carboxamide |
| I-193 | 4-ethoxy-N-(1H-imidazo[4,5-c]pyridin-2-ylmethyl)-2-(6-methoxypyridin-3-yl)quinoline-7-carboxamide |
| I-194 | 4-ethoxy-N-(1H-imidazo[4,5-c]pyridin-2-ylmethyl)-2-(2-methoxypyridin-4-yl)quinoline-7-carboxamide |
| I-195 | 4-ethoxy-2-(2-methoxypyridin-4-yl)-N-[2-(1H-1,2,3-triazol-5-yl)ethyl]quinoline-7-carboxamide |
| I-196 | 2-(4-fluorophenyl)-N-[3-(1H-imidazol-2-yl)propyl]-4-(2-methoxypyridin-4-yl)quinazoline-7-carboxamide |
| I-197 | 2-(4-fluorophenyl)-4-(2-methoxypyridin-4-yl)-N-[3-(4H-1,2,4-triazol-3-yl)propyl]quinazoline-7-carboxamide |
| I-198 | 2-(4-chlorophenyl)-4-ethoxy-N-[3-(4H-1,2,4-triazol-3-yl)propyl]quinoline-7-carboxamide |
| I-199 | 4-ethoxy-2-(5-fluoro-2-methoxyphenyl)-N-[3-(4H-1,2,4-triazol-3-yl)propyl]quinoline-7-carboxamide |
| I-200 | 4-ethoxy-2-(2-methoxypyridin-3-yl)-N-[3-(4H-1,2,4-triazol-3-yl)propyl]quinoline-7-carboxamide |
| I-201 | 4-ethoxy-2-(4-fluorophenyl)-N-[3-(3-methyl-1H-pyrazol-4-yl)propyl]quinoline-7-carboxamide |
| I-202 | 4-ethoxy-2-(2-methylpyridin-4-yl)-N-[3-(4H-1,2,4-triazol-3-yl)propyl]quinoline-7-carboxamide |
| I-203 | 4-ethoxy-2-(4-fluorophenyl)-N-[2-(5-methyl-2H-1,2,3-triazol-4-yl)ethyl]quinoline-7-carboxamide |
| I-204 | 4-ethoxy-2-(4-fluorophenyl)-N-[3-(1H-pyrazol-3-yl)propyl]quinoline-7-carboxamide |
| I-205 | 4-ethoxy-2-(1H-pyrazol-4-yl)-N-[3-(4H-1,2,4-triazol-3-yl)propyl]quinoline-7-carboxamide |
| I-206 | 4-ethoxy-2-(1-methyl-1H-pyrazol-4-yl)-N-[3-(4H-1,2,4-triazol-3-yl)propyl]quinoline-7-carboxamide |
| I-207 | 4-ethoxy-2-phenyl-N-[3-(4H-1,2,4-triazol-3-yl)propyl]quinoline-7-carboxamide |
| I-208 | 4-ethoxy-2-(pyrimidin-5-yl)-N-[3-(4H-1,2,4-triazol-3-yl)propyl]quinoline-7-carboxamide |
| I-209 | 4-ethoxy-2-(pyridin-3-yl)-N-[3-(4H-1,2,4-triazol-3-yl)propyl]quinoline-7-carboxamide |
| I-210 | 4-ethoxy-2-(5-methoxypyridin-3-yl)-N-[3-(4H-1,2,4-triazol-3-yl)propyl]quinoline-7-carboxamide |
| I-211 | 2-(6-chloro-4-methylpyridin-3-yl)-4-ethoxy-N-[3-(4H-1,2,4-triazol-3-yl)propyl]quinoline-7-carboxamide |
| I-212 | 4-ethoxy-2-(4-methoxypyridin-3-yl)-N-[3-(4H-1,2,4-triazol-3-yl)propyl]quinoline-7-carboxamide |
| I-213 | 4-ethoxy-2-(2-methylpyridin-3-yl)-N-[3-(4H-1,2,4-triazol-3-yl)propyl]quinoline-7-carboxamide |
| I-214 | 4-ethoxy-2-(pyridin-4-yl)-N-[3-(4H-1,2,4-triazol-3-yl)propyl]quinoline-7-carboxamide |
| I-215 | 4-ethoxy-N-[3-(4H-1,2,4-triazol-3-yl)propyl]-2-[3-(trifluoromethyl)phenyl]quinoline-7-carboxamide |
| I-216 | 4-ethoxy-N-[3-(4H-1,2,4-triazol-3-yl)propyl]-2-[3-(trifluoromethoxy)phenyl]quinoline-7-carboxamide |
| I-217 | 4-ethoxy-N-[3-(4H-1,2,4-triazol-3-yl)propyl]-2-[6-(trifluoromethyl)pyridin-3-yl]quinoline-7-carboxamide |
| I-218 | 4-ethoxy-N-[3-(4H-1,2,4-triazol-3-yl)propyl]-2-[2-(trifluoromethyl)pyridin-4-yl]quinoline-7-carboxamide |
| I-219 | 4-ethoxy-2-(4-fluorophenyl)-N-[3-(1H-tetrazol-5-yl)propyl]quinoline-7-carboxamide |
| I-220 | N-[3-(5-amino-4H-1,2,4-triazol-3-yl)propyl]-4-ethoxy-2-(4-fluorophenyl)quinoline-7-carboxamide |
| I-221 | 4-ethoxy-2-(4-fluorophenyl)-N-[2-(2H-tetrazol-5-yl)ethyl]quinoline-7-carboxamide |
| I-222 | 4-ethoxy-2-(4-fluorophenyl)-N-[cis-3-(4H-1,2,4-triazol-3-yl)cyclobutyl]quinoline-7-carboxamide |
| I-223 | 4-ethoxy-2-(5-methyl-2-thienyl)-N-[3-(4H-1,2,4-triazol-3-yl)propyl]quinoline-7-carboxamide |
| I-224 | 4-ethoxy-2-(4-fluorophenyl)-N-[3-(1-methyl-1H-imidazol-5-yl)propyl]quinoline-7-carboxamide |
| I-225 | 4-ethoxy-2-(5-fluoro-2-methoxypyridin-4-yl)-N-[3-(4H-1,2,4-triazol-3-yl)propyl]quinoline-7-carboxamide |
| I-226 | 4-ethoxy-N-[3-(1H-imidazol-2-yl)propyl]-2-propylquinoline-7-carboxamide |
| I-227 | 4-ethoxy-2-(4-fluorophenyl)-N-[3-(6-methylpyridin-3-yl)propyl]quinoline-7-carboxamide |
| I-228 | 4-ethoxy-2-(4-fluorophenyl)-N-[3-(pyrimidin-5-yl)propyl]quinoline-7-carboxamide |
| I-229 | 2-(4-fluorophenyl)-4-(2-hydroxyethoxy)-N-[3-(1H-imidazol-2-yl)propyl]quinoline-7-carboxamide |

1. Preparation of Exemplary Compounds

Definitions

AA LCMS method using ammonium acetate
Ac acetate
ADDP 1,1'-(Azodicarbonyl)dipiperidine
tAmPH 2-methyl-2-butanol
Amphos bis(di-tert-butyl(4-dimethylamino)phosphine)
C Celsius
CDCl$_3$ deuterated chloroform
CDI Carbonyldiimidazole
DABCO 1,4-diazabicyclo[5.4.0]octane
DCM dichloromethane
dba dibenzylidineacetone
DDQ 2,3-dichloro-5,6-dicyano-1,4-benzoquinone
DIPEA diisopropylethylamine
DMA dimethylacetamide
DME dimethoxyethane
DMF N,N-dimethylformamide
DMSO dimethylsulfoxide
DPPA diphenylphosphoryl azide
dppf 1,1'-bis(diphenylphosphino) ferrocene
EDCI 1-(3-dimethylaminopropyl)-3-ethylcarbodiimide hydrochloride
Ether diethyl ether EtOAc ethyl acetate
FA LCMS method using formic acid
h hours
HATU (1-[bis(dimethylamino)methylene]-1H-1,2,3-triazolo[4,5-b]pyridinium 3-oxid hexafluorophosphate)
HOBt 1-hydroxybenotriazole
HPLC high pressure liquid chromatography
$IC_{50}$ inhibitory concentration 50%
LCMS liquid chromoatography mass spectrometry
MeCN acetonitrile
m/z mass to charge
min minutes
NBS N-bromosuccinimide
NMP N-methyl-2-pyrrolidone
PE petroleum ether
pic picoline
Ph phenyl
PHPB pyridinium hydrobromideperbromide
PMB para-methoxybenzyl
psi pounds per square inch
rt room temperature
TBTU N,N,N',N'-tetramethyl-O-(7-azabenzotriazol-1-yl) uranium hexafluorophosphate
TEA triethylamine
TFA trifluoroacetic acid
THF tetrahydrofuran
T3P® 2,4,6-tripropyl-1,3,5,2,4,6-trioxatriphosphorinane-2,4,6-trioxide
Xantphos 4,5-bis(diphenylphosphino)-9,9-dimethylxanthene
XPhos 2-dicyclohexylphosphino-2',4',6'-tri-isopropyl-1,1'-biphenyl
XPhos-Pd-G3 methanesulfonato(2-dicyclohexylphosphino-2',4',6'-tri-isopropyl-1,1'-biphenyl)(2'-amino-1,1'-biphenyl-2-yl)palladium(II)
Analytical Methods
NMR Conditions:
$^1$H NMR spectra were collected by the following methods: A) On a 400 MHz Bruker Avance III spectrometer equipped with a 5 mm BBFO probe or B) 400 MHz Bruker Avance II spectrometer equipped with a 5 mm QNP probe for the measurement. Chemical shifts for $^1$H NMR were reported in parts per million (ppm) downfield from tetramethylsilane (6) as the internal standard in deuterated solvent and coupling constants (J) are in Hertz (Hz). The following abbreviations are used for spin multiplicity: s=singlet, d=doublet, t=triplet, q=quartet, m=multiplet and br=broad.
LCMS Conditions:
LCMS spectra were recorded by one of the following methods. A) On a Hewlett-Packard HP 1100 or Agilent 1100 Series LC system connected to a Micromass mass spectromteter using reverse phase C18 columns. Various gradients and run times were selected in order to best characterize the compounds. Mobile phases were based on ACN/water gradients and contained either 0.1% formic acid (methods indicated FA) or 10 mM ammonium acetate (methods indicated AA). One example of a solvent gradient that was used was 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min run. B) LCMS spectra were recorded on an Agilent 1290 Infinity UPLC system connected to an Agilent 6130 mass spectrometer, a Waters Acquity UPLC system connected to a Waters Acquity SQ mass spectrometer, or an Agilent 1100 Series HPLC system connected to a Waters Micromass ZQ mass spectrometer using reverse phase C18 columns.

Preparative HPLC:
Preparative HPLC are conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

One of ordinary skill in the art will recognize that modifications of the gradient, column length, and flow rate are possible and that some conditions may be suitable for compound characterization than others, depending on the chemical species being analyzed.

Example 1: Ethoxy-2-(4-fluorophenyl)-N-[3-(1H-imidazol-2-yl)propyl]quinazoline-7-carboxamide (I-32)

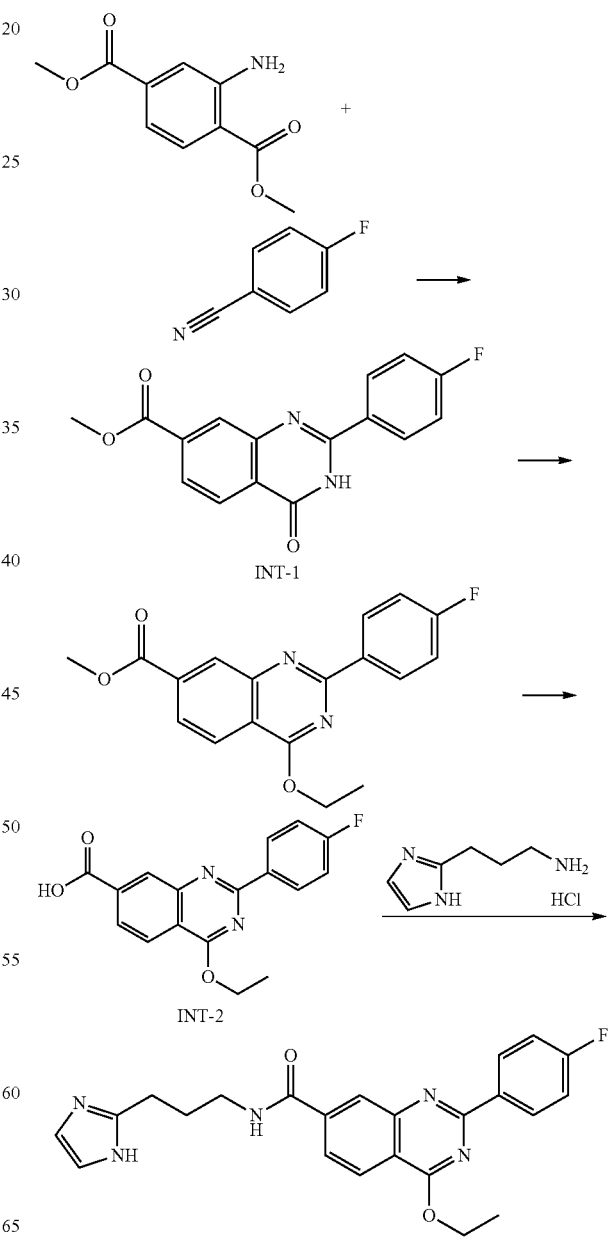

Step 1: Methyl 2-(4-fluorophenyl)-4-oxo-3,4-dihydroquinazoline-7-carboxylate (INT-1)

A 150 ml pressure reactor was loaded with methyl 2 amino-4-carbomethoxybenzoate (3.11 g, 14.9 mmol) and 4-fluorobenzonitrile (1.98 g, 16.4 mmol). 4 M of hydrochloric acid in 1,4-dioxane (35.0 mL, 140 mmol) was added. The tube was sealed and the resulting suspension was stirred at rt for 4 h. The suspension became very thick; it was then heated at 100° C. for 30 h. After cooling, the mixture was poured into 200 mL of water and stirred for 30 min. The solid was collected by filtration, washed with water and ethanol and was dried under vacuum for 15 h to give methyl 2-(4-fluorophenyl)-4-oxo-3,4-dihydroquinazoline-7-carboxylate (3.61 g, 81%) as a light brown solid. LC-MS: (FA) ES+ 299.1; 1H NMR (400 MHz, DMSO-$d_6$) δ 12.78 (s, 1H), 8.32-8.22 (m, 4H), 8.02 (d, J=8.2 Hz, 1H), 7.47-7.38 (m, 2H), 3.95 (s, 3H).

Step 2: Methyl 4-ethoxy-2-(4-fluorophenyl)quinazoline-7-carboxylate

To a mixture of methyl 2-(4-fluorophenyl)-4-oxo-3,4-dihydroquinazoline-7-carboxylate (1.06 g, 3.55 mmol) and potassium carbonate (737 mg, 5.33 mmol) in DMF (18.5 mL, 239 mmol) was added iodoethane (426 uL, 5.33 mmol). The mixture was stirred at rt overnight. The mixture had become very thick. LCMS analysis showed completed reaction. The mixture was partitioned between EtOAc and water. The organic layer was washed with brine ×2, dried over $Na_2SO_4$ and concentrated. The product was purified on ISCO using 0-6% EtOAc/hexane over 25 min to give methyl 4-ethoxy-2-(4-fluorophenyl)quinazoline-7-carboxylate (887 mg, 76%) as a white solid. LC-MS: (FA) ES+ 327.1; 1H NMR (400 MHz, DMSO-d6) δ 8.62-8.55 (m, 2H), 8.45 (d, J=1.5 Hz, 1H), 8.27 (d, J=8.5 Hz, 1H), 8.10 (dd, J=8.5, 1.5 Hz, 1H), 7.45-7.37 (m, 2H), 4.78 (q, J=7.1 Hz, 2H), 3.97 (s, 3H), 1.54 (t, J=7.1 Hz, 3H).

Step 3: 4-Ethoxy-2-(4-fluorophenyl)quinazoline-7-carboxylic acid (INT-2)

To a solution of methyl 4-ethoxy-2-(4-fluorophenyl)quinazoline-7-carboxylate (885 mg, 2.71 mmol) in THF (16.2 mL, 200 mmol) and ethanol (16.2 mL, 277 mmol) cooled in ice bath was added 1.0 M of sodium hydroxide in water (8.14 mL, 8.14 mmol). The mixture was then stirred at rt. The mixture became homogeneous after ~1 h LCMS showed completed reaction. The mixture was added to 100 ml of water. The resulting solution was acidified with 1M HCl to pH ~2. The white solid that precipitated was collected by filtration and was dried under high vacuum to give 4-ethoxy-2-(4-fluorophenyl)quinazoline-7-carboxylic acid (0.923 g, 99%). LC-MS: (FA) ES+ 313.1; 1H NMR (400 MHz, DMSO-$d_6$) δ 13.60 (s, 1H), 8.63-8.56 (m, 2H), 8.45 (d, J=1.5 Hz, 1H), 8.25 (d, J=8.5 Hz, 1H), 8.10 (dd, J=8.5, 1.5 Hz, 1H), 7.44-7.37 (m, 2H), 4.79 (q, J=7.1 Hz, 2H), 1.54 (t, J=7.1 Hz, 3H).

Step 4: 4-Ethoxy-2-(4-fluorophenyl)-N-[3-(1H-imidazol-2-yl)propyl]quinazoline-7-carboxamide To a mixture at rt of 4-ethoxy-2-(4-fluorophenyl)quinazoline-7-carboxylic acid (166 mg, 0.532 mmol) and TBTU (205 mg, 0.638 mmol) in dimethyl sulfoxide (3.0 mL, 42 mmol) was added DIPEA (139 uL, 0.797 mmol). The mixture became homogeneous and was stirred at rt for 5 min. 3-(1H-imidazol-2-yl)-1-propanamine 2HCl (137 mg, 0.691 mmol) and DIPEA (278 uL, 1.59 mmol) were added. The mixture was stirred at rt for 1 h. This reaction mixture was partitioned between EtOAc and 1M $K_2CO_3$ (stirred for 2 h). Separated organics was washed with brine ×2, dried over $Na_2SO_4$ and concentrated. The product was purified on ISCO (12 g silica) using 0-8% MeOH/DCM. Pertinent fractions were concentrated to give 4-ethoxy-2-(4-fluorophenyl)-N-[3-(1H-imidazol-2-yl)propyl]quinazoline-7-carboxamide (158 mg, 71%) as an off white solid. LC-MS: (FA) ES+ 420.2; 1H NMR (400 MHz, DMSO-$d_6$) δ 11.71 (s, 1H), 9.08 (t, J=5.2 Hz, 1H), 8.62-8.56 (m, 2H), 8.46 (d, J=1.5 Hz 1H), 8.23 (d, J=8.5 Hz, 1H), 8.05 (dd, J=8.5, 1.5 Hz, 1H), 7.45-7.38 (m, 2H), 6.99 (s, 1H), 6.79 (s, 1H), 4.79 (q, J=7.1 Hz, 2H), 3.43-3.35 (m, 2H), 2.79-2.75 (m, 2H), 2.01-1.91 (m, 2H), 1.54 (t, J=7.1 Hz, 3H).

The compounds listed in the table below were prepared in an analogous fashion to that described in Example 1 starting from the appropriate starting materials:

| Starting Material Step 1 | Starting Material Step 2 | Compound No. or Name | LCMS Data |
|---|---|---|---|
| 4-fluorobenzonitrile | isopropyl iodide | I-36 | LCMS (ESI+): m/z = 434.2 (M + H) |
| 4-fluorobenzonitrile | 2-bromoethyl ethyl ether | I-37 | LCMS (ESI+): m/z = 450.2 (M + H) |
| 4-chlorobenzonitrile | ethyl iodide | I-38* | LCMS (ESI+): m/z = 436.2 (M + H) |
| 4-fluorobenzonitrile | (bromomethyl)cyclopropane | I-40** | LCMS (ESI+): m/z = 446.2 (M + H) |
| 4-chlorobenzonitrile | methyl iodide | I-10*** | LCMS (ESI+): m/z = 422.1 (M + H) |

*Carboxylic acid in was converted to acid chloride using thionyl chloride in Step 4 followed by coupling with amine, similar to conditions used in Example 7, Step 2

**HATU was used as coupling reagent in Step 4

***T3P ® was used as coupling reagent in Step 4

Example 2: 4-(Ethylamino)-2-(4-fluorophenyl)-N-[3-(1H-imidazol-2-yl)propyl]quinazoline-7-carboxamide (I-41)

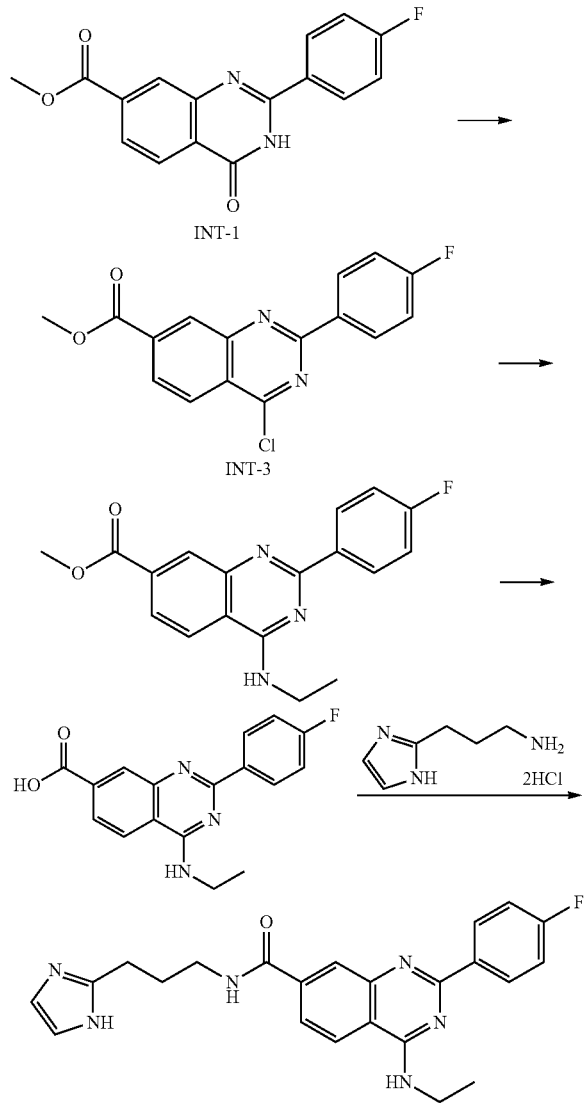

Step 1: Methyl 4-chloro-2-(4-fluorophenyl)quinazoline-7-carboxylate (INT-3)

Microwave tube was charged with methyl 2-(4-fluorophenyl)-4-oxo-3,4-dihydroquinazoline-7-carboxylate (INT-1, described in Example 1; 54 mg, 0.18 mmol), phosphorus pentachloride (110 mg, 0.54 mmol) and 1,2-dichloroethane (1.5 mL, 19 mmol). The reaction mixture was microwaved on 300 watts, 160° C. for 30 min. The resulting solution was diluted with 15 ml of DCM and stirred with 15 ml of 0.1M HCl for 15 min. Separated aqueous was extracted with DCM. Combined organic layers were dried over $MgSO_4$ and concentrated. The residue was dried under vacuum to give methyl 4-chloro-2-(4-fluorophenyl)quinazoline-7-carboxylate (52 mg, 91%) as a light yellow solid. LC-MS: (FA) ES+ 317.1; 1H NMR (400 MHz, $CDCl_3$) δ 8.70-8.68 (m, 1H), 8.59-8.52 (m, 2H), 8.26-8.22 (m, 1H), 8.19-8.15 (m, 1H), 7.18-7.11 (m, 2H), 3.97 (s, 3H).

Step 2: Methyl 4-(ethylamino)-2-(4-fluorophenyl)quinazoline-7-carboxylate

To a suspension of methyl 4-chloro-2-(4-fluorophenyl)quinazoline-7-carboxylate (122 mg, 0.385 mmol) in DCM (3.0 mL, 47 mmol) at 0° C. was added 2.00 M of ethylamine in THF (0.963 mL, 1.93 mmol). The mixture was stirred at rt for 2.5 h. The mixture was diluted with EtOAc and washed with 50% brine. The organic layer was then dried over $Na_2SO_4$ and concentrated. The resulting product was purified on ISCO using 0-20% EtOAc over 25 min to give methyl 4-(ethylamino)-2-(4-fluorophenyl)quinazoline-7-carboxylate (96 mg, 77%) as a white solid. LC-MS: (FA) ES+ 326.1; 1H NMR (400 MHz, Methanol-$d_4$) δ 8.56-8.50 (m, 2H), 8.47-8.44 (m, 1H), 8.21-8.17 (m, 1H), 8.03-7.99 (m, 1H), 7.27-7.20 (m, 2H), 4.01 (s, 3H), 3.83 (q, J=7.2 Hz, 2H), 1.42 (t, J=7.2 Hz, 3H).

Step 3: 4-(Ethylamino)-2-(4-fluorophenyl)quinazoline-7-carboxylic acid

To a solution of methyl 4-(ethylamino)-2-(4-fluorophenyl)quinazoline-7-carboxylate (94.5 mg, 0.290 mmol) in THF (1.7 mL, 21 mmol) and methanol (1.7 mL, 42 mmol) at 5° C. was added 1.0 M of sodium hydroxide in water (0.87 mL, 0.87 mmol) and water (0.85 mL, 47 mmol). The resulting suspension was allowed to warm up to rt and stirred for 3 days. The reaction mixture was added to 30 ml of water and the mixture was acidified with 1M HCl to pH 2-3. The resulting slurry was filtered and the collected solid was washed with little water and dried under vacuum to give 4-(ethylamino)-2-(4-fluorophenyl)quinazoline-7-carboxylic acid (85 mg, 94%) as a white solid. LC-MS: (FA) ES+ 312.1; 1H NMR (400 MHz, DMSO-d6) δ 13.42 (s, 1H), 8.60-8.50 (m, 3H), 8.35 (d, J=8.5 Hz, 1H), 8.26 (d, J=1.5 Hz, 1H), 7.94 (dd, J=8.5, 1.5 Hz, 1H), 7.38-7.31 (m, 2H), 3.77-3.68 (m, 2H), 1.33 (t, J=7.2 Hz, 3H).

Step 4: 4-(Ethylamino)-2-(4-fluorophenyl)-N-[3-(1H-imidazol-2-yl)propyl]quinazoline-7-carboxamide To a mixture of 4-(ethylamino)-2-(4-fluorophenyl)quinazoline-7-carboxylic acid (83 mg, 0.27 mmol), 3-(1H-Imidazol-2-yl)propan-1-amine*2[HCl](68.6 mg, 0.346 mmol) and DIPEA (209 uL, 1.20 mmol) in dimethyl sulfoxide (0.99 mL, 14 mmol) was added HATU (112 mg, 0.293 mmol). The mixture was stirred for 2 h. The reaction mixture was quenched with 50 uL of water and stirred for 15 min. The mixture was then partitioned between 25 ml of diluted ammonia and 25 ml of EtOAc. The separated aqueous layer (some brine was added to help separation) was extracted with EtOAc (25 ml). Combined organic layers were washed with diluted ammonia (×2) and brine (×2), dried over $Na_2SO_4$ and concentrated. The product was purified on ISCO (12 g silica) using 0-10% MeOH/DCM over 25 min. Pure fractions were combined, concentrated and dried under vacuum to give 4-(ethylamino)-2-(4-fluorophenyl)-N-[3-(1H-imidazol-2-yl)propyl]quinazoline-7-carboxamide (77.5 mg, 69%) as a white solid. LC-MS: (FA) ES+ 419.2; 1H NMR (400 MHz, DMSO-d6) δ 11.71 (s, 1H), 8.95 (t, J=5.5 Hz, 1H), 8.58-8.51 (m, 2H), 8.48 (t, J=5.4 Hz, 1H), 8.32 (d, J=8.6 Hz, 1H), 8.25 (d, J=1.7 Hz, 1H), 7.88 (dd, J=8.5, 1.7 Hz, 1H), 7.38-7.31 (m, 2H), 6.99 (s, 1H), 6.78

(s, 1H), 3.76-3.67 (m, 2H), 3.40-3.33 (m, 2H), 2.70 (t, J=7.6 Hz, 2H), 1.98-1.89 (m, 2H), 1.33 (t, J=7.2 Hz, 3H).

The compounds listed in the table below were prepared in an analogous fashion to that described in Example 2 starting from the appropriate starting materials:

| Starting Material Step 2 | Compound No. or Name | LCMS Data |
|---|---|---|
|  | I-39* | LCMS (ESI+): m/z = 433.2 (M + H) |

*TBTU was used as coupling reagent in Step 4

Example 3: 2-(4-Fluorophenyl)-N-(imidazo[1,2-a]pyridin-6-ylmethyl)-4-propyl-quinazoline-7-carboxamide (I-34)

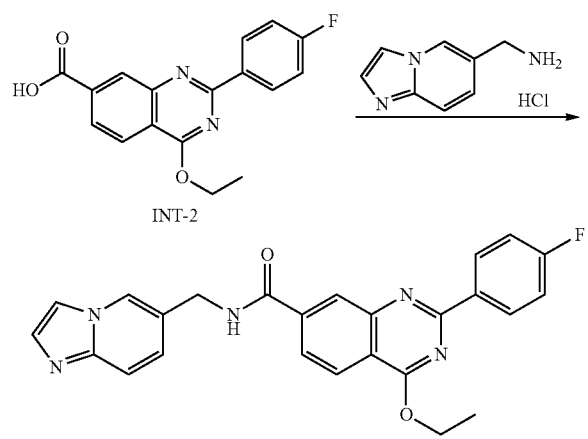

To a heterogeneous mixture of 4-ethoxy-2-(4-fluorophenyl)quinazoline-7-carboxylic acid (INT-2, described in Example 1; 94.0 mg, 0.301 mmol) and TBTU (116 mg, 0.361 mmol) in dimethyl sulfoxide (1.7 mL, 24 mmol) at rt, was added DIPEA (78.6 uL, 0.451 mmol). The mixture became homogeneous and was stirred for 5 min. (Imidazo[1,2-a]pyridin-6-yl)methylamine hydrochloride (76.0 mg, 0.414 mmol) and DIPEA (157 uL, 0.903 mmol) were added. The mixture was stirred at rt overnight. This reaction mixture was partitioned between EtOAc and 1M $K_2CO_3$ and stirred for 30 min. Separated organic layers was washed with brine ×2, dried over $Na_2SO_4$ and concentrated. The product was purified on ISCO (12 g silica) using 0-6% MeOH/DCM. Pertinent fractions were concentrated. The white solid residue was dried under vacuum at 45° C. overnight to give 4-ethoxy-2-(4-fluorophenyl)-N-(imidazo[1,2-a]pyridin-6-ylmethyl)quinazoline-7-carboxamide (56 mg; 42%). LC-MS: (FA) ES+ 442.1; 1H NMR (400 MHz, DMSO-$d_6$) δ 9.48 (t, J=5.8 Hz, 1H), 8.62-8.54 (m, 3H), 8.49-8.51 (m, 1H), 8.26-8.22 (m, 1H), 8.10-8.06 (m, 1H), 7.98 (s, 1H), 7.59-7.54 (m, 2H), 7.45-7.37 (t, 2H), 7.31-7.27 (m, 1H), 4.79 (q, J=7.1 Hz, 2H), 4.55 (d, J=5.8 Hz, 2H), 1.54 (t, J=7.1 Hz, 3H).

The compounds listed in the table below were prepared in an analogous fashion to that described in Example 3 starting from the appropriate starting materials:

| Starting Material Step 1 | Compound No. or Name | LCMS Data |
|---|---|---|
| 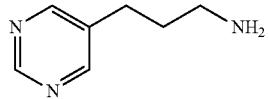 | I-19* | LCMS (ESI+): m/z = 432.2 (M + H) |
| 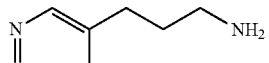 | I-29* | LCMS (ESI+): m/z = 432.2 (M + H) |

*HATU used as coupling reagent, TEA used as base

Example 4: 2-(5-chloro-2-thienyl)-4-ethoxy-N-[3-(1H-imidazol-2-yl)propyl]quinazoline-7-carboxamide (I-35)

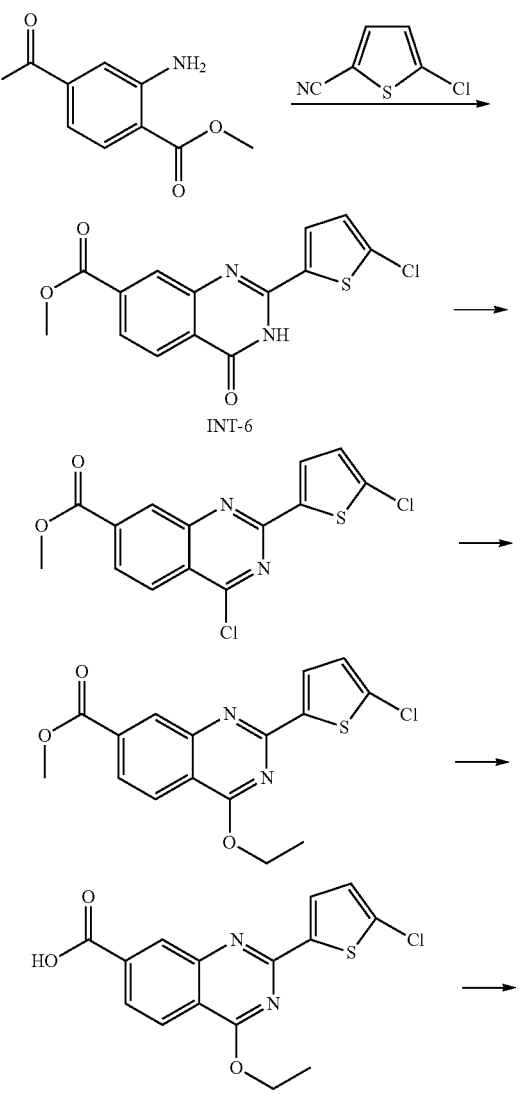

-continued

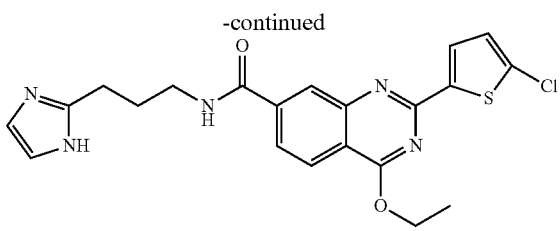

Step 1: Methyl 2-(5-chloro-2-thienyl)-4-oxo-3,4-dihydroquinazoline-7-carboxylate (INT-6)

In a 75 mL pressure tube was loaded methyl 2-amino-4-carbomethoxybenzoate (2.91 g, 13.9 mmol) and 2-chloro-5-cyanothiophene (2.00 g, 13.9 mmol). 4 M of hydrochloric acid in 1,4-dioxane (30.0 mL, 118 mmol) was added. The tube was capped and stirred at rt for 1.5 h. The thick suspension was heated to 100° C. (oil bath) for 15 h with a safety shield. The mixture was cooled to rt, filtered and the cake was washed with EtOH (2 mL×2) then dried in vacuum pump to give methyl 2-(5-chloro-2-thienyl)-4-oxo-3,4-dihydroquinazoline-7-carboxylate as an off-white product (3.38 g, 71%). UPLC-MS/5 min: (FA) ES+ 321.1; $^1$H NMR (400 MHz, CDCl$_3$ plus Methanol-d$_4$) δ 8.54-8.48 (m, 1H), 8.23 (d, J=8.3 Hz, 1H), 8.03 (dd, J=8.3, 1.5 Hz, 1H), 7.90 (d, J=4.2 Hz, 1H), 7.00 (d, J=4.2 Hz, 1H), 3.94 (s, 3H).

Step 2: Methyl 4-chloro-2-(5-chloro-2-thienyl)quinazoline-7-carboxylate

To a suspension of methyl 2-(5-chloro-2-thienyl)-4-oxo-3,4-dihydroquinazoline-7-carboxylate (1.38 g, 4.04 mmol) in anhydrous toluene (5.0 mL, 47 mmol) was added thionyl chloride (5.0 mL, 68 mmol), followed by DMF (20 uL, 0.2 mmol). The suspension was heated to reflux (110° C. heating block) for 0.5 h and the suspension turned into a clear orange solution. The mixture was cooled to rt and turned back to a yellow suspension. The mixture was filtered, and the cake was washed with hexane, dried in vacuum pump to give methyl 4-chloro-2-(5-chloro-2-thienyl)quinazoline-7-carboxylate as a yellow solid product. (1.29 g, 92%). UPLC-MS/5 min: (FA) ES+ 339.0; $^1$H NMR (400 MHz, CDCl$_3$) δ 8.84 (s, 1H), 8.29 (d, J=8.6 Hz, 1H), 8.23 (dd, J=8.7, 1.4 Hz, 1H), 8.20 (d, J=4.0 Hz, 1H), 7.05 (d, J=4.1 Hz, 1H), 4.03 (s, 3H).

Step 3: Methyl 2-(5-chloro-2-thienyl)-4-ethoxyquinazoline-7-carboxylate

Methyl 4-chloro-2-(5-chloro-2-thienyl)quinazoline-7-carboxylate (0.72 g, 2.1 mmol) was suspended in ethanol (10.0 mL, 171 mmol). DIPEA (0.47 mL, 2.7 mmol) was added and the mixture was heated to reflux (95° C., heating block) overnight. The second portions of DIPEA (0.30 mL, 1.7 mmol) and ethanol (5.0 mL, 86 mmol) were added. The mixture was kept refluxing for 23 h. The mixture was cooled to rt. The suspension was filtered and the cake was washed with EtOH (3 mL×2). The filtrate was concentrated in vacuo and the residue was dissolved in DCM, washed with water (3×) then brine, dried over anhydrous Na$_2$SO$_4$, filtered and concentrated. The crude material was chromatographed on a 24 g silica column using EtOAc/hexane (0/100 to 10/90) to give a white solid product but only 40 mg. The product was combined with the solid from filtration (0.44 g), chromatographed in a 40 g silica column using EtOAc/hexane (0/100 to 5/95) and afforded methyl 2-(5-chloro-2-thienyl)-4-ethoxyquinazoline-7-carboxylate as a white solid product (0.295 g, 39%). UPLC-MS/5 min: (FA) ES+ 349.1; $^1$H NMR (400 MHz, CDCl$_3$) δ 8.57 (s, 1H), 8.17 (d, J=8.5 Hz, 1H), 8.06 (dd, J=8.5, 1.5 Hz, 1H), 7.87 (d, J=3.7 Hz, 1H), 6.98 (d, J=4.0 Hz, 1H), 4.71 (q, J=7.1 Hz, 2H), 4.00 (s, 3H), 1.59-1.53 (m, 3H).

Step 4: 2-(5-Chloro-2-thienyl)-4-ethoxyquinazoline-7-carboxylic acid

Methyl 2-(5-chloro-2-thienyl)-4-ethoxyquinazoline-7-carboxylate (0.295 g, 0.846 mmol) was dissolved in THF (10 mL). 1.0 M of sodium hydroxide in water (2.00 mL, 2.00 mmol) was added, followed by water (2.0 mL). The bi-layer solution was stirred at rt for 2 h and turned into a white suspension. The mixture was cooled with an ice bath, neutralized with 1.00 M of hydrochloric acid in water (2.15 mL, 2.15 mmol) to pH ~2.5. The resulting solution was concentrated in vacuo to give an aqueous suspension. 10 mL of EtOAc was added however most of the white solid was not soluble in the bi-layer solvent. The suspension was filtered and the cake was washed with EtOAc then hexane, dried in vacuo to give the first crop of 2-(5-chloro-2-thienyl)-4-ethoxyquinazoline-7-carboxylic acid as a solid product (0.177 g). The filtrate was separated and the aqueous layer was extracted with EtOAc (20 mL×2). The combined EtOAc solution was dried over anhydrous Na$_2$SO$_4$, filtered and the filtrated was concentrated in rotavapor then dried in vacuum pump to give the second crop of solid product (0.109 g, yield from combined crops was 100%). UPLC-MS/1.5 min: (FA) ES+ 335.1. $^1$H NMR (400 MHz, CDCl$_3$+ MeOH-d$_4$) δ 8.91 (s, 1H), 8.45 (s, 1H), 8.15 (q, J=8.5 Hz, 2H), 7.04 (d, J=4.1 Hz, 1H), 4.75 (q, J=7.1 Hz, 2H), 1.55 (t, J=7.1 Hz, 3H).

Step 5: 2-(5-Chloro-2-thienyl)-4-ethoxy-N-[3-(1H-imidazol-2-yl)propyl]quinazoline-7-carboxamide (I-35)

2-(5-Chloro-2-thienyl)-4-ethoxyquinazoline-7-carboxylic acid (0.108 g, 0.323 mmol) was partially dissolved in DCM (8.0 mL). 2.0 M of oxalyl chloride in DCM (0.210 mL, 0.419 mmol) was added, followed by DMF (2.50 uL, 0.0323 mmol). The mixture was stirred at rt under nitrogen atmosphere for 30 min. To the resulting pale orange solution 3-(1H-imidazol-2-yl)-1-propanamine.2HCl (95.8 mg, 0.484 mmol) was added, followed by addition of DIPEA (0.350 mL, 2.01 mmol) dropwise. The resulted brown solution was stirred at rt under a nitrogen atmosphere overnight. The mixture was quenched with 15 mL of water, extracted with 5% MeOH/DCM (50 mL, 10 mL×2). The combined DCM solution was washed with brine, dried over anhydrous Na$_2$SO$_4$, filtered. The filtrate was evaporated in vacuo to give a crude product. The crude product was chromatographed on a 24 g silica column using MeOH/DCM (0/100 to 10/90) to afford 2-(5-chloro-2-thienyl)-4-ethoxy-N-[3-(1H-imidazol-2-yl)propyl]quinazoline-7-carboxamide as an off-white solid product (88.1 mg, 61%). UPLC-MS/5 min: (FA) ES+ 442.1. $^1$H NMR (400 MHz, Methanol-d4) δ 8.26 (d, J=1.2 Hz, 1H), 8.20 (d, J=8.5 Hz, 1H), 7.92 (dd, J=8.5, 1.7 Hz, 1H), 7.88 (d, J=4.0 Hz, 1H), 7.07 (d, J=4.0 Hz, 1H), 6.95 (s, 2H), 4.74 (q, J=7.1 Hz, 2H), 3.47 (t, J=6.8 Hz, 2H), 2.84 (t, J=7.5 Hz, 2H), 2.05 (p, J=7.1 Hz, 2H), 1.57 (t, J=7.1 Hz, 3H).

The compounds listed in the table below were prepared in an analogous fashion to that described in Example 4 starting from the appropriate starting materials:

| Starting Material Step 5 | Compound No. or Name | LCMS Data |
|---|---|---|
| imidazo[1,2-a]pyridine-6-CH2NH2 | I-28 | LCMS (ESI+): m/z = 462.2 (M + H) |

Example 5: N-(3-(1H-imidazol-2-yl)propyl)-4-(ethylthio)-2-(4-fluorophenyl)quinazoline-7-carboxamide (I-27)

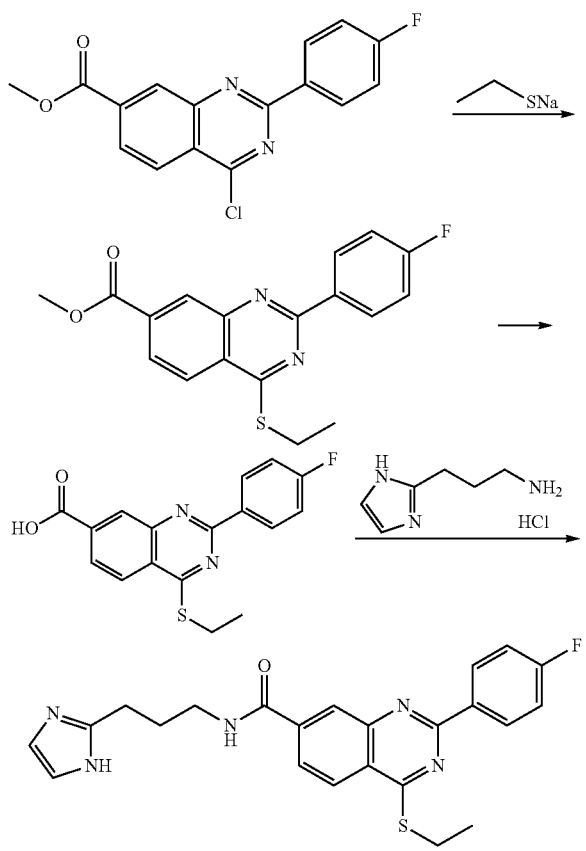

Step 1: Methyl 4-(ethylthio)-2-(4-fluorophenyl)quinazoline-7-carboxylate

A vial was charged with methyl 4-chloro-2-(4-fluorophenyl)quinazoline-7-carboxylate (INT-3, described in Example 2; 65.0 mg, 0.205 mmol) and sodium ethanethiolate (25.9 mg, 0.308 mmol) and DMF (2 mL). The reaction mixture was stirred at rt for 1 h. Water was added, a solid precipitated out of solution and the solid was collected by filtration. The solid was washed with water then dried to give methyl 4-(ethylthio)-2-(4-fluorophenyl)quinazoline-7-carboxylate (69 mg, 98%). LC-MS: (FA) ES+ 343.1

Step 2: 4-(Ethylthio)-2-(4-fluorophenyl)quinazoline-7-carboxylic acid

To a solution of methyl 4-(ethylthio)-2-(4-fluorophenyl)quinazoline-7-carboxylate (67 mg, 0.196 mmol) in THF (2.2 mL) was added 1.0 M of sodium hydroxide in water (3.0 mL) at rt, then the reaction mixture was heated up to 50° C. until the mixture went into solution. The reaction was acidified with 1N HCl to pH 3-4. A solid precipitated out of solution. The solid was collected by filtration. The solid was washed with water, then dried to give 4-(ethylthio)-2-(4-fluorophenyl)quinazoline-7-carboxylic acid (57 mg, 89%). LC-MS: (FA) ES+ 329.1 1H NMR (400 MHz, DMSO-d$_6$) δ 13.69 (s, 1H), 8.68 (m, 5.8 Hz, 2H), 8.52 (s, 1H), 8.28-8.12 (m, 2H), 7.48 (m, 2H), 3.58 (q, J=7.3 Hz, 2H), 1.55 (t, J=7.3 Hz, 3H).

Step 3: N-(3-(1H-imidazol-2-yl)propyl)-4-(ethylthio)-2-(4-fluorophenyl)quinazoline-7-carboxamide To a solution of 4-(ethylthio)-2-(4-fluorophenyl)quinazoline-7-carboxylic acid (57.0 mg, 0.174 mmol) in THF (0.634 mL), 3-(1H-Imidazol-2-yl)propan-1-amine.2[HCl] (51.6 mg, 0.260 mmol), TBTU (72.6 mg, 0.191 mmol) and TEA (121 uL, 0.868 mmol) was added at rt. The reaction mixture was stirred at rt for about 1 h. The mixture was added to 10 ml of water and a solid precipitated out of solution, filtered and collected. The crude solid was purified by HPLC to afford N-(3-(1H-imidazol-2-yl)propyl)-4-(ethylthio)-2-(4-fluorophenyl)quinazoline-7-carboxamide (39 mg, 52%) was obtained. LC-MS: (FA) ES+ 436.1 1H NMR (400 MHz, DMSO-d6) δ 9.11 (br s, 1H) 8.63 (br dd, J=8.22, 5.96 Hz, 2H) 8.48 (s, 1H) 8.17 (br d, J=8.16 Hz, 1H) 8.07 (br d, J=8.28 Hz, 1H) 7.44 (br t, J=8.72 Hz, 2H) 6.90 (s, 2H) 3.53 (m, 2H) 3.34-3.44 (m, 2H) 2.73 (m, 2H) 1.90-2.02 (m, 2H) 1.50 (t, J=7.22 Hz, 3H)

Example 6: N-(3-(1H-imidazol-2-yl)-2-methylpropyl)-4-ethoxy-2-(4-fluorophenyl)quinazoline-7-carboxamide (I-18)

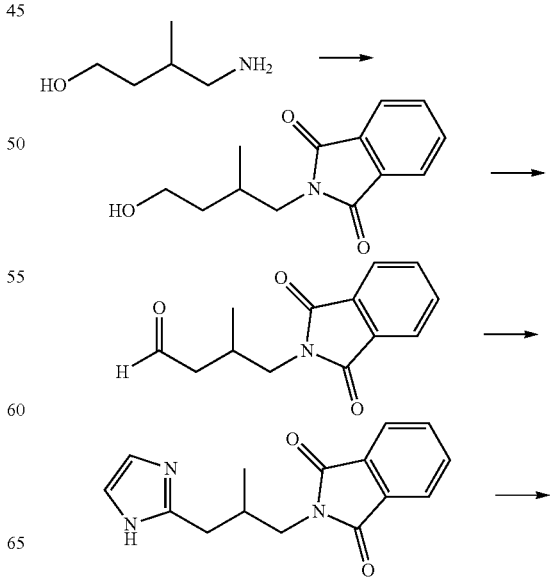

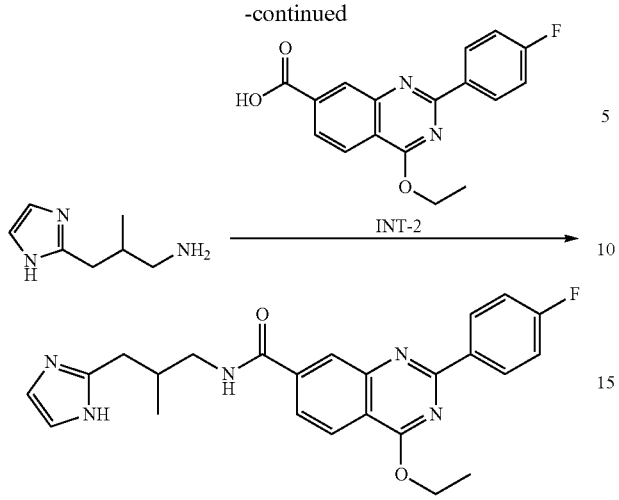

Step 1: 2-(4-Hydroxy-2-methylbutyl)isoindoline-1,3-dione

To a solution of 4-amino-3-methylbutan-1-ol (402 mg, 3.90 mmol) in toluene (8.5 mL) was added phthalic anhydride (577 mg, 3.90 mmol). The mixture was refluxed for 4 h and water was collected in a Dean Stark trap. The reaction mixture was then cooled and concentrated in vacuo. Purification by silica gel chromatography gave 2-(4-hydroxy-2-methylbutyl)isoindoline-1,3-dione (909 mg, 82%). $^1$H NMR (400 MHz, CDCl$_3$) δ 7.80-7.75 (m, 2H), 7.67-7.63 (m, 2H), 3.76-3.47 (m, 4H), 2.12-2.03 (m, 1H), 1.62-1.55 (m, 1H), 1.44-1.35 (m, 1H), 0.90 (d, J=6.8 Hz, 3H).

Step 2: 4-(1,3-Dioxoisoindolin-2-yl)-3-methylbutanal

To a solution of oxalyl chloride (319 uL, 3.77 mmol) in DCM (9.7 mL) in a dry ice/acetone bath was added a solution of DMSO (568 uL, 8.00 mmol) in DCM (2.4 mL), while keeping the internal temperature below −60° C. A solution of 2-(4-hydroxy-2-methylbutyl)isoindoline-1,3-dione (704 mg, 3.02 mmol) in DCM (4.8 mL) was then added over 5 min, and the resulting solution was stirred for 25 min. TEA (2.31 mL, 16.6 mmol) was then added, and the reaction was allowed to warm to rt. Water (12 mL) was added, the layers were separated, and the aqueous layer was extracted with DCM (10 mL). The combined organic layers were washed with water (5 mL) and brine (5 mL), and the organic layer was dried and concentrated in vacuo. Silica gel chromatography gave 4-(1,3-dioxoisoindolin-2-yl)-3-methylbutanal (568 mg, 81%). $^1$H NMR (400 MHz, CDCl$_3$) δ 9.75 (t, J=1.6 Hz, 1H), 7.89-7.85 (m, 2H), 7.77-7.73 (m, 2H), 3.68-3.60 (m, 2H), 2.68-2.53 (m, 2H), 2.39-2.32 (m, 1H), 1.04 (d, J=6.8 Hz, 3 H).

Step 3: 2-(3-(1H-Imidazol-2-yl)-2-methylpropyl)isoindoline-1,3-dione

To a solution of 4-(1,3-dioxoisoindolin-2-yl)-3-methylbutanal (128 mg, 0.554 mmol) in IPA (3.0 mL) was added water (3.0 mL), ammonium bicarbonate (612 mg, 7.74 mmol) and a 7 M solution of ethanedial in water (562 uL, 3.87 mmol). The resulting solution was stirred at rt overnight. DCM (25 mL) and water (3.0 mL) were added and the layers were separated. The aqueous layer was extracted twice with DCM. The combined organic layers were dried and concentrated in vacuo to give 2-(3-(1H-imidazol-2-yl)-2-methylpropyl)isoindoline-1,3-dione (149 mg, 63%). LCMS (ESI+): m/z=270.1 (M+H). $^1$H NMR (400 MHz, DMSO-d$_6$) δ 11.65 (s, 1H), 7.88-7.82 (m, 4H), 6.92 (s, 1H), 6.69 (s, 1H), 3.56-3.47 (m, 2H), 2.69-2.64 (m, 1H), 2.47-2.41 (m, 1H), 2.37-2.28 (m, 1H), 0.81 (d, J=6.8 Hz, 3H).

Step 4: 3-(1H-Imidazol-2-yl)-2-methylpropan-1-amine

To a solution of 2-(3-(1H-imidazol-2-yl)-2-methylpropyl)isoindoline-1,3-dione (54 mg, 0.20 mmol) in ethanol (3.0 mL) was added hydrazine (19 uL, 0.60 mmol) and the resulting solution was heated to 80° C. for 3 h. The mixture was cooled, filtered, and concentrated in vacuo to give 3-(1H-imidazol-2-yl)-2-methylpropan-1-amine (28 mg, 100%) as a crude product which was used without purification in the next step.

Step 5: N-(3-(1H-Imidazol-2-yl)-2-methylpropyl)-4-ethoxy-2-(4-fluorophenyl)quinazoline-7-carboxamide (I-18)

To a solution of 3-(1H-imidazol-2-yl)-2-methylpropan-1-amine (28 mg, 0.20 mmol) in THF (1.0 mL) and DMF (1.0 mL) was added 4-ethoxy-2-(4-fluorophenyl)quinazoline-7-carboxylic acid (INT-2 described in Example 1) (48 mg, 0.15 mmol), TEA (86.0 uL, 0.617 mmol), and N, N, N', N'-tetramethyl-O-(7-azabenzotriazol-1-yl)uranium hexafluorophosphate (HATU) (101 mg, 0.265 mmol) and the resulting mixture was stirred overnight at rt. To the reaction was added EtOAc (10 mL) and water (5 mL). The layers were separated and the aqueous layer was extracted with EtOAc (10 mL). The combined organic layers were washed twice with water (5 mL), and brine (5 mL), then dried and concentrated in vacuo. HPLC purification gave N-(3-(1H-imidazol-2-yl)-2-methylpropyl)-4-ethoxy-2-(4-fluorophenyl)quinazoline-7-carboxamide (4 mg, 6%). LCMS (ESI+): m/z=434.2 (M+H). $^1$H NMR (400 MHz, DMSO-d$_6$) δ 8.65-8.60 (m, 2H), 8.40 (d, J=1.2 Hz, 1H), 8.29 (d, J=8.4 Hz, 1H), 7.99 (dd, J=8.4, 1.6 Hz, 1H), 7.30-7.24 (m, 2H), 7.17 (s, 2H), 4.87-4.82 (m, 2H), 3.42 (dd, J=6.4, 4.4 Hz, 2H), 2.99 (dd, J=14.8, 6.4 Hz, 1H), 2.77 (dd, J=14.8, 8.0 Hz, 1H), 2.38-2.31 (m, 1H), 1.61 (t, J=6.8 Hz, 3 H), 1.02 (d, J=6.8 Hz, 3H).

Example 7: 2-(4-Chlorophenyl)-4-ethyl-N-[3-(1H-imidazol-2-yl)propyl]quinazoline-7-carboxamide (I-33)

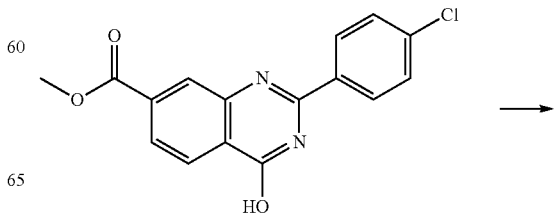

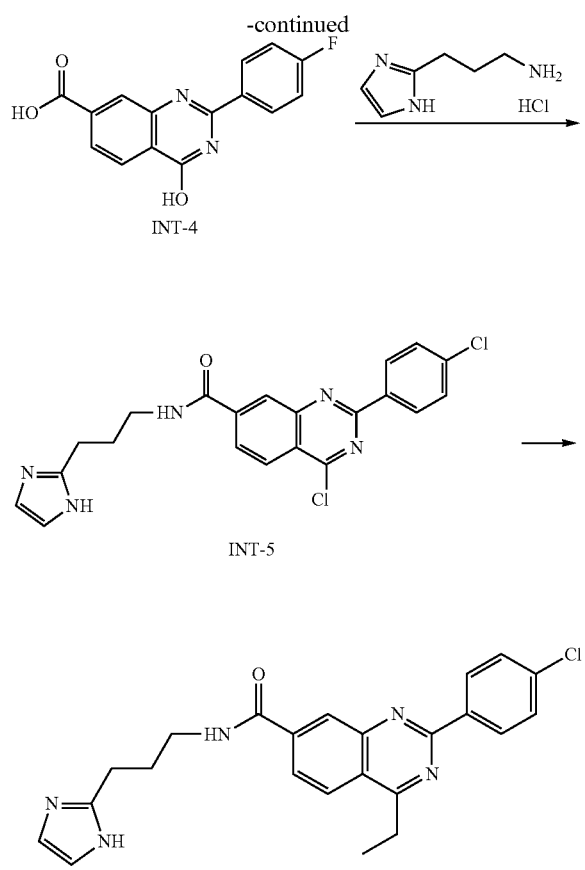

Step 1: 2-(4-Chlorophenyl)-4-hydroxy-quinazoline-7-carboxylic acid (INT-4)

To a solution of methyl 2-(4-chlorophenyl)-4-hydroxy-quinazoline-7-carboxylate (prepared similarly to INT-1 described in Example 1, Step 1, using 4-chlorobenzonitrile) (5.0 g, 16 mmol) in THF (130 ml, 1600 mmol) cooled in ice bath was added 1.0 M of sodium hydroxide in water (40 mL, 40 mmol). The resulting suspension was stirred at 35° C. for 3 h. The mixture was added to 100 ml of water. The resulting solution was acidified with 1 M HCl to pH ~2. The white solid that precipitated was collected by filtration and was dried under high vacuum to give 2-(4-chlorophenyl)-4-hydroxy-quinazoline-7-carboxylic acid (4.73 g; 99%) as white solid. LCMS (ESI+): m/z=301.1 (M+H). $^1$H NMR (400 MHz, DMSO-d6) δ 8.34-8.24 (m, 4H), 8.07 (d, J=8.2 Hz, 1H), 7.72 (d, J=8.7 Hz, 2H).

Step 2: 4-Chloro-2-(4-chlorophenyl)-N-[3-(1H-imidazol-2-yl)propyl]quinazoline-7-carboxamide (INT-5)

To a suspension of 2-(4-chlorophenyl)-4-hydroxy-quinazoline-7-carboxylic acid (1.90 g, 6.32 mmol) in thionyl chloride (4.61 mL, 63.2 mmol) was added ~5 drops of DMF. The mixture was then stirred at reflux for 1 h, cooled to rt, and evaporated solvent, and dried on hi-vacuum for 2 h to afford crude 4-chloro-2-(4-chlorophenyl)quinazoline-7-carbonyl chloride as yellow solid. The solid was dissolved in the mixture of THF (51.2 mL, 632 mmol) and DMF (7.34 mL, 94.8 mmol), followed by the solution of TEA (2.64 mL, 19.0 mmol), and 3-(1H-imidazol-2-yl)-1-propanamine 2HCl (1.44 g, 7.27 mmol) in DMF (9.78 mL, 126 mmol). The mixture was stirred at rt for overnight. Half of the volume of solvent was removed by rotovap, and the remaining solvent was diluted with water, and a precipitate formed. The resulting slurry was filtered and the collected solid was washed with a little water and dried under vacuum to give 4-chloro-2-(4-chlorophenyl)-N-[3-(1H-imidazol-2-yl)propyl]quinazoline-7-carboxamide (2.30 g; 85%) as yellow solid. LCMS (ESI+): m/z=426.3 (M+H). $^1$H NMR (400 MHz, DMSO-d$_6$) δ 9.21 (s, 1H), 8.62 (s, 1H), 8.52 (d, J=8.7 Hz, 2H), 8.39 (d, J=8.6 Hz, 1H), 8.24 (d, J=8.6 Hz, 1H), 8.15 (s, 1H), 7.70 (d, J=8.6 Hz, 2H), 6.91 (s, 2H), 3.41 (q, J=6.5 Hz, 2H), 2.73 (t, J=7.5 Hz, 2H), 2.07-1.82 (m, 2H)

Step 3: 2-(4-Chlorophenyl)-4-ethyl-N-[3-(1H-imidazol-2-yl)propyl]quinazoline-7-carboxamide (I-33)

To a suspension of 4-chloro-2-(4-chlorophenyl)-N-[3-(1H-imidazol-2-yl)propyl]quinazoline-7-carboxamide (60 mg, 0.10 mmol), acetylacetone iron (III) salt (4.90 mg, 0.0140 mmol) in THF (1 mL, 20 mmol) was added 2.0 M ethylmagnesium chloride in THF (0.350 mL, 0.70 mmol) dropwise over 10 min at −10° C. (bath) and stirred for overnight. The reaction mixture was quenched by water, and extracted with EtOAc 3×30 ml, washed with brine, dried, and concentrated. Purification by HPLC provided 2-(4-chlorophenyl)-4-ethyl-N-[3-(1H-imidazol-2-yl)propyl]quinazoline-7-carboxamide (14.0 mg; 20%) as formic acid salt. LCMS (ESI+): m/z=420.2 (M+H). $^1$H NMR (400 MHz, DMSO-d$_6$) δ=9.11 (brt, J=5.3 Hz, 1H), 8.65-8.58 (m, 2H), 8.54 (d, J=1.4 Hz, 1H), 8.43 (d, J=8.5 Hz, 1H), 8.17 (s, 1H), 8.11 (dd, J=1.6, 8.5 Hz, 1H), 7.67 (d, J=8.7 Hz, 2H), 6.91 (s, 2H), 3.50-3.31 (m, 4H), 2.73 (t, J=7.5 Hz, 2H), 1.97 (br t, J=7.2 Hz, 2H), 1.47 (t, J=7.4 Hz, 3H)

The compounds listed in the table below were prepared in an analogous fashion to that described in Example 7 starting from the appropriate starting materials:

| Starting Material Step 1 | Starting Material Step 3 | Compound No. or Name | LCMS Data |
| --- | --- | --- | --- |
| INT-1 | ![isobutyl-MgCl] | I-21 | LCMS (ESI+): m/z = 448.3 (M + H) |
| INT-1 | ![cyclopropyl-MgBr] | I-31 | LCMS (ESI+): m/z = 432.2 (M + H) |
| INT-4* | MeMgCl | I-63 | LCMS (ESI+): m/z = 407.1 (M + H) |

*3-(4H-1,2,4-triazol-3-yl)propanamine HCl was used in Step 2

Example 8: 2-(4-Chlorophenyl)-N-[3-(1H-imidazol-2-yl)propyl]-4-(methoxymethyl)quinazoline-7-carboxamide (I-25)

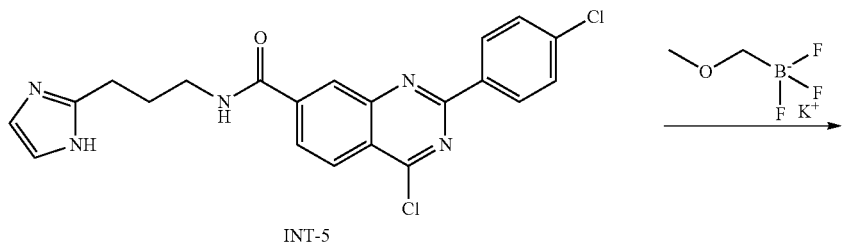

INT-5

4-Chloro-2-(4-chlorophenyl)-N-[3-(1H-imidazol-2-yl)propyl]quinazoline-7-carboxamide (200 mg, 0.0005 mol) (INT-5 described in Example 7), potassiummethoxymethyltrifluoroborate (214 mg, 0.00141 mol) dicesium carbonate (458 mg, 0.00141 mol) and SiliaCat® DPP-Pd(0.260 mmol/g loading; 361 mg, 0.0000938 mol) were weighed into a 2-5 mL microwave vial purged with nitrogen 5 min then added 1,4-dioxane (7.65 mL, 0.0980 mol) and water (1.69 mL, 0.0938 mol). The mixture was heated at 155° C. for 80 min under microwave irradiation. After cooling, the reaction mixture was poured into EtOAc and water. The layers were separated and the aqueous layer was extracted two more times with EtOAc. The combined organic layer was dried over anhydrous $MgSO_4$ and concentrated in vacuo, and purified by HPLC to give 2-(4-chlorophenyl)-N-[3-(1H-imidazol-2-yl)propyl]-4-(methoxymethyl)quinazoline-7-carboxamide (20.0 mg, 10%) as a white solid. LCMS (ESI+): m/z=436.2 (M+H). $^1$H NMR (400 MHz, DMSO-$d_6$) δ 9.12 (s, 1H), 8.63-8.56 (m, 3H), 8.45 (d, J=8.6 Hz, 1H), 8.16 (s, 1H), 8.13 (d, J=8.7 Hz, 1H), 7.68 (d, J=8.6 Hz, 2H), 6.91 (s, 2H), 5.13 (s, 2H), 3.48 (s, 3H), 3.32-3.44 (m, 2H), 2.73 (t, J=7.5 Hz, 2H), 2.01-1.93 (m, 2H).

The compounds listed in the table below were prepared in an analogous fashion to that described in Example 8 starting from the appropriate starting materials:

| Reagent Step 1 | Compound No. or Name | LCMS Data |
|---|---|---|
| ethoxymethyl trifluoroborate | I-20 | LCMS (ESI+): m/z = 450.2 (M + H) |
| thiomorpholinomethyl trifluoroborate | I-26 | LCMS (ESI+): m/z = 507.2 (M + H) |
| tert-butoxymethyl trifluoroborate | I-30 | LCMS (ESI+): m/z = 478.2 (M + H) |

Example 9: 2-(5-Chloro-2-thienyl)-4-ethyl-N-[3-(1H-imidazol-2-yl)propyl]quinazoline-7-carboxamide (I-22)

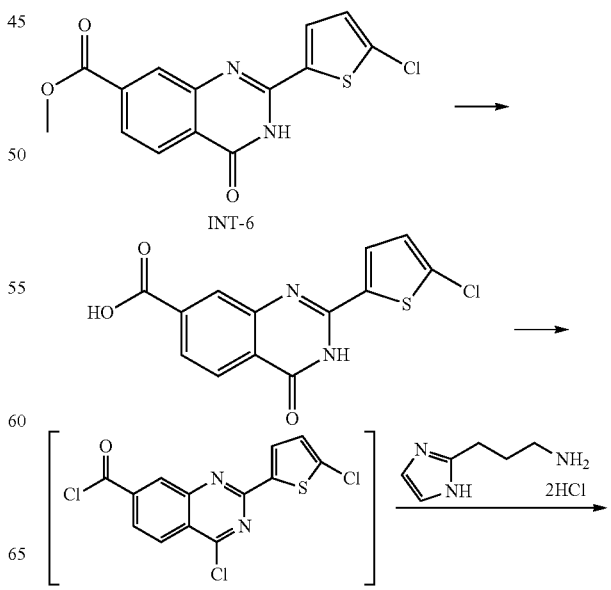

INT-6

-continued

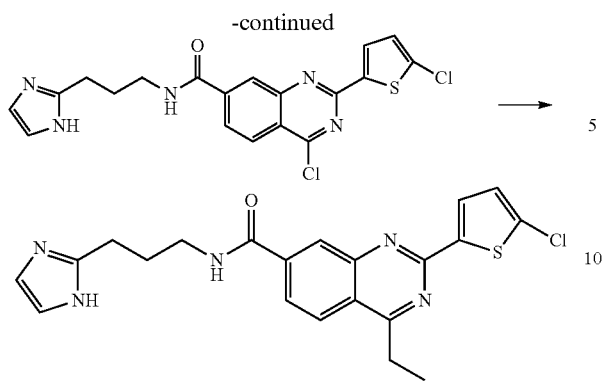

Step 1: 2-(5-Chloro-2-thienyl)-4-oxo-3,4-dihydroquinazoline-7-carboxylic acid Methyl 2-(5-chloro-2-thienyl)-4-oxo-3,4-dihydroquinazoline-7-carboxylate (1.99 g, 6.20 mmol) (INT-6 described in Example 4) was suspended in THF (40 mL). 1.0 M of sodium hydroxide in water (12.5 mL, 12.5 mmol) was added and the resulted bi-layer cloudy solution was stirred at rt for 22 h. To the single layer solution was added 1.0 M of sodium hydroxide in water (12.5 mL, 12.5 mmol) and the cloudy solution was stirred at rt for 6 h. UPLC-MS showed conversion completed. The mixture was cooled with an ice bath, acidified with 1.00 M of hydrochloric acid in water (25 mL, 25 mmol) to pH ~2. The resulting pale yellow solid was collected by filtration and washed with water, dried in air overnight then in lyophilizer for 5 h to give 2-(5-chloro-2-thienyl)-4-oxo-3,4-dihydroquinazoline-7-carboxylic acid (1.85 g, 97%). UPLC-MS/1.5 min: (FA) ES−: 305.0. $^1$H NMR (400 MHz, DMSO-$d_6$) δ 12.89 (s, 1H), 8.20 (d, J=8.2 Hz, 1H), 8.12 (d, J=4.1 Hz, 1H), 8.08 (s, 1H), 7.95 (dd, J=8.2, 1.6 Hz, 1H), 7.30 (d, J=4.1 Hz, 1H).

Step 2: 4-Chloro-2-(5-chloro-2-thienyl)-N-[3-(1H-imidazol-2-yl)propyl]quinazoline-7-carboxamide A mixture of 2-(5-chloro-2-thienyl)-4-oxo-3,4-dihydroquinazoline-7-carboxylic acid (1.00 g, 3.26 mmol), thionyl chloride (8.0 mL, 110 mmol), DMF (0.050 mL, 0.64 mmol) in DCM (5.0 mL) was heated to reflux (95° C., heating block) for 1 h, cooled to rt overnight. The mixture became a yellow suspension. The suspension was rotavaped and azeotroped with anhydrous DCM to give a yellow solid intermediate 4-chloro-2-(5-chloro-2-thienyl)quinazoline-7-carbonyl chloride (1.09 g, crude 97%).

A mixture of the intermediate 4-chloro-2-(5-chloro-2-thienyl)quinazoline-7-carbonyl chloride (0.802 g, 3.17 mmol) and 3-(1H-imidazol-2-yl)-1-propanamine 2HCl (0.465 g, 2.35 mmol) were suspended in anhydrous DCM (10 mL, 200 mmol). DIPEA (1.70 mL, 9.78 mmol) was added and the resulted pale brown solution was stirred at rt for 1 h and the mixture turned into a pale orange suspension. The suspension was filtered and the solid was washed with DCM (3 mL×4), dried in vacuum pump to give the first crop of 4-chloro-2-(5-chloro-2-thienyl)-N-[3-(1H-imidazol-2-yl)propyl]quinazoline-7-carboxamide (0.633 g). The filtrate was diluted with DCM (30 mL) and water (70 mL) to give a bilayer suspension, filtered and washed with DCM, dried in vacuo to give the second crop of product (0.134 g, combined yield from both crops was 52%). UPLC-MS/5 min: (FA) ES+ 432.1. $^1$H NMR (400 MHz, DMSO-d6) δ 9.19 (t, J=5.3 Hz, 1H), 8.51 (s, 1H), 8.32 (d, J=8.7 Hz, 1H), 8.18 (d, J=8.7 Hz, 1H), 7.94 (d, J=3.9 Hz, 1H), 7.32 (d, J=4.0 Hz, 1H), 6.91 (d, J=4.8 Hz, 2H), 3.38 (d, J=6.2 Hz, 2H), 2.72 (t, J=7.4 Hz, 2H), 2.00-1.92 (m, 2H).

Step 3: 2-(5-Chloro-2-thienyl)-4-ethyl-N-[3-(1H-imidazol-2-yl)propyl]quinazoline-7-carboxamide (I-22)

A pale yellow suspension of 4-chloro-2-(5-chloro-2-thienyl)-N-[3-(1H-imidazol-2-yl)propyl]quinazoline-7-carboxamide (129 mg, 0.298 mmol) and ferric acetylacetonate (10.5 mg, 0.0298 mmol) in anhydrous THF (8.0 mL, 99 mmol) was cooled with an ice-brine bath (−5° C.). 2.0 M of ethylmagnesium chloride in ether (1.20 mL, 2.40 mmol) (already a white suspension) was dropwise added over 3 min. The suspension turned into a black-grey cloudy solution and was stirred with cooling for 5 min. The mixture turned into a brown solution and was quenched with aqueous saturated NH$_4$Cl solution (10 mL), and extracted with EtOAc (20 mL×4). The combined EtOAc solution was washed with brine, dried over anhydrous Na$_2$SO$_4$, filtered and evaporated in vacuo to give a crude product (114 mg). The crude product was submitted to HPLC purification. 2-(5-Chloro-2-thienyl)-4-ethyl-N-[3-(1H-imidazol-2-yl)propyl]quinazoline-7-carboxamide was obtained as a powder as a formic acid salt (48.0 mg, 34%). HPLC-MS/20 min: (FA) ES+ 426.1. $^1$H NMR (400 MHz, Methanol-$d_4$) δ 8.42 (s, 1H), 8.36-8.32 (m, 1H), 8.28 (d, J=8.6 Hz, 1H), 7.98 (dd, J=8.6, 1.5 Hz, 1H), 7.91 (d, J=4.0 Hz, 1H), 7.20 (s, 2H), 7.07 (d, J=4.0 Hz, 1H), 3.51 (t, J=6.8 Hz, 2H), 3.36 (q, J=7.5 Hz, 2H), 2.97 (t, J=7.5 Hz, 2H), 2.10 (p, J=6.9 Hz, 2H), 1.48 (t, J=7.4 Hz, 3H).

The compounds listed in the table below were prepared in an analogous fashion to that described in Example 9 starting from the appropriate starting materials:

| Starting Material Step 3 | Compound No. or Name | LCMS Data |
|---|---|---|
| ![](MgCl isobutyl) | I-23 | LCMS (ESI+): m/z = 454.0 (M + H) |
| ![](MgCl propyl) | I-24 | LCMS (ESI+): m/z = 440.1 (M + H) |

Example 10 2-(4-Chlorophenyl)-N-[3-(1H-imidazol-2-yl)propyl]-4-propylquinazoline-7-carboxamide (I-4)

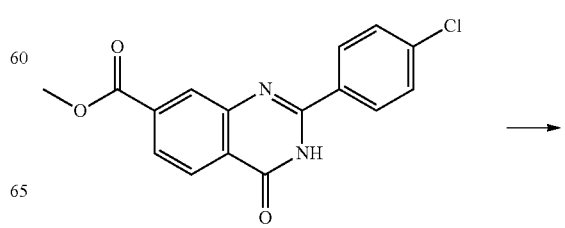

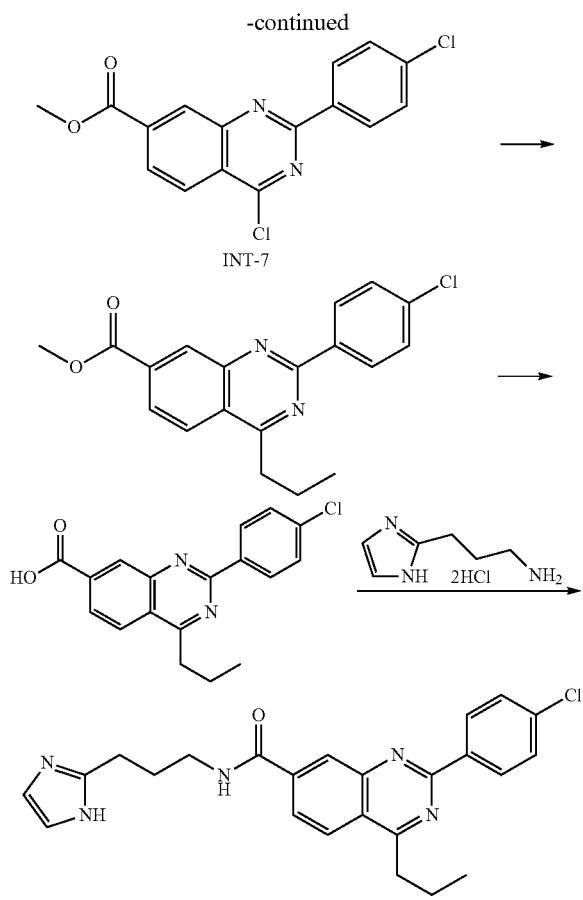

Step 1: Methyl 4-chloro-2-(4-chlorophenyl)quinazoline-7-carboxylate (INT-7)

To a suspension of methyl 2-(4-chlorophenyl)-4-oxo-3,4-dihydroquinazoline-7-carboxylate (7.03 g, 22.4 mmol), and phosphorus pentachloride (8.66 g, 41.6 mmol) in 1,2-dichloroethane (127 mL) was added DMF (438 µL, 5.65 mmol). The reaction mixture was stirred and heated at 80° C. for 2 h. After cooling, the resulting solution was concentrated to thick slurry. 10 ml of DCM were added, the mixture was stirred and cooled in an ice bath and 200 mL of cold water were added gradually. The suspension was stirred for 20 min and was filtered. The collected solid was washed with water, DCM (10 mL) and ether (30 mL), and dried under vacuum to give methyl 4-chloro-2-(4-chlorophenyl)quinazoline-7-carboxylate (6.56 g, 84% yield) as a white solid. LC-MS: (FA) ES+ 333.1; $^1$H NMR (400 MHz, CDCl$_3$) δ 8.80-8.78 (m, 1H), 8.61-8.55 (m, 2H), 8.34 (dd, J=8.7, 0.6 Hz, 1H), 8.27 (dd, J=8.7, 1.6 Hz, 1H), 7.56-7.51 (m, 2H), 4.07 (s, 3H).

Step 2: Methyl 2-(4-chlorophenyl)-4-propyl-quinazoline-7-carboxylate

To a suspension of methyl 4-chloro-2-(4-chlorophenyl)quinazoline-7-carboxylate (1.77 g, 5.31 mmol) and acetylacetone iron (III) salt (208 mg, 0.591 mmol) in THF (71 mL, 880 mmol) at −10° C. was added 2.0 M propyl magnesium chloride in ether (5.61 mL, 11.2 mmol) over 10 min drop wise. After 30 min the mixture was quenched with 2M aqueous NH$_4$Cl (50 ml) then diluted with water (50 ml) and extracted with 100 ml of EtOAc/ether (1:1). The separated aqueous layer was washed with 50 ml of EtOAc. The combined organics were washed with brine, dried over Na$_2$SO$_4$ and concentrated. The resulting product was purified on ISCO (80 g silica; dry load) using 20-75% DCM/Hexane over 25 min to give methyl 2-(4-chlorophenyl)-4-propyl-quinazoline-7-carboxylate (1.25 g, 69%) as an off white solid. LC-MS: (FA) ES+ 341.1; $^1$H NMR (400 MHz, DMSO-d$_6$) δ 8.61-8.57 (m, 2H), 8.56-8.54 (m, 1H), 8.49 (d, J=8.7 Hz, 1H), 8.14 (dd, J=8.7, 1.7 Hz, 1H), 7.68-7.64 (m, 2H), 3.98 (s, 3H), 3.42-3.35 (m, 2H), 2.01-1.90 (m, 2H), 1.07 (t, J=7.4 Hz, 3H).

Step 3: 2-(4-Chlorophenyl)-4-propyl-quinazoline-7-carboxylic acid

To a suspension of methyl 2-(4-chlorophenyl)-4-propyl-quinazoline-7-carboxylate (1.24 g, 3.66 mmol) in THF (22 mL) and methanol (22 mL) was added 1.0 M of sodium hydroxide in water (11.0 mL, 11.0 mmol). The resulting heterogeneous mixture was then stirred at rt overnight. The mixture was added to 200 ml of water under stirring. The resulting solution was acidified with 1M HCl to pH ~3.5. The white solid that precipitated was collected by filtration and was dried under high vacuum to give 2-(4-chlorophenyl)-4-propyl-quinazoline-7-carboxylic acid (1.16 g, 3.55 mmol, 96%) as an off white solid. LC-MS: (FA) ES+ 327.1; $^1$H NMR (400 MHz, DMSO-d6) δ 13.67 (s, 1H), 8.62-8.56 (m, 2H), 8.54-8.52 (m, 1H), 8.47-8.43 (m, 1H), 8.16-8.14 (m, 1H), 7.68-7.63 (m, 2H), 3.42-3.34 (m, 4H), 2.02-1.89 (m, 2H), 1.07 (t, J=7.4 Hz, 3H).

Step 4: 2-(4-Chlorophenyl)-N-[3-(1H-imidazol-2-yl)propyl]-4-propylquinazoline-7-carboxamide (I-4)

A mixture of 2-(4-chlorophenyl)-4-propyl-quinazoline-7-carboxylic acid (545 mg, 1.67 mmol) and 3-(1H-imidazol-2-yl)-1-propanamine 2HCl (513 mg, 2.59 mmol) in pyridine (8.62 mL) was stirred at rt for 5 min. To the resulting thick mixture was added T3P® (1.68 M in EtOAc, 2.44 mL, 4.11 mmol). The mixture was then stirred for 1 h. 1.5 mL of water was added and the mixture was concentrated in vacuo (at 40° C.). The thick liquid residue that remained was diluted with 20 mL of water under stirring. The light suspension mixture was slowly made basic by addition of 4 M aqueous K$_2$CO$_3$ to pH 10-11. The resulting suspension was stirred for 1 h. The solid was filtered off, washed with water and was dried under vacuum to give 750 mg of light purple solid. Purification on ISCO (24 g silica; dry load) using 0-8% MeOH in DCM gave 2-(4-chlorophenyl)-N-[3-(1H-imidazol-2-yl)propyl]-4-propyl-quinazoline-7-carboxamide as an off white solid (605 mg, 1.47 mmol, 83%). LC-MS: (FA) ES+ 434.1; $^1$H NMR (400 MHz, DMSO-d6) δ 11.73 (s, 1H), 9.12 (t, J=5.4 Hz, 1H), 8.61-8.57 (m, 2H), 8.53 (d, J=1.5 Hz, 1H), 8.44 (d, J=8.7 Hz, 1H), 8.10 (dd, J=8.7, 1.7 Hz, 1H), 7.69-7.64 (m, 2H), 6.89 (s, 2H), 3.43-3.34 (m, 4H), 2.72 (t, J=7.5 Hz, 2H), 2.03-1.89 (m, 4H), 1.06 (t, J=7.4 Hz, 3H).

The compounds listed in the table below were prepared in an analogous fashion to that described in Example 10 starting from the appropriate starting materials:

| Starting Material Step 4 | Compound No. or Name | LCMS Data |
|---|---|---|
| <img> imidazole-ethylamine structure </img> | I-1* | LCMS (ESI+): m/z = 434.1 (M + H) |

195
-continued

| Starting Material Step 4 | Compound No. or Name | LCMS Data |
|---|---|---|
| [triazole-propylamine] | I-7** | LCMS (ESI+): m/z = 435.1 (M + H) |
| [imidazopyridine-methylamine] | I-8** | LCMS (ESI+): m/z = 456.1 (M + H) |
| [imidazopyridine-methylamine] | I-9** | LCMS (ESI+): m/z = 457.2 (M + H) |
| [imidazole-propylamine] | I-16*** | LCMS (ESI+): m/z = 418.2 (M + H) |

*HATU coupling reagent, TEA base and THF solvent used in Step 4
**TEA base and DMF solvent used in Step 4
***INT-1 used in Step 1; HATU coupling reagent, TEA base and THF solvent used in Step 4

The compounds listed in the table below were prepared in an analogous fashion to that described in Example 10 starting from the appropriate starting materials:

| Starting Material Step 2 | Compound No. or Name | LCMS Data |
|---|---|---|
| [benzylboronic acid] | I-53 | LCMS (ESI+): m/z = 482.2 (M + H) |

Example 11: N-(3-(1H-Imidazol-2-yl)propyl)-2-(4-chlorophenyl)-4-ethoxyquinoline-7-carboxamide (I-13)

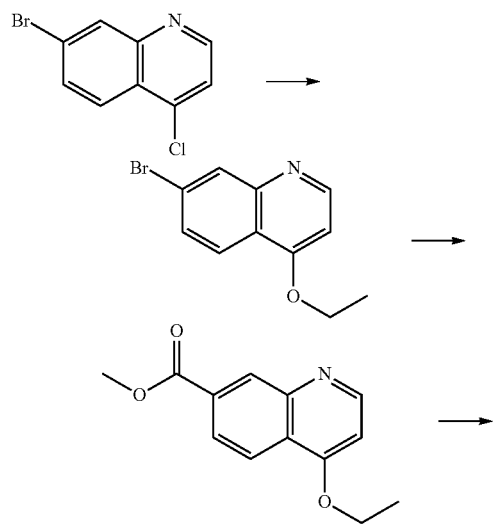

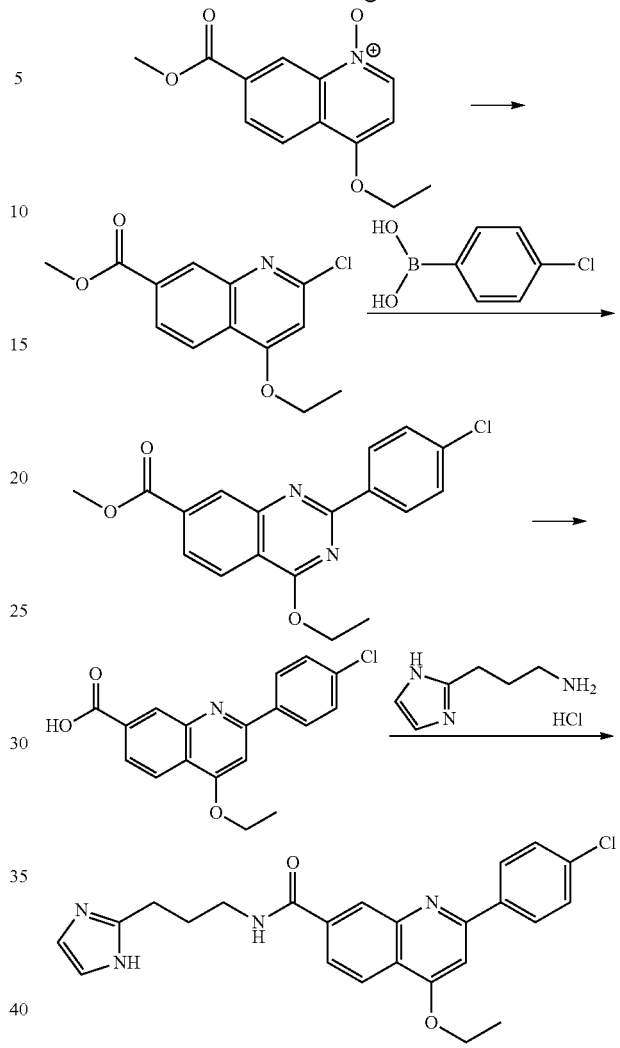

Step 1: 7-Bromo-4-ethoxyquinoline

A round bottom flask was charged with NaH (60:40, sodium hydride:mineral oil, 1.65 g, 41.2 mmol) and N-methylpyrrolidinone (68.9 mL). The suspension was cooled in an ice bath then dry ethanol (9.63 mL, 165 mmol) was added. The mixture was then stirred at rt for 10 min (gas generation observed). The pinkish mixture was cooled in ice bath again then 7-bromo-4-chloroquinoline (5.0 g, 20.6 mmol) was added. That mixture was then stirred at rt for about 2 h. LCMS showed completed reaction. The mixture was added to cold NaHCO$_3$ saturated solution, and solid precipitated out. The mixture was filtered to collect solid. The solid was washed 3 times with water and then dried to give 7-bromo-4-ethoxyquinoline (5.20 g, 100%). LC-MS: (FA) ES+ 252.0. 1H NMR (400 MHz, DMSO-d6) δ 8.75 (d, J=5.2 Hz, 1H), 8.15 (d, J=1.9 Hz, 1H), 8.09 (d, J=8.9 Hz, 1H), 7.71 (dd, J=8.9, 2.0 Hz, 1H), 7.07 (d, J=5.3 Hz, 1H), 4.33 (q, J=7.0 Hz, 2H), 1.49 (t, J=7.0 Hz, 3H).

Step 2: Methyl 4-ethoxyquinoline-7-carboxylate

To a round-bottom flask was added 7-bromo-4-ethoxyquinoline (2.5 g, 9.92 mmol), TEA (13.8 mL, 99.2 mmol), methanol (60 mL) and dimethyl sulfoxide (60 mL) [all solvents pre-degassed]. Then 1,3-bis(diphenylphosphino) propane (818 mg, 1.98 mmol) and palladium (II) acetate (445 mg, 1.98 mmol) were added. The flask was purged with carbon monoxide twice and left under a balloon of carbon monoxide as it was heated at 70° C. for 3 h, then the reaction mixture was kept in rt overnight. After removing methanol under reduced pressure water was added. The resulting precipitate was filtered and then purified by silica gel column chromatography (0 to 80% EtOAc/hexane) to yield methyl 4-ethoxyquinoline-7-carboxylate (1.75 g, 77%). LC-MS: (FA) ES+ 232.1. $^1$H NMR (400 MHz, DMSO-d6) δ 8.84 (d, J=5.2 Hz, 1H), 8.52 (s, 1H), 8.27 (d, J=8.7 Hz, 1H), 8.05 (dd, J=8.7, 1.6 Hz, 1H), 7.14 (d, J=5.2 Hz, 1H), 4.35 (q, J=7.0 Hz, 2H), 3.95 (s, 3H), 1.50 (t, J=7.0 Hz, 3H).

Step 3: Methyl 4-ethoxy-7-(methoxycarbonyl)quinoline 1-oxide

To a solution of methyl 4-ethoxyquinoline-7-carboxylate (3.50 g, 15.1 mmol) in DCM (76.9 mL, 1.20E3 mmol) was added m-chloroperbenzoic acid (6.78 g, 30.3 mmol) at 0° C. The reaction mixture was stirred at rt for 2 h. The reaction mixture was then partitioned between saturated NaHCO$_3$ and DCM. The separated organic layer was washed three times with 1N NaOH, then washed with brine, dried over Na$_2$SO$_4$/MgSO$_4$, and concentrated to give methyl 4-ethoxy-7-(methoxycarbonyl)quinoline 1-oxide (3.34 g, 89%) LC-MS: (FA) ES+ 248.1 1H NMR (400 MHz, DMSO-d6) δ 9.11 (d, J=1.5 Hz, 1H), 8.58 (d, J=6.9 Hz, 1H), 8.32 (d, J=8.7 Hz, 1H), 8.20 (dd, J=8.7, 1.7 Hz, 1H), 7.11 (d, J=6.9 Hz, 1H), 4.34 (q, J=7.0 Hz, 2H), 3.97 (s, 3H), 1.49 (t, J=7.0 Hz, 3H).

Step 4: Methyl 2-chloro-4-ethoxyquinoline-7-carboxylate

A solution of methyl 4-ethoxyquinoline-7-carboxylate 1-oxide (3.34 g, 13.5 mmol) in DMF (50.4 mL) was cooled in an ice bath. 2.0 M of oxalyl chloride in DCM (13.5 mL, 27.0 mmol) was added dropwise (gas evolution was observed). After a few min the resulting light brown suspension was allowed to warm up to rt and then the suspension was heated at 35-40° C. for 2 h. The reaction mixture was quenched with water and then was extracted with DCM twice. The combined organic layers were washed three times with water, dried over Na$_2$SO$_4$, and concentrated. The residue was dried under vacuum to give methyl 2-chloro-4-ethoxyquinoline-7-carboxylate (2.69 g, 74.9%). LC-MS: (FA) ES+ 266.1 1H NMR (400 MHz, DMSO-d6) δ 8.38 (dd, J=1.7, 0.5 Hz, 1H), 8.24-8.20 (m, 1H), 8.06 (dd, J=8.6, 1.7 Hz, 1H), 7.21 (s, 1H), 4.38 (q, J=7.0 Hz, 2H), 3.94 (s, 3H), 1.49 (t, J=7.0 Hz, 3H).

Step 5: Methyl 2-(4-chlorophenyl)-4-ethoxyquinoline-7-carboxylate

A microwave vial was charged with methyl 2-chloro-4-ethoxyquinoline-7-carboxylate (200.00 mg, 0.75 mmol), 4-chlorophenylboronic acid (140 mg, 0.90 mmol), cesium carbonate (736 mg, 2.26 mmol), and SiliaCat® DPP-Pd (0.260 mmol/g loading; 579.04 mg, 0.150 mmol). The vial was purged with nitrogen and then 1,4-dioxane (12 mL) and water (3 mL) were added. The vial was sealed and the reaction mixture was stirred in the microwave at 110° C. for 45 min. The reaction mixture was filtered to remove resin. The filtrate was concentrated and purified on a silica gel column (0 to 30% EtOAc/hexane) to give methyl 2-(4-chlorophenyl)-4-ethoxyquinoline-7-carboxylate (110 mg, 43%). LC-MS: (FA) ES+ 342.1 $^1$H NMR (400 MHz, DMSO-d6) δ 8.57 (d, J=1.3 Hz, 1H), 8.37 (d, J=8.7 Hz, 2H), 8.26 (d, J=8.6 Hz, 1H), 8.04 (dd, J=8.6, 1.7 Hz, 1H), 7.68 (s, 1H), 7.64 (d, J=8.6 Hz, 2H), 4.50 (q, J=7.0 Hz, 2H), 3.96 (s, 3H), 1.54 (t, J=7.0 Hz, 3H).

Step 6: 2-(4-Chlorophenyl)-4-ethoxyquinoline-7-carboxylic acid

To a suspension of methyl 2-(4-chlorophenyl)-4-ethoxyquinoline-7-carboxylate (110 mg, 0.32 mmol) in THF (2.0 mL) and methanol (2.0 mL) was added 1.0 M of sodium hydroxide in water (1.0 mL, 1.0 mmol). The reaction mixture was stirred at rt. The reaction mixture turned into a clear solution in 2 h. The resulting solution was diluted with water and acidified with 1M HCl to pH ~3.5. A white solid precipitated out of solution. The solid was filtered, washed with water, and dried to afford 2-(4-chlorophenyl)-4-ethoxyquinoline-7-carboxylic acid (88 mg, 82%). LCMS: (FA) ES+ 328.1 1H NMR (400 MHz, DMSO-d$_6$) δ 13.39 (s, 1H), 8.60 (d, J=1.3 Hz, 1H), 8.42 (d, J=8.6 Hz, 2H), 8.28 (d, J=8.6 Hz, 1H), 8.08 (dd, J=8.6, 1.6 Hz, 1H), 7.71 (s, 1H), 7.68 (d, J=8.6 Hz, 2H), 4.55 (q, J=6.9 Hz, 2H), 1.59 (t, J=6.9 Hz, 3H).

Step 7: N-(3-(1H-Imidazol-2-yl)propyl)-2-(4-chlorophenyl)-4-ethoxyquinoline-7-carboxamide To a solution of 2-(4-chlorophenyl)-4-ethoxyquinoline-7-carboxylic acid (88.0 mg, 0.27 mmol) in THF (1.3 mL) was added 3-(1H-imidazol-2-yl)propan-1-amine.2 [HCl](79.8 mg, 0.40 mmol), TBTU (112 mg, 0.30 mmol), TEA (190 uL, 1.3 mmol) at rt. The reaction mixture was stirred at rt overnight. To the mixture was added 2 mL 1N NaOH and 10 ml of water. The resulting precipitate was filtered and purified by HPLC to yield N-(3-(1H-imidazol-2-yl)propyl)-2-(4-chlorophenyl)-4-ethoxyquinoline-7-carboxamide (75 mg, 58%) LCMS: (FA) ES+ 435.1; $^1$H NMR (400 MHz, DMSO-d$_6$) δ 8.99 (m, 1H), 8.54 (d, J=1.4 Hz, 1H), 8.36 (d, J=8.7 Hz, 2H), 8.20 (d, J=8.6 Hz, 1H), 8.18 (s, 1H), 7.98 (dd, J=8.6, 1.7 Hz, 1H), 7.64 (m, 2H), 6.92 (s, 2H), 4.49 (q, J=7.0 Hz, 2H), 3.39 (q, J=6.7 Hz, 2H), 2.73 (t, J=7.5 Hz, 2H), 1.96 (m, 2H), 1.54 (t, J=7.0 Hz, 3H).

The compounds listed in the table below were prepared in an analogous fashion to that described in Example 11 starting from the appropriate starting materials:

| Starting Material Step 5 | Starting Material Step 7 | Compound No. or Name | LCMS Data |
|---|---|---|---|
| HO-B(OH)-C$_6$H$_4$-F | N-methylimidazole-CH$_2$CH$_2$NH$_2$ | I-2 | LCMS (ESI+): m/z = 419.2 (M + H) |

| Starting Material Step 5 | Starting Material Step 7 | Compound No. or Name | LCMS Data |
|---|---|---|---|
| 4-fluorophenylboronic acid | 3-(1H-1,2,4-triazol-5-yl)propan-1-amine | I-5 | LCMS (ESI+): m/z = 420.2 (M + H) |
| 4-fluorophenylboronic acid | 2-(1-methyl-1H-imidazol-4-yl)ethanamine | I-6 | LCMS (ESI+): m/z = 419.6 (M + H) |
| 5-chloro-2-fluorophenylboronic acid | 3-(1H-imidazol-2-yl)propan-1-amine | I-11 | LCMS (ESI−): m/z = 451.1 (M − H) |
| 5-fluoro-2-methoxypyridin-4-ylboronic acid | 3-(1H-imidazol-2-yl)propan-1-amine | I-12 | LCMS (ESI+): m/z = 450.1 (M + H) |
| 4-fluorophenylboronic acid | (3H-imidazo[4,5-c]pyridin-2-yl)methanamine | I-14 | LCMS (ESI+): m/z = 442.1 (M + H) |
| 4-fluorophenylboronic acid | 3-(1H-imidazol-2-yl)propan-1-amine | I-15 | LCMS (ESI+): m/z = 419.2 (M + H) |
| 4-fluorophenylboronic acid | 3-(1H-pyrazol-1-yl)propan-1-amine | I-43 | LCMS (ESI+): m/z = 419.2 (M + H) |
| 4-fluorophenylboronic acid | 3-(thiazol-2-yl)propan-1-amine | I-44 | LCMS (ESI+): m/z = 436.1 (M + H) |
| 4-fluorophenylboronic acid | 3-(pyridazin-4-yl)propan-1-amine | I-45 | LCMS (ESI+): m/z = 431.2 (M + H) |

| Starting Material Step 5 | Starting Material Step 7 | Compound No. or Name | LCMS Data |
|---|---|---|---|
| 4-fluorophenylboronic acid | 1H-pyrazol-5-ylethylamine | I-46 [a] | LCMS (ESI+): m/z = 405.2 (M + H) |
| 4-fluorophenylboronic acid | 4-(2-aminoethyl)benzonitrile | I-47 [a] | LCMS (ESI+): m/z = 440.2 (M + H) |
| 4-fluorophenylboronic acid | 1H-pyrazol-4-ylethylamine | I-48 | LCMS (ESI+): m/z = 405.2 (M + H) |
| 4-fluorophenylboronic acid | (1H-benzimidazol-2-yl)methylamine | I-54 [a] | LCMS (ESI+): m/z = 441.2 (M + H) |
| 4-fluorophenylboronic acid | 2-(1H-1,2,4-triazol-1-yl)ethylamine | I-55 [a] | LCMS (ESI+): m/z = 406.2 (M + H) |
| 5-fluoro-2-methoxypyridin-4-ylboronic acid | 3-(4-methyl-1H-1,2,3-triazol-5-yl)propylamine | I-68 [b,e] | LCMS (ESI+): m/z = 465.2 (M + H) |
| 2-methoxypyridin-4-ylboronic acid | [1,2,4]triazolo[1,5-a]pyridin-6-ylmethylamine | I-70 [b,d,t] | LCMS (ESI+): m/z = 455 (M + H) |
| 2-methoxypyridin-4-ylboronic acid | 3-(4-methyl-1H-1,2,3-triazol-5-yl)propylamine | I-71 [b,d,t] | LCMS (ESI+): m/z = 447 (M + H) |

-continued

| Starting Material Step 5 | Starting Material Step 7 | Compound No. or Name | LCMS Data |
|---|---|---|---|
| | | I-74 [b,e] | LCMS (ESI+): m/z = 439.1 (M + H) |
| | | I-75 [b,e,t] | LCMS (ESI+): m/z = 431.2 (M + H) |
| | | I-76 [b,e,t] | LCMS (ESI+): m/z = 433.2 (M + H) |
| | | I-77 [b,e,t] | LCMS (ESI+): m/z = 417.2 (M + H) |
| | | I-79 [b,e] | LCMS (ESI+): m/z = 458.1 (M + H) |
| | | I-80 [b,e] | LCMS (ESI+): m/z = 447.1 (M + H) |
| | | I-83 [b,d,t] | LCMS (ESI−): m/z = 431 (M − H) |
| | | I-84 [b,e] | LCMS (ESI+): m/z = 442.1 (M + H) |

-continued
| Starting Material Step 5 | Starting Material Step 7 | Compound No. or Name | LCMS Data |
|---|---|---|---|
| 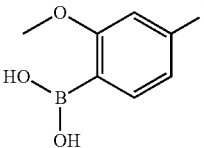 | 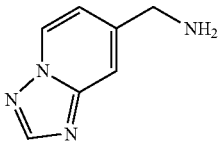 | I-85 [b,e] | LCMS (ESI+): m/z = 472.2 (M + H) |
| 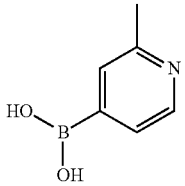 | 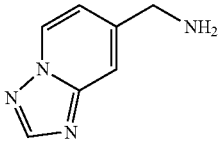 | I-86 [b,e] | LCMS (ESI+): m/z = 439.1 (M + H) |
| 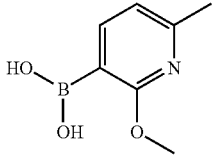 | 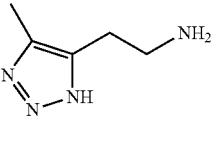 | I-87 [b,e,g,t] | LCMS (ESI+): m/z = 447.2 (M + H) |
| 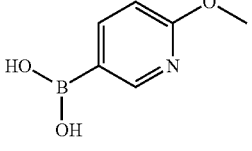 | 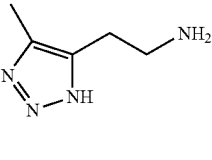 | I-88 [b,e,g,t] | LCMS (ESI+): m/z = 433.2 (M + H) |
| 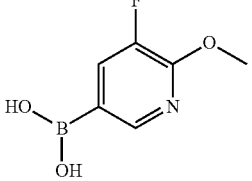 | 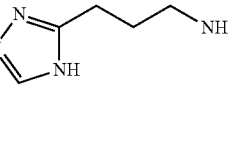 | I-89 [b,e] | LCMS (ESI+): m/z = 451.2 (M + H) |
| 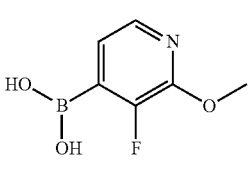 | 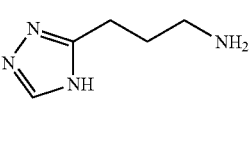 | I-90 [b,e] | LCMS (ESI+): m/z = 451.2 (M + H) |
| 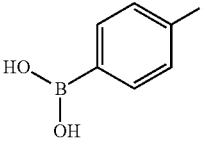 | 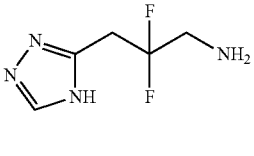 [SMILES: NCC(F)(F)Cc1nnc[nH]1] | I-91 [b] | LCMS (ESI+): m/z = 456 (M + H) |
| 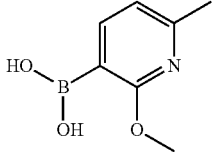 | 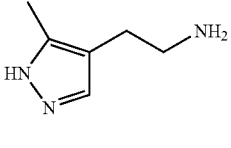 | I-92 [b,e,g,t] | LCMS (ESI+): m/z = 446.2 (M + H) |
| 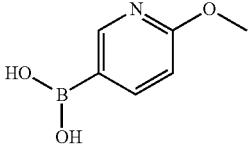 | 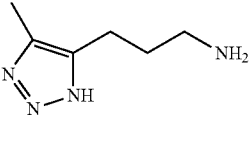 | I-93 [b,e,g,t] | LCMS (ESI+): m/z = 447.2 (M + H) |

-continued

| Starting Material Step 5 | Starting Material Step 7 | Compound No. or Name | LCMS Data |
|---|---|---|---|
| | | I-94 [b,e,g,t] | LCMS (ESI+): m/z = 461.2 (M + H) |
| | | I-95 [b,e,t] | LCMS (ESI+): m/z = 433.2 (M + H) |
| | | I-96 [b,e,t] | LCMS (ESI+): m/z = 433.2 (M + H) |
| | | I-97 [b,e,t] | LCMS (ESI+): m/z = 447.2 (M + H) |
| | | I-98 [b,e,t] | LCMS (ESI+): m/z = 432.1 (M + H) |
| | | I-99 [b,d,g,t] | LCMS (ESI+): m/z = 439.2 (M + H) |
| | | I-100 [b,d,t] | LCMS (ESI+): m/z = 432 (M + H) |
| | | I-101 [b,e,g,t] | LCMS (ESI+): m/z = 433.2 (M + H) |

-continued

| Starting Material Step 5 | Starting Material Step 7 | Compound No. or Name | LCMS Data |
|---|---|---|---|
| (6-methoxypyridin-3-yl)boronic acid | 3-(1H-1,2,3-triazol-5-yl)propan-1-amine | I-102 [b,e,g,t] | LCMS (ESI+): m/z = 433.2 (M + H) |
| (2-methoxy-6-methylpyridin-3-yl)boronic acid | 3-(1H-1,2,3-triazol-5-yl)propan-1-amine | I-103 [b,e,g,t] | LCMS (ESI+): m/z = 447.2 (M + H) |
| (2-methoxy-6-methylpyridin-3-yl)boronic acid | 3-(1H-pyrazol-5-yl)propan-1-amine | I-104 [b,e,g,t] | LCMS (ESI+): m/z = 446.2 (M + H) |
| (2-methoxypyridin-3-yl)boronic acid | 3-(1H-1,2,3-triazol-5-yl)propan-1-amine | I-105 [b,e] | LCMS (ESI+): m/z = 433.2 (M + H) |
| (4-fluoro-2-methoxyphenyl)boronic acid | 3-(4-methyl-1H-1,2,3-triazol-5-yl)propan-1-amine | I-106 [b,e] | LCMS (ESI+): m/z = 464.2 (M + H) |
| (4-fluorophenyl)boronic acid | 2-(1H-1,2,3-triazol-5-yl)ethan-1-amine | I-107 [b,e] | LCMS (ESI+): m/z = 406.2 (M + H) |
| (4-fluoro-2-methoxyphenyl)boronic acid | 2-(1H-1,2,3-triazol-5-yl)ethan-1-amine | I-108 [b,d,f,t] | LCMS (ESI+): m/z = 436.1 (M + H) |
| (6-methylpyridin-3-yl)boronic acid | 3-(1H-1,2,3-triazol-5-yl)propan-1-amine | I-110 [b,e,t] | LCMS (ESI+): m/z = 417.2 (M + H) |
| (6-methylpyridin-3-yl)boronic acid | 3-(1H-pyrazol-5-yl)propan-1-amine | I-111 [b,e,t] | LCMS (ESI+): m/z = 416.2 (M + H) |

| Starting Material Step 5 | Starting Material Step 7 | Compound No. or Name | LCMS Data |
|---|---|---|---|
| 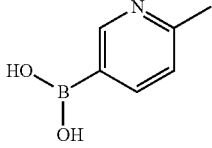 | 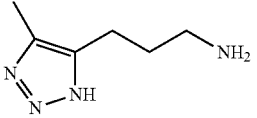 | I-112 b,e,t | LCMS (ESI+): m/z = 431.2 (M + H) |
| 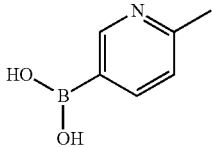 | 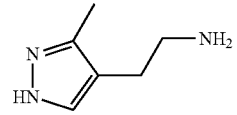 | I-113 b,e,t | LCMS (ESI+): m/z = 416.2 (M + H) |
| 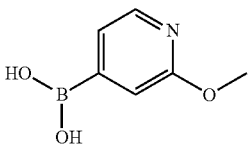 | 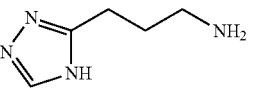 | I-114 b,d,t | LCMS (ESI−): m/z = 431 (M − H) |
| 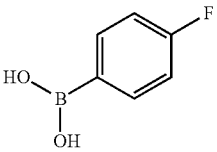 | 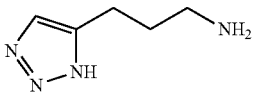 | I-115 c,e | LCMS (ESI+): m/z = 420.1 (M + H) |
| 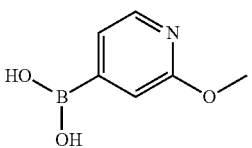 | 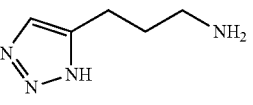 | I-116 b,d,t | LCMS (ESI+): m/z = 433 (M + H) |
| 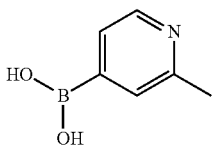 | 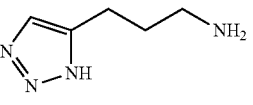 | I-117 b,e,t | LCMS (ESI+): m/z = 417.2 (M + H) |
| 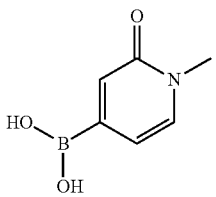 | 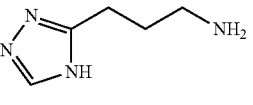 | I-118 b,e,t | LCMS (ESI+): m/z = 433.2 (M + H) |
| 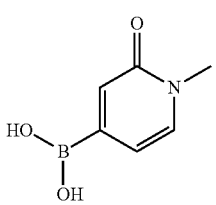 | 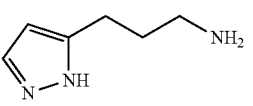 | I-119 b,e,t | LCMS (ESI+): m/z = 432.2 (M + H) |
| 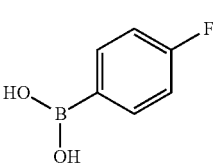 | 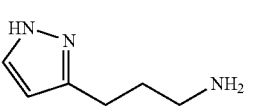 | I-120 b,e | LCMS (ESI+): m/z = 449.2 (M + H) |

| Starting Material Step 5 | Starting Material Step 7 | Compound No. or Name | LCMS Data |
|---|---|---|---|
| 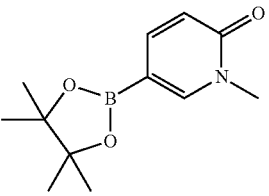 | 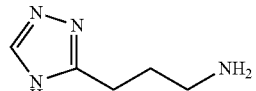 | I-122 [b,e,t] | LCMS (ESI+): m/z = 433.2 (M + H) |
| 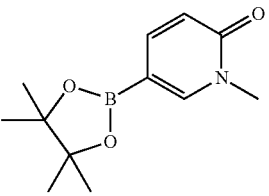 | 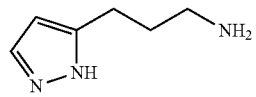 | I-123 [b,e,t] | LCMS (ESI+): m/z = 432.2 (M + H) |
| 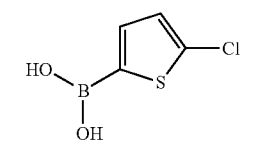 | 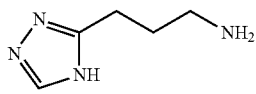 | I-125 [b,e] | LCMS (ESI+): m/z = 442.1 (M + H) |
| 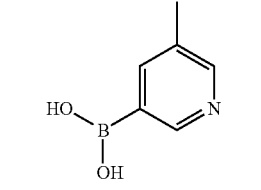 | 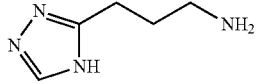 | I-127 [b,e] | LCMS (ESI+): m/z = 417.2 (M + H) |
| 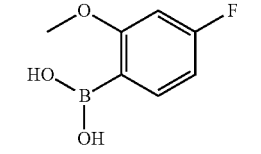 | 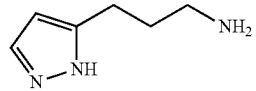 | I-128 [b,e] | LCMS (ESI+): m/z = 449.2 (M + H) |
| 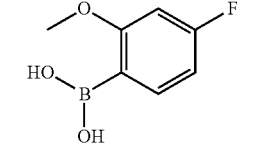 | 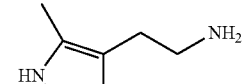 | I-129 [b,e] | LCMS (ESI+): m/z = 449.2 (M + H) |
| 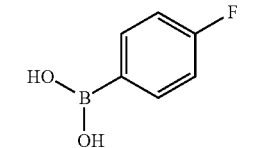 | 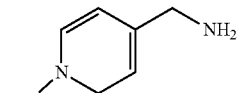 | I-130 [b,d,f,t] | LCMS (ESI+): m/z = 442.2 (M + H) |
| 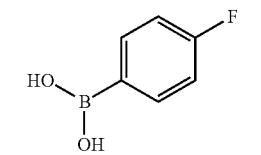 | 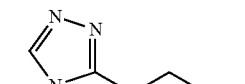 | I-131 [b,e,g,t] | LCMS (ESI+): m/z = 406.2 (M + H) |
| 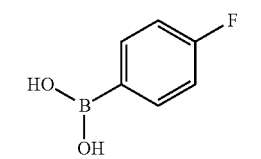 | 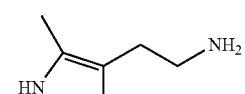 | I-132 [b,e,t] | LCMS (ESI+): m/z = 419.2 (M + H) |

-continued

| Starting Material Step 5 | Starting Material Step 7 | Compound No. or Name | LCMS Data |
|---|---|---|---|
| (HO)₂B-C₆H₄-F (4-fluorophenylboronic acid) | 4-methyl-1H-1,2,3-triazol-5-yl ethylamine | I-133 [b,e,g,t] | LCMS (ESI+): m/z = 434.2 (M + H) |
| (HO)₂B-C₆H₄-F (4-fluorophenylboronic acid) | 3-amino-1H-pyrazol-5-yl ethylamine | I-134 [b] | LCMS (ESI−): m/z = 418 (M − H) |
| 2-methoxy-6-methylpyridin-4-yl boronic acid | 1H-1,2,4-triazol-3-yl propylamine | I-136 [b,e,t] | LCMS (ESI+): m/z = 447.2 (M + H) |
| 3-(methylsulfonyl)phenylboronic acid | 1H-1,2,4-triazol-3-yl propylamine | I-137 [b,e,t] | LCMS (ESI+): m/z = 480.2 (M + H) |
| 6-methoxy-2-methylpyridin-3-yl boronic acid | 1H-1,2,4-triazol-3-yl propylamine | I-138 [b,d,t] | LCMS (ESI−): m/z = 445 (M − H) |
| 3-methoxypyridin-4-yl boronic acid | 1H-1,2,4-triazol-3-yl propylamine | I-139 [b,d,t] | LCMS (ESI−): m/z = 431 (M − H) |
| (HO)₂B-C₆H₄-F (4-fluorophenylboronic acid) | 3-amino-1H-1,2,4-triazol-5-yl methylamine | I-141 [b,e,g,t] | LCMS (ESI+): m/z = 407.1 (M + H) |
| (HO)₂B-C₆H₄-F (4-fluorophenylboronic acid) | 3-amino-1H-1,2,4-triazol-5-yl ethylamine | I-142 [b] | LCMS (ESI−): m/z = 419 (M − H) |
| 2,6-dimethoxypyridin-3-yl boronic acid | 1H-1,2,4-triazol-3-yl propylamine | I-143 [b,d,t] | LCMS (ESI+): m/z = 463 (M + H) |

-continued
| Starting Material Step 5 | Starting Material Step 7 | Compound No. or Name | LCMS Data |
|---|---|---|---|
| 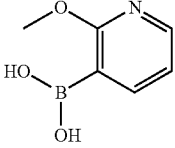 | 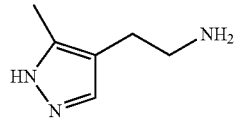 | I-144 [b,e,t] | LCMS (ESI+): m/z = 432.2 (M + H) |
| 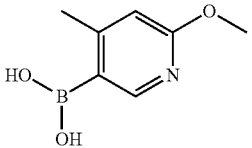 | 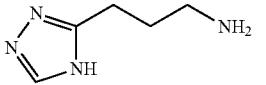 | I-145 [b,d,t] | LCMS (ESI−): m/z = 445 (M − H) |
| 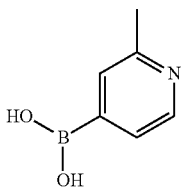 | 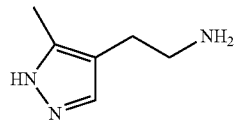 | I-146 [b,e,t] | LCMS (ESI+): m/z = 416.2 (M + H) |
| 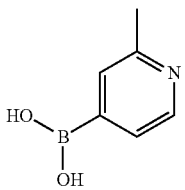 | 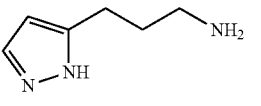 | I-149 [b,e,t] | LCMS (ESI+): m/z = 416.2 (M + H) |
| 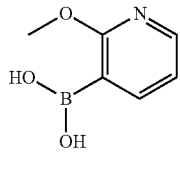 | 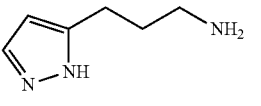 | I-150 [b,e,t] | LCMS (ESI+): m/z = 432.2 (M + H) |
| 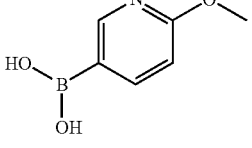 | 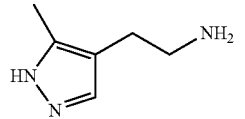 | I-153 [b,e,g,t] | LCMS (ESI+): m/z = 432.2 (M + H) |
| 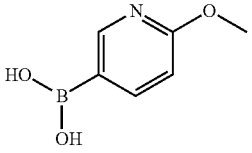 | 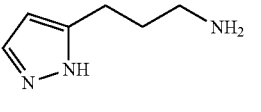 | I-154 [b,e,g,t] | LCMS (ESI+): m/z = 432.2 (M + H) |
| 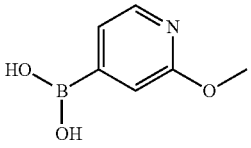 | 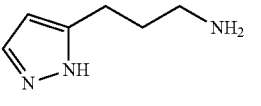 | I-155 [b,d,t] | LCMS (ESI+): m/z = 432 (M + H) |
| 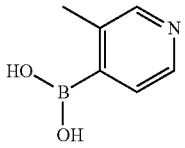 | 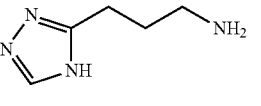 | I-158 [b,e] | LCMS (ESI+): m/z = 415.2 (M + H) |

-continued
| Starting Material Step 5 | Starting Material Step 7 | Compound No. or Name | LCMS Data |
|---|---|---|---|
|  |  | I-159 [b,e,t] | LCMS (ESI+): m/z = 447 (M + H) |
| 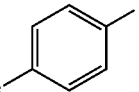 | 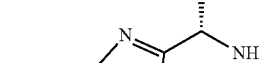 | I-160 [b,e,g,t] | LCMS (ESI+): m/z = 456.1 (M + H) |
|  | 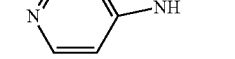 | I-161 [b,e,t] | LCMS (ESI+): m/z = 451.2 (M + H) |
| 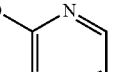 | 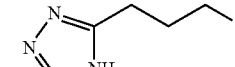 | I-164 [b,e,t] | LCMS (ESI−): m/z = 465, 467 (M − H) |
|  |  | I-165 [b,d,f,t] | LCMS (ESI+): m/z = 450.2 (M + H) |
| 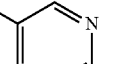 | 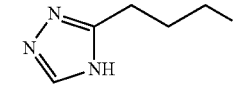 | I-166 [b,d,t] | LCMS (ESI−): m/z = 465, 467 (M − H) |
|  |  | I-167 [b,d,g,t] | LCMS (ESI+): m/z = 439.2 (M + H) |
| 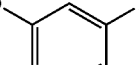 | 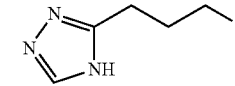 | I-168 [b,d,g,t] | LCMS (ESI+): m/z = 403.2 (M + H) |
|  |  | I-169 [b,d,g,t] | LCMS (ESI+): m/z = 403.2 (M + H) |

-continued

| Starting Material Step 5 | Starting Material Step 7 | Compound No. or Name | LCMS Data |
|---|---|---|---|
| 4-fluoro-2-methoxyphenylboronic acid | 2-(4H-1,2,4-triazol-3-yl)ethan-1-amine | I-170 [b,d,f,t] | LCMS (ESI+): m/z = 436.2 (M + H) |
| (2-methylpyridin-4-yl)boronic acid | 2-(4H-1,2,4-triazol-3-yl)ethan-1-amine | I-172 [b,e,t] | LCMS (ESI+): m/z = 403.2 (M + H) |
| (6-methylpyridin-3-yl)boronic acid | 3-(4H-1,2,4-triazol-3-yl)propan-1-amine | I-173 [b,d,g,t] | LCMS (ESI+): m/z = 417.2 (M + H) |
| (2-methoxy-6-methylpyridin-3-yl)boronic acid | (1H-imidazo[4,5-c]pyridin-2-yl)methanamine | I-174 [b,e,g,t] | LCMS (ESI+): m/z = 469.2 (M + H) |
| (5-chlorothiophen-2-yl)boronic acid | (1H-imidazo[4,5-c]pyridin-2-yl)methanamine | I-175 [b,e] | LCMS (ESI+): m/z = 464.1 (M + H) |
| (5-chlorothiophen-2-yl)boronic acid | 2-(2H-1,2,3-triazol-4-yl)ethan-1-amine | I-176 [b,e] | LCMS (ESI+): m/z = 428.1 (M + H) |
| (5-chlorothiophen-2-yl)boronic acid | 2-(4H-1,2,4-triazol-3-yl)ethan-1-amine | I-177 [b,e] | LCMS (ESI+): m/z = 428.1 (M + H) |
| (4-fluorophenyl)boronic acid | (1-methyl-1H-imidazo[4,5-c]pyridin-2-yl)methanamine | I-178 [b,e,t] | LCMS (ESI+): m/z = 456.2 (M + H) |
| (5-fluoro-2-methoxyphenyl)boronic acid | (1-methyl-1H-imidazo[4,5-c]pyridin-2-yl)methanamine | I-179 [b,e,t] | LCMS (ESI+): m/z = 486.2 (M + H) |

-continued

| Starting Material Step 5 | Starting Material Step 7 | Compound No. or Name | LCMS Data |
|---|---|---|---|
| 2-methoxypyridin-3-yl boronic acid | 2-(1H-1,2,4-triazol-3-yl)ethan-1-amine | I-180 [b,e,t] | LCMS (ESI+): m/z = 419.2 (M + H) |
| 2-methylpyridin-4-yl boronic acid | 2-(1H-1,2,3-triazol-4-yl)ethan-1-amine | I-181 [b,e,t] | LCMS (ESI+): m/z = 403.2 (M + H) |
| 5-fluoro-2-methoxyphenyl boronic acid | 2-(1H-1,2,4-triazol-3-yl)ethan-1-amine | I-182 [b,e,t] | LCMS (ESI−): m/z = 434 (M − H) |
| 2-methoxy-6-methylpyridin-3-yl boronic acid | 3-(1H-1,2,4-triazol-3-yl)propan-1-amine | I-183 [b,e,g,t] | LCMS (ESI+): m/z = 447.2 (M + H) |
| 5-fluoro-2-methoxyphenyl boronic acid | 2-(1H-1,2,3-triazol-4-yl)ethan-1-amine | I-184 [b,e,t] | LCMS (ESI−): m/z = 434 (M − H) |
| 6-methoxypyridin-3-yl boronic acid | 2-(1H-1,2,3-triazol-4-yl)ethan-1-amine | I-185 [b,e,g,t] | LCMS (ESI+): m/z = 419.2 (M + H) |
| 6-methoxypyridin-3-yl boronic acid | 2-(1H-1,2,4-triazol-3-yl)ethan-1-amine | I-186 [b,e,g,t] | LCMS (ESI+): m/z = 419.2 (M + H) |
| 5-fluoro-2-methoxyphenyl boronic acid | (3H-imidazo[4,5-c]pyridin-2-yl)methanamine | I-187 [b,e,t] | LCMS (ESI+): m/z = 472 (M + H) |
| 5-fluoro-2-methoxypyridin-4-yl boronic acid | (3H-imidazo[4,5-c]pyridin-2-yl)methanamine | I-188 [b,e] | LCMS (ESI+): m/z = 473.2 (M + H) |

-continued
| Starting Material Step 5 | Starting Material Step 7 | Compound No. or Name | LCMS Data |
|---|---|---|---|
| 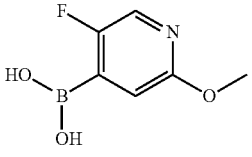 | 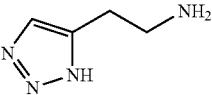 | I-189 [b,e] | LCMS (ESI+): m/z = 437.2 (M + H) |
| 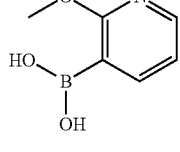 | 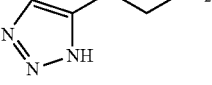 | I-190 [b,e,t] | LCMS (ESI+): m/z = 419.2 (M + H) |
| 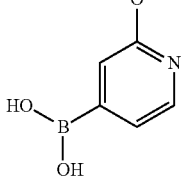 | 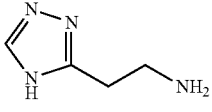 | I-191 [b,d,t] | LCMS (ESI−): m/z = 417 (M − H) |
| 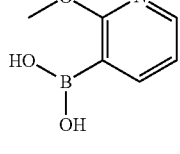 | 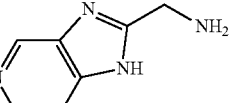 | I-192 [a,e,t] | LCMS (ESI+): m/z = 455.2 (M + H) |
| 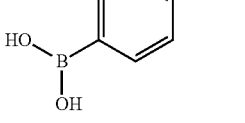 | 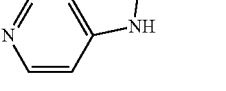 | I-193 [b,e,g,t] | LCMS (ESI+): m/z = 455.2 (M + H) |
| 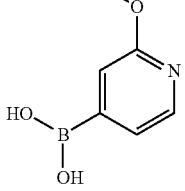 | 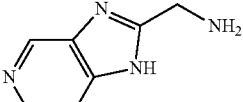 | I-194 [b,d,t] | LCMS (ESI+): m/z = 455 (M + H) |
| 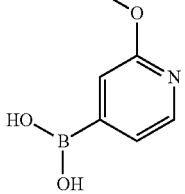 | 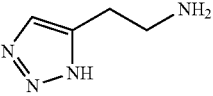 | I-195 [b,d,t] | LCMS (ESI+): m/z = 419 (M + H) |
| 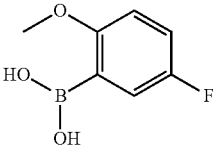 | 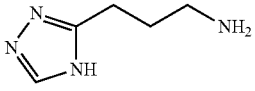 | I-199 [b,e,t] | LCMS (ESI−): m/z = 448 (M − H) |

-continued
| Starting Material Step 5 | Starting Material Step 7 | Compound No. or Name | LCMS Data |
|---|---|---|---|
| 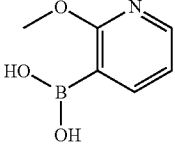 | 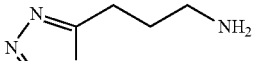 | I-200 [b,e,t] | LCMS (ESI+): m/z = 433.2 (M + H) |
| 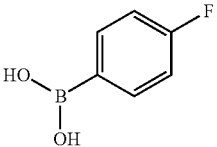 | 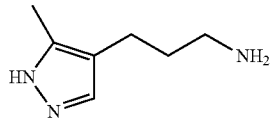 | I-201 [b,e,g,t] | LCMS (ESI+): m/z = 433.2 (M + H) |
| 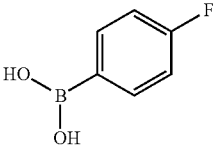 | 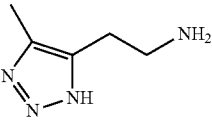 | I-203 [b,e,g,t] | LCMS (ESI+): m/z = 420.2 (M + H) |
| 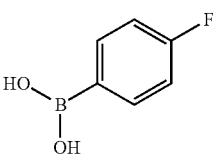 | 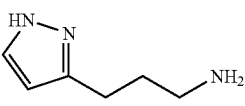 | I-204 [b] | LCMS (ESI+): m/z = 419 (M + H) |
| 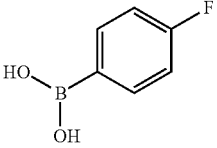 | 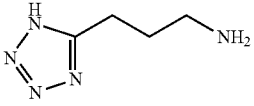 | I-219 b | LCMS (ESI+): m/z = 421 (M + H) |
| 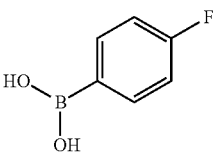 | 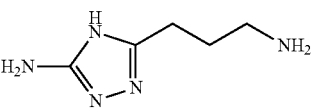 | I-220 [b,e,t] | LCMS (ESI+): m/z = 435.1 (M + H) |
| 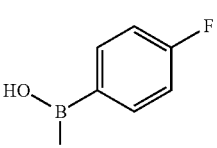 | 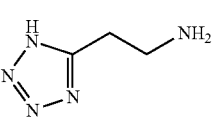 | I-221 [b] | LCMS (ESI+): m/z = 407.1 (M + H) |
| 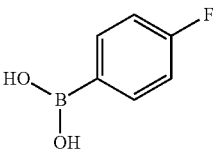 | 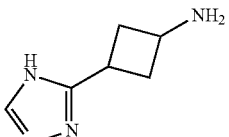 | I-222 [b,e,g,t] | LCMS (ESI+): m/z = 432.2 (M + H) |
| 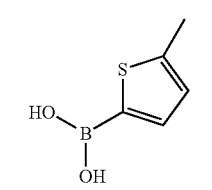 | 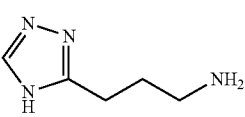 | I-223 [b,e] | LCMS (ESI+): m/z = 423.2 (M + H) |

-continued

| Starting Material Step 5 | Starting Material Step 7 | Compound No. or Name | LCMS Data |
|---|---|---|---|
| (4-fluorophenyl boronic acid) | (6-methyl-5-(3-aminopropyl)pyridine) | I-227 [b,e,g,t] | LCMS (ESI+): m/z = 444.2 (M + H) |
| (3-fluoro-4-boronic acid phenyl) | (5-(3-aminopropyl)pyrimidine) | I-228 [b,e,g,t] | LCMS (ESI+): m/z = 431.2 (M + H) |

[a]* T3P ® as coupling reagent and pyridine as solvent/base used in Step 7
[b]** HATU coupling reagent was used in Step 7
[c]***** EDC/HOBT coupling reagents and DMF solvent were used in Step 7
[d]*** Pd/Xphos catalyst was used in Step 5
[e]**** Pd(dppf)Cl$_2$ catalyst was used in Step 5
[f] Potassium phosphate base used in Step 5
[g] Potassium carbonate base used in Step 5
[t] Thermal heating used in Step 5

The compounds listed in the table below were prepared in an analogous fashion to that described in Example 11 starting from the appropriate starting materials:

| Starting Material Step 1 | Starting Material Step 5 | Compound No. or Name | LCMS Data |
|---|---|---|---|
| (isopropanol) | (4-fluorophenyl boronic acid) | I-17 | LCMS (ESI+): m/z = 433.2 (M + H) |

Example 12: 2-(4-Chlorophenyl)-N-[cis-3-(1H-imidazol-2-yl)cyclobutyl]-4-propyl-quinazoline-7-carboxamide (I-3)

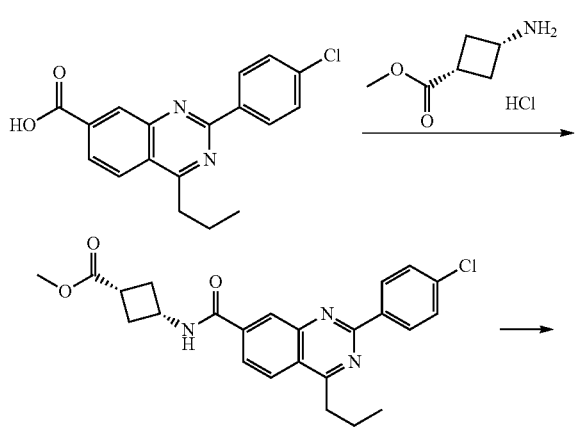

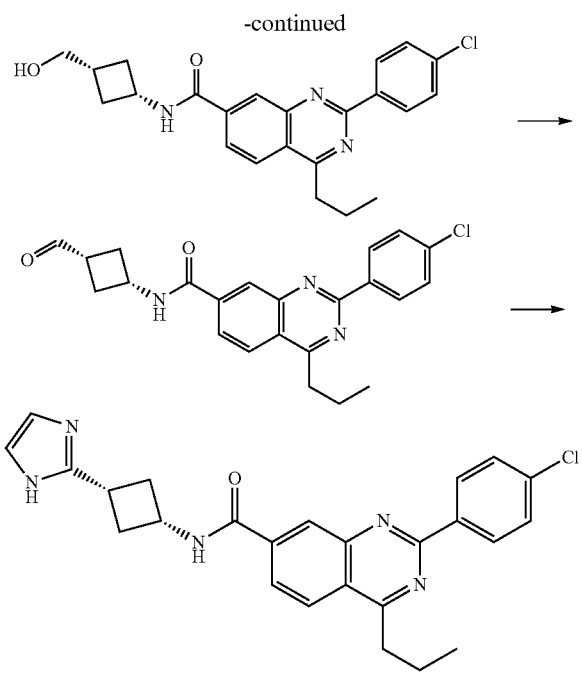

Step 1: Methyl cis-3-[[2-(4-chlorophenyl)-4-propyl-quinazoline-7-carbonyl]amino]cyclobutanecarboxylate A mixture of 2-(4-chlorophenyl)-4-propyl-quinazoline-7-carboxylic acid (255.0 mg, 0.7803 mmol, prepared as described in Example 10) and methyl cis-3-amino-cyclobutanecarboxylate hydrochloride (167 mg, 0.978 mmol) in pyridine (4.03 mL) was stirred at rt for 5 min. To the resulting mixture was added T3P® (1.68 mol/L) in EtOAc (1.14 mL, 1.92 mmol). The mixture was then stirred at rt for 1.5 h. 1 mL of water was added to quench the reaction. The mixture was stirred for 10 min and was concentrated in vacuo to wet residue. Water was added gradually to mixture under stirring. The mixture was stirred over the weekend which led to a fine suspension. The off white solid was filtered off and dried under vacuum to give methyl 3-[[2-(4-chlorophenyl)-4-propyl-quinazoline-7-carbonyl]amino]cyclobutane-carboxylate (288 mg, 0.6248 mmol, 80%). LCMS: (FA) ES+ 438.2; $^1$H NMR (400 MHz, DMSO-d$_6$) δ 9.18 (d, J=7.6 Hz, 1H), 8.61-8.55 (m, 3H), 8.43 (d, J=8.6 Hz, 1H), 8.09 (dd, J=8.6, 1.7 Hz, 1H), 7.69-7.64 (m, 2H), 4.48 (m, 1H), 3.64 (s, 3H), 3.40-3.34 (m, 2H), 2.99-2.87 (m, 1H), 2.58-2.45 (m, 1H), 2.40-2.30 (m, 2H), 2.00-1.94 (m, 2H), 1.06 (t, J=7.4 Hz, 4H).

Step 2: 2-(4-Chlorophenyl)-N-[cis-3-(hydroxymethyl)cyclobutyl]-4-propyl-quinazoline-7-carboxamide To a solution of methyl cis-3-[[2-(4-chlorophenyl)-4-propyl-quinazoline-7-carbonyl]amino]cyclobutanecarboxylate (50.0 mg, 0.114 mmol) in THF (1.00 mL) at 0° C. was added lithium aluminum hydride in THF (95 μL, 0.190 mmol, 2.00 mol/L) dropwise. The mixture was stirred for 30 min and was quenched with 0.5 ml of 0.5 M aqueous citric acid. The mixture was then diluted with EtOAc. The separated organic layer was washed with brine, dried over Na$_2$SO$_4$ and concentrated. The product was purified on 4 g silica gel column using 0-6% MeOH/DCM over 25 min to give 2-(4-chlorophenyl)-N-[3-(hydroxymethyl)cyclobutyl]-4-propyl-quinazoline-7-carboxamide (24.0 mg, 0.059 mmol, 51%) as an off white solid. LCMS: (FA) ES+ 410.1; $^1$H NMR (400 MHz, DMSO-d$_6$) δ 7.84-7.80 (m, 2H), 7.66 (s, 1H), 7.56 (d, J=8.7 Hz, 1H), 7.26-7.22 (m, 1H), 6.78-6.73 (m, 2H), 3.72-3.62 (m, 1H), 2.78 (d, J=6.0 Hz, 2H), 2.63-2.56 (m, 2H), 1.76-1.67 (m, 2H), 1.54-1.44 (m, 1H), 1.29-1.20 (m, 2H), 1.18-1.08 (m, 2H), 0.34 (t, J=7.4 Hz, 3H).

Step 3: 2-(4-Chlorophenyl)-N-(cis-3-formylcyclobutyl)-4-propyl-quinazoline-7-carboxamide To a solution of 2-(4-chlorophenyl)-N-[cis-3-(hydroxymethyl)cyclobutyl]-4-propyl-quinazoline-7-carboxamide (23.0 mg, 0.0561 mmol) in DCM (2.00 mL) at rt was added Dess-Martin periodinane (35.7 mg, 0.0842 mmol). The reaction mixture was stirred for 1 h. LCMS analysis showed around 50% conversion. Additional Dess-Martin periodinane (25 mg, 0.059 mmol) was added. The reaction mixture was stirred for 1 h. LCMS analysis showed around 75% conversion. Additional Dess-Martin periodinane (15 mg, 0.03537 mmol) was added. After 1 h, the reaction mixture was quenched with 0.5 M aqueous Na$_2$S$_2$O$_3$. The mixture was stirred few minutes and was extracted with EtOAc. The separated organic phase was washed with brine twice, dried over Na$_2$SO$_4$, and concentrated. The product was purified on 4 g silica gel column using 0-4% MeOH/DCM over 25 min to give 2-(4-chlorophenyl)-N-(3-formylcyclobutyl)-4-propyl-quinazoline-7-carboxamide (15.5 mg, 0.0380 mmol, 68%) as an off white solid. LC-MS: (FA) ES+ 408.1; $^1$H NMR (400 MHz, DMSO-d$_6$) δ 9.67 (d, J=2.0 Hz, 1H), 9.14 (d, J=7.6 Hz, 1H), 8.66-8.50 (m, 3H), 8.43 (d, J=8.7 Hz, 1H), 8.09 (dd, J=8.7, 1.7 Hz, 1H), 7.69-7.64 (m, 2H), 4.48-4.62 (m, 1H), 3.43-3.35 (m, 2H), 3.08-2.94 (m, 1H), 2.54-2.40 (m, 2H), 2.27-2.39 (m, 2H), 1.90-2.02 (m, 2H), 1.06 (t, J=7.4 Hz, 3H).

Step 4: 2-(4-Chlorophenyl)-N-[cis-3-(1H-imidazol-2-yl)cyclobutyl]-4-propyl-quinazoline-7-carboxamide (I-3)

To a suspension of 2-(4-chlorophenyl)-N-(cis-3-formylcyclobutyl)-4-propyl-quinazoline-7-carboxamide (14.0 mg, 0.0343 mmol) in isopropyl alcohol (400 μL) and water (400 μL) was added ammonium bicarbonate (13.0 mg, 0.164 mmol) and 7 M of ethanedial in water (14.0 μL, 0.0123 mmol, 8.8 mol/L). The resulting suspension was stirred at rt overnight. The resulting suspension was filtered and the collected solid was dried under vacuum. The product was purified on 4 g silica gel column using 0-6% MeOH/DCM over 25 min to give 2-(4-chlorophenyl)-N-[3-(1H-imidazol-2-yl)cyclobutyl]-4-propyl-quinazoline-7-carboxamide (3.5 mg, 0.0078 mmol, 23% yield) as an off white solid. LCMS: (FA) ES+ 446.1; $^1$H NMR (400 MHz, DMSO-d6) δ 11.71 (s, 1H), 9.22 (d, J=7.5 Hz, 1H), 8.62-8.56 (m, 3H), 8.43 (d, J=8.9 Hz, 1H), 8.12 (d, J=8.3 Hz, 1H), 7.69-7.64 (m, 2H), 6.99 (s, 1H), 6.81 (s, 1H), 4.55-4.43 (m, 1H), 3.29-3.17 (m, 1H), 2.71-2.59 (m, 2H), 2.39-2.51 (m, 2H), 2.03-1.90 (m, 2H), 1.07 (t, J=7.3 Hz, 3H).

Example 13: 4-Ethoxy-2-(4-fluorophenyl)-N-{[trans-(1,2)-2-(1H-imidazol-2-yl)cyclopropyl]methyl}quinoline-7-carboxamide (first eluting enantiomer (Chiralpak ID Peak 1) I-50 and second eluting enantiomer (Chiralpak ID Peak 2) I-51)

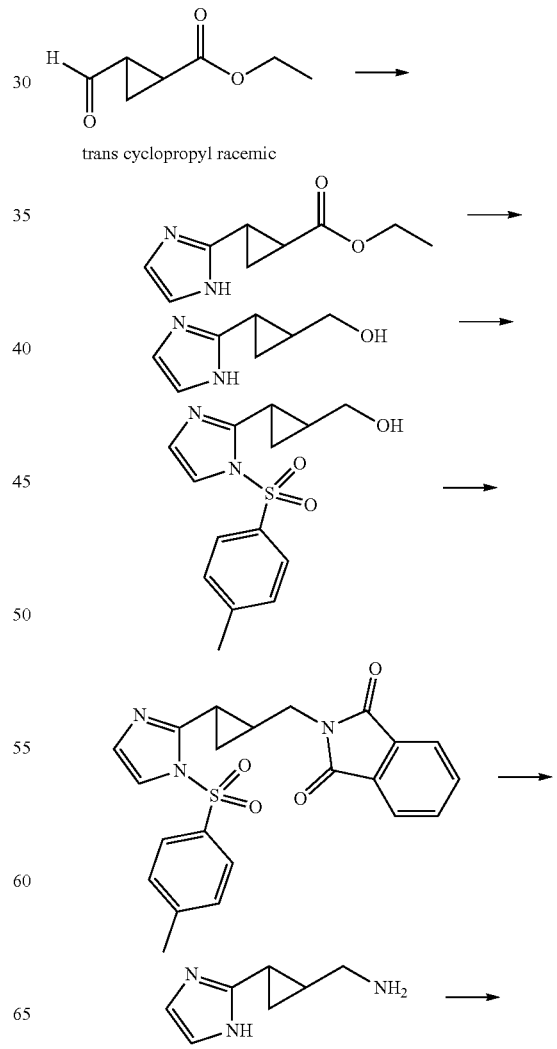

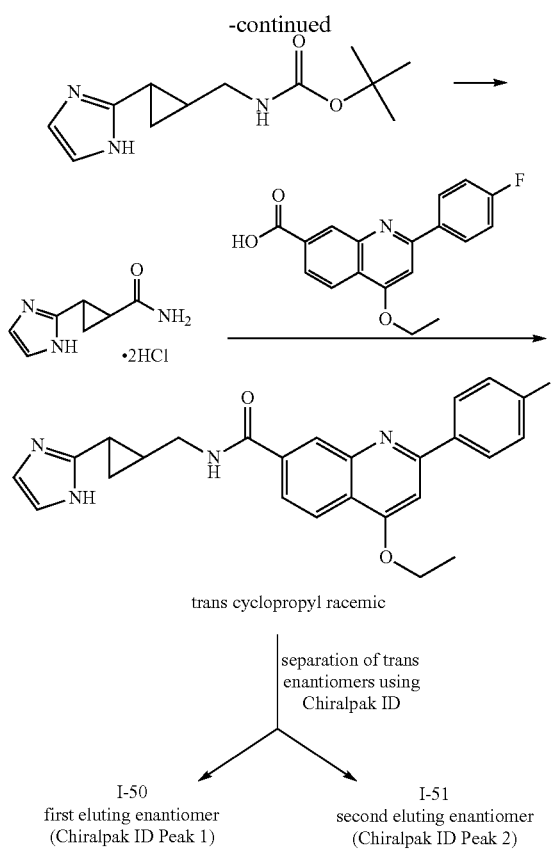

trans cyclopropyl racemic separation of trans enantiomers using Chiralpak ID

I-50
first eluting enantiomer
(Chiralpak ID Peak 1)

I-51
second eluting enantiomer
(Chiralpak ID Peak 2)

Step 1: Trans-rac-ethyl 2-(1H-imidazol-2-yl)cyclopropanecarboxylate

To a solution of trans-rac-ethyl 2-formylcyclopropanecarboxylate (696 mg, 4.90 mmol) in IPA (13 mL) was added water (13 mL) and ammonium bicarbonate (1.16 g, 14.7 mmol), followed by a 8.8 M solution of ethanedial in water (1.06 mL, 9.32 mmol), and the resulting solution was stirred overnight at rt. The reaction mixture was filtered, and the filtrate was diluted with DCM (40 mL) and water (5 mL). The layers were separated and the aqueous layer was extracted with DCM (15 mL). The combined organic layers were washed with brine, dried, filtered and concentrated in vacuo. Purification by silica gel chromatography gave trans-rac-ethyl 2-(1H-imidazol-2-yl)cyclopropanecarboxylate (882 mg, 48%). LCMS (ESI+): m/z=181.1 $^1$H NMR (400 MHz, CDCl$_3$) δ 8.97 (bs, 1H), 6.95 (s, 2H), 4.16 (q, J=7.2 Hz, 2H), 2.58-2.53 (m, 1H), 2.24-2.20 (m, 1H), 1.67-1.63 (m, 1H), 1.60-1.56 (m, 1H), 1.28 (t, J=7.2 Hz, 3H).

Step 2: Trans-rac-(2-(1H-imidazol-2-yl)cylopropyl)methanol

To a solution of trans-rac-ethyl 2-(1H-imidazol-2-yl)cyclopropanecarboxylate (2.57 g, 14.3 mmol) in THF (41 mL) was added a 1.0 M solution of LAH in THF (28.5 mL, 28.5 mmol) and the resulting solution was heated at 60° C. for 2 h. The reaction mixture was cooled and quenched with water (1.07 mL), 15% aqueous NaOH (1.07 mL), and water (3.15 mL). The reaction mixture was filtered and concentrated in vacuo. Silica gel chromatography gave trans-rac-(2-(1H-imidazol-2-yl)cyclopropyl)methanol (1.97 g, 87%). $^1$H NMR (400 MHz, DMSO-d$_6$) δ 11.65 (bs, 1H), 6.79 (s, 2H), 4.64 (s, 1H), 3.45-3.31 (m, 2H), 1.82-1.78 (m, 1H), 1.45-1.38 (m, 1H), 0.93-0.89 (m, 1H), 0.82-0.77 (m, 1H).

Step 3: Trans-rac-(2-(1-tosyl-1H-imidazol-2-yl)cyclopropyl)methanol

To a solution of trans-rac-(2-(1H-imidazol-2-yl)cyclopropyl)methanol (1.52 g, 11.0 mmol) in THF (50 mL) was added a solution of potassium carbonate (3.07 g, 22.0 mmol) in water (10 mL) followed by p-toluenesulfonyl chloride (2.14 g, 11.0 mmol) and the reaction mixture was stirred vigorously overnight. Most of the THF was removed in vacuo, and the aqueous layer was extracted twice with EtOAc (25 mL). The combined organic layers were washed with brine (10 mL), dried, filtered and concentrated in vacuo. Silica gel chromatography gave trans-rac-(2-(1-tosyl-1H-imidazol-2-yl)cyclopropyl)methanol (3.22 g, 93%). LCMS (ESI+): m/z=293.1 (M+H). $^1$H NMR (400 MHz, CDCl$_3$) δ 7.85-7.82 (m, 2H), 7.40-7.38 (m, 3H), 6.88 (d, J=1.2 Hz, 1H), 3.79 (dd, J=11.2, 5.6 Hz, 1H), 3.41 (dd, J=11.2, 7.6 Hz, 1H), 2.47 (s, 3H), 2.30 (bs, 1H), 2.28-2.23 (m, 1H), 1.73-1.64 (m, 1H), 1.38-1.33 (m, 1H), 0.97-0.92 (m, 1H).

Step 4: Trans-rac-2-((2-(1-tosyl-1H-imidazol-2-yl)cyclopropyl)methyl)isoindoline-1,3-dione To a solution of trans-rac-(2-(1-tosyl-1H-imidazol-2-yl)cyclopropyl)methanol (2.99 g, 10.2 mmol) in THF (60 mL) was added phthalimide (1.82 g, 12.3 mmol) and triphenylphosphine (3.25 g, 12.3 mmol). The mixture was stirred for 5 min, and then cooled in an ice bath. A solution of diethyl azodicarboxylate (2.01 mL, 12.3 mmol) in THF (10 mL) was then added over 5 min, and the resulting solution was stirred for 30 min. The reaction mixture was concentrated in vacuo. Silica gel chromatography gave trans-rac-2-((2-(1-tosyl-1H-imidazol-2-yl)cyclopropyl)methyl)isoindoline-1,3-dione (4.31 g, 54%). LCMS (ESI+): m/z=422.1 (M+H). $^1$H NMR (400 MHz, CDCl$_3$) δ 7.89-7.85 (m, 2H), 7.84-7.81 (m, 2H), 7.76-7.71 (m, 2H), 7.40-7.38 (m, 2H), 7.35 (d, J=1.6 Hz, 1H), 6.82 (d, J=1.6 Hz, 1H), 3.75 (dd, J=14.4, 7.2 Hz, 1H), 3.64 (dd, J=14.4, 7.2 Hz, 1H), 2.47 (s, 3H), 2.46-2.41 (m, 1H), 1.90-1.81 (m, 1H), 1.27-1.22 (m, 1H), 1.10-1.06 (m, 1H).

Step 5: Trans-rac-(2-(1H-imidazol-2-yl)cycloproyl)methanamine

To a solution of trans-rac-2-((2-(1-tosyl-1H-imidazol-2-yl)cyclopropyl)methyl)isoindoline-1,3-dione (2.34 g, 5.55 mmol) in ethanol (44 mL) was added hydrazine (2.79 mL, 88.8 mmol) and the resulting solution was heated overnight at 76° C. The reaction mixture was cooled, filtered and concentrated in vacuo to give crude trans-rac-(2-(1H-imidazol-2-yl)cyclopropyl)methanamine which was used without purification in the next step. LCMS (ESI+): m/z=138.1 (M+H).

Step 6: Trans-rac-tert-butyl ((2-(1H-imidazol-2-yl)cyclopropyl)methyl)carbamate

To a solution of trans-rac-(2-(1H-imidazol-2-yl)cyclopropyl)methanamine in methanol (27 mL) was added TEA (3.67 mL, 26.1 mmol), DMAP (51 mg, 0.42 mmol) and di-tert-butyl dicarbonate (6.1 mL, 26 mmol) and the resulting solution was stirred overnight at rt. The reaction mixture was concentrated in vacuo. Silica gel chromatography gave trans-rac-tert-butyl ((2-(1H-imidazol-2-yl)cyclopropyl)methyl)carbamate (839 mg, 63% for 2-steps). LCMS (ESI+): m/z=238.1 (M+H). $^1$H NMR (400 MHz, DMSO-$d_6$) δ 6.99 (t, J=5.6 Hz, 1H), 6.84 (s, 2H), 2.97-2.94 (m, 2H), 1.84-1.80 (m, 1H), 1.44-1.37 (m, 1H), 1.38 (s, 9H), 0.94-0.89 (m, 1H), 0.83-0.79 (m, 1H).

Step 7: Trans-rac-(2-(1H-imidazol-2-yl)cyclopropyl)methanamine, dihydrochloride salt To a solution of trans-rac-tert-butyl ((2-(1H-imidazol-2-yl)cyclopropyl)methyl)carbamate (821 mg, 3.46 mmol) in MeOH (9 mL) was added a 4 M solution of HCl in dioxane (8.7 mL, 35 mmol) and the resulting solution was stirred at rt for 3 h. The reaction mixture was concentrated in vacuo. The residue was dissolved in MeOH (3 mL) and EtOAc (10 mL) was then added. The precipitate that formed was filtered and washed with EtOAc to give trans-rac-(2-(1H-imidazol-2-yl)cyclopropyl)methanamine, dihydrochloride salt (727 mg, 67%). LCMS (ESI+): m/z=138.1 (M+H). $^1$H NMR (400 MHz, DMSO-$d_6$) δ 14.46 (s, 1H), 8.35 (s, 2H), 7.52 (s, 2H), 3.06-2.99 (m, 1H), 2.82-2.75 (m, 1H), 2.43-2.38 (m, 1H), 1.89-1.80 (m, 1H), 1.59-1.54 (m, 1H), 1.34-1.29 (m, 1H).

Step 8: 4-Ethoxy-2-(4-fluorophenyl)-N-{[trans-(1,2)-2-(1H-imidazol-2-yl)cyclopropyl]methyl}quinoline-7-carboxamide (I-50, first eluting enantiomer (Chiralpak ID Peak 1) and I-51, second eluting enantiomer (Chiralpak ID Peak 2))

To a mixture of 4-ethoxy-2-(4-fluorophenyl)quinoline-7-carboxylic acid (82 mg, 0.26 mmol) (INT-2 described in Example 1) in THF (1.4 mL) was added trans-rac-(2-(1H-imidazol-2-yl)cyclopropyl)methanamine, dihydrochloride salt (83 mg, 0.40 mmol), TEA (184 uL, 1.32 mmol), and N,N,N',N'-tetramethyl-O-(7-azabenzotriazol-1-yl)uranium hexafluorophosphate (HATU) (110 mg, 0.290 mmol) and the mixture was stirred at rt for 3 h. To the reaction mixture was added water (5 mL) and EtOAc (10 mL). The layers were separated and the aqueous layer was extracted twice with EtOAc (5 mL). The combined organic layers were washed with brine (5 mL), dried, filtered, and concentrated in vacuo. Silica gel chromatography gave trans-rac-N-((2-(1H-imidazol-2-yl)cyclopropyl)methyl)-4-ethoxy-2-(4-fluorophenyl) quinoline-7-carboxamide. LCMS (ESI+): m/z=431.1 (M+H). $^1$H NMR (400 MHz, Methanol-d4) δ 8.47-8.46 (m, 1H), 8.31-8.29 (m, 1H), 8.20-8.17 (m, 2H), 7.95-7.92 (m, 1H), 7.42 (s, 1H), 7.32-7.27 (m, 2H), 6.91 (s, 2H), 4.46 (q, J=7.2 Hz, 2H), 3.55-3.49 (m, 2H), 2.09-2.05 (m, 1H), 1.77-1.68 (m, 1H), 1.63 (t, J=7.2 Hz, 3H), 1.24-1.20 (m, 1H), 1.13-1.08 (m, 1H).

The trans enantiomers were separated on a Chiralpak ID (10×250 mm 5 micron column from Chiral Technologies) column using a Jasco semi-prep SFC instrument. Solvent: 65/35 $CO_2$/0.3% DEA in IPA at 10 mL/min at 40° C. I-50 refers to the faster moving (first eluting) enantiomer (Chiralpak ID Peak 1), and I-51 refers to the slower moving (second eluting) enantiomer (Chiralpak ID Peak 2). Retention times of the separated enantiomers on analytical chiral HPLC (Chiralpak ID 4.6×100 mm 5 micron, Flow Rate: 4 mL/min, Time: 10 min, Solvent: 30% [0.3% DEA in IPA]/70% $CO_2$, BPR: 10 MPa were 5.47 min and 6.89 min. The absolute configurations of the separated peaks were not determined.

The compound listed in the table below was prepared in an analogous fashion to that described in Example 13 starting from the appropriate starting materials, as a racemic mixture of the two trans enantiomers:

| Starting Material Step 8 | Compound No. or Name | LCMS Data |
|---|---|---|
| (structure shown) | I-59 (trans cyclopropyl racemic) | LCMS (ESI+): m/z = 446.1 (M + H) |

Example 14: 2-(4-Chlorophenyl)-4-(4-fluorophenyl)-N-[3-(1H-imidazol-2-yl)propyl]quinazoline-7-carboxamide (I-57)

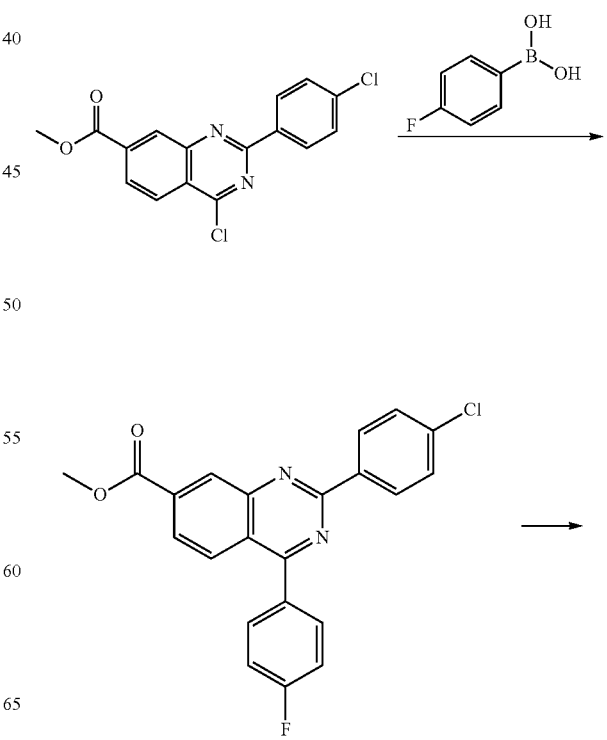

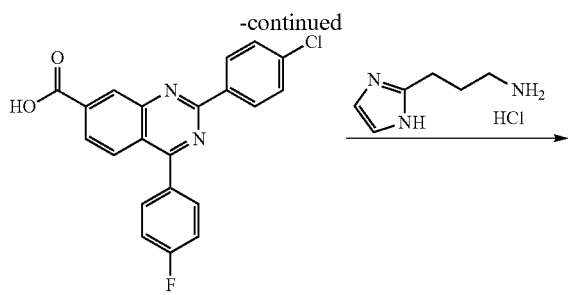

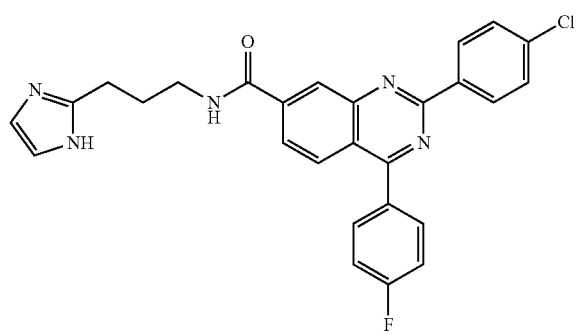

Step 1: Methyl 2-(4-chlorophenyl)-4-(4-fluorophenyl)quinazoline-7-carboxylate

To a solution in a pressure tube of methyl 4-chloro-2-(4-chlorophenyl)quinazoline-7-carboxylate (215 mg, 0.6453 mmol), (4-fluorophenyl)boronic acid (107 mg, 0.764 mmol), dppf (16.9 mg, 0.0208 mmol) in 1,4-dioxane (2.50 mL) was added 2 M aqueous potassium carbonate (600 μL, 1.20 mmol). The pressure tube was purged with nitrogen (×3), sealed and was stirred at 95° C. for 2 h. The resulting semi-solidified mixture was diluted with 2 mL of dioxane and the resulting suspension was added to 30 mL of water and stirred for 15 min. The solid was filtered off and dried under vacuum to give 266 mg of crude material. The product was purified on ISCO (12 g silica; solid load) using 20-70% DCM/hexane over 25 min to give methyl 2-(4-chlorophenyl)-4-(4-fluorophenyl)quinazoline-7-carboxylate (177 mg, 66%). LCMS: (FA) ES+ 393.1; $^1$H NMR (400 MHz, DMSO-$d_6$) δ 8.66-8.59 (m, 3H), 8.22-8.26 (m, 1H), 8.14-8.18 (m, 1H), 8.04-7.97 (m, 2H), 7.70-7.64 (m, 2H), 7.57-7.49 (m, 2H), 3.99 (s, 3H).

Step 2: 2-(4-Chlorophenyl)-4-(4-fluorophenyl)quinazoline-7-carboxylic acid

To a suspension of methyl 2-(4-chlorophenyl)-4-(4-fluorophenyl)quinazoline-7-carboxylate (156.0 mg, 0.3971 mmol) in THF (2.75 mL) and methanol (2.75 mL) was added 1.000 M of sodium hydroxide in water (1.38 mL, 1.38 mmol). The resulting heterogeneous mixture was stirred at rt overnight. The mixture was diluted with 25 ml of water. The resulting slurry was acidified with 1M HCl to pH ~3.5. The solid was collected by filtration and was dried under high vacuum to give 2-(4-chlorophenyl)-4-(4-fluorophenyl)quinazoline-7-carboxylic acid (150 mg, 95%) as an off white solid. LCMS: (FA) ES+ 379.0; $^1$H NMR (400 MHz, DMSO-$d_6$) δ 13.72 (s, 1H), 8.63-8.57 (m, 3H), 8.23-8.12 (m, 2H), 8.03-7.96 (m, 2H), 7.67-7.62 (m, 2H), 7.48-7.55 (m, 2H).

Step 3: 2-(4-Chlorophenyl)-4-(4-fluorophenyl)-N-[3-(1H-imidazol-2-yl)propyl]quinazoline-7-carboxamide (I-57)

A mixture of 2-(4-chlorophenyl)-4-(4-fluorophenyl)quinazoline-7-carboxylic acid (149 mg, 0.374 mmol) and 3-(1H-imidazol-2-yl)-1-propanamine 2HCl (135 mg, 0.682 mmol) in pyridine (3.44 ml) was stirred at rt for 5 min. To the resulting heterogeneous mixture was added T3P® (1.68 mol/1) in EtOAc (620 μl, 1.04 mmol). The reaction mixture was stirred at rt for 1 h. 500 ul of water were added to quench the reaction mixture. After stirring for 15 min, the mixture was concentrated on the rotovap, (bath temperature at 40° C.). The residue was mixed with 20 ml of water and the resulting suspension was made basic to pH 10 with 1 M aqueous $K_2CO_3$. The suspension was extracted with EtOAc×2. The combined organic layer was dried over $Na_2SO_4$ and concentrated. The crude product was purified on ISCO (12 silica, dryload) using 0-8% DCM/MeOH over 25 min to give 2-(4-chlorophenyl)-4-(4-fluorophenyl)-N-[3-(1H-imidazol-2-yl)propyl]quinazoline-7-carboxamide (159 mg, 83%) as a white solid. LCMS: (FA) ES+ 486.1; $^1$H NMR (400 MHz, DMSO-$d_6$) δ 11.73 (s, 1H), 9.19 (t, J=5.5 Hz, 1H), 8.65-8.60 (m, 3H), 8.21-8.17 (m, 1H), 8.14-8.09 (m, 1H), 8.04-7.98 (m, 2H), 7.71-7.65 (m, 2H), 7.56-7.49 (m, 2H), 6.99 (s, 1H), 6.79 (s, 1H), 3.44-3.37 (m, 2H), 2.75-2.69 (m, 2H), 2.02-1.92 (m, 2H).

The compounds listed in the table below were prepared in an analogous fashion to that described in Example 14 starting from the appropriate starting materials, as a racemic mixture of the two trans enantiomers:

| Starting Material Step 1 | Reagent Step 1 | Reagent Step 3 | Compound No. or Name | LCMS Data |
|---|---|---|---|---|
| INT-3 | ![structure] | ![structure] | I-162 | LCMS (ESI+): m/z = 468.2 (M + H) |

-continued

| Starting Material Step 1 | Reagent Step 1 | Reagent Step 3 | Compound No. or Name | LCMS Data |
|---|---|---|---|---|
| INT-3 | (structure) | (structure) | I-196 | LCMS (ESI+): m/z = 483.2 (M + H) |
| INT-3 | (structure) | (structure) | I-197 | LCMS (ESI+): m/z = 484.2 (M + H) |

Example 15: N-(3-(1H-Imidazol-2-yl)propyl)-2-cyclopropyl-4-ethoxyquinoline-7-carboxamide (I-58)

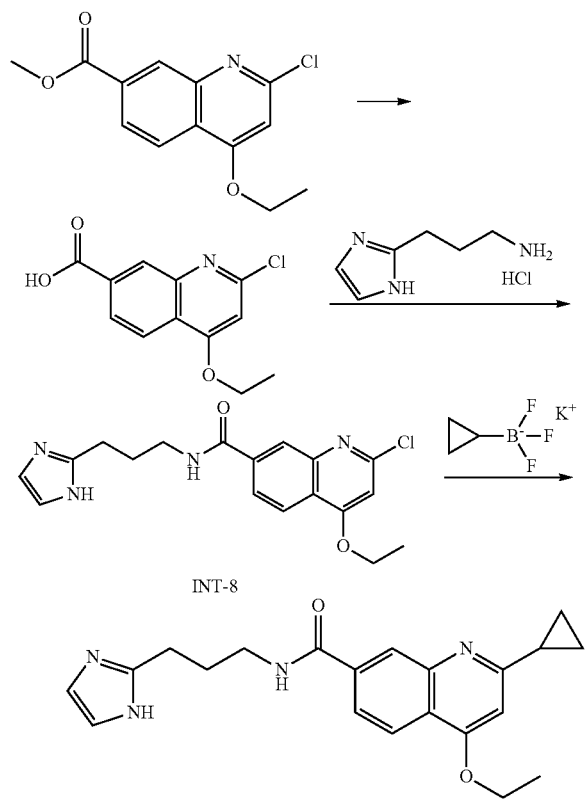

Step 1: 2-Chloro-4-ethoxyquinoline-7-carboxylic acid

To a solution of methyl 2-chloro-4-ethoxyquinoline-7-carboxylate (2.27 g, 8.53 mmol, prepared as described in Example 11) in THF (50 mL) was added 1.0 M of sodium hydroxide in water (25 mL) and water (25 mL). The resulting suspension was stirred under ice/water bath then left in the refrigerator overnight. The suspension turned into a solution. The reaction mixture was diluted with water, and then pH was adjusted with 1N HCl to pH 2-3. Solid precipitated out of the solution. The solid was filtered and collected and washed with water twice. Solid was dried to give 2-chloro-4-ethoxyquinoline-7-carboxylic acid 2.0 g (93%). LCMS: (FA) ES+ 252.0 $^1$H NMR (400 MHz, DMSO-$d_6$) δ ppm 13.46 (br s, 1H) 8.38 (s, 1H) 8.23 (d, J=8.53 Hz, 1H) 8.08 (d, J=7.79 Hz, 1H) 7.21 (s, 1H) 4.40 (q, J=6.90 Hz, 2H) 1.50 (t, J=6.96 Hz, 3H)

Step 2: N-(3-(1H-Imidazol-2-yl)propyl)-2-chloro-4-ethoxyquinoline-7-carboxamide (INT-8)

THF (37 ml) and TEA (5.1 mL, 36.4 mmol) were added into a flask with 2-chloro-4-ethoxy-quinoline-7-carboxylic acid (1.83 g, 7.3 mmol), 3-(1H-imidazol-2-yl)propan-1-amine dihydrochloride (1.58 g, 8.0 mmol) and HATU (2.84 g, 7.47 mmol). The reaction mixture was stirred at rt for 2 h. After adding ice/water, the reaction mixture was extracted with EtOAc twice. The combined organic layers were washed with brine then dried to afford crude N-(3-(1H-imidazol-2-yl)propyl)-2-chloro-4-ethoxyquinoline-7-carboxamide (2.61 g, 100%). The crude material was used without purification in the next step. LCMS: (FA) ES+ 359.2

Step 3: N-(3-(1H-Imidazol-2-yl)propyl)-2-cyclopropyl-4-ethoxyquinoline-7-carboxamide (I-58)

Into a microwave vial was added potassium cyclopropyltrifluoroborate (530.0 mg, 3.58 mmol), N-(3-(1H-imidazol-2-yl)propyl)-2-chloro-4-ethoxyquinoline-7-carboxamide (200.0 mg, 0.56 mmol), tetrakis(triphenylphosphine)palladium(0) (26.7 mg, 0.023 mmol), 2 M of sodium carbonate in water (700 μL, 1 mmol) and 1,4-dioxane (1.7 mL, 22 mmol). The vial was sealed and the mixture was degassed. The reaction mixture was heated in the microwave at 150° C. for 1 h. To the reaction mixture was added water and the mixture was extracted with EtOAc twice. Combined organic layers were washed with brine, dried, and then evaporated.

The crude material was purified by HPLC to afford N-(3-(1H-imidazol-2-yl)propyl)-2-cyclopropyl-4-ethoxyquinoline-7-carboxamide 4.89 mg (2.4%). LCMS: (FA) ES+ 365.5 ¹H NMR (400 MHz, Methanol-d₄) δ ppm 8.27-8.40 (m, 2H) 8.23 (br d, J=8.53 Hz, 1H) 7.84 (br d, J=8.53 Hz, 1H) 7.33 (s, 2H) 6.77 (s, 1H) 4.36 (q, J=6.90 Hz, 2H) 3.53 (br t, J=6.53 Hz, 2H) 3.05 (br t, J=7.28 Hz, 2H) 2.27 (br d, J=5.52 Hz, 1H) 2.13 (br t, J=7.03 Hz, 2H) 1.59 (br t, J=6.90 Hz, 3H) 1.10-1.23 (m, 4H)

Example 16: N-(3-(1H-Imidazol-2-yl)propyl)-2,4-diethoxyquinoline-7-carboxamide (I-61)

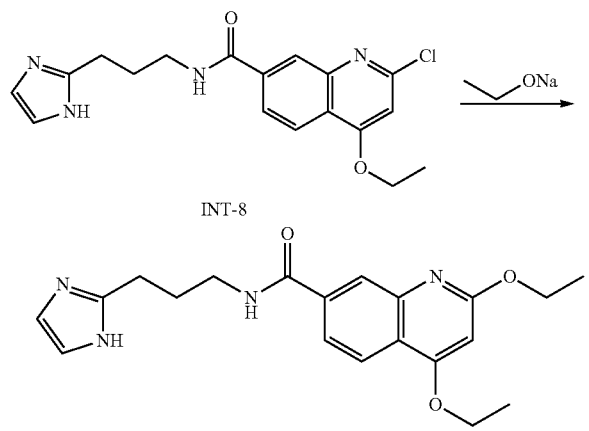

2-Chloro-4-ethoxy-N-[3-(1H-imidazol-2-yl)propyl]quinoline-7-carboxamide (70 mg, 0.2 mmol, INT-8 as described in Example 15) and 21% sodium ethoxide in ethanol (0.73 mL, 2.0 mmol) was added in a flask and heated at 60° C. overnight, LCMS showed clean and complete conversion. Solvent was removed and water was added then the mixture was extracted with EtOAc twice. Combined organic layers were washed with brine, dried then evaporated to afford crude residue. The crude material was purified through HPLC purification to afford N-(3-(1H-imidazol-2-yl)propyl)-2,4-diethoxyquinoline-7-carboxamide 50 mg (70%). LCMS: (FA) ES+ 369.2; ¹H NMR (400 MHz, DMSO-d₆) δ ppm 8.92 (br s, 1H) 8.23 (s, 1H) 8.19 (s, 1H) 8.06 (br d, J=8.53 Hz, 1H) 7.83 (br d, J=7.91 Hz, 1H) 6.89 (s, 2H) 6.51 (s, 1H) 4.47 (m, 2H) 4.24-4.34 (m, 2H) 3.20-3.52 (m, 2H) 2.66-2.74 (m, 2H) 1.94 (m, 2H) 1.48 (m, 3H) 1.40 (m, 3H).

Example 17: 4-Ethoxy-N-[3-(1H-imidazol-2-yl)propyl]-2-(pyrrolidin-1-yl)quinoline-7-carboxamide (I-62)

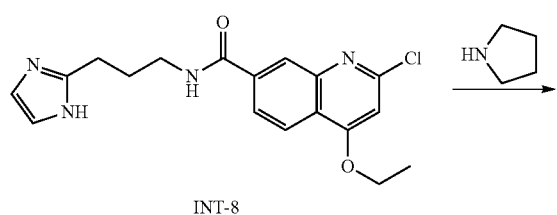

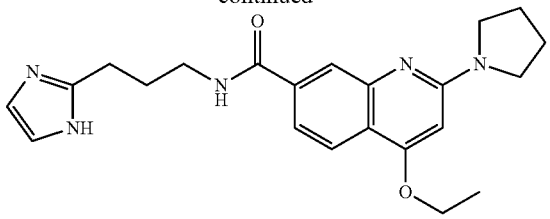

2-Chloro-4-ethoxy-N-[3-(1H-imidazol-2-yl)propyl]quinoline-7-carboxamide (70 mg, 0.20 mmol, INT-8 as described in Example 15) and pyrrolidine (1.0 mL, 12 mmol) was added together and heated in the microwave at 100° C. for 30 min. Solvent was removed. The crude mixture was purified using preparative HPLC to afford 4-ethoxy-N-[3-(1H-imidazol-2-yl)propyl]-2-(pyrrolidin-1-yl)quinoline-7-carboxamide 35 mg (46%) LCMS: (FA) ES+ 394.2; ¹H NMR (400 MHz, DMSO-d₆) δ ppm 8.80 (s, 1H) 8.17 (s, 1H) 8.02 (s, 1H) 7.90 (m, 1H) 7.56 (m, 1H) 6.91 (s, 2H) 6.26 (s, 1H) 4.29 (m, 2H) 3.22-3.60 (m, 6H) 2.70 (m, 2H) 1.71-2.04 (m, 6H) 1.49 (m, 3H).

The compounds listed in the table below were prepared in an analogous fashion to that described in Example 17 starting from the appropriate starting materials:

| Starting Material Step 1 | Compound No. or Name | LCMS Data |
|---|---|---|
| ⌇⌇NH₂ | I-42* | LCMS (ESI+): m/z = 368.2 (M + H) |

*DMF was used as co-solvent; the ethyl amine Step 1 Starting Material was 2.0M in THF Example 18: N-(3-(1H-Imidazol-2-yl)propyl)-4-ethoxy-2-(ethylthio)quinoline-7-carboxamide (I-49)

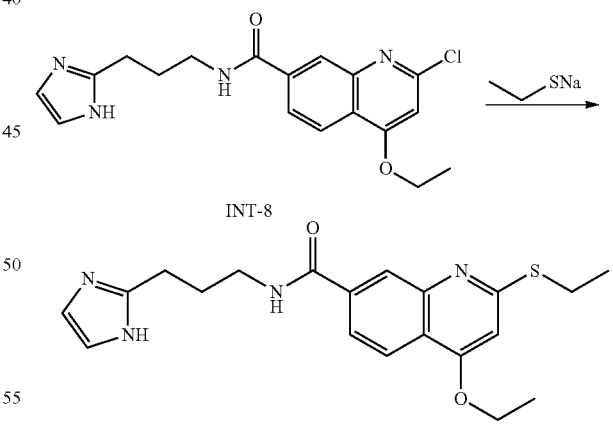

2-Chloro-4-ethoxy-N-[3-(1H-imidazol-2-yl)propyl]quinoline-7-carboxamide (300 mg, 0.8361 mmol, INT-8, described in Example 15), sodium ethanethiolate (352 mg, 4.181 mmol), DMF (3 mL) was added together and allowed to stir at rt for 1 h. Water was added to the reaction mixture and a lot of solid precipitated out of solution. The mixture was filtered to collect the solid and the solid was purified by HPLC purification to afford N-(3-(1H-imidazol-2-yl)propyl)-4-ethoxy-2-(ethylthio)quinoline-7-carboxamide (110 mg, 34%) LCMS: (FA) ES+ 385.2 ¹H NMR (400 MHz, DMSO-$d_6$) δ ppm 8.99 (m, 1H) 8.32 (s, 1H) 8.17 (s, 1H) 8.09 (d, J=8.41 Hz, 1H) 7.89 (d, J=8.41 Hz, 1H) 6.92 (s, 2H) 6.89 (s, 1H) 4.30 (m, 2H) 3.37 (m, 2H) 3.31 (m, 2H) 2.72 (m, 2H) 1.95 (m, 2H) 1.48 (t, J=6.90 Hz, 3H) 1.39 (t, J=7.28 Hz, 3H)

Example 19: 4-Ethoxy-2-(4-fluorophenyl)-N-[cis-3-(1H-imidazol-2-yl)cyclobutyl]quinoline-7-carboxamide (I-60)

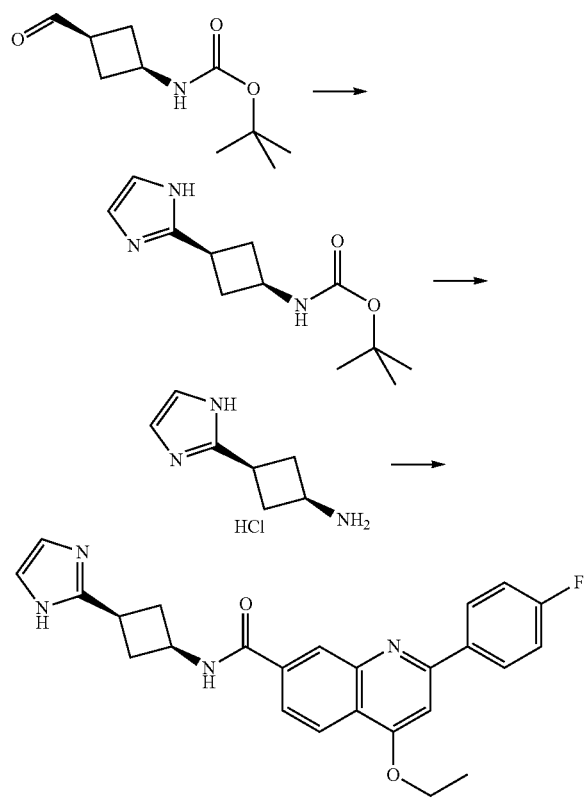

Step 1: tert-Butyl N-[cis-3-(1H-imidazol-2-yl)cyclobutyl]carbamate

To a solution of tert-butyl N-cis-(3-formylcyclobutyl)carbamate (443 mg, 2.22 mmol, prepared as described in WO2013/149121) in methyl alcohol (9.5 mL) cooled in ice bath was added ammonium hydroxide (28% mass %) (2.40 mL, 20.0 mmol) and dropwise 8.8 M of ethanedial in water (0.325 mL, 2.86 mmol). The resulting solution was stirred at rt for 15 h. The resulting orange mixture was concentrated to a wet solid. 15 mL of water were added to the solid mass and after mixing and stirring for 30 min, a suspension was obtained. The solid was filtered off, washed with water and dried under vacuum at 40° C. to give tert-butyl N-[3-(1H-imidazol-2-yl)cyclobutyl]carbamate (475 mg, 90%) as a brown solid. LCMS: (FA) ES+ 238.1; $^1$H NMR (400 MHz, DMSO-$d_6$) δ 11.61 (s, 1H), 7.12 (d, J=8.1 Hz, 1H), 6.95 (s, 1H), 6.75 (s, 1H), 3.96-3.84 (m, 1H), 2.99-3.09 (m, 1H), 2.50-2.42 (m, 2H), 2.06-2.16 (m, 2H), 1.38 (s, 9H).

Step 2: cis-3-(1H-Imidazol-2-yl)cyclobutanamine dihydrochloride

To a solution of tert-butyl N-[cis-3-(1H-imidazol-2-yl)cyclobutyl]carbamate (472 mg, 1.99 mmol) in methanol (2.5 mL) cooled in ice bath was added 4 M hydrochloric acid in dioxane (5.00 mL, 20.0 mmol). The resulting solution was then stirred at rt for 1.5 h. The mixture was added to ether (25 mL), stirred for 15 min and filtered. The collected solid was dried by suction under nitrogen, and then under vacuum to give 3-(1H-imidazol-2-yl)cyclobutanamine dihydrochloride (410 mg, 98%) as a light brown solid.

Step 3: 4-Ethoxy-2-(4-fluorophenyl)-N-[cis-3-(1H-imidazol-2-yl)cyclobutyl]quinoline-7-carboxamide (I-60)

A mixture of 4-ethoxy-2-(4-fluorophenyl)quinoline-7-carboxylic acid (125 mg, 0.402 mmol, prepared in analogous way as described in Example 11, using 4-fluorophenylboronic acid) and cis-3-(1H-imidazol-2-yl)cyclobutanamine dihydrochloride (135 mg, 0.643 mmol) in pyridine (2.50 mL) was stirred at rt for 5 min. T3P® (1.68 mol/L) in EtOAc (604 μL, 1.01 mmol) was added. The reaction mixture was stirred at rt for 20 h. 500 uL of water were added to quench the reaction mixture. The mixture was stirred at rt for 15 min and was concentrated on rotovap (at 40° C.). The residue was suspended in 10 mL of water and the resulting suspension was made basic with 1M NaOH to pH 12. The suspension was extracted with EtOAc. The separated organic layer was washed with 1M aqueous $K_2CO_3$ (×2), then brine, was dried over $Na_2SO_4$ and concentrated. The product was purified on ISCO (12 g silica, dryload) using 0-8% MeOH/DCM over 25 min to give 4-ethoxy-2-(4-fluorophenyl)-N-[3-(1H-imidazol-2-yl)cyclobutyl]quinoline-7-carboxamide (90 mg, 52%) as an off white solid. LCMS: (FA) ES+ 431.2 $^1$H NMR (400 MHz, DMSO-$d_6$) δ 11.71 (s, 1H), 9.09 (d, J=7.4 Hz, 1H), 8.58 (d, J=1.4 Hz, 1H), 8.41-8.35 (m, 2H), 8.18 (d, J=8.6 Hz, 1H), 7.99 (dd, J=8.6, 1.7 Hz, 1H), 7.61 (s, 1H), 7.44-7.36 (m, 2H), 7.01-6.98 (m, 1H), 6.82-6.80 (m, 1H), 4.55-4.43 (m, 3H), 3.27-3.16 (m, 1H), 2.69-2.59 (m, 2H), 2.48-2.38 (m, 2H), 1.53 (t, J=7.0 Hz, 3H).

Example 20: 2-(3,4-difluorophenyl)-4-ethoxy-N-[3-(1H-imidazol-2-yl)propyl]quinoline-7-carboxamide (I-52)

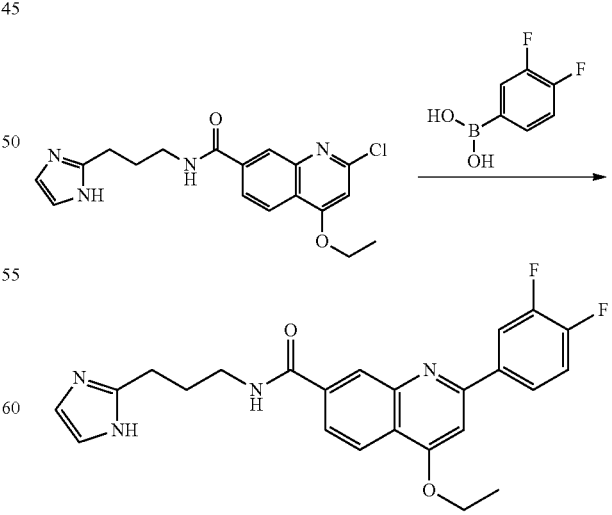

Microwave tube was charged with 2-chloro-4-ethoxy-N-[3-(1H-imidazol-2-yl)propyl]quinoline-7-carboxamide (300 mg, 0.836 mmol), 3,4-difluorophenylboronic acid (158 mg, 1.0 mmol), Pd-dppf (92 mg, 0.113 mmol), 1,4-dioxane (11 mL) and 2.0 M of potassium carbonate in water (1.43 mL, 2.85 mmol). The reaction mixture was flushed with nitrogen twice then heated at 110° C. for 35 min with microwave irradiation. The reaction mixture was quenched with water (5 mL) and then extracted with EtOAc (2×10 mL). The combined organic layers were washed with brine, dried over Na$_2$SO$_4$, filtered and evaporated to dryness. The crude material was purified by HPLC. N-(3-(1H-imidazol-2-yl)propyl)-2-(3,4-difluorophenyl)-4-ethoxyquinoline-7-carboxamide was obtained (138 mg, 38%). LC-MS: (FA) ES+ 437.2 $^1$H NMR (400 MHz, DMSO-d$_6$) δ ppm 9.00 (br s, 1H), 8.55 (s, 1H), 8.41 (m, 1H), 8.21-8.28 (m, 2H), 8.00 (m, 1H), 7.60-7.71 (m, 2H), 6.90 (br s, 2H), 4.51 (m, 2H), 3.39 (m, 2H), 2.72 (m, 2H), 1.96 (m, 2H), 1.55 (t, J=6.90 Hz, 3H).

The compound listed in the table below was prepared in an analogous fashion to that described in Example 20 starting from the appropriate starting materials:

| Starting Material | Compound No. or Name | LCMS Data |
|---|---|---|
| ![structure] | I-56 | LCMS (ESI+): m/z = 453.1 (M + H) |

Example 21: N-(3-(4H-1,2,4-yriazol-3-yl)propyl)-2-(4-chlorophenyl)-4-((2-methoxyethoxy)methyl)quinazoline-7-carboxamide (I-64)

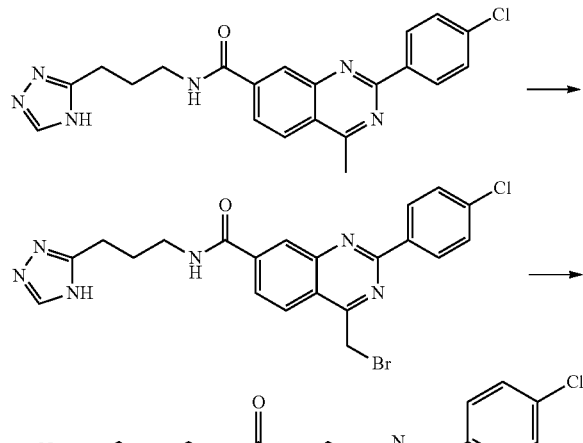

Step 1: N-(3-(4H-1,2,4-triazol-3-yl)propyl)-4-(bromomethyl)-2-(4-chlorophenyl)quinazoline-7-carboxamide To a solution of N-(3-(4H-1,2,4-triazol-3-yl)propyl)-2-(4-chlorophenyl)-4-methylquinazoline-7-carboxamide (271 mg, 0.67 mmol; I-63, prepared according to Example 7) in acetic acid (8.0 mL) was added bromine solution in acetic acid (0.88 M, 1.88 mL) and the solution was allowed to stir at 65° C. Additional bromine solution was added in 30 (0.300 mL) and 60 min (0.200 mL). 30 min after the last bromine addition the reaction was cooled and quenched by adding saturated aqueous sodium bisulfite solution (0.5 mL). The reaction was concentrated in vacuo. Purification by silica gel chromatography followed by preparative HPLC gave N-(3-(4H-1,2,4-triazol-3-yl)propyl)-4-(bromomethyl)-2-(4-chlorophenyl)quineazoline-7-carboxamide (25 mg, 8%). LC-MS: (FA) ES+ 487.0, 485.1.

Step 2: N-(3-(4H-1,2,4-yriazol-3-yl)propyl)-2-(4-chlorophenyl)-4-((2-methoxyethoxy)methyl)quinazoline-7-carboxamide To a solution of N-(3-(4H-1,2,4-triazol-3-yl)propyl)-4-(bromomethyl)-2-(4-chlorophenyl)quinazoline-7-carboxamide (25.3 mg, 0.0521 mmol) in 2-methoxyethanol (2.0 mL) was added 1.0 M aqueous sodium hydroxide (0.130 mL) and the resulting solution was stirred for 10 minutes. The solution was neutralized to pH 7 with 1N formic acid solution. The resulting solution was concentrated in vacuo and purified by prep reverse phase HPLC to give N-(3-(4H-1,2,4-yriazol-3-yl)propyl)-2-(4-chlorophenyl)-4-((2-methoxyethoxy)methyl)quinazoline-7-carboxamide (6.5 mg, 26%). LC-MS: (FA) ES+ 481.1; $^1$H NMR (Methanol-d$_4$, 400 MHz) δ 8.55-8.51 (m, 2H), 8.42-8.39 (m, 2H), 7.96-7.94 (m, 1H), 7.47-7.43 (m, 2H), 8.05 (bs, 1H), 5.13 (s, 2H), 3.75-3.73 (m, 2H), 3.54-3.51 (m, 2H), 3.45-3.42 (m, 2H), 3.25 (s, 3H), 2.85-2.81 (m, 2H), 2.06-2.01 (m, 2H).

Example 22: 4-(2-methoxyethoxy)-2-(2-methylpyridin-4-yl)-N-([1,2,4]triazolo[1,5-a]pyridin-7-ylmethyl)quinoline-7-carboxamide (I-69)

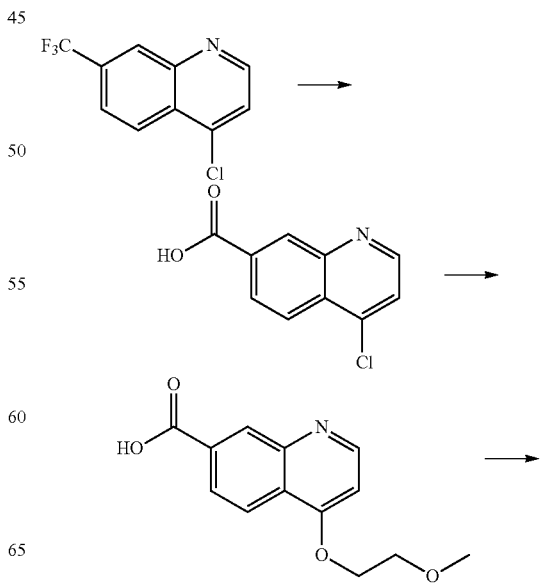

-continued

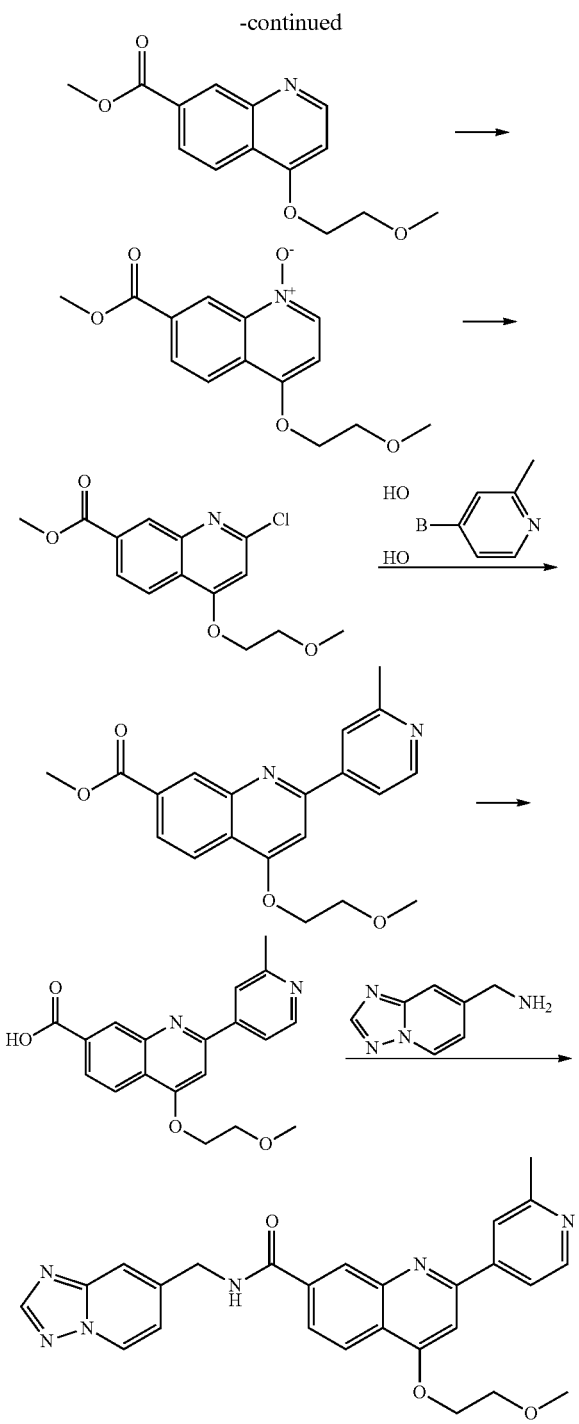

Step 1: 4-chloroquinoline-7-carboxylic acid

A mixture of 4-chloro-7-(trifluoromethyl)quinoline (44.0 g, 189 mmol) and sulfuric acid (440 mL) was allowed to stir at 200° C. for 4 h. The reaction mixture was cooled to room temperature, then poured into ice water (2000 mL). The pH was adjusted to 3 by addition of 1N NaOH. The resulting precipitate was collected by filtration and washed with water (200 mL×2), and dried under high vacuum to give 4-chloroquinoline-7-carboxylic acid (30.0 g, 77%) as a beige solid. LC-MS: (FA) ES+ 208.0; $^1$H NMR (400 MHz, DMSO-$d_6$) δ 8.97 (d, J=4.6 Hz, 1H), 8.63 (d, J=1.3 Hz, 1H), 8.33 (d, J=8.8 Hz, 1H), 8.23 (dd, J=1.6, 8.7 Hz, 1H), 7.92 (d, J=4.6 Hz, 1H).

Step 2: 4-(2-methoxyethoxy)quinoline-7-carboxylic acid

To a mixture of 4-chloroquinoline-7-carboxylic acid (6.70 g, 32.3 mmol) in 2-methoxyethanol (159 mL, 2.02 mol) and 1,4-dioxane (67.0 mL) was added potassium tert-butoxide (1M solution in THF, 96.8 mL, 96.8 mmol). The reaction was allowed to stir at 100° C. for 16 h. The reaction was cooled to room temperature, then quenched with water. The mixture was concentrated to remove organic solvents, then diluted with water and pH was adjusted to 4.5 by addition of 1N HCl. The mixture was allowed to stand at room temperature overnight, and the resulting precipitate was collected by filtration and washed with water and dried under high vacuum to give 4-(2-methoxyethoxy)quinoline-7-carboxylic acid (5.69 g, 71%) as a beige solid. LC-MS: (AA) ES+ 248.1; $^1$H NMR (400 MHz, DMSO-$d_6$) δ 13.31 (br s, 1H), 8.83 (d, J=5.1 Hz, 1H), 8.50 (d, J=1.4 Hz, 1H), 8.24 (d, J=8.7 Hz, 1H), 8.05 (dd, J=1.6, 8.7 Hz, 1H), 7.16 (d, J=5.3 Hz, 1H), 4.46-4.39 (m, 2H), 3.84 (dd, J=3.6, 5.2 Hz, 2H), 3.40-3.37 (m, 3H).

Step 3: Methyl 4-(2-methoxyethoxy)quinoline-7-carboxylate

To a mixture of 4-(2-methoxyethoxy)quinoline-7-carboxylic acid (1.00 g, 4.05 mmol) and DMF (0.0273 mL, 0.352 mmol) in THF (20.0 mL) was added oxalyl chloride (2M solution in DCM, 6.07 mL, 12.1 mmol) dropwise. The reaction mixture was allowed to stir at rt for 6 hours. Then MeOH (5.00 mL) was added and the reaction was allowed to stir at rt for 16 hours. The mixture was distributed between EtOAc and saturated aqueous sodium bicarbonate. The layers were separated and the aqueous layer was extracted twice with EtOAc. The combined organic layer was then washed with saturated aqueous sodium bicarbonate followed by brine. The organic layer was dried over anhydrous sodium sulfate then filtered and concentrated to give methyl 4-(2-methoxyethoxy)quinoline-7-carboxylate (0.825 g, 78% yield) as an off-white solid. LC-MS: (AA) ES+ 262.1; $^1$H NMR (400 MHz, DMSO-$d_6$) δ 8.84 (d, J=5.3 Hz, 1H), 8.52 (d, J=1.5 Hz, 1H), 8.27 (d, J=8.8 Hz, 1H), 8.06 (dd, J=1.8, 8.7 Hz, 1H), 7.18 (d, J=5.3 Hz, 1H), 4.46-4.39 (m, 2H), 3.94 (s, 3H), 3.90-3.78 (m, 2H), 3.38 (s, 3H).

Step 4: Methyl 4-(2-methoxyethoxy)quinoline-7-carboxylate 1-oxide

To a solution of methyl 4-(2-methoxyethoxy)quinoline-7-carboxylate (5.22 g, 20.0 mmol) in DCM (224 mL) at 0° C. was added 3-chloroperoxybenzoic acid (6.89 g, 40.0 mmol). The reaction mixture was allowed to warm to room temperature and stir for 16 hours. The reaction was then distributed between DCM and saturated aqueous sodium sulfite solution. The layers were separated and the organic layer was washed with saturated aqueous sodium bicarbonate solution three times, followed by brine. The organic layer was dried over anhydrous sodium sulfate then filtered and concentrated to give methyl 4-(2-methoxyethoxy)quinoline-7-carboxylate 1-oxide (5.12 g, 92%) as a yellow solid. LC-MS: (AA) ES+ 278.1; $^1$H NMR (400 MHz, DMSO-$d_6$) δ 9.10 (d, J=1.4 Hz, 1H), 8.59 (d, J=6.9 Hz, 1H), 8.30 (d, J=8.7 Hz, 1H), 8.21 (dd, J=1.6, 8.7 Hz, 1H), 7.14 (d, J=6.9 Hz, 1H), 4.41 (dd, J=3.6, 5.2 Hz, 2H), 3.96 (s, 3H), 3.82 (dd, J=3.5, 5.1 Hz, 2H), 3.39-3.36 (m, 3H).

Step 5: Methyl 2-chloro-4-(2-methoxyethoxy)quinoline-7-carboxylate

To a solution of methyl 4-(2-methoxyethoxy)quinoline-7-carboxylate 1-oxide (5.12 g, 18.5 mmol) in DMF (107 mL) at 0° C. was added oxalyl chloride (2M solution in DCM, 20.7 mL, 41.4 mmol) slowly. After stirring at 0° C. for 5 minutes, the reaction mixture was allowed to stir at 38° C. for 16 h. The mixture was allowed to cool to room temperature, and then ice water and DCM was added to the mixture. After pH was adjusted to 7 with addition of saturated aqueous sodium bicarbonate solution, the layers were separated and the aqueous layer was extracted with DCM twice. The combined organic layer was washed with 10% aqueous lithium chloride solution three times, followed by water and then brine. The organic layer was dried over anhydrous sodium sulfate, filtered and concentrated under reduced pressure. The residue was azeotroped twice with toluene to remove DMF, then dried under vacuum to give methyl 2-chloro-4-(2-methoxyethoxy)quinoline-7-carboxylate (4.79 g, 88% yield) as an off-white solid. LC-MS: (AA) ES+ 296.1; $^1$H NMR (400 MHz, DMSO-$d_6$) δ 8.41 (d, J=1.3 Hz, 1H), 8.24 (d, J=8.7 Hz, 1H), 8.10 (dd, J=1.6, 8.7 Hz, 1H), 7.28 (s, 1H), 4.46-4.51 (m, 2H), 3.94 (s, 3H), 3.80-3.85 (m, 2H), 3.42-3.34 (m, 3H).

Step 6: Methyl 4-(2-methoxyethoxy)-2-(2-methylpyridin-4-yl)quinoline-7-carboxylate To a mixture of methyl 2-chloro-4-(2-methoxyethoxy)quinoline-7-carboxylate (0.194 g, 0.656 mmol), (2-methyl-4-pyridyl)boronic acid (0.112 g, 0.820 mmol) and cesium carbonate (0.359 g, 1.10 mmol) was added 1,4-dioxane (5.20 mL) and water (0.780 mL). The reaction mixture was stirred under nitrogen atmosphere for 5 minutes, then 1,1'-bis(diphenylphosphino)ferrocenedichloropalladium(II) (0.0268 g, 0.0328 mmol) was added. The reaction mixture was allowed to stir at 110° C. for 1 hr. The reaction was cooled to room temperature then diluted with DCM. The mixture was filtered over Celite and the solid was washed with DCM. The filtrate was concentrated under reduced pressure, and the residue was diluted with EtOAc and water. The layers were separated and the aqueous layer was extracted with EtOAc twice. The combined organic layer was then dried over anhydrous sodium sulfate then concentrated under reduced pressure. The crude material was purified by silica gel chromatography to give methyl 4-(2-methoxyethoxy)-2-(2-methylpyridin-4-yl)quinoline-7-carboxylate (0.140 g, 61%) as a yellow solid. LC-MS: (AA) ES+ 353.1; $^1$H NMR (400 MHz, DMSO-$d_6$) δ 8.64 (d, J=5.2 Hz, 1H), 8.62 (s, 1H), 8.28 (d, J=8.7 Hz, 1H), 8.16 (s, 1H), 8.12-8.04 (m, 2H), 7.78 (s, 1H), 4.66-4.55 (m, 2H), 3.96 (s, 3H), 3.93-3.83 (m, 2H), 3.41 (s, 3H), 2.62 (s, 3H).

Step 7: 4-(2-methoxyethoxy)-2-(2-methylpyridin-4-yl)quinoline-7-carboxylic acid To a solution of methyl 4-(2-methoxyethoxy)-2-(2-methylpyridin-4-yl)quinoline-7-carboxylate (0.131 g, 0.372 mmol) in THF (1.2 mL) and methanol (1.2 mL) was added 1N sodium hydroxide (1.11 mL, 1.11 mmol). The reaction mixture was allowed to stir at rt for 3 days, then the mixture was concentrated. 1N aqueous hydrogen chloride was added to adjust pH to 6. The mixture was concentrated to dryness and then purified by HPLC to give 4-(2-methoxyethoxy)-2-(2-methylpyridin-4-yl)quinoline-7-carboxylic acid (0.100 g, 80% yield) as a white solid. LC-MS: (AA) ES+ 339.1; $^1$H NMR (400 MHz, DMSO-$d_6$) δ 8.63 (d, J=5.3 Hz, 1H), 8.54 (s, 1H), 8.14-8.20 (m, 2H), 8.06-8.10 (m, 2H), 7.72 (s, 1H), 4.56-4.61 (m, 2H), 3.85-3.90 (m, 2H), 3.41 (s, 3H), 2.62 (s, 3H).

Step 8: 4-(2-methoxyethoxy)-2-(2-methylpyridin-4-yl)-N-([1,2,4]triazolo[1,5-a]pyridin-7-ylmethyl)quinoline-7-carboxamide To a mixture of 4-(2-methoxyethoxy)-2-(2-methylpyridin-4-yl)quinoline-7-carboxylic acid (0.050 g, 0.148 mmol) and [1,2,4]triazolo[1,5-a]pyridine-7-ylmethanamine (0.024 g, 0.163 mmol) in THF (1.8 mL) at room temperature was added TEA (0.103 mL, 0.739 mmol) followed by HATU (0.062 g, 0.163 mmol). The reaction mixture was allowed to stir at room temperature for 16 hours. The reaction was distributed between EtOAc and 1N NaOH. The layers were separated and the aqueous layer was extracted with EtOAc. The combined organic layer was washed with saturated sodium bicarbonate followed by brine. The organic layer was dried over anhydrous sodium sulfate then filtered and concentrated. The residue was purified by HPLC to give 4-(2-methoxyethoxy)-2-(2-methylpyridin-4-yl)-N-([1,2,4]triazolo[1,5-a]pyridin-7-ylmethyl)quinoline-7-carboxamide (0.016 g, 23%) as a white solid. LC-MS: (AA) ES+ 469.2; $^1$H NMR (400 MHz, methanol-$d_4$) δ 8.80 (d, J=7.0 Hz, 1H), 8.62 (s, 1H), 8.60 (d, J=5.2 Hz, 1H), 8.38-8.43 (m, 2H), 8.13 (s, 1H), 8.08-8.02 (m, 2H), 7.78 (s, 1H), 7.63 (s, 1H), 7.32 (dd, J=1.4, 7.0 Hz, 1H), 4.87-4.79 (m, 2H), 4.69-4.52 (m, 2H), 4.03-3.96 (m, 2H), 3.54 (s, 3H), 2.70 (s, 3H).

The compound listed in the table below was prepared in an analogous fashion to that described in Example 22 starting from the appropriate starting materials:

| Material in Step 6 | Compound No. or Name | LCMS Data |
|---|---|---|
| (boronic acid structure shown) | I-67 | LCMS (ESI+): m/z = 485.2 (M + H) |

Example 23: 2-(4-chlorophenyl)-4-[1-fluoropropyl]-N-[3-(1H-imidazol-2-yl)propyl]quinazoline-7-carboxamide (I-72)

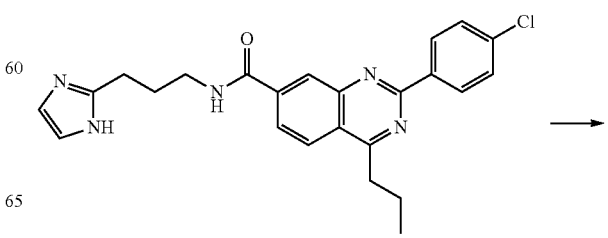

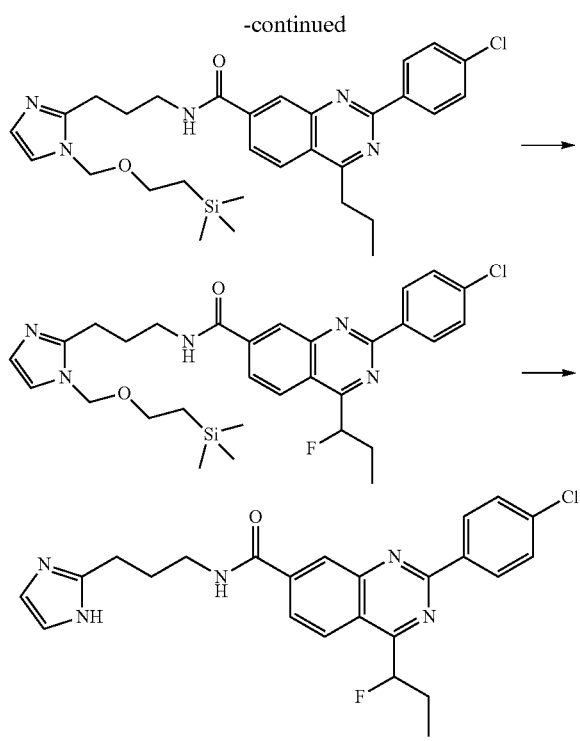

Step 1: 2-(4-chlorophenyl)-4-propyl-N-[3-[1-(2-trimethylsilylethoxymethyl)imidazol-2-yl]propyl]quinazoline-7-carboxamide To a solution of 2-(4-chlorophenyl)-N-[3-(1H-imidazol-2-yl)propyl]-4-propyl-quinazoline-7-carboxamide (176 mg, 0.405 mmol) in DMF (2.50 mL) was added sodium hydride in mineral oil (60%) (18 mg, 0.446 mmol) at 0° C. The mixture was warmed to rt and allowed to stir for 10 min. The mixture was cooled back to 0° C. and 2-(trimethylsilyl)ethoxymethyl chloride (79 µL, 0.446 mmol) was added. The reaction was slowly warmed to rt and allowed to stir overnight, and then was distributed between saturated aqueous sodium bicarbonate solution and EtOAc. The aqueous layer was extracted with EtOAc. The combined organic layer was washed with brine (×2), dried over $Na_2SO_4$, filtered and concentrated. Purification by column chromatography provided 2-(4-chlorophenyl)-4-propyl-N-[3-[1-(2-trimethylsilylethoxymethyl)imidazol-2-yl]propyl]quinazoline-7-carboxamide as a white solid (172 mg, 75.2% yield). LC-MS: (FA) ES+ 564; $^1$H NMR (400 MHz, $CDCl_3$) δ 9.25 (br s, 1H), 8.61-8.68 (m, 2H), 8.59 (d, J=1.25 Hz, 1H), 8.07-8.20 (m, 2H), 7.46-7.55 (m, 2H), 7.14 (d, J=1.25 Hz, 1H), 6.98 (d, J=1.51 Hz, 1H), 5.25 (s, 2H), 3.62-3.71 (m, 2H), 3.52 (dd, J=7.78, 8.78 Hz, 2H), 3.29-3.39 (m, 2H), 2.94-3.03 (m, 2H), 2.17-2.30 (m, 2H), 1.96-2.13 (m, 2H), 1.13 (t, J=7.40 Hz, 3H), 0.84-0.98 (m, 2H), −0.02 (s, 9H).

Step 2: 2-(4-chlorophenyl)-4-[1-fluoropropyl]-N-[3-[1-(2-trimethylsilylethoxymethyl)imidazol-2-yl]propyl]quinazoline-7-carboxamide To a solution of 2-(4-chlorophenyl)-4-propyl-N-[3-[1-(2-trimethylsilylethoxymethyl)imidazol-2-yl]propyl]quinazoline-7-carboxamide (55 mg, 0.0975 mmol) in MeCN (1.00 mL) was added N-fluoro-N-chloromethyl-triethylenediamine-bis(tetrafluoroborate) (51.8 mg, 0.146 mmol). The solution was allowed to stir at rt for 2 days. The mixture was distributed between saturated aqueous sodium bicarbonate solution and EtOAc. The aqueous layer was extracted with EtOAc. The combined organic layer was washed with brine, dried over $Na_2SO_4$, filtered and concentrated. The crude mixture was purified by silica gel chromatography to provide 2-(4-chlorophenyl)-4-[1-fluoropropyl]-N-[3-[1-(2-trimethylsilylethoxymethyl)imidadazol-2-yl]propyl]quinazoline-7-carboxamide as a colorless syrup (22 mg, used directly in the following step). LC-MS: (FA) ES+ 582.

Step 3: 2-(4-chlorophenyl)-4-[1-fluoropropyl]-N-[3-(1H-imidazol-2-yl)propyl]quinazoline-7-carboxamide A solution of 2-(4-chlorophenyl)-4-[1-fluoropropyl]-N-[3-[1-(2-trimethylsilylethoxymethyl)imidazol-2-yl]propyl]quinazoline-7-carboxamide (22 mg, 0.038 mmol) in 4M hydrochloric acid in 1,4-dioxane (1.00 mL, 4.00 mmol) was allowed to stir at rt overnight. The reaction was distributed between saturated aqueous sodium bicarbonate solution and EtOAc. The aqueous layer was extracted with EtOAc. The combined org layer was dried over $Na_2SO_4$, filtered and concentrated. Purification by HPLC provided 2-(4-chlorophenyl)-4-[1-fluoropropyl]-N-[3-(1H-imidazol-2-yl)propyl]quinazoline-7-carboxamide as a yellow solid (7.0 mg, 16% yield over 2 steps). LC-MS: (FA) ES+ 452, 454; $^1$H NMR (400 MHz, Methanol-$d_4$) δ 8.63 (d, J=8.56 Hz, 2H), 8.55 (d, J=1.47 Hz, 1H), 8.52 (d, J=8.68 Hz, 1H), 8.08 (dd, J=1.71, 8.80 Hz, 1H), 7.57 (d, J=8.56 Hz, 2H), 6.99 (s, 2H), 6.02-6.29 (m, 1H), 3.51 (t, J=6.97 Hz, 2H), 2.87 (t, J=7.52 Hz, 2H), 2.22-2.47 (m, 2H), 2.03-2.15 (m, 2H), 1.18 (t, J=7.46 Hz, 3H).

Example 24: N-(3-(4H-1,2,4-triazol-3-yl)propyl)-2-(4-fluorophenyl)-4-(2-methoxyethoxy)quinoline-7-carboxamide (I-124)

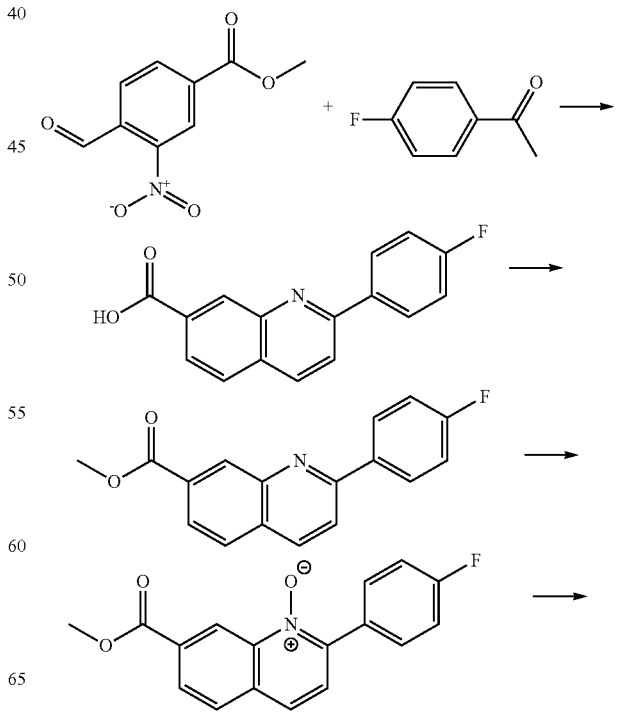

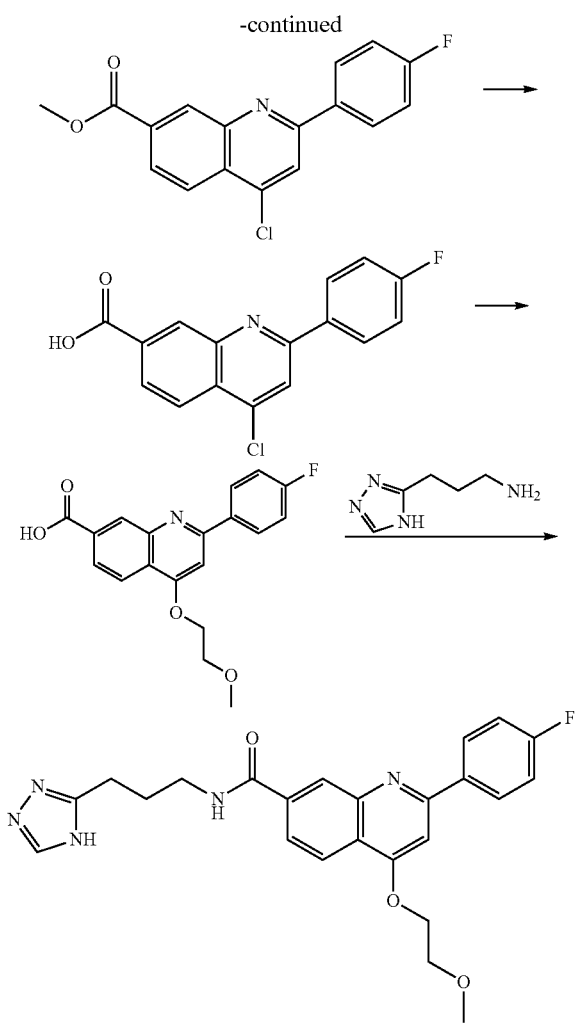

Step 1: 2-(4-fluorophenyl)quinoline-7-carboxylic acid

Iron power (1.3 g, 234.7 mmol), water (5.0 mL), concentrated HCl (0.39 mL, 4.5 mmol) were added consecutively to a solution of methyl 4-formyl-3-nitrobenzoate (5.0 g, 23.9 mmol) in ethanol (62 mL), and the mixture was allowed to stir at 95° C. for 90 min. Then 4'-Fluoroacetophenone (3.24 g, 23.5 mmol) and solid KOH (4.0 g, 70.3 mmol) were added cautiously and the mixture was allowed to stir at 95° C. for another 90 min. The warm mixture was filtered, and the filtrate was acidified to pH 1 with 6N HCl. The resulting solid was filtered and washed with water then dried under vacuum to give 2-(4-fluorophenyl)quinoline-7-carboxylic acid (3.5 g, 73% yield) UPLC-MS/1.5 min: (FA) ES+ 268.1 $^1$H NMR (400 MHz, DMSO-$d_6$) δ ppm 13.33 (br s, 1H) 8.62 (s, 1H) 8.56 (d, J=8.78 Hz, 1H) 8.38 (dd, J=8.66, 5.65 Hz, 2H) 8.29 (d, J=8.66 Hz, 1H) 8.04-8.15 (m, 2H) 7.41 (t, J=8.85 Hz, 2H)

Step 2: Methyl 2-(4-fluorophenyl)quinoline-7-carboxylate

Into a round bottom flask was added 2-(4-fluorophenyl) quinoline-7-carboxylic acid (1.00 g, 3.74 mmol), THF (20 mL) and DMF (4 µL, 0.05 mmol). To the stirred suspension was added oxalyl chloride (5.6 mL, 11.2 mmol, 2.00 mol/L in DCM). The reaction mixture was allowed to stir at room temperature overnight. Then methanol (10 mL, 300 mmol) was added and the mixture was allowed to stir for 5 min. The reaction mixture was distributed between water and EtOAc. The aqueous layer was extracted with EtOAc (2×). The combined organic layer was washed with water (3×) and brine then dried over $Na_2SO_4$ and concentrated to give methyl 2-(4-fluorophenyl)quinoline-7-carboxylate (1.29 g; crude material was used directly in next step) UPLC-MS/1.5 min: (FA) ES+ 282.1 $^1$H NMR (400 MHz, DMSO-$d_6$) δ ppm 8.64 (s, 1H) 8.57 (d, J=8.66 Hz, 1H) 8.38 (dd, J=8.85, 5.58 Hz, 2H) 8.30 (d, J=8.78 Hz, 1H) 8.04-8.18 (m, 2H) 7.41 (t, J=8.85 Hz, 2H) 3.96 (s, 3H)

Step 3: Methyl 2-(4-fluorophenyl)quinoline-7-carboxylate 1-oxide

To a solution of methyl 2-(4-fluorophenyl)quinoline-7-carboxylate (1.09 g, 3.87 mmol) in DCM (22 mL) at rt was added mCPBA (1.98 g, 8.8 mmol). The reaction mixture was allowed to stir at rt overnight. The reaction mixture was partitioned between saturated aqueous $NaHCO_3$ and DCM. The separated organic layer was washed with 1N aqueous NaOH three times, then brine. The organics were dried over $Na_2SO_4$, and concentrated to give crude methyl 2-(4-fluorophenyl)quinoline-7-carboxylate 1-oxide (1.03 g, 89% yield) UPLC-MS/1.5 min: (FA) ES+ 298.1 $^1$H NMR (400 MHz, DMSO-$d_6$) δ ppm 9.22 (s, 1H) 8.18-8.28 (m, 2H) 8.11-8.16 (m, 2H) 8.08 (d, J=8.66 Hz, 1H) 7.91 (d, J=8.78 Hz, 1H) 7.38-7.44 (m, 2H) 3.97 (s, 3H)

Step 4: methyl 4-chloro-2-(4-fluorophenyl)quinoline-7-carboxylate

A solution of methyl 2-(4-fluorophenyl)quinoline-7-carboxylate 1-oxide (1.03 g, 3.46 mmol) in DMF (20 mL) was cooled in ice bath. 2.00 M of oxalyl chloride in DCM (4.17 mL, 8.33 mmol, 2.00 mol/L) was added dropwise. After a few minutes the resulting suspension was allowed to warm up to room temperature. Then the reaction mixture was allowed to stir at 38° C. for 2 hours. The mixture was distributed between water and DCM. The aqueous phase was extracted with DCM, then the combined organic layer was washed with water 3 times, dried over $Na_2SO_4$, filtered and concentrated to give methyl 4-chloro-2-(4-fluorophenyl)quinoline-7-carboxylate (1.06 g, 97% yield) UPLC-MS/1.5 min: (FA) ES+ 316.1

Step 5: 4-chloro-2-(4-fluorophenyl)quinoline-7-carboxylic acid

To a solution of methyl 4-chloro-2-(4-fluorophenyl)quinoline-7-carboxylate (1.16 g, 3.67 mmol) in THF (26 mL) at 0° C. was added 1.0 M Sodium hydroxide in water (13 mL) and water (13 mL). The resulting suspension was allowed to stand at 0° C. overnight. The reaction mixture was diluted with water, and then acidified to pH 2.5 using 1N aqueous HCl. The resulting solid was collected by filtration then washed with water and dried under vacuum to give 4-chloro-2-(4-fluorophenyl)quinoline-7-carboxylic acid (742 mg, 74% yield). UPLC-MS/1.5 min: (FA) ES+ 302.0 $^1$H NMR (400 MHz, DMSO-$d_6$) δ ppm 13.53 (br, H) 8.66 (s, 1H) 8.56 (s, 1H) 8.43 (dd, J=8.78, 5.52 Hz, 2H) 8.32 (d, J=8.66 Hz, 1H) 8.20 (dd, J=8.66, 1.51 Hz, 1H) 7.42 (t, J=8.85 Hz, 2H)

Step 6: 2-(4-fluorophenyl)-4-(2-methoxyethoxy) quinoline-7-carboxylic acid

To a solution of 4-chloro-2-(4-fluorophenyl)quinoline-7-carboxylic acid (548 mg, 1.82 mmol) in 2-methoxyethanol (1.43 mL, 18.2 mmol) and 1,4-dioxane (2 mL) was added potassium tert-butoxide in THF (5.4 mL, 5.4 mmol, 1.0 mol/L). The reaction mixture was allowed to stir at 100° C. overnight. After cooling to rt, the reaction mixture was diluted with water and then acidified to pH 5-6 using 1N aqueous HCl. The resulting solid was filtered and then washed with water followed by EtOAc and ether and dried under vacuum to give 2-(4-fluorophenyl)-4-(2-methoxyethoxy)quinoline-7-carboxylic acid (267 mg, 43% yield) UPLC-MS/1.5 min: (FA) ES+ 342.1 $^1$H NMR (400 MHz, DMSO-$d_6$) δ ppm 13.31 (br s, 1H) 8.54 (d, J=1.13 Hz, 1H) 8.40 (dd, J=8.78, 5.65 Hz, 2H) 8.22 (d, J=8.53 Hz, 1H) 8.03 (dd, J=8.66, 1.51 Hz, 1H) 7.69 (s, 1H) 7.40 (t, J=8.85 Hz, 2H) 4.54-4.62 (m, 2H) 3.84-3.91 (m, 2H) 3.40 (s, 3H).

Step 7: N-(3-(4H-1,2,4-triazol-3-yl)propyl)-2-(4-fluorophenyl)-4-(2-methoxyethoxy)quinoline-7-carboxamide To a solution of 2-(4-fluorophenyl)-4-(2-methoxyethoxy)quinoline-7-carboxylic acid (157 mg, 0.46 mmol) and 3-(4H-1,2,4-triazol-3-yl)propan-1-amine hydrochloride (90 mg, 0.55 mmol) and HATU (192 mg, 0.51 mmol) in THF (2.3 mL) was added TEA (0.32 mL, 2.30 mmol). The reaction mixture was stirred at rt for 2 h. The mixture was distributed between water and EtOAc, then the aqueous phase was extracted with EtOAc. The combined organic layer was washed with water 3 times, dried over $Na_2SO_4$ and concentrated. The residue was purified by HPLC to give N-(3-(4H-1,2,4-triazol-3-yl)propyl)-2-(4-fluorophenyl)-4-(2-methoxyethoxy)quinoline-7-carboxamide (92 mg, 45% yield) UPLC-MS/1.5 min: (FA) ES+ 450.2 $^1$H NMR (400 MHz, DMSO-$d_6$) δ ppm 8.87 (t, J=5.58 Hz, 1H) 8.53 (d, J=1.38 Hz, 1H) 8.34-8.42 (m, 2H) 8.19 (d, J=8.53 Hz, 1H) 7.97 (dd, J=8.60, 1.69 Hz, 1H) 7.66 (s, 1H) 7.40 (m, 2H) 4.58 (m, 2H) 3.88 (m, 2H) 3.41 (s, 3H) 3.37-3.43 (m, 2H) 2.78 (br t, J=7.65 Hz, 2H) 1.98 (m, 2H).

The compound listed in the table below was prepared in an analogous fashion to that described in Example 24 starting from the appropriate starting materials:

| Alcohol in Step 6 | Amine in Step 7 | Compound No. or Name | LCMS Data |
|---|---|---|---|
| | | I-66 | LCMS (ESI+): m/z = 464.2 (M + H) |
| | | I-81 | LCMS (ESI+): m/z = 486.2 (M + H) |
| | | I-82 | LCMS (ESI+): m/z = 472.2 (M + H) |
| | | I-109 | LCMS (ESI+): m/z = 450.2 (M + H) |
| | | I-120 | LCMS (ESI+): m/z = 449.2 (M + H) |
| | | I-126 | LCMS (ESI+): m/z = 449.2 (M + H) |
| | | I-156 | LCMS (ESI+): m/z = 449.2 (M + H) |

-continued

| Alcohol in Step 6 | Amine in Step 7 | Compound No. or Name | LCMS Data |
|---|---|---|---|
| HO~~OH | [imidazol-2-yl-propyl-NH2] | I-229 | LCMS (ESI+): m/z = 435.1 (M + H) |

Example 25: 2-(3,6-dihydro-2H-pyran-4-yl)-4-ethoxy-N-[3-(4H-1,2,4-triazol-3-yl)propyl]quinoline-7-carboxamide (I-140)

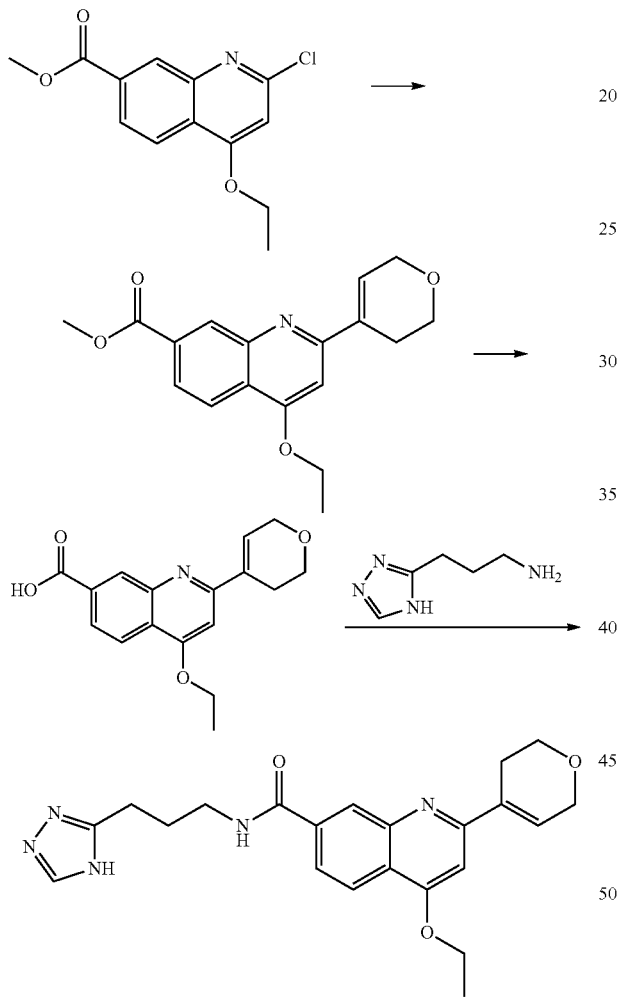

Step 1: methyl 2-(3,6-dihydro-2H-pyran-4-yl)-4-ethoxyquinoline-7-carboxylate A mixture of methyl 2-chloro-4-ethoxyquinoline-7-carboxylate (874 mg, 3.29 mmol; prepared according to Example 11), 3,6-dihydropyran-4-boronic acid, pinacol ester (1.06 g, 4.93 mmol), bis(di-tert-butyl(4-dimethylaminophenyl)phosphine)dichloropalladium(II) (233 mg, 0.329 mmol), potassium acetate (1.13 g, 11.5 mmol) was placed into a pressure tube. Dioxane (22.6 mL) and water (4.5 mL) were added and the suspension was purged with argon and was allowed to stir at 105° C. overnight. The reaction was allowed to cool at rt and was partitioned between EtOAc (50 ml) and water (10 mL). The organic layer was washed with water (10 mL), dried over MgSO$_4$, filtered and concentrated in vacuo. Purification by column chromatography gave methyl 2-(3,6-dihydro-2H-pyran-4-yl)-4-ethoxyquinoline-7-carboxylate (1.03 g, 81%). LC-MS: (FA) ES+ 314.1; $^1$H NMR (CDCl$_3$, 400 MHz) δ 8.72 (s, 1H), 8.23 (d, J=8.5 Hz, 1H), 8.05 (dd, J=8.7, 1.6 Hz, 1H), 7.28 (m, 1H), 6.95 (s, 1H), 4.46-4.43 (m, 2H), 4.34-4.29 (m, 2H), 4.02-3.99 (m, 2H), 4.00 (s, 3H), 2.86-2.83 (m, 2H), 1.61 (t, J=6.9 Hz, 3H).

Step 2: 2-(3,6-dihydro-2H-pyran-4-yl)-4-ethoxyquinoline-7-carboxylic acid

To a solution of methyl 2-(3,6-dihydro-2H-pyran-4-yl)-4-ethoxyquinoline-7-carboxylate (524 mg, 1.67 mmol) in THF (9 mL) and ethanol (9 mL) was added 1.0 M aqueous NaOH solution (4.63 mL) and the resulting solution was allowed to stir at rt overnight. Water (10 mL) was added and the resulting solution was acidified to pH 3.5 with 1 M HCl aqueous solution. The mixture was concentrated in vacuo to a slurry and the resulting precipitate was filtered off, washed with water and dried to give 2-(3,6-dihydro-2H-pyran-4-yl)-4-ethoxyquinoline-7-carboxylic acid (335 mg, 67%). LC-MS: (FA) ES+ 300.1; $^1$H NMR (DMSO-d$_6$, 400 MHz) δ 13.41 (br s, 1H), 8.59-8.56 (m, 1H), 8.23 (br d, J=8.5 Hz, 1H), 8.06-8.03 (m, 1H), 7.40 (br s, 1H), 7.08 (br s, 1H), 4.49-4.44 (m, 2H), 4.37 (br d, J=2.5 Hz, 2H), 3.87-3.87 (m, 2H), 2.74-2.72 (m, 2H), 1.51 (t, J=7.0 Hz, 3H).

Step 3: 2-(3,6-dihydro-2H-pyran-4-yl)-4-ethoxy-N-[3-(4H-1,2,4-triazol-3-yl)propyl]quinoline-7-carboxamide To a solution of 2-(3,6-dihydro-2H-pyran-4-yl)-4-ethoxyquinoline-7-carboxylic acid (208 mg, 0.695 mmol) in THF (3.0 mL) was added HATU (291 mg, 0.765 mmol), TEA (0.484 mL, 3.48 mmol) and 3-(4H-1,2,4-triazol-3-yl)propan-1-amine hydrochloride (136 mg, 0.834 mmol). The resulting mixture was allowed to stir at rt overnight. The reaction was partitioned between aqueous saturated sodium bicarbonate (10 mL) and EtOAc (10 mL). The aqueous layer was extracted with EtOAc (5 mL). The combined organic layer was dried over MgSO$_4$, filtered and concentrated in vacuo. Purification by column chromatography gave 2-(3,6-dihydro-2H-pyran-4-yl)-4-ethoxy-N-[3-(4H-1,2,4-triazol-3-yl)propyl]quinoline-7-carboxamide (193 mg, 68%). LC-MS: (FA) ES+ 408.2; $^1$H NMR (DMSO-d$_6$, 400 MHz) δ 13.65 (br s, 1H), 8.87-8.85 (m, 1H), 8.41 (d, J=1.5 Hz, 1H), 8.14 (d, J=8.5 Hz, 1H), 7.92 (dd, J=8.5, 1.8 Hz, 1H), 7.79 (br s, 1H), 7.31 (s, 1H), 6.98 (br s, 1H), 4.42-4.33 (m, 4H), 3.88-3.86 (m, 2H), 3.39-3.35 (m, 2H), 2.78-2.72 (m, 4H), 2.00-1.92 (m, 2H), 1.51 (t, J=7.0 Hz, 3H).

Example 26: 4-ethoxy-2-(tetrahydro-2H-pyran-4-yl)-N-[3-(4H-1,2,4-triazol-3-yl)propyl]quinoline-7-carboxamide (I-135)

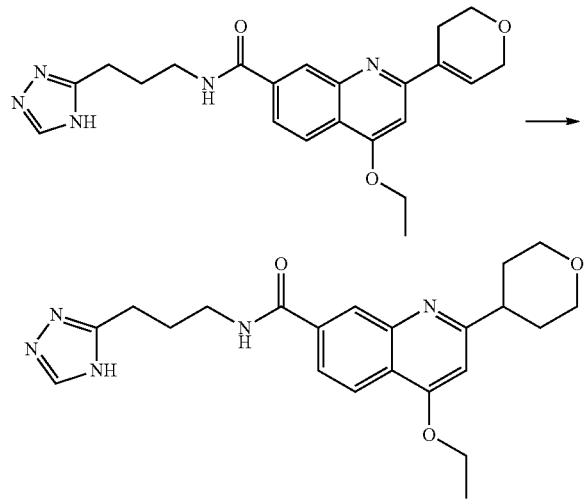

To a Paar bottle containing 10% Pd/C (40.0 mg) under argon was added a solution of 2-(3,6-dihydro-2H-pyran-4-yl)-4-ethoxy-N-[3-(4H-1,2,4-triazol-3-yl)propyl]quinoline-7-carboxamide (91 mg, 0.223 mmol) in MeOH (20 mL) and the resulting mixture was allowed to stir under hydrogen at 50 psi for 3 days. The catalyst was filtered through a bed of Celite® and the filtrate was concentrated in vacuo. Purification by column chromatography gave 4-ethoxy-2-(tetrahydro-2H-pyran-4-yl)-N-[3-(4H-1,2,4-triazol-3-yl)propyl]quinoline-7-carboxamide (41 mg, 44%). LC-MS: (FA) ES+ 410.2; $^1$H NMR (Methanol-$d_4$, 400 MHz) δ 8.27 (d, J=1.5 Hz, 1H), 8.14 (d, J=8.7 Hz, 1H), 8.02 (br s, 1H), 7.79-7.76 (m, 1H), 6.86 (s, 1H), 4.30-4.25 (m, 2H) 4.03-3.99 (m, 2H), 3.56-3.50 (m, 2H), 3.43-3.39 (m, 2H), 3.08-3.00 (m, 1H), 2.84-2.80 (m, 2H), 2.04-1.90 (m, 4H), 1.82-1.77 (m, 2H), 1.51 (t, J=7.0 Hz, 3H).

Example 27: 2-(4-fluorophenyl)-4-(1H-imidazol-1-yl)-N-[3-(4H-1,2,4-triazol-3-yl)propyl]quinoline-7-carboxamide (I-148)

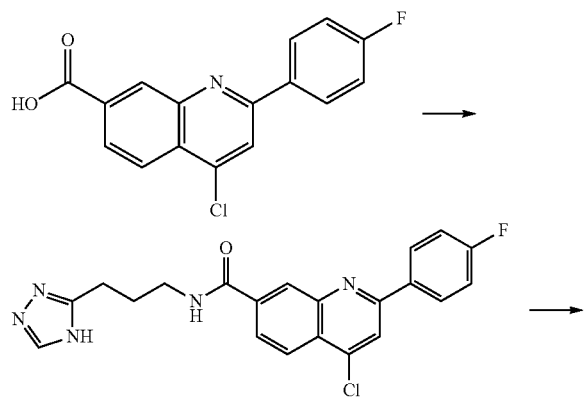

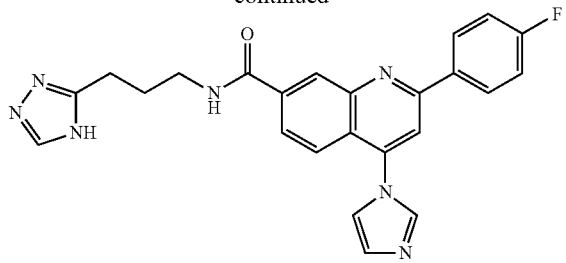

Step 1: 4-chloro-2-(4-fluorophenyl)-N-[3-(4H-1,2,4-triazol-3-yl)propyl]quinoline-7-carboxamide A mixture of 4-chloro-2-(4-fluorophenyl)quinoline-7-carboxylic acid (420 mg, 1.39 mmol), 3-(1H-1,2,4-triazol-3-yl)propan-1-amine hydrochloride (249 mg, 1.53 mmol), TEA (0.58 mL, 4.18 mmol) and HATU (556 mg, 1.46 mmol) in 7 mL of THF was allowed to stir at rt for 2 h. Water was added to the mixture and the resulting suspension was allowed to stir for some time. The solid was collected by filtration and was dried under vacuum to give 4-chloro-2-(4-fluorophenyl)-N-[3-(4H-1,2,4-triazol-3-yl)propyl]quinoline-7-carboxamide (527 mg, 92% yield). UPLC-MS: (FA) ES+ 410.1.

Step 2: 2-(4-fluorophenyl)-4-(1H-imidazol-1-yl)-N-[3-(4H-1,2,4-triazol-3-yl)propyl]quinoline-7-carboxamide To a solution of 4-chloro-2-(4-fluorophenyl)-N-[3-(4H-1,2,4-triazol-3-yl)propyl]quinoline-7-carboxamide (50.00 mg, 0.122 mmol) in 1 mL of DMSO was added imidazole (16.6 mg, 0.24 mmol) and potassium tert-butoxide (0.22 mL, 0.22 mmol, 1.00 M) in THF. The reaction mixture was subjected to microwave irradiation at 120° C. for 30 min. The reaction was diluted with water and was extracted with EtOAc twice. Combined organic layer was washed with brine and was concentrated to dryness. The crude product was purified by HPLC to give 2-(4-fluorophenyl)-4-(1H-imidazol-1-yl)-N-[3-(4H-1,2,4-triazol-3-yl)propyl]quinoline-7-carboxamide (15 mg, 28% yield). UPLC-MS: (FA) ES+ 442.2: $^1$H NMR (400 MHz, DMSO-$d_6$), δ ppm 8.90-9.03 (m, 1H), 8.72 (s, 1H), 8.48 (dd, J=8.78, 5.52 Hz, 2H), 8.35 (s, 1H), 8.28 (s, 1H), 8.10 (dd, J=8.72, 1.57 Hz, 1H), 7.89 (d, J=8.66 Hz, 1H), 7.85 (s, 1H), 7.44 (t, J=8.78 Hz, 2H), 7.31 (s, 1H), 3.37-3.49 (m, 2H), 2.80 (m, 2H), 2.00 (m, 2H).

Example 28: 4-(ethylamino)-2-(4-fluorophenyl)-N-[3-(4H-1,2,4-triazol-3-yl)propyl]quinoline-7-carboxamide (I-151)

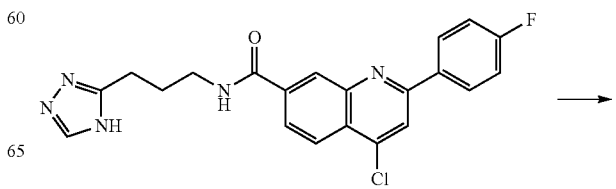

-continued

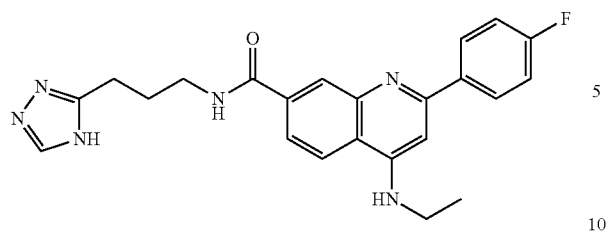

A sealed tube was charged with 4-chloro-2-(4-fluorophenyl)-N-[3-(4H-1,2,4-triazol-3-yl)propyl]quinoline-7-carboxamide (50 mg, 0.122 mmol) and ethylamine in THF (625 µL, 1 mmol, 2 M). The reaction mixture was subjected to microwave irradiation at 160° C. for 6 h. The mixture was then concentrated and the product was purified by HPLC to give 4-(ethylamino)-2-(4-fluorophenyl)-N-[3-(4H-1,2,4-triazol-3-yl)propyl]quinoline-7-carboxamide (15 mg, 29% yield). UPLC-MS: (FA) ES+ 419.2; $^1$H NMR (400 MHz, DMSO-$d_6$) δ ppm 8.78 (m, 1H), 8.38 (d, J=1.38 Hz, 1H), 8.25-8.33 (m, 3H), 8.15 (s, 1H), 7.82 (dd, J=8.60, 1.57 Hz, 1H), 7.34 (t, J=8.85 Hz, 2H), 7.28 (m, 1H), 7.00 (s, 1H), 3.46 (m, 2H), 3.38 (m, 2H), 2.78 (m, 2H), 1.97 (m, 2H), 1.33 (t, J=7.15 Hz, 3H).

Example 29: N-(3-(4H-1,2,4-triazol-3-yl)propyl)-4-(4-fluorophenyl)-2-(2-methylpyridin-4-yl)quinoline-7-carboxamide (I-157)

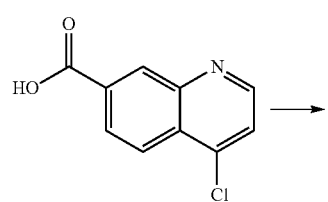

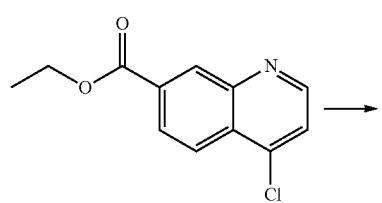

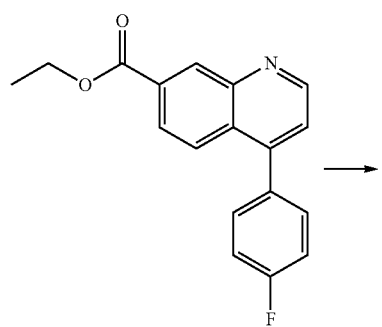

-continued

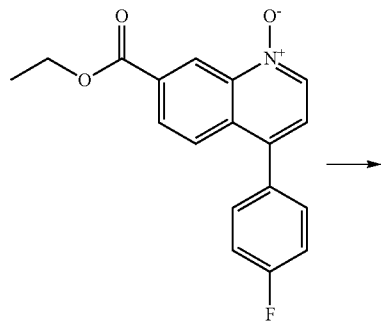

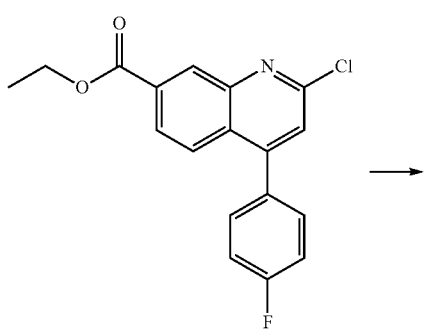

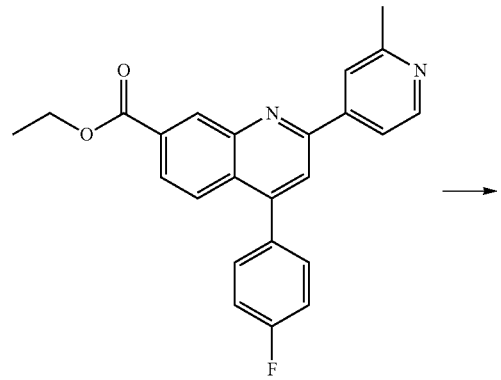

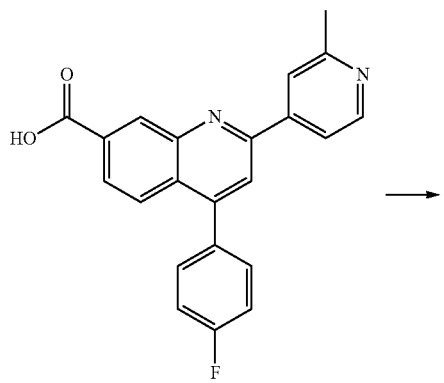

-continued

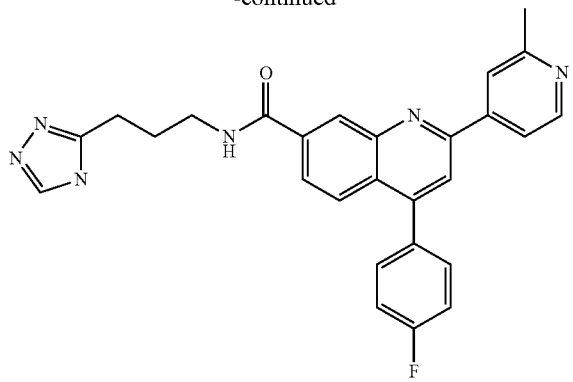

Step 1: Ethyl 4-chloroquinoline-7-carboxylate

To a mixture of 4-chloroquinoline-7-carboxylic acid (25.0 g, 2.89 mmol) and DMF (0.092 mL, 1.20 mmol) in THF (500 mL) was added oxalyl chloride (2M solution in DCM, 180 mL, 360 mmol) dropwise. The reaction was allowed to stir at rt for 16 h. The mixture was concentrated under reduced pressure then EtOH (300 mL) was added. After stirring at rt for 5 min the mixture was concentrated in vacuo. Water (300 mL) was added and the mixture was allowed to stir at rt for 0.5 hr. The solid was collected by filtration and dried under vacuum to give ethyl 4-chloroquinoline-7-carboxylate (21.9 g, 78% yield) as an off-white solid. LC-MS: (FA) ES+ 236.0; $^1$H NMR (400 MHz, CDCl$_3$) δ 8.75-8.85 (m, 2H), 8.15-8.25 (m, 2H), 7.50-7.58 (m, 1H), 4.40-4.50 (m, 2H), 1.40-1.50 (m, 3H).

Step 2: Ethyl 4-(4-fluorophenyl)quinoline-7-carboxylate

A 250 mL pressure vessel was charged ethyl 4-chloroquinoline-7-carboxylate (2.43 g, 10.1 mmol), 4-fluorophenylboronic acid (2.16 g, 15.2 mmol), cesium carbonate (11.5 g, 35.4 mmol), [1,1'-bis(diphenylphosphino)ferrocene]palladium(II)dichloride (752 mg, 0.915 mmol) and dioxane (130 mL). The mixture was degassed with argon and the container was sealed. After stirring at 105° C. for 2 hours the reaction was cooled, filtered and concentrated in vacuo. The residue was distributed between EtOAc (200 mL) and water (40 mL). The layers were separated and the aqueous layer was extracted with EtOAc (40 mL). The combined organic layers were dried over MgSO$_4$, filtered and concentrated in vacuo. Purification by silica gel chromatography gave ethyl 4-(4-fluorophenyl)quinoline-7-carboxylate (2.49 g, 83%). LC-MS: (FA) ES+ 296.1; $^1$H NMR (DMSO-d$_6$, 400 MHz) δ 9.07 (d, J=4.3 Hz, 1H), 8.67-8.66 (m, 1H), 8.10-8.06 (m, 1H), 7.98-7.95 (m, 1H), 7.66-7.60 (m, 3H), 7.48-7.42 (m, 2H), 4.44-4.39 (m, 2H), 1.41-1.37 (m, 3H).

Step 3: 7-(Ethoxycarbonyl)-4-(4-fluorophenyl)quinoline 1-oxide

To a solution of ethyl 4-(4-fluorophenyl)quinoline-7-carboxylate (3.25 g, 11.0 mmol) in DCM (67 mL) was added m-chloroperozybenzoic acid (5.90 g, 26.0 mmol) and the resulting mixture was allowed to stir at room temperature for 2 hours. The reaction was quenched with saturated sodium bicarbonate solution (50 mL). The layers were separated, and the organic layer was washed three times with 1N NaOH solution, then once with brine. The organic layer was dried over MgSO$_4$, filtered and concentrated in vacuo to give 7-(ethoxycarbonyl)-4-(4-fluorophenyl)quinoline 1-oxide (3.08 g, 90%). LC-MS: (FA) ES+ 312.1; $^1$H NMR (DMSO-d$_6$, 400 MHz) δ 9.17-9.16 (m, 1H), 8.73-8.71 (m, 1H), 8.17-8.15 (m, 1H), 8.01-7.99 (m, 1H), 7.65-7.60 (m, 2H), 7.56-7.54 (m, 1H), 7.46-7.41 (m, 2H), 4.45-4.39 (m, 2H), 1.41-1.36 (m, 3H).

Step 4: ethyl 2-chloro-4-(4-fluorophenyl)quinoline-7-carboxylate

To a solution of 7-(ethoxycarbonyl)-4-(4-fluorophenyl) quinoline 1-oxide (2.61 g, 8.38 mmol) in DCM (25 mL) was added phosphoryl chloride (1.56 mL, 16.8 mmol) and the resulting solution was allowed to stir at 45° C. for 2 hours. The reaction was cooled and quenched by the addition of saturated aqueous sodium bicarbonate (10 mL), and the mixture was stirred for 20 minutes. The layers were separated and the organic layer was washed with brine (10 mL). The organic layer was dried over MgSO$_4$, filtered and concentrated in vacuo to give ethyl 2-chloro-4-(4-fluorophenyl)quinoline-7-carboxylate oxide (1.44 g, 52%). LC-MS: (FA) ES+ 330.1; $^1$H NMR (DMSO-d$_6$, 400 MHz) δ 8.54 (d, J=1.3 Hz, 1H), 8.78 (dd, J=8.8, 1.8 Hz, 1H), 7.95 (d, J=8.8 Hz, 1H), 7.70-7.65 (m, 3H), 7.49-7.43 (m, 2H), 4.40 (q, J=7.3 Hz, 2H), 1.30 (t, J=7.3 Hz, 3H).

Step 5: ethyl 4-(4-fluorophenyl)-2-(2-methylpyridin-4-yl)quinoline-7-carboxylate A pressure vessel was charged with ethyl 2-chloro-4-(4-fluorophenyl)quinoline-7-carboxylate (368 mg, 1.12 mmol), 2-methylpyridine-4-boronic acid (232 mg, 1.67 mmol), cesium carbonate (1.27 g, 3.91 mmol), [1,1'-bis(diphenylphosphino)ferrocene]palladium(II)dichloride (114 mg, 0.139 mmol) and 1,4-dioxane (20 mL). The mixture was degassed with argon, and then the container was sealed. After stirring at 100° C. for 2 hours. The reaction was cooled, filtered and concentrated in vacuo. The residue was distributed between EtOAc (30 mL) and water (10 mL). The layers were separated and the aqueous layer was extracted with EtOAc (10 mL). The combined organic layers were dried over MgSO$_4$, filtered and concentrated in vacuo. Purification by silica gel chromatography gave ethyl 4-(4-fluorophenyl)-2-(2-methylpyridin-4-yl)quinoline-7-carboxylate (431 mg, 36%). LC-MS: (FA) ES+ 387.2; $^1$H NMR (CDCl$_3$, 400 MHz) δ 9.00 (d, J=1.5 Hz, 1H), 8.72-8.70 (m, 1H), 8.18-8.15 (m, 1H), 8.05 (br s, 1H), 7.98-7.91 (m, 3H), 7.59-7.54 (m, 2H), 7.34-7.28 (m, 2H), 4.50 (q, J=7.3 Hz, 2H), 2.76 (s, 3H), 1.50 (t, J=7.3 Hz, 3H).

Step 6: 4-(4-fluorophenyl)-2-(2-methylpyridin-4-yl) quinoline-7-carboxylic acid To a solution of ethyl 4-(4-fluorophenyl)-2-(2-methylpyridin-4-yl)quinoline-7-carboxylate (153 mg, 0.396 mmol) in THF (2.7 mL) and ethanol (2.7 mL) was added 1.0 M aqueous solution of sodium hydroxide (1.31 mL) and the resulting solution was allowed to stir at room temperature overnight. Water (10 mL) was added and the resulting solution was acidified to pH 3.5 with 1 M HCl. The volatiles were removed in vacuo and the resulting solution was extracted with EtOAc (2×20 mL). The combined organic layers were dried over MgSO$_4$, filtered and concentrated in vacuo to give 4-(4-fluorophenyl)-2-(2-methylpyridin-4-yl)

quinoline-7-carboxylic acid (71 mg, 50%). LC-MS: (FA) ES+ 359.1; $^1$H NMR (DMSO-$d_6$, 400 MHz) δ 13.38 (br s, 1H), 8.75 (d, J=1.5 Hz, 1H), 8.65 (d, J=5.3 Hz, 1H), 8.28 (s, 1H), 8.23 (s, 1H), 8.15-8.10 (m, 2H), 7.98 (d, J=8.8 Hz, 1H), 7.77-7.73 (m, 2H), 7.51-7.47 (m, 2H), 2.62 (s, 3H).

Step 7: N-(3-(4H-1,2,4-triazol-3-yl)propyl)-4-(4-fluorophenyl)-2-(2-methylpyridin-4-yl)quinoline-7-carboxamide To a solution 4-(4-fluorophenyl)-2-(2-methylpyridin-4-yl)quinoline-7-carboxylic acid (69.0 mg, 0.192 mmol) in THF (1.0 mL) was added HATU (88 mg, 0.231 mmol), TEA (0.134 mL, 0.963 mmol) and 3-(4H-1,2,4-triazol-3-yl)propan-1-amine HCl (38 mg, 0.231 mmol). The resulting mixture was allowed to stir at room temperature overnight. The reaction was distributed between aqueous saturated sodium bicarbonate (10 mL) and EtOAc (10 mL). The layers were separated and the aqueous layer was extracted with EtOAc (5 mL). The organic layers were dried over MgSO$_4$, filtered and concentrated in vacuo. Purification by silica gel chromatography gave N-(3-(4H-1,2,4-triazol-3-yl)propyl)-4-(4-fluorophenyl)-2-(2-methylpyridin-4-yl)quinoline-7-carboxamide (47 mg, 52%). LC-MS: (FA) ES+ 467.2; $^1$H NMR (Methanol-$d_4$, 400 MHz) δ 8.59 (m, H), 8.51-8.49 (m, 1H), 8.10-8.09 (m, 1H), 8.06 (br s, 1H), 8.02-8.00 (m, 2H), 7.92-7.91 (m, 2H), 7.60-7.56 (m, 2H), 7.30-7.24 (m, 2H), 3.47-3.43 (m, 2H), 2.87-2.82 (m, 2H), 2.58 (s, 3H), 2.06-2.00 (m, 2H).

Example 30: 2-(4-fluorophenyl)-4-propyl-N-[3-(4H-1,2,4-triazol-3-yl)propyl]quinoline-7-carboxamide (I-171)

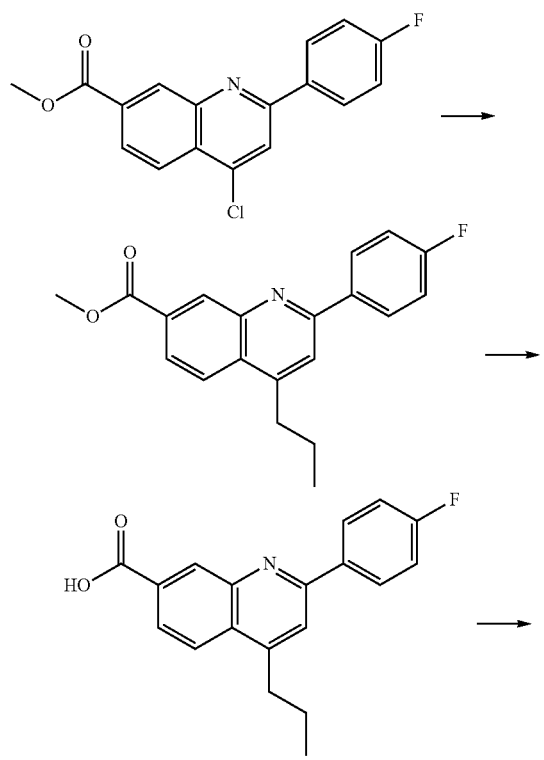

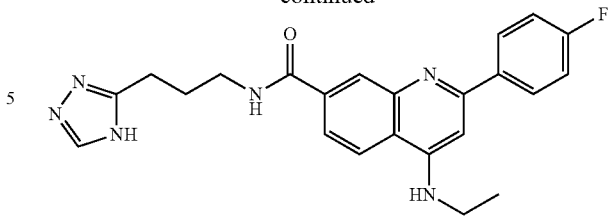

Step 1: methyl 2-(4-fluorophenyl)-4-propylquinoline-7-carboxylate

To a suspension of methyl 4-chloro-2-(4-fluorophenyl)quinoline-7-carboxylate (172 mg, 0.54 mmol), 2-allyl-4,4,5,5-tetramethyl-1,3,2-dioxaborolane (114 mg, 0.68 mmol), XPhos (13 mg, 0.027 mmol) and Xphos Pd G3 (12 mg, 0.014 mmol) in 4 mL dioxane in a pressure tube was added 1.25 M aqueous potassium phosphate solution (0.65 mL, 0.82 mmol). The mixture was purged three times with nitrogen and was allowed to stir at 80° C. for 1 h. The reaction mixture was diluted with water and was extracted with EtOAc twice. Combined organic layer was concentrated to give crude product as an orange gum. The crude product was dissolved in 4 mL of methanol. The solution was purged with nitrogen and palladium on carbon (17 mg) was added. The reaction mixture was then purged with hydrogen (1 atm) and was allowed to stir at rt for 1 hr. The reaction mixture was filtered through a bed of Celite® and the filtrate was concentrated. The crude product was purified by column chromatography to give methyl 2-(4-fluorophenyl)-4-propylquinoline-7-carboxylate (112 mg, 63% yield) UPLC-MS: (FA) ES+ 324.1 $^1$H NMR (400 MHz, DMSO-$d_6$) δ ppm 8.63 (d, J=1.38 Hz, 1H), 8.38 (dd, J=8.85, 5.58 Hz, 2H), 8.29 (d, J=8.78 Hz, 1H), 8.14 (s, 1H), 8.06 (dd, J=8.72, 1.69 Hz, 1H), 7.40 (t, J=8.85 Hz, 2H), 3.96 (s, 3H), 3.16 (t, J=7.65 Hz, 2H), 1.72-1.88 (m, 2H), 1.02 (t, J=7.28 Hz, 3H).

Step 2 2-(4-fluorophenyl)-4-propylquinoline-7-carboxylic acid

To a suspension of methyl 2-(4-fluorophenyl)-4-propylquinoline-7-carboxylate (450 mg, 1.39 mmol) in 7.9 mL of THF and 7.9 mL of methanol was added 1 M NaOH (3.95 mL, 3.95 mmol) and water (3.95 mL). The mixture was allowed to stir at rt for 2 h. The resulting solution was diluted with water and was acidified with 1M aqueous HCl solution to pH ~3.5. The resulting suspension was filtered and the collected white solid was washed with water and dried to give 2-(4-fluorophenyl)-4-propylquinoline-7-carboxylic acid (408 mg, 95% yield). UPLC-MS (FA) ES+ 310.1; $^1$H NMR (400 MHz, DMSO-$d_6$) δ ppm 13.30 (s, 1H), 8.61 (d, J=1.51 Hz, 1H), 8.33-8.42 (m, 2H), 8.26 (d, J=8.66 Hz, 1H), 8.11 (s, 1H), 8.06 (dd, J=8.66, 1.76 Hz, 1H), 7.40 (t, J=8.91 Hz, 2H), 3.10-3.21 (m, 2H), 1.79 (m, 2H), 1.02 (t, J=7.34 Hz, 3H).

Step 3: 2-(4-fluorophenyl)-4-propyl-N-[3-(4H-1,2,4-triazol-3-yl)propyl]quinoline-7-carboxamide To a mixture of 2-(4-fluorophenyl)-4-propyl-quinoline-7-carboxylic acid (100 mg, 0.32 mmol), 3-(4H-1,2,4-triazol-3-yl)propan-1-amine hydrochloride (63 mg, 0.39 mmol) and HATU (135 mg, 0.36 mmol) in 2 mL of THF was added TEA (0.225 mL, 1.6 mmol). The mixture was allowed to stir at rt for 2 h. Water was added to the mixture and the resulting suspension was filtered. The collected solid was dried and was purified by HPLC to give 2-(4-fluorophenyl)-4-propyl-N-[3-(4H-1,2,4-triazol-3-yl)propyl]quinoline-7-carboxamide (80 mg, 59% yield) UPLC-MS min: (FA) ES+ 418.2; $^1$H NMR (400 MHz, DMSO-$d_6$) δ ppm 8.88 (br, 1H), 8.59 (d, J=1.38 Hz, 1H), 8.36 (dd, J=8.85, 5.58 Hz, 2H), 8.23 (d, J=8.78 Hz, 1H), 8.07 (s, 1H), 8.01 (dd, J=8.66, 1.63 Hz, 1H), 7.40 (t, J=8.91 Hz, 2H), 3.41 (m, 2H), 3.15 (t, J=7.65 Hz, 2H), 2.79 (br t, J=7.34 Hz, 2H), 1.99 (m, 2H), 1.71-1.87 (m, 2H), 1.02 (t, J=7.34 Hz, 3H).

The compounds listed in the table below were prepared in an analogous fashion to that described in Example 30 starting from the appropriate starting materials:

| Amine in Step 3 | Compound No. or Name | LCMS Data |
|---|---|---|
|  | I-47 | LCMS (ESI+): M/Z = 417.2 (M + H) |
|  | I-152 | LCMS (ESI+): m/z = 417.2 (M + H) |
|  | I-163 | LCMS (ESI+): m/z = 417.2 (M + H) |

Example 31: N-(3-(1H-imidazol-2-yl)propyl)-2-(4-chlorophenyl)-4-ethoxyquinoline-7-carboxamide (I-198)

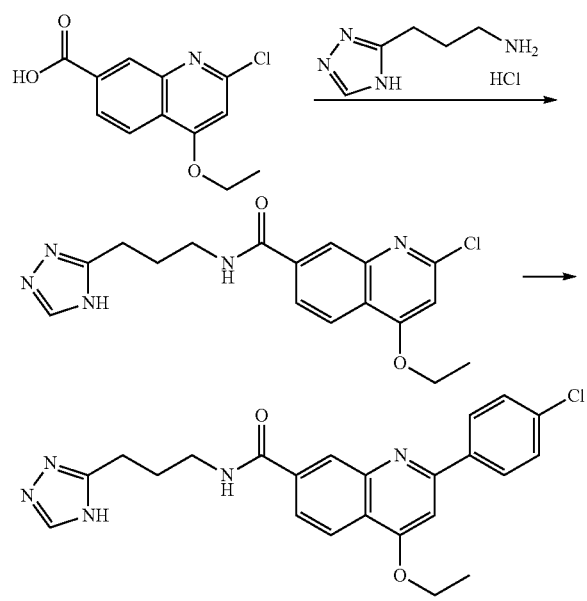

Step 1: N-(3-(4H-1,2,4-triazol-3-yl)propyl)-2-chloro-4-ethoxyquinoline-7-carboxamide Into a flask with 2-chloro-4-ethoxy-quinoline-7-carboxylic acid (1.0 g, 4.0 mmol), 3-(4H-1,2,4-triazol-3-yl)propan-1-amine hydrochloride (711 mg, 4.4 mmol) and HATU (1.6 g, 4.2 mmol) was added THF (20 mL) followed by TEA (1.67 mL, 11.9 mmol). The reaction mixture was stirred at rt for 2 h. The reaction mixture was distributed between ice water and EtOAc, and the aqueous phase was separated then extracted with EtOAc. The organic solutions were combined, washed with brine, then dried over $Na_2SO_4$, filtered and concentrated. The crude residue was triturated with water. The resulting solid was collected by filtration and dried under vacuum to give N-(3-(4H-1,2,4-triazol-3-yl)propyl)-2-chloro-4-ethoxyquinoline-7-carboxamide (1.2 g, yield: 85%) UPLC-MS/1.5 min: (FA) ES+ 360.2

Step 2: N-(3-(1H-imidazol-2-yl)propyl)-2-(4-chlorophenyl)-4-ethoxyquinoline-7-carboxamide Into a microwave vial charged with 2-chloro-4-ethoxy-N-[3-(4H-1,2,4-triazol-3-yl)propyl]quinoline-7-carboxamide (250.0 mg, 0.69 mmol), (4-chlorophenyl)boronic acid (275 mg, 1.76 mmol), SiliaCat DPP-Pd (685 mg, 0.178 mmol, 0.260 mmol/g loading) and cesium carbonate (453, 1.39 mmol) was added 1,4-dioxane (14.5 mL) and water (3.6 mL). The vial was sealed and flushed under nitrogen then subjected to microwave irradiation at 125° C. for 1 hr. The reaction mixture mixture was filtered, then the filtrate was distributed between EtOAc and water. The aqueous layer was extracted with EtOAc twice. The combined organic solutions were dried over $Na_2SO_4$, filtered and evaporated. The crude compound was purified by column chromatography, followed by HPLC purification to give N-(3-(1H-imidazol-2-yl)propyl)-2-(4-chlorophenyl)-4-ethoxyquinoline-7-carboxamide (93 mg, yield: 31%) UPLC-MS/1.5 min: (FA) ES+ 436.2 $^1$H NMR (400 MHz, DMSO-$d_6$) δ ppm 8.87 (br s, 1H) 8.53 (s, 1H) 8.36 (d, J=8.66 Hz, 2H) 8.20 (d, J=8.66 Hz, 1H) 7.97 (dd, J=8.60, 1.57 Hz, 1H) 7.57-7.70 (m, 3H) 4.49 (m, 2H) 3.39 (m, 2H) 2.66-2.87 (m, 2H) 1.91-2.04 (m, 2H) 1.54 (t, J=6.96 Hz, 3H)

The compounds listed in the table below were prepared in an analogous fashion to that described in Example 31 starting from the appropriate starting materials:

| Boronic acid in Step 3 | Compound No. or Name | LCMS Data |
|---|---|---|
|  | I-205 | LCMS (ESI+): m/z = 392.3 (M + H) |
|  | I-206 | LCMS (ESI+): m/z = 406.3 (M + H) |

-continued

| Boronic acid in Step 3 | Compound No. or Name | LCMS Data |
|---|---|---|
| phenylboronic acid | I-207 | LCMS (ESI+): m/z = 402.3 (M + H) |
| pyrimidin-5-ylboronic acid | I-208 | LCMS (ESI+): m/z = 404.3 (M + H) |
| pyridin-3-ylboronic acid | I-209 | LCMS (ESI+): m/z = 403.3 (M + H) |
| (5-methoxypyridin-3-yl)boronic acid | I-210 | LCMS (ESI+): m/z = 433.3 (M + H) |
| (6-chloro-4-methylpyridin-3-yl)boronic acid | I-211 | LCMS (ESI+): m/z = 451.2 (M + H) |
| (4-methoxypyridin-3-yl)boronic acid | I-212 | LCMS (ESI+): m/z = 433.4 (M + H) |
| (2-methylpyridin-3-yl)boronic acid | I-213 | LCMS (ESI+): m/z = 417.3 (M + H) |
| pyridin-4-ylboronic acid | I-214 | LCMS (ESI+): m/z = 403.3 (M + H) |
| (3-(trifluoromethyl)phenyl)boronic acid | I-215 | LCMS (ESI+): m/z = 470.3 (M + H) |

-continued

| Boronic acid in Step 3 | Compound No. or Name | LCMS Data |
|---|---|---|
| (3-(trifluoromethoxy)phenyl)boronic acid | I-216 | LCMS (ESI+): m/z = 486.3 (M + H) |
| (6-(trifluoromethyl)pyridin-3-yl)boronic acid | I-217 | LCMS (ESI+): m/z = 471.3 (M + H) |
| (2-(trifluoromethyl)pyridin-4-yl)boronic acid | I-218 | LCMS (ESI+): m/z = 471.3 (M + H) |
| (5-methylthiophen-2-yl)boronic acid | I-223 | LCMS (ESI+): m/z = 422.3 (M + H) |
| (5-fluoro-2-methoxypyridin-4-yl)boronic acid | I-225 | LCMS (ESI+): m/z = 451.2 (M + H) |

Example 32: N-(3-(1H-imidazol-2-yl)propyl)-4-ethoxy-2-propylquinoline-7-carboxamide (I-226)

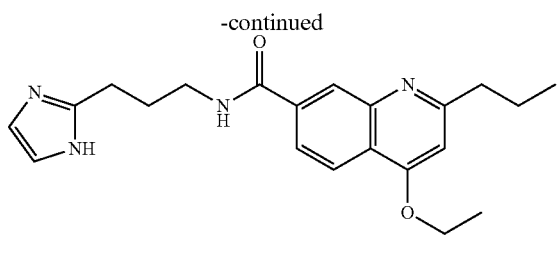

To a solution of 2-chloro-4-ethoxy-N-[3-(1H-imidazol-2-yl)propyl]quinoline-7-carboxamide (INT-8; 586.0 mg, 1.6 mmol), 2-allyl-4,4,5,5-tetramethyl-1,3,2-dioxaborolane (343 mg, 2.0 mmol), X-Phos (40 mg, 0.08 mmol) and XPhos-Pd-G3 (36 mg, 0.04 mmol) in 1,4-dioxane (14 mL) was added 1.25 M potassium phosphate in water (1.96 mL, 2.45 mmol). The reaction mixture was purged with $N_2$ and stirred at 80° C. for 1 hr. The reaction mixture was partitioned between EtOAc and water, then extracted with EtOAc twice. The organic layers were combined and evaporated. The crude material was dissolved in methanol (10 mL). The flask was purged with nitrogen, then added 10% palladium on carbon (60 mg). The reaction mixture was purged with hydrogen then stirred at rt for 1 hr under hydrogen (1 atm balloon). The reaction mixture was filtered through celite and the filtrate was evaporated. The crude mixture was purified by HPLC to give N-(3-(1H-imidazol-2-yl)propyl)-4-ethoxy-2-propylquinoline-7-carboxamide (170 mg, yield: 28%) UPLC-MS/5.0 min: (FA) ES+ 367.2 $^1$H NMR (400 MHz, DMSO-$d_6$) δ ppm 8.90 (m, 1H) 8.41 (d, J=1.38 Hz, 1H) 8.15 (s, 1H) 8.13 (d, J=8.66 Hz, 1H) 7.91 (dd, J=8.66, 1.76 Hz, 1H) 6.98 (s, 1H) 6.91 (s, 2H) 4.33 (m, 2H) 3.30-3.42 (m, 2H) 2.81-2.95 (m, 2H) 2.71 (m, 2H) 1.94 (m, 2H) 1.74-1.86 (m, 2H) 1.49 (t, J=6.96 Hz, 3H) 0.96 (t, J=7.34 Hz, 3H)

Example 33: 4-ethoxy-3-fluoro-2-(4-fluorophenyl)-N-[3-(1H-1,2,3-triazol-4-yl)propyl]quinoline-7-carboxamide (I-73)

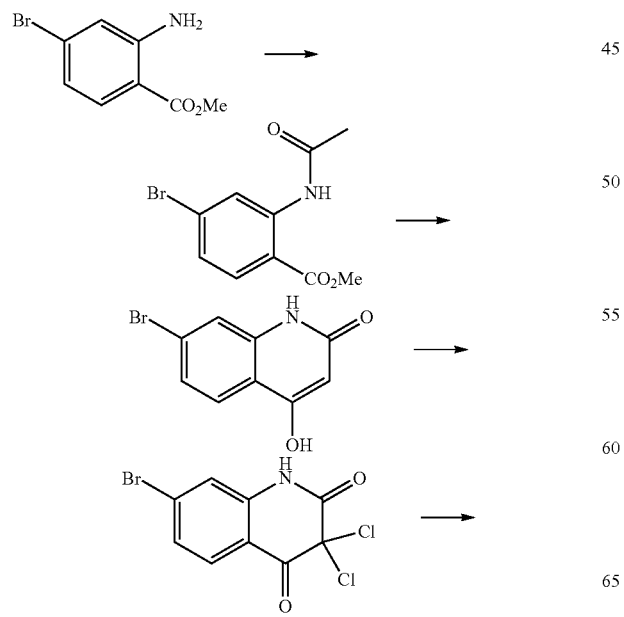

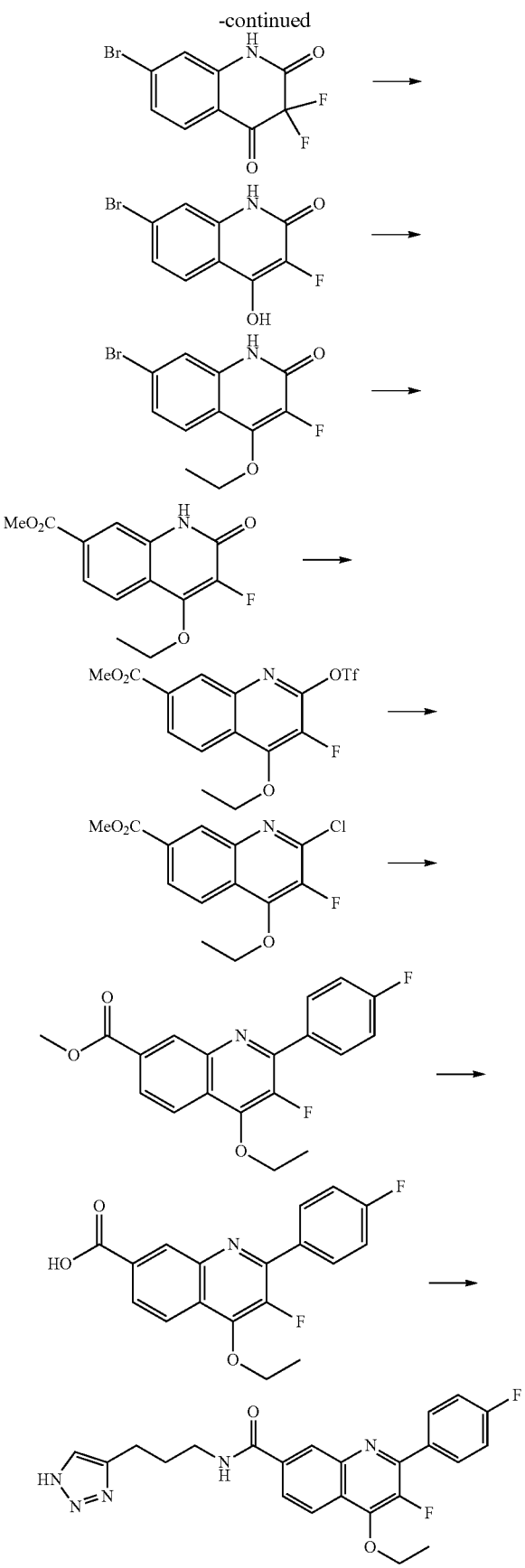

Step 1: methyl 2-acetamido-4-bromobenzoate

To a suspension of methyl 2-amino-4-bromobenzoate (150 g, 652 mmol) in toluene (1500 mL) was added acetic anhydride (99.8 g, 978 mmol) at 23° C. The mixture was allowed to stir at 80° C. for 15 h. The reaction mixture was concentrated under reduced pressure and the residual solid was washed with PE/EtOAc (1100 mL, 10:1) and dried to give methyl 2-acetamido-4-bromobenzoate (153 g, 86% yield) as a light yellow solid. $^1$H NMR (400 MHz, CDCl$_3$) δ 11.08 (br s, 1H), 8.97 (s, 1H), 7.89-7.85 (m, 1H), 7.40 (s, 1H), 7.23-7.20 (m, 1H), 3.93 (s, 3H), 2.24 (s, 3H).

Step 2: 7-bromo-4-hydroxyquinolin-2(1H)-one

Two reactions of the same scale were performed in parallel. To solutions of potassium bis(trimethylsilyl)amide in THF (548 mL, 548 mmol) were added suspensions of methyl 2-acetamido-4-bromobenzoate (50 g, 183 mmol) in THF (500 mL) dropwise at −78° C. under nitrogen atmosphere. After stirring at this temperature for 1 h the mixtures were allowed to warm to 10° C. within 1 h. The reactions were then combined and the mixture was quenched with water (3000 mL). The aqueous layer was washed with EtOAc (1000 mL×2). The separated aqueous layer was cooled to 10° C. and the pH was adjusted to 2.5-3.5 with the addition of 5N HCl aqueous solution resulting in a yellow precipitate. The solid was collected by filtration, washed with EtOAc (1000 mL) and dried under vacuum to give 7-bromo-4-hydroxyquinolin-2(1H)-one (80.0 g, 90.9% yield) as an off-white solid. LCMS: (FA) ES+ 241.7; $^1$H NMR (400 MHz, DMSO-d$_6$) δ 11.52 (br s, 1H), 11.26 (s, 1H), 7.67-7.63 (m, 1H), 7.40 (s, 1H), 7.27-7.24 (m, 1H), 5.72 (s, 1H).

Step 3: 7-bromo-3,3-dichloroquinoline-2,4(1H,3H)-dione

Two reactions of the same scale were performed in parallel. Suspensions of 7-bromo-4-hydroxyquinolin-2(1H)-one (115 g, 479 mmol) in dioxane (1400 mL) were warmed to 40-50° C. To the mixtures was added SO$_2$Cl$_2$ (192 g, 1.43 mol) dropwise with vigorous stirring so that the temperature did not exceed 60° C. After 40 min of stirring the mixtures were poured into ice/water (2 L) and combined. The mixture was extracted with EtOAc (1600 mL×3). The combined organic layers was dried over Na$_2$SO$_4$ and concentrated under reduced pressure. The crude product was purified by column chromatography on silica gel to give 7-bromo-3,3-dichloroquinoline-2,4(1H,3H)-dione (280 g, 94% yield) as a yellow solid. $^1$H NMR (400 MHz, DMSO-d$_6$) δ 11.53 (s, 1H), 7.83-7.79 (m, 1H), 7.40-7.38 (m, 1H), 7.32 (s, 1H).

Step 4: 7-bromo-3,3-difluoroquinoline-2,4(1H,3H)-dione

Two reactions of the same scale were performed in parallel. Mixtures of 7-bromo-3,3-dichloroquinoline-2,4 (1H,3H)-dione (140 g, 453 mmol), KF (78.4 g, 1.35 mol), and 18-crown-6 (11.9 g, 45.3 mmol) in MeCN (1.70 L) were allowed to stir at 80° C. for 3 h. The two reaction mixtures were combined and filtered, and the filtrate was concentrated under reduced pressure. The residue was purified by column chromatography on silica gel to give 7-bromo-3,3-difluoroquinoline-2,4(1H,3H)-dione (185 g, 74% yield) as a yellow solid. $^1$H NMR (400 MHz, DMSO-d$_6$) δ 11.48 (s, 1H), 7.77-7.73 (m, 1H), 7.40-7.37 (m, 1H), 7.31-7.30 (m, 1H).

Step 5: 7-bromo-3-fluoro-4-hydroxyquinolin-2(1H)-one

Two reactions of the same scale were performed in parallel. To solutions of 7-bromo-3,3-difluoroquinoline-2,4 (1H,3H)-dione (92 g, 333 mmol) in AcOH (1100 mL) was added Zn (43.5 g, 666 mmol) by portions. The mixtures were allowed to stir at 80° C. for 1 h. The two reaction mixtures were combined and concentrated under reduced pressure. HCl (1.5 L, 1M in water) was added and the mixture was stirred for 20 min. The resulting solid was filtered, washed with EtOAc (100 mL×2), and dried to give 7-bromo-3-fluoro-4-hydroxyquinolin-2(1H)-one (150 g, 88% yield) as a gray-white solid. $^1$H NMR (400 MHz, DMSO-d$_6$) δ 11.78 (s, 1H), 7.74-7.71 (m, 1H), 7.43-7.42 (m, 1H), 7.35-7.32 (m, 1H).

Step 6: 7-bromo-4-ethoxy-3-fluoroquinolin-2(1H)-one

To a suspension of 7-bromo-3-fluoro-4-hydroxyquinolin-2(1H)-one (84 g, 325 mmol) and K$_2$CO$_3$ (67.3 g, 487 mmol) in DMF (1.0 L) was added iodoethane (75.9 g, 487 mmol) dropwise at 20° C. The reaction mixture was allowed to stir at 85° C. for 1 h. The mixture was poured into water (1200 mL) and the resulting suspension was filtered. The collected solid was washed with EtOAc (150 mL×2) and dried under reduced pressure to give 7-bromo-4-ethoxy-3-fluoroquinolin-2(1H)-one (65 g, 70% yield) as a white solid. LC-MS: (FA) ES+ 286.0; $^1$H NMR (400 MHz, DMSO-d$_6$) δ 7.72-7.69 (m, 1H), 7.45 (s, 1H), 7.40-7.36 (m, 1H), 4.51-4.45 (m, 2H), 1.40-1.36 (m, 3H).

Step 7: methyl 4-ethoxy-3-fluoro-2-oxo-1,2-dihydroquinoline-7-carboxylate

Four reactions of the same scale were performed in parallel. To mixtures of 7-bromo-4-ethoxy-3-fluoroquinolin-2(1H)-one (20 g, 69.9 mmol) and TEA (21.1 g, 209 mmol) were added 600 mL of DMF/MeOH (1:1). The mixtures were purged with CO (×3), then Pd(dppf)Cl$_2$ (10.1 g, 13.9 mmol) and Xantphos (8.04 g, 13.9 mmol) were added. The mixtures were allowed to stir under CO (50 psi) at 80° C. for 5 h. The four reactions were combined and filtered. The collected solid was washed with MeOH (500 mL) and dried under reduced pressure to give crude methyl 4-ethoxy-3-fluoro-2-oxo-1,2-dihydroquinoline-7-carboxylate (90 g, 121% yield) as a yellow solid, which was used for the next step without further purification. LC-MS: (FA) ES+ 265.9; $^1$H NMR (400 MHz, DMSO-d$_6$) δ 12.19 (s, 1H), 7.90-7.87 (m, 2H), 7.74-7.71 (m, 1H), 4.51-4.48 (m, 2H), 3.85 (s, 3H), 1.40-1.36 (m, 3H).

Step 8: methyl 4-ethoxy-3-fluoro-2-(((trifluoromethyl)sulfonyl)oxy)quinoline-7-carboxylate Two reactions of the same scale were performed in parallel. To suspensions of methyl 4-ethoxy-3-fluoro-2-oxo-1,2-dihydroquinoline-7-carboxylate (45 g, 169 mmol) in DCM (500 mL) were added pyridine (40.1 g, 507 mmol) and Tf$_2$O (95.3 g, 338 mmol) dropwise at 0° C. The mixture was allowed to stir at rt for 4 h. The two reactions were combined and concentrated under reduced pressure to give crude methyl 4-ethoxy-3-fluoro-2-(((trifluoromethyl)sulfonyl)

oxy)quinoline-7-carboxylate (150 g), which was used for the next step without further purification. LC-MS: (FA) ES+ 397.9.

Step 9: methyl 2-chloro-4-ethoxy-3-fluoroquinoline-7-carboxylate

Two reactions of the same scale were performed in parallel. Solutions of methyl 4-ethoxy-3-fluoro-2-(((trifluoromethyl)sulfonyl)oxy)quinoline-7-carboxylate (67 g, 337 mmol) in 4M HCl in EtOAc (400 mL) were allowed to stir at rt for 30 min. The two reactions were combined and the pH was adjusted to 7 by addition of aqueous NaHCO$_3$ solution. The mixture was extracted with EtOAc (400 mL×3). The combined organic layers was dried over Na$_2$SO$_4$ and concentrated under reduced pressure. The crude product was purified by column chromatography on silica gel to give methyl 2-chloro-4-ethoxy-3-fluoroquinoline-7-carboxylate (6.5 g, 6.79% yield) as a white solid. LC-MS: (FA) ES+ 284.1; $^1$H NMR (400 MHz, DMSO-d$_6$) δ 8.58 (s, 1H), 8.16-8.13 (m, 1H), 8.09-8.06 (m, 1H), 4.69-4.61 (m, 2H), 3.96 (s, 3H), 1.54-1.50 (m, 3H).

Step 10: methyl 4-ethoxy-3-fluoro-2-(4-fluorophenyl)quinoline-7-carboxylate

A 10 mL pressure tube was charged with a mixture of methyl 2-chloro-4-ethoxy-3-fluoroquinoline-7-carboxylate (100 mg, 0.352 mmol), 4-fluorophenylboronic acid (80.0 mg, 0.555 mmol), 2-dicyclohexylphosphino-2',4',6'-tri-isopropyl-1,1'-biphenyl (XPhos) (12.5 mg, 0.0262 mmol) and methanesulfonato(2-dicyclohexylphosphino-2',4',6'-tri-isopropyl-1,1'-biphenyl)(2'-amino-1,1'-biphenyl-2-yl)palladium(II) (XPhos-Pd-G3), (10.0 mg, 0.012 mmol), in 1,4-dioxane (3.50 mL, 44.8 mmol), and 2.0 M of potassium carbonate solution in water (380 μL, 0.760 mmol). The reaction container was purged with nitrogen and sealed. The reaction was allowed to stir at 80° C. for 2.5 h. After cooling the mixture was partitioned between EtOAc and water. Separated aqueous was extracted with EtOAc. The combined organic layers was washed with brine, dried over Na$_2$SO$_4$ and concentrated. The residue was purified on silica gel column to give methyl 4-ethoxy-3-fluoro-2-(4-fluorophenyl)quinoline-7-carboxylate (118 mg, 97.5% yield) as a white solid. LC-MS: (FA) ES+ 344.1; $^1$H NMR (400 MHz, DMSO-d$_6$) δ 8.59-8.56 (m, 1H), 8.30-8.25 (m, 1H), 8.12-8.03 (m, 3H), 7.46-7.39 (m, 2H), 4.69-4.61 (m, 2H), 3.95 (s, 3H), 1.52-1.47 (m, 3H).

Step 11: 4-ethoxy-3-fluoro-2-(4-fluorophenyl)quinoline-7-carboxylic acid

To a solution of methyl 4-ethoxy-3-fluoro-2-(4-fluorophenyl)quinoline-7-carboxylate (113 mg, 0.329 mmol) in THF (2.00 mL) and methanol (1.00 mL) was added 1.0 M sodium hydroxide aqueous solution (1.00 mL, 1.00 mmol,) at room temperature. The resulting suspension was allowed to stir at room temperature for 1.5 h. The mixture was diluted with 10 ml of water and was acidified to pH ~4-5 with the addition of 1M HCl aqueous solution. The resulting slurry was stirred overnight. The solid was then filtered off and dried under vacuum at 40° C. for 3 h. to give 4-ethoxy-3-fluoro-2-(4-fluorophenyl)quinoline-7-carboxylic acid (109 mg, 97.9% yield) as a white solid. LC-MS: (FA) ES+ 330.1; $^1$H NMR (400 MHz, DMSO-d$_6$) δ 13.39 (br s, 1H), 8.55 (s, 1H), 8.27-8.22 (m, 1H), 8.12-8.01 (m, 3H), 7.46-7.38 (m, 2H), 4.68-4.59 (m, 2H), 1.52-1.44 (m, 3H).

Step 12: 4-ethoxy-3-fluoro-2-(4-fluorophenyl)-N-[3-(1H-1,2,3-triazol-4-yl)propyl]quinoline-7-carboxamide To a mixture of 4-ethoxy-3-fluoro-2-(4-fluorophenyl)quinoline-7-carboxylic acid (48 mg, 0.146 mmol) and 3-(1H-triazol-5-yl)propan-1-amine; hydrochloride (39.3 mg, 0.241 mmol,) in DMF (440 μL) and THF (1.3 mL) was added N,N-diisopropylethylamine (131 μL, 0.754 mmol). After a few minutes of stirring HATU (62.0 mg, 0.163 mmol) was added. The mixture was allowed to stir at room temperature for 2 h. Water (1.0 mL) was added and the mixture was stirred for another few minutes. The mixture was then partitioned between EtOAc and brine. The separated aqueous layer was extracted with EtOAc. The combined organic layer was washed with brine, dried over Na$_2$SO$_4$, and concentrated. The crude product was purified on silica gel column. Drying under vacuum at 40° C. overnight gave 4-ethoxy-3-fluoro-2-(4-fluorophenyl)-N-[3-(1H-1,2,3-triazol-4-yl)propyl]quinoline-7-carboxamide (I-73) (51 mg, 0.117 mmol, 80.0% yield) as a white solid. LC-MS: (FA) ES+ 438.1; $^1$H NMR (400 MHz, DMSO-d$_6$) δ 14.70 (br s, 1H), 8.91-8.84 (m, 1H), 8.59-8.54 (m, 1H), 8.24-8.18 (m, 1H), 8.08-8.02 (m, 3H), 7.69-7.62 (m, 1H), 7.47-7.39 (m, 2H), 4.66-4.60 (m, 2H), 3.42-3.35 (m, 2H), 2.77-2.70 (m, 2H), 1.96-1.87 (m, 2H), 1.51-1.45 (m, 3H).

The compounds listed in the table below were prepared in an analogous fashion to that described in Example 33 starting from the appropriate starting materials:

| Reagent Step 10 | Reagent Step 12 | Compound No. or Name | LCMS Data |
|---|---|---|---|
| 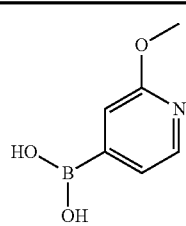 | 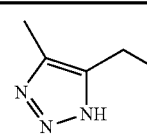 | I-65 | LCMS (ESI+): m/z = 465.2 (M + H) |

| Reagent Step 10 | Reagent Step 12 | Compound No. or Name | LCMS Data |
|---|---|---|---|
| (4-fluorophenyl boronic acid structure) | (triazole-propylamine structure) | I-78 | LCMS (ESI+): m/z = 438.2 (M + H) |

Example 34: Preparation of 3-(4-methyl-1H-1,2,3-triazol-5-yl)propan-1-amine dihydrochloride (CAP-1)

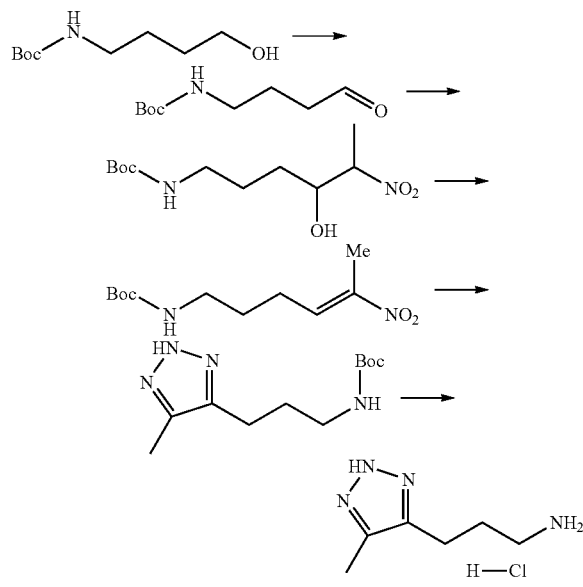

Step 1: tert-Butyl (4-oxobutyl)carbamate

To a solution of DMSO (7.35 ml) in DCM (118 ml) cooled in a dry ice/ethanol bath was added oxalyl chloride (25.9 ml, 51.7 mmol, 2.0 M in DCM) over 15-20 min using syringe pump and the mixture was stirred for another 5 min. A solution of tert-butyl (4-hydroxybutyl)carbamate (8.17 g, 43.2 mmol) in DCM (69.5 ml) was then added over ~25 min. After 15 min of stirring N,N-diisopropylethylamine (22.5 ml, 129 mmol) was added over 8 min. After 5 min of stirring the reaction mixture was allowed to warm up to 0° C. over 25 min and was allowed to stir at 0° C. for 15 min. The mixture was concentrated to around 50% of the original volume while cooling. Water (120 mL) was added and after 3-5 minutes of stirring the mixture was extracted with 300 mL of ether. The organic layer was washed with water (80 mL×3) and brine (80 mL×2), dried over $Na_2SO_4$ and concentrated. The residue was dried under vacuum to give tert-butyl (4-oxobutyl)carbamate (8.10 g, 100% weight yield as crude material) as a light yellow oil. 1H NMR (400 MHz, DMSO-$d_6$) δ 9.65 (s, 1H), 6.85 (br s, 1H), 2.95-2.85 (m, 2H), 2.47-2.35 (m, 2H), 1.68-1.56 (m, 2H), 1.37 (s, 9H).

Step 2: tert-Butyl (4-hydroxy-5-nitrohexyl)carbamate

To a solution of tert-butyl (4-oxobutyl)carbamate (8.10 g, 43.3 mmol) in nitroethane (16.2 mL, 226 mmol) was added TEA (1.10 mL, 7.86 mmol) dropwise. The mixture was allowed to stir at room temperature for 16 h. The mixture was concentrated, coevaporated with toluene twice and dried under vacuum to give 10.25 g of crude material as an orange thick oil. The product was purified on silica gel column to give tert-butyl (4-hydroxy-5-nitrohexyl)carbamate (7.71 g, 67.9% yield) as a white solid.

Step 3: tert-Butyl (E)-(5-nitrohex-4-en-1-yl)carbamate

To a solution of tert-butyl (4-hydroxy-5-nitrohexyl)carbamate (7.71 g, 29.4 mmol) in DCM (39 mL) cooled in ice water bath was added methanesulfonyl chloride (2.57 mL, 33.3 mmol) rapidly followed by TEA (16.4 mL, 118 mmol) dropwise. The resulting orange thick suspension was allowed to stir at 0° C. for 15-20 min. The mixture was diluted with 150 mL of DCM and was washed successively with water (75 mL), 0.5M citric acid aqueous solution (75 mL), and water (75 mL). The organic layer was dried over $Na_2SO_4$ and concentrated to give 6.7 g of crude material. Purification on a silica gel column gave tert-butyl (E)-(5-nitrohex-4-en-1-yl)carbamate (4.02 g, 56.0% yield) as a light yellow oil that solidified over time. LC-MS: (FA) ES– 243.2; $^1$H NMR (400 MHz, DMSO-$d_6$) δ 7.14-7.06 (m, 1H), 6.87 (br s, 1H), 2.99-2.91 (m, 2H), 2.28-2.20 (m, 2H), 2.13-2.09 (m, 3H), 1.61-1.51 (m, 2H), 1.37 (s, 9H).

Step 4: tert-Butyl (3-(4-methyl-1H-1,2,3-triazol-5-yl)propyl)carbamate

To a stirred solution of sodium azide (4.28 g, 65.8 mmol) in DMSO (56.0 mL) was added a solution of tert-butyl (E)-(5-nitrohex-4-en-1-yl)carbamate (4.02 g, 16.4 mmol) in dimethyl sulfoxide (10.0 mL) at 80° C. The mixture was allowed to stir at 80-85° C. for 2.5 hr. After cooling to room temperature the mixture was partitioned between EtOAc (200 mL) and water (300 ml). The separated aqueous layer was extracted with EtOAc (100 ml×2). Combined organic layer was washed with brine (×2), dried over $Na_2SO_4$, filtered and concentrated to give 4.1 g of crude material. The product was purified on a silica gel column to give tert-butyl (3-(4-methyl-1H-1,2,3-triazol-5-yl)propyl)carbamate (1.77 g, 45% yield). LC-MS: (FA) ES+ 241.2; $^1$H NMR (400 MHz, DMSO-$d_6$) δ 6.84 (br s, 1H), 2.97-2.89 (m, 2H), 2.58-2.51 (m, 2H), 2.16 (s, 3H), 1.72-1.61 (m, 2H), 1.38 (s, 9H).

Step 5: 3-(4-methyl-1H-1,2,3-triazol-5-yl)propan-1-amine dihydrochloride

A solution of tert-butyl (3-(4-methyl-1H-1,2,3-triazol-5-yl)propyl)carbamate (2.17 g, 9.03 mmol) in methanol (11.8 mL) was cooled in ice bath. To the solution was added hydrogen chloride in dioxane (23.6 mL, 94.3 mmol, 4.0 M) over 2-3 min and the resulting mixture was allowed to stir at room temperature for 2.5 h. Ether (75 mL) was added and the resulting suspension was allowed to stir for 1 hr. The solid was filtered and dried under vacuum overnight to give 3-(4-methyl-1H-1,2,3-triazol-5-yl)propan-1-amine dihydrochloride (1.81 g, 8.48 mmol, 93.9% yield) as a light tan solid. LC-MS: (FA) ES+ 141.2; $^1$H NMR (400 MHz, DMSO-d$_6$) δ 8.02 (br s, 3H), 2.88-2.74 (m, 2H) 2.70-2.62 (m, 2H), 2.21 (s, 3H), 1.93-1.84 (m, 2H).

Example 35: Preparation of 2-(4-methyl-1H-1,2,3-triazol-5-yl)ethan-1-amine dihydrochloride (CAP-2)

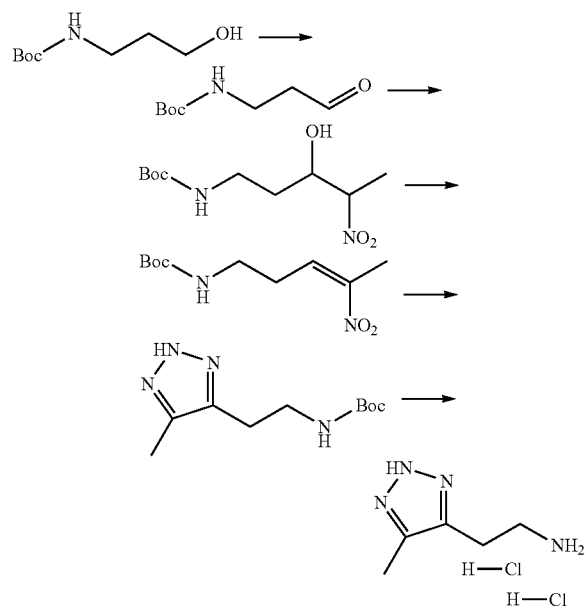

Step 1: tert-Butyl (3-oxopropyl)carbamate

To a solution of DMSO (5.05 mL, 71.1 mmol) in DCM (75.0 mL) at −78° C. was added oxalyl chloride (17.1 mL, 34.2 mmol, 2.00 mmol/mL) over 10 min. by syringe pump. The mixture was stirred for an additional 5 min and a solution of tert-butyl (3-hydroxypropyl)carbamate (5.00 g, 28.5 mmol) in DCM (36.0 mL) was added over 15 min. After 30 min. DIPEA (15.0 mL, 86.1 mmol) was added over 10 min. The mixture was stirred for additional 10 min., was allowed to warm up to 0° C. and stir at that temperature for 15 min. Water (100 mL) was added and the mixture was stirred for 3-5 min. The reaction mixture was then extracted with 400 mL of ether. The separated organic layer was washed with water (100 mL×2) and brine, then dried over Na$_2$SO$_4$ and concentrated to give tert-butyl (3-oxopropyl) carbamate (4.84 g, 97.9% yield) as a light yellow oil. $^1$H NMR (400 MHz, CDCl$_3$) δ 9.83 (s, 1H), 4.91 (br s, 1H), 3.47-3.41 (m, 2H), 2.76-2.70 (m, 2H), 1.45 (s, 9H).

Step 2: tert-Butyl (3-hydroxy-4-nitropentyl)carbamate

To a solution of tert-butyl (3-oxopropyl)carbamate (4.84 g, 27.9 mmol) in nitroethane (12.5 mL, 173 mmol) was added TEA (801 µL, 5.75 mmol) dropwise. The mixture was allowed to stir at room temperature overnight. The reaction mixture was then concentrated, coevaporated with toluene twice and dried under vacuum to give tert-butyl (3-hydroxy-4-nitropentyl)carbamate (6.97 g, quantitative yield). This material was used in the next step without further purification.

Step 3: tert-Butyl (Z)-(4-nitropent-3-en-1-yl)carbamate

To a solution of tert-butyl N-(3-hydroxy-4-nitro-pentyl) carbamate (5.70 g, 23.0 mmol) in DCM (30.6 mL) at 0° C. was added methanesulfonyl chloride (2.02 mL, 26.2 mmol) rapidly followed by TEA (12.9 mL, 92.5 mmol). The reaction mixture was allowed to stir for 15-20 min at 0° C. The mixture was then diluted with 150 mL of DCM and the organic layer was washed successively with water (75 mL), 0.5M aqueous citric acid (2×75 mL) and 1:1 brine-water mixture. The organic solution was dried over Na$_2$SO$_4$ and concentrated. The residue was purified by column chromatography to give tert-butyl (Z)-(4-nitropent-3-en-1-yl)carbamate (2.91 g, 55.0% yield) as a light yellow solid. LC-MS: (FA) ES-229.2; $^1$H NMR (400 MHz, DMSO-d6) δ 7.05-7.11 (m, 1H), 6.91-7.04 (m, 1H), 3.12-3.08 (m, 2H), 2.40-2.34 (m, 2H), 2.10 (s, 3H), 1.37 (s, 9H).

Step 4: tert-Butyl (2-(4-methyl-1H-1,2,3-triazol-5-yl)ethyl)carbamate

To a stirred solution of tert-butyl (Z)-(4-nitropent-3-en-1-yl)carbamate (3.49 g, 15.1 mmol) in DMSO (55.0 mL) at room temperature was added sodium azide (3.90 g, 60.0 mmol). The mixture was allowed to stir at 85° C. for 1.5 h. After cooling to rt, the reaction mixture was added to water (275 mL) and then extracted with EtOAc (150 and 100 mL). Combined organics were washed with water (50 mL×2) and brine (50 mL×2) then dried over Na$_2$SO$_4$ and concentrated. The crude product was purified by column chromatography to give tert-butyl (2-(4-methyl-1H-1,2,3-triazol-5-yl)ethyl) carbamate (2.37 g, 69.2% yield). LC-MS: (FA) ES+ 227.1; $^1$H NMR (400 MHz, methanol-d4) δ 3.23-3.13 (m, 2H), 2.73-2.67 (m, 2H), 2.18 (s, 3H), 1.31 (s, 9H)

Step 5: 2-(4-Methyl-1H-1,2,3-triazol-5-yl)ethan-1-amine dihydrochloride

To a solution of tert-butyl (2-(4-methyl-1H-1,2,3-triazol-5-yl)ethyl)carbamate (2.37 g, 10.5 mmol) in methanol (13.1 mL) at 0° C. was added hydrogen chloride in 1,4-dioxane (26.3 mL, 105 mmol, 4.00 mol/L) over 2-3 min. and the mixture was allowed to stir at room temperature for 2.25 h. Then ether (70 mL) was added gradually and the resulting suspension was allowed to stir at rt for 1 hr. The light brown solid was filtered off and dried under vacuum at 40° C. overnight to give 2-(4-methyl-1H-1,2,3-triazol-5-yl)ethan-1-amine dihydrochloride (2.15 g, 100% yield). LC-MS: (FA) ES+ 127.0; $^1$H NMR (400 MHz, DMSO-d$_6$) δ 8.08 (br s, 3H), 3.10-2.99 (m, 2H), 2.95-2.87 (m, 2H), 2.21 (s, 3H).

Example 36: Preparation of 3-(3-methyl-1H-pyrazol-4-yl)propan-1-amine dihydrochloride (CAP-3)

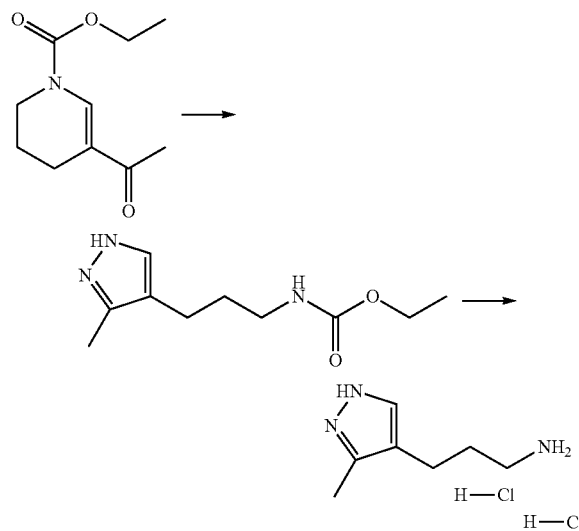

To a solution of ethyl 5-acetyl-3,4-dihydropyridine-1 (2H)-carboxylate (150 mg, 0.761 mmol) in 1-butanol (7.5 mL, 82 mmol) was added hydrazine monohydrochloride (154 mg, 2.24 mmol). The reaction mixture was heated to reflux for 1.5 h. An aliquot was taken from the reaction then evaporated and dried in order to confirm the formation of the intermediate ethyl (3-(3-methyl-1H-pyrazol-4-yl)propyl) carbamate. LC-MS: (FA) ES+ 212.2; $^1$H NMR (400 MHz, DMSO-$d_6$) δ 7.87 (s, 1H), 7.14 (br s, 1H), 4.04-3.90 (m, 2H), 3.00-2.93 (m, 2H), 2.42-2.35 (m, 2H), 2.25 (s, 3H), 1.69-1.55 (m, 2H), 1.17-1.11 (m, 3H). The reaction mixture was neutralized by addition of 2.3 mL 1M aqueous NaOH (2.3 mL) and then concentrated and dried under vacuum. Added concentrated hydrogen chloride (1.9 mL, 23 mmol, 12.0 mol/L) to the residue and the mixture was heated to reflux for 4 h. The mixture was diluted with water (4 mL) then concentrated in vacuo. The residue was coevaporated with toluene and dried under vacuum to give 3-(3-methyl-1H-pyrazol-4-yl)propan-1-amine dihydrochloride (174 mg, 61% yield, contaminated with ~25% of the intermediate described above) $^1$H NMR (400 MHz, DMSO-$d_6$) δ 8.17 (br s, 3H), 7.91 (s, 1H), 2.82-2.67 (m, 2H), 2.50-2.44 (m, 2H), 2.27 (m, 3H), 1.87-1.76 (m, 2H). The product was used in the next step without further purification.

Example 37: Preparation of cis-3-(4H-1,2,4-triazol-3-yl)cyclobutan-1-amine dihydrochloride (CAP-4)

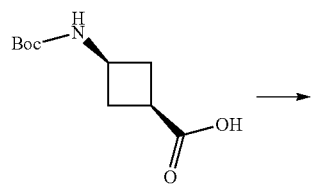

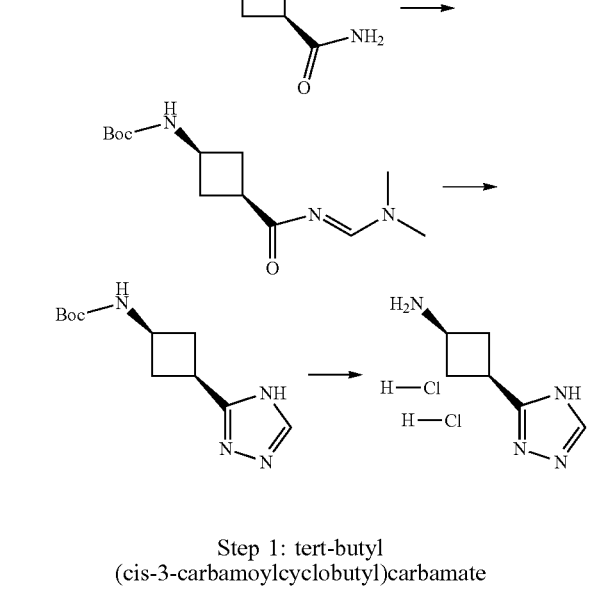

Step 1: tert-butyl (cis-3-carbamoylcyclobutyl)carbamate

To a solution of cis-3-((tert-butoxycarbonyl)amino)cyclobutane-1-carboxylic acid (453 mg, 2.04 mmol) and N,N-diisopropylethylamine (891 µL, 5.11 mmol) in THF (9.90 mL, 122 mmol) cooled to 0° C. was added ethyl chloroformate (215 µL, 2.25 mmol). After stirring at room temperature for 1 h ammonium hydroxide solution (550 µL, 8.09 mmol, 14.7 M) was added. The mixture was allowed to stir at room temperature for 1 hour. The reaction mixture was then partitioned between EtOAc and water. The organic layer was washed with water and brine, dried over $Na_2SO_4$, and concentrated to give tert-butyl (cis-3-carbamoylcyclobutyl)carbamate (303 mg, 69% yield) as a white solid. $^1$H NMR (400 MHz, DMSO-$d_6$) δ 7.22-7.03 (m, 2H), 6.71 (br s, 1H), 3.87-3.72 (m, 1H), 2.27-2.16 (m, 2H), 2.00-1.90 (m, 2H), 1.36 (s, 9H).

Step 2: tert-butyl [cis-3-(4H-1,2,4-triazol-3-yl)cyclobutyl]carbamate

A suspension of tert-butyl (cis-3-carbamoylcyclobutyl)carbamate (301 mg, 1.40 mmol) in N,N-dimethylformamide dimethyl acetal (4.00 mL) was allowed to stir at 100° C. for 2 hours. The mixture was cooled, concentrated and dried under vacuum. The residue was dissolved in 1,4-dioxane (2.1 mL), and then hydrazine monohydrate (85 µL, 1.774 mmol) and acetic acid (200 µL, 3.49 mmol) were added. The resulting heterogeneous mixture was allowed to stir at 90° C. for 2 hours. The resulting homogeneous mixture was concentrated, coevaporated with toluene (×2) and the residue was dried under vacuum to give tert-butyl [cis-3-(4H-1,2,4-triazol-3-yl)cyclobutyl]carbamate (369 mg, 99.2% yield). LC-MS: (FA) ES+ 239.2; $^1$H NMR (400 MHz, DMSO-$d_6$) δ 8.05 (br s, 1H), 7.25-7.18 (m, 1H), 4.02-3.87 (m, 1H), 3.21-3.06 (m, 1H), 2.57-2.55 (m, 1H), 2.19-2.09 (m, 2H), 1.37 (s, 9H).

Step 3: cis-3-(4H-1,2,4-triazol-3-yl)cyclobutanamine dihydrochloride

To a solution tert-butyl [cis-3-(4H-1,2,4-triazol-3-yl)cyclobutyl]carbamate (369 mg, 1.55 mmol) in methanol (1.95 mL) cooled in ice bath was added hydrogen chloride in 1,4-dioxane (3.91 mL, 15.6 mmol, 4.0 M). The resulting solution was allowed to stir at room temperature for 1.5 hours. To the resulting suspension was added 25 mL of diethylether and the resulting mixture was stirred for 15 min. The solid was filtered off and dried under vacuum to give cis-3-(4H-1,2,4-triazol-3-yl)cyclobutanamine dihydrochloride (306 mg, 84.3% yield) as a light yellow solid. LC-MS: (FA) ES+ 139.1; $^1$H NMR (400 MHz, DMSO-$d_6$) δ 8.61 (br s, 1H), 8.27 (br s, 3H), 3.78-3.68 (m, 1H), 3.53-3.42 (m, 1H), 2.68-2.57 (m, 2H), 2.53-2.42 (m, 2H).

Example 38: Preparation of 3-(1H-1,2,3-triazol-5-yl)propan-1-amine, dihydrochloride salt (CAP-5)

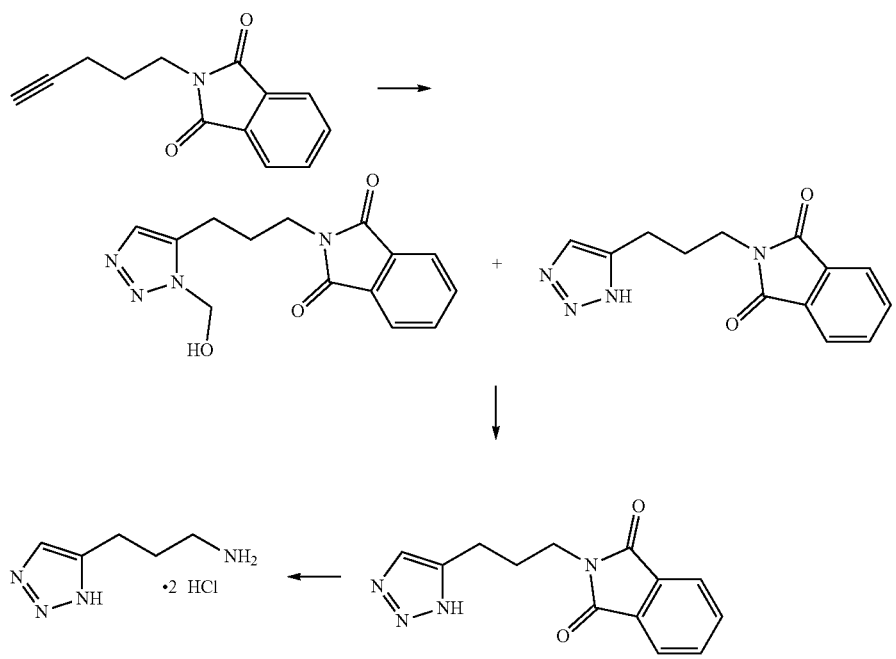

Step 1: Mixture of 2-(3-(1-(hydroxymethyl)-1H-1,2,3-triazol-5-yl)propyl)isoindoline-1,3-dione and 2-(3-(1H-1,2,3-triazol-5-yl)propyl)isoindoline-1,3-dione To a flask containing 1,4-dioxane (88 mL) was added 37% formaldehyde in water (85 mL, 1.14 mol) followed by acetic acid (9.8 mL, 171 mmol), and the resulting solution was allowed to stir at room temperature for 15 min. Sodium azide (11.1 g, 171 mmol) was then added followed by N-(4-pentynyl)phthalimide (25.0 g, 114 mmol), and the mixture was allowed to stir at rt for 10 min. Sodium ascorbate (4.50 g, 22.7 mmol) was then added followed by a solution of cupric sulfate (908 mg, 5.7 mmol) in water (4.8 mL), and the resulting mixture was allowed to stir at rt overnight. To the reaction mixture was added water (300 mL) and EtOAc (500 mL). The layers were separated and the aqueous layer was extracted with EtOAc (100 mL). The combined organic layer was dried (MgSO$_4$), filtered and concentrated in vacuo. The crude compound was purified by column chromatography to give a mixture of 2-(3-(1-(hydroxymethyl)-1H-1,2,3-triazol-5-yl)propyl)isoindoline-1,3-dione and 2-(3-(1H-1,2,3-triazol-5-yl)propyl)isoindoline-1,3-dione (31 g) which was used directly in the following step. LC-MS: (FA) ES+ 287.1, 257.1.

Step 2: 2-(3-(1H-1,2,3-triazol-5-yl)propyl)isoindoline-1,3-dione

To a solution of the mixture of 2-(3-(1-(hydroxymethyl)-1H-1,2,3-triazol-5-yl)propyl)isoindoline-1,3-dione and 2-(3-(1H-1,2,3-triazol-5-yl)propyl)isoindoline-1,3-dione (31 g) in chloroform (500 mL) was added manganese dioxide (89 g, 1.0 mol) and the mixture was allowed to stir at 62° C. for 2 days. The reaction was cooled slightly, then filtered while still hot through a bed of silica gel (250 mL). The bed was then washed with hot EtOAc (1 L). The filtrate was concentrated in vacuo to give 2-(3-(1H-1,2,3-triazol-5-yl)propyl)isoindoline-1,3-dione (16.5 g, 56% 2-step yield). LC-MS: (FA) ES+ 257.1; $^1$H NMR (Methanol-$d_4$, 400 MHz) δ 7.86-7.78 (m, 4H), 7.65 (s, 1H), 3.77-3.73 (m, 2H), 2.82-2.74 (m, 2H), 2.11-2.02 (m, 2H).

Step 3: 3-(1H-1,2,3-triazol-5-yl)propan-1-amine, dihydrochloride salt

To a solution of 2-(3-(1H-1,2,3-triazol-5-yl)propyl)isoindoline-1,3-dione (16.5 g, 64.4 mmol) in ethanol (410 mL) was added hydrazine (40.0 mL, 1.03 mol) and the resulting solution was allowed to stir at 70° C. for 90 minutes. The reaction was cooled, and the solids were filtered and washed with ethanol (100 mL). The filtrate was concentrated in vacuo to give crude 3-(1H-1,2,3-triazol-5-yl)propan-1-amine (8.8 g), which was dissolved in MeOH (88 mL) and filtered. To the filtrate was added 4M HCl in 1,4-dioxane (33.8 mL) and then stirred for 15 minutes. EtOAc (176 mL) was added and the mixture was stirred for 30 min. The solids were filtered, washed with EtOAc (50 mL) and dried to give 3-(1H-1,2,3-triazol-5-yl)propan-1-amine, dihydrochloride salt (12.0 g, 93% 2 step yield). LC-MS: (FA) ES+ 127.1; $^1$H NMR (Methanol-$d_4$, 400 MHz) δ 8.47 (s, 1H), 3.09-3.04 (m, 4H), 2.19-2.11 (m, 2H).

Example 39: Preparation of 2-(3-methyl-1H-pyrazol-4-yl)ethanamine dihydrochloride (CAP-6)

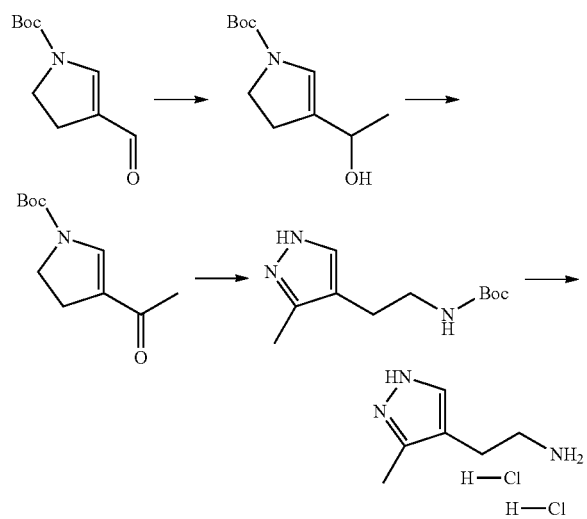

Step 1: tert-butyl 4-(1-hydroxyethyl)-2,3-dihydro-1H-pyrrole-1-carboxylate

To a solution of tert-butyl 4-formyl-2,3-dihydropyrrole-1-carboxylate (prepared following the procedure described in Greshock, T. J., Funk, R. L. *J. Am. Chem. Soc.* 2006, 128, 4946-4947; 6.04 g, 30.6 mmol) in THF (150 mL) cooled in acetone-dry ice bath was added 1.6M methyllithium in diethyl ether (21.1 mL, 33.7 mmol). The mixture was allowed to stir at −78° C. for 20 min. The reaction was quenched by addition of ~100 mL of saturated NaHCO$_3$ aqueous solution. The mixture was allowed to stir at rt for few minutes, and then distributed between water and diethyl ether. The aqueous layer was extracted with ether. The combined organic layers was washed with brine, dried over Na$_2$SO$_4$ and concentrated. The residue was dried to give tert-butyl 4-(1-hydroxyethyl)-2,3-dihydro-1H-pyrrole-1-carboxylate (6.52 g, 99.8% yield) as a yellow oil. $^1$H NMR (400 MHz, methanol-d$_4$) δ 6.40-6.45 (m, 1H), 4.37-4.42 (m, 1H), 3.69-3.79 (m, 2H), 2.59-2.76 (m, 2H), 1.49 (s, 9H), 1.30-1.32 (m, 3H).

Step 2: tert-butyl 4-acetyl-2,3-dihydro-1H-pyrrole-1-carboxylate

To a solution of tert-butyl 4-(1-hydroxyethyl)-2,3-dihydro-1H-pyrrole-1-carboxylate (6.52 g, 30.6 mmol) in DCM (100 mL) cooled in ice bath was added 4 Å molecular sieves powder (dried at 140° C. overnight under vacuum, 15.0 g), N-methyl morpholine-N-oxide (6.09 g, 52.0 mmol) and tetrapropylammonium perruthenate (1.07 g, 3.06 mmol). The reaction mixture was then allowed to stir at 0° C. for 3 h. To the mixture was added saturated NaHCO$_3$ aqueous solution (150 mL), DCM and Celite®, and the mixture was filtered. The aqueous layer was extracted with DCM (2×25 mL). The combined organic layers was dried over Na$_2$SO$_4$, filtered, and concentrated. Purification by column chromatography provided tert-butyl 4-acetyl-2,3-dihydro-1H-pyrrole-1-carboxylate (4.29 g, 66.4% yield) as a light yellow waxy solid. $^1$H NMR (400 MHz, methanol-d$_4$) δ 7.43-7.80 (m, 1H), 3.84 (t, J=9.54 Hz, 2H), 2.78 (t, J=9.80 Hz, 2H), 2.26 (s, 3H), 1.52 (s, 9H).

Step 3: tert-butyl N-[2-(3-methyl-1H-pyrazol-4-yl)ethyl]carbamate

To a solution of tert-butyl 4-acetyl-2,3-dihydro-1H-pyrrole-1-carboxylate (4.29 g, 20.3 mmol) in 1-butanol (80.0 mL, 873 mmol) in a round flask equipped with condenser was added hydrazine hydrate (2.96 mL, 60.9 mmol). The mixture was allowed to stir at 120° C. for 2 days. The solution was concentrated. The resulting syrup was purified by column chromatography to give tert-butyl N-[2-(3-methyl-1H-pyrazol-4-yl)ethyl]carbamate (3.63 g, 77.8% yield). LC-MS: (FA) ES+ 226; $^1$H NMR (400 MHz, CDCl$_3$) δ 7.37 (s, 1H), 4.59 (br s, 1H), 3.25-3.37 (m, 2H), 2.63 (t, J=6.90 Hz, 2H), 2.27 (s, 3H), 1.46 (s, 9H).

Step 4: 2-(3-methyl-1H-pyrazol-4-yl)ethanamine dihydrochloride

To a solution of tert-butyl N-[2-(3-methyl-1H-pyrazol-yl)ethyl]carbamate (3.63 g, 16.1 mmol) in methanol (20.0 mL) was added 4.0 M hydrogen chloride in dioxane (40.3 mL, 161 mmol) over 2 min at 0° C. After a few minutes the mixture allowed to stir at rt. After 1 h diethyl ether (100 mL) was added slowly and the resulting suspension was allowed to stir for 1 h. The resulting light yellow solid was filtered off, washed with diethyl ether, and dried under air for 2 h to give 2-(3-methyl-1H-pyrazol-4-yl)ethanamine dihydrochloride (3.06 g, 95.9% yield). LC-MS: (FA) ES+ 126; $^1$H NMR (400 MHz, methanol-d$_4$) δ 8.08 (s, 1H), 3.18 (t, J=7.53 Hz, 2H), 2.91 (t, J=7.65 Hz, 2H), 2.44 (s, 3H).

Example 40: Preparation of 3-(2-aminoethyl)-1H-pyrazol-5-amine hydrochloride (CAP-7)

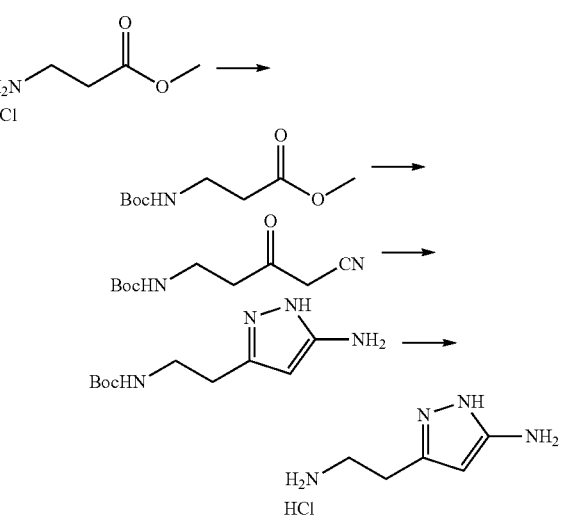

Step 1: methyl 3-[(tert-butoxycarbonyl)amino]propanoate

To a suspension of methyl 3-aminopropanoate hydrochloride (5.0 g, 35.8 mmol) in 40 mL of DCM was added TEA (7.24 g, 71.6 mmol). The mixture was allowed to stir at 0°

C. and di-tert-butyl dicarbonate (7.81 g, 35.8 mmol) was added. The mixture was allowed stir at 15° C. for 20 h. Water (60 mL) was added and then the mixture was extracted with DCM (30 mL×3). The combined organic layers was dried over Na$_2$SO$_4$, filtered and concentrated. Purification by column chromatograghy provided methyl 3-[(tert-butoxycarbonyl)amino]propanoate (4.5 g, 61.8% yield) as light yellow oil. $^1$H NMR (400 MHz, CDCl$_3$) δ 5.03 (br s, 1H), 3.65 (s, 3H), 3.34-3.35 (m, 2H), 2.48 (t, J=6.0 Hz, 2H), 1.38 (s, 9H).

Step 2: tert-butyl (4-cyano-3-oxobutyl)carbamate

To a solution of n-BuLi (2.5M in hexane, 34.3 mL, 85.9 mmol) in THF at −78° C. under nitrogen was added dropwise a solution of MeCN (3.52 g, 85.9 mmol) in 50 mL of THF. The mixture was allowed to stir for 1 h at −78° C. A solution of methyl 3-((tert-butoxycarbonyl)amino)propanoate (7.0 g, 34.4 mmol) in 20 mL THF was then added dropwise. The resulting mixture was allowed to warm to −50° C. over 30 min. The reaction was quenched by addition of acetic acid (15 mL). Water (150 mL) was added and the mixture was extracted with EtOAc (50 mL×3). The combined organic layers was dried over Na$_2$SO$_4$, filtered and concentrated. Purification by column chromatograghy gave tert-butyl (4-cyano-3-oxobutyl)carbamate (6.0 g, 82.1% yield) as a yellow oil. $^1$H NMR (400 MHz, CDCl$_3$) δ 5.00 (br s, 1H), 3.49-3.53 (m, 2H), 3.33-3.38 (m, 2H), 2.78 (t, J=6.0 Hz, 2H), 1.37 (s, 9H).

Step 3: tert-butyl [2-(5-amino-1H-pyrazol-3-yl)ethyl]carbamate

To a solution of tert-butyl (4-cyano-3-oxobutyl)carbamate (6.0 g, 28.2 mmol) in ethanol (60 mL) under nitrogen was added hydrazine (1.8 g, 28.2 mmol). The mixture was allowed to stir at 80° C. for 16 h and then was concentrated. The product was purified by column chromatograghy to give tert-butyl [2-(5-amino-1H-pyrazol-3-yl)ethyl]carbamate (5.0 g, 78.3% yield) as a yellow oil. $^1$H NMR (400 MHz, CDCl$_3$) δ 5.44 (s, 1H), 4.91 (br s, 1H), 3.34-3.36 (m, 2H), 2.73 (t, J=6.8 Hz, 2H), 1.42 (s, 9H).

Step 4: 3-(2-aminoethyl)-1H-pyrazol-5-amine hydrochloride

A solution of tert-butyl [2-(5-amino-1H-pyrazol-3-yl)ethyl]carbamate (5 g, 22 mmol) in 50 mL of 4M HCl solution in methanol was allowed to stir at 20° C. for 2 h. The mixture was filtered. The collected solid was washed with EtOAc (20 mL) and dried to provide 3-(2-aminoethyl)-1H-pyrazol-5-amine hydrochloride (2.5 g, 70% yield) as a white solid. LC-MS: (FA) ES+ 127; 1H NMR (400 MHz, DMSO-d6) δ 8.37 (br s, 3H), 5.84 (s, 1H), 3.09-3.11 (m, 2H), 2.96 (t, J=6.8 Hz, 2H).

Example 41: Preparation of 2,2-difluoro-3-(4H-1,2,4-triazol-3-yl)propan-1-amine hydrochloride (CAP-8)

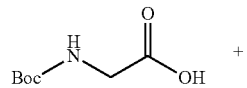

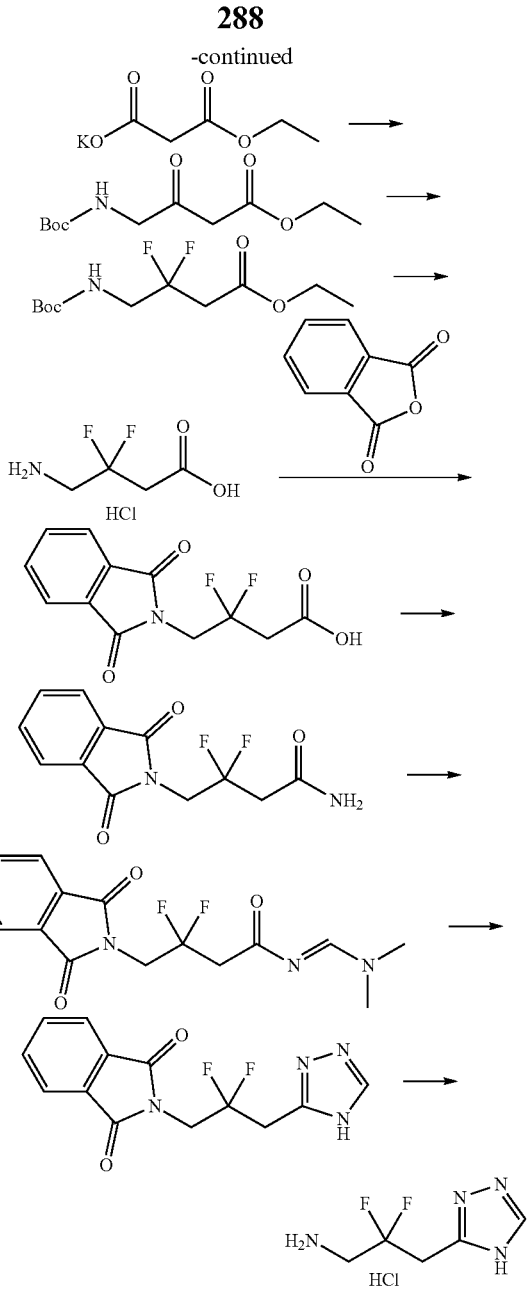

Step 1: ethyl 4-((tert-butoxycarbonyl)amino)-3-oxobutanoate

To a solution of [(tert-butoxycarbonyl)amino]acetic acid (47 g, 268 mmol) in THF (470 mL) was added CDI (47.6 g, 294 mmol), and the resulting solution was allowed to stir at 30° C. for 4 h. Treatment of potassium 3-ethoxy-3-oxopropanoate (54.6 g, 321 mmol) with magnesium chloride (35.7 g, 375 mmol) and TEA (40.6 g, 402 mmol) in THF (540 mL) at 30° C. for 4 h generated the dianion as its magnesium chelate. To this solution was added the imidazolide solution, and a gummy precipitate began to form immediately. After stirring at 30° C. for 72 h, the reaction was poured into ice-cold 1 M HCl aqueous solution (1000 mL) and extracted with EtOAc (800 mL×2). The combined organic layers was washed with saturated NaHCO$_3$ aqueous solution (800 mL) and brine (800 mL), was dried over Na$_2$SO$_4$, filtered and concentrated to give crude product. Purification by column chromatography gave ethyl 4-[(tert-butoxycarbonyl)amino]-3-oxobutanoate (49 g, 75% yield) as a red oil. $^1$H NMR (400 MHz, CDCl$_3$) δ 5.18 (br s, 1H), 4.20 (q, J=7.2 Hz, 2H), 4.11-4.14 (m, 2H), 3.48 (s, 2H), 1.45 (s, 9H), 1.29 (t, J=6.8 Hz, 3H).

Step 2: ethyl 4-[(tert-butoxycarbonyl)amino]-3,3-difluorobutanoate

To a solution of ethyl 4-[(tert-butoxycarbonyl)amino]-3-oxobutanoate (47 g, 191 mmol) in DCM (490 mL) was added DAST (48 g, 297 mmol), and the resulting solution was allowed to stir at 15° C. After 17 h another batch of DAST (34 g, 211 mmol) was added. After 3 h the reaction was poured into ice-water (1000 mL) and extracted with DCM (500 mL×2). The combined organic layers was washed with saturated NaHCO$_3$ aqueous solution (800 mL×2) and brine (800 mL), dried over Na$_2$SO$_4$, filtered and concentrated in vacuo to give crude product. Purification by column chromatography gave ethyl 4-[(tert-butoxycarbonyl)amino]-3,3-difluorobutanoate (12 g, 24% yield) as a white solid. $^1$H NMR (400 MHz, CDCl$_3$) δ 4.87 (s br, 1H), 4.21 (q, J=7.6 Hz, 2H), 3.67-3.75 (td, J=13.6 Hz, 6.8 Hz, 2H), 2.96 (t, J=15.2 Hz, 2H), 1.46 (s, 9H), 1.29 (t, J=7.6 Hz, 3H).

Step 3: 4-amino-3,3-difluorobutanoic acid hydrochloride

A solution of ethyl 4-[(tert-butoxycarbonyl)amino]-3,3-difluorobutanoate (12.9 g, 48.2 mmol) in 6M HCl aqueous solution (60 mL) was allowed to stir at 100° C. for 17 h. The reaction mixture was then concentrated in vacuo to give crude product 4-amino-3,3-difluorobutanoic acid hydrochloride (8 g, quantitative) as a pale yellow solid. $^1$H NMR (400 MHz, methanol-d4) δ 3.76 (t, J=16 Hz, 2H), 2.24 (t, J=14.8 Hz, 2H).

Step 4: 4-(1,3-dioxo-1,3-dihydro-2H-isoindol-2-yl)-3,3-difluorobutanoic acid

A mixture of 4-amino-3,3-difluorobutanoic acid hydrochloride (8 g, 45.5 mmol), phthalic anhydride (10.1 g, 68.2 mmol) and sodium acetate (5.59 g, 68.2 mmol) in acetic acid (76 mL) was allowed to stir at 120° C. for 2.5 h. The mixture was concentrated and distributed between 1M HCl aqueous solution (300 mL) and EtOAc (300 mL). The mixture was extracted with EtOAc (300 mL×2). Combined organic layer was dried and concentrated to give crude product (14 g). The crude product was dissolved in ethanol (10 mL) and EtOAc (25 mL) and PE (80 mL) were added dropwise. The resulting mixture was allowed to stir at 20° C. for 30 min. The suspension was filtered and the collected solid was washed with PE (30 mL×2) and dried to give 4-(1,3-dioxo-1,3-dihydro-2H-isoindol-2-yl)-3,3-difluorobutanoic acid as a white solid (9.1 g, 75% yield). LC-MS: ES+ 270. $^1$H NMR (400 MHz, methanol-d$_4$) δ 7.92-7.94 (m, 2H), 7.85-7.87 (m, 2H), 4.34 (t, J=14.0 Hz, 2H), 3.10 (t, J=15.2 Hz, 2H).

Step 5: 4-(1,3-dioxo-1,3-dihydro-2H-isoindol-2-yl)-3,3-difluorobutanamide

To a solution of 4-(1,3-dioxo-1,3-dihydro-2H-isoindol-2-yl)-3,3-difluorobutanoic acid (7.22 g, 26.8 mmol) in THF (75 mL) was added oxalyl chloride (20.3 g, 160 mmol) at 20° C. The resulting mixture was allowed to stir at 80° C. for 2.5 h, then the reaction was concentrated to give the acyl chloride. To a solution of ammonium hydroxide (7.32 mL, 53.6 mmol) in THF (200 mL) at −65° C. was added dropwise a solution of the previously described acyl chloride in THF (40 mL). The reaction was allowed to stir at −65° C. for 1 h. Water (150 mL) was added and the mixture was extracted with DCM/MeOH (10:1, 330 mL×4). The combined organic layers was dried, filtered and concentrated to provide 4-(1,3-dioxo-1,3-dihydro-2H-isoindol-2-yl)-3,3-difluorobutanamide (7.0 g, 97% yield) as a white solid. LC-MS: ES+ 269. $^1$H NMR (400 MHz, methanol-d4) δ 7.92-7.94 (m, 2H), 7.85-7.87 (m, 2H), 4.32 (t, J=14.8 Hz, 2H), 2.99 (t, J=16.0 Hz, 2H).

Step 6: N-[(E)-(dimethylamino)methylene]-4-(1,3-dioxo-1,3-dihydro-2H-isoindol-2-yl)-3,3-difluorobutanamide A mixture of 4-(1,3-dioxo-1,3-dihydro-2H-isoindol-2-yl)-3,3-difluorobutanamide (6.3 g, 23.4 mmol) and 1,1-dimethoxy-N,N-dimethylmethanamine (5.57 g, 46.8 mmol) in toluene (200 mL) was allowed to stir at 65° C. for 2 h. The reaction was cooled and water (200 mL) was added. The mixture was extracted with EtOAc (200 mL×2). The combined organic layers was washed with brine, dried over Na$_2$SO$_4$, filtered and concentrated. The crude product was dissolved in EtOAc (10 mL), then PE (100 mL) was added dropwise. The resulting solid was filtered off and dried to give N-[(E)-(dimethylamino)methylene]-4-(1,3-dioxo-1,3-dihydro-2H-isoindol-2-yl)-3,3-difluorobutanamide (6.2 g, 82% yield) as a pale yellow solid. $^1$H NMR (400 MHz, CDCl$_3$) δ 8.50 (s, 1H), 7.87-7.90 (m, 2H), 7.73-7.76 (m, 2H), 4.50 (t, J=15.2 Hz, 2H), 3.11-3.19 (m, 8H).

Step 7: 2-[2,2-difluoro-3-(4H-1,2,4-triazol-3-yl)propyl]-1H-isoindole-1,3(2H)-dione To a solution of N-[(E)-(dimethylamino)methylene]-4-(1,3-dioxo-1,3-dihydro-2H-isoindol-2-yl)-3,3-difluorobutanamide (4.1 g, 12.6 mmol) in 150 mL of acetic acid was added hydrazine (1.89 g, 50.4 mmol) at 20° C. The reaction was allowed to stir at 90° C. for 2.5 h. 1 M NaOH aqueous solution was added to the reaction to pH 9, and the resulting mixture was extracted with EtOAc (200 mL×3). The combined organic layers was dried over Na$_2$SO$_4$, filtrated and concentrated to provide 2-[2,2-difluoro-3-(4H-1,2,4-triazol-3-yl)propyl]-1H-isoindole-1,3(2H)-dione (3.0 g, 81% yield) as a yellow solid. LC-MS: ES+ 293. $^1$H NMR (400 MHz, DMSO-d$_6$) δ 13.97 (s, 1H), 7.87-7.93 (m, 4H), 4.26 (t, J=14.8 Hz, 2H), 3.49-3.50 (m, 2H).

Step 8: 2,2-difluoro-3-(4H-1,2,4-triazol-3-yl)propan-1-amine hydrochloride

A solution of 2-[2,2-difluoro-3-(4H-1,2,4-triazol-3-yl)propyl]-1H-isoindole-1,3(2H)-dione (3.0 g, 10.2 mmol) in 6 M HCl aqueous solution (50 mL) was stirred at 100° C. for 17 h. The reaction was allowed to cool and was washed with DCM (60 mL×3). Concentration of the aqueous layer provided crude product. The crude product was suspended in MeOH/DCM/EtOAc (0.02:1:5, 30 mL) and was allowed to stir for 30 min. The resulting solid was filtered off and dried to give 2,2-difluoro-3-(4H-1,2,4-triazol-3-yl)propan-1-amine hydrochloride (1.2 g, 61% yield) as a pale yellow solid. LC-MS: ES+ 163. $^1$H NMR (400 MHz, methanol-d4) δ 9.21 (s, 1H), 3.69-3.84 (m, 4H).

The following building blocks that were not available from commercial sources were prepared according to listed references:

| Reagent Structure | Compound ID | Literature Reference |
|---|---|---|
| H₂N-[structure] | CAP-9 | Jia et al *J.Med.Chem* 2014, 57, 7577 |
| H₂N-[structure] | CAP-10 | Jia et al *J.Med.Chem* 2014, 57, 7577 |
| H₂N-[structure] | CAP-11 | Jia et al *J.Med.Chem* 2014, 57, 7577 |
| H₂N-[structure] | CAP-12 | Jia et al *J.Med.Chem* 2014, 57, 7577 |

Biological Data

Example 20: NAMPT Enzyme Assay

To measure the inhibition of NAMPT activity hNAMPT protein stock and anti 6His-Tb (Cisbio; Cat. No. 61HISTLB) is diluted to 3× final concentration with assay buffer (50 mM Tris-HCl (pH 7.5), 1 mM DTT, 100 mM NaCl, 10 mM MgCl₂, 0.005% Tween 20). To this solution is added a test compound or vehicle control (DMSO) and BodiPY ligand (structure below). The plate is shaken for 1-2 min sealed and incubated for 1 h at rt in the dark. The TR-FRET signal is measured using BMG Pherastar (Lanthascreen protocol on BMG Pherastar). Excitation was carried out at 320 nm, and the ratio of emission of BodiPY (520 nm) to terbium (486 nm) was determined. Concentration response curves are generated by calculating the excitation increase in test compound-treated samples relative to DMSO-treated controls.

For the assay method described above, test compound percent inhibition values at a single concentration are calculated relative to control (DMSO) treated samples. Compound concentration response curves are fitted to generate $IC_{50}$ values from those curves. One skilled in the art will appreciate that these values generated either as percentage inhibition at a single concentration or $IC_{50}$ values are subject to experimental variation.

Structure of BODIPY Ligand:

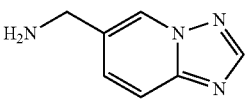 [SMILES: NCc1ccc2ncnn2c1]

Compounds of the invention were assayed at a concentration of 1 µM with the % inhibition values as shown in the table below (Table 2). Additionally, compounds of the invention inhibit NAMPT with the following $IC_{50}$ ranges: (A)<10 nM; (B) 10 nM to <50 nM; (C) 50 nM to <100 nM; or (D) greater than 100 nM.

TABLE 2

NAMPT Inhibition of Compounds of the Invention

| Compound | Concentration (µM) | Percent Inhibition | IC50 |
|---|---|---|---|
| I-1 | 1 | >99 | A |
| I-2 | 1 | >99 | A |
| I-3 | 1 | 94 | B |
| I-4 | 1 | 99 | A |
| I-5 | 1 | 100 | A |
| I-6 | 1 | 94 | C |
| I-7 | 1 | 97 | B |
| I-8 | 1 | 98 | A |
| I-9 | 1 | 93 | A |
| I-10 | 1 | 100 | A |
| I-11 | 1 | >99 | A |
| I-12 | 1 | >99 | A |
| I-13 | 1 | >99 | A |
| I-14 | 1 | >99 | A |
| I-15 | 1 | >99 | A |
| I-16 | 1 | 100 | A |
| I-17 | 1 | 99 | A |
| I-18 | 1 | 99 | B |
| I-19 | 1 | >99 | A |

TABLE 2-continued

NAMPT Inhibition of Compounds of the Invention

| Compound | Concentration (μM) | Percent Inhibition | IC50 |
|---|---|---|---|
| I-20 | 1 | 98 | B |
| I-21 | 1 | 99 | B |
| I-22 | 1 | >99 | B |
| I-23 | 1 | >99 | B |
| I-24 | 1 | >99 | A |
| I-25 | 1 | 99 | A |
| I-26 | 1 | 89 | D |
| I-27 | 1 | 98 | A |
| I-28 | 1 | 99 | A |
| I-29 | 1 | 100 | A |
| I-30 | 1 | 91 | C |
| I-31 | 1 | 97 | B |
| I-32 | 1 | >99 | A |
| I-33 | 1 | 97 | B |
| I-34 | 1 | 97 | A |
| I-35 | 1 | >99 | A |
| I-36 | 1 | >99 | A |
| I-37 | 1 | >99 | A |
| I-38 | 1 | >99 | A |
| I-39 | 1 | 96 | B |
| I-40 | 1 | >99 | A |
| I-41 | 1 | 92 | D |
| I-42 | 1 | 83 | D |
| I-43 | 1 | 99 | A |
| I-44 | 1 | 97 | A |
| I-45 | 1 | 100 | A |
| I-46 | 1 | 97 | B |
| I-47 | 1 | 47 | A |
| I-48 | 1 | 97 | B |
| I-49 | 1 | 98 | A |
| I-50 | 1 | 99 | A |
| I-51 | 1 | 98 | B |
| I-52 | 1 | 99 | A |
| I-53 | 1 | 93 | B |
| I-54 | 0.33 | 96 | A |
| I-55 | 1 | 93 | C |
| I-56 | 1 | 99 | A |
| I-57 | 1 | 99 | A |
| I-58 | 1 | 96 | B |
| I-59 | 1 | 90 | C |
| I-60 | 1 | 99 | A |
| I-61 | 1 | 99 | A |
| I-62 | 1 | 95 | C |
| I-63 | 1 | 77 | D |
| I-64 | 1 | 91 | C |
| I-65 | 1 | 91 | C |
| I-66 | 1 | 94 | B |
| I-67 | 1 | 85 | D |
| I-68 | 1 | 92 | B |
| I-69 | 1 | 86 | D |
| I-70 | 1 | 99 | A |
| I-71 | 1 | 97 | B |
| I-72 | 1 | 98 | A |
| I-73 | 1 | 100 | A |
| I-74 | 1 | 100 | A |
| I-75 | 1 | 94 | B |
| I-76 | 1 | 93 | C |
| I-77 | 1 | 97 | B |
| I-78 | 1 | 99 | A |
| I-79 | 1 | 99 | A |
| I-80 | 1 | 98 | A |
| I-81 | 1 | 67 | D |
| I-82 | 1 | 100 | A |
| I-83 | 1 | 96 | B |
| I-84 | 1 | 99 | A |
| I-85 | 1 | 100 | A |
| I-86 | 1 | 99 | A |
| I-87 | 1 | 94 | B |
| I-88 | 1 | 97 | B |
| I-89 | 1 | 96 | B |
| I-90 | 1 | 97 | B |
| I-91 | 1 | 80 | D |
| I-92 | 1 | 95 | B |
| I-93 | 1 | 99 | B |
| I-94 | 1 | 97 | B |
| I-95 | 1 | >99 | A |
| I-96 | 1 | >99 | A |
| I-97 | 1 | >99 | B |
| I-98 | 1 | 99 | C |
| I-99 | 1 | >99 | A |
| I-100 | 1 | 92 | C |
| I-101 | 1 | 96 | B |
| I-102 | 1 | 99 | A |
| I-103 | 1 | >99 | B |
| I-104 | 1 | 95 | B |
| I-105 | 1 | 100 | B |
| I-106 | 1 | 100 | B |
| I-107 | 1 | 99 | A |
| I-108 | 1 | 99 | B |
| I-109 | 1 | 100 | B |
| I-110 | 1 | 100 | A |
| I-111 | 1 | 97 | B |
| I-112 | 1 | 99 | B |
| I-113 | 1 | 97 | B |
| I-114 | 1 | 97 | B |
| I-115 | 1 | >99 | A |
| I-116 | 1 | 98 | A |
| I-117 | 1 | 100 | A |
| I-118 | 1 | 99 | B |
| I-119 | 1 | 100 | B |
| I-120 | 1 | 94 | B |
| I-121 | 1 | >99 | A |
| I-122 | 1 | >99 | B |
| I-123 | 1 | >99 | B |
| I-124 | 1 | 92 | C |
| I-125 | 1 | 100 | A |
| I-126 | 1 | 91 | C |
| I-127 | 1 | 87 | C |
| I-128 | 1 | 96 | B |
| I-129 | 1 | 96 | B |
| I-130 | 1 | 100 | A |
| I-131 | 1 | 99 | B |
| I-132 | 1 | >99 | A |
| I-133 | 1 | >99 | A |
| I-134 | 1 | 93 | B |
| I-135 | 1 | 71 | D |
| I-136 | 1 | 98 | A |
| I-137 | 1 | 97 | B |
| I-138 | 1 | 89 | C |
| I-139 | 1 | 99 | B |
| I-140 | 1 | 91 | C |
| I-141 | 1 | 82 | D |
| I-142 | 1 | 89 | D |
| I-143 | 1 | 97 | B |
| I-144 | 1 | 94 | B |
| I-145 | 1 | 86 | D |
| I-146 | 1 | 87 | C |
| I-147 | 1 | 92 | C |
| I-148 | 1 | 99 | A |
| I-149 | 1 | 96 | B |
| I-150 | 1 | 95 | B |
| I-151 | 1 | 61 | D |
| I-152 | 1 | 84 | D |
| I-153 | 1 | 98 | B |
| I-154 | 1 | 96 | B |
| I-155 | 1 | 98 | B |
| I-156 | 1 | 100 | A |
| I-157 | 1 | 89 | C |
| I-158 | 1 | 97 | B |
| I-159 | 1 | 99 | B |
| I-160 | 1 | 60 | D |
| I-161 | 1 | 97 | B |
| I-162 | 1 | 94 | B |
| I-163 | 1 | 97 | A |
| I-164 | 1 | 97 | A |
| I-165 | 1 | 99 | B |
| I-166 | 1 | 94 | B |
| I-167 | 1 | >99 | A |
| I-168 | 1 | 95 | B |
| I-169 | 1 | 97 | B |

TABLE 2-continued

NAMPT Inhibition of Compounds of the Invention

| Compound | Concentration (µM) | Percent Inhibition | IC50 |
|---|---|---|---|
| I-170 | 1 | 93 | C |
| I-171 | 1 | 97 | B |
| I-172 | 1 | 71 | D |
| I-173 | 1 | 98 | B |
| I-174 | 1 | >99 | A |
| I-175 | 0.33 | 98 | A |
| I-176 | 1 | 99 | B |
| I-177 | 1 | 97 | B |
| I-178 | 1 | 99 | A |
| I-179 | 1 | 95 | C |
| I-180 | 1 | 83 | D |
| I-181 | 1 | 86 | D |
| I-182 | 1 | 77 | D |
| I-183 | 1 | 94 | C |
| I-184 | 1 | 91 | C |
| I-185 | 1 | 98 | B |
| I-186 | 1 | 99 | B |
| I-187 | 1 | >99 | A |
| I-188 | 1 | 99 | A |
| I-189 | 1 | 74 | D |
| I-190 | 1 | 94 | C |
| I-191 | 1 | 79 | D |
| I-192 | 1 | 100 | A |
| I-193 | 1 | >99 | A |
| I-194 | 1 | 100 | A |
| I-195 | 1 | 89 | C |
| I-196 | 1 | 100 | A |
| I-197 | 1 | 97 | B |
| I-198 | 1 | 94 | A |
| I-199 | 1 | 100 | B |
| I-200 | 1 | 95 | B |
| I-201 | 1 | 98 | A |
| I-202 | 1 | 98 | B |
| I-203 | 1 | 98 | A |
| I-204 | 1 | 100 | A |
| I-205 | 1 | 63 | D |
| I-206 | 1 | 66 | D |
| I-207 | 1 | 96 | B |
| I-208 | 1 | 86 | D |
| I-209 | 1 | 92 | C |
| I-210 | 1 | 94 | B |
| I-211 | 1 | 50 | D |
| I-212 | 1 | 69 | D |
| I-213 | 1 | 87 | D |
| I-214 | 1 | 97 | B |
| I-215 | 1 | 93 | C |
| I-216 | 1 | 92 | C |
| I-217 | 1 | 94 | B |
| I-218 | 1 | 93 | C |
| I-219 | 1 | 85 | D |
| I-220 | 1 | 92 | C |
| I-221 | 1 | 53 | D |
| I-222 | 1 | 96 | B |
| I-223 | 1 | >99 | B |
| I-224 | 1 | >99 | A |
| I-225 | 1 | 97 | B |
| I-226 | 1 | 86 | D |
| I-227 | 1 | 100 | A |
| I-228 | 1 | 94 | A |
| I-229 | 1 | 99 | A |

To measure PC3 growth inhibition, PC3 cells that were maintained in RPMI1640 growth medium (Life Technologies; Cat. No. 11875) at 37° C. under 5% $CO_2$ are trypsinized and diluted at a density of $8\times10^4$ cells/ml, 25 ul per well of cells and plated in 384-well black tissue culture plate. The cells are incubated overnight at 37° C. under 5% $CO_2$. For each measurement, a test compound or vehicle DMSO control is diluted with AIM serum free medium and added to the cell plate. The cell plate is incubated for 72 hours at 37° C. under 5% $CO_2$. 25 µl Cell-titer glo solution (Promega; Cat. No. G8462) is added and the cell plates are incubated for 10 minutes protected from light. The luminescence is measured. Concentration response curves are generated by calculating the luminescence increase in test compound-treated samples relative to DMSO-treated controls. Percentage remaining viability values at a single concentration, growth inhibition ($GI_{50}$) or cell viability ($LD_{50}$) values are determined from those curves. One skilled in the art will appreciate that these values are subject to experimental variation.

TABLE 3

PC3 Growth Inhibition of Compounds of the Invention

| Compound | Concentration (µM) | Percent Viability |
|---|---|---|
| I-1 | 1.667 | 2 |
| I-2 | 1.667 | 2 |
| I-3 | 1.667 | 2 |
| I-4 | 1.667 | 1 |
| I-5 | 1.667 | 1 |
| I-6 | 1.667 | 1 |
| I-7 | 1.667 | 1 |
| I-8 | 1.667 | 1 |
| I-9 | 1.667 | 1 |
| I-10 | 1.667 | 1 |
| I-11 | 1.667 | 1 |
| I-12 | 1.667 | 1 |
| I-13 | 1.667 | 0 |
| I-14 | 1.667 | 1 |
| I-15 | 1.667 | 2 |
| I-16 | 1.667 | 0 |
| I-17 | 1.667 | 0 |
| I-18 | 1.667 | 0 |
| I-19 | 1.667 | 1 |
| I-20 | 1.667 | 1 |
| I-21 | 1.667 | 0 |
| I-22 | 1.667 | 1 |
| I-23 | 1.667 | 1 |
| I-24 | 1.667 | 1 |
| I-25 | 1.667 | 0 |
| I-26 | 1.667 | 1 |
| I-27 | 1.667 | 1 |
| I-28 | 1.667 | 1 |
| I-29 | 1.667 | 1 |
| I-30 | 1.667 | 1 |
| I-31 | 1.667 | 1 |
| I-32 | 1.667 | 2 |
| I-33 | 1.667 | 1 |
| I-34 | 1.667 | 1 |
| I-35 | 1.667 | 1 |
| I-36 | 1.667 | 2 |
| I-37 | 1.667 | 2 |
| I-38 | 1.667 | 2 |
| I-39 | 1.667 | 2 |
| I-40 | 1.667 | 3 |
| I-41 | 1.667 | 2 |
| I-42 | 1.667 | 11 |
| I-43 | 1.667 | 77 |
| I-44 | 1.667 | 58 |
| I-45 | 1.667 | 8 |
| I-46 | 1.667 | 3 |
| I-47 | 1.667 | 99 |
| I-48 | 1.667 | 4 |
| I-49 | 1.667 | 5 |
| I-50 | 1.667 | 3 |
| I-51 | 1.667 | 4 |
| I-52 | 1.667 | 4 |
| I-53 | 1.667 | 4 |
| I-54 | 1.667 | 94 |
| I-55 | 1.667 | 86 |
| I-56 | 1.667 | 1 |
| I-57 | 1.667 | 1 |
| I-58 | 1.667 | 1 |
| I-59 | 1.667 | 2 |
| I-60 | 1.667 | 1 |
| I-61 | 1.667 | 2 |
| I-62 | 1.667 | 2 |
| I-63 | 1.667 | 7 |
| I-64 | 1.667 | 1 |

TABLE 3-continued

PC3 Growth Inhibition of Compounds of the Invention

| Compound | Concentration (µM) | Percent Viability |
|---|---|---|
| I-65 | 1.667 | 1 |
| I-66 | 1.667 | 2 |
| I-67 | 1.667 | 3 |
| I-68 | 1.667 | 1 |
| I-69 | 1.667 | 4 |
| I-70 | 1.667 | 1 |
| I-71 | 1.667 | 2 |
| I-72 | 1.667 | 1 |
| I-73 | 1.667 | 1 |
| I-74 | 1.667 | 1 |
| I-75 | 1.667 | 1 |
| I-76 | 1.667 | 11 |
| I-77 | 1.667 | 1 |
| I-78 | 1.667 | 2 |
| I-79 | 1.667 | 2 |
| I-80 | 1.667 | 2 |
| I-81 | 1.667 | 2 |
| I-82 | 1.667 | 2 |
| I-83 | 1.667 | 2 |
| I-84 | 1.667 | 1 |
| I-85 | 1.667 | 2 |
| I-86 | 1.667 | 2 |
| I-87 | 1.667 | 2 |
| I-88 | 1.667 | 1 |
| I-89 | 1.667 | 2 |
| I-90 | 1.667 | 1 |
| I-91 | 1.667 | 2 |
| I-92 | 1.667 | 2 |
| I-93 | 1.667 | 2 |
| I-94 | 1.667 | 1 |
| I-95 | 1.667 | 1 |
| I-96 | 1.667 | 1 |
| I-97 | 1.667 | 2 |
| I-98 | 1.667 | 1 |
| I-99 | 1.667 | 2 |
| I-100 | 1.667 | 2 |
| I-101 | 1.667 | 2 |
| I-102 | 1.667 | 2 |
| I-103 | 1.667 | 2 |
| I-104 | 1.667 | 2 |
| I-105 | 1.667 | 2 |
| I-106 | 1.667 | 2 |
| I-107 | 1.667 | 2 |
| I-108 | 1.667 | 3 |
| I-109 | 1.667 | 2 |
| I-110 | 1.667 | 2 |
| I-111 | 1.667 | 2 |
| I-112 | 1.667 | 2 |
| I-113 | 1.667 | 2 |
| I-114 | 1.667 | 2 |
| I-115 | 1.667 | 2 |
| I-116 | 1.667 | 2 |
| I-117 | 1.667 | 2 |
| I-118 | 1.667 | 2 |
| I-119 | 1.667 | 2 |
| I-120 | 1.667 | 2 |
| I-121 | 1.667 | 2 |
| I-122 | 1.667 | 2 |
| I-123 | 1.667 | 2 |
| I-124 | 1.667 | 2 |
| I-125 | 1.667 | 2 |
| I-126 | 1.667 | 2 |
| I-127 | 1.667 | 2 |
| I-128 | 1.667 | 2 |
| I-129 | 1.667 | 2 |
| I-130 | 1.667 | 2 |
| I-131 | 1.667 | 3 |
| I-132 | 1.667 | 3 |
| I-133 | 1.667 | 2 |
| I-134 | 1.667 | 3 |
| I-135 | 1.667 | 4 |
| I-136 | 1.667 | 2 |
| I-137 | 1.667 | 2 |
| I-138 | 1.667 | 2 |
| I-139 | 1.667 | 2 |
| I-140 | 1.667 | 2 |
| I-141 | 1.667 | 9 |
| I-142 | 1.667 | 14 |
| I-143 | 1.667 | 2 |
| I-144 | 1.667 | 2 |
| I-145 | 1.667 | 2 |
| I-146 | 1.667 | 2 |
| I-147 | 1.667 | 2 |
| I-148 | 1.667 | 1 |
| I-149 | 1.667 | 2 |
| I-150 | 1.667 | 2 |
| I-151 | 1.667 | 3 |
| I-152 | 1.667 | 2 |
| I-153 | 1.667 | 2 |
| I-154 | 1.667 | 3 |
| I-155 | 1.667 | 2 |
| I-156 | 1.667 | 2 |
| I-157 | 1.667 | 5 |
| I-158 | 1.667 | 1 |
| I-159 | 1.667 | 2 |
| I-160 | 1.667 | >99 |
| I-161 | 1.667 | 2 |
| I-162 | 1.667 | 2 |
| I-163 | 1.667 | 2 |
| I-164 | 1.667 | 2 |
| I-165 | 1.667 | 1 |
| I-166 | 1.667 | 2 |
| I-167 | 1.667 | 2 |
| I-168 | 1.667 | 2 |
| I-169 | 1.667 | 3 |
| I-170 | 1.667 | 2 |
| I-171 | 1.667 | 2 |
| I-172 | 1.667 | 6 |
| I-173 | 1.667 | 2 |
| I-174 | 1.667 | 1 |
| I-175 | 1.667 | 2 |
| I-176 | 1.667 | 4 |
| I-177 | 1.667 | 3 |
| I-178 | 1.667 | 2 |
| I-179 | 1.667 | 2 |
| I-180 | 1.667 | 2 |
| I-181 | 1.667 | 9 |
| I-182 | 1.667 | 5 |
| I-183 | 1.667 | 2 |
| I-184 | 1.667 | 6 |
| I-185 | 1.667 | 2 |
| I-186 | 1.667 | 4 |
| I-187 | 1.667 | 3 |
| I-188 | 1.667 | 3 |
| I-189 | 1.667 | >99 |
| I-190 | 1.667 | 5 |
| I-191 | 1.667 | 10 |
| I-192 | 1.667 | 3 |
| I-193 | 1.667 | 3 |
| I-194 | 1.667 | 3 |
| I-195 | 1.667 | 19 |
| I-196 | 1.667 | 1 |
| I-197 | 1.667 | 3 |
| I-198 | 1.667 | 3 |
| I-199 | 1.667 | 2 |
| I-200 | 1.667 | 1 |
| I-201 | 1.667 | 3 |
| I-202 | 1.667 | 1 |
| I-203 | 1.667 | 2 |
| I-204 | 1.667 | 2 |
| I-205 | 1.667 | 4 |
| I-206 | 1.667 | 2 |
| I-207 | 1.667 | 2 |
| I-208 | 1.667 | 2 |
| I-209 | 1.667 | 1 |
| I-210 | 1.667 | 1 |
| I-211 | 1.667 | 3 |
| I-212 | 1.667 | 2 |
| I-213 | 1.667 | 1 |
| I-214 | 1.667 | 1 |

TABLE 3-continued

PC3 Growth Inhibition of Compounds of the Invention

| Compound | Concentration (μM) | Percent Viability |
|---|---|---|
| I-215 | 1.667 | 1 |
| I-216 | 1.667 | 1 |
| I-217 | 1.667 | 2 |
| I-218 | 1.667 | 2 |
| I-219 | 1.667 | 3 |
| I-220 | 1.667 | 2 |
| I-221 | 1.667 | 89 |
| I-222 | 1.667 | 4 |
| I-223 | 1.667 | 3 |
| I-224 | 1.667 | 2 |
| I-225 | 1.667 | 2 |
| I-226 | 1.667 | 14 |
| I-227 | 1.667 | 6 |
| I-228 | 1.667 | 5 |
| I-229 | 1.667 | 2 |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed:

1. A chemical entity chosen from compounds of formula I:

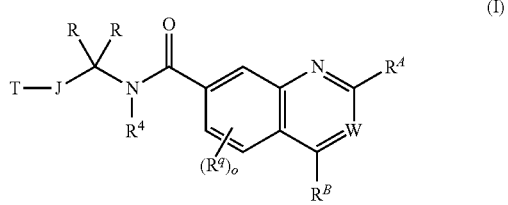

and pharmaceutically acceptable salts thereof, wherein:
$R^A$ is

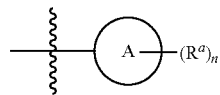

or $YR^C R^D R^E$;
$R^B$ is $XR^1 R^2 R^3$;
W is N, CH or $CR^q$;
Y is selected from C, O, S, and N, provided that (1) when Y is N, then one of $R^C$, $R^D$, and $R^E$ is absent and the remaining two of $R^C$, $R^D$, and $R^E$ are both not hydrogen and (2) when Y is O or S, then two of $R^C$, $R^D$, and $R^E$ are absent and the remaining one of $R^C$, $R^D$, and $R^E$ is not hydrogen;
$R^C$, $R^D$, and $R^E$ are each independently selected from hydrogen; linear or branched $C_{1-6}$ aliphatic, wherein 1 or 2 methylene units of the $C_{1-6}$ aliphatic are optionally and independently replaced by O, S, S(O), S(O)$_2$, or N($R^{25}$); (CH$_2$)$_q$-6-10-membered aryl; (CH$_2$)$_r$-3-10-membered cycloaliphatic; (CH$_2$)$_x$-4-10-membered heterocycle having 1-5 heteroatoms independently selected from nitrogen, oxygen, and sulfur, and (CH$_2$)$_b$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^e$;
X is selected from halogen, C, O, S, and N, provided that (1) when X is N, then one of $R^1$, $R^2$, and $R^3$ is absent; (2) when X is halogen, then $R^1$, $R^2$, and $R^3$ are absent, and (3) when X is O or S, then two of $R^1$, $R^2$, and $R^3$ are absent and the remaining one of $R^1$, $R^2$, and $R^3$ is not hydrogen;
$R^1$, $R^2$, and $R^3$ are each independently selected from hydrogen; linear or branched $C_{1-6}$ aliphatic, wherein 1 or 2 methylene units of the $C_{1-6}$ aliphatic are optionally and independently replaced by O, S, S(O), S(O)$_2$, or N($R^{19}$); (CH$_2$)$_s$-6-10-membered aryl; (CH$_2$)$_t$-3-10-membered cycloaliphatic; (CH$_2$)$_u$-4-10-membered heterocycle having 1-5 heteroatoms independently selected from nitrogen, oxygen, and sulfur, and (CH$_2$)$_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more $R^k$;
or wherein any two of $R^1$, $R^2$, and $R^3$ taken together with the atom X to which they are bound, when X is C or N, form a ring selected from 4-10-membered heterocycle having 1-5 heteroatoms independently selected from nitrogen, oxygen and sulfur and 3-10-membered cycloaliphatic, wherein the ring is optionally substituted with one or more $R^b$;
or wherein $R^1$, $R^2$, and $R^3$ taken together with the atom X to which they are bound, when X is C, form a ring selected from 5-10-membered heteroaryl having 1-4 heteroatoms independently selected from nitrogen, oxygen, and sulfur and 6-10-membered aryl, wherein the ring is optionally substituted with one or more $R^b$;
or wherein $R^1$, $R^2$, and $R^3$ taken together with the atom X to which they are bound, when X is N, form a 5-10-membered heteroaryl ring having 1-5 heteroatoms independently selected from nitrogen, oxygen, and sulfur, wherein the ring is optionally substituted with one or more $R^b$;

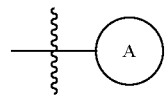

is a ring selected from 3-7-membered saturated, partially unsaturated, and aromatic monocyclic ring having 0-3 heteroatoms independently selected from nitrogen, oxygen, and sulfur and 8-10-membered saturated, partially unsaturated, and aromatic bicyclic ring having 0-5 heteroatoms independently selected from nitrogen, oxygen, and sulfur;
each occurrence of $R^a$ is independently selected from linear or branched $C_{1-6}$ aliphatic and $Z_1$—$R^8$;
or wherein two $R^a$ taken together with the atom or atoms to which they are bound, form a ring selected from 4-10-membered heterocycle having 1-5 heteroatoms independently selected from nitrogen, oxygen, and sulfur and 3-6-membered cycloaliphatic, wherein the ring is optionally substituted with one or more $R^P$;
each occurrence of $R^P$ is independently selected from CN, CH$_3$, CF$_3$, CH$_2$F, CF$_2$H, NH$_2$, NH(linear or branched $C_{1-3}$ aliphatic), N(linear or branched $C_{1-3}$ aliphatic)$_2$, OH, halogen, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $Z_1$ is independently selected from a direct bond, $C_{1-3}$ alkylene chain, O, $N(R^{16})$, S, S(O), $S(O)_2$, C(O), $CO_2$, $C(O)NR^{16}$, $N(R^{16})C(O)$, $N(R^{16})CO_2$, $S(O)_2NR^{16}$, $N(R^{16})S(O)_2$, $OC(O)N(R^{16})$, $N(R^{16})C(O)NR^{16}$, $N(R^{16})S(O)_2N(R^{16})$, and OC(O), wherein the alkylene chain is optionally substituted with one or more $R^h$;

each occurrence of $R^h$ is independently selected from CN, $CH_3$, $CF_3$, $CH_2F$, $CF_2H$, OH, halogen, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $R^b$ is independently selected from linear or branched $C_{1-6}$ aliphatic and $Z_2$—$R^6$;

or wherein two $R^b$ taken together with the atom or atoms to which they are bound, form a 3-7-membered saturated, partially unsaturated, or aromatic monocyclic ring having 0-3 heteroatoms independently selected from nitrogen, oxygen, and sulfur, wherein the ring is optionally substituted with one or more $R^c$;

each occurrence of $R^c$ is independently selected from linear or branched $C_{1-6}$ aliphatic, $CF_3$, $CF_2H$, $CH_2F$, halogen, $OR^{12}$, $(CH_2)_v$—$C(O)R^9$, and $(CH_2)_w$—$NR^{10}C(O)R^{11}$;

each occurrence of $Z_2$ is independently selected from direct bond, $C_{1-3}$ alkylene chain, O, $N(R^{17})$, S, S(O), $S(O)_2$, C(O), $CO_2$, $C(O)NR^{17}$, $N(R^{17})C(O)$, $N(R^{17})CO_2$, $S(O)_2NR^{17}$, $N(R^{17})S(O)_2$, $OC(O)N(R^{17})$, $N(R^{17})C(O)NR^{17}$, $N(R^{17})S(O)_2N(R^{17})$, and OC(O), wherein the alkylene chain is optionally substituted with one or more $R^i$;

each occurrence of $R^i$ is independently selected from CN, $CH_3$, $CF_3$, $CH_2F$, $CF_2H$, halogen, OH, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;

each occurrence of $R^k$ is independently selected from linear or branched $C_{1-6}$ aliphatic and $Z_3$—$R^{23}$;

each occurrence of $Z_3$ is independently selected from direct bond, $C_{1-3}$ alkylene chain, O, $N(R^{24})$, S, S(O), $S(O)_2$, C(O), $CO_2$, $C(O)NR^{24}$, $N(R^{24})C(O)$, $N(R^{24})CO_2$, $S(O)_2NR^{24}$, $N(R^{24})S(O)_2$, $OC(O)N(R^{24})$, $N(R^{24})C(O)NR^{24}$, $N(R^{24})S(O)_2N(R^{24})$, and OC(O), wherein the alkylene chain is optionally substituted with one or more $R^n$;

each occurrence of $R^n$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

each occurrence of $R^e$ is independently selected from linear or branched $C_{1-6}$ aliphatic and $Z_4$—$R^{22}$;

each occurrence of $Z_4$ is independently selected from direct bond, $C_{1-3}$ alkylene chain, O, $N(R^{20})$, S, S(O), $S(O)_2$, C(O), $CO_2$, $C(O)NR^{20}$, $N(R^{20})C(O)$, $N(R^{20})CO_2$, $S(O)_2NR^{20}$, $N(R^{20})S(O)_2$, $OC(O)N(R^{20})$, $N(R^{20})C(O)NR^{20}$, $N(R^{20})S(O)_2N(R^{20})$, and OC(O), wherein the alkylene chain is optionally substituted with one or more $R^t$;

each occurrence of $R^t$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;

J is selected from a direct bond; linear or branched $C_{1-6}$ aliphatic, wherein 1 or 2 methylene units of J are optionally and independently replaced by O, S, or $N(R^{13})$ and further wherein the $C_{1-6}$ aliphatic is optionally substituted with one or more $R^j$;

each occurrence of $R^j$ is independently selected from fluorine, $CH_3$, $CF_3$, $CH_2F$, $CF_2H$, OH, $OCH_3$, $OCF_3$, $OCH_2F$, $OCF_2H$, O(linear or branched $C_{2-3}$ aliphatic), $NH_2$, NH(linear or branched $C_{1-3}$ aliphatic), N(linear or branched $C_{1-3}$ aliphatic)$_2$, and linear or branched $C_{2-3}$ aliphatic, wherein the $C_{2-3}$ aliphatic is optionally substituted with one or more F;

or wherein two $R^j$ taken together with the atom or atoms to which they are bound form a ring selected from 3-6-membered heterocycle having 1 heteroatom selected from nitrogen, oxygen, and sulfur and 3-6-membered cycloaliphatic ring, wherein the ring is optionally substituted with one or more $R^m$;

each occurrence of R is independently selected from hydrogen and linear or branched $C_{1-3}$ aliphatic, wherein the $C_{1-3}$ aliphatic is optionally substituted with one or more F;

or wherein one of $R^j$ and one of R taken together with the atoms to which they are bound form a ring selected from 3-6-membered heterocycle having 1 heteroatom selected from nitrogen, oxygen, and sulfur and 3-6-membered cycloaliphatic, wherein the ring is optionally substituted with one or more $R^m$;

$R^4$ is selected from hydrogen and linear or branched $C_{1-6}$ aliphatic;

or wherein one of R and $R^4$ taken together with the atoms to which they are bound, form a 4-10-membered heterocycle ring having 1-5 heteroatoms independently selected from nitrogen, oxygen, and sulfur, wherein the ring is optionally substituted with one or more $R^m$;

or wherein one of $R^j$ and $R^4$ taken together with the atoms to which they are bound, form a 4-10-membered heterocycle ring having 1-5 heteroatoms independently selected from nitrogen, oxygen, and sulfur, wherein the ring is optionally substituted with one or more $R^m$;

each occurrence of $R^m$ is independently selected from halogen, $CF_3$, $CF_2H$, $CH_2F$, and linear or branched $C_{1-6}$ aliphatic, or wherein two $R^m$ taken together with the atom or atoms to which they are bound, form a 3-7-membered saturated, partially unsaturated, or aromatic monocyclic ring having 1-3 heteroatoms independently selected from nitrogen, oxygen, and sulfur, wherein the ring is optionally substituted with one or more $R^h$;

each occurrence of $R^h$ is independently selected from halogen, $CF_3$, $CF_2H$, $CH_2F$, linear or branched $C_{1-6}$ aliphatic, $C(O)N(R^{18})_2$, OH, and O(linear or branched $C_{1-6}$ aliphatic);

each occurrence of $R^5$ is independently selected from hydrogen, $CF_3$, $CF_2H$, $CH_2F$, and linear or branched $C_{1-6}$ aliphatic;

each occurrence of $R^6$ is independently selected from CN, halogen, $OR^7$, $N(R^{19})_2$, linear or branched $C_{1-6}$ aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the aryl, heteroaryl, heterocycle, and cycloaliphatic are optionally substituted with one or more $R^c$;
each occurrence of $R^7$ is independently selected from hydrogen, $CF_3$, $CF_2H$, $CH_2F$, linear or branched $C_{1-6}$ aliphatic, and 6-10-membered aryl;
each occurrence of $R^8$ is independently selected from CN, halogen, $OR^5$, $N(R^{21})_2$, linear or branched $C_{1-6}$ aliphatic, 6-10-membered aryl, 3-10-membered cycloaliphatic, 5-10-membered heteroaryl having 1-5 heteroatoms independently selected from nitrogen, oxygen, and sulfur, and 4-10-membered heterocycle having 1-5 heteroatoms independently selected from nitrogen, oxygen and sulfur, wherein the aryl, cycloaliphatic, heteroaryl, and heterocycle are optionally substituted with one or more $R^g$;
each occurrence of $R^g$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic) and linear or branched $C_{2-3}$ aliphatic, wherein the $C_{2-3}$ aliphatic is optionally substituted with one or more F;
each occurrence of $R^9$ is independently selected from OH, O(linear or branched $C_{1-6}$ aliphatic), $N(R^{15})_2$, and linear or branched $C_{1-6}$ aliphatic;
each occurrence of $R^{10}$ is independently selected from hydrogen and linear or branched $C_{1-6}$ aliphatic;
each occurrence of $R^{11}$ is independently selected from OH, $OC_{1-6}$aliphatic, $N(R^{14})_2$, and $C_{1-6}$ aliphatic;
each occurrence of $R^{12}$ is independently selected from hydrogen and linear or branched $C_{1-6}$ aliphatic;
each occurrence of $R^{13}$ is independently selected from hydrogen and linear or branched $C_{1-6}$ aliphatic;
each occurrence of $R^{14}$ is independently selected from hydrogen and linear or branched $C_{1-6}$ aliphatic;
each occurrence of $R^{15}$ is independently selected from hydrogen and linear or branched $C_{1-6}$ aliphatic;
each occurrence of $R^{16}$ is independently selected from hydrogen and linear or branched $C_{1-6}$ aliphatic;
each occurrence of $R^{17}$ is independently selected from hydrogen and linear or branched $C_{1-6}$ aliphatic;
each occurrence of $R^{18}$ is independently selected from hydrogen and linear or branched $C_{1-6}$ aliphatic;
each occurrence of $R^{19}$ is independently selected from hydrogen and linear or branched $C_{1-3}$ aliphatic;
each occurrence of $R^{20}$ is independently selected from hydrogen and linear or branched $C_{1-6}$ aliphatic;
each occurrence of $R^{21}$ is independently selected from hydrogen and linear or branched $C_{1-6}$ aliphatic;
each occurrence of $R^{22}$ is independently selected from CN, halogen, $OR^{28}$, $N(R^{29})_2$, and linear or branched $C_{1-6}$ aliphatic; 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic;
each occurrence of $R^{23}$ is independently selected from CN, halogen, $OR^{30}$, $SR^{30}$, $N(R^{26})_2$, and linear or branched $C_{1-6}$aliphatic;
each occurrence of $R^{24}$ is independently selected from hydrogen and linear or branched $C_{1-6}$ aliphatic;
each occurrence of $R^{25}$ is independently selected from hydrogen and linear or branched $C_{1-3}$ aliphatic;
each occurrence of $R^{26}$ is independently selected from hydrogen and linear or branched $C_{1-3}$ aliphatic;
each occurrence of $R^{27}$ is independently selected from hydrogen and linear or branched $C_{1-3}$ aliphatic;
each occurrence of $R^{28}$ is independently selected from hydrogen, $CF_3$, $CF_2H$, $CH_2F$, linear or branched $C_{1-6}$ aliphatic, and 6-10-membered aryl;
each occurrence of $R^{29}$ is independently selected from hydrogen and linear or branched $C_{1-3}$ aliphatic;
each occurrence of $R^{30}$ is independently selected from hydrogen, $CF_3$, $CF_2H$, $CH_2F$, linear or branched $C_{1-6}$ aliphatic, and 6-10-membered aryl;
T is $(CH_2)_s$-6-10-membered aryl or $(CH_2)_z$-5-10-membered monocyclic or bicyclic heteroaryl having 1-5 heteroatoms independently selected from nitrogen, oxygen, and sulfur, wherein the aryl or heteroaryl are optionally substituted with one or more $R^d$,
each occurrence of $R^d$ is independently selected from CN, halogen, $N(R^{27})_2$, and linear or branched $C_{1-6}$ aliphatic;
or wherein taken together two $R^d$ together with the atom or atoms to which they are bound, form a 4-10-membered heterocycle ring having 1-5 heteroatoms independently selected from nitrogen, oxygen, and sulfur;
each occurrence of $R^q$ is independently selected from CN, $CH_3$, $CF_3$, $CF_2H$, $CH_2F$, halogen, OH, $OCH_3$, $OCF_3$, $OCH_2F$, $OCF_2H$, O(linear or branched $C_{2-3}$ aliphatic), and linear or branched $C_{2-3}$ aliphatic, wherein the $C_{2-3}$ aliphatic is optionally substituted with one or more F;
b is 0, 1, 2, or 3;
n is 0, 1, 2, 3, 4, or 5;
o is 0, 1, 2, or 3;
p is 0, 1, 2, or 3;
r is 0, 1, 2, or 3;
s is 0, 1, 2, or 3;
t is 0, 1, 2, or 3;
q is 0, 1, 2, or 3;
u is 0, 1, 2, or 3;
x is 0, 1, 2, or 3;
v is 0, 1, 2, or 3;
w is 0, 1, 2, or 3; and
z is 0, 1, 2, or 3,
further provided that when $R^B$ is a tertiary amine or methyl and J is a direct bond, then T is not phenyl or 3-pyridine, wherein the phenyl and 3-pyridine are optionally substituted with one of more $R^d$.

2. The chemical entity of claim 1 chosen from compounds of formula II, compounds of formula III:

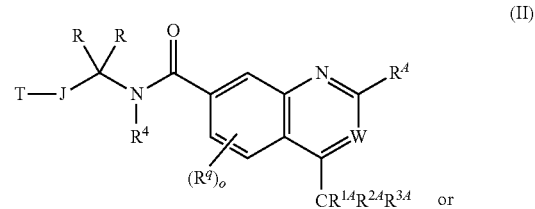

(II)

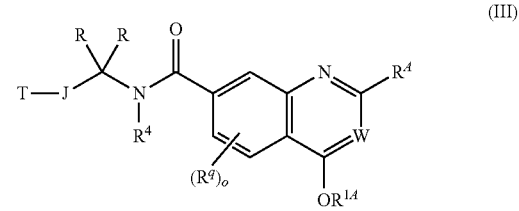

(III)

and pharmaceutically acceptable salts thereof, wherein $R^{1A}$, $R^{2A}$, and $R^{3A}$ are each independently selected from hydrogen; linear or branched $C_{1-6}$aliphatic, wherein 1 or 2 methylene units of the $C_{1-6}$ aliphatic are optionally and independently replaced by O, S, S(O), S(O)$_2$, or N(R$^{19}$); (CH$_2$)$_s$-6-10-membered aryl; (CH$_2$)$_t$-3-10-membered cycloaliphatic; (CH$_2$)$_u$-4-10-membered heterocycle having 1-5 heteroatoms independently selected from nitrogen, oxygen, and sulfur, and (CH$_2$)$_p$-5-10-membered heteroaryl having 1-5 heteroatoms independently selected from nitrogen, oxygen, and sulfur, wherein the $C_{1-6}$ aliphatic, aryl, cycloaliphatic, heterocycle, and heteroaryl are optionally substituted with one or more R$^k$, provided that for formula III, R$^{1A}$ is not hydrogen and provided that for formula II, when R$^{1A}$, R$^{2A}$, and R$^{3A}$ are each hydrogen and J is a direct bond, the T is not phenyl or 3-pyridine, wherein the phenyl and 3-pyridine are optionally substituted with one or more R$^d$;

or wherein any two of R$^{1A}$, R$^{2A}$, and R$^{3A}$ taken together with the carbon atom to which they are bound, form a ring selected from 4-10-membered heterocycle having 1-5 heteroatoms independently selected from nitrogen, oxygen and sulfur and 3-10-membered cycloaliphatic, wherein the ring is optionally substituted with one or more R$^b$;

or wherein R$^{1A}$, R$^{2A}$, and R$^{3A}$ taken together with the carbon atom to which they are bound form a ring selected from 5-10-membered heteroaryl having 1-4 heteroatoms independently selected from nitrogen, oxygen, and sulfur, and 6-10-membered aryl, wherein the ring is optionally substituted with one or more R$^b$;

each occurrence of R$^b$ is independently selected from linear or branched $C_{1-6}$ aliphatic and Z$_2$—R$^6$;

or wherein two R$^b$ taken together with the atom or atoms to which they are bound, form a ring selected from 3-7-membered saturated, partially unsaturated, or aromatic monocyclic ring having 0-3 heteroatoms independently selected from nitrogen, oxygen, and sulfur, wherein the ring is optionally substituted with one or more R$^c$;

each occurrence of R$^c$ is independently selected from linear or branched $C_{1-6}$ aliphatic, CF$_3$, CF$_2$H, CH$_2$F, halogen, OR$^{12}$, (CH$_2$)$_v$—C(O)R$^9$, and (CH$_2$)$_w$—NR$^{10}$C(O)R$^{11}$;

each occurrence of Z$_2$ is independently selected from direct bond, $C_{1-3}$ alkylene chain, O, N(R$^{17}$), S, S(O), S(O)$_2$, C(O), CO$_2$, C(O)NR$^{17}$, N(R$^{17}$)C(O), N(R$^{17}$)CO$_2$, S(O)$_2$NR$^{17}$, N(R$^{17}$)S(O)$_2$, OC(O)N(R$^{17}$), N(R$^{17}$)C(O)NR$^{17}$, N(R$^{17}$)S(O)$_2$N(R$^{17}$), and OC(O), wherein the alkylene chain is optionally substituted with one or more R$^i$;

each occurrence of R$^i$ is independently selected from CN, CH$_3$, CF$_3$, CH$_2$F, CF$_2$H, halogen, OH, OCH$_3$, OCF$_3$, OCH$_2$F, OCF$_2$H, O(linear or branched $C_{2-3}$ aliphatic) and linear or branched $C_{2-3}$ aliphatic, wherein the $C_{2-3}$ aliphatic is optionally substituted with one or more F;

each occurrence of R$^k$ is independently selected from linear or branched $C_{1-6}$ aliphatic and Z$_3$—R$^{23}$;

each occurrence of Z$_3$ is independently selected from direct bond, $C_{1-3}$ alkylene chain, O, N(R$^{24}$), S, S(O), S(O)$_2$, C(O), CO$_2$, C(O)NR$^{24}$, N(R$^{24}$)C(O), N(R$^{24}$)CO$_2$, S(O)$_2$NR$^{24}$, N(R$^{24}$)S(O)$_2$, OC(O)N(R$^{24}$), N(R$^{24}$)C(O)NR$^{24}$, N(R$^{24}$)S(O)$_2$N(R$^{24}$), and OC(O), wherein the alkylene chain is optionally substituted with one or more R$^n$;

each occurrence of R$^n$ is independently selected from CN, CH$_3$, CF$_3$, CF$_2$H, CH$_2$F, halogen, OH, OCH$_3$, OCF$_3$, OCH$_2$F, OCF$_2$H, O(linear or branched $C_{2-3}$ aliphatic), and linear or branched $C_{2-3}$ aliphatic, wherein the $C_{2-3}$ aliphatic is optionally substituted with one or more F;

each occurrence of R$^6$ is independently selected from CN, halogen, OR$^7$, N(R$^{19}$)$_2$, linear or branched $C_{1-6}$ aliphatic, 6-10-membered aryl, 5-10-membered heteroaryl having 1-5 heteroatoms independently selected from nitrogen, oxygen, and sulfur, 4-10-membered heterocycle having 1-5 heteroatoms independently selected from nitrogen, oxygen and sulfur, and 3-10-membered cycloaliphatic, wherein the aryl, heteroaryl, heterocycle, and cycloaliphatic is optionally substituted with one or more R$^c$;

each occurrence of R$^7$ is independently selected from hydrogen, CF$_3$, CF$_2$H, CH$_2$F, linear or branched $C_{1-6}$ aliphatic, and 6-10-membered aryl;

each occurrence of R$^9$ is independently selected from OH, O(linear or branched $C_{1-6}$ aliphatic), N(R$^{15}$)$_2$, and linear or branched $C_{1-6}$ aliphatic;

each occurrence of R$^{10}$ is independently selected from hydrogen and linear or branched $C_{1-6}$ aliphatic;

each occurrence of R$^{11}$ is independently selected from OH, OC$_{1-6}$aliphatic, N(R$^{14}$)$_2$, and $C_{1-6}$ aliphatic;

each occurrence of R$^{12}$ is independently selected from hydrogen and linear or branched $C_{1-6}$ aliphatic;

each occurrence of R$^{14}$ is independently selected from hydrogen and linear or branched $C_{1-6}$ aliphatic;

each occurrence of R$^{15}$ is independently selected from hydrogen and linear or branched $C_{1-6}$ aliphatic;

each occurrence of R$^{17}$ is independently selected from hydrogen and linear or branched $C_{1-6}$ aliphatic;

each occurrence of R$^{19}$ is independently selected from hydrogen and linear or branched $C_{1-3}$ aliphatic;

each occurrence of R$^{23}$ is independently selected from CN, halogen, OR$^{30}$, SR$^{30}$, N(R$^{26}$)$_2$, and linear or branched $C_{1-6}$aliphatic;

each occurrence of R$^{24}$ is independently selected from hydrogen and linear or branched $C_{1-6}$ aliphatic;

each occurrence of R$^{26}$ is independently selected from hydrogen and linear or branched $C_{1-3}$ aliphatic;

each occurrence of R$^{30}$ is independently selected from hydrogen, CF$_3$, CF$_2$H, CH$_2$F, linear or branched $C_{1-6}$ aliphatic, and 6-10-membered aryl;

p is 0, 1, 2, or 3;

s is 0, 1, 2, or 3;

t is 0, 1, 2, or 3;

u is 0, 1, 2, or 3;

v is 0, 1, 2, or 3; and w is 0, 1, 2, or 3.

3. The chemical entity of claim 2 chosen from compounds of formula II and pharmaceutically acceptable salts thereof, wherein R$^{1A}$, R$^{2A}$, and R$^{3A}$ are each independently selected from hydrogen; linear or branched $C_{1-6}$aliphatic, wherein 1 or 2 methylene units of the $C_{1-6}$aliphatic are optionally and independently replaced by O, provided that when R$^{1A}$, R$^{2A}$, and R$^{3A}$ are each hydrogen and J is a direct bond, the T is not phenyl or 3-pyridine, wherein the phenyl and 3-pyridine are optionally substituted with one or more R$^d$.

4. The chemical entity of claim 2 chosen from compounds of formula III and pharmaceutically acceptable salts thereof, wherein R$^{1A}$ is selected from a linear or branched $C_{1-6}$aliphatic, wherein 1 or 2 methylene units of the $C_{1-6}$ aliphatic are optionally and independently replaced by O, and (CH$_2$)$_t$-3-7-membered cycloaliphatic.

5. The chemical entity of claim 1 chosen from compounds of formula VI:

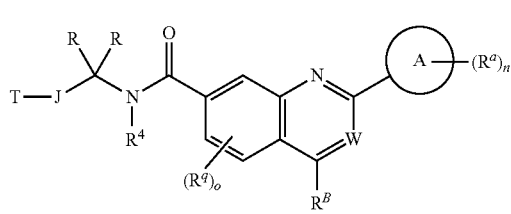

(VI)

and pharmaceutically acceptable salts thereof.

6. The chemical entity of claim 5, wherein

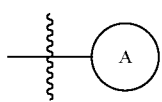

is a ring selected from a 5- or 6-membered saturated, partially unsaturated, monocyclic ring having 0-3 heteroatoms independently selected from nitrogen, oxygen, and sulfur.

7. The chemical entity of claim 1, wherein J is selected from direct bond, $C_1$ aliphatic, and $C_2$ aliphatic and further wherein, the aliphatic are optionally substituted with one or more $R^j$; or J is selected from $C_1$ aliphatic and $C_2$ aliphatic, wherein the aliphatic are substituted with one or more $R^j$ and one of $R^j$ and one of R taken together with the atoms to which they are bound form a 3-6-membered cycloaliphatic ring; or J is $C_2$ aliphatic, wherein the aliphatic is substituted with two or more $R^j$ and two $R^j$ taken together with the atom or atoms to which they are bound form a 3-6-membered cycloaliphatic ring.

8. The chemical entity of claim 1 chosen from compounds of formula XIV, compounds of formula XV:

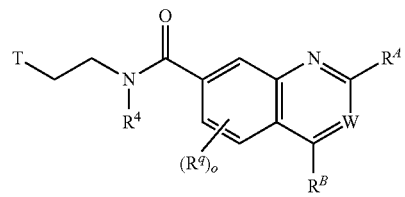

(XIV)

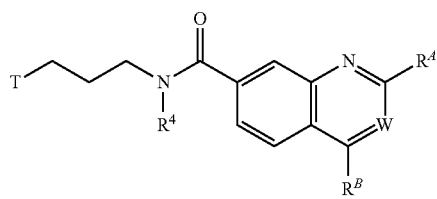

(XV)

and pharmaceutically acceptable salts thereof.

9. The chemical entity of claim 1, wherein T is $(CH_2)_s$-6-10-membered aryl, wherein the aryl is optionally substituted with one or more $R^d$.

10. The chemical entity of claim 1, wherein T is a 5-9-membered heteroaryl ring having 1-2 heteroatoms independently selected from nitrogen and sulfur, wherein the ring is optionally substituted with one or more $R^d$.

11. The chemical entity of claim 10, wherein T is a 5-membered heteroaryl ring having two nitrogen heteroatoms and the ring is optionally substituted with one or more $R^d$.

12. The chemical entity of claim 1, wherein

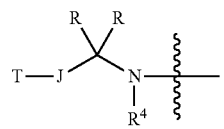

is selected from

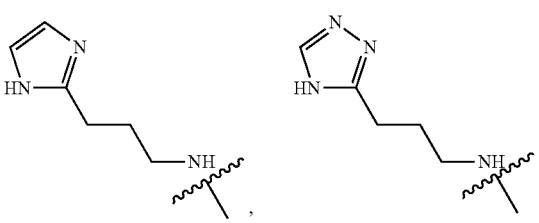

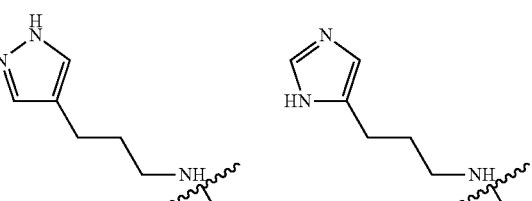

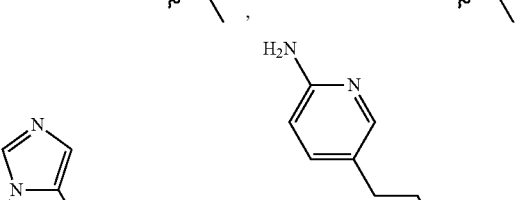

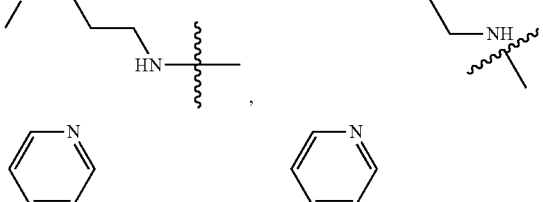

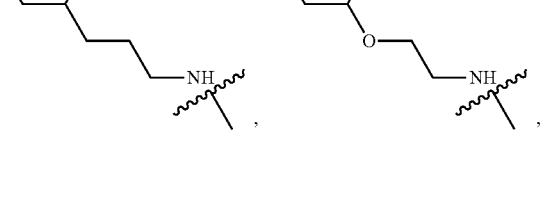

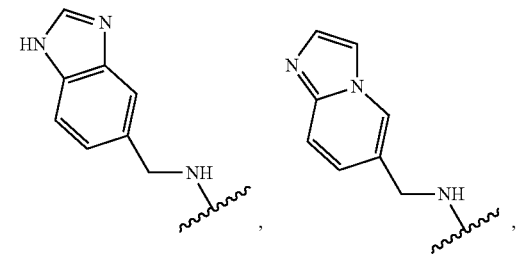

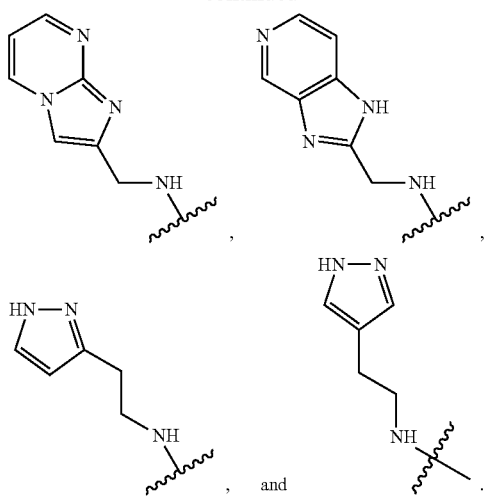
13. A chemical entity chosen from the following compounds and pharmaceutically acceptable salts thereof:
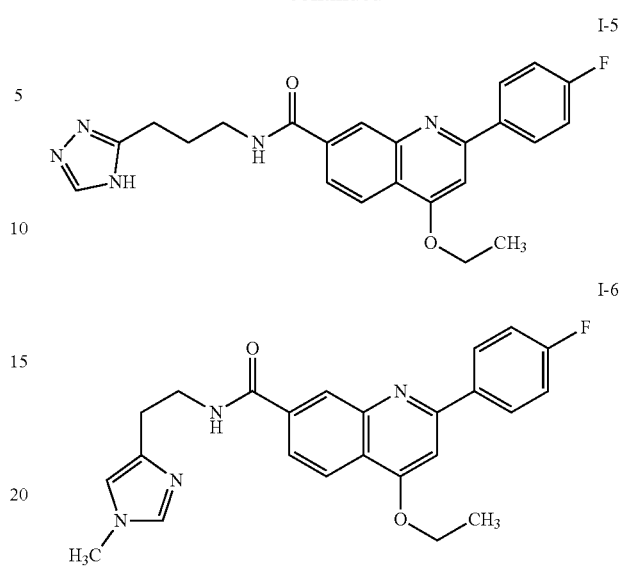
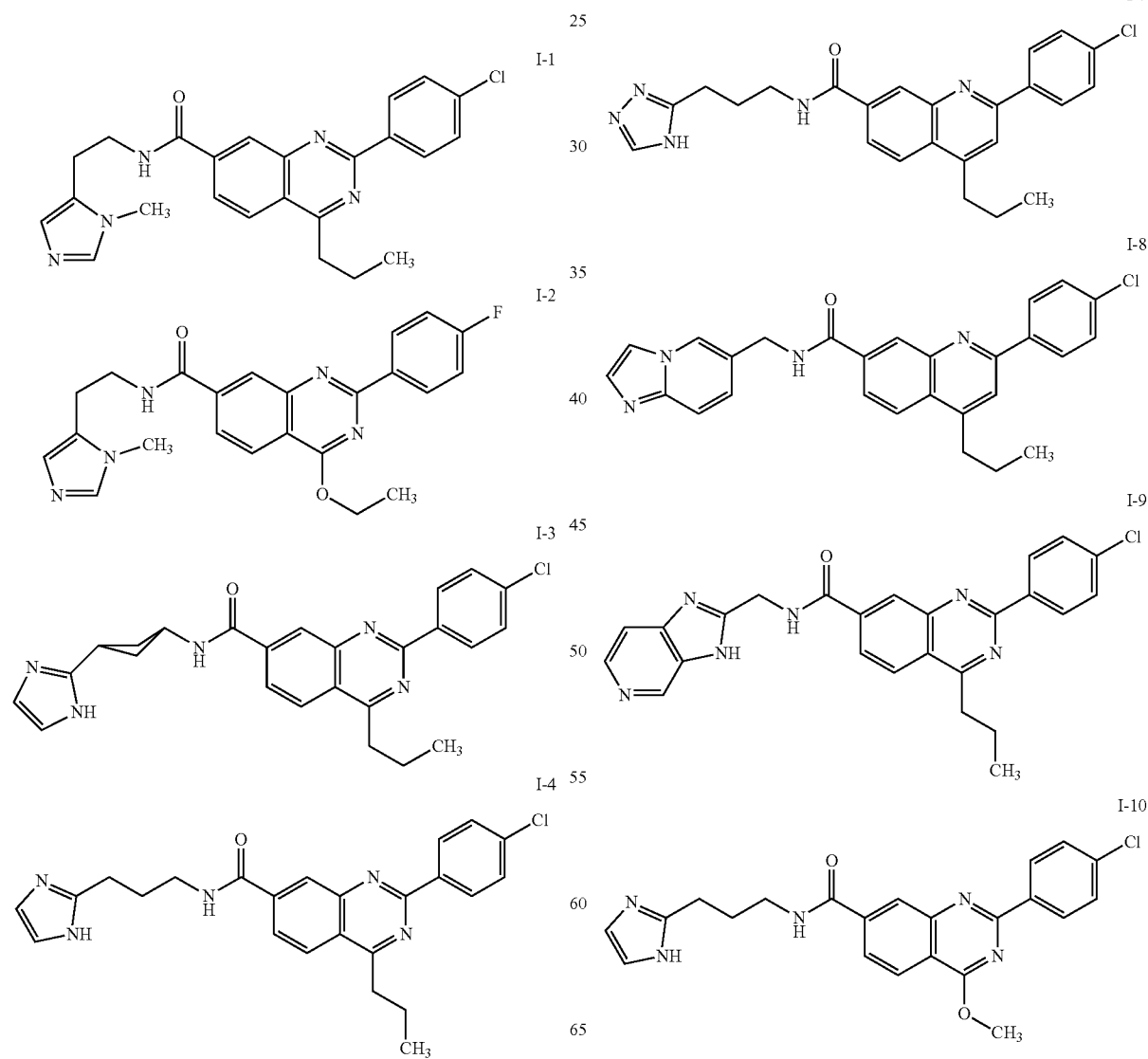

311
-continued
I-11
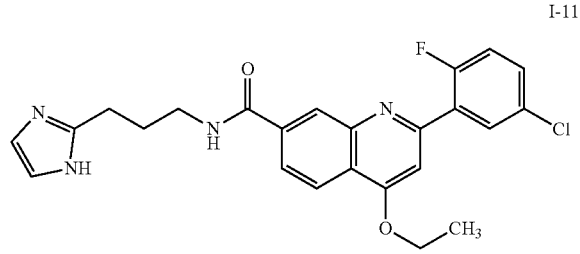
I-12
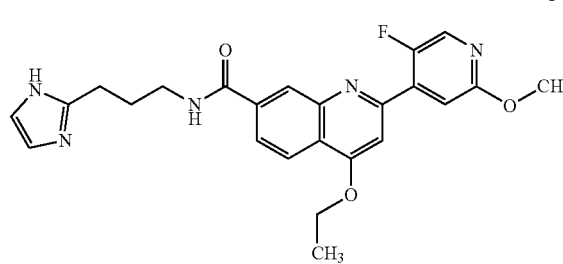
I-13
I-14
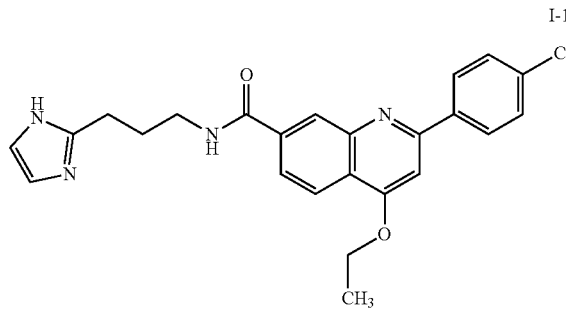
I-15
I-16
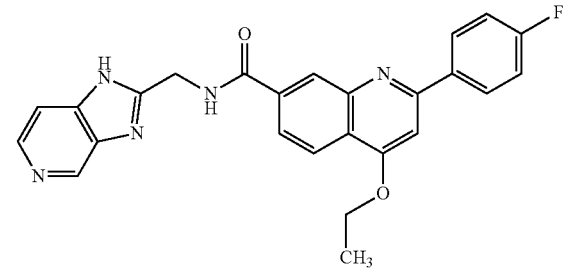
312
-continued
I-17
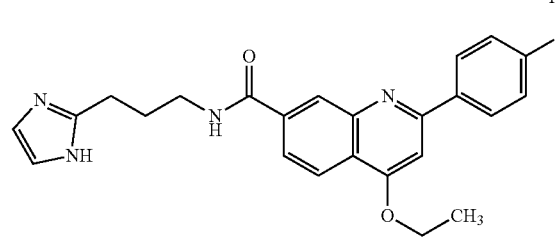
I-18
I-19
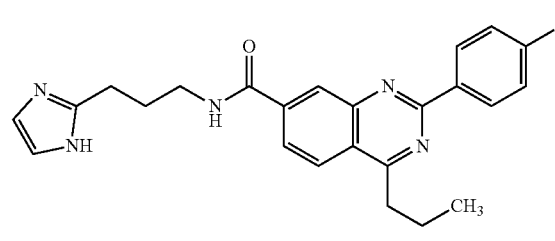
I-20
I-21

I-22 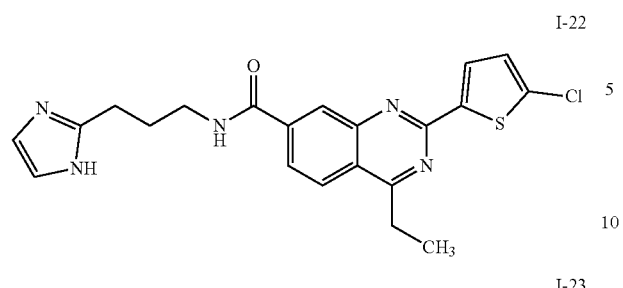
I-23 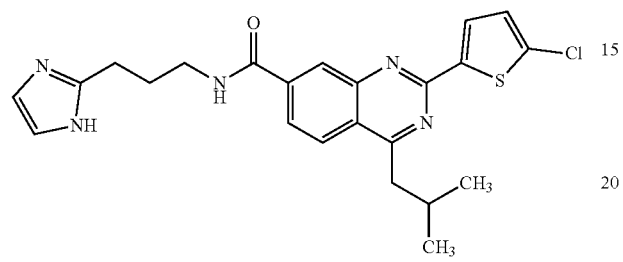
I-24 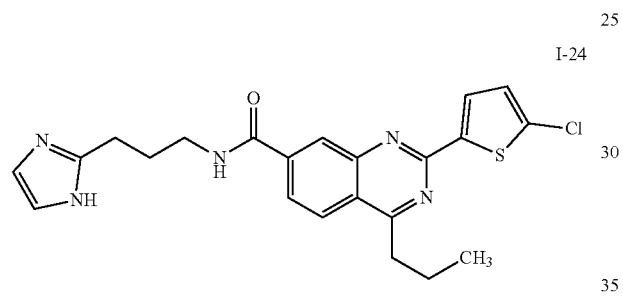
I-25 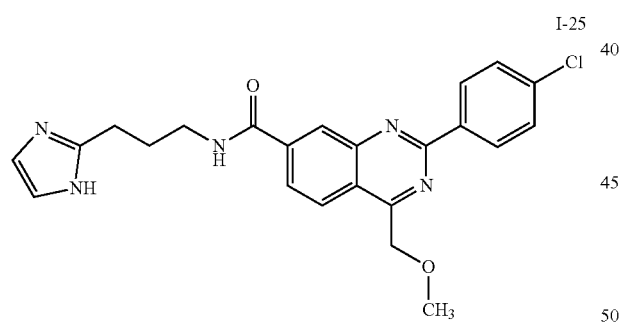
I-26 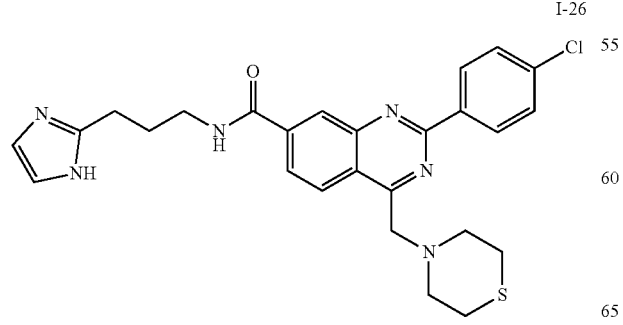
I-27 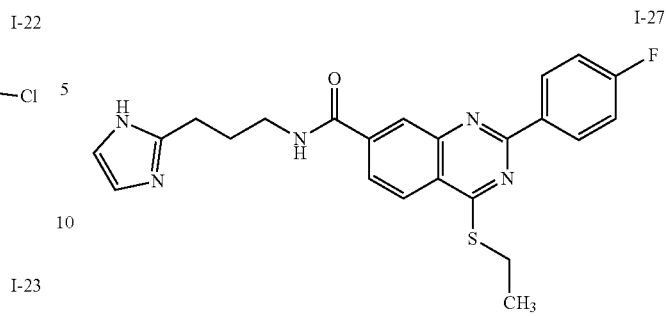
I-28
I-29
I-30
I-31
I-32

I-33
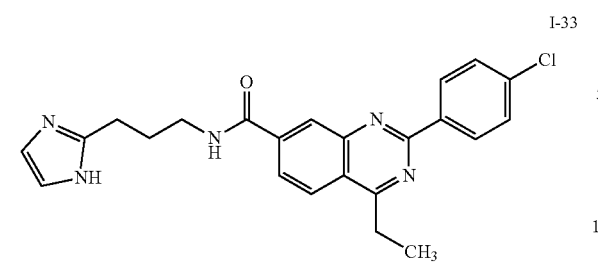
I-34
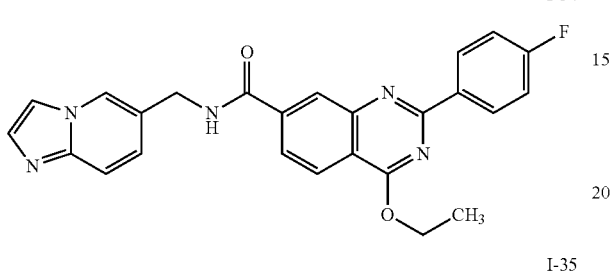
I-35
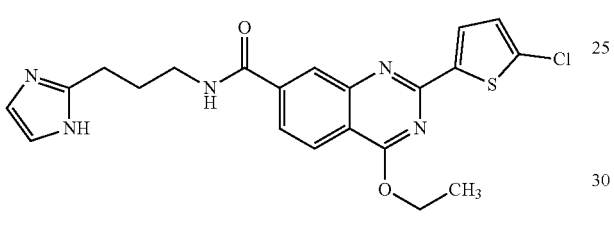
I-36
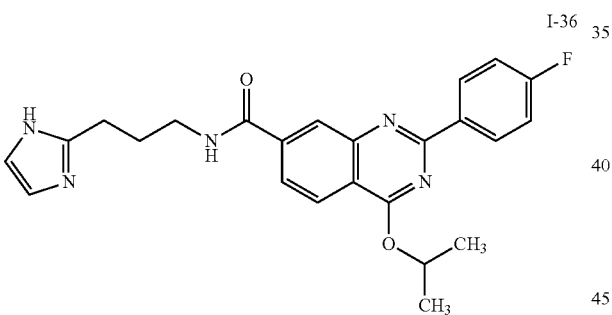
I-37
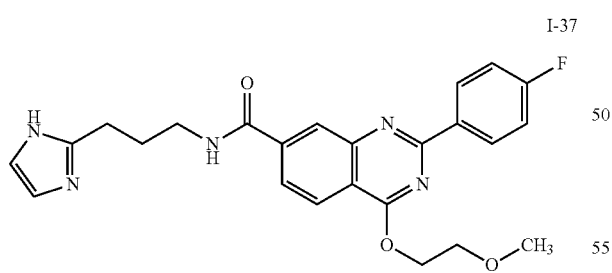
I-38
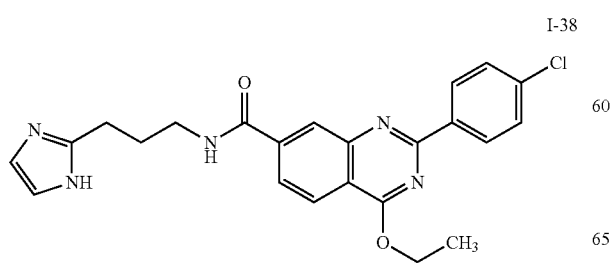
I-39
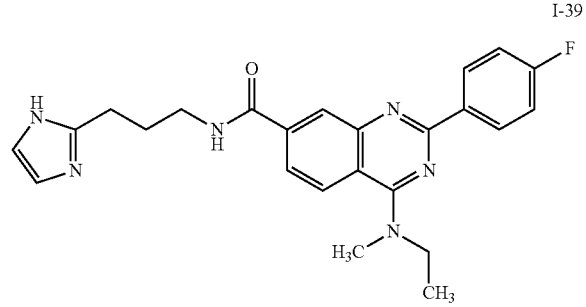
I-40
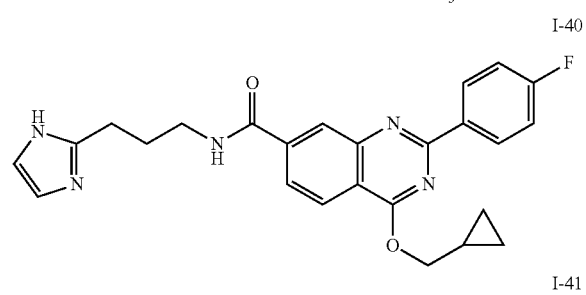
I-41
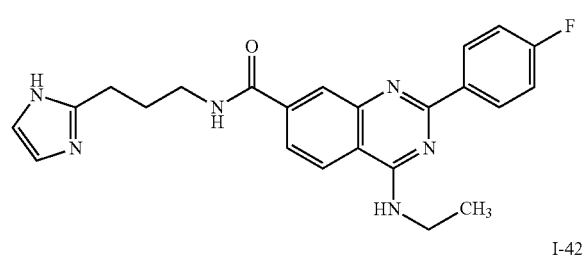
I-42
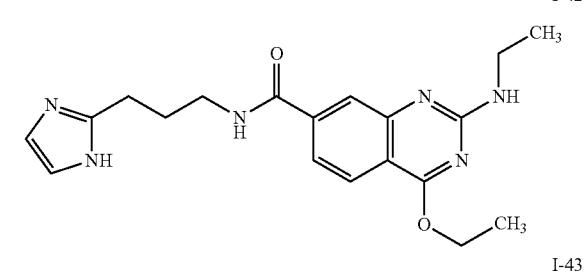
I-43
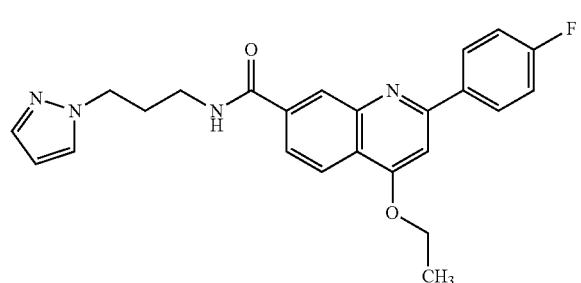
I-44
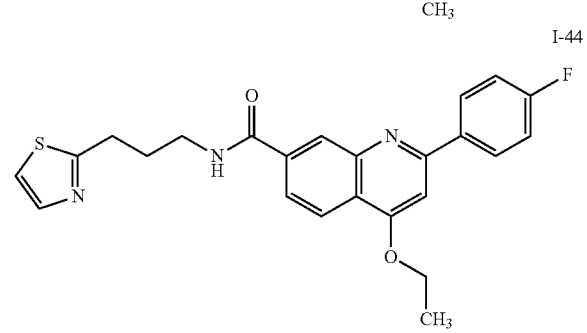

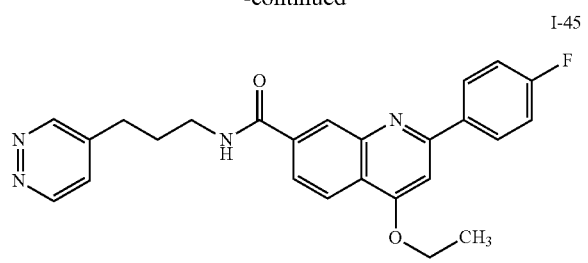

| I-55 | I-60 |
| I-56 | I-61 |
| I-57 | I-62 |
| I-58 | I-63 |
| I-59 | I-64 | cis-cyclobutyl (I-60)

trans cyclopropyl (racemic) (I-59)

I-65
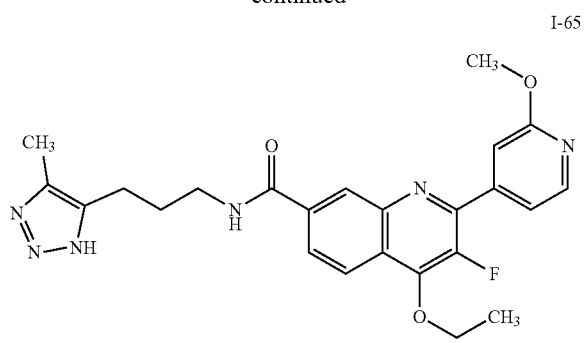
I-66
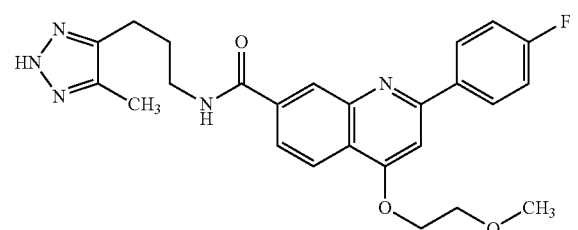
I-67
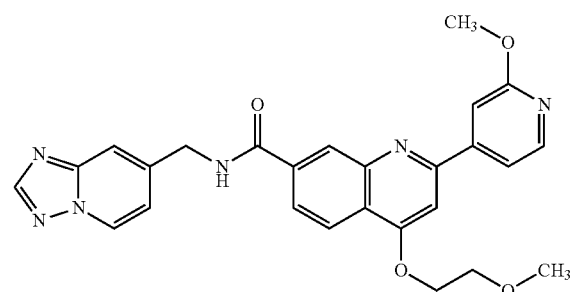
I-68
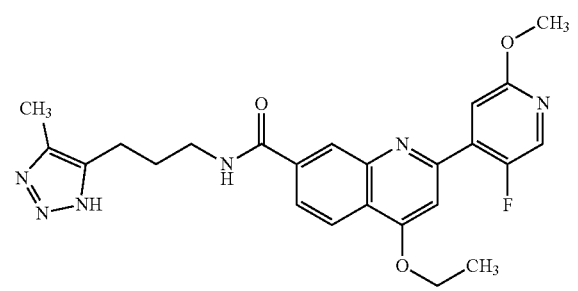
I-69
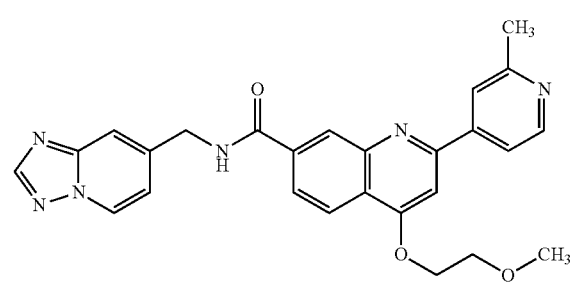
I-70
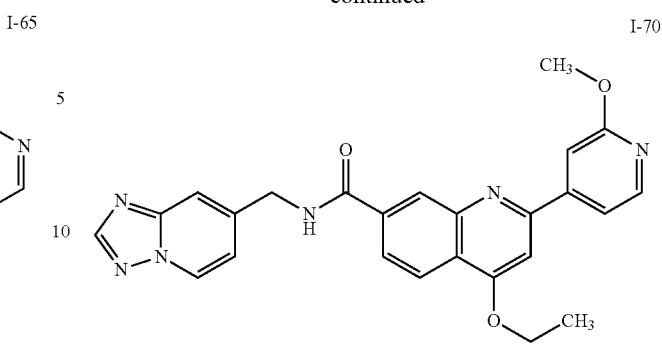

-continued
I-75
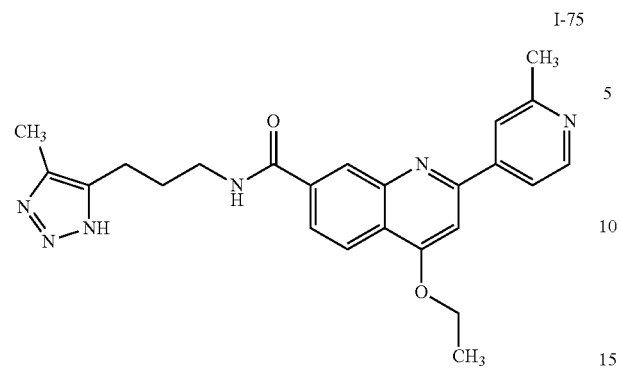
I-76
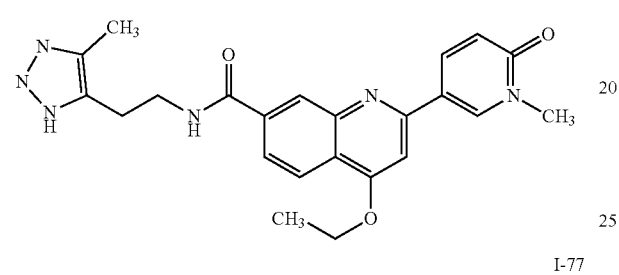
I-77
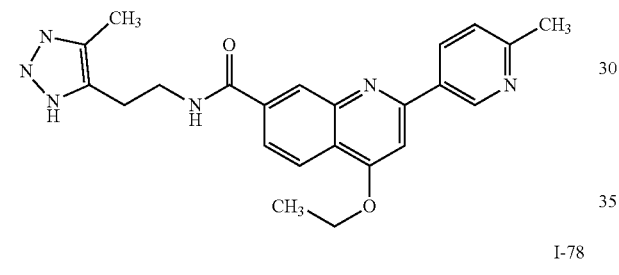
I-78
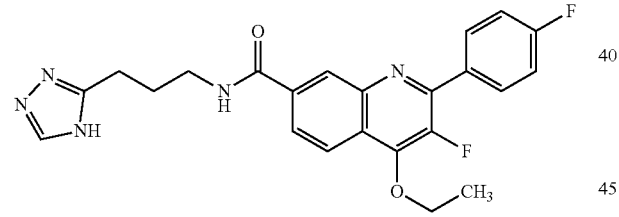
I-79
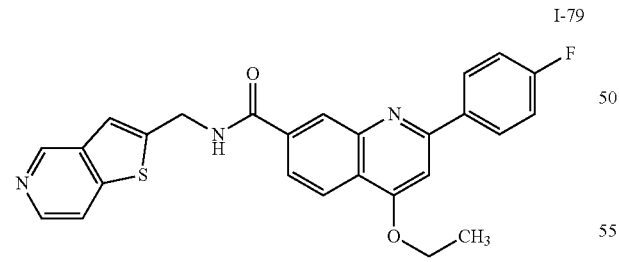
I-80
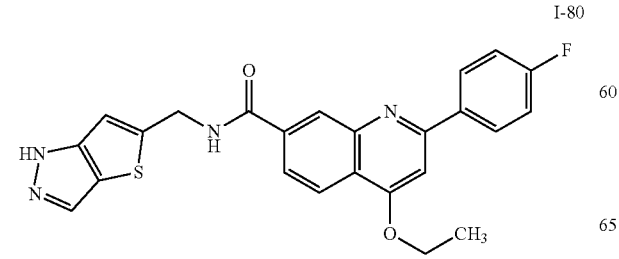
-continued
I-81
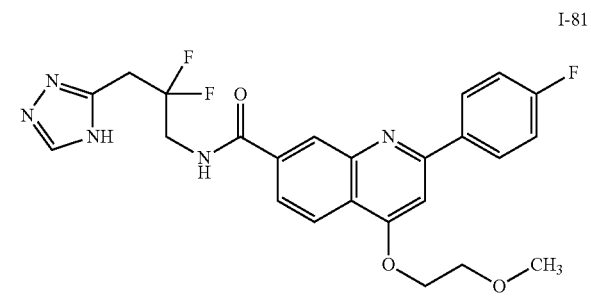
I-82
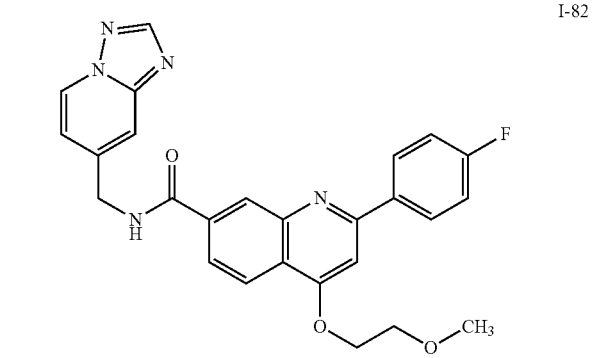
I-83
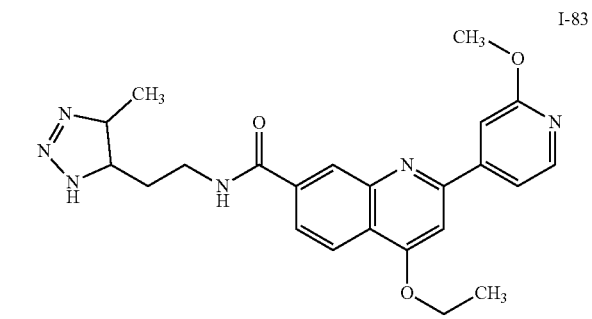
I-84
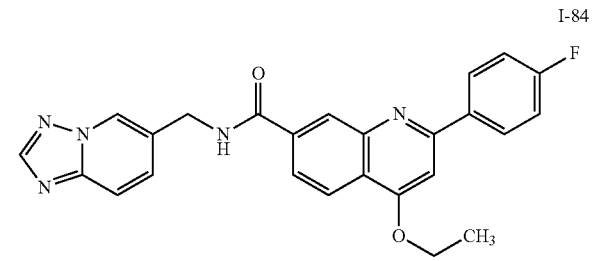
I-85
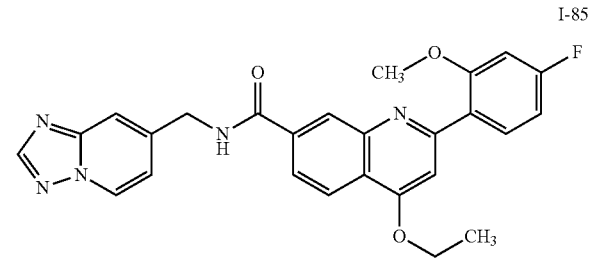

I-86
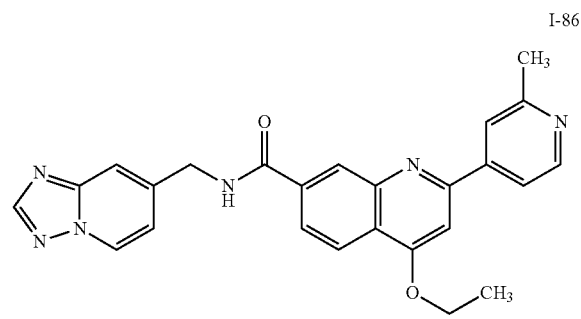
I-87
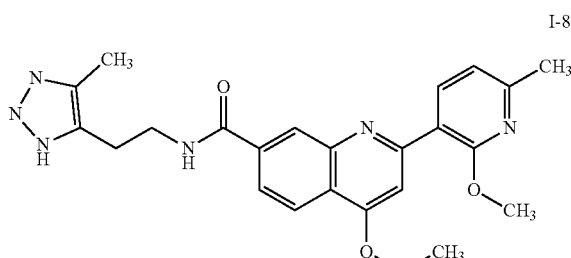
I-88
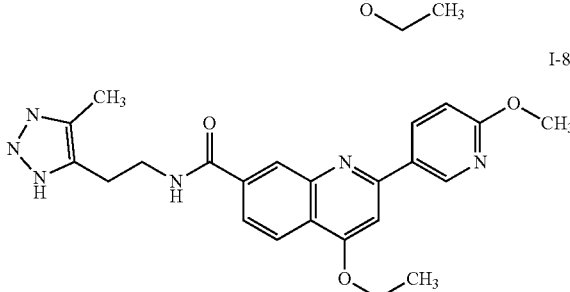
I-89
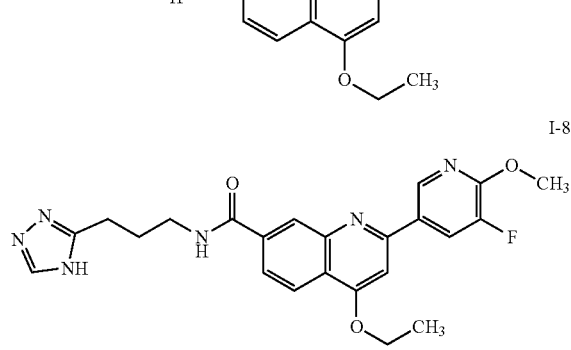
I-90
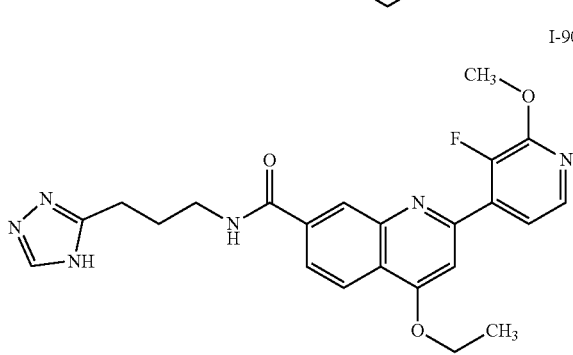
I-91
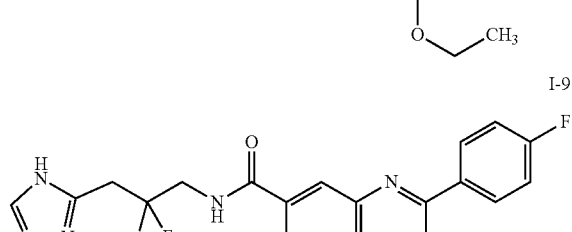
I-92
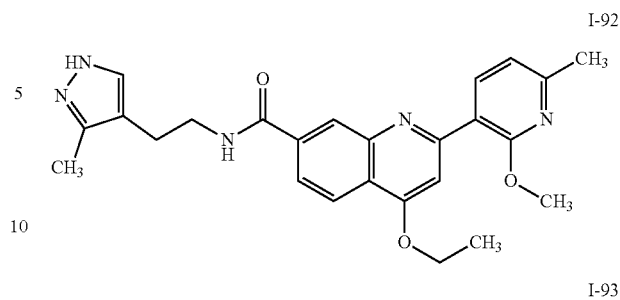
I-93
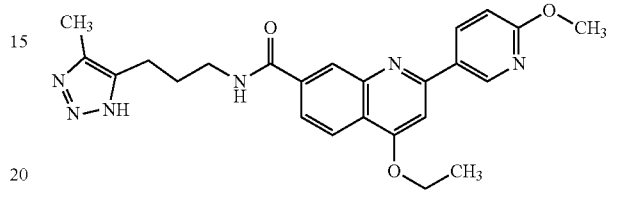
I-94
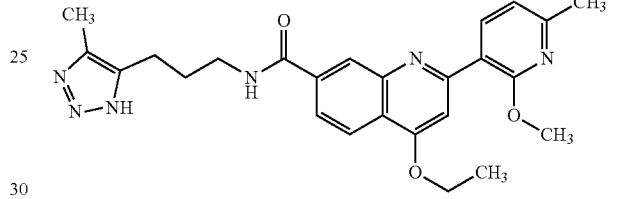
I-95
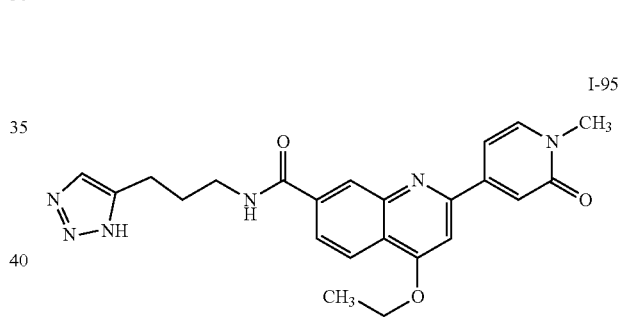
I-96
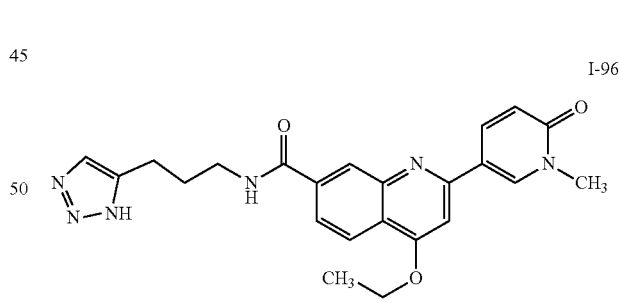
I-97
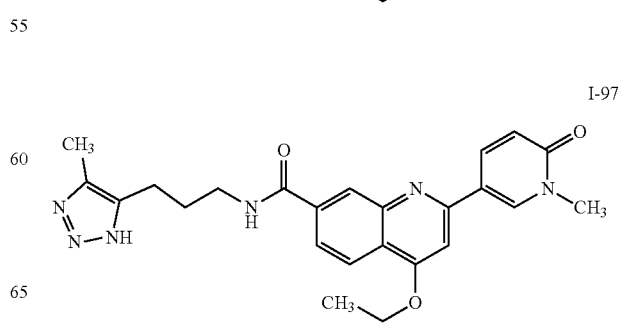

I-98
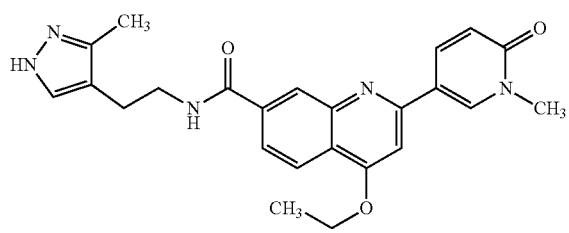
I-99
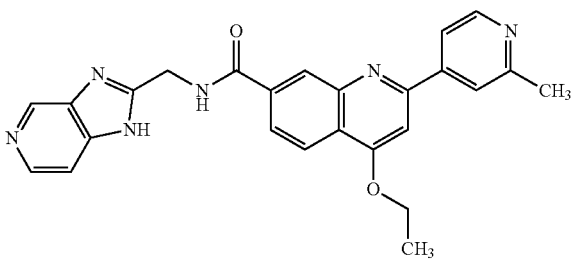
I-100
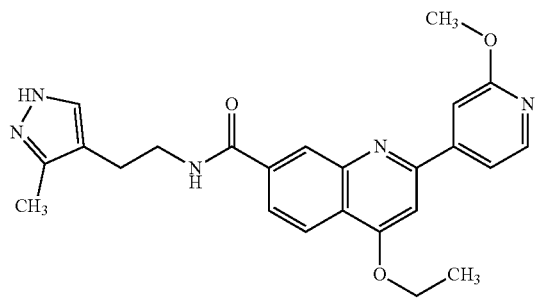
I-101
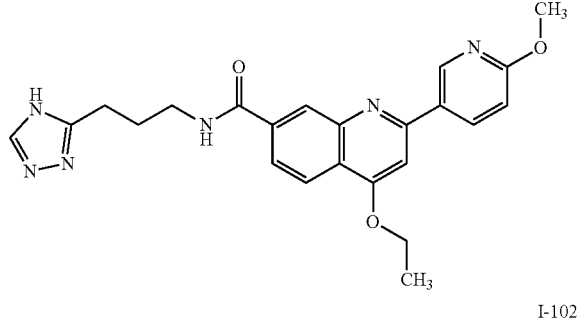
I-102
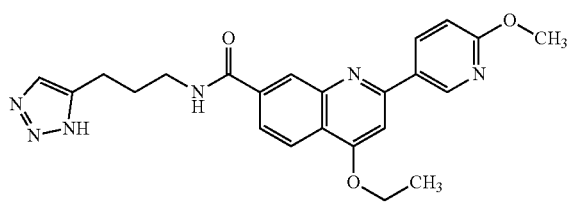
I-103
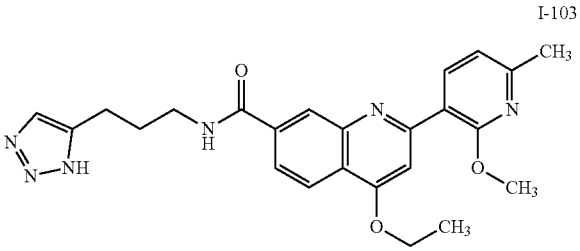
I-104
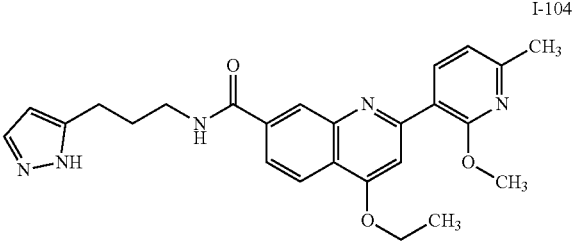
I-105
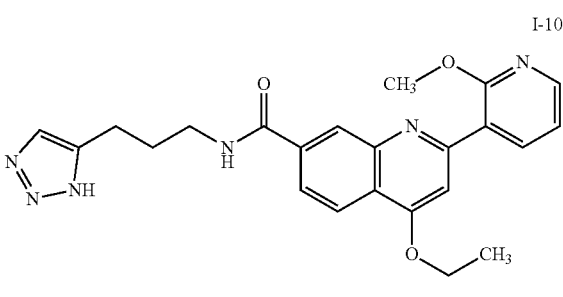
I-106
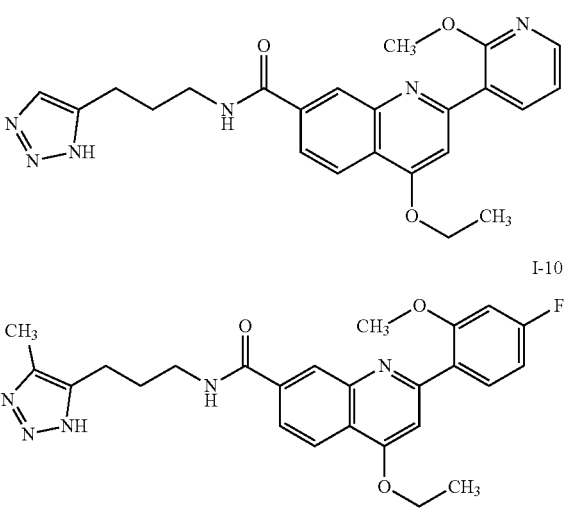
I-107
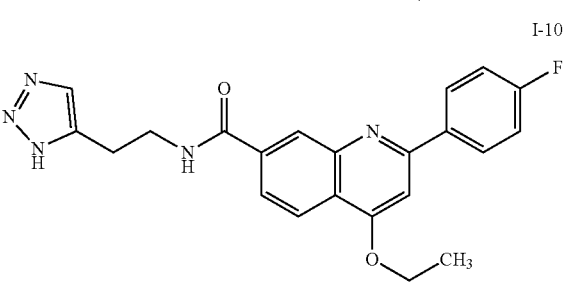
I-108
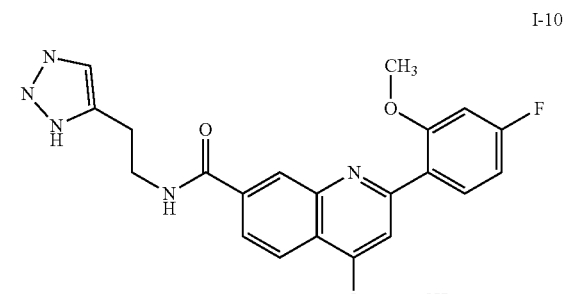
I-109
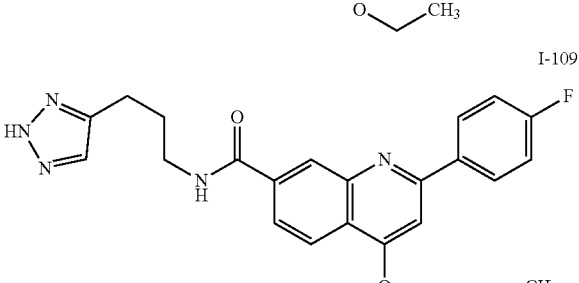

-continued
I-110
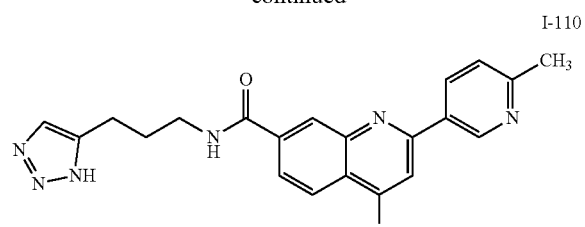
I-111
I-112
I-113
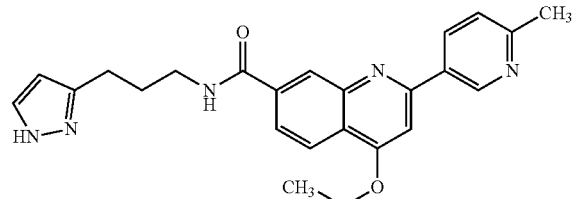
I-114
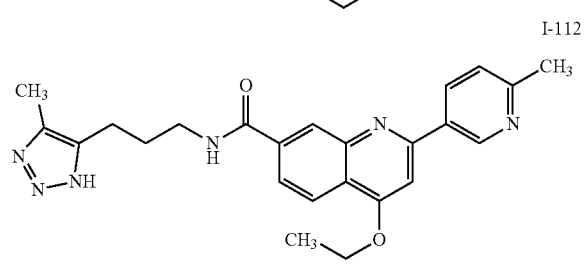
I-115
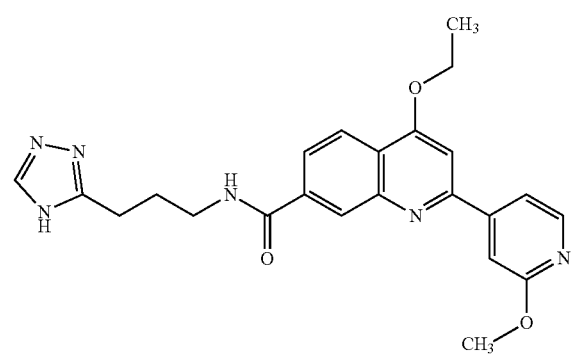
-continued
I-116
I-117
I-118
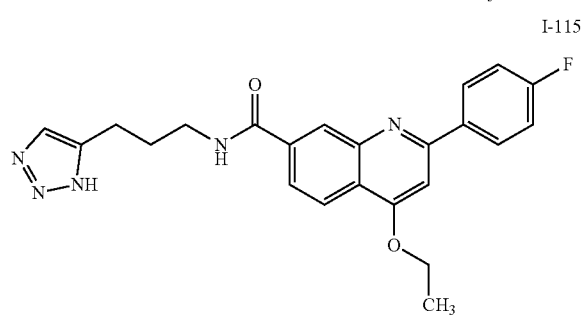
I-119
I-120
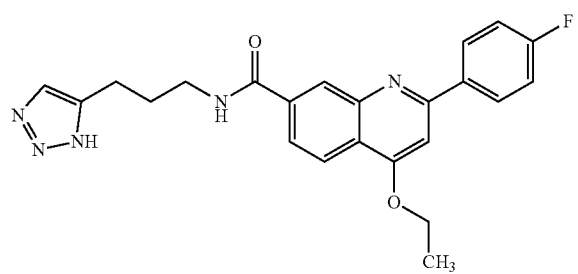

331 332
-continued -continued
I-121
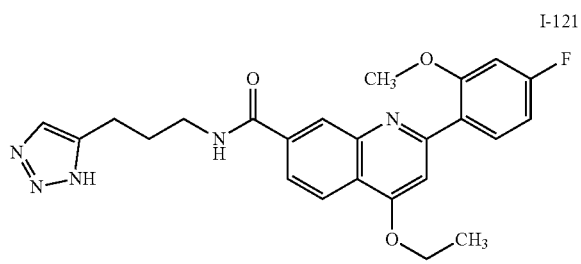
I-127
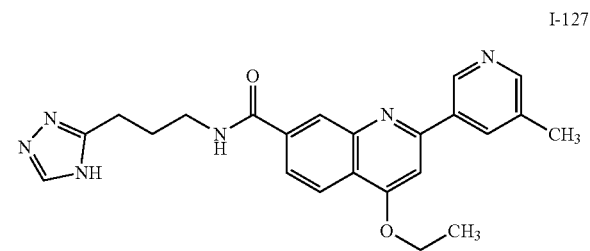
I-122
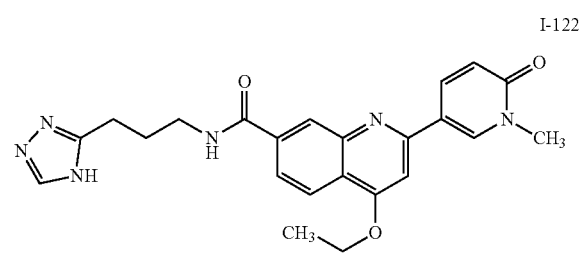
I-128
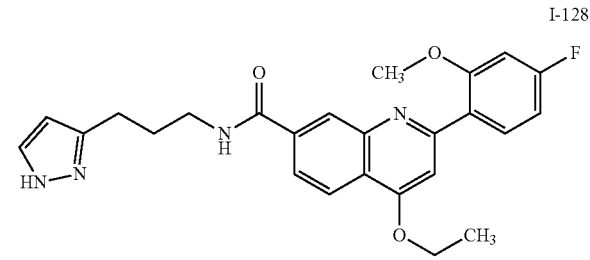
I-123
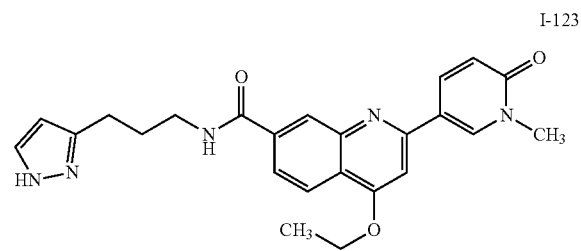
I-129
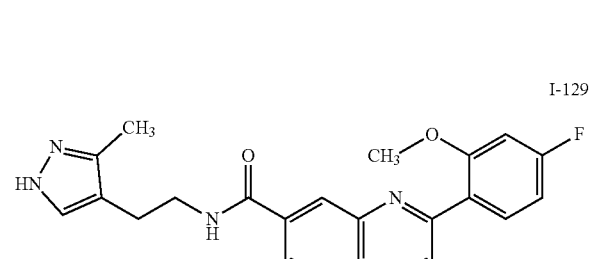
I-124
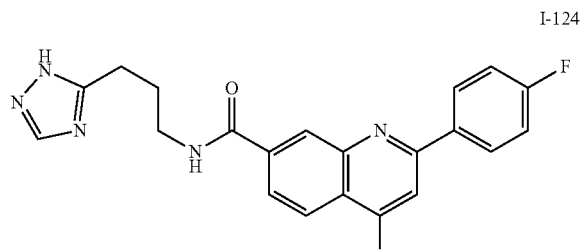
I-130
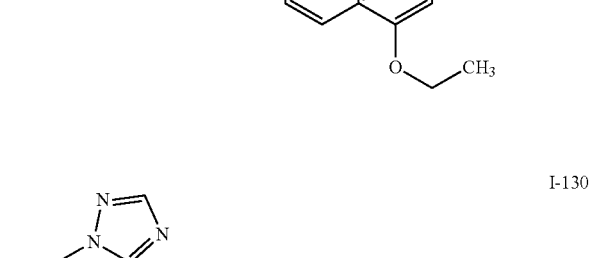
I-125
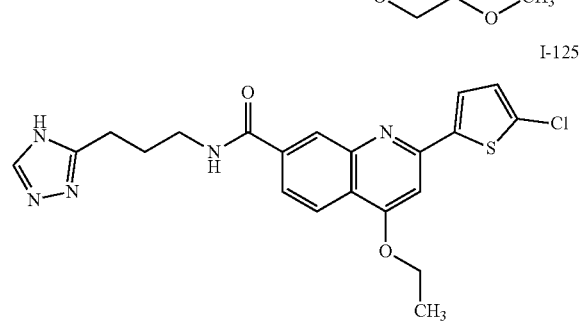
I-126
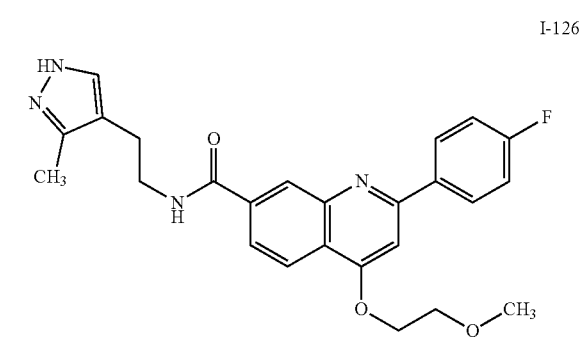
I-131
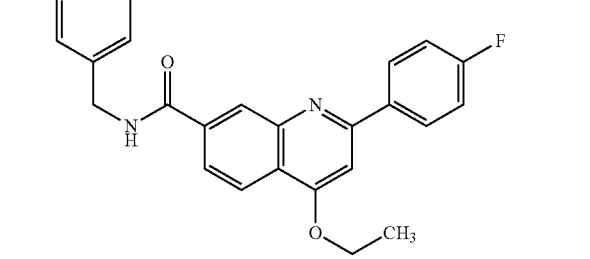
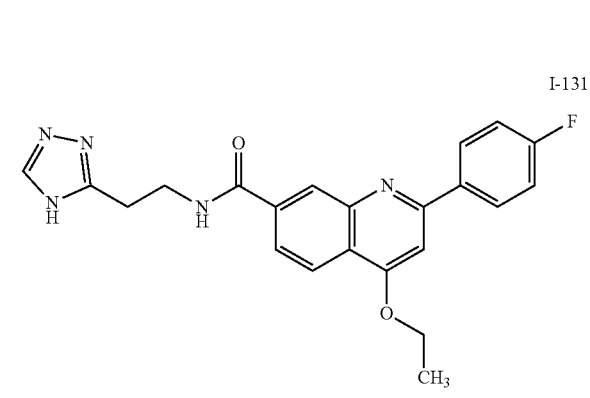

-continued

I-132

I-133

I-134

I-135

I-136

I-137

-continued

I-138

I-139

I-140

I-141

I-142

I-143

I-144
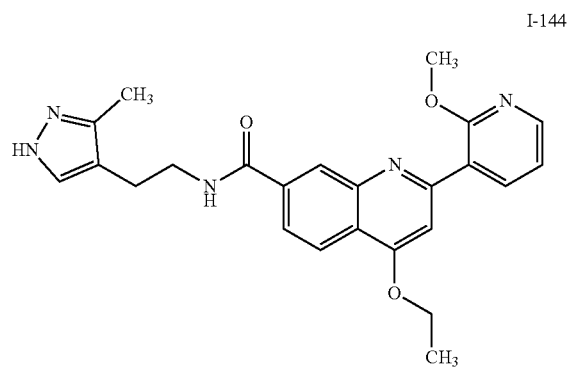
I-145
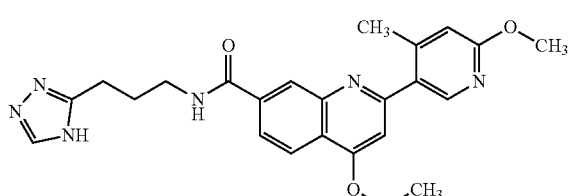
I-146
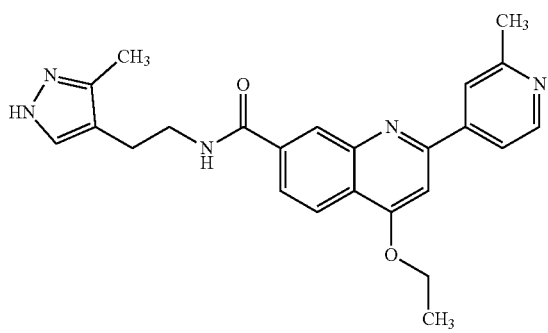
I-147
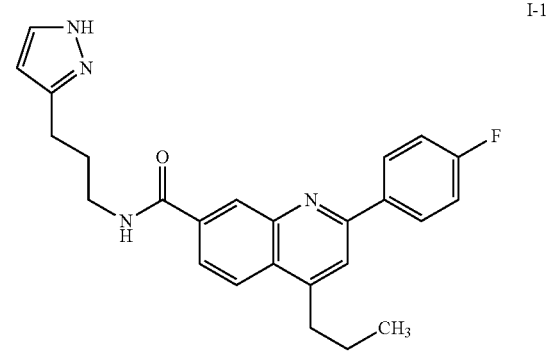
I-148
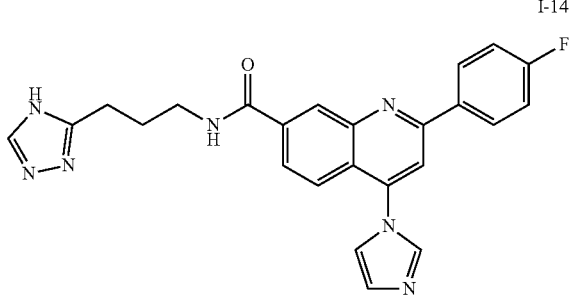
I-149
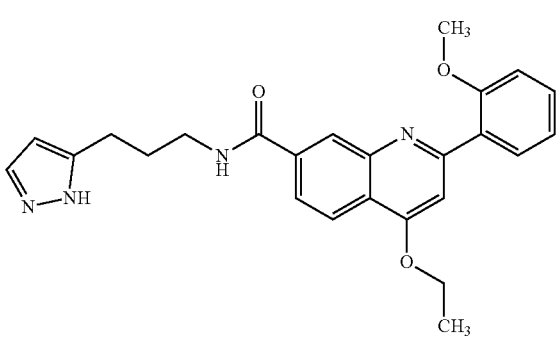
I-150
I-151
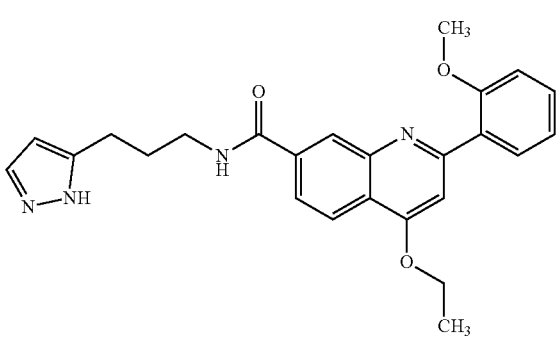
I-152
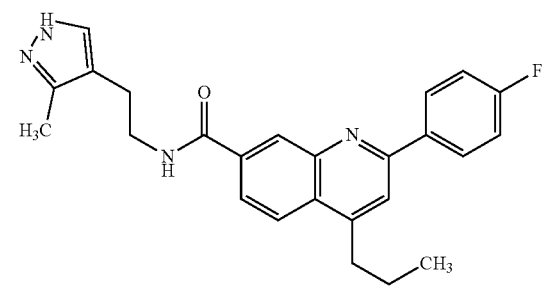
I-153
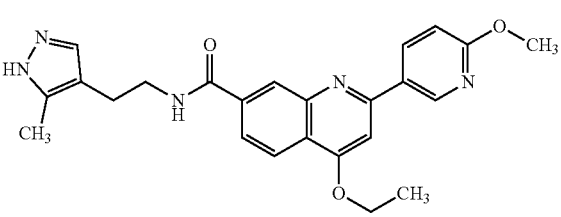

I-154
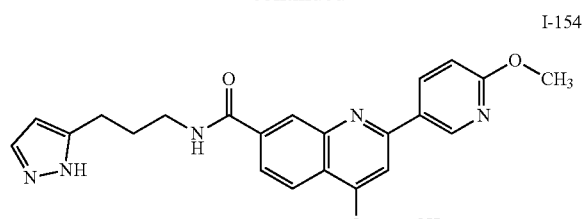
I-155
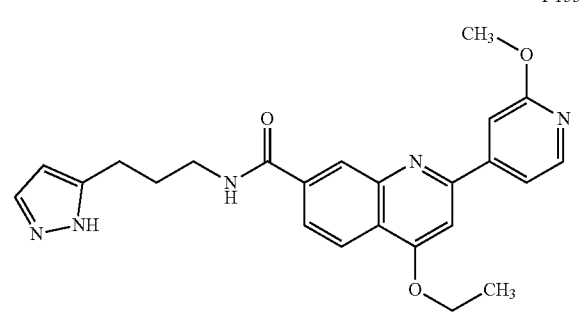
I-156
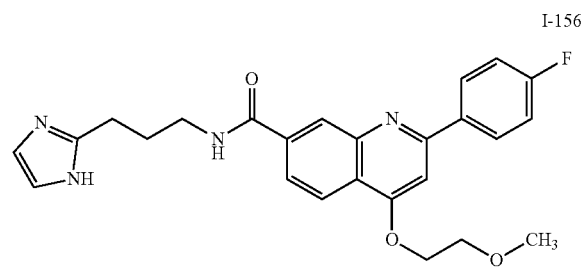
I-157
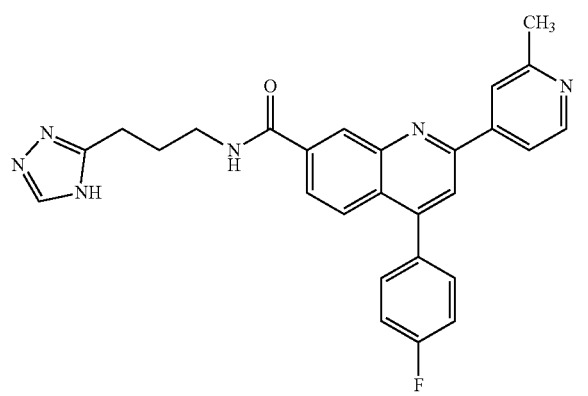
I-158
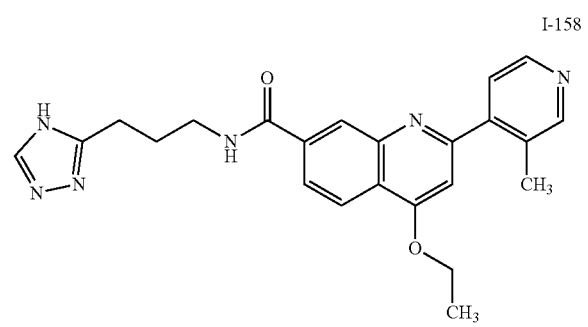
I-159
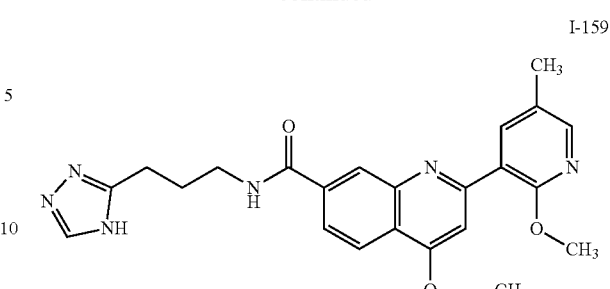
I-160
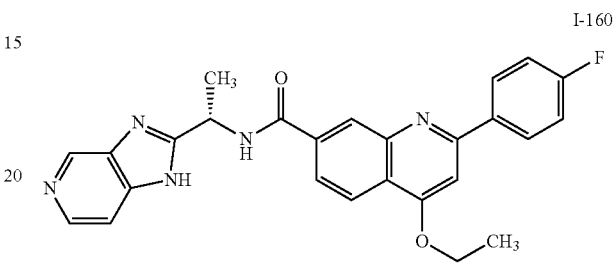
I-161
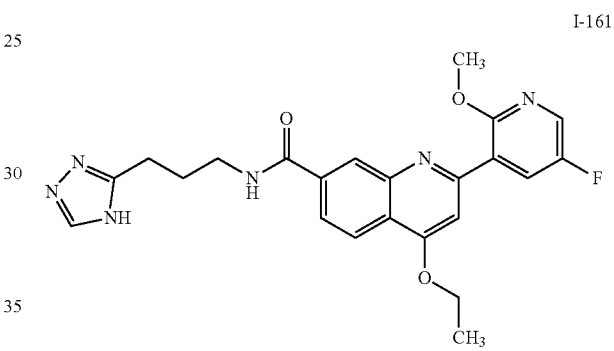
I-162
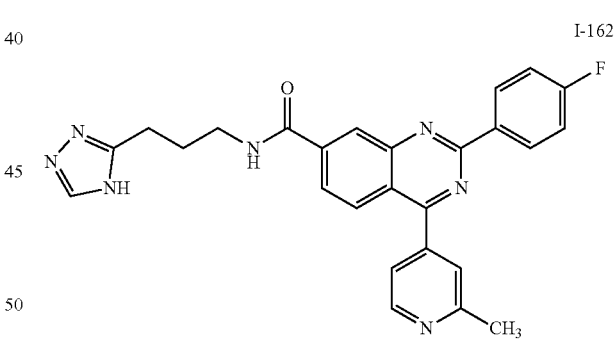
I-163
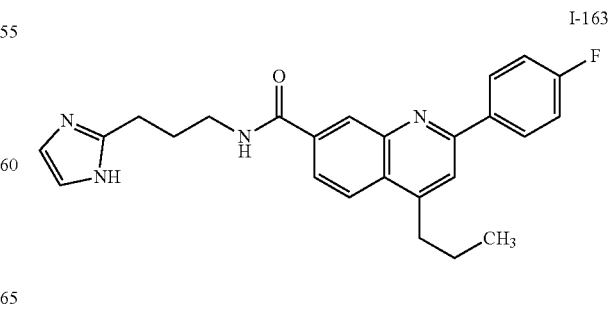

-continued
I-164
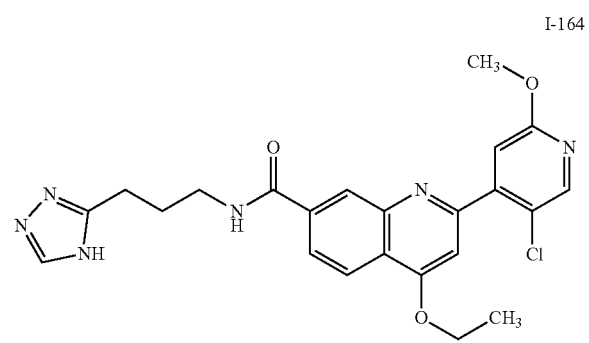
I-165
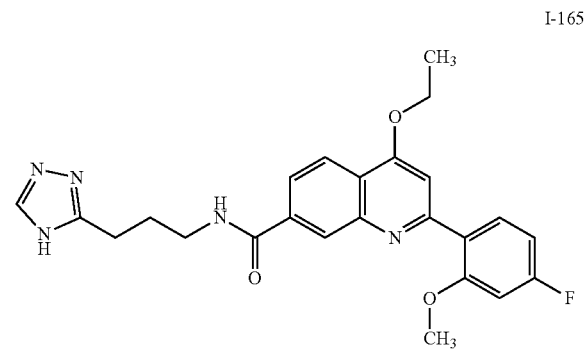
I-166
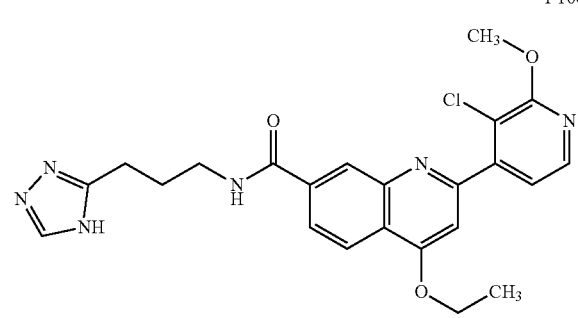
I-167
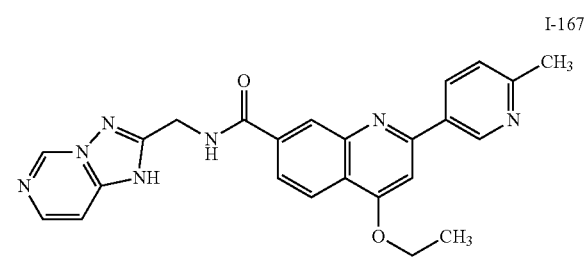
I-168
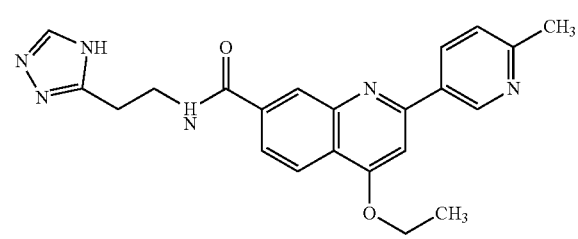
-continued
I-169
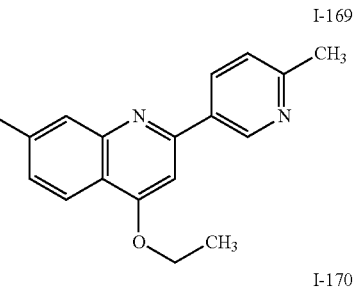
I-170
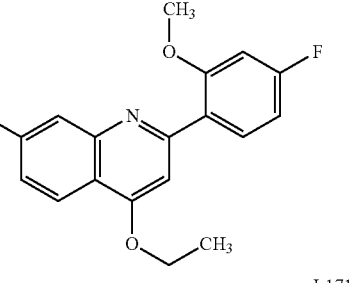
I-171
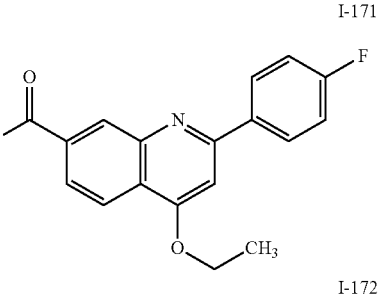
I-172
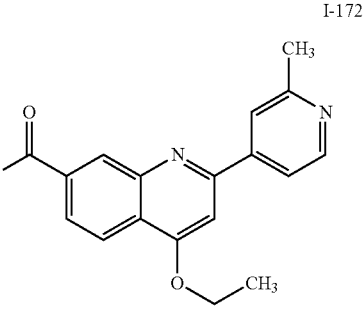
I-173
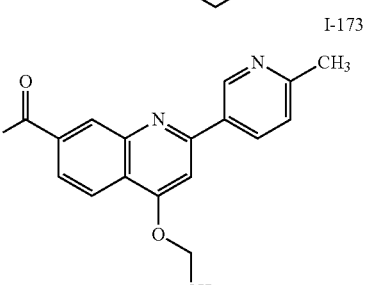
I-174
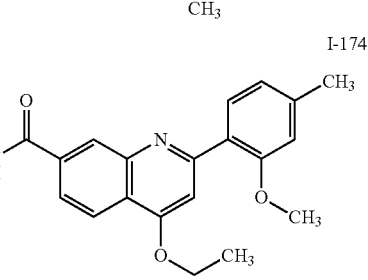

I-175
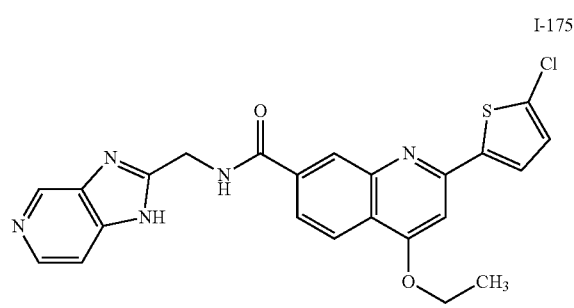
I-176
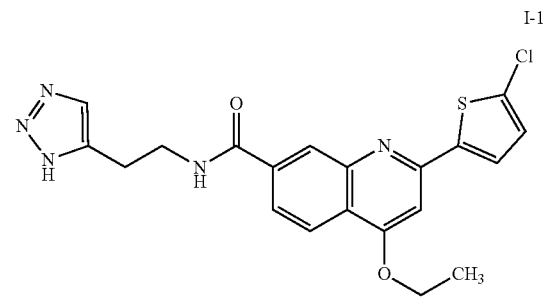
I-177
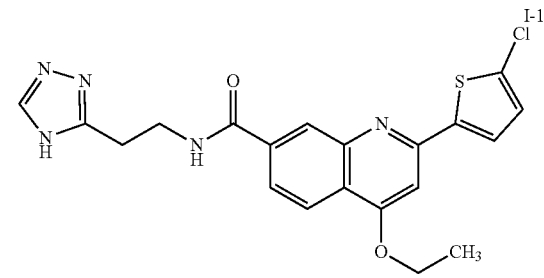
I-178
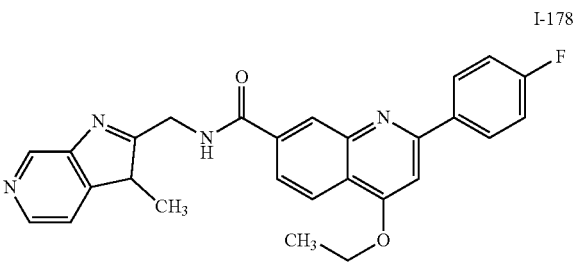
I-179
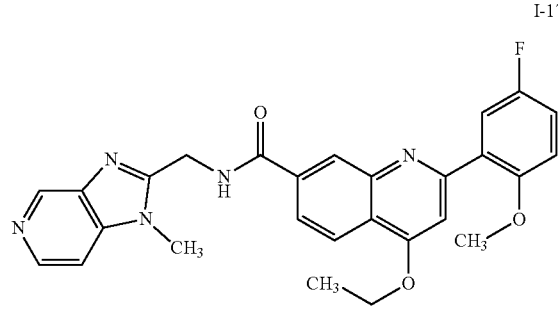
I-180
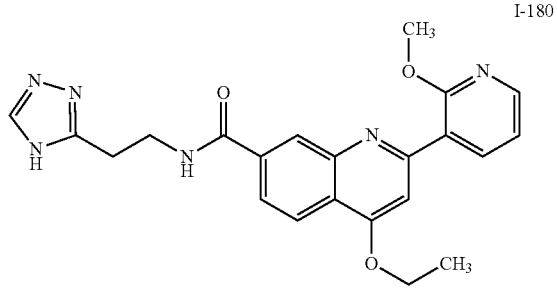
I-181
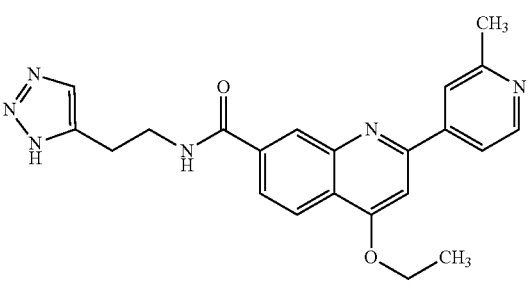
I-182
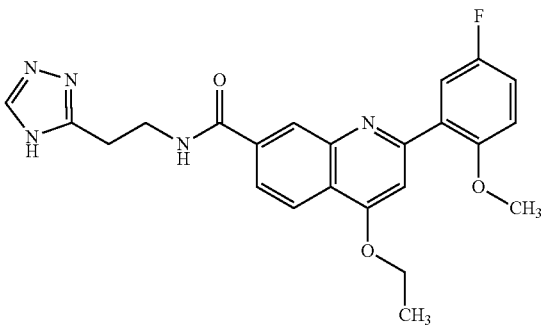
I-183
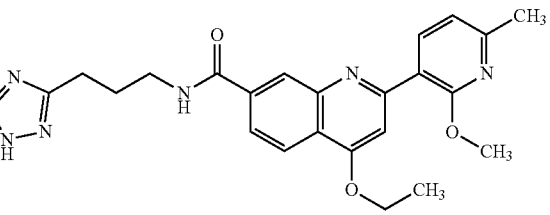
I-184
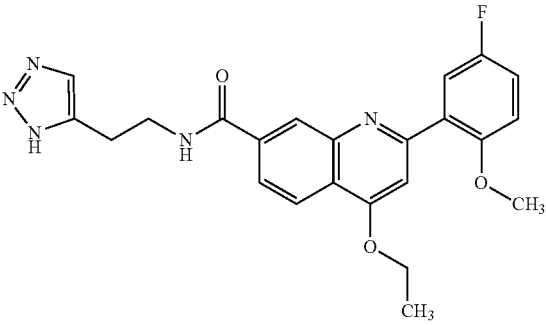

I-185
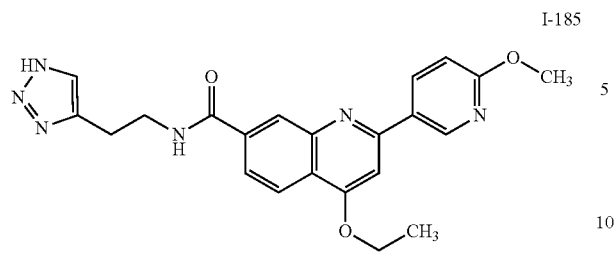
I-186
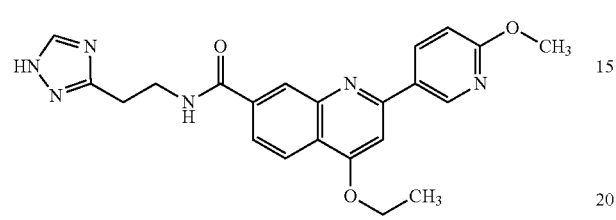
I-187
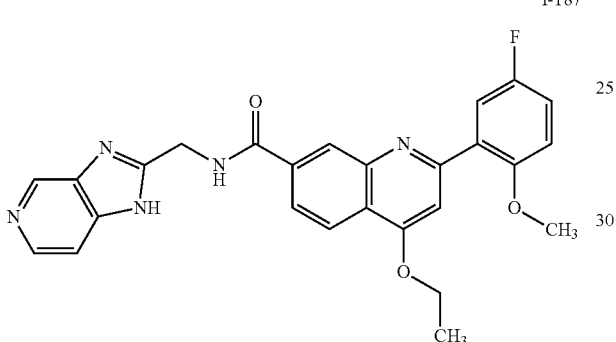
I-188
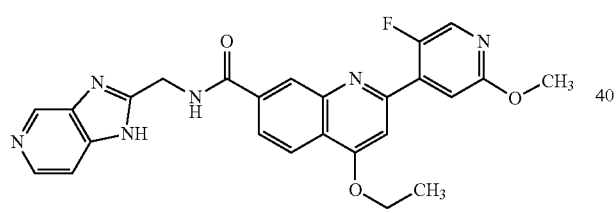
I-189
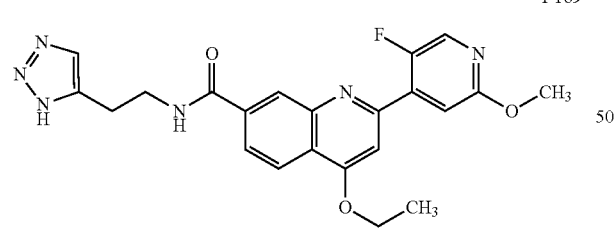
I-190
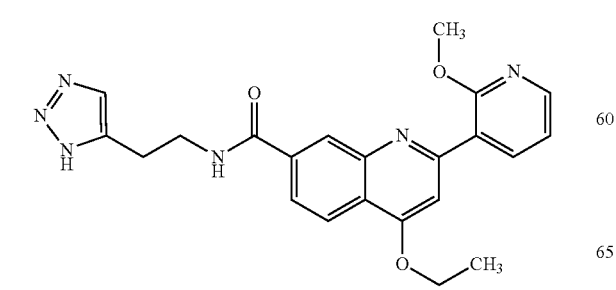
I-191
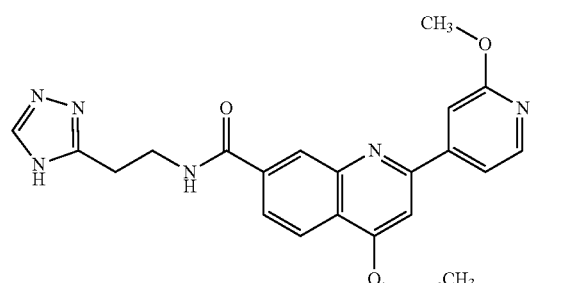
I-192
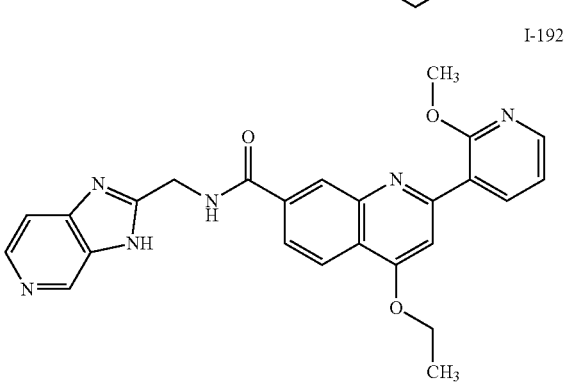
I-193
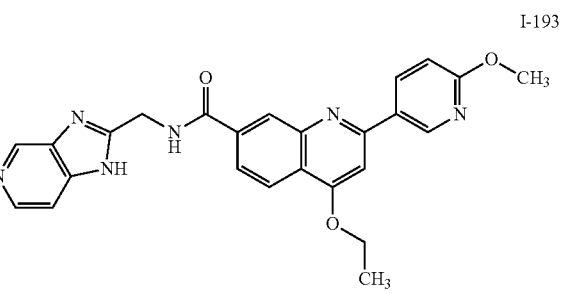
I-194
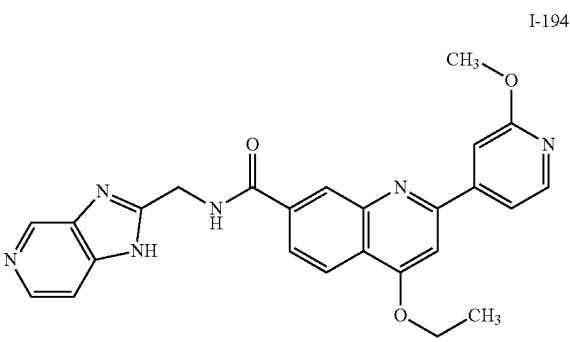
I-195
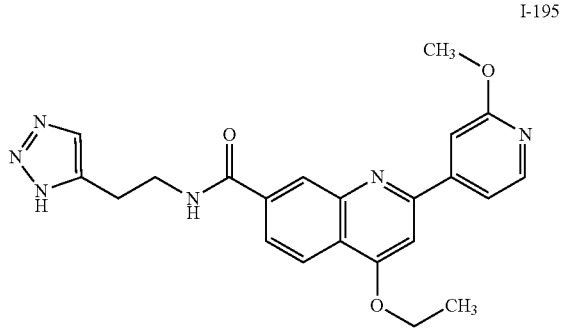

-continued
I-196
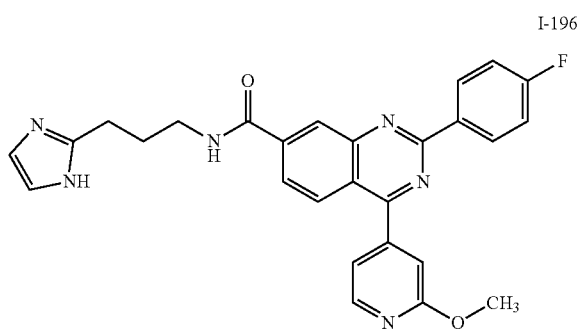
I-197
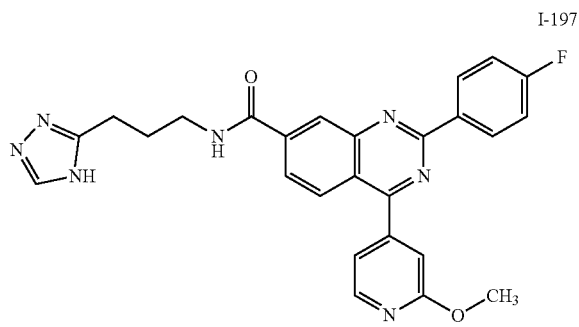
I-198
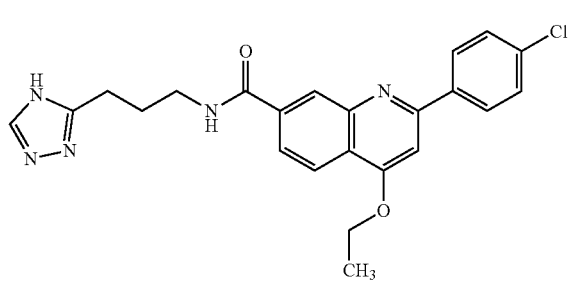
I-199
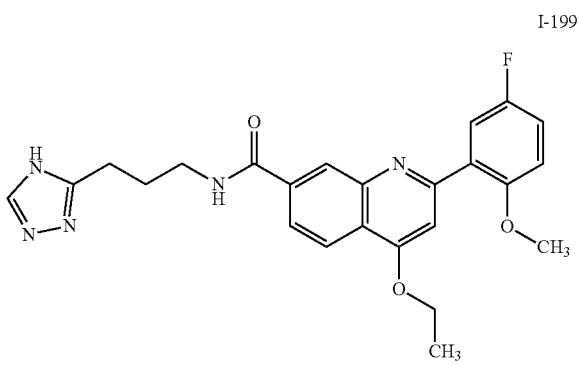
I-200
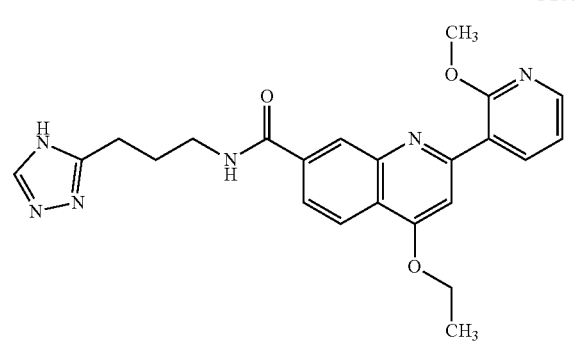
-continued
I-201
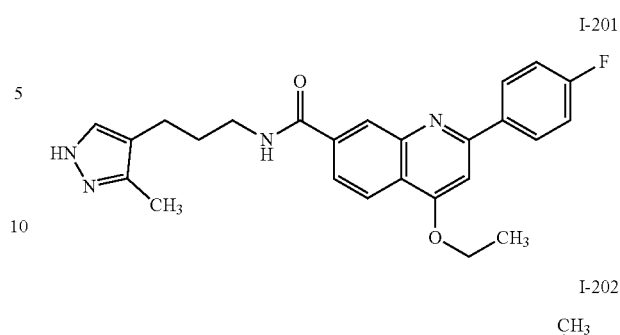
I-202
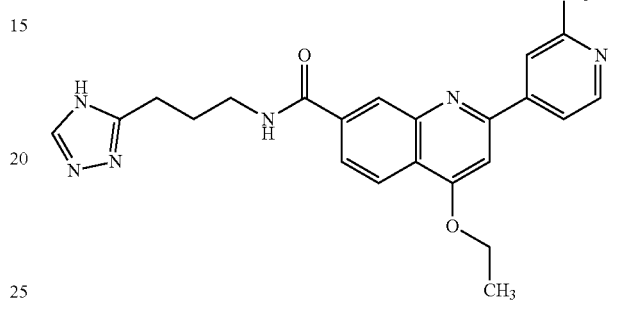
I-203
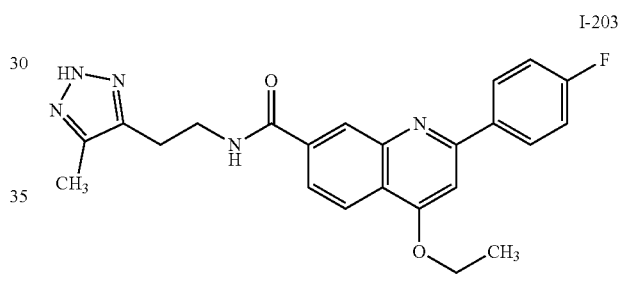
I-204
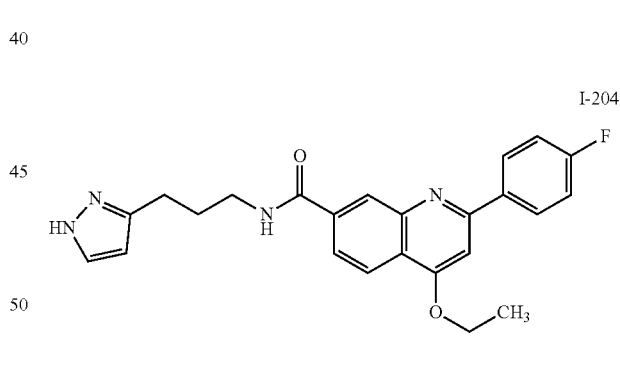
I-205
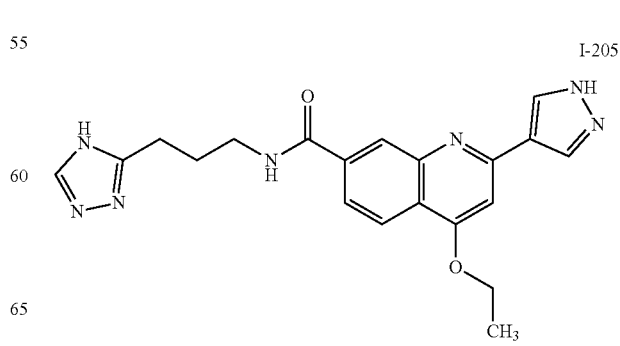

I-206
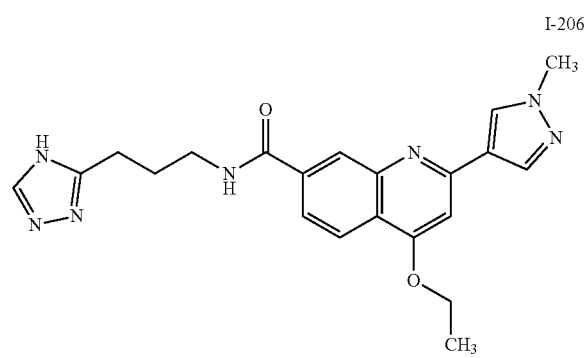
I-211
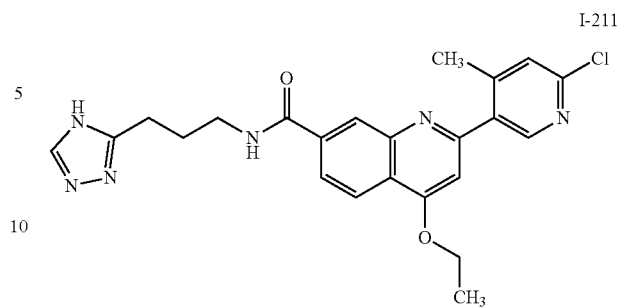
I-207
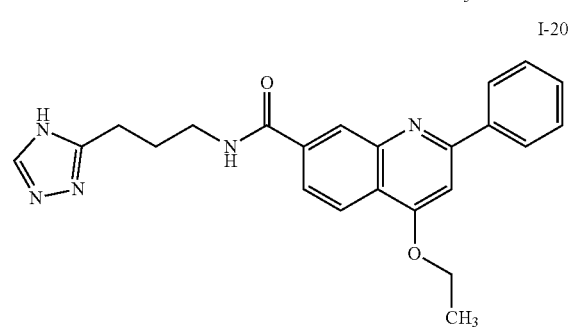
I-212
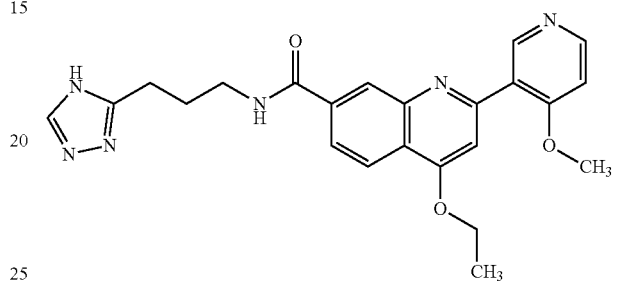
I-208
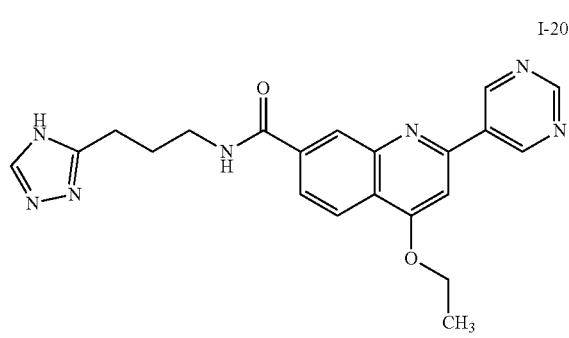
I-213
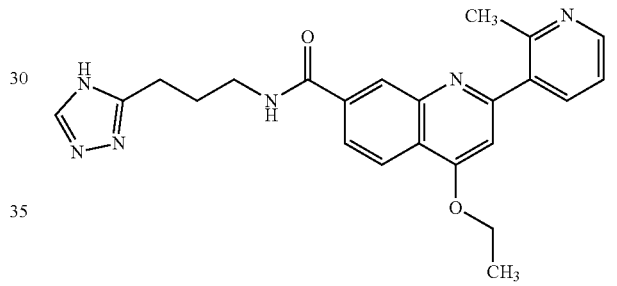
I-209
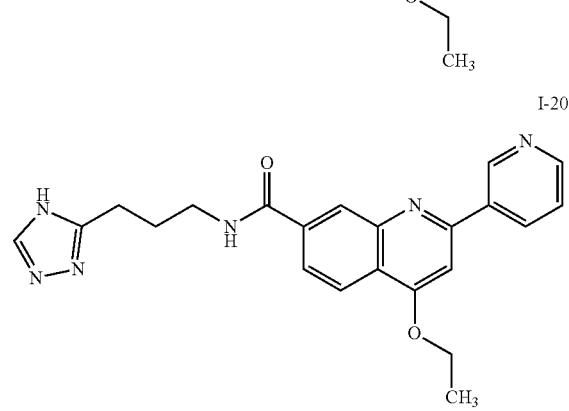
I-214
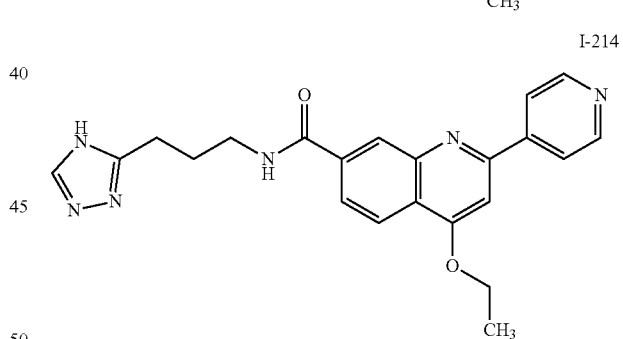
I-210
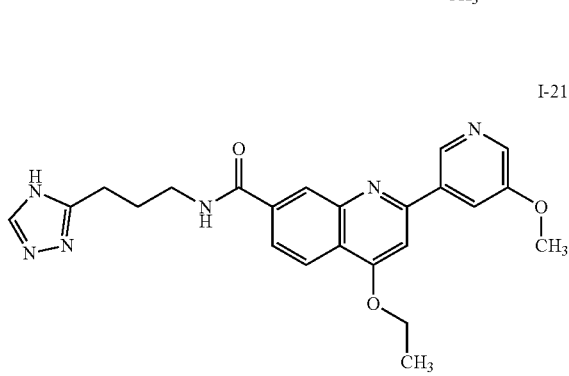
I-215
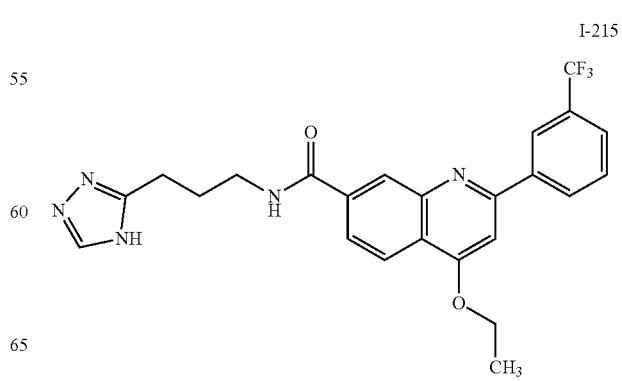

I-216
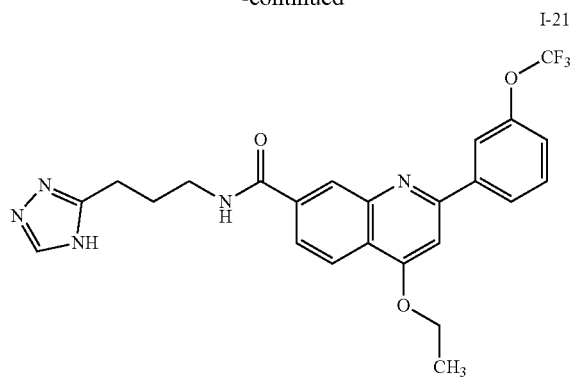
I-217
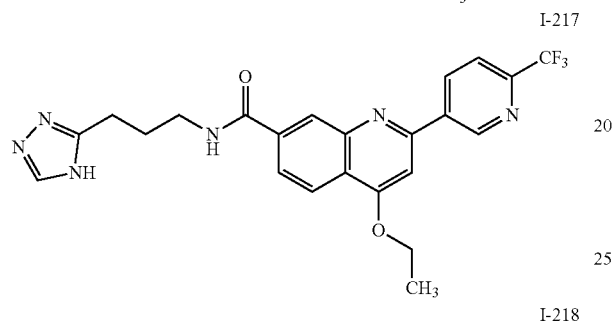
I-218
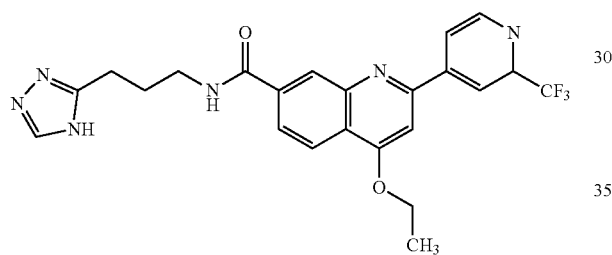
I-219
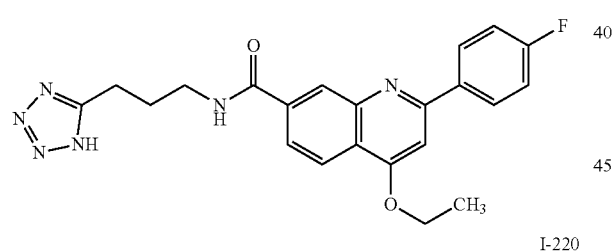
I-220
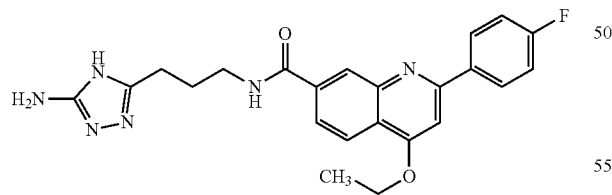
I-221
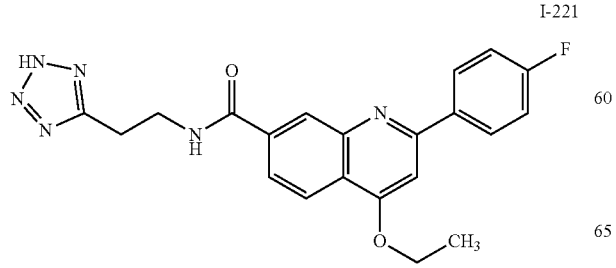
I-222
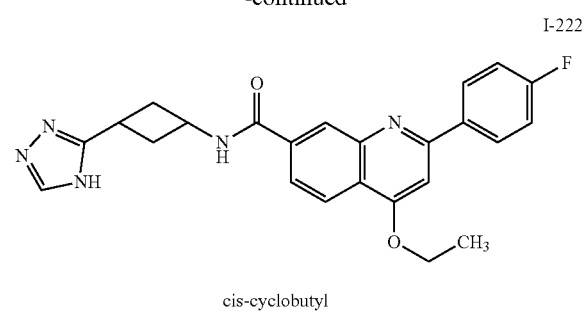
cis-cyclobutyl
I-223
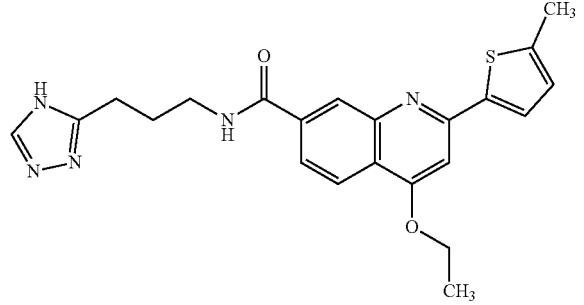
I-224
I-225
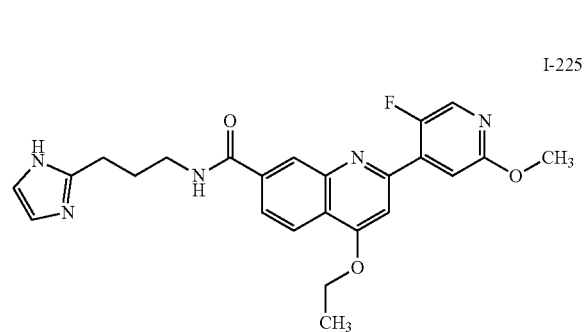
I-226
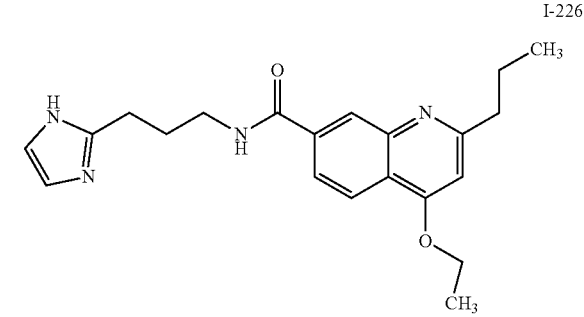

-continued

I-227

I-228

I-229

14. The chemical entity of claim 2 chosen from compounds of formula III and pharmaceutically acceptable salts thereof, wherein:
   J is linear $C_{1-6}$ aliphatic, wherein 1-2 methylene units of J are optionally and independently replaced by O, S, or $N(R^{13})$;
   T is 5-10-membered heteroaryl having 1-5 heteroatoms independently selected from nitrogen, oxygen, and sulfur, wherein the aryl and heteroaryl are optionally substituted with one or more $R^d$;
   R is hydrogen;
   $R^A$ is wherein is a 5- or 6-membered aromatic monocyclic ring having 0-3 heteroatoms independently selected from nitrogen, oxygen, and sulfur;

n is 0, 1, 2, or 3;
$R^a$ is $Z_1$—$R^8$;
$Z_1$ is a direct bond;
$R^8$ is independently selected from halogen, $R^5$ and $OR^5$;
W is CH;
$R^q$ is hydrogen;
$R^{1A}$ is linear or branched $C_{1-6}$ aliphatic, wherein 1 or 2 methylene units of the $C_{1-6}$ aliphatic are optionally and independently replaced by O, S or $N(R^{19})$; and wherein the $C_{1-6}$ aliphatic is optionally substituted with one or more $R^k$;
each occurrence of $R^k$ is independently selected from linear or branched $C_{1-6}$ aliphatic and $Z_3$—$R^{23}$;
each occurrence of $Z_3$ is independently selected from direct bond, and $C_{1-3}$ alkylene chain; and
each occurrence of $R^{23}$ is independently selected from CN, halogen, $OR^{30}$, $SR^{30}$, $N(R^{26})_2$, and linear or branched $C_{1-6}$ aliphatic.

15. The chemical entity of claim 14 chosen from compounds of formula III and pharmaceutically acceptable salts thereof, wherein:

$R^A$ is and
$R^{1A}$ is linear or branched $C_{1-6}$ aliphatic, wherein 1 or 2 methylene units of the $C_{1-6}$ aliphatic are optionally and independently replaced by O, S or NH.

16. The chemical entity of claim 15, wherein:
$OR^{1A}$ is selected from

, and

.

17. The chemical entity of claim 14, wherein:
$R^A$ is selected from

,

-continued
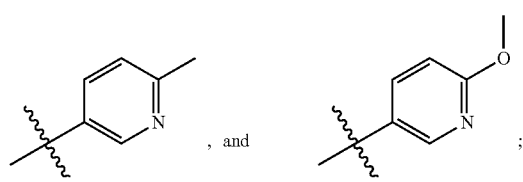, and
$OR^{1A}$ is selected from
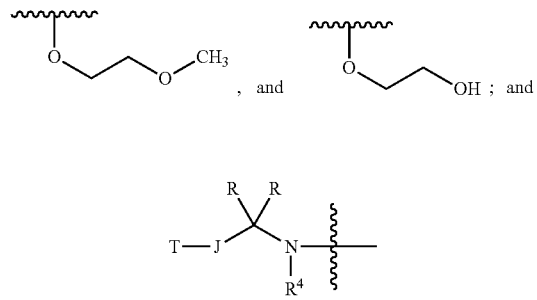, and
is selected from
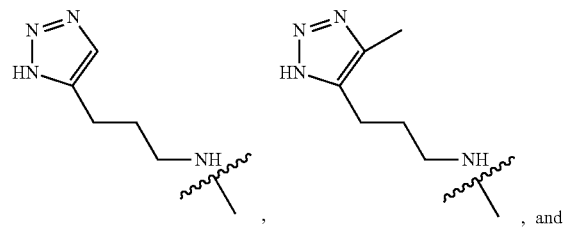
18. The chemical entity of claim 17, selected from:
-continued
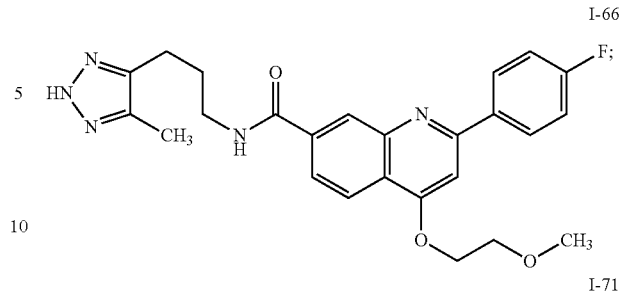
I-66
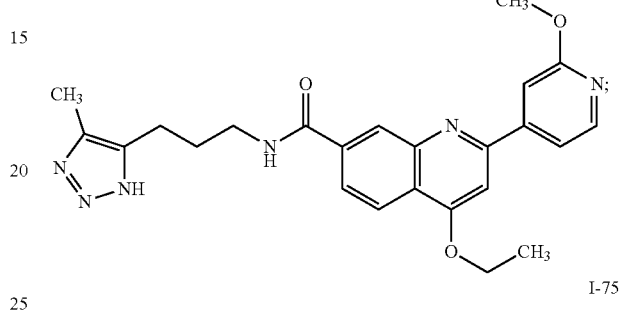
I-71
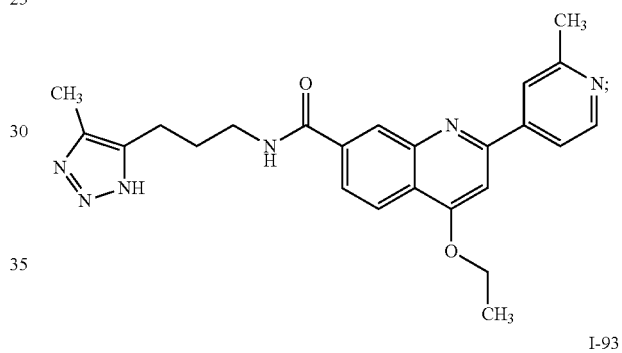
I-75
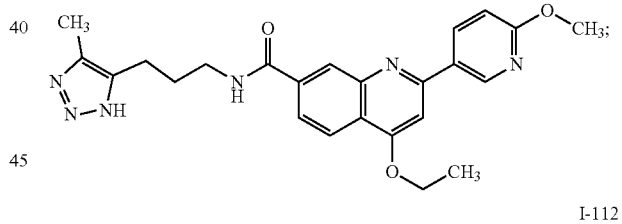
I-93
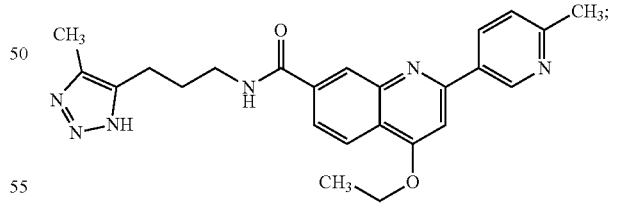
I-112
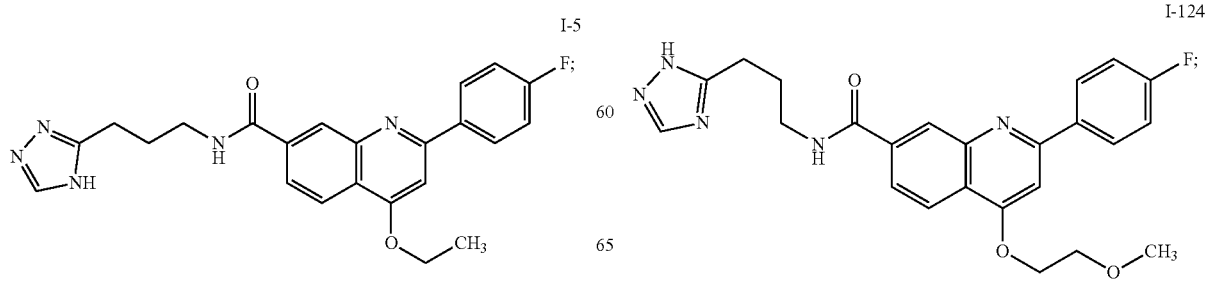
I-5, I-124

I-126

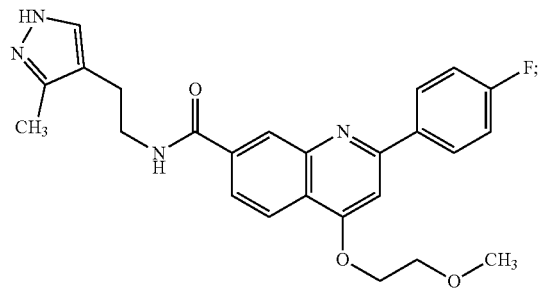

I-115

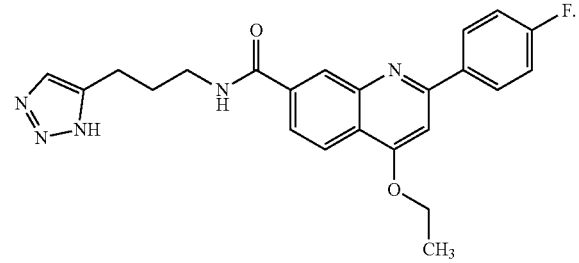

-continued
and

I-229

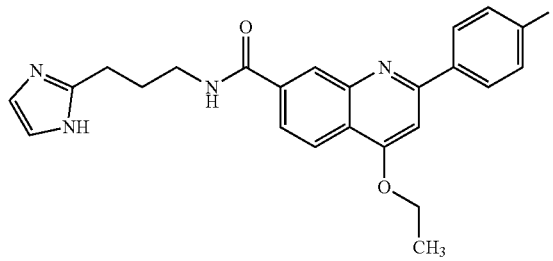

19. A pharmaceutical composition comprising a chemical entity of claim 1 and a pharmaceutically acceptable carrier.

20. The pharmaceutical composition of claim 19, further comprising another therapeutic agent.

21. A method of inhibiting abnormal cell growth or treating a hyperproliferative disorder in a subject in need thereof comprising administering to the subject in need thereof an effective amount of a chemical entity of claim 1.

22. A method of treating cancer, arthritis, endotoxic shock, or autoimmune encephalitis in a subject in need thereof comprising administering to the subject an effective amount of a chemical entity of claim 1.

23. A method for inhibiting nicotinamide phosphoribosyltransferase (NAMPT) in a cell comprising contacting the cell with an effective amount of a chemical entity of claim 1.

* * * * *